US008962642B2

(12) United States Patent
Mortimore et al.

(10) Patent No.: US 8,962,642 B2
(45) Date of Patent: *Feb. 24, 2015

(54) 5-CYANO-4-(PYRROLO[2,3B]PYRIDINE-3-YL)-PYRIMIDINE DERIVATIVES USEFUL AS PROTEIN KINASE INHIBITORS

(71) Applicant: Vertex Pharmaceuticals Incorporated, Cambridge, MA (US)

(72) Inventors: Michael Mortimore, Abingdon (GB); Stephen Clinton Young, Oxford (GB); Simon Robert Lorrie Everitt, Abingdon (GB); Ronald Knegtel, Abingdon (GB); Joanne Louise Pinder, Abingdon (GB); Alistair Peter Rutherford, Abingdon (GB); Steven Durrant, Abingdon (GB); Guy Brenchley, West Hanney (GB); Jean-Damien Charrier, Abingdon (GB); Michael O'Donnell, Abingdon (GB)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/961,218

(22) Filed: Aug. 7, 2013

(65) Prior Publication Data

US 2014/0045812 A1 Feb. 13, 2014

Related U.S. Application Data

(62) Division of application No. 13/477,663, filed on May 22, 2012, now Pat. No. 8,530,489, which is a division of application No. 12/448,489, filed as application No. PCT/US2007/026190 on Dec. 21, 2007, now Pat. No. 8,247,421.

(60) Provisional application No. 60/876,307, filed on Dec. 21, 2006, provisional application No. 60/922,291, filed on Apr. 6, 2007, provisional application No. 60/947,707, filed on Jul. 3, 2007, provisional application No. 60/989,014, filed on Nov. 19, 2007.

(51) Int. Cl.
*A01N 43/54* (2006.01)
*A61K 31/505* (2006.01)
*C07D 471/04* (2006.01)

(52) U.S. Cl.
CPC .................... *C07D 471/04* (2013.01)
USPC ............ 514/274; 514/275; 544/316; 544/331

(58) Field of Classification Search
USPC .................. 514/269, 274, 275; 544/316, 331
See application file for complete search history.

(56) References Cited

U.S. PATENT DOCUMENTS

| 5,304,121 | A | 4/1994 | Sahatjian |
| 5,338,849 | A | 8/1994 | Festal et al. |
| 5,886,026 | A | 3/1999 | Hunter et al. |
| 6,099,562 | A | 8/2000 | Ding et al. |
| 6,265,403 | B1 | 7/2001 | Fraley et al. |
| 6,900,201 | B2 * | 5/2005 | Noe et al. ................... 514/227.8 |
| 7,135,550 | B2 | 11/2006 | Come et al. |
| 7,507,826 | B2 | 3/2009 | Salituro et al. |
| 7,767,816 | B2 | 8/2010 | Farmer et al. |
| 7,795,259 | B2 | 9/2010 | Binch et al. |
| 8,163,917 | B2 * | 4/2012 | Farmer et al. ................. 546/113 |
| 8,247,421 | B2 * | 8/2012 | Mortimore et al. ........... 514/256 |
| 8,530,489 | B2 | 9/2013 | Mortimore et al. |
| 2002/0147189 | A1 | 10/2002 | Cai et al. |
| 2003/0153560 | A1 | 8/2003 | Salituro et al. |
| 2004/0009968 | A1 | 1/2004 | Binch et al. |
| 2004/0009996 | A1 | 1/2004 | Moon et al. |
| 2004/0043388 | A1 | 3/2004 | Come et al. |
| 2004/0044203 | A1 * | 3/2004 | Wittman et al. ................ 544/55 |
| 2004/0236110 | A1 * | 11/2004 | Ladouceur et al. ........ 546/277.4 |
| 2005/0137201 | A1 | 6/2005 | Aronov et al. |
| 2005/0148603 | A1 | 7/2005 | Jimenez et al. |
| 2006/0003968 | A1 | 1/2006 | Green et al. |
| 2006/0122185 | A1 | 6/2006 | Green et al. |
| 2006/0122213 | A1 | 6/2006 | Pierard et al. |
| 2006/0183761 | A1 | 8/2006 | Ledeboer et al. |
| 2006/0183911 | A1 | 8/2006 | Charrier et al. |
| 2006/0258662 | A1 | 11/2006 | Binch et al. |
| 2007/0043063 | A1 | 2/2007 | Salituro et al. |

(Continued)

FOREIGN PATENT DOCUMENTS

| EP | 0557171 | 8/1993 |
| WO | 88/01997 | 3/1988 |

(Continued)

OTHER PUBLICATIONS

Alvarez, Mercedes, et al., "Synthesis of 3-Aryl- and 3-Heteroaryl-7-azaindoles", Synthesis, Thieme Stuttgart, New York, No. 4, 1999, pp. 615-620.
Berge, Stephen M., et al., "Pharmaceutical Salts" Journal of Pharmaceutical Sciences, vol. 66, No. 1, Jan. 1977, pp. 1-19.
Chitaley, Kanchan, et al., "Antagonism of Rho-kinase stimulates rat penile erection via a nitric oxide-independent pathway", Nature Medicine, Nature Publishing Group, vol. 7, No. 1, Jan. 2001, pp. 119-122.
Eto, Masato, et al., "Thrombin Suppresses Endothelial Nitric Oxide Synthase and Upregulates Endothelin-Converting Enzyme-1 Expression by Distinct Pathways", Circulation Research, vol. 89, 2001, pp. 583-590.

(Continued)

*Primary Examiner* — Alexander R Pagano
(74) *Attorney, Agent, or Firm* — Booyong S. Lim

(57) ABSTRACT

The present invention relates to compounds useful as inhibitors of protein kinase. The invention also provides pharmaceutically acceptable compositions comprising said compounds and methods of using the compositions in the treatment of various disease, conditions, or disorders. The invention also provides processes for preparing compounds of the inventions.

32 Claims, No Drawings

(56) References Cited

U.S. PATENT DOCUMENTS

| | | | |
|---|---|---|---|
| 2007/0135466 | A1 | 6/2007 | Ledeboer et al. |
| 2007/0203142 | A1 | 8/2007 | Farmer et al. |
| 2007/0207995 | A1 | 9/2007 | Salituro et al. |
| 2007/0213327 | A1 | 9/2007 | Collier et al. |
| 2009/0048250 | A1 | 2/2009 | Aronov et al. |
| 2009/0088445 | A1 | 4/2009 | Ledeboer et al. |
| 2009/0118278 | A1 | 5/2009 | Forester et al. |
| 2009/0176763 | A1 | 7/2009 | Salituro et al. |
| 2009/0291937 | A1 | 11/2009 | Jimenez et al. |
| 2010/0311743 | A1 | 12/2010 | Farmer et al. |
| 2011/0224197 | A1 | 9/2011 | Henkel et al. |
| 2012/0258958 | A1* | 10/2012 | Salituro et al. ........... 514/217.06 |

FOREIGN PATENT DOCUMENTS

| | | |
|---|---|---|
| WO | 95/33748 | 12/1995 |
| WO | 99/21859 | 5/1999 |
| WO | 00/40581 | 7/2000 |
| WO | 00/43393 | 7/2000 |
| WO | 01/01986 | 1/2001 |
| WO | 02/051837 | 7/2002 |
| WO | 02/072587 | 9/2002 |
| WO | 02/085896 | 10/2002 |
| WO | 02/085911 | 10/2002 |
| WO | 02/088131 | 11/2002 |
| WO | 02/088135 | 11/2002 |
| WO | 02/088140 | 11/2002 |
| WO | 02/088144 | 11/2002 |
| WO | 02/092602 | 11/2002 |
| WO | 03/000688 | 1/2003 |
| WO | 03/091246 | 11/2003 |
| WO | 03/101990 | 12/2003 |
| WO | 2004/013140 | 2/2004 |
| WO | 2004/016609 | 2/2004 |
| WO | 2004/016610 | 2/2004 |
| WO | 2004/043388 | 5/2004 |
| WO | 2004/076454 | 9/2004 |
| WO | 2004/078756 | 9/2004 |
| WO | 2004/082638 | 9/2004 |
| WO | 2004/089913 | 10/2004 |
| WO | 2004/106298 | 12/2004 |
| WO | 2005/000813 A1 | 1/2005 |
| WO | 2005/028475 | 3/2005 |
| WO | 2005/044181 | 5/2005 |
| WO | 2005/062795 | 7/2005 |
| WO | 2005/085244 | 9/2005 |
| WO | 2005/095400 A1 | 10/2005 |
| WO | WO 2005095400 A1 * | 10/2005 |
| WO | 2005/105213 | 11/2005 |
| WO | 2006/009755 | 1/2006 |
| WO | 2006/015123 | 2/2006 |
| WO | 2006/030031 | 3/2006 |
| WO | WO2006/038001 | 4/2006 |
| WO | WO 2006/050076 | 5/2006 |
| WO | 2006/124863 A2 | 11/2006 |
| WO | 2006/127587 | 11/2006 |
| WO | 2007/002433 | 1/2007 |
| WO | WO 2007/084557 | 7/2007 |
| WO | WO 2007/107221 | 9/2007 |
| WO | WO 2007084557 A3 * | 9/2007 |
| WO | 2007/117494 | 10/2007 |
| WO | 2008/005457 | 1/2008 |
| WO | 2008/005457 A2 | 1/2008 |
| WO | 2008/112642 | 9/2008 |
| WO | 2008/112646 | 9/2008 |
| WO | 2008/112651 | 9/2008 |
| WO | 2009/145814 | 3/2009 |

OTHER PUBLICATIONS

Eto, Yasuhiro, et al., "Gene transfer of dominant negative Rho kinase suppresses neointimal formation after balloon injury in pigs", Am. J. Physiol. Heart Circ. Physiol., Ameican Physiological Society, vol. 278, 2000, pp. H1744-H1750.

Fernandez, David, et al., "Synthesis of Polyheterocyclic Nitrogen-Containing Marine Natural Products#", Monatshefte Fur Chemie, Chemical Monthly, AU, vol. 135, 2004, pp. 615-627.
Fournier, Alyson E., et al., "Rho Kinase Inhibition Enhances Axonal Regeneration in the Injured CNS", The Journal of Neuriscience, vol. 23, No. 4, Feb. 15, 2003, pp. 1416-1423.
Fresneda, Pilar M., et al., "Synthesis of the indole alkaloids meridianins from the tunicate Aplidium meridianum", Tetrahedron, Pergamon, vol. 57, No. 12, 2001, pp. 2355-2363.
Genda, Takuya, et al., "Cell Motility Mediated by Rho and Rho-Associated Protein Kinase Plays a Critical Role in Intrahepatic Metastasis of Human Hepatocellular Carcinoma", Hepatology, vol. 30, No. 4, Oct. 1999, pp. 1027-1036.
Herbert, R., et al., "1H-Pyrrolo[2,3-b]pyridines. Part II. Fragmentation of Some 1H-Pyrrolo[2,3-b]pyridines induced by Electron Impact", J. Chem. Soc., Phys. Org., 1970, pp. 459-463.
Hernandez-Perera, Octavio, et al., "Involvement of Rho GTPases in the Transcriptional Inhibition of Preproendothelin-1 Gene Expression by Simvastatin in Vascular Endothelial Cells", Circulation Research, vol. 87, 2000, pp. 616-622.
Honjo, Meguni, et al., "Effects of Protein Kinase Inhibitor, HA1077 on Intraocular Pressure and Outflow Facility in Rabbit Eyes", Arch. Ophthalmol, vol. 119, Aug. 2001, pp. 1171-1178.
Hoshijima, Masahiko, et al., "The Low Molecular Weight GTPase Rho Regulates Myofibril Formation and Organization in Neonatal Rat Ventricular Myocytes", The Journal of Biological Chemistry, USA, vol. 273, No. 13, Mar. 27, 1998, pp. 7725-7730.
Ikeda, Fusao, et al., "Reduction of Hepatic Ischemia/Reperfusion-Induced Injury by a Specific ROCK/Rho Kinase Inhibitor Y-27632", Journal of Surgical Research, Elsevier Science (USA), vol. 109, 2003, pp. 155-160.
International Search Report issued for PCT Application No. PCT/US2005/010846 Dated Aug. 19, 2005.
International Search Report issued for PCT Application No. PCT/US2007/001225 Dated Jul. 20, 2007.
International Search Report issued for PCT Application No. PCT/US2009/001534 Dated Apr. 2, 2010.
Ishibashi, Toshiyuki, et al., "Inhibition of Rho/Rho-kinase signaling downregulates plasminogen activator inhibitor-1 synthesis in cultured human monocytes", Biochimica Et Biophysica Acta, Elsevier, vol. 1590, 2002, pp. 123-130.
Itoh, Kazuyuki, et al., "An essential part for Rho-associated kinase in the transcellular invasion of tumor cells", Nature Medicine, vol. 5, No. 2, Feb. 1999, pp. 221-225.
Kelly, Terence A., et al., "Novel Non-Nucleoside Inhibitors of Human Immunodeficiency Virus Type 1 Reverse Transcriptase. 6. 2-Indol-3-yl and 2-Azaindol-3-yl-dipyridodiazepinones1", Journal of Medicinal Chemistry, vol. 40, No. 15, 1997, pp. 2430-2433.
Kupittayanant, S., et al., "The effects of inhibiting Rho-associated kinase with Y-27632 on force and intracellular calcium in human myometrium", Pflugers Arch—Eur J Physiol, vol. 443, 2001, pp. 112-114.
Kuwahara, Koichiro, et al., "The effects of the selective Rock inhibitor, Y27632, on ET-1-induced hypertrophic response in nenatal rat cardiac myocytes—possible involvement of Rho/ROCK pathway in cardiac muscle cell hypertrophy" Federation of European Biochemial Societies Letters, vol. 452, 1999, pp. 314-318.
Laufs, Ulrich, et al., "Post-transcriptional Regulation of Endothelial Nitric Oxide Synthase mRNA Stability by Rho GTPase", The Journal of Biological Chemistry, USA, vol. 273, No. 37, Sep. 11, 1998, pp. 24266-24271.
Lowery, Drew M., et al., "Structure and function of Polo-like Kinases", Oncogene, Nature Publishing Group, vol. 24, 2005, pp. 248-259.
Masumoto, Akihiro, et al., "Suppression of Coronary Artery Spasm by the Rho-Kinase Inhibitor Fasudil in Patients With Vasospastic Angina", Circulation, vol. 105, 2002, pp. 1545-1547.
Mills, Thomas M., et al., "Effect of Rho-kinase inhibition on vasoconstriction in the penil circulation", J. Appl. Physiol., vol. 91, 2001, pp. 1269-1273.
Mizunuma, Kazuyuki, et al., "Prevention of Ischemia-Reperfusion-Induced Hepatic Microcirculatory Disruption by Inhibiting Stellate

(56) References Cited

OTHER PUBLICATIONS

Cell Contraction Using Rock Inhibitor1", Transplantation, USA, vol. 75, No. 5, Mar. 15, 2003, pp. 579-586.
Morishige, Kunio, et al., "Asenovirus-Mediated Transfer of Dominant-Negative Rho-Kinase Induces a Regression of Coronary Arteriosclerosis in Pigs In Vivo", Arterioscler. Thromb. Vasc. Biol., vol. 21, Apr. 2001, pp. 548-554.
Niiro, Naohisa, et al., "Up-Regulation of rho A and rho-Kinase mRHAs in the Rat Myometrium during Pregnancy", Biochemiacl and Biophysical Rearch Communications, vol. 230, 1997, pp. 356-359.
Pungpo, Pornpan, et al., "Three-dimensional quantitative structure-activity relationship study on HIV-1 reverse transcriptase inhibitors in the class of dipyridodiazepinone derivatives, using comparative molecular field analysis" Journal of Molecular Graphics and Modeling, Elsevier Science Inc., vol. 18, 2000, pp. 581-590.
Rao, P. Vasantha, et al., "Modulation of Aqueous Humor Outflow Facility by the Rho Kinase-Specific Inhibitor Y-27632", Investigative Ophthalmology & Visual Science, vol. 42, No. 5, Apr. 2001, pp. 1029-1037.
Rees, Rowland W., et al., "Y-27632, A Rho-Kinase Inhibitor, Inhibits Proliferation and Adrenergic Contraction of Prostatic Smooth Muscle Cells", The Journal of Urology, USA, vol. 170, Dec. 2003, pp. 2517-2522.
Retzer, Michaela, et al., "Mildly oxidised low density lipoprotein induces platelet shape change via Rho-kinase-dependent phosphorylation of myosin light chain and moesin", Federation of European Biochemial Societies Letters, vol. 466, 2000, pp. 70-74.
Sah, Valerie P., et al., "Rho is Required for Gαq and α1-Adrenergic Receptor Signaling in Cardiomyocytes", The Journal of Biological Chemistry, USA, vol. 27, No. 49, Dec. 6, 1996, pp. 31185-31190.
Satoh, Shin-Ichi, et al., "Antiischemic Properties of Fasudil in Experimental Models of Vasospastic Angina", Jpn. J. Pharmacol., vol. 87, 2001, pp. 34-40.
Sawada, Naoki, et al., "Inhibition of Rho-Associated Kinase Results in Suppression of Neointimal Formation of Balloon-Injured Arteries", Circulation, vol. 101, May 2, 2000, pp. 2030-2023.
Segain, Jean-Pierre, et al., "Rho Kinase Blockade Prevents Inflammation Via Nuclear Factor κB Inhibition: Evidence in Crohn's Disease and Experimental Colitis", Gastroenterology, vol. 124, No. 5, May 2003, pp. 1180-1187.
Shibata, Rei, et al., Role of Rho-Associated Kinase in Neointima Formation After Vascular Injury, Circulation, vol. 130, Jan. 16, 2001, pp. 284-289.
Shimokawa, Hiroaki, et al., "Rho-kinase as a Novel Therapeutic Target in Treatment of Cardiovascilar Diseases", Journal of Cardiovascular Pharmacology, vol. 39, No. 3, 2002, pp. 319-327.
Shimokawa, Hiroaki, et al., "Anti-anginal Effect of Fasudil, a Rho-Kinase Inhibitor, in Patients With Stable Effort Angina: A Multicenter Study", Journal of Cardiovascular Pharmacology, vol. 40, No. 5, 2002, pp. 751-761.
Shimokawa, Hiroaki, et al., "Long-term inhibition of Rho-kinase induces a regression of arteriosclerotic coronary lesions in a percine model in vivo", Cardiovascular Research, Elsevier, vol. 51, 2001, pp. 169-177.
Somlyo, Avril V., et al., Rho-Kinase Inhibitor Retards Migration and in Vivo Dissemination of Human Prostate Cancer Cells, Biochemical and Biophysical Research Communications, vol. 269, No. 3, 2000, pp. 652-659.
Tahara, Masahiro, et al., "RhoA/Rho-Kinase Cascade Is Involved in Oxytocin-Induced Rat Uterine Contraction", Endocrinology, vol. 143, No. 3, Mar. 2002, pp. 920-929.
Utsunomiya, T., et al., "Antianginal effects of hydroxyfasudil, a Rho-kinase inhibitor, in a canine model of effort angina", British Journal of Pharmacology, vol. 134, No. 8, 2001, pp. 1724-1730.
Written Opinion of the International Searching Authority issued for PCT Application No. PCT/US2005/010846 Dated Aug. 19, 2005.
Written Opinion of the International Searching Authority issued for PCT Application No. PCT/US2007/026190 Dated May 20, 2008.
Written Opinion of the International Searching Authority issued for PCT Application No. PCT/US2009/001534 Dated Apr. 2, 2008.
Yanazume, Tetsuhiko, et al., "Rho/ROCK Pathway Contributes to the Activation of Extracellular Signal-regulated Kinase/GTA-4 during Myocardial Cell Hypertrophy", The Journal of Biological Chemistry, USA, vol. 277, No. 10, Mar. 8, 2002, pp. 8618-8625.
Zhou, Yan, et al., "Nonsteroidal Anti-Inflamatory Drugs Can Lower Amyloidogenic Aβ42 by Inhibiting Rho", Science, vol. 302, No. 14, Nov. 2003, pp. 1215-1218.
Alexei S Karpov et al., "Concise Synthesis of Meridianins by Carbonylative Alkynylation and a Four-Component Pyrimidine Synthesis", Angewandte Chemie, International Edition, Wiley VCH Verlag, Weinheim, DE, 2005, pp. 6951-6956, vol. 44.
Bettayeb, K et al, "Meriolins, a New Class of . Cell Death-Inducing Kinase Inhibitors with Enhanced Selectivity for Cyclin-Dependent Kinases", Cancer Research, Sep. 1, 2007, pp. 8325-8334, vol. 67, No. 17.
WO 2008/079346, International Search Report, (PCT/US2007/026190 May 20, 2008).
WO 2008/079346, International Preliminary Report on Patentability, (Jun. 24, 2009).

\* cited by examiner

5-CYANO-4-(PYRROLO [2,3B] PYRIDINE-3-YL)-PYRIMIDINE DERIVATIVES USEFUL AS PROTEIN KINASE INHIBITORS

CROSS-REFERENCE

This application is a divisional application of U.S. application Ser. No. 13/477,663, filed on May 22, 2012 which claims priority to: U.S. application Ser. No. 12/448,489, filed on Jun. 22, 2009; PCT Application No. PCT/US2007/026190, filed Dec. 21, 2006; U.S. Application No. 60/876,307, filed on Dec. 21, 2006; U.S. Application No. 60/922,291, filed on Apr. 6, 2007; U.S. Application No. 60/947,707, filed on Jul. 3, 2007; and U.S. Application No. 60/989,014, filed on Nov. 19, 2007. The entire contents of these applications are incorporated herein by reference.

TECHNICAL FIELD OF THE INVENTION

The present invention relates to compounds useful as inhibitors of protein kinases. The invention also provides pharmaceutically acceptable compositions comprising the compounds of the invention and methods of using the compositions in the treatment of various disorders. The invention also provides processes for preparing the compounds of the invention.

BACKGROUND OF THE INVENTION

The search for new therapeutic agents has been greatly aided in recent years by a better understanding of the structure of enzymes and other biomolecules associated with diseases. One important class of enzymes that has been the subject of intensive study is protein kinases.

Protein kinases constitute a large family of structurally related enzymes that are responsible for the control of a variety of signal transduction processes within the cell (see Hardie, G. et al., *The Protein Kinase Facts Book, I and II*, Academic Press, San Diego, Calif.: 1995). Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids etc). Sequence motifs have been identified that generally correspond to each of these kinase families (see, e.g., Hanks, S. K., Hunter, T., *FASEB J.*, 1995, 9, 576-596; Knighton et al., *Science*, 1991, 253, 407-414; Hiles et al, *Cell*, 1992, 70, 419-429; Kunz et al, *Cell*, 1993, 73, 585-596; Garcia-Bustos et. al., *EMBO J.*, 1994, 13, 2352-2361).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., shock, heat shock, ultraviolet radiation, bacterial endotoxin, and $H_2O_2$), cytokines (e.g., interleukin-1 (IL-1) and tumor necrosis factor alpha (TNF-a), and growth factors (e.g., granulocyte macrophage-colony stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, survival and regulation of the cell cycle.

Many diseases are associated with abnormal cellular responses triggered by protein kinase-mediated events as described above. These diseases include, but are not limited to, cancer, autoimmune diseases, inflammatory diseases, bone diseases, metabolic diseases, neurological and neurodegenerative diseases, cardiovascular diseases, allergies and asthma, Alzheimer's disease and hormone related diseases. Accordingly, there has been a substantial effort in medicinal chemistry to find protein kinase inhibitors that are effective as therapeutic agents.

The Polo-like kinases (PLK) belong to a family of serine/threonine kinases that are highly conserved across the species, ranging from yeast to man (reviewed in Lowery, D. M. et al., *Oncogene*, 2005, 24; 248-259). The PLK kinases have multiple roles in cell cycle, including control of entry into and progression through mitosis.

PLK1 is the best characterized of the PLK family members. PLK1 is widely expressed and is most abundant in tissues with a high mitotic index. Protein levels of PLK1 rise and peak in mitosis (Hamanaka, R. et al., *J. Biol. Chem.*, 1995, 270, 21086-21091). The reported substrates of PLK1 are all molecules that are known to regulate entry and progression through mitosis, and include CDC25C, cyclin B, p53, APC, BRCA2 and the proteasome. PLK1 is upregulated in multiple cancer types and the expression levels correlate with severity of disease (Macmillan, J C et al., *Ann. Surg. Oncol.*, 2001, 8, 729-740). PLK1 is an oncogene and can transform NIH-3T3 cells (Smith, M. R. et al., *Biochem. Biophys. Res. Commun.*, 1997, 234, 397-405). Depletion or inhibition of PLK1 by siRNA, antisense, microinjection of antibodies, or transfection of a dominant negative construct of PLK1 into cells, reduces proliferation and viability of tumour cells in vitro (Guan, R. et al., *Cancer Res.*, 2005, 65, 2698-2704; Liu, X. et al., *Proc. Nat'l. Acad. Sci. USA*, 2003, 100, 5789-5794; Fan, Y. et al., *World J. Gastroenterol.*, 2005, 11, 4596-4599; Lane, H. A. et al., *J. Cell Biol* 1996, 135, 1701-1713; Wada, M. et al., *Biochem. Biophys. Res. Commun.*, 2007, 357(2): 353-359; Rizki, A. et al., *Cancer Res.*, 2007, 67 (23): 11106-11100). Tumour cells that have been depleted of PLK1 have activated spindle checkpoints and defects in spindle formation, chromosome alignment and separation and cytokinesis. Loss in viability has been reported to be the result of an induction of apoptosis. In contrast, normal cells have been reported to maintain viability on depletion of PLK1. In vivo knock down of PLK1 by siRNA or the use of dominant negative constructs leads to growth inhibition or regression of tumours in xenograft models.

PLK2 is mainly expressed during the G1 phase of the cell cycle and is localized to the centrosome in interphase cells. PLK2 knockout mice develop normally, are fertile and have normal survival rates, but are around 20% smaller than wild type mice. Cells from knockout animals progress through the cell cycle more slowly than in normal mice (Ma, S. et al., *Mol. Cell. Biol.*, 2003, 23, 6936-6943). Depletion of PLK2 by siRNA or transfection of kinase inactive mutants into cells blocks centriole duplication. Downregulation of PLK2 also sensitizes tumour cells to taxol and promotes mitotic catastrophe, in part by suppression of the p53 response (Burns, T. F. et al., *Mol. Cell. Biol.*, 2003, 23, 5556-5571).

PLK3 is expressed throughout the cell cycle and increases from G1 to mitosis. Expression is upregulated in highly proliferating ovarian tumours and breast cancer and is associated with a worse prognosis (Weichert, W. et al., *Br. J. Cancer,*

2004, 90, 815-821; Weichert, W et al., *Virchows. Arch.*, 2005, 446, 442-450). In addition to regulation of mitosis, PLK3 is believed to be involved in Golgi fragmentation during the cell cycle and in the DNA-damage response Inhibition of PLK3 by dominant negative expression is reported to promote p53-independent apoptosis after DNA damage and suppresses colony formation by tumour cells (Li, Z. et. al., *J. Biol. Chem.*, 2005, 280, 16843-16850).

PLK4 is structurally more diverse from the other PLK family members. Depletion of this kinase causes apoptosis in cancer cells (Li, J. et. al., *Neoplasia*, 2005, 7, 312-323). PLK4 knockout mice arrest at E7.5 with a high fraction of cells in mitosis and partly segregated chromosomes (Hudson, J. W. et. al., *Current Biology*, 2001, 11, 441-446).

Molecules of the protein kinase family have been implicated in tumour cell growth, proliferation and survival. Accordingly, there is a great need to develop compounds useful as inhibitors of protein kinases. The evidence implicating the PLK kinases as essential for cell division is strong. Blockade of the cell cycle is a clinically validated approach to inhibiting tumour cell proliferation and viability. It would therefore be desirable to develop compounds that are useful as inhibitors of the PLK family of protein kinases (e.g., PLK1, PLK2, PLK3 and PLK4), that would inhibit proliferation and reduce viability of tumour cells, particularly as there is a strong medical need to develop new treatments for cancer.

SUMMARY OF THE INVENTION

Compounds of this invention are useful as inhibitors of PLK protein kinases and in some embodiments, as inhibitors of PLK1 protein kinases. These compounds are as defined herein.

These compounds, and pharmaceutically acceptable salts thereof, are useful for treating or preventing a variety of diseases, disorders or conditions, including, but not limited to, an autoimmune, inflammatory, proliferative, or hyperproliferative disease, a neurodegenerative disease, or an immunologically-mediated disease. The compounds provided by this invention (and pharmaceutically acceptable salts and pharmaceutically acceptable derivatives thereof) are also useful for the study of kinases in biological and pathological phenomena; the study of intracellular signal transduction pathways mediated by such kinases; and the comparative evaluation of new kinase inhibitors.

DETAILED DESCRIPTION OF THE INVENTION

Compounds of the Invention
This invention provides a compound of formula I:

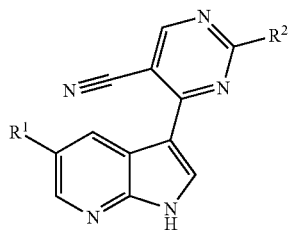

I or a pharmaceutically acceptable salt thereof; wherein:
$R^1$ is —H, halogen, $C_{1-6}$ aliphatic optionally substituted with 1-3 $R^3$, —O($C_{1-6}$ aliphatic) optionally substituted with 1-3 $R^3$, or —N(H)R;

Each R is independently H, $C_{1-6}$ aliphatic, aryl, heteroaryl, $C_{3-8}$ cycloalkyl, or 4-12 membered heterocyclic ring optionally containing 1-3 groups selected from —N($R^{17}$)—, —O—, or —S—; wherein each of the aliphatic, aryl, heteroaryl, cycloalkyl, and heterocyclic ring are optionally substituted with 1-3 of Q;

Each Q is independently selected from halogen, hydroxy, $C_{1-6}$ alkyl, benzyl, oxo, —$CF_3$, W, —CN, —$NH_2$, —N(H)—W, —N(W)$_2$, —N(H)—$SO_2$—W, —S(O)$_2$—N(H)—W, —S(O)$_2$—N(W)$_2$, —C(O)—W, —C(O)—N(W)$_2$, —N(H)—C(O)—W, —O—C(O)—W, —C(O)—O—W, —$SO_2$—W, SW or —OW;

Two Q can be linked together to form a 4- to 8-membered carbocyclic or heterocyclic ring optionally substituted with $C_{1-3}$ alkyl or $CF_3$;

Each W is independently selected from —H, $C_{1-6}$ alkyl, aralkyl, cycloalkyl or heterocyclic ring; each $C_{1-6}$ alkyl, aralkyl, cycloalkyl or heterocyclic ring is optionally substituted with 1-3 of halogen, —$OR^6$, —CN, $C_{1-6}$ alkyl or $NR^{18}R^{19}$; or One W, together with the nitrogen atom to which it is attached and a carbon atom of R, form a 4- to 8-membered ring; or Two W, together with the same or different nitrogen atom or carbon atom to which they are attached, form a 4- to 8-membered heterocyclic ring;

Each $R^{18}$ and $R^{19}$ is independently hydrogen or $C_{1-3}$ alkyl; or $R^{18}$ and $R^{19}$, together with the nitrogen atom to which they are attached, form a 4- to 8-memebered heterocyclic ring, optionally substituted with $C_{1-3}$ alkyl or $CF_3$;

Two W can be linked together to form a 4- to 8-membered cycloalkyl or heterocycloalkyl optionally substituted with $C_{1-3}$ alkyl or $CF_3$;

$R^2$ is —$NR^4R^5$, —$OR^6$, —$SR^6$, or —$NR^{10}R^{11}$;

Each $R^3$ is independently halogen, $C_{1-6}$ alkyl, aryl, or heteroaryl;

Each $R^4$ is independently —H or $C_{1-6}$ aliphatic optionally substituted with 1-3 $R^7$;

Each $R^5$ is independently $C_{1-6}$ aliphatic optionally substituted with 1-4 $R^7$ or a 4- to 8-membered monocyclic or 6- to 10-membered bicyclic ring optionally substituted with 1-4 $R^2$, or $R^4$ and $R^5$ can be joined together to form a monocyclic or bicyclic ring optionally substituted with 1-3 $R^9$;

Each $R^6$ is independently H, $C_{1-6}$ alkyl, -L-aryl, or -L-heteroaryl, wherein each of the $C_{1-6}$ alkyl, -L-aryl, or -L-heteroaryl is optionally and independently substituted with 1-3 $R^8$;

L is $C_{0-3}$ alkyl;

Each $R^7$ is independently oxo, alkyl, halogen, —CN, —$OR^9$, —$SR^9$, —N($R^9$)$_2$, $C_{3-8}$ cycloalkyl, aryl, heteroaryl or a 4- to 8-membered heterocyclic ring containing 1-3 groups selected from —N($R^{17}$)—, —O—, or —S—, wherein each alkyl, cycloalkyl, 4-8 membered heterocyclic monocyclic or bicyclic ring, aryl, and heteroaryl is optionally and independently substituted with 1-3 $R^8$, or Two $R^7$ on the same atom or adjacent atoms is joined to form a carbocyclic ring or a 4-8 membered heterocyclic ring containing 1-3 groups selected from —N($R^{17}$)—, —O—, or —S—, wherein each of the carbocyclic ring and the 4- to 8-membered heterocyclic ring is optionally and independently substituted with 1-3 $R^8$;

Each $R^8$ is independently —R, -Q, —$R^9$, —$OR^9$, —N($R^9$)$_2$, halogen, or —CN;

Each $R^9$ is independently —H, —N($R^{16}$)$_2$, $C_{3-6}$ carbocyclic ring, $C_{3-6}$ heterocyclic ring, or $C1\_3$ aliphatic, wherein $C_{3-6}$ carbocyclic ring, $C_{3-6}$ heterocyclic ring and $C_{1-3}$ aliphatic are each optionally substituted with 1-3 Q; or Two $R^9$ groups together with the N atom to which they are bound form a 4-8 membered ring additionally containing 1 or 2 groups each indpednetly selected from —N($R^{17}$)—, —O—, or —S—, wherein the 4- to 8-membered ring is optionally and independently substituted with 1-3 of W;

Each $R^{16}$ is independently hydrogen or $C_{1-6}$ alkyl, or

Two $R^{16}$ groups together with the N atom to which they are bound form a 4- to 8-membered ring containing 1 or 2 groups selected from $NR^{17}$, O, or S;

Each $R^{17}$ is independently, hydrogen, $Q_1$ or $C_{1-4}$ aliphatic or cycloaliphatic, wherein each $C_{1-4}$ aliphatic or cycloaliphatic is optionally substituted with 1-3 of Q;

$Q_1$ is $C1\_6$ alkyl, benzyl, —S(O)$_2$—N(H)—W, —S(O)$_2$—N(W)$_2$, —C(O)—W, —C(O)—N(W)$_2$, —C(O)—N(H)—W, —N(H)—C(O)—W, —O—C(O)—W, —C(O)—O—W, or —SO$_2$—W;

$R^{10}$ is —H or $C_1$-$C_6$ aliphatic optionally substituted with 1-3 $R^7$;

$R^{11}$ is —C($R^{12}R^{13}$)C(=O)N$R^{14}R^{15}$;

Each of $R^{12}$ and $R^{13}$ is independently H or $C_{1-6}$ aliphatic optionally substituted with 1-3 $R^7$; or $R^{12}$ and $R^{13}$ can be joined together to form a ring optionally substituted with 1-3 $R^9$; or $R^{10}$ and $R^{12}$ can be joined together to form a ring optionally substituted with 1-3 $R^9$; and Each $R^{14}$ and $R^{15}$ is independently H, $C_{1-6}$ alkyl, carbocyclic, or heterocyclic optionally substituted with 1-3 $R^7$; or $R^{14}$ and $R^{15}$ can be joined together to form a ring optionally substituted with 1-3 $R^9$.

In some embodiments, $R^4$ is H or $C_{1-4}$ alkyl and $R^5$ is selected from —CH$_3$,

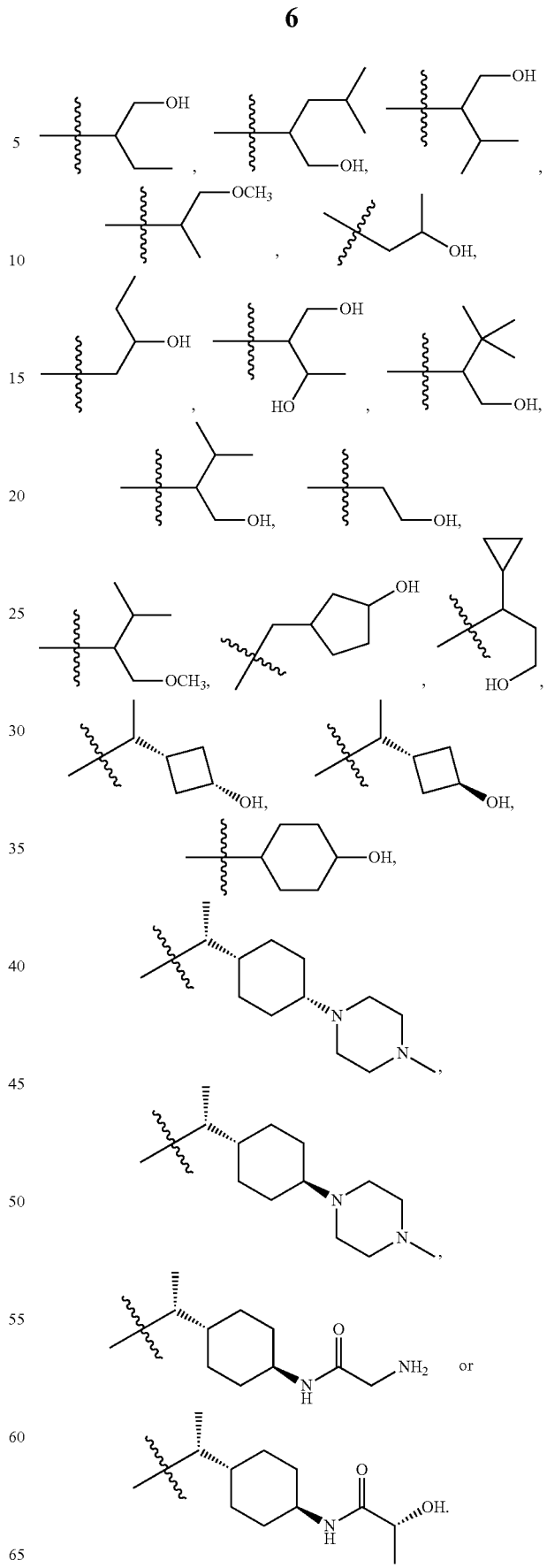

In some embodiments, $R^4$ is H or $C_{1-4}$ alkyl and $R^5$ is a hydroxyalkyl, hydroxcycloalkyl or alkoxyalkyl selected from In some embodiments, $R^4$ is H or $C_{1-4}$ alkyl and $R^5$ is a substituted alkyl selected from
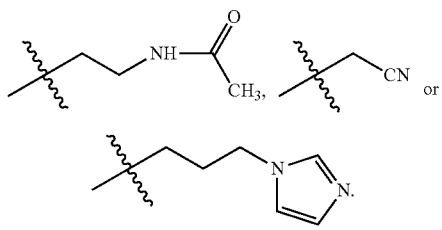
In some embodiments, $R^4$ is H or $C_{1-4}$ alkyl, and $R^5$ is an aryl or aralkyl selected from
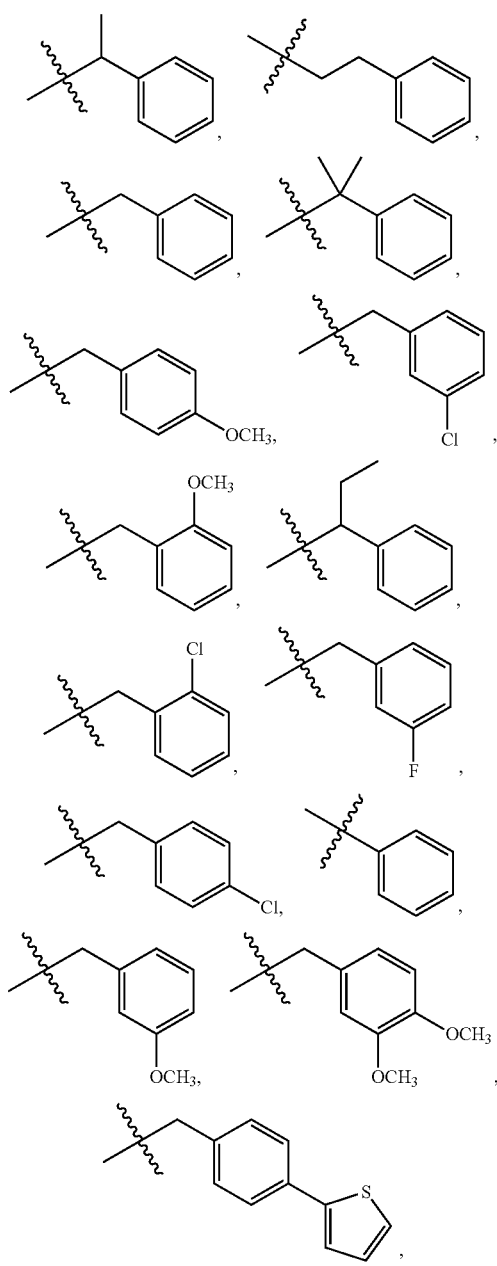
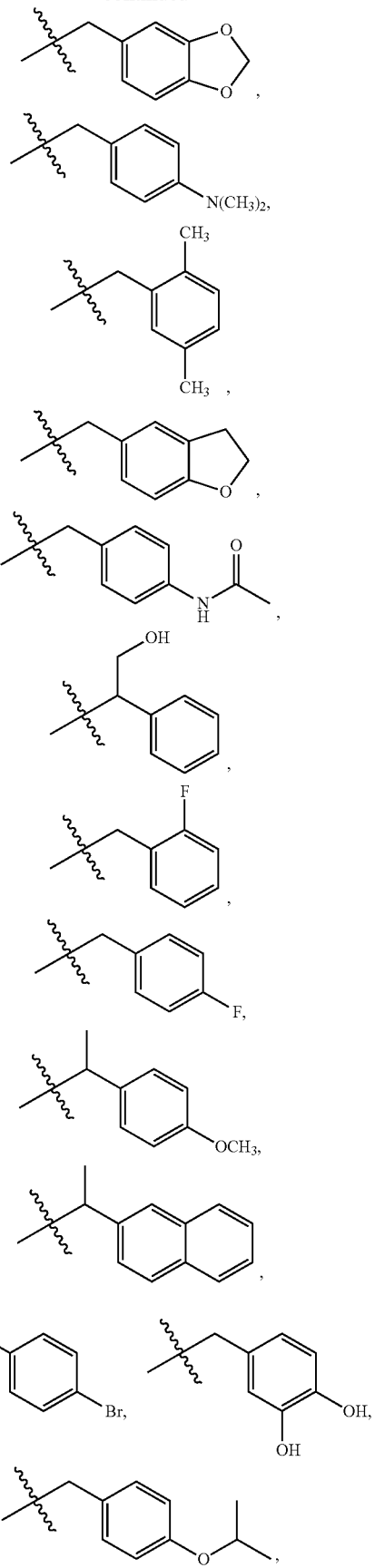

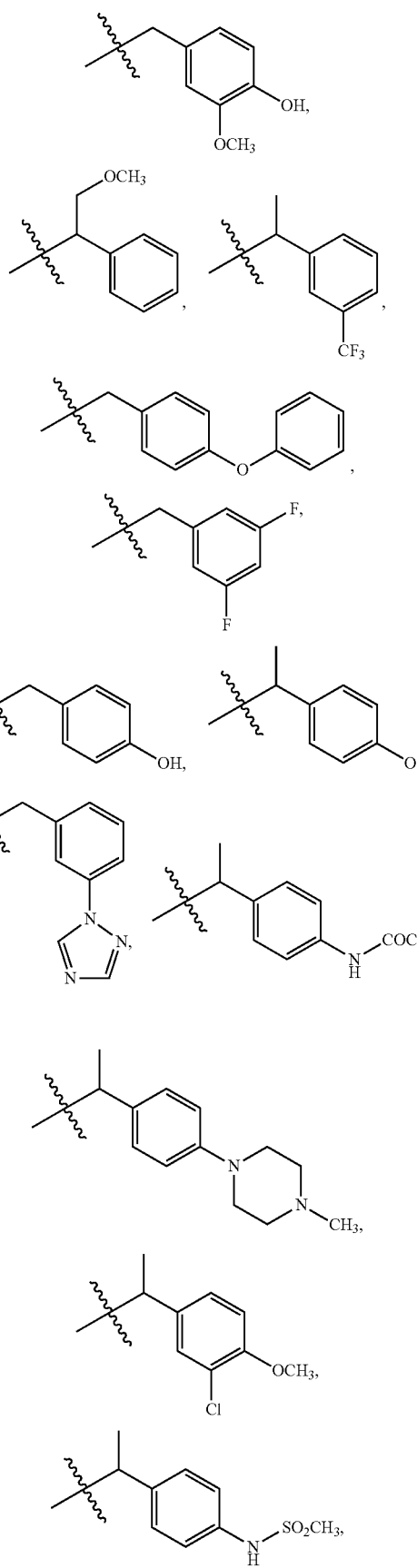
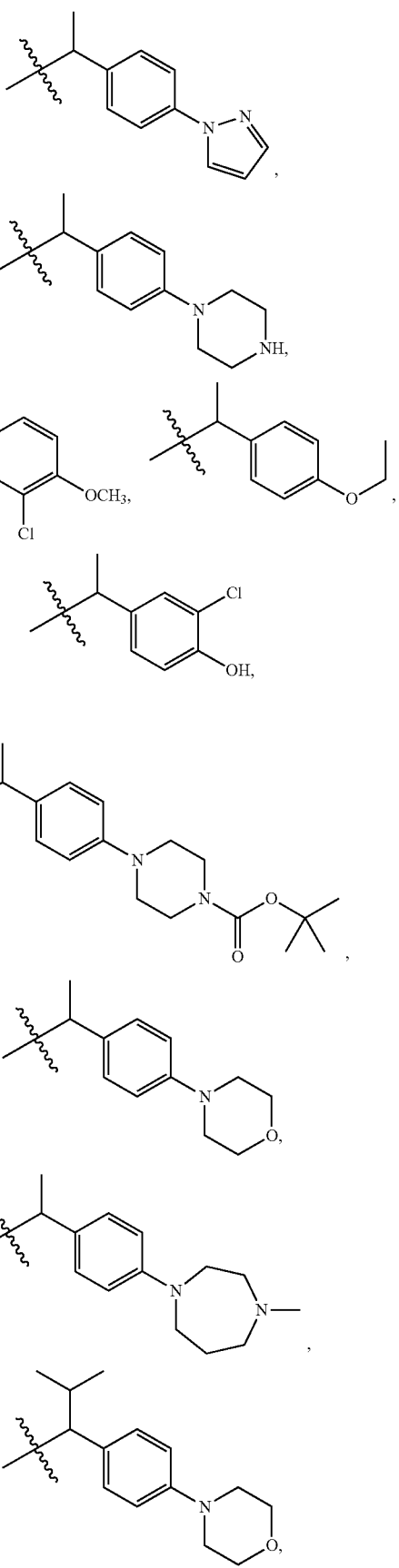

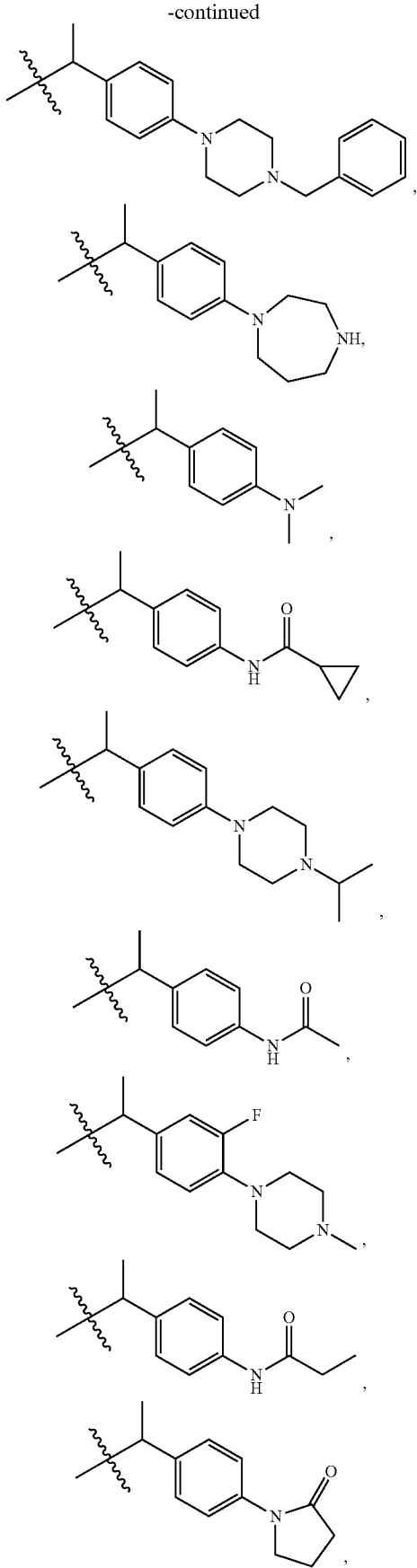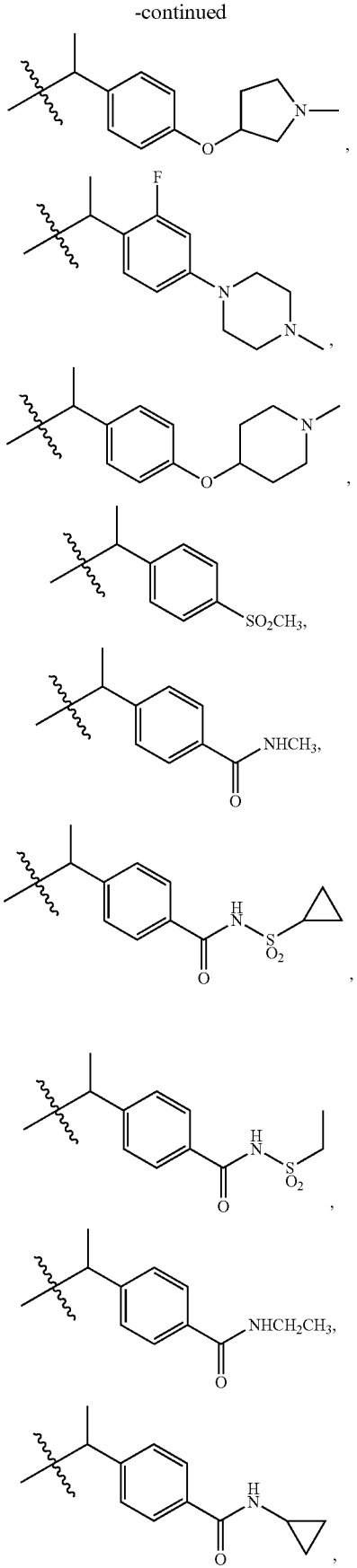

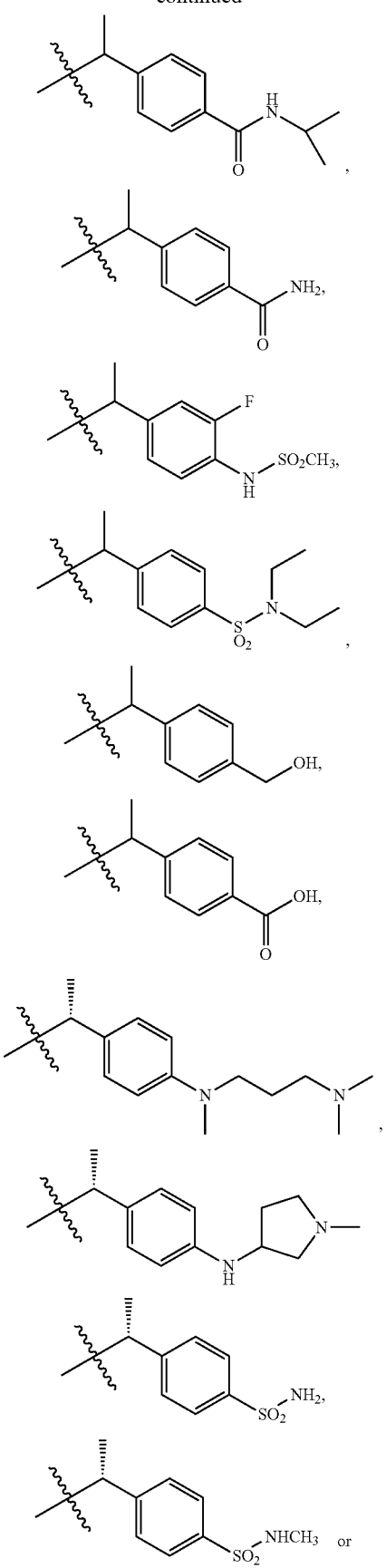
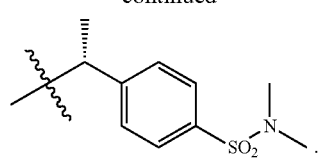
In some embodiments, $R^4$ is H or $C_{1-4}$ alkyl and $R^5$ is an optionally substituted heteroaralkyl selected from
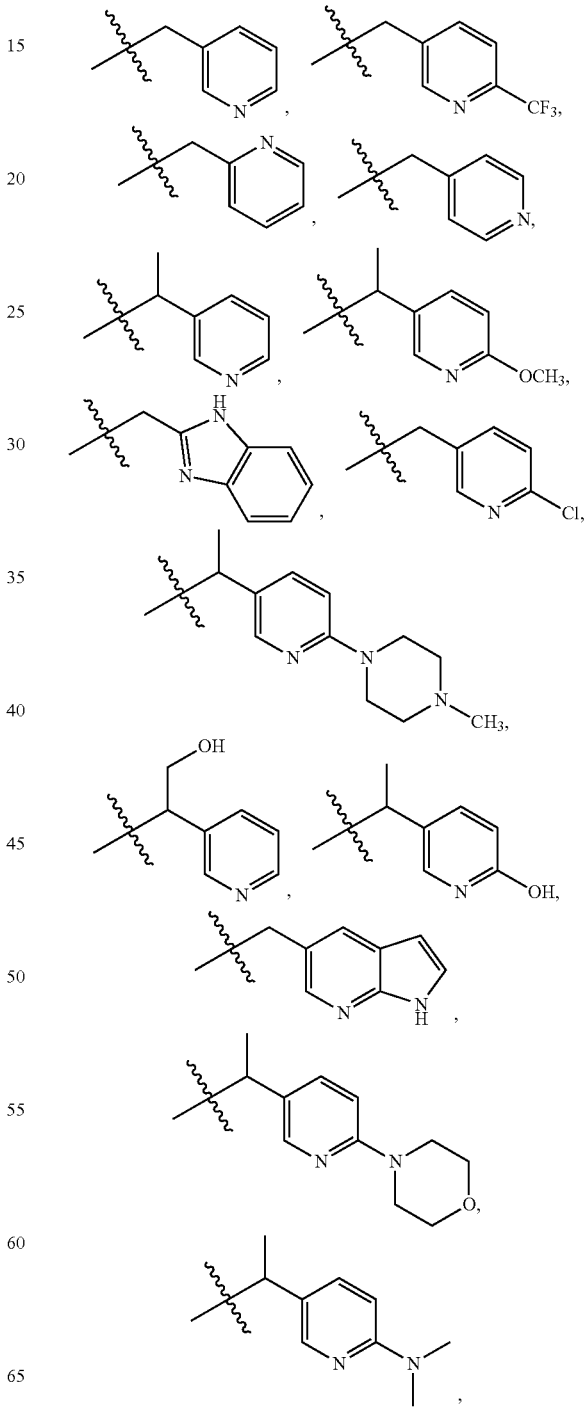

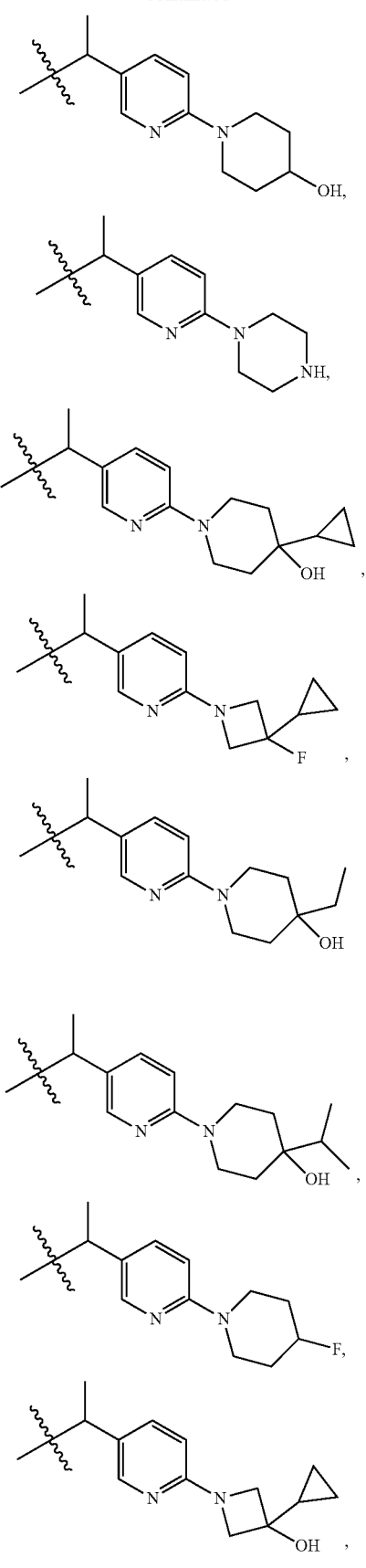
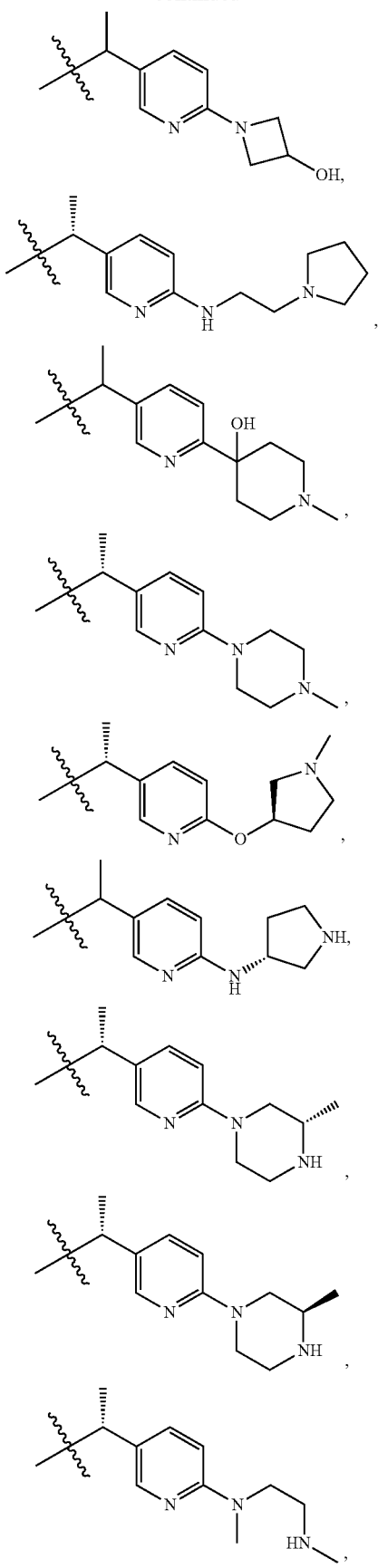

17
-continued
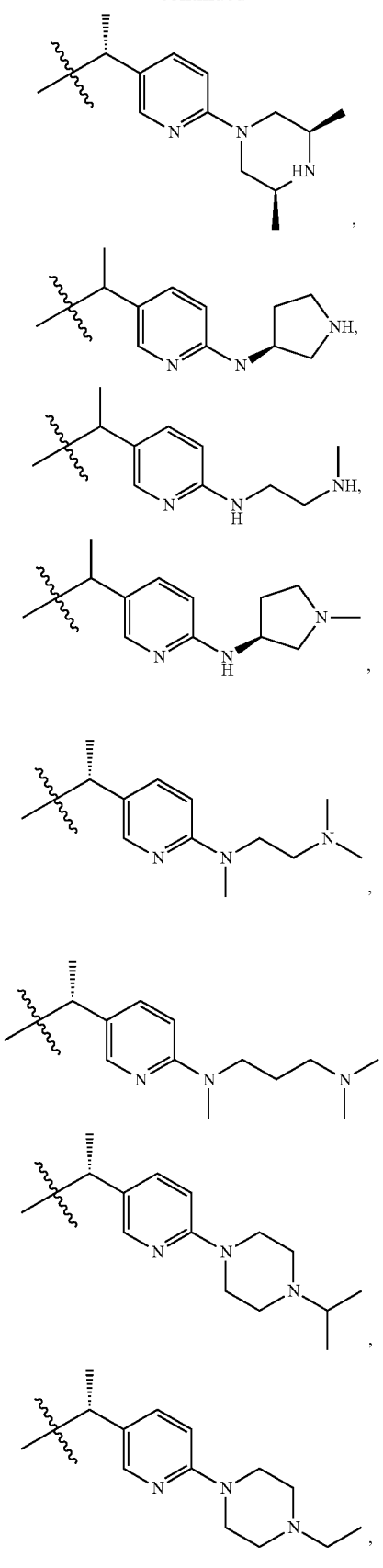
18
-continued
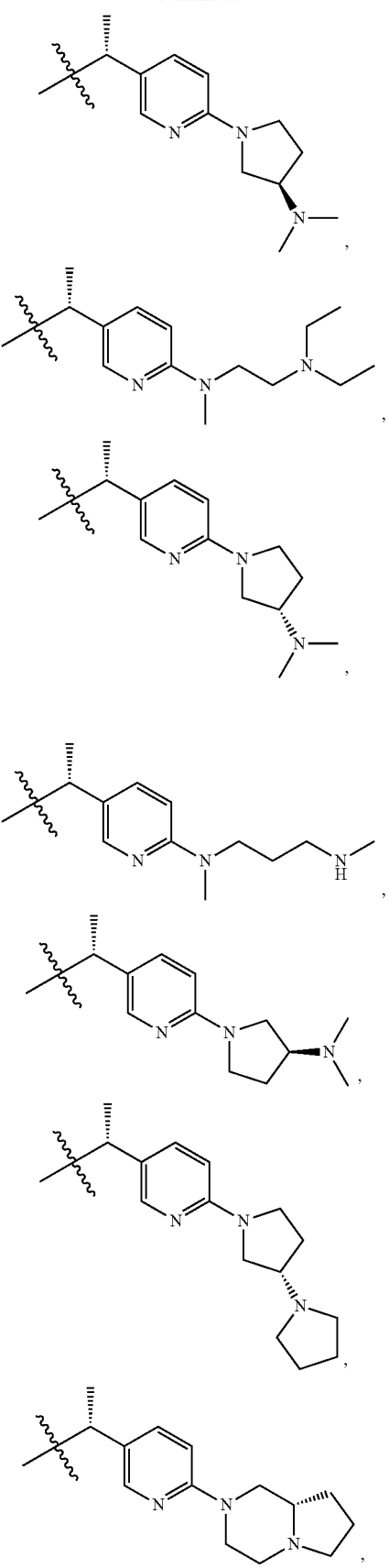

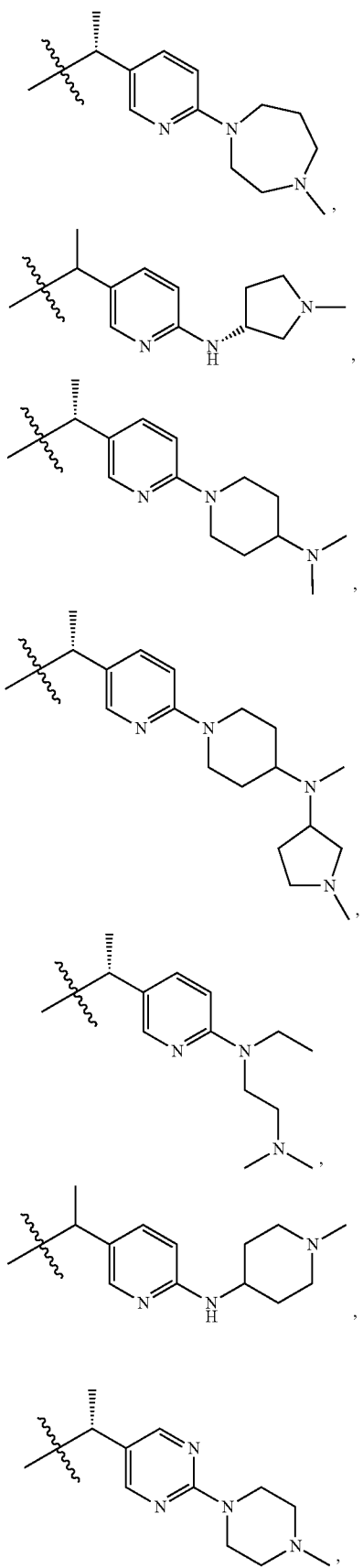
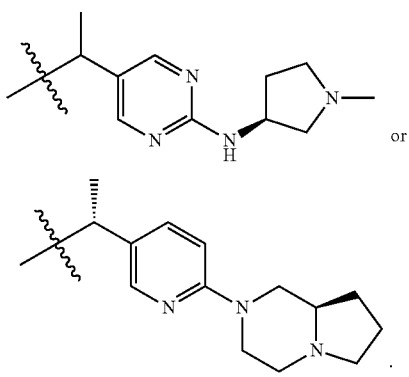
In some embodiments, $R^4$ is H and $R^5$ is an optionally substituted aralkyl or heteroaralkyl, which give compounds of formula Ic
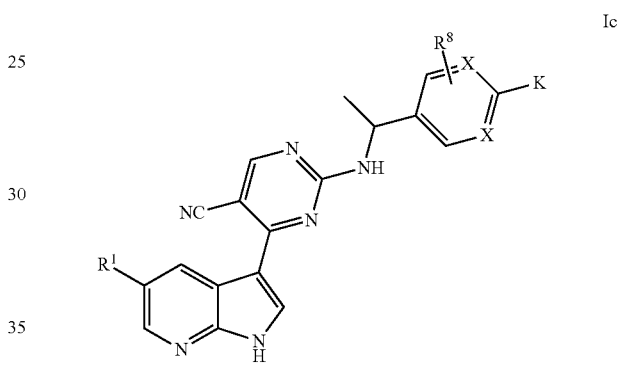
wherein each X is independently $CR^8$ or N and K is $-OR^6$, $-SR^6$, or $-N(R^9)_2$.
In some embodiments, $R^4$ is H or $C_{1-4}$ alkyl and $R^5$ is a cycloalkyl or cycloalkyl(alkyl), each optionally substituted, and selected from
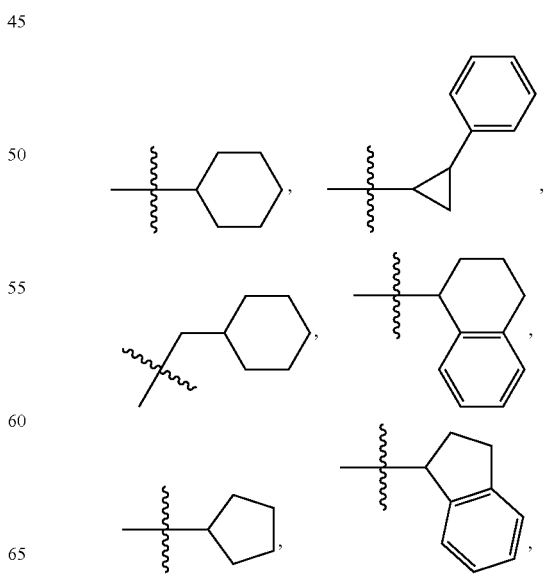

-continued
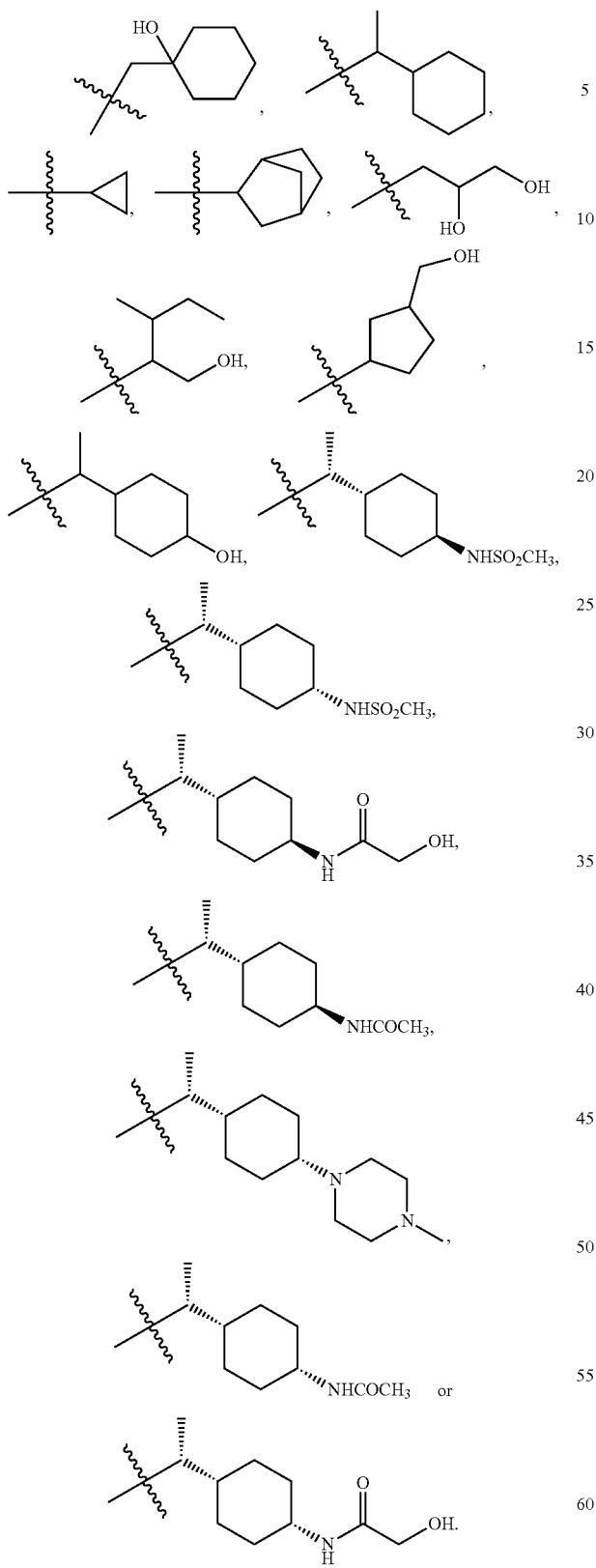
In other embodiments, $R^4$ is H and $R^5$ is an amino substituted cycloalkyl(alkyl), which give the compounds of formula Ib
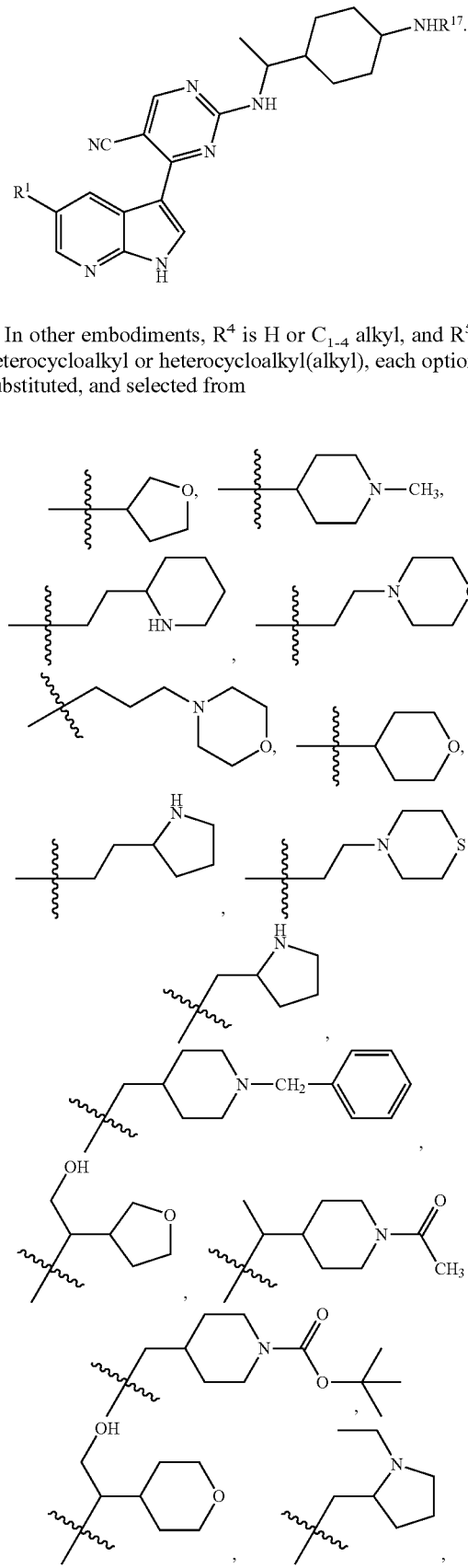
In other embodiments, $R^4$ is H or $C_{1-4}$ alkyl, and $R^5$ is a heterocycloalkyl or heterocycloalkyl(alkyl), each optionally substituted, and selected from

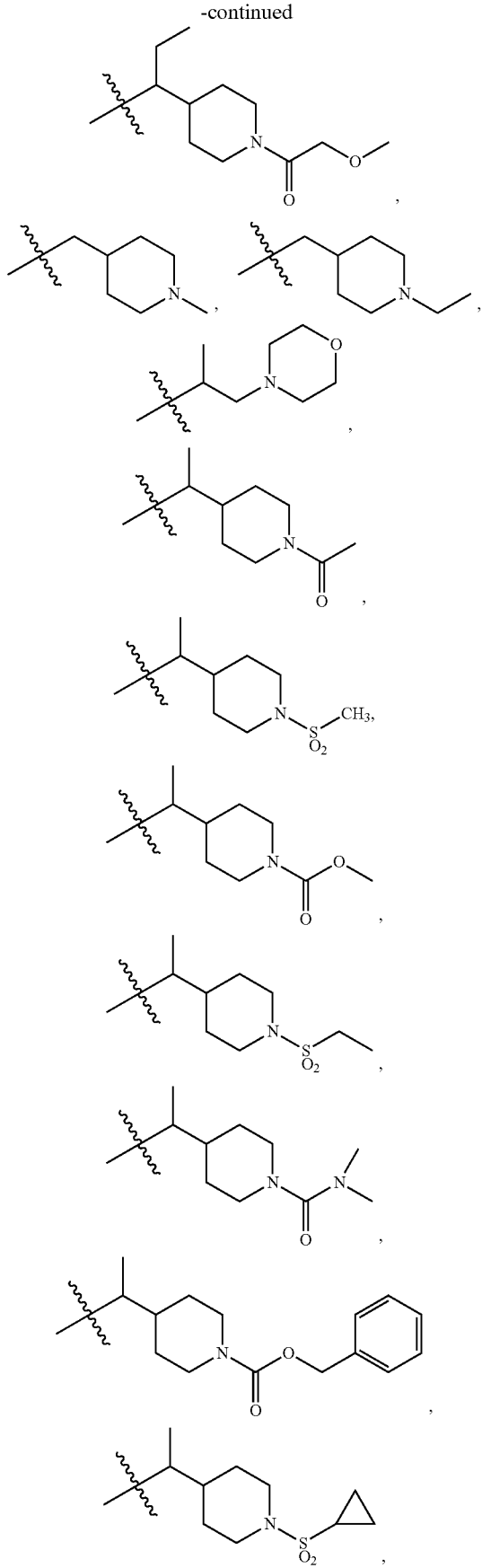
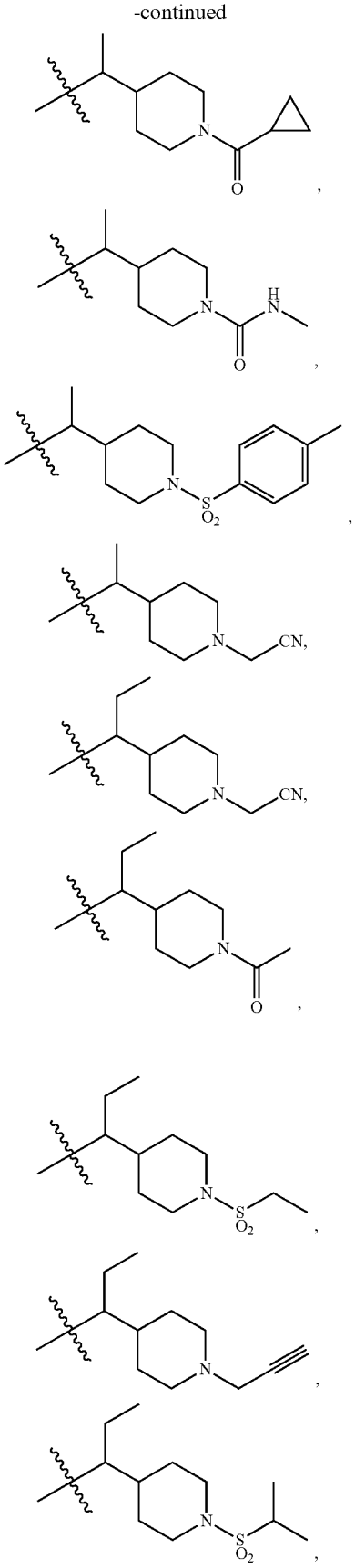

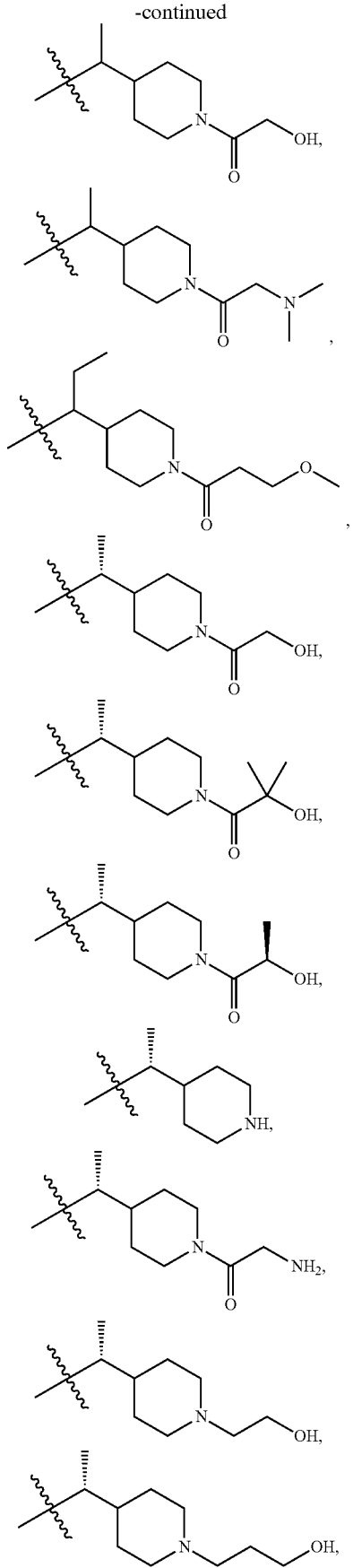
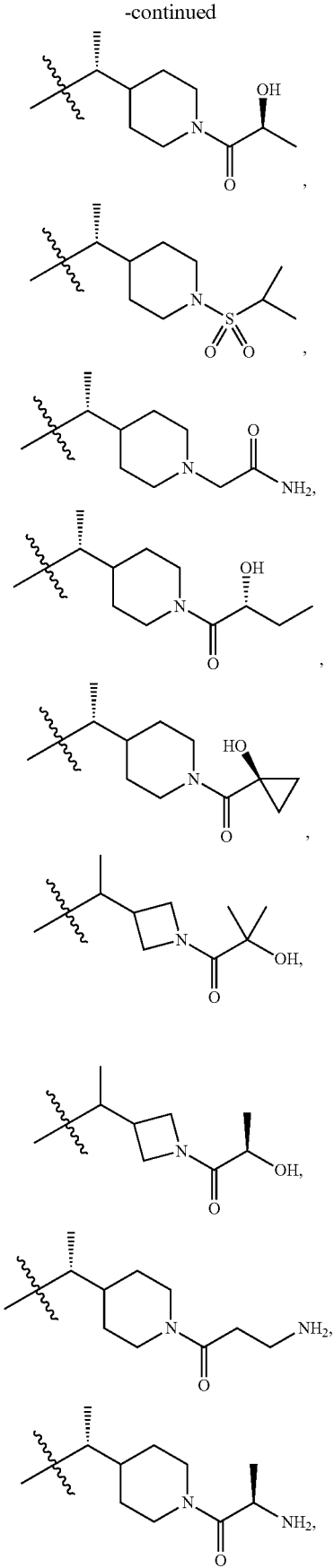

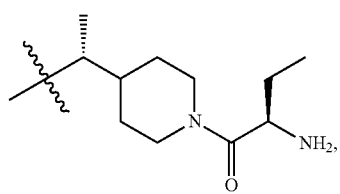
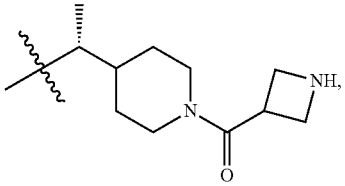
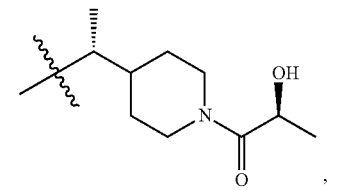
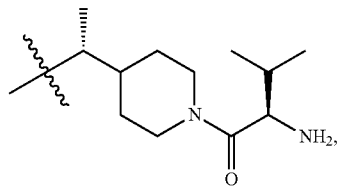
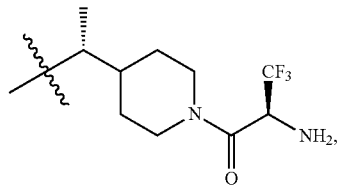
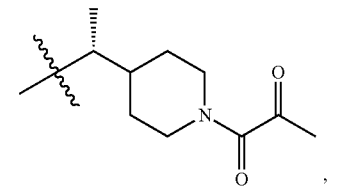
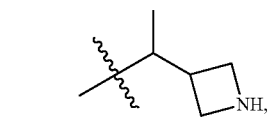
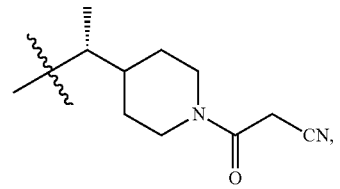
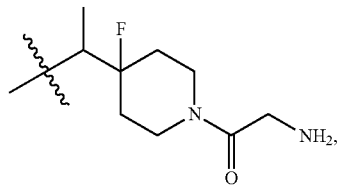
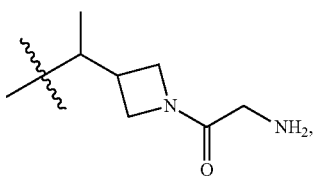
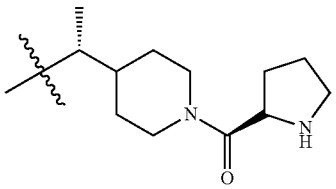
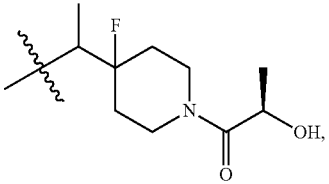
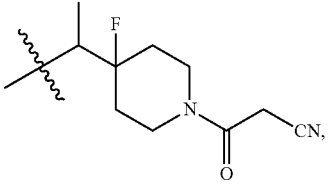
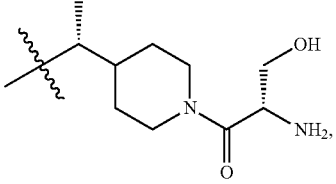
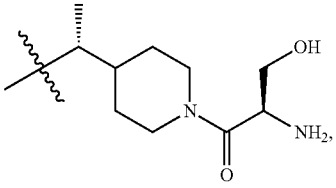
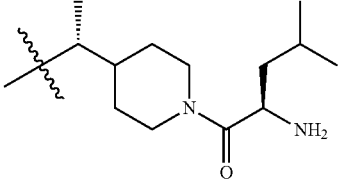
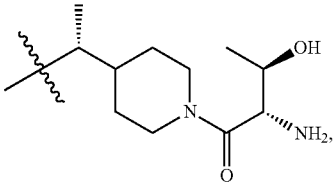
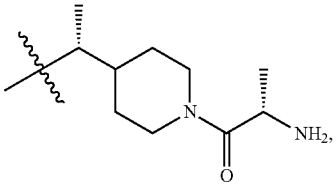

29
-continued
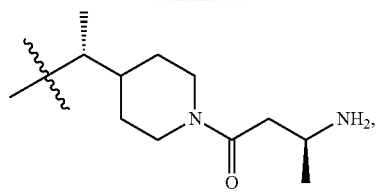
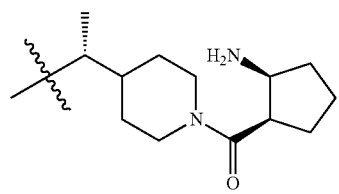
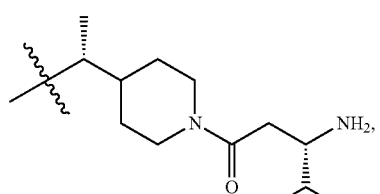
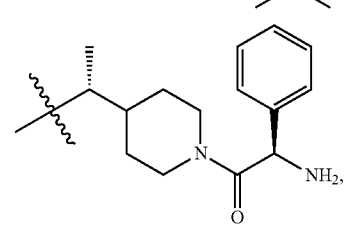
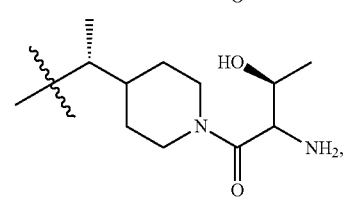
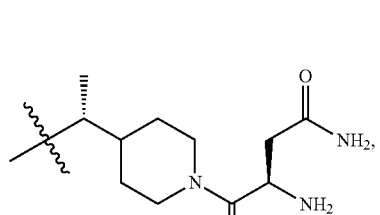
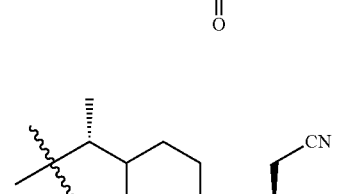
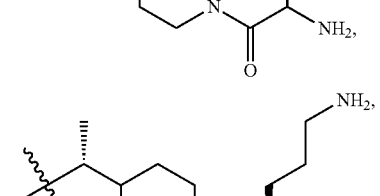
30
-continued
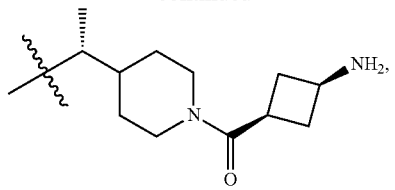
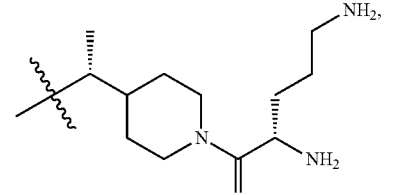
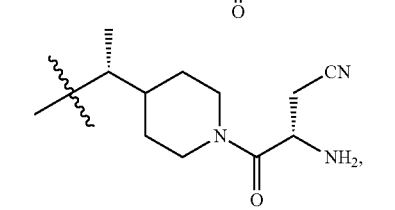
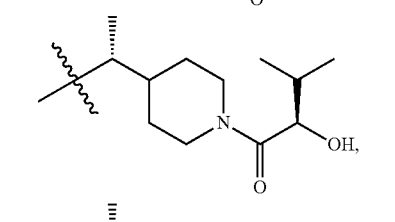
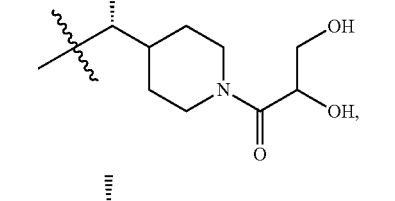
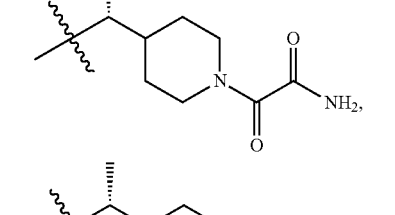
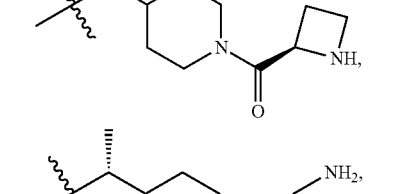
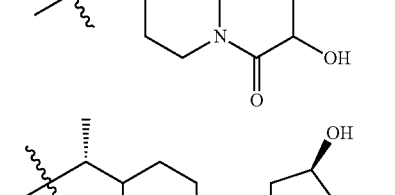 or

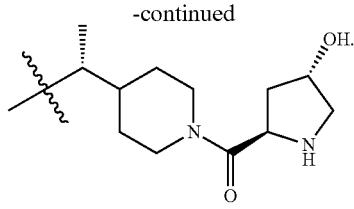

In some embodiments, R⁴ is H and R⁵ is a heterocycloalkyl (alkyl), which give the compounds of formula Ia

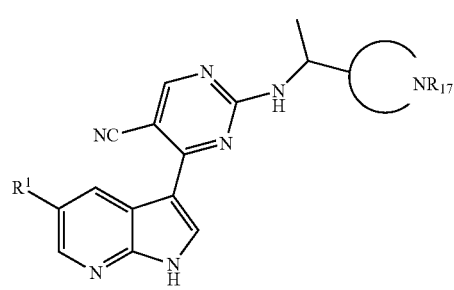

Ia wherein

represents a 4- to 8-membered nitrogen containing heterocyclic ring.

In one embodiment, R⁴ and R⁵ are joined together to form

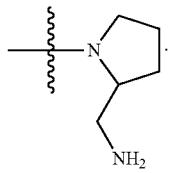 [SMILES: *N1CCCC1CN ; "."]

In other embodiments, R² is —NR¹⁰R¹¹ wherein R¹⁰ is H and R¹¹ is selected from

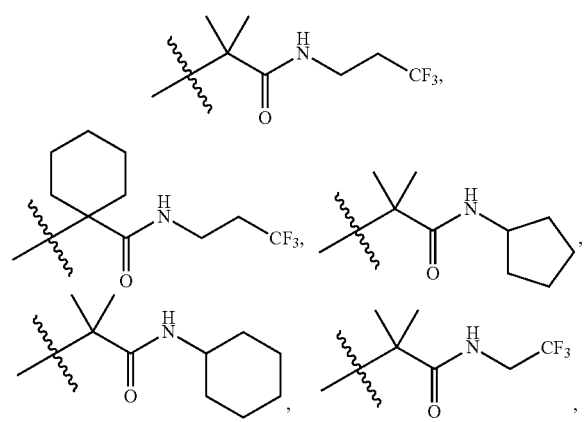

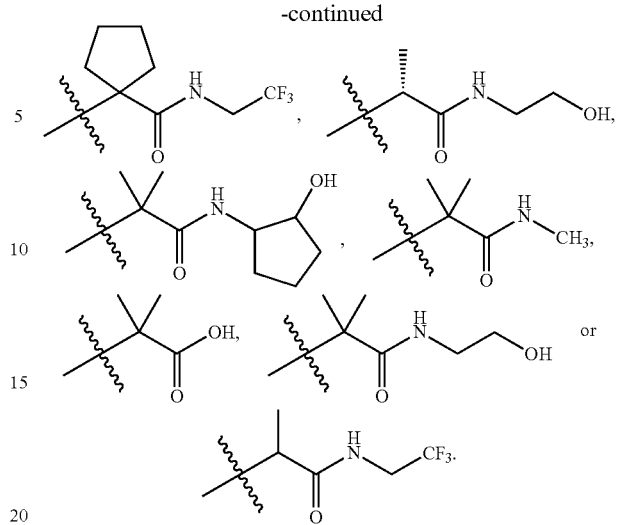

In another embodiment, R² is —SR⁶ wherein R⁶ is selected from CH₃—,

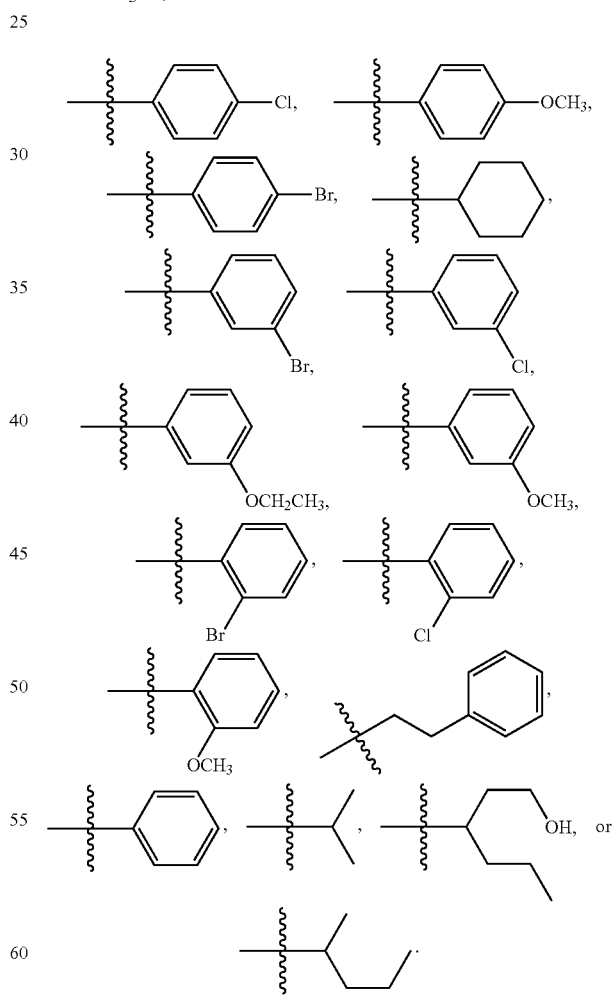

In some embodiments, the compounds of this invention have one of more of the following features: R⁷ is a 4- to 10-membered heterocyclic monocyclic or bicyclic ring optionally substituted with 1-3 of R⁸; R⁷ is a 4- to 6-membered heterocyclic monocyclic ring optionally substituted with 1-3 of $R^8$; $R^8$ is Q; Q is selected from —C(O)—W, —C(O)—N(W)$_2$, —C(O)—O—W, or —SO$_2$—W; Q is —C(O)—W.

In some embodiments, the compounds of this invention have one of more of the following features: $R^7$ is a $C_3$-$C_8$ carbocycle optionally substituted with 1-3 $R^8$; one $R^8$ is Q; Q is selected from hydroxy, —NH$_2$, —N(H)—W, |—N(W)$_2$, —N(H)—SO$_2$—W, —C(O)—N(W)$_2$, —N(H)—C(O)—W, or —O—C(O)—W; Q is —N(H)—C(O)—W.

In some embodiments, the compounds of this invention have one of more of the following features: $R^1$ is halogen (e.g., —Cl); $R^1$ is $C_{1-6}$ aliphatic (e.g., alkyl, alkenyl, or alkynyl) optionally substituted with 1-3 of $R^3$, and each $R^3$ is independently halo, aryl, or heteroaryl; $R^1$ is methyl optionally substituted with 1-3 $R^3$ and each $R^3$ is independently halo; $R^1$ is —CF$_3$; $R^1$ is —CH$_3$; $R^1$ is —NHR and R is H, $C_{1-6}$ aliphatic (e.g., alkyl), aryl, or $C_{3-8}$ cycloalkyl.

In some embodiments, the compounds of this invention have one or more of the following features: $R^2$ is —NR$^4$R$^5$ or —NR$^{10}$R$^{11}$; $R^2$ is —NR$^4$R$^5$, K wherein $R^4$ is H or $C_{1-6}$ aliphatic optionally substituted with 1-3 $R^7$, and $R^5$ is $C_{1-6}$ aliphatic optionally substituted with 1-4 $R^7$ or a 3- to 6-membered monocyclic or 6- to 10-membered bicyclic ring optionally substituted with 1-4 $R^7$; $R^4$ is H or $C_{1-6}$ aliphatic, and $R^5$ is $C_{1-6}$ alkyl that is optionally substituted with 1-4 of $R^7$; $R^4$ is H, and $R^5$ is $C_{1-4}$ alkyl and optionally substituted with 1-4 $R^7$; $R^5$ is ethyl substituted at the carbon atom attached to the nitrogen atom with $R^7$; $R^7$ is an aryl or heteroaryl, and is optionally substituted with 1-3 of $R^8$; $R^7$ is phenyl, pyridyl, or pyrimidyl, and is optionally substituted with 1-3 of $R^8$; $R^7$ is phenyl optionally substituted with 1-3 of $R^8$; $R^7$ is phenyl optionally substituted at the ortho- or meta-position with $R^8$ and also optionally substituted at the para-position with $R^8$ (e.g., the optional substituent $R^8$ at an ortho- or meta-position, when present, is halo).

In some embodiments of the compounds of this invention, $R^7$ is phenyl substituted at the para-position with —R or —N(R$^9$)$_2$;

R is 4- to 8-membered heterocyclic ring optionally containing 1-3 groups each independently selected from —N(R$^{17}$)—, —O—, or —S—, and the heterocyclic ring is optionally substituted with 1-3 of Q;

Each Q is independently selected from halogen, hydroxy, $C_{1-6}$ alkyl, benzyl, —CF$_3$, W, —C(O)—W, —C(O)—N(W)$_2$, —C(O)—O—W;

Each W is independently selected from —H, $C_{1-6}$ alkyl, or cycloalkyl;

Each $R^9$ is independently —H, $C_{3-6}$ heterocyclic ring, or $C_{1-3}$ aliphatic, wherein $C_{3-6}$ heterocyclic ring and $C_{1-3}$ aliphatic are each optionally substituted with 1-3 Q; or Two $R^9$ groups together with the N atom to which they are bound form a 4- to 8-membered ring containing additional 1 or 2 groups each independently selected from —N(R$^{17}$)—, —O—, or —S—, wherein the 4- to 8-membered ring is optionally and independently substituted with 1-3 of W.

In still some embodiments of the compounds of this invention, $R^7$ is optionally substituted at an ortho-position with fluoride.

In some embodiments, the compounds of this inventions have the following features:

R is 5- to 7-membered heterocyclic ring optionally containing 2 nitrogen atoms and optionally substituted with 1-3 of Q;

Each $R^9$ is independently —H, $C_{3-6}$ heterocyclic ring, or $C_{1-3}$ aliphatic, wherein $C_{3-6}$ heterocyclic ring and $C_1$-$C_3$ aliphatic are each optionally substituted with 1-3 Q; or Two $R^9$ groups together with the N atom to which they are bound form a 6- to 7-membered ring containing an additional nitrogen atom and optionally substituted with 1-3 of W.

Still some of the compounds of this invention have one or more of the following features: R is piperazine optionally substituted with 1-3 of Q; $R^7$ is

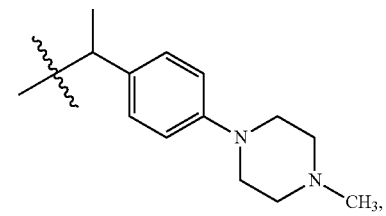

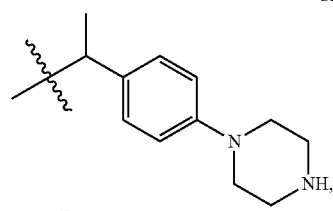

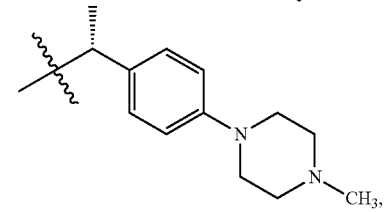

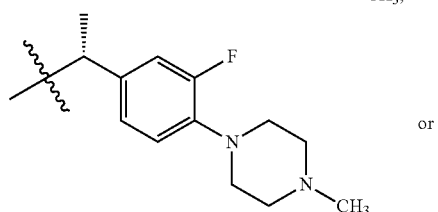

or

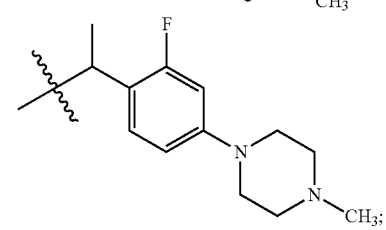

$R^7$ is phenyl substituted at the para-position with —OR$^9$; $R^9$ is —H, $C_{3-6}$ heterocycloalkyl ring, or $C_{1-3}$ alkyl, wherein $C_{3-6}$ heterocycloalkyl ring and $C_{1-3}$ alkyl are each optionally substituted with 1-3 Q; $R^9$ is pyrrolidinyl or piperidinyl and optionally substituted with 1-3 Q; $R^9$ is

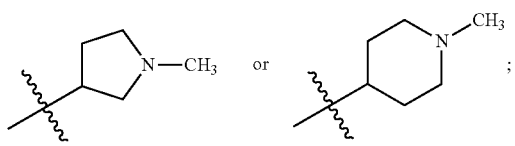

R⁹ is

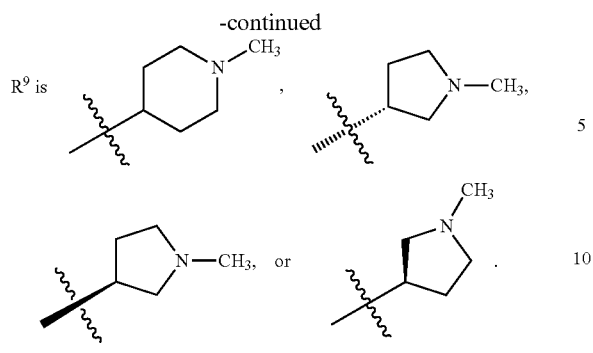

Still some of the compounds of this invention have one or more of the following features: R⁷ is pyrimidinyl optionally substituted with 1-3 of R⁸; R⁷ is 5-pyrimidyl optionally substituted at the 2-position with R⁸; R⁸ is —R⁹, —OR⁹, —SR⁹, —N(R⁹)₂, halogen, or —CN; Each R⁹ is independently —H, C₃₋₆ carbocyclic ring, C₃₋₆ heterocyclic ring, or C₁₋₃ aliphatic, wherein C₃₋₆ carbocyclic ring, C₃₋₆ heterocyclic ring and C₁₋₃ aliphatic are each optionally substituted with 1-3 Q; R⁷ is

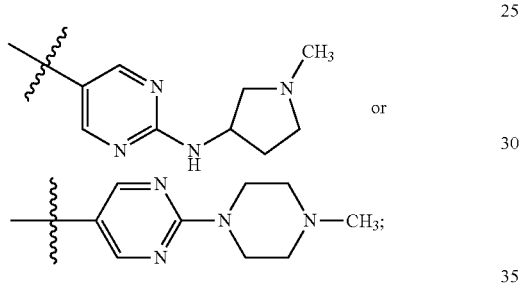

R⁷ is pyridinyl optionally substituted with 1-3 of R⁸; R⁷ is 3-pyridinyl optionally substituted with 1-3 of R⁸; R⁷ is 3-pyridinyl optionally substituted at the 6-position with R⁸; R⁸ is -Q, —R⁹, —OR⁹, —N(R⁹)₂, halogen, or —CN; each R⁹ is independently —H, C₃₋₆ heterocyclic ring, or C₁₋₃ aliphatic, wherein C₃₋₆ heterocyclic ring and C₁₋₃ aliphatic are each optionally substituted with 1-3 Q; or two R⁹ groups together with the N atom to which they are bound form a 4- to 8-membered heterocycloalkyl ring optioanlly containing an additional 1 or 2 groups selected from —N(R¹⁷)—, —O—, or —S—, wherein the 4- to 8-membered heterocycloalkyl ring is optionally and independently substituted with 1-3 of W; each R¹⁷ is independently, hydrogen, or C₁₋₄ aliphatic, wherein each C₁₋₄ aliphatic is optionally substituted with 1-3 of Q; each Q is independently selected from halogen, hydroxy, C₁₋₆ alkyl, —CF₃, —NH₂, —N(H)—W, or —N(W)₂;

each W is independently selected from —H, C₁₋₆ alkyl, aralkyl, cycloalkyl or heterocyclic ring; each C₁₋₆ alkyl, aralkyl, cycloalkyl or heterocyclic ring is optionally substituted with 1-3 of halogen, —OR⁶, —CN, C₁₋₆ alkyl or —NR¹⁸R¹⁹; or one W group, together with the nitrogen atom to which it is attached and a carbon atom of R, form a 4- to 8-membered ring; or two W groups, together with the same or different nitrogen atom or carbon atom to which they are attached, form a 4- to 8-membered heterocyclic ring.

Some other embodiments of the compounds of this invention have one or more of the following features: R⁷ is

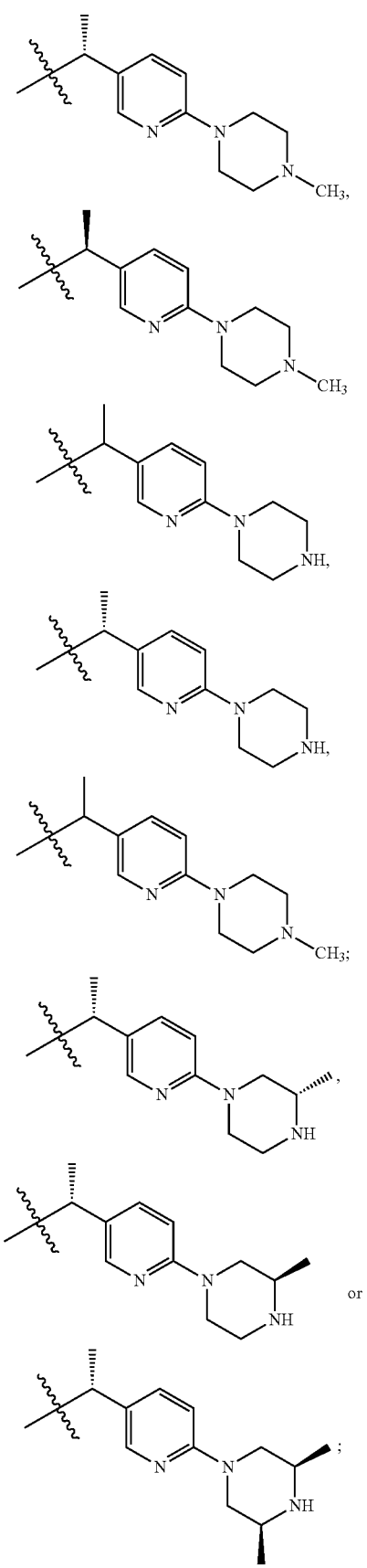

one R⁸ is aryl, heteroaryl, C₃-C₈ cycloalkyl, or 4- to 8-membered heterocyclic ring each optionally substituted with 1-3 of Q; R⁸ is a 4- to 8-membered heterocyclic ring optionally substituted with 1-3 of Q; one R⁸ is a 5- to 6-membered heterocyclic ring optionally substituted with 1-3 of Q; one R⁸ is a piperazine ring optionally substituted with 1-3 of Q; one R⁸ is Q; Q is —NHW, —NW₂, —NH—SO₂W, —NH—COW, —CO—NHW, —CO—NW₂, —SO₂NHW, —SO₂—NW₂, —SW, —OW, or —W; Q is —NHW, —NW₂ or —OW; W is C₁₋₆ alkyl, aralkyl, cycloalkyl or heterocyclic ring; each C₁₋₆ alkyl, aralkyl, cycloalkyl or heterocyclic ring is optionally substituted with 1-3 of halogen, —OR⁶, —CN, C₁₋₆ alkyl, C₁₋₆ alkyl or —NR¹⁸R¹⁹; W is C₁₋₆ alkyl or heterocyclic ring; each C₁₋₆ alkyl, aralkyl, cycloalkyl or heterocyclic ring is optionally substituted with 1-3 of halogen, —OR⁶, —CN, C₁₋₆ alkyl, C₁₋₆ alkyl or —NR¹⁸R¹⁹; one R⁸ is —R⁹, —OR⁹ or —N(R⁹)₂; R⁹ is independently H, C₃₋₆ carbocyclic ring, C₃₋₆ heterocyclic ring, or C₁₋₃ aliphatic, wherein C₃₋₆ carbocyclic ring, C₃₋₆ heterocyclic ring and C₁₋₃ aliphatic are each optionally substituted with 1-3 Q; or two R⁹ groups, together with the N atom to which they are bound, form a 4- to 8-membered ring optionally containing additional 1 or 2 groups selected from —N(R¹⁷)—, —O—, or —S—, wherein the 4- to 8-membered ring is optionally and independently substituted with 1-3 of W.

Still some other compounds of this invention have one or more of the following features: R⁷ is a 4- to 10-membered heterocyclic monocyclic or bicyclic ring optionally substituted with 1-3 of R⁸; R⁷ is a 4- to 6-membered heterocyclic monocyclic ring optionally substituted with 1-3 of R⁸; R⁸ is Q; Q is selected from —C(O)—W, —C(O)—N(W)₂—C(O)—O—W or —SO₂—W; Q is selected from —C(O)—W.

Still some other compounds of this invention have one or more of the following features: R⁷ is a C₃₋₈ carbocycle optionally substituted with 1-3 R⁸; one R⁸ is Q; Q is selected from hydroxy, —NH₂, —N(H)—W, —N(W)₂, —N(H)—SO₂—W, —C(O)—N(W)₂, —N(H)—C(O)—W, or —O—C(O)—W; Q is selected from —N(H)—C(O)—W; R² is —NR¹⁰R¹¹; R¹⁰ is —H and R¹¹ is —C(R¹²R¹³)C(=O)NR¹⁴R¹⁵; R¹² is H; R¹³ is C₁₋₃ alkyl; R¹⁴ is H; and R¹⁵ is alkyl substituted with trifluoromethyl or hydroxy, or R¹⁵ is cycloalkyl substituted with hydroxy; R¹⁵ is

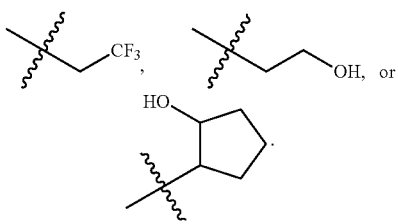

Still some other compounds of this invention have one or more of the following features: R² is –OR⁶ or —SR⁶; R⁶ is optionally substituted phenyl.

Specific examples of the compounds of this invention include compounds I-1 through I-304 or pharmaceutically acceptable salts thereof; compounds IA-0 through IA-13 or pharmaceutically acceptable salts thereof; compounds II-0 through II-17 or pharmaceutically acceptable salts thereof; and compounds EG4, EG5, EG6, EG7 and EG8 or pharmaceutically acceptable salts thereof. The structures of these specific compounds are show hereinafter.

In another aspect, the invention features compounds of formula Id

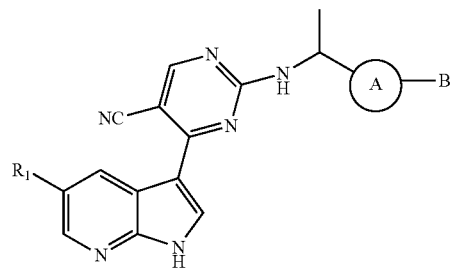

or a pharmacetucally acceptable salt thereof, wherein:
A is phenyl, pyridinyl, or pyrmidinyl;
B is —NR'R";
R' is H or C₁₋₄ alkyl;
R" is a C₂₋₄ aliphatic substituted with —NH₂ or —NHCH₃; or
R" is an N-heterocycloaliphatic optionally substituted on N with CH₃; or
R' and R" together with the N to which they are attached form a 5- to 7-membered heterocycloaliphatic ring containing two N atoms.

Compounds of formula Id show selectivity for PLK1 over PLK2 and PLK3.

In some embodiments, R¹ is trifluoromethyl.

In some embodiments, R' is H or methyl and R" is 2-amino- or 2-methylamino-ethane.

In other embodiments, B is piperazinyl or diazepanyl, optionally substituted at the 4-position with methyl.

In certain embodiments, R' is H or methyl, and R" is pyrrolidine or piperidine and is optionally substituted at N with methyl.

In certain embodiments, R" is a C₂₋₄ aliphatic substituted with —NH₂ or —NHCH₃.

In certain embodiments, R" is cyclohexyl substituted with —NH₂ or —NHCH₃.

In certain embodiments, R" is piperazine or pyrrolidine.

The compounds of this invention include those described herein, and are further illustrated by the classes, subclasses, and species disclosed herein.

Another aspect of this invention provides a pharmaceutical composition containing one of the compounds described above, and a pharmaceutically acceptable carrier, adjuvant, or vehicle. The composition may further include another therapeutic agent selected from the group consisting of synthetic small molecule VEGF receptor antagonists, small molecule growth factor receptor antagonists, inhibitors of the EGF receptor and/or VEGF receptor and/or integrin receptors or any other protein tyrosine kinase receptors which are not classified under the synthetic small-molecules, inhibitors directed to EGF receptor and/or VEGF receptor and/or integrin receptors or any other protein tyrosine kinase receptors, which are fusion proteins, compounds which interact with nucleic acids and which are classified as alkylating agents or platinum compounds, compounds which interact with nucleic acids and which are classified as anthracyclines, as DNA intercalators or as DNA cross-linking agents, including DNA minor-groove binding compounds, anti-metabolites, naturally occurring, semi-synthetic or synthetic bleomycin type antibiotics, inhibitors of DNA transcribing enzymes, and especially the topoisomerase I or topoisomerase II inhibitors, chromatin modifying agents, mitosis inhibitors, anti-mitotic agents, cell-cycle inhibitors, proteasome inhibitors, enzymes, hormones, hormone antagonists, hormone inhibitors, inhibitors of steroid biosynthesis, steroids, cytokines, hypoxia-selective cytotoxins, inhibitors of cytokines, lymphokines, antibodies directed against cytokines, oral and parenteral tolerance induction agents, supportive agents, chemical radiation sensitizers and protectors, photo-chemically activated drugs, synthetic poly- or oligonucleotides, optionally modified or conjugated, non-steroidal anti-inflammatory drugs, cytotoxic antibiotics, antibodies targeting growth factors or their receptors, antibodies targeting the surface molecules of cancer cells, inhibitors of metalloproteinases, metals, inhibitors of oncogenes, inhibitors of gene transcription or of RNA translation or protein expression, complexes of rare earth elements, compounds which reduces the transport of hyaluronan mediated by one or more ABC transporters, and photo-chemotherapeutic agents.

Still, the pharmaceutical compositions of this invention may further contains another therapeutic agent selected from the group consisting of a small molecule VEGF receptor antagonist such as vatalanib (PTK-787/ZK222584), SU-5416, SU-6668, SU-11248, SU-14813, AZD-6474, AZD-2171, CP-547632, CEP-7055, AG-013736, IM-842 or GW-786034, a dual EGFR/HER2 antagonist such as gefitinib, erlotinib, CI-1033 or GW-2016, an EGFR antagonist such as iressa (ZD-1839), tarceva (OSI-774), PKI-166, EKB-569, HKI-272 or herceptin, an antagonist of the mitogen-activated protein kinase such as BAY-43-9006 or BAY-57-9006, a quinazoline derivative such as 4-[(3-chloro-4-fluorophenyl)amino]-6-{[4-(N,N-dimethylamino)-1-oxo-2-bute-n-1-yl]amino}-7-((S)-tetrahydrofuran-3-yloxy)-quinazoline or 4-[(3-chloro-4-fluoro-phenyl)amino]-6-{[4-(homomorpholin-4-yl)-1-oxo-2-bu-ten-1-yl]amino}-7-[(S)-(tetrahydrofuran-3-yl)oxy]-quinazoline, or a pharmaceutically acceptable salt thereof, a protein kinase receptor antagonist which is not classified under the synthetic small molecules such as atrasentan, rituximab, cetuximab, Avastin™ (bevacizumab), IMC-1C11, erbitux (C-225), DC-101, EMD-72000, vitaxin, imatinib, a protein tyrosine kinase inhibitor which is a fusion protein such as VEGFtrap, an alkylating agent or a platinum compound such as melphalan, cyclophosphamide, an oxazaphosphorine, cisplatin, carboplatin, oxaliplatin, satraplatin, tetraplatin, iproplatin, mitomycin, streptozocin, carmustine (BCNU), lomustine (CCNU), busulfan, ifosfamide, streptozocin, thiotepa, chlorambucil, a nitrogen mustard such as mechlorethamine, an ethyleneimine compound, an alkylsulphonate, daunorubicin, doxorubicin (adriamycin), liposomal doxorubicin (doxil), epirubicin, idarubicin, mitoxantrone, amsacrine, dactinomycin, distamycin or a derivative thereof, netropsin, pibenzimol, mitomycin, CC-1065, a duocarmycin, mithramycin, chromomycin, olivomycin, a phtalanilide such as propamidine or stilbamidine, an anthramycin, an aziridine, a nitrosourea or a derivative thereof, a pyrimidine or purine analogue or antagonist or an inhibitor of the nucleoside diphosphate reductase such as cytarabine, 5-fluorouracile (5-FU), pemetrexed, tegafur/uracil, uracil mustard, fludarabine, gemcitabine, capecitabine, mercaptopurine, cladribine, thioguanine, methotrexate, pentostatin, hydroxyurea, or folic acid, a phleomycin, a bleomycin or a derivative or salt thereof, CHPP, BZPP, MTPP, BAPP, liblomycin, an acridine or a derivative thereof, a rifamycin, an actinomycin, adramycin, a camptothecin such as irinotecan or topotecan, an amsacrine or analogue thereof, a tricyclic carboxamide, an histonedeacetylase inhibitor such as SAHA, MD-275, trichostatin A, CBHA, LAQ824, or valproic acid, an anti-cancer drug from plants such as paclitaxel (taxol), docetaxel or taxotere, a vinca alkaloid such as navelbine, vinblastin, vincristin, vindesine or vinorelbine, a tropolone alkaloid such as colchicine or a derivative thereof, a macrolide such as maytansine, an ansamitocin or rhizoxin, an antimitotic peptide such as phomopsin or dolastatin, an epipodophyllotoxin or a derivative of podophyllotoxin such as etoposide or teniposide, a steganacin, an antimitotic carbamate derivative such as combretastatin or amphetinile, procarbazine, a proteasome inhibitor such as bortezomib, an enzyme such as asparaginase, pegylated asparaginase (pegaspargase) or a thymidine-phosphorylase inhibitor, a gestagen or an estrogen such as estramustine (T-66) or megestrol, an anti-androgen such as flutamide, casodex, anandron or cyproterone acetate, an aromatase inhibitor such as aminogluthetimide, anastrozole, formestan or letrozole, a GNrH analogue such as leuprorelin, buserelin, goserelin or triptorelin, an anti-estrogen such as tamoxifen or its citrate salt, droloxifene, trioxifene, raloxifene or zindoxifene, a derivative of 17.beta.-estradiol such as ICI 164,384 or ICI 182,780, aminoglutethimide, formestane, fadrozole, finasteride, ketoconazole, a LH-RH antagonist such as leuprolide, a steroid such as prednisone, prednisolone, methylprednisolone, dexamethasone, budenoside, fluocortolone or triamcinolone, an interferon such as interferon .beta., an interleukin such as IL-10 or IL-12, an anti-TNF.alpha. antibody such as etanercept, an immunomodulatory drug such as thalidomide, its R- and S-enantiomers and its derivatives, or revimid (CC-5013), a leukotrien antagonist, mitomycin C, an aziridoquinone such as BMY-42355, AZQ or EO-9, a 2-nitroimidazole such as misonidazole, NLP-1 or NLA-1, a nitroacridine, a nitroquinoline, a nitropyrazoloacridine, a "dual-function" nitro aromatic such as RSU-1069 or RB-6145, CB-1954, a N-oxide of nitrogen mustard such as nitromin, a metal complex of a nitrogen mustard, an anti-CD3 or anti-CD25 antibody, a tolerance induction agent, a biphosphonate or derivative thereof such as minodronic acid or its derivatives (YM-529, Ono-5920, YH-529), zoledronic acid monohydrate, ibandronate sodium hydrate or clodronate disodium, a nitroimidazole such as metronidazole, misonidazole, benznidazole or nimorazole, a nitroaryl compound such as RSU-1069, a nitroxyl or N-oxide such as SR-4233, an halogenated pyrimidine analogue such as bromodeoxyuridine, iododeoxyuridine, a thiophosphate such as WR-272 1, a photo-chemically activated drug such as porfimer, photofrin, a benzoporphyrin derivative, a pheophorbide derivative, merocyanin 540 (MC-540) or tin etioporpurin, an ant-template or an anti-sense RNA or DNA such as oblimersen, a non-steroidal inflammatory drug such as acetylsalicyclic acid, mesalazin, ibuprofen, naproxen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen, indomethacin, sulindac, tolmetin, zomepirac, nabumetone, diclofenac, fenclofenac, alclofenac, bromfenac, ibufenac, aceclofenac, acemetacin, fentiazac, clidanac, etodolac, oxpinac, mefenamic acid, meclofenamic acid, flufenamic acid, nifluminic acid, tolfenamic acid, diflunisal, flufenisal, piroxicam, tenoxicam, lomoxicam, nimesulide, meloxicam, celecoxib, rofecoxib, or a pharmaceutically acceptable salt of a non-steroidal inflammatory drug, a cytotoxic antibiotic, an antibody targeting the surface molecules of cancer cells such as apolizumab or 1D09C3, an inhibitor of metalloproteinases such as TIMP-1 or TIMP-2, Zinc, an inhibitor of oncogenes such as P53 and Rb, a complex of rare earth elements such as the heterocyclic complexes of lanthanides, a photo-chemotherapeutic agent such as PUVA, an inhibitor of the transcription factor complex ESX/DRIP130/Sur-2, an inhibitor of HER-2 expression, such as the heat shock protein HSP90 modulator geldanamycin and its derivative 17-allylaminogeldanamycin or 17-AAG, a compound which reduces the transport of hyaluronan mediated by one or more ABC transporters selected from a P-glycoprotein (P-gp) inhibitor molecule or inhibitor peptide, an MRP 1 inhibitor, an antibody directed against and capable of blocking the ABC transporter, an antisense oligomer, iRNA, siRNA or aptamer directed against one or more ABC transporters, or a therapeutic agent selected from IM-842, tetrathiomolybdate, squalamine, combrestatin A4, TNP-470, marimastat, neovastat, bicalutamide, abarelix, oregovomab, mitumomab, TLK-286, alemtuzumab, ibritumomab, temozolomide, denileukin diftitox, aldesleukin, dacarbazine, floxuridine, plicamycin, mitotane, pipobroman, plicamycin, tamLoxifen and testolactone.

The pharmaceutical composition of this invention may still further contains another therapeutic agent selected from the group consisting of an anti-cancer drug from plants such as paclitaxel (taxol), docetaxel or taxotere, a vinca alkaloid such as navelbine, vinblastin, vincristin, vindesine or vinorelbine, a vinca alkaloid such as navelbine, vinblastin, vincristin, vindesine or vinorelbine, an alkylating agent or a platinum compound such as melphalan, cyclophosphamide, an oxazaphosphorine, cisplatin, carboplatin, oxaliplatin, satraplatin, tetraplatin, iproplatin, mitomycin, streptozocin, carmustine (BCNU), lomustine (CCNU), busulfan, ifosfamide, streptozocin, thiotepa, chlorambucil, a nitrogen mustard such as mechlorethamine, an immunomodulatory drug such as thalidomide, its R- and S-enantiomers and its derivatives, or revimid (CC-5013)), an ethyleneimine compound, an alkylsulphonate, daunorubicin, doxorubicin (adriamycin), liposomal doxorubicin (doxil), epirubicin, idarubicin, mitoxantrone, amsacrine, dactinomycin, distamycin or a derivative thereof, netropsin, pibenzimol, mitomycin, CC-1065, a duocarmycin, mithramycin, chromomycin, olivomycin, a phtalanilide such as propamidine or stilbamidine, an anthramycin, an aziridine, a nitrosourea or a derivative thereof, a pyrimidine or purine analogue or antagonist or an inhibitor of the nucleoside diphosphate reductase such as cytarabine, 5-fluorouracile (5-FU), pemetrexed, tegafur/uracil, uracil mustard, fludarabine, gemcitabine, capecitabine, mercaptopurine, cladribine, thioguanine, methotrexate, pentostatin, hydroxyurea, or folic acid, an acridine or a derivative thereof, a rifamycin, an actinomycin, adramycin, a camptothecin such as irinotecan or topotecan, an amsacrine or analogue thereof, a tricyclic carboxamide, an histonedeacetylase inhibitor such as SAHA, MD-275, trichostatin A, CBHA, LAQ824, or valproic acid, a proteasome inhibitor such as bortezomib, a small molecule VEGF receptor antagonist such as vatalanib (PTK-787/ZK222584), SU-5416, SU-6668, SU-11248, SU-14813, AZD-6474, AZD-2171, CP-547632, CEP-7055, AG-013736, IM-842 or GW-786034, an antagonist of the mitogen-activated protein kinase such as BAY-43-9006 or BAY-57-9006, a dual EGFR/HER2 antagonist such as gefitinib, erlotinib, CI-1033 or GW-2016, an EGFR antagonist such as iressa (ZD-1839), tarceva (OSI-774), PKI-166, EKB-569, HKI-272 or herceptin, a quinazoline derivative such as 4-[(3-chloro-4-fluorophenyl)amino]-6-{[4-(N,N-dimethylamino)-1-oxo-2-bute-n-1-yl]amino}-7-((S)-tetrahydrofuran-3-yloxy)-quinazoline or 4-[(3-chloro-4-fluoro-phenyl)amino]-6-{[4-(homomorpholin-4-yl)-1-oxo-2-bu-ten-1-yl]amino}-7-[(S)-(tetrahydrofuran-3-yl)oxy]-quinazoline, or a pharmaceutically acceptable salt thereof, an inhibitor of the transcription factor complex ESX/DRIP130/Sur-2, an inhibitor of HER-2 expression, such as the heat shock protein HSP90 modulator geldanamycin and its derivative 17-allylaminogeldanamycin or 17-AAG, a protein kinase receptor antagonist which is not classified under the synthetic small molecules such as atrasentan, rituximab, cetuximab, Avastin™ (bevacizumab), IMC-1C11, erbitux (C-225), DC-1 01, EMD-72000, vitaxin, imatinib, a P-glycoprotein (P-gp) inhibitor molecule such as zosuquidar (LY 335973), its salts (especially the trichloride salt) and its polymorphs, cyclosporin A, verapamil or its R-isomer, tamoxifen, quinidine, d-alpha tocopheryl polyethylene glycol 1000 succinate, VX-710, PSC833, phenothiazine, GF120918 (II), SDZ PSC 833, TMBY, MS-073, S-9788, SDZ 280-446, XR(9051) and functional derivatives, analogues and isomers of these, or an antibody targeting the surface molecules of cancer cells such as apolizumab or ID09C3.

In some embodiments, the compositions of this invention may further include 4-[(3-chloro-4-fluorophenyl)amino]-6-{[4-(N,N-dimethylamino)-1-oxo-2-bute-n-1-yl]amino}-7-((S)-tetrahydrofuran-3-yloxy)-quinazoline, 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline, 4-[(3-chloro-4-fluoro-phenyl)amino]-6-{[4-(homomorpholin-4-yl)-1-oxo-2-buten-1-yl]amino}-7-[(S)-(tetrahydrofuran-3-yl)oxy]-quinazoline, 4-[(3-chloro-4-fluoro-phenyl)amino]-6-{[4-(homomorpholin-4-yl)-1-oxo-2-bu-ten-1-yl]amino}-7-[(S)-(tetrahydrofuran-3-yl)oxy]-quinazoline, 3-Z-[1-(4-(N-((4-methyl-piperazin-1-yl)-methylcarbonyl)-N-methyl-amino)-anilino-)-1-phenyl-methylene]-6-methoxycarbonyl-2-indolinone, 3-Z-[1-(4-(N-((4-methyl-piperazin-1-yl)-methylcarbonyl)-N-methyl-amino)-a-nilino)-1-phenyl-methylene]-6-methoxycarbonyl-2-indolinone, 3-Z-[1-(4-dimethylaminomethylanilino)-1-(4-(2-carboxyethyl)phenyl)methyle-ne]-6-fluoro-2-indolinone, or a pharmaceutically acceptable salt thereof.

The compounds of this invention can be used to inhibit PLK protein kinase activity in a biological sample.

Thus, the invention further provides a method of inhibiting PLK protein kinase activity in a patient, which includes administering to the patient one of the compounds described above or one of the compositions described above.

Another aspect of this invention provides a method of treating a proliferative disorder, a neurodegenerative disorder, an autoimmune disorder, an inflammatory disorder, or an immunologically mediated disorder in a patient. The method includes administering to the patient in need thereof a therapeutically effective amount of one of the compounds or compositions described above. This method may further include administering to the patient an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating destructive bone disorders, an agent for treating liver disease, an antiviral agent, an agent for treating blood disorders, an agent for treating diabetes, or an agent for treating immunodeficiency disorders, wherein (1) said additional therapeutic agent is appropriate for the disease being treated, and (2) said additional therapeutic agent is administered together with said composition as a single dosage form or separately from said composition as part of a multiple dosage form.

Still in another aspect, the invention provides a method of treating an oncological disease in a patient, which includes administering to the patient in need thereof a therapeutically effective amount of a compound or a pharmaceutical composition of those described above. Examples of the oncological disease include, but are not limited to, refractory or relapsed multiple myeloma, acute or chronic myelogenous leukaemia, myelodysplastic syndrome, myeloproliferativesyndromes, acute lymphoblastic leukaemia, Hodgkin's and non-Hodgkin's lymphoma.

The invention further provides a method of treating solid tumor, melanoma, myeloma, leukemia, lymphoma, neuroblastoma, or a cancer selected from colon, breast, gastric, ovarian, cervical, lung, central nervous system (CNS), renal, prostate, bladder, or pancreatic, in a patient by administering to said patient one of the compounds or pharmaceutical compositions described above.

The invention still further provides a method of treating cancer in a patient, which includes administering to the patient one of the compounds or pharmaceutical compositions described above. Examples of the cancer include urogenital cancer, lung cancer, gastrointestinal cancer, head and neck cancer, malignant mesothelioma, breast cancer, malignant melanoma, childhood cancer and bone or soft tissue sarcoma.

The invention also relates to a method of treating a disease involving cell proliferation, migration or apoptosis of cancer cells, or angiogenesis, in a human or non-human mammalian body, by administering simultaneously, separately or sequentially to the patient a therapeutically effective amount of one of the compounds or pharmaceutical compositions described above. Examples of such disease include Coeliac disease, diabetes mellitus type 1 (IDDM), systemic lupus erythematosus (SLE), Sjögren's syndrome, multiple sclerosis (MS), Hashimoto's thyroiditis, Graves' disease, idiopathic thrombocytopenic purpura, and rheumatoid arthritis (RA).

Also within the scope of the invention is a process for preparing a compound of formula I

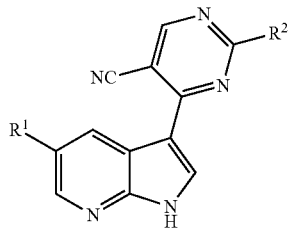

I or a pharmaceutically acceptable salt thereof, wherein the variables $R^1$ and $R^2$ are as defined above. This process includes contacting a mixture of a boronate ester of formula 8

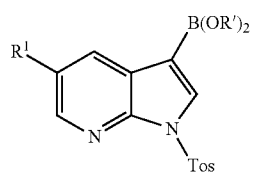

8

(wherein each R' is independently $C_1$-$C_3$ alkyl or two R' together with the atoms to which they are attached form a 5 or 6 membered ring optionally substituted with 1 to 4 methyl groups), a pyrimidine of formula 7

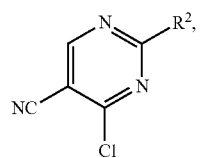

7 and an alkali metal carbonate with a palladium catalyst in a suitable solvent. An example of the suitable palladium catalyst is bis-(tri-tert-butylphosphine)palladium(0) and an example of the suitable solvent is dioxane and the alkali metal carbonate is potassium carbonate. To practice this process, the pyrimidine can be 4-chloro-2-(methylthio)pyrimidine-5-carbonitrile, and the boronate ester can be 5-Trifluoromethyl-3-(4,4,5,5-tetramethyl-1,3,2-dioxoborolan-2-yl)-1-tosyl-1H-pyrrolo[2,3-b]pyridine.

In some embodiments of the process of this invention, $R^2$ is —$SCH_3$.

The process of this invention may further includes the steps of:

(a) oxidizing a compound of formula 26

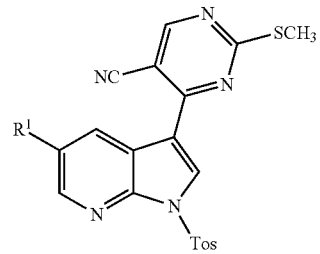

26

(wherein $R^1$ is as previously described) with chlorine in aqueous ethanol to provide a compound of formula 27

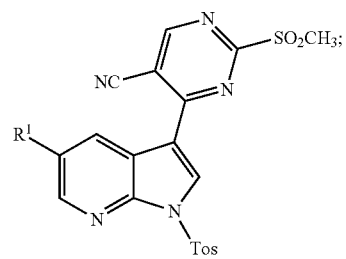

27

(b) reacting a compound of formula 27 with a compound of formula $R^2H$, wherein $R^2$ is $HNR^4R^5$, $HOR^6$ or $HSR^6$ and $R^4$, $R^5$ and $R^6$ are as previously described, in the presence of microwave irradiation to provide a compound of formula 28

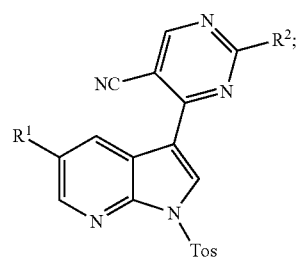

28 and c) removing the Tos protecting group to provide compounds of formula I.

DEFINITIONS

As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As described herein, a specified number range of atoms includes any integer therein. For example, a group having from 1-4 atoms could have 1, 2, 3, or 4 atoms.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

The term "stable", as used herein, refers to compounds that are not substantially altered when subjected to conditions to allow for their production, detection, recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched), branched, or cyclic substituted or unsubstituted hydrocarbon chain that is completely saturated or that contains one or more units of unsaturation that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. Suitable aliphatic groups include, but are not limited to, linear or branched, substituted or unsubstituted alkyl, alkenyl, or alkynyl groups. Specific examples include, but are not limited to, methyl, ethyl, isopropyl, n-propyl, sec-butyl, vinyl, n-butenyl, ethynyl, and tert-butyl.

As used herein, the term "$C_{0-3}$ alkyl" refers to either a bond or a $C_{1-3}$ alkyl. Other carbon number ranges containing zero have the same meaning.

It should be understood that if the aliphatic is alkenyl or alkynyl, then the aliphatic group has at least 2 carbon atoms.

The term "oxo" for substituent refers to the group "=O" which replace, e.g., two hydrogen atoms on a carbon atom of a methylen group to form —C(O)— (equivalent to —C(=O)—), i.e., a carbonyl group.

The term "cycloaliphatic" or "carbocyclic" refers to a monocyclic $C_{3-8}$ hydrocarbon or bicyclic $C_{7-12}$ hydrocarbon that is completely saturated or that contains one or more units of unsaturation, but which is not aromatic, that has a single point of attachment to the rest of the molecule wherein any individual ring in said bicyclic ring system has 3-7 members. Suitable cycloaliphatic groups include, but are not limited to, cycloalkyl, bicycloalkyl, cycloalkenyl and bicycloalkenyl groups. Specific examples include, but are not limited to, cyclohexyl, bicycle[2.2.1]heptanyl, cyclopropenyl, and cyclobutyl. The term "heteroaliphatic", as used herein, means aliphatic groups wherein one or two carbon atoms are independently replaced by one or more of oxygen, sulfur, nitrogen, phosphorus, or silicon. Heteroaliphatic groups may be substituted or unsubstituted, branched or unbranched, cyclic or acyclic, and include "heterocycle", "heterocyclyl", "heterocycloaliphatic", or "heterocyclic" groups.

The term "heterocycle", "heterocyclyl", or "heterocyclic" as used herein means nonaromatic, monocyclic, bicyclic, or tricyclic ring systems in which one or more ring members are an independently selected heteroatom. A heterocyclic ring includes heterocycloaliphatic, which in turn includes heterocycloalkyl, heterocycloalkenyl, and heterocycloalkynyl. In some embodiments, the "heterocycle", "heterocyclyl", or "heterocyclic" group has three to fourteen ring members in which one or more ring members is a heteroatom independently selected from oxygen, sulfur, nitrogen, or phosphorus, and each ring in the system contains 3 to 7 ring members.

Suitable heterocycles include, but are not limited to, 3-1H-benzimidazol-2-one, 3-(1-alkyl)-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 4-piperidinyl, 1-pyrazolinyl, 3-pyrazolinyl, 4-pyrazolinyl, 2-thiazolidinyl, 3-thiazolidinyl, 4-thiazolidinyl, 1-imidazolidinyl, 2-imidazolidinyl, 4-imidazolidinyl, indolinyl, tetrahydroquinolinyl, tetrahydroisoquinolinyl, benzothiolane, benzodithiane, and 1,3-dihydro-imidazol-2-one.

Cyclic groups, (e.g., cycloaliphatic and heterocycles), can be linearly fused, bridged, or spirocyclic.

The term "heteroatom" means one or more of oxygen, sulfur, nitrogen, or phosphorus, (including, any oxidized form of nitrogen, sulfur, or phosphorus; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation.

The term "nonaromatic", as used herein, describes rings that are either saturated or partially unsaturated.

The term "aromatic", as used herein, describes rings that are fully unsaturated.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl", "haloaliphatic", and "haloalkoxy" mean alkyl, alkenyl or alkoxy, as the case may be, substituted with one or more halogen atoms. The terms "halogen", "halo", and "hal" mean F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic". Suitable heteroaryl rings include, but are not limited to, 2-furanyl, 3-furanyl, N-imidazolyl, 2-imidazolyl, 4-imidazolyl, 5-imidazolyl, benzimidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, benzofuryl, benzothiophenyl, indolyl (e.g., 2-indolyl), pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

When the term "ortho", "meta", or "para" is used to identify the position of a substituent on a 6-member ring system, it is relative to the atom by which this ring system is attached to the core of the compound of formula. For instance, a phenyl substituted at the ortho-position with methyl, at the meta-position with fluoro, and at the para-position with isopropyl is

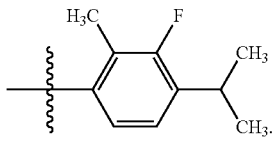

The term "protecting group" and "protective group" as used herein, are interchangeable and refer to an agent used to temporarily block one or more desired reactive sites in a multifunctional compound. In certain embodiments, a protecting group has one or more, or preferably all, of the following characteristics: a) is added selectively to a functional group in good yield to give a protected substrate that is b) stable to reactions occurring at one or more of the other reactive sites; and c) is selectively removable in good yield by reagents that do not attack the regenerated, deprotected functional group. Exemplary protecting groups are detailed in Greene, T. W., Wuts, P. G in "Protective Groups in Organic Synthesis", Third Edition, John Wiley & Sons, New York: 1999 (and other editions of the book), the entire contents of which are hereby incorporated by reference. The term "nitrogen protecting group", as used herein, refers to an agents used to temporarily block one or more desired nitrogen reactive sites in a multifunctional compound. Preferred nitrogen protecting groups also possess the characteristics exemplified above, and certain exemplary nitrogen protecting groups are also detailed in Chapter 7 in Greene, T. W., Wuts, P. G in "Protective Groups in Organic Synthesis", Third Edition, John Wiley & Sons, New York: 1999, the entire contents of which are hereby incorporated by reference.

In some embodiments, an alkyl or aliphatic chain can be optionally interrupted with another atom or group. This means that a methylene unit of the alkyl or aliphatic chain is optionally replaced with said other atom or group. Examples of such atoms or groups would include, but are not limited to, —NR—, —O—, —S—, $CO_2$—, —OC(O)—, —C(O)CO—, —C(O)—, —C(O)NR—, —C(=N—CN)—, —NRCO—, —NRC(O)O—, —$SO_2$NR—, —$NRSO_2$—, —NRC(O) NR—, —OC(O)NR—, —$NRSO_2$NR—, —SO—, or —$SO_2$—, wherein R is defined herein. Unless otherwise specified, the optional replacements form a chemically stable compound. Optional interruptions can occur both within the chain and at either end of the chain; i.e., both at the point of attachment and/or also at the terminal end. Two optional replacements can also be adjacent to each other within a chain so long as it results in a chemically stable compound. The optional interruptions or replacements can also completely replace all of the carbon atoms in a chain. For example, a $C_3$ aliphatic can be optionally interrupted or replaced by —NR—, —C(O)—, and —NR— to form —NRC(O)NR— (a urea).

As used herein, the term "1-3" (or other similar numerical terms) refers to a range of 1 to 3.

Unless otherwise specified, if the replacement or interruption occurs at the terminal end, the replacement atom is bound to an H on the terminal end. For example, if —$CH_2CH_2CH_3$ were optionally interrupted with —O—, the resulting compound could be —$OCH_2CH_3$, —$CH_2OCH_3$, or —$CH_2CH_2OH$.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention.

Unless otherwise stated, all tautomeric forms of the compounds of the invention are within the scope of the invention.

Unless otherwise stated, a substituent can freely rotate around any rotatable bonds. For example, a substituent drawn as

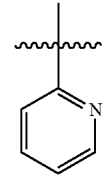

also represents

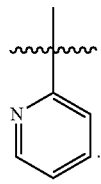

Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

The following abbreviations are used:
PG protecting group
LG leaving group
DCM dichloromethane
Ac acetyl
DMF dimethylformamide
EtOAc ethyl acetate
DMSO dimethyl sulfoxide
MeCN acetonitrile
TCA trichloroacetic acid
ATP adenosine triphosphate
EtOH ethanol
Ph phenyl
Me methyl
Et ethyl
Bu butyl
DEAD diethylazodicarboxylate
HEPES 4-(2-hydroxyethyl)-1-piperazineethanesulfonic acid
BSA bovine serum albumin
DTT dithiothreitol
MOPS 4-morpholinepropanesulfonic acid
NMR nuclear magnetic resonance
HPLC high performance liquid chromatography
LCMS liquid chromatography-mass spectrometry
TLC thin layer chromatography
Rt retention time Synthesis of the Compounds The compounds of this invention may, in general, be prepared by methods such as those depicted in the schemes below. Unless otherwise indicated, all variables in the following schemes are as defined herein.

Scheme 1

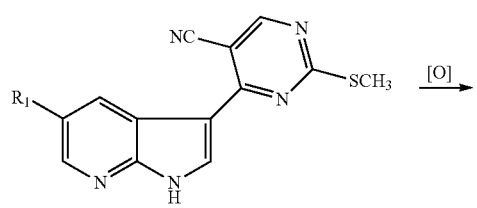

1

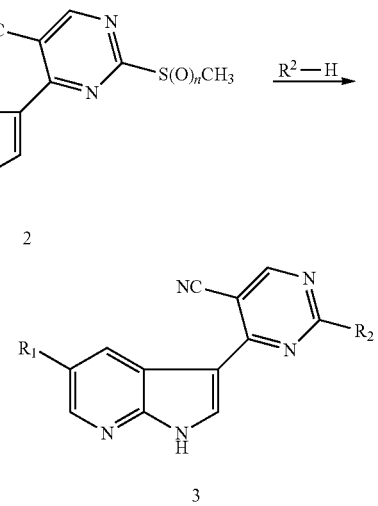

Referring to Scheme 1, oxidation of compound 1 to provide compound 2 can be achieved with a known oxidizing agent such as oxone or m-CPBA or chlorine gas in a solvent such as aqueous alcohol, acetonitrile or dichloromethane. Displacement with $R^2$—H, wherein $R^2$—H is $HNR^4R^5$, $HOR^6$ or $HSR^6$, to give compound 3 can be achieved thermally or using microwave heating in a solvent such as dioxane, tetrahydrofuran, ethanol, isopropanol or butanol.

An alternative method for preparing compounds of the invention is illustrated in Scheme 2.

Scheme 2

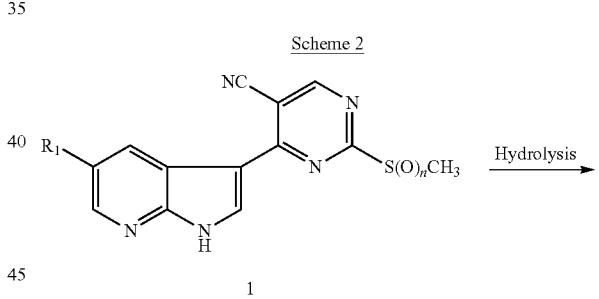

1

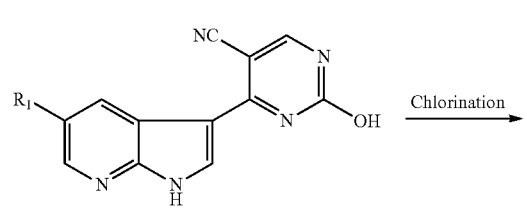

2-2

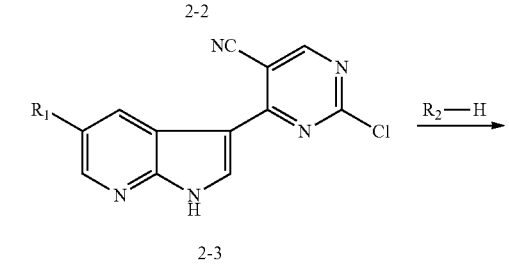

2-3

-continued

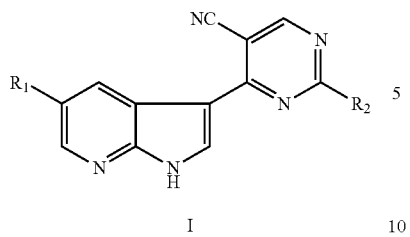

I

Referring to Scheme 2, hydrolysis of compound 1 can be achieved by water in the presence of a base such as triethylamine or ethyldiisopropylamine in a solvent such as acetonitrile, tetrahydrofuran or dioxane to provide compound 2-2. Chlorination of compound 2-2 to provide compound 2-3 can be achieved by phosphorous oxychloride in a solvent such as toluene. Reaction of compound 2-3 with $R^2$—H, wherein $R^2$—H is $HNR^4R^5$, $HOR^6$ or $HSR^6$, can be achieved thermally or using microwave heating in a solvent such as dioxane, tetrahydrofuran, ethanol, isopropanol or butanol to provide compound I.

In some instances, the azaindole 1-nitrogen is optionally protected with an arylsulphonate, such as tosyl or benzene sulphonate, a silyl group such as tert-butyldimethylsilyl or triisopropylsilyl, or is left unprotected. If the nitrogen is protected by a sulphonate group then it can be removed in a subsequent step by treatment with base such as aqueous sodium hydroxide, lithium hydroxide or potassium carbonate in a solvent such as methanol, ethanol or isoproanol. If the nitrogen is protected by a silyl group then it can be removed in a subsequent step by treatment with aqueous acid such as hydrochloric acid or sulphuric acid in a solvent such as methanol, ethanol, isopropanol, tetrahydrofuran or dioxane.

An alternative method for preparing compounds of the invention is shown in Scheme 3.

Scheme 3

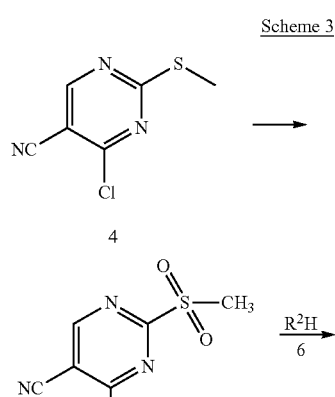

-continued

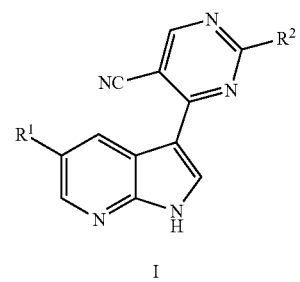

I

Referring to Scheme 3, oxidation of compound 4 can be achieved by a range of standard oxidising agents such as oxone or mCPBA in a solvent such as acetonitrile or dichloromethane. Reaction of compound 5 with compound 6 may be carried as described in Scheme I to provide compound 7. The coupling reaction of compound 7 with compound 8, wherein —B(OR')$_2$ can be a boronic acid —B(OH)$_2$, a boronate ester such as —B(OMe)$_2$ or a cyclic boronate ester such as

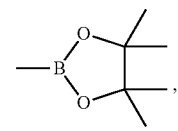

provides compound I.

The azaindole nitrogen may be protected with an arylsulphonate, such as tosyl or benzene sulphonate, a silyl group such as tert-butyldimethylsilyl or triisopropylsilyl, or is left unprotected. If the nitrogen is protected by a sulphonate group then it can be removed in a subsequent step by treatment with base such as aqueous sodium hydroxide, lithium hydroxide or potassium carbonate in a solvent such as methanol, ethanol or isoproanol. If the nitrogen is protected by a silyl group then it can be removed in a subsequent step by treatment with aqueous acid such as hydrochloric acid, sulphuric acid in a solvent such as methanol, ethanol, isoproanol, tetrahydrofuran or dioxane.

Compounds of the invention wherein $R^1$ is —NHR and R is aryl may be prepared as illustrated in Scheme 4.

Scheme 4

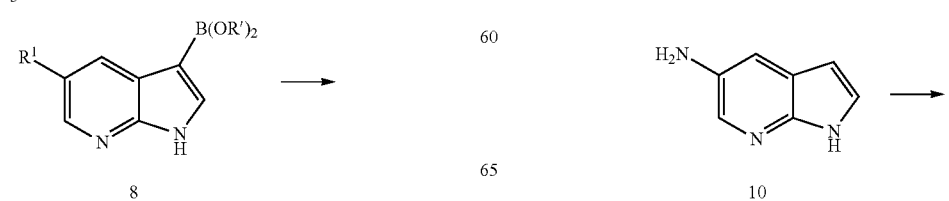

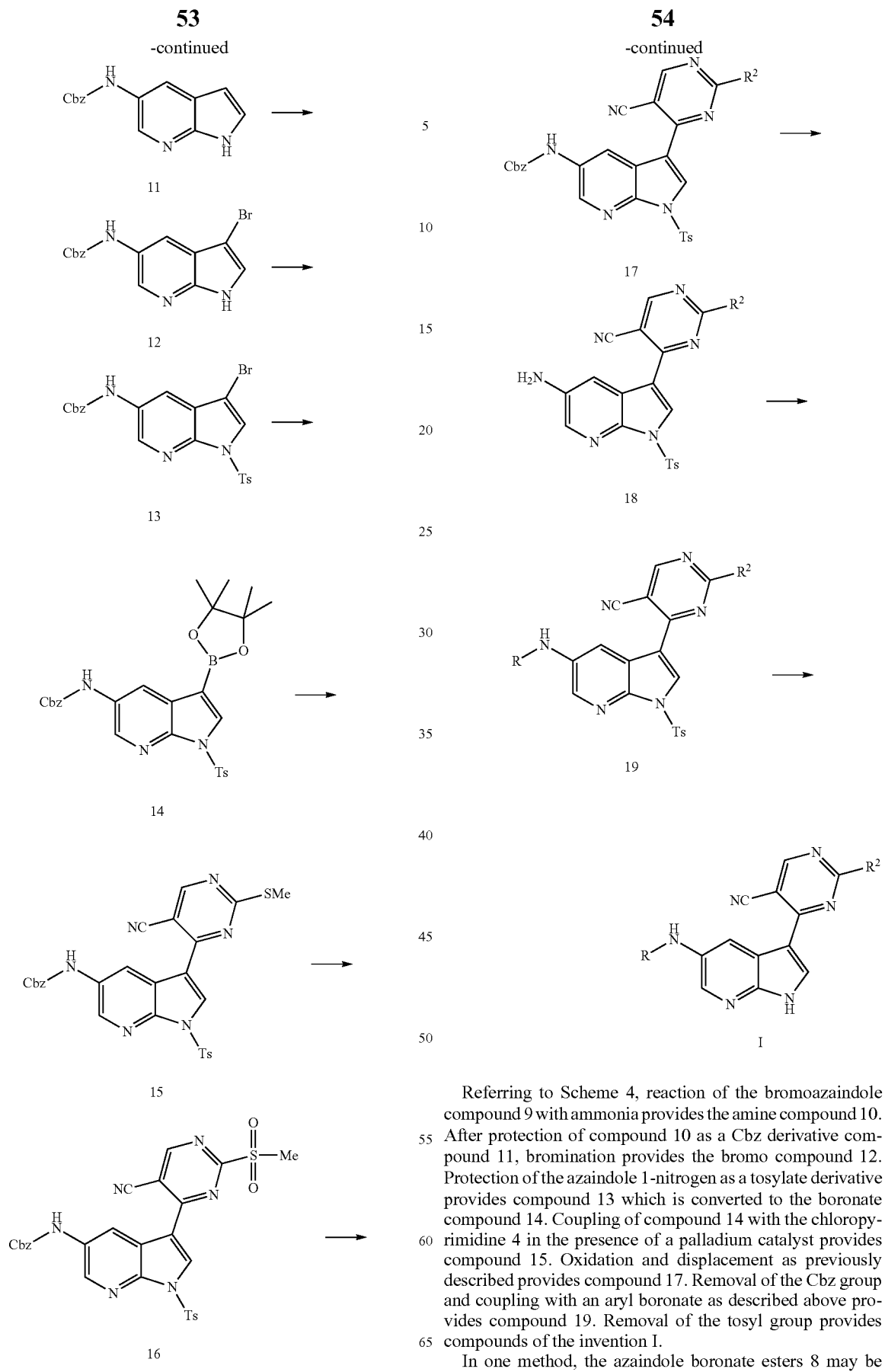

Referring to Scheme 4, reaction of the bromoazaindole compound 9 with ammonia provides the amine compound 10. After protection of compound 10 as a Cbz derivative compound 11, bromination provides the bromo compound 12. Protection of the azaindole 1-nitrogen as a tosylate derivative provides compound 13 which is converted to the boronate compound 14. Coupling of compound 14 with the chloropyrimidine 4 in the presence of a palladium catalyst provides compound 15. Oxidation and displacement as previously described provides compound 17. Removal of the Cbz group and coupling with an aryl boronate as described above provides compound 19. Removal of the tosyl group provides compounds of the invention I.

In one method, the azaindole boronate esters 8 may be prepared as illustrated in Scheme 5.

Scheme 5

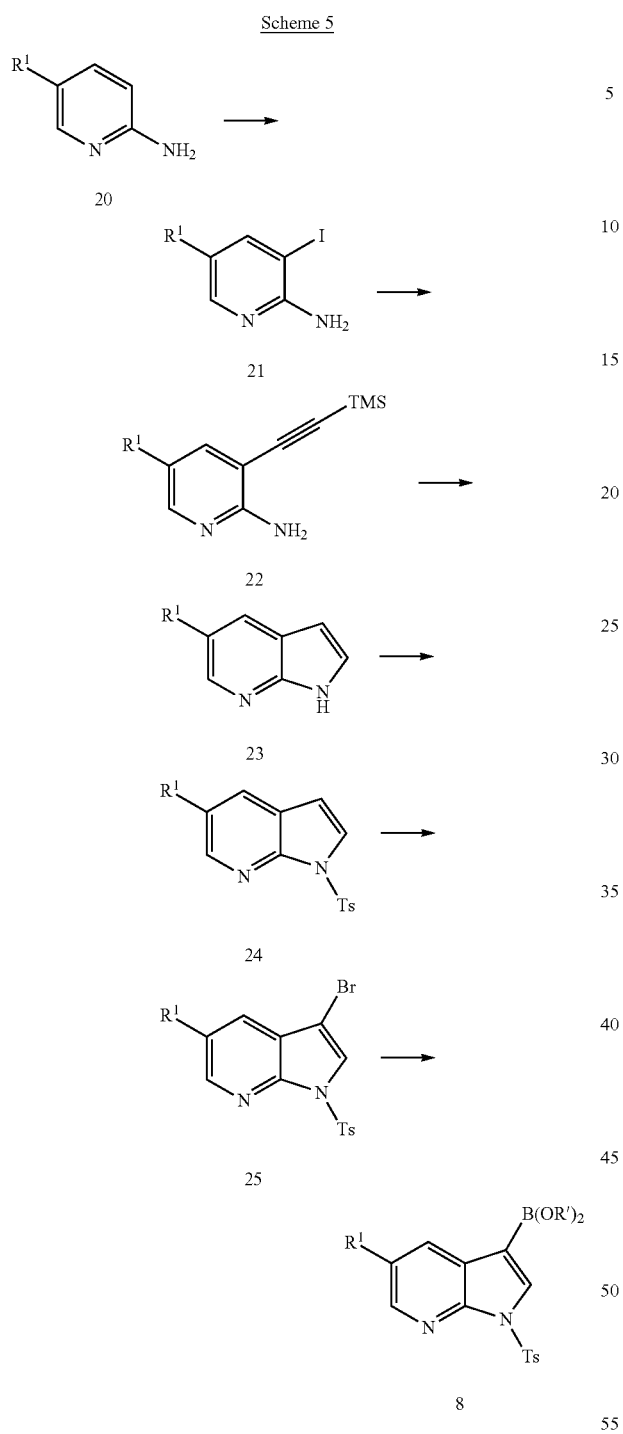

Scheme 6

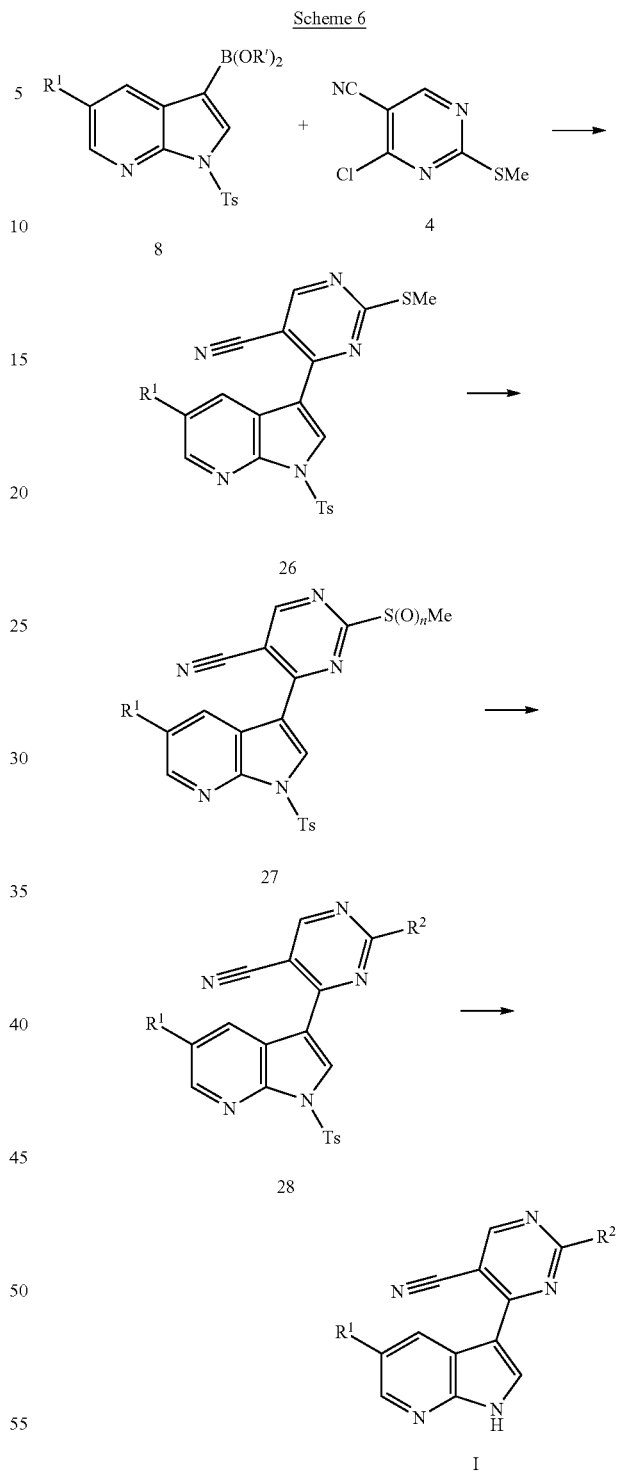

Referring to Scheme 5, an aminopyridine compound 20 is iodinated to provide the iodo compound 21. Reaction of compound 21 with trimethylsilylacetylene provides compound 22 which can be cyclized to provide the azaindole compound 23. Protection of compound 23 as a tosylate followed by bromination provides the bromoazaindole compound 25. Reaction of compound 25 with a diboronate in the presence of a palladium catalyst provides boronate intermediates compound 8.

Another method for preparing the compounds is illustrated in Scheme 6.

Referring to Scheme 6, coupling of compound 8 with the chloropyrimidine compound 4 in the presence of a palladium catalyst provides compound 26. Oxidation by m-CPBA or chlorine and displacement as previously described provides compound 28. Compounds of formula I of this invention are obtained by removal of the tosyl group.

In some embodiments, the compounds may be prepared as illustrated in Scheme 7.

Scheme 7

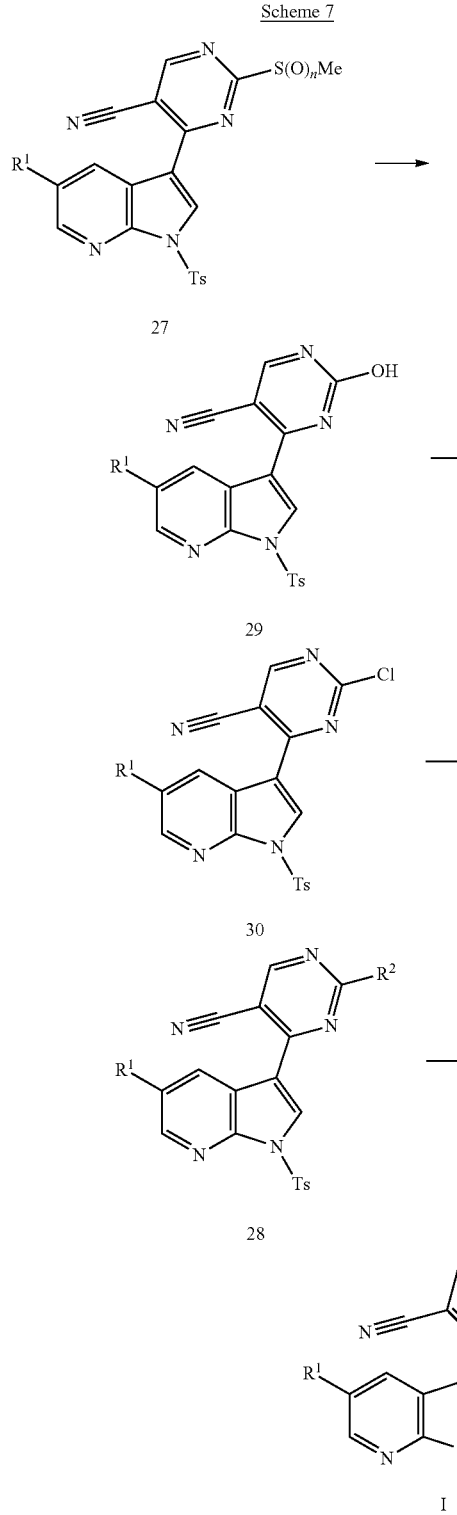

Referring to Scheme 7, hydrolysis of compound 27 (n=2) furnishes compound 29 which is chlorinated under conditions known in the art to provide compound 30. Displacement of chloropyrimidine compound 30 with an appropriate $R^2$—H, as previously described, provides compound 28. Compounds of formula I of this invention are obtained by removal of the tosyl group.

In other embodiments, the compounds may be prepared as illustrated in Scheme 8.

Scheme 8

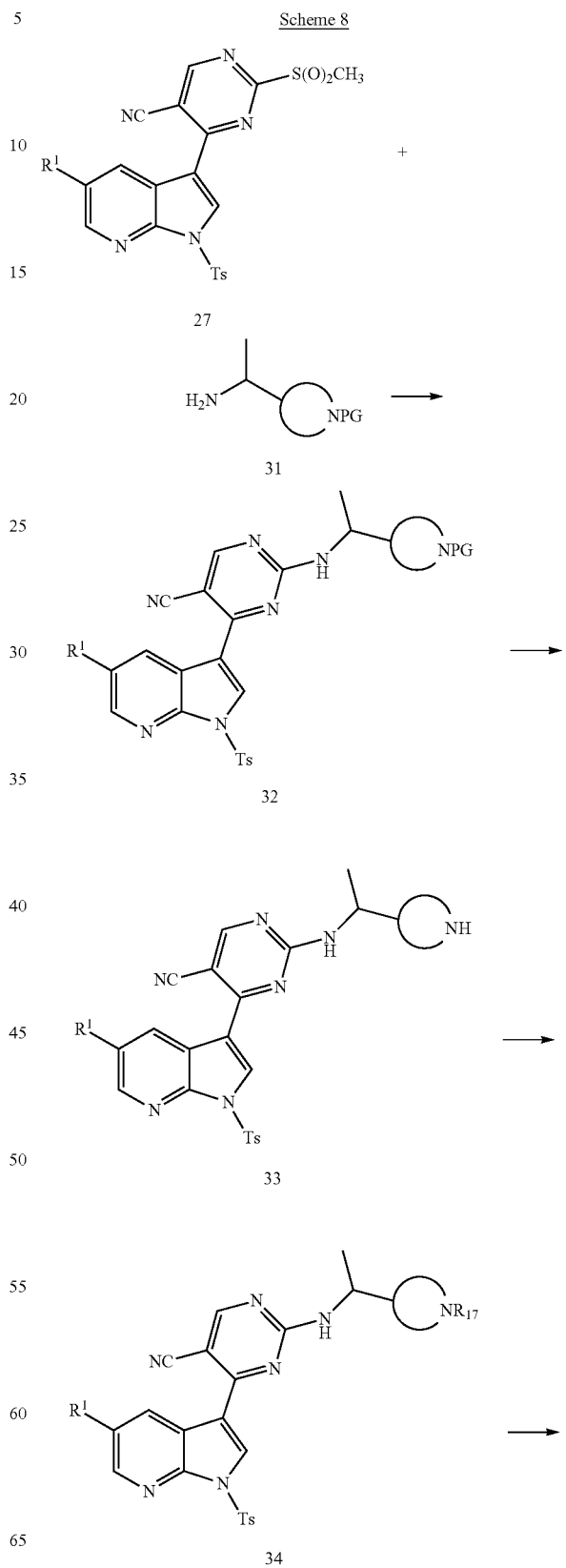

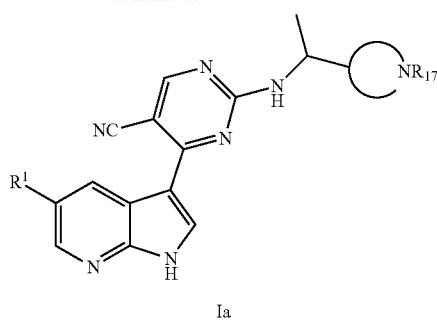

Ia

Referring to Scheme 8,

represents a 4 to 8 membered optionally substituted nitrogen heterocycle wherein PG is a protecting group. Reaction of compound 27 with amine compound 31 followed by deprotection provides compound 33. Further modifications of compound 33 may be achieved by known reactions such as, for example, acylation, alkylation, and reductive amination to provide intermediates compound 34. Compounds of formula Ia of this invention are then obtained by removal of the tosyl group.

In certain embodiments, compounds of the invention are prepared by modification of substituents as illustrated in Scheme 9.

Scheme 9

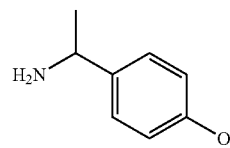

35

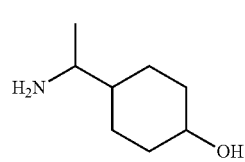

36

+

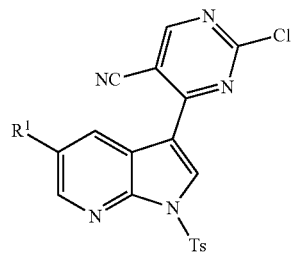

30

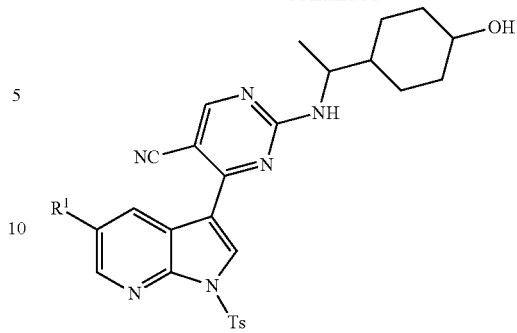

37

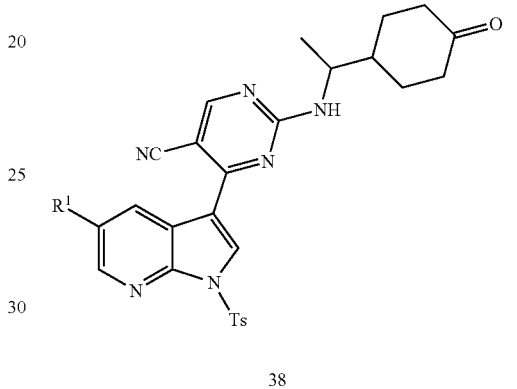

38

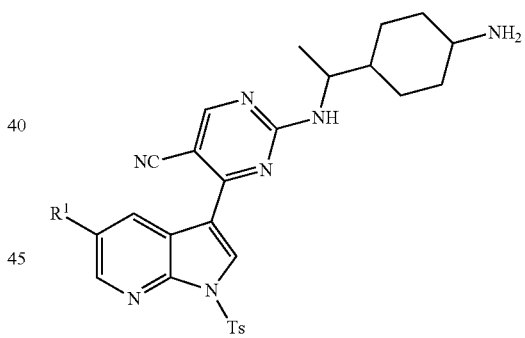

39

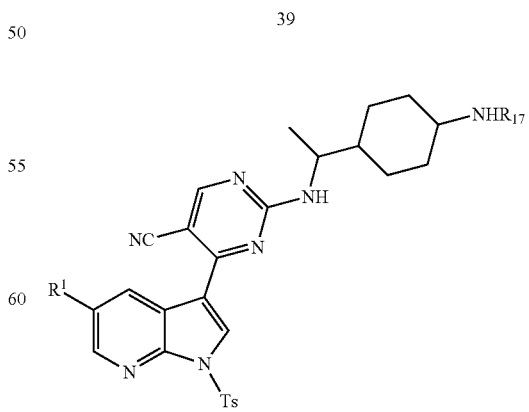

40

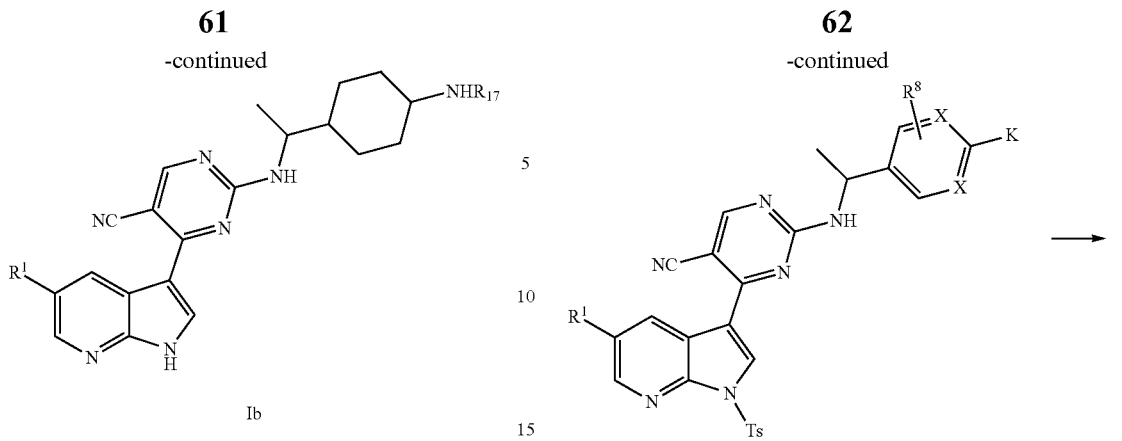

Referring to Scheme 9, hydrogenation of compound 35 in the presence of $PtO_2$ furnishes compound 36. Reaction of compound 30 with amine compound 36 provides compound 37. Subsequent oxidation of alcohol compound 37 to compound 38 followed by reductive amination of compound 38 provides compound 39. Further modifications of compound 39 may be achieved by known reactions such as, for example, acylation, alkylation, and reductive amination to provide intermediates compound 40. Compounds of formula Ib of this invention are then obtained by removal of the tosyl group.

In other embodiments, compounds of the invention are prepared by modification of substituents as illustrated in Scheme 10.

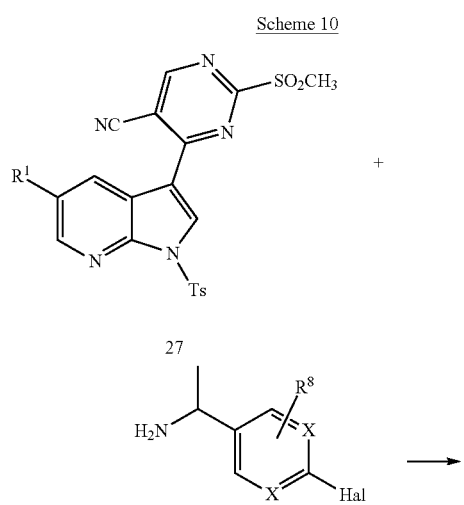

Referring to Scheme 10, reaction of compound 27 with an amine compound 41, wherein Hal represents F, Cl, Br or I and each X is independently $CR^8$ or N, provides compound 42. Reaction of compound 42 with H-K wherein K is $-OR^6$, $-SR^6$, or $-N(R^9)_2$ can be achieved thermally using conventional heating or microwave irradiation, in a solvent such as dioxane, tetrahydrofuran, ethanol, isopropanol or butanol. In the case where H-K is $HN(R^9)_2$ the reaction can be achieved via Buchwald coupling conditions. Compounds of formula Ic of this invention are then obtained by removal of the tosyl group of compound 43. The chiral version of compound 41 can be prepared using known methods: *Tetrahedron Asymmetry* 2006, 17, 3163-9.

An alternative method for preparing the compounds is illustrated in Scheme 11.

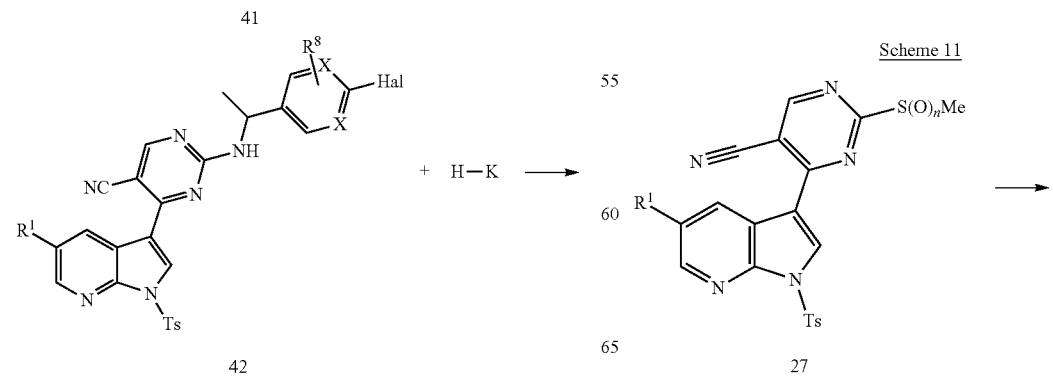

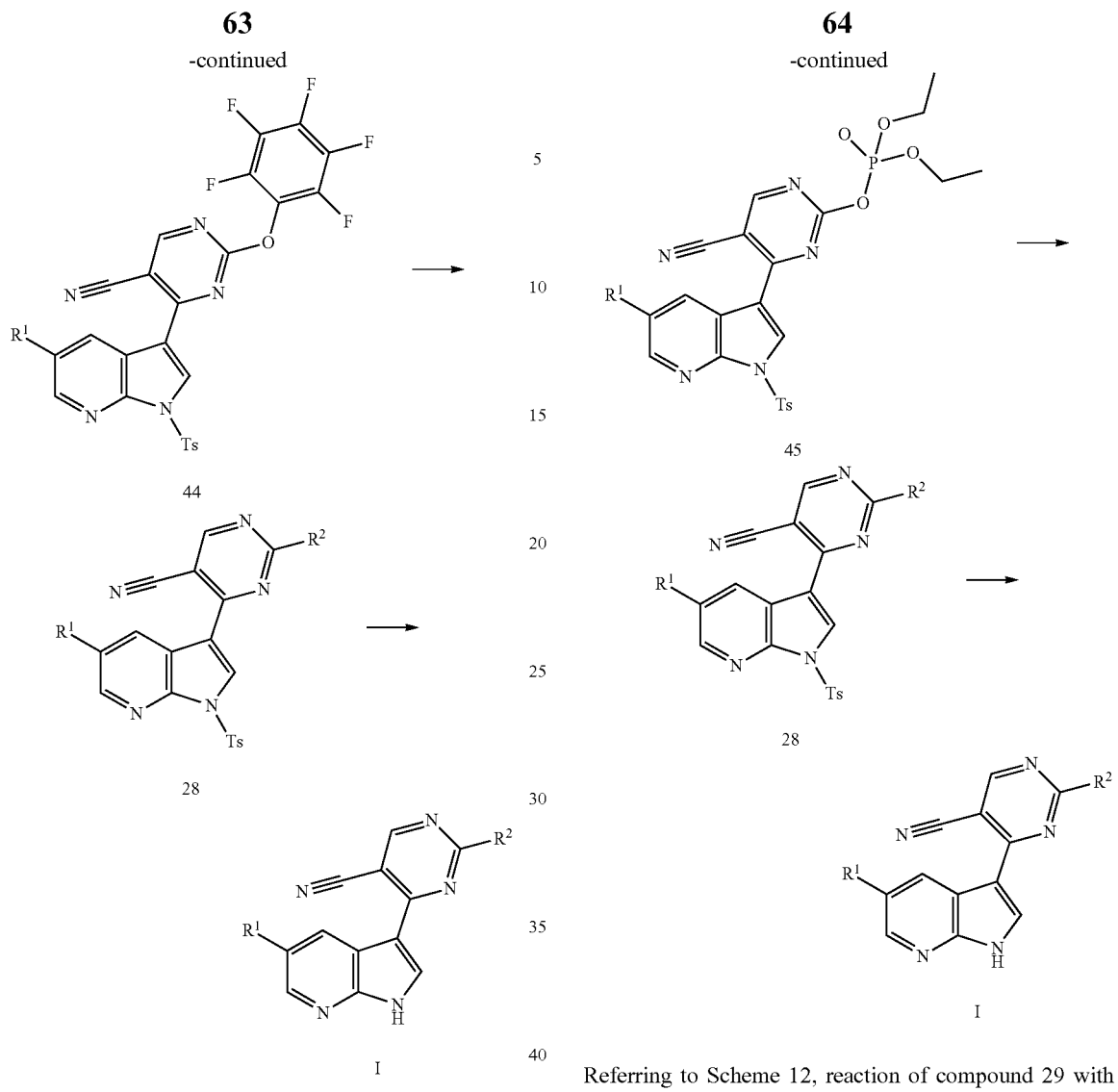

Referring to Scheme 11, reaction of compound 27 with pentafluorophenol provides compound 44, which can be displaced with a series of HNR², under similar conditions as described previously in Scheme 10. Compounds of formula I of this invention are obtained by removal of the tosyl group of compound 28.

A further method for preparing the compounds is illustrated in Scheme 12.

Referring to Scheme 12, reaction of compound 29 with diethylchlorophosphate provides compound 45. Reaction of compound 45 with HR² under conditions similar to those previously described provides the intermediate compound 28. Compounds of formula I of this invention are then obtained by removal of the tosyl group of compound 28.

An alternative method for preparing compounds of fomula Ib is illustrated in Scheme 13.

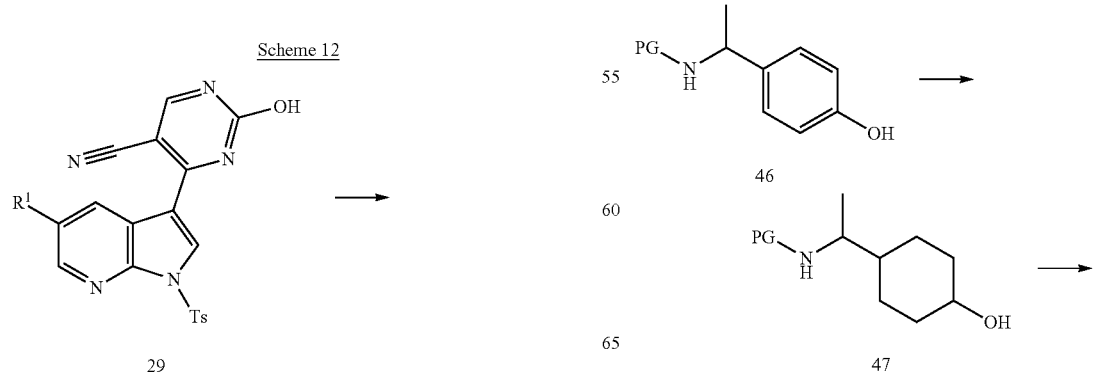

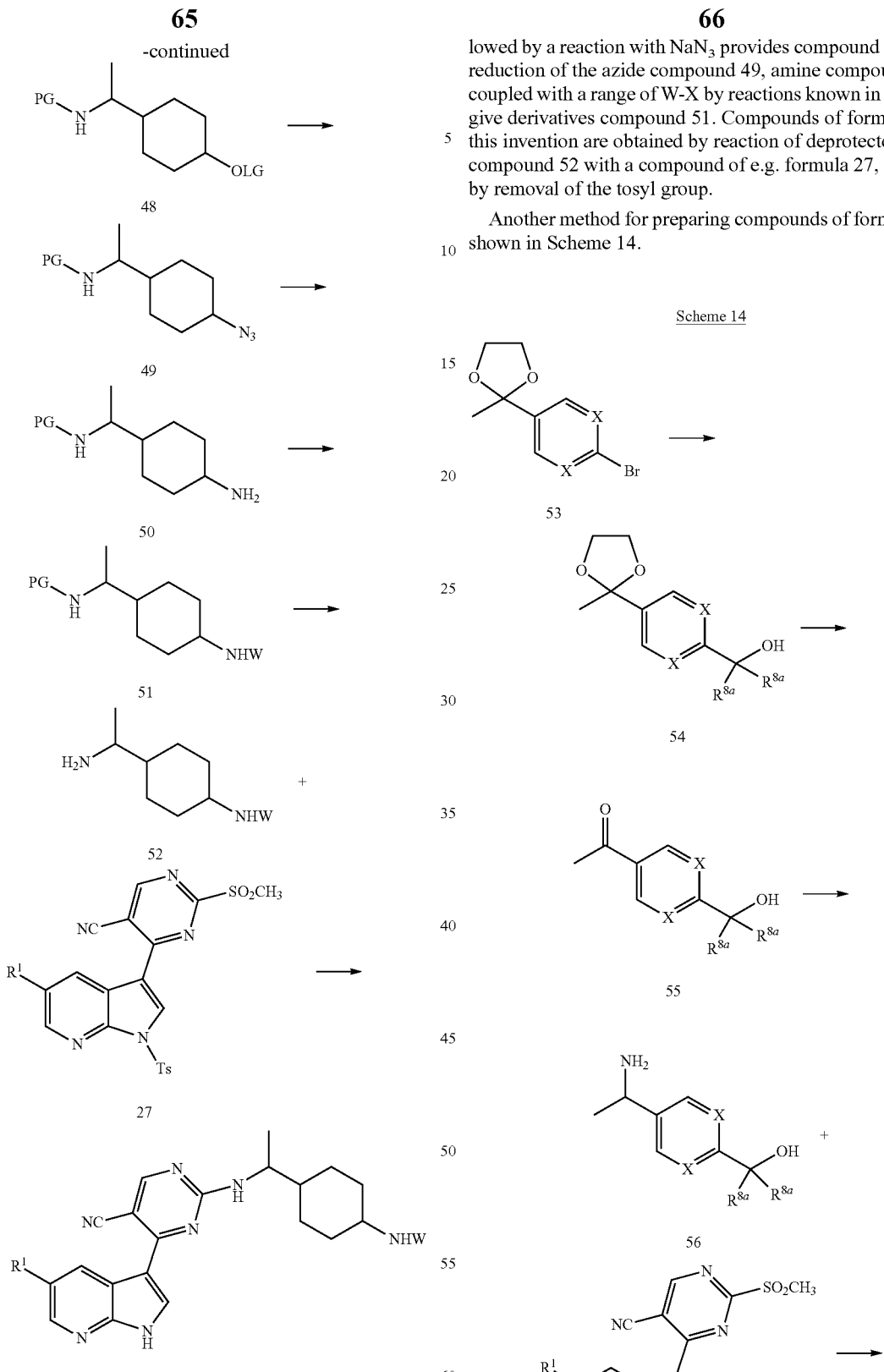

lowed by a reaction with NaN₃ provides compound 49. After reduction of the azide compound 49, amine compound 50 is coupled with a range of W-X by reactions known in the art to give derivatives compound 51. Compounds of formula Ib of this invention are obtained by reaction of deprotected amine compound 52 with a compound of e.g. formula 27, followed by removal of the tosyl group.

Another method for preparing compounds of formula Ia is shown in Scheme 14.

Referring to Scheme 13, hydrogenation of compound 46, wherein PG is a suitable protecting group (e.g. Boc), in the presence of rhodium on alumina furnishes compound 47. Activation of alcohol compound 47 with a suitable leaving group LG1 (e.g., Tos or Mes) to provide compound 48 fol-

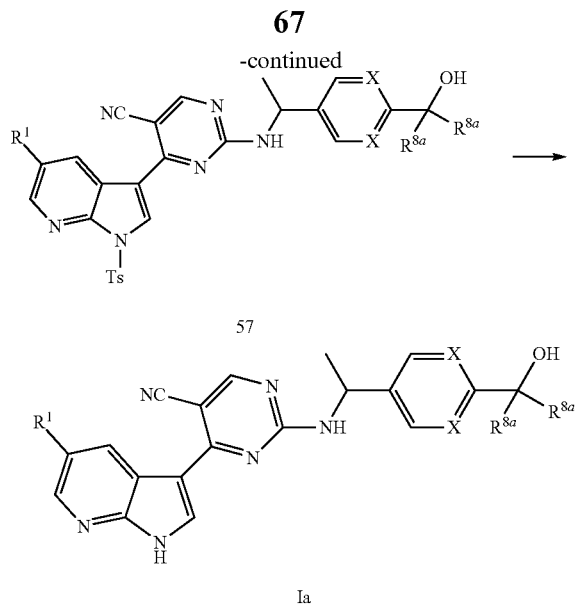

Referring to Scheme 14, each X is independently CR$^8$ or N and R$^{8a}$ is R$^8$ or two R$^{8a}$ together with the atom to which they are attached may form a 5- to 7-membered heterocyclic ring. Starting material 53 (see, e.g., *Bioorg. Med. Chem.*, 2005, 13, 6763) is lithiated and reacted with ketones R$^{8a}$C(O)R$^{8a}$. Amines compound 56 are formed after deprotection of ketals compound 54, followed by reductive amination of intermediates compound 55. Reaction of compound 56 with compound 27 provides intermediate compound 57. Compounds of formula Ia of this invention are obtained by removal of the tosyl group.

Schemes 1 through 14 above depict synthetic methods that may be used to provide compounds of this invention. Accordingly, this invention also provides processes for preparing a compound of this invention according to Schemes 1 through 14.

Use of the Compounds

The present invention provides compounds that are useful for the treatment of diseases, disorders, and conditions including, but not limited to, autoimmune diseases, inflammatory diseases, proliferative and hyperproliferative diseases, immunologically-mediated diseases, bone diseases, metabolic diseases, neurological and neurodegenerative diseases, cardiovascular diseases, hormone related diseases, allergies, asthma, and Alzheimer's disease. Another aspect of this invention provides compounds that are inhibitors of protein kinases, and thus are useful for the treatment of the diseases, disorders, and conditions, along with other uses described herein. In another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable salt or pharmaceutically acceptable derivative thereof.

As used herein, a "pharmaceutically acceptable derivative" is an adduct or derivative which, upon administration to a patient in need, is capable of providing, directly or indirectly, a compound as otherwise described herein, or a metabolite or residue thereof. Examples of pharmaceutically acceptable derivatives include, but are not limited to, pharmaceutically acceptable prodrugs.

As used herein, the term "pharmaceutically acceptable salt" refers to salts of a compound which are, within the scope of sound medical judgment, suitable for use in contact with the tissues of humans and lower animals without undue toxicity, irritation, allergic response and the like, and are commensurate with a reasonable benefit/risk ratio.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. These salts can be prepared in situ during the final isolation and purification of the compounds. Acid addition salts can be prepared by first reacting the purified compound in its free-based form with a suitable organic or inorganic acid, and then isolating the salt thus formed.

Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, salicylate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-4}$alkyl)$_4$ salts. This invention also envisions the quaternization of any basic nitrogen-containing groups of the compounds disclosed herein. Water or oil-soluble or dispersible products may be obtained by such quaternization.

Base addition salts can be prepared by first reacting the purified compound in its acid form with a suitable organic or inorganic base, and then isolating the salt thus formed. Base addition salts include alkali or alkaline earth metal salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate. Other acids and bases, while not in themselves pharmaceutically acceptable, may be employed in the preparation of salts useful as intermediates in obtaining the compounds of the invention and their pharmaceutically acceptable acid or base addition salts.

As described herein, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. *Remington's Pharmaceutical Sciences*, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other nontoxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

One aspect of this invention provides a method for the treatment or lessening the severity of a disease selected from an autoimmune disease, an inflammatory disease, a proliferative or hyperproliferative disease, such as cancer, an immunologically-mediated disease, a bone disease, a metabolic disease, a neurological or neurodegenerative disease, a cardiovascular disease, allergies, asthma, Alzheimer's disease, or a hormone related disease, comprising administering an effective amount of a compound, or a pharmaceutically acceptable composition comprising a compound, to a subject in need thereof. The term "cancer" includes, but is not limited to the following cancers: breast; ovary; cervix; prostate; testis, genitourinary tract; esophagus; larynx, glioblastoma; neuroblastoma; stomach; skin, keratoacanthoma; lung, epidermoid carcinoma, large cell carcinoma, small cell carcinoma, lung adenocarcinoma; bone; colon, adenoma; pancreas, adenocarcinoma; thyroid, follicular carcinoma, undifferentiated carcinoma, papillary carcinoma; seminoma; melanoma; sarcoma; bladder carcinoma; liver carcinoma and biliary passages; kidney carcinoma; myeloid disorders; lymphoid disorders, Hodgkin's, hairy cells; buccal cavity and pharynx (oral), lip, tongue, mouth, pharynx; small intestine; colon-rectum, large intestine, rectum; brain and central nervous system; and leukemia.

In certain embodiments, an "effective amount" of the compound or pharmaceutically acceptable composition is that amount effective in order to treat said disease. The compounds and compositions, according to the method of the present invention, may be administered using any amount and any route of administration effective for treating or lessening the severity of said disease. In some embodiments, said disease is selected from a proliferative disorder, a neurodegenerative disorder, an autoimmune disorder, and inflammatory disorder, and an immunologically-mediated disorder. In some embodiments, said disease is a proliferative disorder. In some embodiments, said disease is cancer.

In other embodiments of this invention, said disease is a protein-kinase mediated condition. In some embodiments, said protein kinase in PLK.

The term "protein kinase-mediated condition", as used herein means any disease or other deleterious condition in which a protein kinase plays a role. Such conditions include, without limitation, autoimmune diseases, inflammatory diseases, proliferative and hyperproliferative diseases, immunologically-mediated diseases, bone diseases, metabolic diseases, neurological and neurodegenerative diseases, cardiovascular diseases, hormone related diseases, allergies, asthma, and Alzheimer's disease.

The term "PLK-mediated condition", as used herein means any disease or other deleterious condition in which PLK plays a role. Such conditions include, without limitation, a proliferative disorder, such as cancer, a neurodegenerative disorder, an autoimmune disorder, and inflammatory disorder, and an immunologically-mediated disorder.

In some embodiments, the compounds and compositions of the invention are inhibitors of protein kinases. As inhibitors of protein kinases, the compounds and compositions of this invention are particularly useful for treating or lessening the severity of a disease, condition, or disorder where a protein kinase is implicated in the disease, condition, or disorder. In one aspect, the present invention provides a method for treating or lessening the severity of a disease, condition, or disorder where a protein kinase is implicated in the disease state. In another aspect, the present invention provides a method for treating or lessening the severity of a disease, condition, or disorder where inhibition of enzymatic activity is implicated in the treatment of the disease. In another aspect, this invention provides a method for treating or lessening the severity of a disease, condition, or disorder with compounds that inhibit enzymatic activity by binding to the protein kinase. In some embodiments, said protein kinase is PLK.

The activity of the compounds as protein kinase inhibitors may be assayed in vitro, in vivo or in a cell line. In vitro assays include assays that determine inhibition of either the kinase activity or ATPase activity of the activated kinase. Alternate in vitro assays quantitate the ability of the inhibitor to bind to the protein kinase and may be measured either by radiolabelling the inhibitor prior to binding, isolating the inhibitor/kinase complex and determining the amount of radiolabel bound, or by running a competition experiment where new inhibitors are incubated with the kinase bound to known radioligands.

The protein kinase inhibitors or pharmaceutical salts thereof may be formulated into pharmaceutical compositions for administration to animals or humans. These pharmaceutical compositions, which comprise an amount of the protein inhibitor effective to treat or prevent a protein kinase-mediated condition and a pharmaceutically acceptable carrier, are another embodiment of the present invention. In some embodiments, said protein kinase-mediated condition is a PLK-mediated condition. In some embodiments, a PLK1-mediated condition.

The exact amount of compound required for treatment will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

In addition to the compounds of this invention, pharmaceutically acceptable derivatives or prodrugs of the compounds of this invention may also be employed in compositions to treat or prevent the above-identified disorders.

A "pharmaceutically acceptable derivative or prodrug" means any pharmaceutically acceptable ester, salt of an ester or other derivative of a compound of this invention which, upon administration to a recipient, is capable of providing, either directly or indirectly, a compound of this invention or an inhibitorily active metabolite or residue thereof. Particularly favoured derivatives or prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

Pharmaceutically acceptable prodrugs of the compounds of this invention include, without limitation, esters, amino acid esters, phosphate esters, metal salts and sulfonate esters.

Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a nontoxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers commonly used include, but are not limited to, lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include, but are not limited to, cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of protein kinase inhibitor that may be combined with the carrier materials to produce a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of inhibitor will also depend upon the particular compound in the composition.

According to another embodiment, the invention provides methods for treating or preventing a protein kinase-mediated condition (in some embodiments, a PLK-mediated condition) comprising the step of administering to a patient one of the above-described pharmaceutical compositions. The term "patient", as used herein, means an animal, preferably a human.

Preferably, that method is used to treat or prevent a condition selected from cancers such as cancers of the breast, colon, prostate, skin, pancreas, brain, genitourinary tract, lymphatic system, stomach, larynx and lung, including lung adenocarcinoma and small cell lung cancer; stroke, diabetes, myeloma, hepatomegaly, cardiomegaly, Alzheimer's disease, cystic fibrosis, and viral disease, or any specific disease described above.

Another aspect of the invention relates to inhibiting protein kinase activity in a patient, which method comprises administering to the patient a compound of formula I or a composition comprising said compound.

Depending upon the particular protein kinase-mediated conditions to be treated or prevented, additional drugs, which are normally administered to treat or prevent that condition, may be administered together with the inhibitors of this invention. For example, chemotherapeutic agents or other anti-proliferative agents may be combined with the protein kinase inhibitors of this invention to treat proliferative diseases.

Those additional agents may be administered separately, as part of a multiple dosage regimen, from the protein kinase inhibitor-containing compound or composition. Alternatively, those agents may be part of a single dosage form, mixed together with the protein kinase inhibitor in a single composition.

In some embodiments, said protein kinase inhibitor is a PLK kinase inhibitor. In other embodiments, said protein kinase inhibitor is a PLK1 kinase inhibitor.

This invention may also be used in methods other than those involving administration to a patient.

One aspect of the invention relates to inhibiting protein kinase activity in a biological sample or a patient, which method comprises contacting said biological sample with a compound of formula I or a composition comprising said compound. The term "biological sample", as used herein, means an in vitro or an ex vivo sample, including, without limitation, cell cultures or extracts thereof; biopsied material obtained from a mammal or extracts thereof; and blood, saliva, urine, feces, semen, tears, or other body fluids or extracts thereof.

Inhibition of protein kinase activity in a biological sample is useful for a variety of purposes that are known to one of skill in the art. Examples of such purposes include, but are not limited to, blood transfusion, organ-transplantation, and biological specimen storage.

Another aspect of this invention relates to the study of protein kinases in biological and pathological phenomena; the study of intracellular signal transduction pathways mediated by such protein kinases; and the comparative evaluation of new protein kinase inhibitors. Examples of such uses include, but are not limited to, biological assays such as enzyme assays and cell-based assays.

The compounds of this invention may be prepared in general by methods known to those skilled in the art. Those compounds may be analyzed by known methods, including but not limited to LCMS (liquid chromatography mass spectrometry) and NMR (nuclear magnetic resonance). Compounds of this invention may be also tested according to these examples. It should be understood that the specific conditions shown below are only examples, and are not meant to limit the scope of the conditions that can be used for making, analyzing, or testing the compounds of this invention. Instead, this invention also includes conditions known to those skilled in that art for making, analyzing, and testing the compounds of this invention.

All references cite in this document are incorporated herein by reference.

EXAMPLES

Mass spec. samples may be analyzed on a MicroMass Quattro Micro mass spectrometer operated in single MS mode with electrospray ionization. Samples may be introduced into the mass spectrometer using chromatography.

¹H-NMR spectra may be recorded at 400 MHz using a Bruker DPX 400 instrument.

Preparation 1: 5-Trifluoromethyl-3-(4,4,5,5-tetramethyl-1,3,2-dioxaborolan-2-yl)-1-tosyl-1H-pyrrolo[2,3-b]pyridine

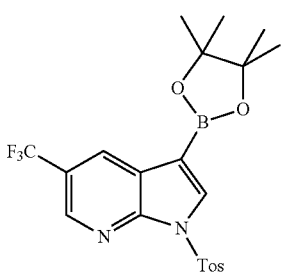

Step 1: 3-Iodo-5-Trifluoromethylpyridin-2-amine

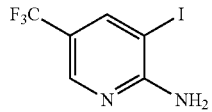

To 2-amino 5-trifluoromethylpyridine, (50 g, 308 mmol) was added acetic acid (500 mL), followed by pre-mixed water (35 mL) and concentrated sulfuric acid (5 mL) and stirred until completely solubilised. Periodic acid (13.3 g, 58 mmol) was added followed by iodine (31.2 g, 123 mmol) and then the reaction mixture was heated to 85° C. for 18 hours.

The reaction mixture was allowed to cool to room temperature and then carefully basified with 4M NaOH solution to pH 10-14. This gave a precipitate which was isolated by filtration and stirred in water (1 litre), filtered and dried to give the product as a brown powder (61.38 g, 69%).

Step 2: 5-Trifluoromethyl-3-((trimethylsilyl)ethynyl)pyridin-2-amine

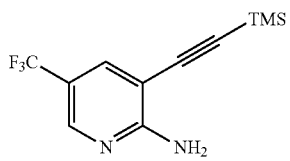 [SMILES: C[Si](C)(C)C#Cc1cc(C(F)(F)F)cnc1N]

To a stirred solution of 3-Iodo-5-trifluoromethylpyridin-2-amine (61.38 g, 213 mmol) in anhydrous THF (200 mL) under a nitrogen atmosphere was added Pd(PPh)₃Cl₂ (1.5 g, 2.1 mmol), and copper iodide (0.406 g, 2.1 mmol) and the reaction mixture degassed under nitrogen. The reaction mixture was cooled in an ice bath and TMS acetylene (36 mL, 256 mmol) was added dropwise over 30 minutes. Upon complete addition the reaction was allowed to warm to room temperature and monitored until the reaction was complete. The mixture was diluted with ethyl acetate (200 mL) and filtered through silica washed through with 4×150 mL ethyl acetate. The filtrates were concentrated and the solid was triturated from heptane (250 mL) to give 56 g of product.

Step 3: 5-Trifluoromethyl-1H-pyrrolo[2,3-b]pyridine

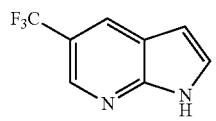 [SMILES: FC(F)(F)c1cnc2[nH]ccc2c1]

To a stirred solution of potassium tert-butoxide (53.6 g, 479 mmol) in anhydrous NMP (200 mL) under a nitrogen atmosphere at 80° C. was added a solution of 5-trifluoromethyl-3-((trimethylsilyl)ethynyl)pyridin-2-amine (62 g, 239 mmol) in NMP (100 mL) at a rate to maintain the internal temperature below 100° C. After complete addition the reaction was deemed complete by LCMS. The reaction mixture was allowed to cool to room temperature and poured carefully into saturated brine (700 mL) cooled in an ice bath to 10° C. The precipitate that formed was aged for 45 min at this temperature and isolated by filtration through buchner funnel. The collected precipitate was stirred in ethyl acetate (1 litre) and water then filtered through celite to remove insoluble polymeric material and organic layer was separated. The aqueous layer was further extracted with ethyl acetate and the combined organic layers dried over magnesium sulfate and concentrated to give a brown solid which was triturated by stirring for an hour in hot heptane and then cooling before filtration, to afford 5-Trifluoromethyl-1H-pyrrolo[2,3-b]pyridine as a crystalline solid (26.38 g, 59% yield).

Step 4: 5-Trifluoromethyl-1-tosyl-1H-pyrrolo[2,3-b]pyridine

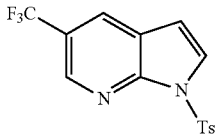 [SMILES: Cc1ccc(S(=O)(=O)n2ccc3cc(C(F)(F)F)cnc32)cc1]

To a stirred solution of sodium hydride (6.2 g, 156 mmol, 60% dispersion), tosyl chloride (27 g, 141.8 mmol), in anhydrous THF (200 mL) under a nitrogen atmosphere was added a solution of 5-trifluoromethyl-1H-pyrrolo[2,3-b]pyridine (26.38 g, 141.8 mmol) in THF (150 mL) dropwise at a rate which maintained the internal temperature of the reaction below 40° C. The reaction mixture was stirred overnight at room temperature and analysis by LCMS showed no starting material remained after this time. The reaction mixture was concentrated to remove most of THF and diluted with DCM and water. The organic layer was separated and the aqueous layer further extracted with DCM. The organic layers are combined and washed with brine, dried over magnesium sulphate and concentrated to a volume which was appropriate to load onto the top of a silica plug (300 mL) pre-wet with DCM, and the silica was washed with 2.5 L DCM. The filtrate was concentrated to give the product as a slightly brown solid (44.1 g, 92% yield).

Step 5: 3-Bromo-5-Trifluoromethyl-1-tosyl-1H-pyrrolo[2,3-b]pyridine

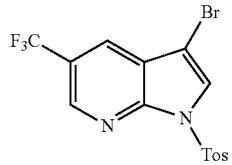

To a stirred solution of 5-trifluoromethyl-1-tosyl-1H-pyrrolo[2,3-b]pyridine (53.7 g, 158 mmol) in DCM (250 mL) was added a solution of bromine (16 mL, 316 mmol) in DCM (50 mL) dropwise. No significant exotherm was observed. After an hour at room temperature, the reaction mixture had thickened and stirring ceased. The reaction was deemed complete by tlc and was diluted with 1.2 litres of DCM and 50:50 saturated bicarbonate: saturated sodium thiosulfate aqueous solution. The organic layer was separated and further washed with the 50:50 aqueous mixture, dried over magnesium sulfate and evaporated. The crude yellow solid was triturated with diethyl ether and solid isolated and dried to give the product as a yellow powder (59 g, 59% yield)

Step 6: 5-Trifluoromethyl-3-(4,4,5,5-tetramethyl-1,3,2-dioxaborolan-2-yl)-1-tosyl-1H-pyrrolo[2,3-b]pyridine

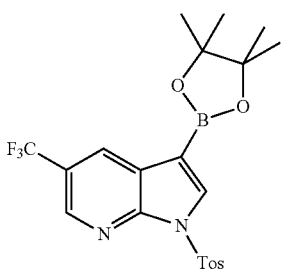

To a mixture of 3-Bromo-5-trifluoromethyl-1-tosyl-1H-pyrrolo[2,3-b]pyridine (5 g, 11.9 mmol), bis-(pinacolato)diboron (40 g, 95.5 mmol), potassium acetate (28.1 g, 266.7 mmol) was added 1,4-dioxane (800 mL). The reaction mixture was stirred vigorously while nitrogen gas was purged through the solution for 2 hours. After this time tetrakis(triphenylphosphine) palladium (10 mol %) was added in one portion and the reaction mixture brought to reflux after an hour. After 4 hours more tetrakis(triphenylphosphine)palladium (10 mol %) added and the reaction mixture refluxed under nitrogen overnight. Heating continued until TLC confirmed no starting material remained. The reaction mixture was allowed to cool then diluted with an equivalent volume of petroleum ether. Solid potassium acetate was removed by filtration through celite. The filtrate was evaporated to dryness and the residue suspended in 20% ethyl acetate 80% petroleum ether and filtered through a plug of Florisil, eluting with 3 volumes followed by one volume 30% ethyl acetate 70% petroleum ether. The mixture was concentrated and triturated with heptane to give an off-white powder (35.72 g, 80% yield)

Preparation 2: 2-(methylthio)-4-(1-tosyl-5-(trifluoromethyl)-1H-pyrrolo[2,3-b]pyridin-3-yl)pyrimidine-5-carbonitrile

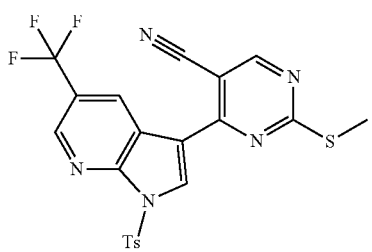 [SMILES: CSc1ncc(C#N)c(-c2cn(S(=O)(=O)c3ccc(C)cc3)c3ncc(C(F)(F)F)cc23)n1]

A mixture of 5-trifluoro-3-(4,4,5,5-tetramethyl-1,3,2-dioxaborolan-2-yl)-1-tosyl-1H-pyrrolo[2,3-b]pyridine (415 mg, 1.08 mmol, 1.0 Eq.) and 4-chloro-2-(methylthio)pyrimidine-5-carbonitrile (146 mg, 1.08 mmol, 1.0 Eq.) was suspended in toluene (20 mL) and EtOH (5 mL) and treated with 2M $K_2CO_3$ (1.62 mL, 3.24 mmol, 3.0 Eq.). The mixture was sonicated under an atmosphere of nitrogen for 20 min and then treated with $Pd(PPh_3)_4$ (75 mg, 0.06 mmol, 0.1 eq.). After sonication for a further 5 minutes the reaction was heated under microwave conditions at 130° C. for 15 minutes. The reaction was diluted with EtOAc and washed with brine. The organic phase was dried over $MgSO_4$ and concentrated in vacuo. The crude product was purified by column chromatography (ISCO Companion™, 80 g column, 0-100% EtOAc/Petroleum Ether). The product was seen to precipitate out in the collection tubes and was filtered off. Further product was obtained by concentration of the fractions and trituration with $Et_2O$ to give the title compound as an off-white solid (195 mg, 40%).

Preparation 2a: 2-(methylthio)-4-(1-tosyl-5-(trifluoromethyl)-1H-pyrrolo[2,3-b]pyridin-3-yl)pyrimidine-5-carbonitrile; alternate procedure 5-Trifluoromethyl-3-(4,4,5,5-tetramethyl-1,3,2-dioxoborolan-2-yl)-1-tosyl-1H-pyrrolo[2,3-b]pyridine (50 g, 107.2 mmol) and 4-chloro-2-(methylthio)pyrimidine-5-carbonitrile (39.8 g, 214.4 mmol) were dissolved in dioxane (900 mL). Potassium carbonate (44.45 g, 321.6 mmol) was added followed by water (135 mL). The mixture was degassed 3 times with vacuum/nitrogen cycles, then bis-(tri-tert-butylphosphine)palladium(0) (Strem, 5.0 g, 9.78 mmol) was added. After 30 minutes an additional 50 mL of water was added. A thick precipitate formed. The mixture was filtered and the product washed with water. The product was dried in a vacuum oven at 60° C. for 18 hours. This gave 2-(methylthio)-4-(1-tosyl-5-(trifluoromethyl)-1H-pyrrolo[2,3-b]pyridin-3-yl)pyrimidine-5-carbonitrile as an off-white solid (48.1 g, 91%).

¹H NMR (DMSO-d₆, 400 MHz) δ 2.07 (3H, s), 2.65 (3H, s), 7.49 (2H, d), 8.12 (2H, d), 8.93 (1H, s), 9.03 (1H, s), 9.12 (1H, s), 9.17 (1H, s); MS (ES⁺) 490, (ES⁻) 488.

Preparation 3: 2-(methylsulfonyl)-4-(1-tosyl-5-(trifluoromethyl)-1H-pyrrolo[2,3-b]pyridin-3-yl)pyrimidine-5-carbonitrile

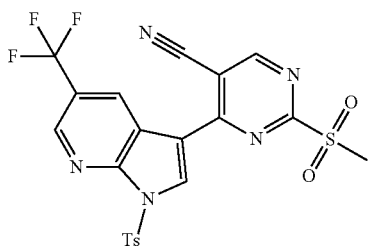 [SMILES: Cc1ccc(S(=O)(=O)n2cc(-c3nc(S(C)(=O)=O)ncc3C#N)c3cc(C(F)(F)F)cnc32)cc1]

2-(methylthio)-4-(1-tosyl-5-(trifluoromethyl)-1H-pyrrolo[2,3-b]pyridin-3-yl)pyrimidine-5-carbonitrile (50 mg, 0.1 mmol) in DCM (10 mL) was treated with MCPBA (38 mg, 0.22 mmol, 2.2 Eq) and allowed to stir overnight at room temperature. The mixture was concentrated in vacuo and treated with EtOAc. The insoluble material was filtered off and the resultant filtrate was concentrated to give the title compound which was taken forward (33 mg, 63%).

Example 1

2-(benzylamino)-4-(5-(trifluoromethyl)-1H-pyrrolo[2,3-b]pyridin-3-yl)pyrimidine-5-carbonitrile

I-1

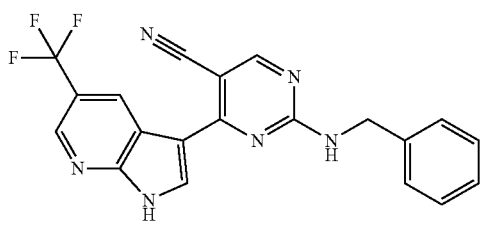

2-(methylsulfonyl)-4-(1-tosyl-5-(trifluoromethyl)-1H-pyrrolo[2,3-b]pyridin-3-yl)pyrimidine-5-carbonitrile (50 mg, 0.096 mmol) was heated with benzylamine (2 luL, 0.19 mmol, 2.0 Eq.) and DIPEA (50 uL, 0.29 mmol, 3.0 Eq.) in THF (2 mL) under microwave conditions at 100° C. for 10 minutes. The reaction was concentrated and the residue dissolved in THF (5 mL). LiOH.H₂O (20 mg, 0.48 mmol, 5.0 Eq.) in water (1 mL) was added and the reaction stirred for 1 hour. The reaction mixture was concentrated and the residue treated with MeOH. The obtained white precipitate was isolated by filtration and dried under vacuum (13 mg, 36% over 2 steps).

MS (ES⁺) m/e=395. ¹H NMR (DMSO) 4.67 (2H, d), 4.74 (2H, d), 7.21-7.38 (10H, m), 8.68 (1H, s), 8.72-8.74 (5H, m), 8.86 (1H, t), 8.93 (1H, s), 9.03 (1H, t), 9.27 (1H, s), 12.77 (2H, vbrs). [1:1 Mixture of rotamers]

Example 2

2-((R)-1-(6-(4-methylpiperazin-1-yl)pyridin-3-yl)ethylamino)-4-(5-(trifluoromethyl)-1H-pyrrolo[2,3-b]pyridin-3-yl)pyrimidine-5-carbonitrile I-147 and
2-((S)-1-(6-(4-methylpiperazin-1-yl)pyridin-3-yl)ethylamino)-4-(5-(trifluoromethyl)-1H-pyrrolo[2,3-b]pyridin-3-yl)pyrimidine-5-carbonitrile (I-129)

I-147

I-129

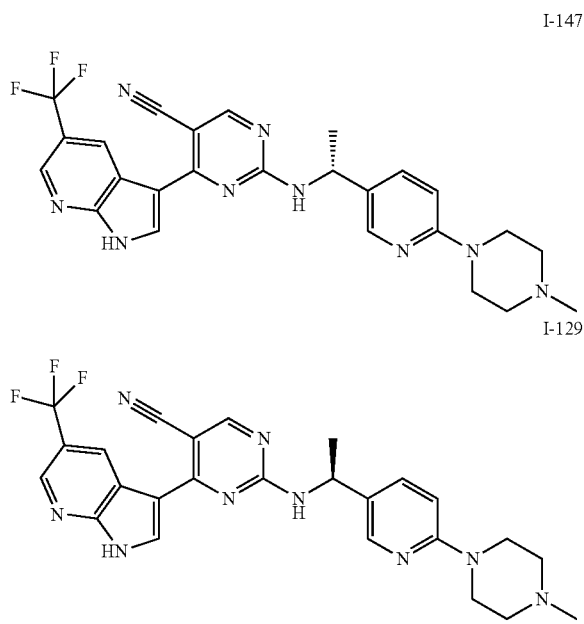

Step 1: 2-(methylsulfonyl)-4-(1-tosyl-5-(trifluoromethyl)-1H-pyrrolo[2,3-b]pyridin-3-yl)pyrimidine-5-carbonitrile

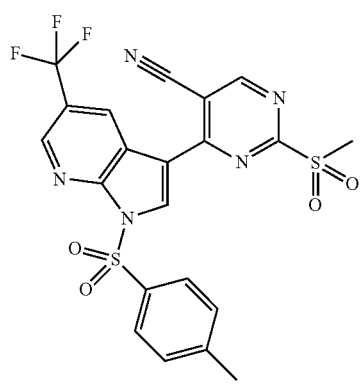 [SMILES: Cc1ccc(S(=O)(=O)n2cc(-c3nc(S(C)(=O)=O)ncc3C#N)c3cc(C(F)(F)F)cnc32)cc1]

2-(Methylsulfonyl)-4-(1-tosyl-5-(trifluoromethyl)-1H-pyrrolo[2,3-b]pyridin-3-yl)pyrimidine-5-carbonitrile (1.4 g, 2.86 mmol) was suspended in ethanol (60 mL) and water (4 mL). The mixture was cooled in an ice bath, and chlroine gas was slowly bubbled through the solution for 20 minutes. After addition, the suspension was stirred for another 30 minutes at 0° C. The reaction mixture was allowed to vent for 15 minutes, then, ether (100 mL) was added and the solid was filtered off. The solid was dried under vacuo to give a light pink solid (1.3 g, 87% yield).

MS (ES+) 522.

Step 2: 2-((R)-(1-(6-chloropyridin-3-yl)ethylamino)-4-(1-tosyl-5-(trifluoromethyl)-1H-pyrrolo[2,3-b]pyridin-3-yl)pyrimidine-5-carbonitrile

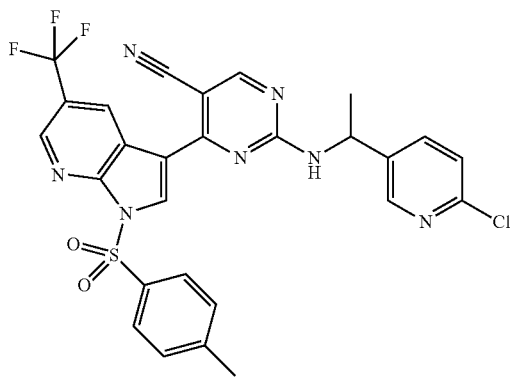 [SMILES: Cc1ccc(S(=O)(=O)n2cc(-c3nc(NC(C)c4ccc(Cl)nc4)ncc3C#N)c3cc(C(F)(F)F)cnc32)cc1]

Diisopropylethylamine (730 µl, 4.2 mmol) was added to a mixture of 2-(methylsulfonyl)-4-(1-tosyl-5-(trifluoromethyl)-1H-pyrrolo[2,3-b]pyridin-3-yl)pyrimidine-5-carbonitrile (330 mg, 2.1 mmol) and 1-(6-chloropyridin-3-yl)ethanamine (described in the literature: EP 375907 (B1)) (500 mg, 1 mmol) in tetrahydrofuran (3 mL). The reaction mixture was heated under microwave irradiation at 110° C. for 15 minutes. The reaction mixture was partitioned between EtOAc and water. The organic phase was dried over magnesium sulphate, filtered and evaporated to dryness. The residue was purified on silica gel by flash column chromatography to afford the title compound as a wax (345 mg, 58% yield).

MS (ES+) 598.

Step 3: 2-((R)-1-(6-(4-methylpiperazin-1-yl)pyridin-3-yl)ethylamino)-4-(5-(trifluoromethyl)-1H-pyrrolo[2,3-b]pyridin-3-yl)pyrimidine-5-carbonitrile I-147 and 2-((S)-1-(6-(4-methylpiperazin-1-yl)pyridin-3-yl)ethylamino)-4-(5-(trifluoromethyl)-1H-pyrrolo[2,3-b]pyridin-3-yl)pyrimidine-5-carbonitrile I-129

I-147

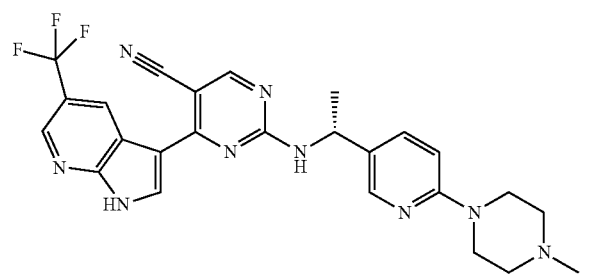

-continued

I-129

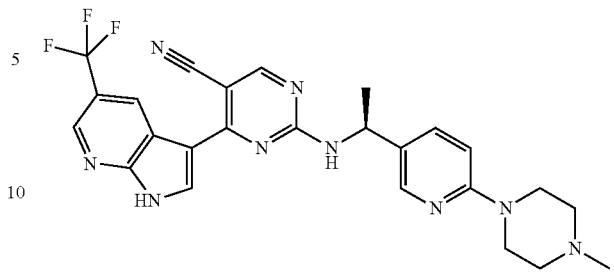

A mixture of 2-(1-(6-chloropyridin-3-yl)ethylamino)-4-(1-tosyl-5-(trifluoromethyl)-1H-pyrrolo[2,3-b]pyridin-3-yl)pyrimidine-5-carbonitrile (157 mg, 0.26 mmol) and N-methylpiperazine (2 mL) was heated under microwave irradiation at 180° C. for 40 minutes. The reaction mixture was partitioned between EtOAc and water. The organic phase was dried over sodium sulphate, filtered and evaporated to dryness. The residue was purified on silica gel by flash column chromatography to afford the title compound as an off-white solid (52 mg, 39% yield).

The two enantiomers were separated using a Berger Minigram SFC system [250×4.6 mm Daicel Chiralcel OD-H column; 4 mLs/min flowrate; co-solvent was 32% Methanol (with 0.25% TEA (Tri-ethyl amine) modifier added); column temperature: 35° C.].

Data for I-147 (first eluted):
$^1$H NMR (DMSO-d$_6$, 400 MHz) δ 1.54 (3H, m), 2.00 (3H, m), 2.32-2.37 (4H, m), 3.38 (4H, m), 5.19-5.26 (1H, m), 6.77-6.84 (1H, m), 7.56-7.62 (1H, m), 8.08-8.16 (1H, m), 8.70-8.77 (4H, m), 9.01-9.19 (1H, m), 12.98 (1H, m) mixture of rotamers; MS (ES+) 508, (ES−) 506.

Data for I-129 (second eluted):
$^1$H NMR (DMSO-d$_6$, 400 MHz) δ 1.54 (3H, m), 2.18 (3H, m), 2.33-2.37 (4H, m), 3.38-3.43 (4H, m), 5.18-5.27 (1H, m), 6.77-6.84 (1H, m), 7.56-7.62 (1H, m), 8.08-8.16 (1H, m), 8.70-8.77 (4H, m), 9.04-9.18 (1H, m), 12.98 (1H, m) mixture of rotamers; MS (ES+) 508, (ES−) 506.

Example 3

N-((1R,4r)-4-((1R)-1-(5-cyano-4-(5-(trifluoromethyl)-1H-pyrrolo[2,3-b]pyridin-3-yl)pyrimidin-2-ylamino)ethyl)cyclohexyl) methanesulfonamide I-202 and N-((1S,4s)-4-((1R)-1-(5-cyano-4-(5-(trifluoromethyl)-1H-pyrrolo[2,3-b]pyridin-3-yl)pyrimidin-2-ylamino)ethyl)cyclohexyl)methanesulfonamide I-203

I-202

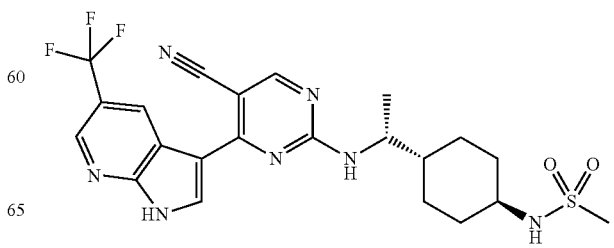

-continued

I-203

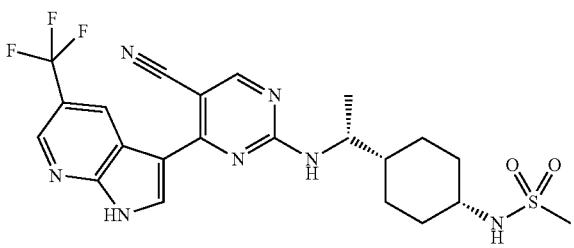

Step 1: 2-hydroxy-4-(1-tosyl-5-(trifluoromethyl)-1H-pyrrolo[2,3-b]pyridin-3-yl)pyrimidine-5-carbonitrile

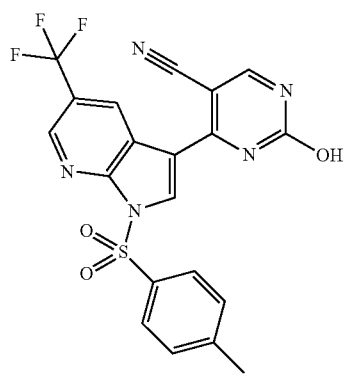 [SMILES: Cc1ccc(S(=O)(=O)n2cc(-c3nc(O)ncc3C#N)c3cc(C(F)(F)F)cnc32)cc1]

DIPEA (7.421 g, 10.00 mL, 57.42 mmol) was added to a suspension of 2-(methylsulfonyl)-4-(1-tosyl-5-(trifluoromethyl)-1H-pyrrolo[2,3-b]pyridin-3-yl)pyrimidine-5-carbonitrile (1 g, 1.918 mmol) in acetonitrile (20 mL). The reaction mixture was stirred for 1 hour then water (5 mL) was added. The mixture was allowed to stir at room temperature for 18 hours. The reaction mixture was concentrated in vacuo to give the desired product (880 mg, quantitative yield).

MS (ES⁺) 460, (ES⁻) 458.

Step 2: 2-chloro-4-(1-tosyl-5-(trifluoromethyl)-1H-pyrrolo[2,3-b]pyridin-3-yl)pyrimidine-5-carbonitrile

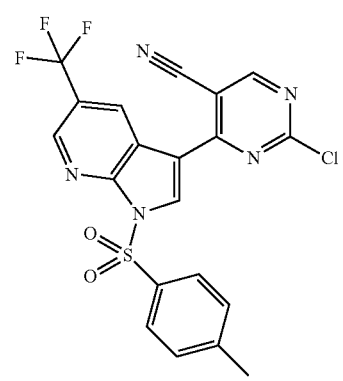 [SMILES: Cc1ccc(S(=O)(=O)n2cc(-c3nc(Cl)ncc3C#N)c3cc(C(F)(F)F)cnc32)cc1]

2-hydroxy-4-(1-tosyl-5-(trifluoromethyl)-1H-pyrrolo[2,3-b]pyridin-3-yl)pyrimidine-5-carbonitrile (880.2 mg, 1.916 mmol) was cooled down with an ice bath. Phosphorus oxy-chloride (2.938 g, 1.786 mL, 19.16 mmol) was added dropwise and the reaction mixture was stirred for 30 minutes at 0° C. and then allowed to warm up to rt and stirred at room temperature for 18 hours. The reaction mixture was quenched by slow addition onto ice. After 1 hour of stirring, the mixture was extracted into ethyl acetate. The organic layer was dried over magnesium sulfate, filtered and concentrated in vacuo to afford a pale orange solid. The solid was triturated further in EtOAc and filtered off (715.4 mg, 78% yield)

MS (ES⁺) 478.

Step 3: (R)-4-(1-aminoethyl)cyclohexanol

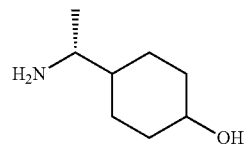

A slurry of platinum oxide (285.5 mg, 1.257 mmol) in water (2.9 mL) was added to 4-[(1R)-1-Aminoethyl]phenol (5.025 g, 36.63 mmol) in methanol (100 mL). Acetic acid (2.9 mL) was added to the reaction mixture. The reaction mixture was hydrogenated in a Parr hydrogenator at 60 psi for 18 hours. The platinum oxide was filtered off and the mother liquors were concentrated in vacuo leaving a colourless oil (8.44 g, crude: predominantly product contaminated with some (R)-1-cyclohexylethanamine and some starting material).

The crude mixture was dissolved in THF (35 mL) and MeCN (7 mL). NaOH (73.32 mL of 0.5 M, 36.66 mmol) was added followed by di-tert-butyl dicarbonate (12.00 g, 54.99 mmol) in portions. The reaction mixture was allowed to stir at ambient temperature for 18 hours. The reaction mixture was extracted with EtOAc (3 times). The combined organic extracts were washed twice with 1M HCl and brine, dried over magnesium sulfate, filtered and concentrated in vacuo. The residue was purified on silica gel by flash column chromatography to afford tert-butyl(R)-1-(4-hydroxycyclohexyl)ethylcarbamate as a white solid (4.49 g, 50% yield).

Tert-butyl(R)-1-(4-hydroxycyclohexyl)ethylcarbamate (4.49 g, 18.45 mmol) was dissolved in dichloromethane (25 mL) and cooled to 0° C. under nitrogen. HCl 2M in Ether (27.68 mL of 2 M, 55.35 mmol) was added and the reaction allowed to warm slowly to ambient temperature for 18 hours. The reaction mixture was concentrated in vacuo. The crude mixture was dissolved in MeOH (25 mL). MP-Carbonate was added (11.75 g, 36.90 mmol) and the reaction mixture was stirred for 3 hours. The resin was filtered and the mother liquors were concentrated to dryness to afford the title compound as an off white solid (2.39 g, 90% yield).

MS (ES⁺) 144.

Step 4: 2-((R)-1-(4-hydroxycyclohexyl)ethylamino)-4-(1-tosyl-5-(trifluoromethyl)-1H-pyrrolo[2,3-b]pyridin-3-yl)pyrimidine-5-carbonitrile

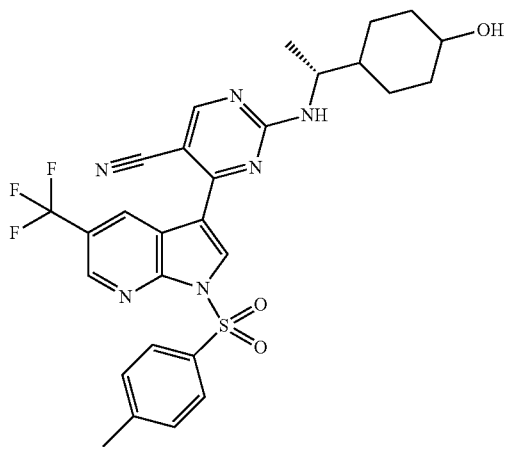 [SMILES: Cc1ccc(S(=O)(=O)n2cc(-c3nc(N[C@H](C)C4CCC(O)CC4)ncc3C#N)c3cc(C(F)(F)F)cnc32)cc1]

4-((R)-1-aminoethyl)cyclohexanol (309.4 mg, 2.16 mmol) was dissolved in THF (10 mL) and DMF (4 mL) and stirred over molecular sieves for 10 minutes. Diisopropylethylamine (376.3 μL, 2.160 mmol) was added, followed by 2-chloro-4-(1-tosyl-5-(trifluoromethyl)-1H-pyrrolo[2,3-b]pyridin-3-yl)pyrimidine-5-carbonitrile (516.1 mg, 1.080 mmol). The reaction mixture was stirred under nitrogen at ambient temperature for 18 hours. The molecular sieves was removed by filtration and washed with EtOAc. The filtrate was washed with water, dried over magnesium sulfate, filtered and concentrated in vacuo. The residue was purified on silica gel by flash column chromatography (ISCO Companion|, 80 g column, 0-100% EtOAc/DCM) to afford the title compound as a yellow solid (558 mg, 88% yield).

MS (ES$^+$) 585, (ES$^-$) 583.

Step 5: 2-((R)-1-(4-oxocyclohexyl)ethylamino)-4-(1-tosyl-5-(trifluoromethyl)-1H-pyrrolo[2,3-b]pyridin-3-yl)pyrimidine-5-carbonitrile

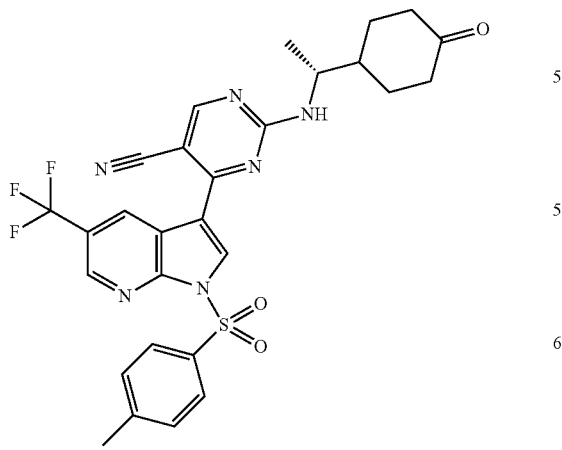

2-((R)-1-(4-hydroxycyclohexyl)ethylamino)-4-(1-tosyl-5-(trifluoromethyl)-1H-pyrrolo[2,3-b]pyridin-3-yl)pyrimidine-5-carbonitrile (442 mg, 0.7561 mmol) was dissolved in dichloromethane (20 mL) and cooled down to 0° C. Dess-Martin periodinane (384.8 mg, 0.9073 mmol) was added and the reaction was allowed to warm up to room temperature. The mixture was stirred for 18 hours. The reaction mixture was partitioned between dichloromethane and a 1:1 saturated solution of sodium hydrosulfite and sodium hydrogen carbonate. The aqueous phase was further extracted with dichloromethane. The combined organic phases were dried over magnesium sulfate, filtered and concentrated to dryness. The residue was purified on silica gel by flash column chromatography (ISCO Companion|, 40 g column, 0-20% EtOAc/DCM) to afford the title compound as a white solid (411 mg, 93% yield).

MS (ES$^+$) 583, (ES$^-$) 581.

Step 6: 2-((R)-1-(4-aminocyclohexyl)ethylamino)-4-(1-tosyl-5-(trifluoromethyl)-1H-pyrrolo[2,3-b]pyridin-3-yl)pyrimidine-5-carbonitrile

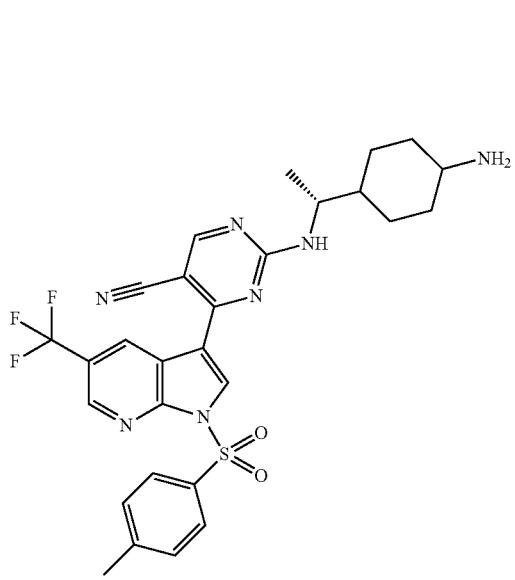 [SMILES: Cc1ccc(S(=O)(=O)n2cc(-c3nc(N[C@H](C)C4CCC(N)CC4)ncc3C#N)c3cc(C(F)(F)F)cnc32)cc1]

2-((R)-1-(4-oxocyclohexyl)ethylamino)-4-(1-tosyl-5-(trifluoromethyl)-1H-pyrrolo[2,3-b]pyridin-3-yl)pyrimidine-5-carbonitrile (105 mg, 0.1802 mmol) was dissolved in methanol (5 mL) and dichloromethane (5 mL). Ammonium acetate (138.9 mg, 118.7 μL, 1.802 mmol), followed by sodium triacetoxyborohydride (38.19 mg, 0.1802 mmol) were added and the reaction mixture was stirred for 4 hours at room temperature. The mixture was partitioned between dichloromethane and a saturated solution of sodium bicarbonate. The aqueous phase was extracted with dichloromethane. The organic layer was dried over magnesium sulfate, filtered and concentrated to dryness to afford the desired product as a yellow solid (95 mg, 90% yield).

MS (ES$^+$) 584, (ES$^-$) 582.

Step 7: N-((1R,4r)-4-((1R)-1-(5-cyano-4-(5-(trifluoromethyl)-1H-pyrrolo[2,3-b]pyridin-3-yl)pyrimidin-2-ylamino)ethyl)cyclohexyl)methanesulfonamide I-202 and N-((1S,4s)-4-((1R)-1-(5-cyano-4-(5-(trifluoromethyl)-1H-pyrrolo[2,3-b]pyridin-3-yl)pyrimidin-2-ylamino)ethyl)cyclohexyl)methanesulfonamide I-203

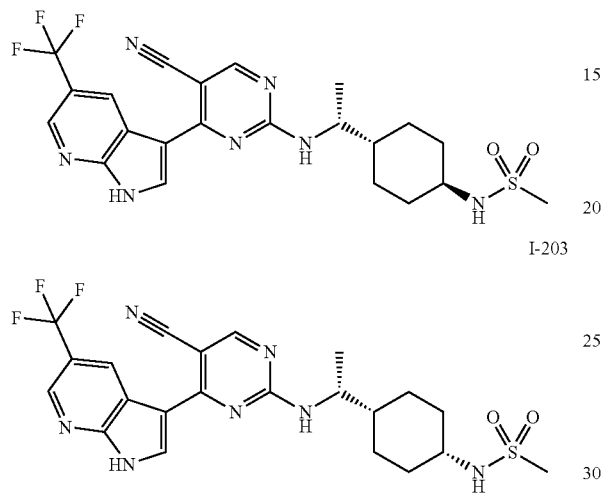

2-((R)-1-(4-aminocyclohexyl)ethylamino)-4-(1-tosyl-5-(trifluoromethyl)-1H-pyrrolo[2,3-b]pyridin-3-yl)pyrimidine-5-carbonitrile (95 mg, 0.1628 mmol) was dissolved in THF (5 mL) and diisopropylethylamine (25.25 mg, 34.03 μL, 0.1954 mmol) was added. The reaction mixture was cooled down to 0° C. under nitrogen and methanesulfonylchloride (15.12 μL, 0.1954 mmol) was added. The reaction mixture was allowed to warm up to ambient temperature and was stirred at that temperature for 1 hour. An aqueous solution of lithium hydroxide (651.2 μL of 1 M, 0.6512 mmol) was added and the reaction stirred at room temperature for 3 hours. The mixture was partitioned between ethyl acetate and water. The aqueous phase was acidified to pH1 with 1M HCl. The aqueous phase was extracted with ethyl acetate. The organic layer was dried over magnesium sulfate, filtered and concentrated to dryness. The cis and trans isomers were separated by reverse phase preparative HPLC [Waters Sunfire C18, 10 μM, 100 Å column, gradient 10%-95% B (solvent A: 0.05% TFA in water; solvent B: $CH_3CN$) over 16 minutes at 25 mL/min] and the resulting fractions were basified by passing them through a bicarbonate cartridge. Concentration under vacuo afforded the desired products (I-202: 12 mg, 27% yield; I-203: 16 mg, 37% yield).

Data for I-202 (first eluted):

$^1$H NMR (DMSO-$d_6$, 400 MHz) δ 1.19-1.27 (7H, m), 1.85-1.97 (2H, m), 2.06-2.10 (2H, m), 2.91 (3H, s), 3.16-3.22 (1H, m), 4.08-4.17 (2H, m), 5.47-5.55 (1H, m), 8.43-8.50 (1H, m), 8.65-8.80 (2H, m), 9.02-9.14 (1H, m), 10.07 (1H, br d); MS (ES$^+$) 508, (ES$^-$) 506.

Data for I-203 (second eluted):

$^1$H NMR (DMSO-$d_6$, 400 MHz) δ 1.39-1.86 (11H, m), 2.97 & 3.00 (3H rotamers), 3.70-3.74 (1H, m), 4.27-4.32 (1H, s), 4.46-4.58 (1H, m), 5.49-5.64 (1H, m), 8.48-8.58 (1H, m), 8.71-8.88 (2H, m), 9.10-9.23 (1H, m), 9.56-10.10 (1H, m); MS (ES$^+$) 508, (ES$^-$) 506.

Example 4

2-((R)-1-(1-(2-hydroxyacetyl)piperidin-4-yl)ethylamino)-4-(5-(trifluoromethyl)-1H-pyrrolo[2,3-b]pyridin-3-yl)pyrimidine-5-carbonitrile I-205

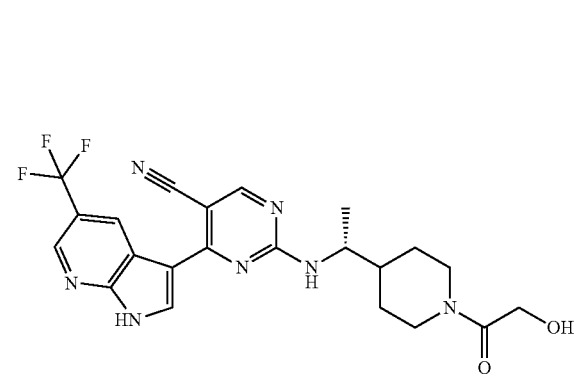 [SMILES: C[C@@H](Nc1ncc(C#N)c(-c2c[nH]c3ncc(C(F)(F)F)cc23)n1)C1CCN(C(=O)CO)CC1]

Step 1: tert-butyl 4-(1-aminoethyl)piperidine-1-carboxylate

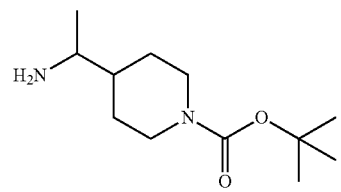 [SMILES: CC(N)C1CCN(C(=O)OC(C)(C)C)CC1]

A mixture of tert-butyl 4-acetylpiperidine-1-carboxylate (145 g, 0.64 mol) and ammonium acetate (225 g, 2.9 mol) in methanol (2 L) was stirred at room temperature for 1.5 hours. Sodium cyanoborohydride (30 g, 0.48 mol) was added in one portion and the stirring was continued overnight at room temperature. The reaction mixture was poured in 2N aq. NaOH (2 L) and extracted with dichloromethane (2×1 L). The combined extracts were washed with water (1 L), brine (0.3 L), and evaporated to dryness. The residue was dissolved in TBME (1.5 L), dried over sodium sulfate, filtered, and evaporated to dryness under reduced pressure. The residue was purified by bulb to bulb distillation at 180° C. and 0.1 mbar to afford the title compound as a colorless oil that partly solidified upon standing (131 g, 90% yield).

¹H NMR (CDCl₃, 300 MHz) δ 4.21-4.08 (2H, m), 2.75-2.58 (3H, m), 1.78-1.60 (2H, m), 1.45 (9H, s), 1.44-1.05 (5H, m), 1.04 (3H, d).

Step 2: (R)- and (S)-tert-butyl 4-(1-aminoethyl)piperidine-1-carboxylate

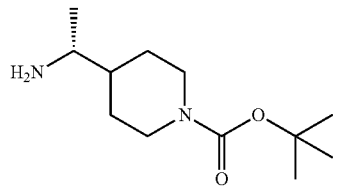

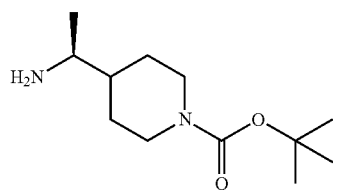

A suspension of tert-butyl 4-(1-aminoethyl)piperidine-1-carboxylate (40 g, 175 mmol) and (S)-(+)-mandelic acid (27 g, 177 mmol) in acetone (400 mL) was heated until a clear solution was obtained. The solution was allowed to cool down to room temperature during 5 hours. The newly formed precipitate was isolated and rinsed with some acetone (30 mL). The material was recrystallized twice from 300 mL acetone and some ethanol (around 25 mL). After drying, 18 g of salt was obtained which was treated in an acid base separation, 100 mL dichloromethane and 100 mL 1N aq. NaOH. The two layers were separated and the organic layer washed with 40 mL 1N aq. NaOH and water, dried over sodium sulfate, filtered and concentrated in vacuo to afford (S)-tert-butyl 4-(1-aminoethyl)piperidine-1-carboxylate (9.0 g, 99+% ee, 22.5% yield).

From the mother liquor of the above mentioned first crystallization tert-butyl 4-(1-aminoethyl)piperidine-1-carboxylate (20 g, 88 mmol) could be isolated (enriched in the other enantiomer). To the material was added (R)-(−)-mandelic acid (14 g, 92 mmol) and acetone (300 mL). The mixture was heated until a clear solution was obtained and allowed to cool to room temperature while stirring. The obtained precipitate was collected, rinsed with some acetone and recrystallized once as described above. After acid base separation, (R)-tert-butyl 4-(1-aminoethyl)piperidine-1-carboxylate was obtained (7.5 g, 99+% ee, 19% yield).

E.e. was determined as followed: sample (one drop) of the amine and one drop 1-naphthyl isocyanate in 1 mL dichloromethane was mixed and left for 1 day at room temperature (most of the dichloromethane was evaporated). The sample was concentrated and 5 mL ethanol was added and heated short to 50-60 degrees. 1 mL sample was used. Chiracel OJ-H, eluent Heptane/EtOH/Et₂NH (85/15/0.2), Rf 11.8 and 13.0 min.

Step 3: 2-(perfluorophenoxy)-4-(1-tosyl-5-(trifluoromethyl)-1H-pyrrolo[2,3-b]pyridin-3-yl)pyrimidine-5-carbonitrile

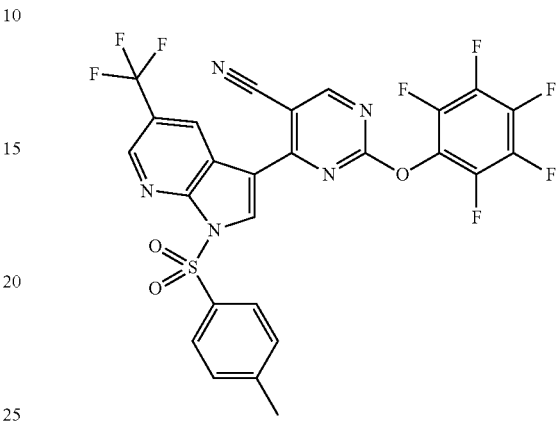

2-(Methylthio)-4-(1-tosyl-5-(trifluoromethyl)-1H-pyrrolo[2,3-b]pyridin-3-yl)pyrimidine-5-carbonitrile (150 mg, 0.31 mmol) was dissolved in dichloromethane at room temperature. Meta-chloroperbenzoic acid (110 mg, 0.64 mmol) was added in one portion and the reaction was stirred for 5 minutes. Pentafluorophenol (285 mg, 1.55 mmol) was added and the solution was stirred at room temperature for 3 hours. The crude mixture was washed with a diluted solution of sodium bicarbonate and brine. The organic phase was dried over magnesium sulfate, filtered and concentrated in vacuo. The residue was purified on silica gel by flash column chromatography to afford the title compound as a solid (60 mg, 31% yield).

¹H NMR (CDCl₃, 400 MHz): δ 2.44 (3H, s), 7.38 (2H, d), 8.21 (2H, d), 8.47 (1H, s), 8.78 (1H, s), 8.95 (1H, s), 9.32 (1H, s); MS (ES⁺) 626.

Step 4: tert-butyl 4-((1R)-1-(5-cyano-4-(1-tosyl-5-(trifluoromethyl)-1H-pyrrolo[2,3-b]pyridin-3-yl)pyrimidin-2-ylamino)ethyl)piperidine-1-carboxylate

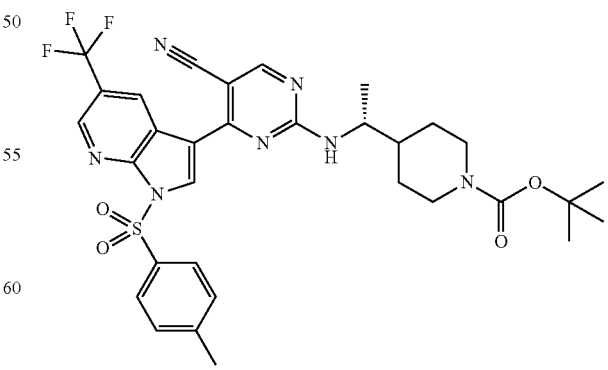

(R)-tert-butyl 4-(1-aminoethyl)piperidine-1-carboxylate (43.82 mg, 0.19 mmol) was added to a solution of 2-(perfluorophenoxy)-4-(1-tosyl-5-(trifluoromethyl)-1H-pyrrolo[2,3- b]pyridin-3-yl)pyrimidine-5-carbonitrile (100 mg, 0.16 mmol) and the reaction mixture was stirred at room temperature for 2 hours. The crude mixture was concentrated to dryness and the resulting residue was purified on silica gel by flash column chromatography to afford the title compound (70 mg, 65% yield).

MS (ES⁻) 668.

This intermediate could also be prepared by step 3B and 4B.

Step 3B: 5-cyano-4-(1-tosyl-5-(trifluoromethyl)-1H-pyrrolo[2,3-b]pyridin-3-yl)pyrimidin-2-yl diethyl phosphate.

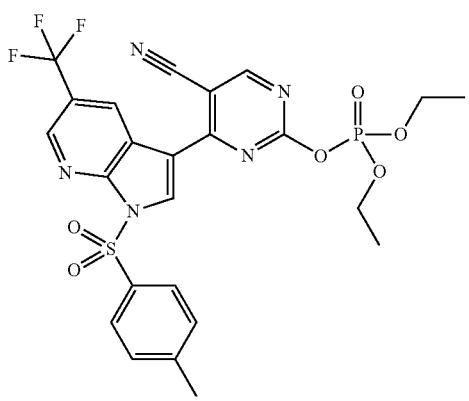 [SMILES: CCOP(=O)(OCC)Oc1ncc(C#N)c(-c2cn(S(=O)(=O)c3ccc(C)cc3)c3ncc(C(F)(F)F)cc23)n1]

2-hydroxy-4-(1-tosyl-5-(trifluoromethyl)-1H-pyrrolo[2,3-b]pyridin-3-yl)pyrimidine-5-carbonitrile (87% pure, 1.23 g, 2.329 mmol) in dry THF (24.60 mL) was stirred at −25° C. and treated with potassium t-butoxide (2.795 mL of 1.0 M, 2.795 mmol) in THF. The reaction mixture was warmed up to 0° C. for 20 minutes, cooled to −50° C. and treated with diethylchlorophosphate (482.3 mg, 403.9 µL, 2.795 mmol). The reaction mixture was stirred at −40° C. for 20 minutes and at room temperature for 2 hours. The reaction mixture was diluted with ice cold ethyl acetate (60 mL), cooled in ice and shaken quickly with ice cold water containing 1M HCl (2.8 mL, 2.8 mmol), basified with aqueous NaHCO₃ and extracted into ethyl acetate. The organic extracts were dried over magnesium sulfate and concentrated to give a pale yellow solid which was triturated with ether and filtered to give a pale yellow solid (810 mg). The mother liquors were concentrated in vacuo and the residue purified on silica gel by flash column chromatography to afford a colourless solid (219 mg) (total: 1.029 g, 74% yield).

¹H NMR (DMSO-d₆, 400 MHz) δ 1.19-1.28 (6H, m), 2.33 (3H, s), 4.17-4.27 (4H, m), 7.51 (2H, d), 8.15 (2H, d), 8.94 (1H, s), 9.24 (1H, s), 9.41 (1H, s), 9.48 (1H, s); MS (ES⁺) 596.

Step 4B: tert-butyl 4-((1R)-1-(5-cyano-4-(1-tosyl-5-(trifluoromethyl)-1H-pyrrolo[2,3-b]pyridin-3-yl)pyrimidin-2-ylamino)ethyl)piperidine-1-carboxylate

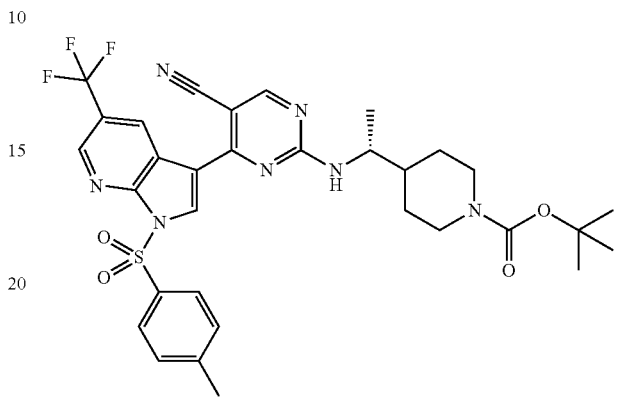

5-cyano-4-(1-tosyl-5-(trifluoromethyl)-1H-pyrrolo[2,3-b]pyridin-3-yl)pyrimidin-2-yl diethyl phosphate (200 mg, 0.3359 mmol) was treated with a solution of (R)-tert-butyl 4-(1-aminoethyl)piperidine-1-carboxylate (76.70 mg, 0.3359 mmol) in THF (2 mL), and diisopropylethylamine (70.22 µL, 0.4031 mmol). The reaction mixture was stirred at room temperature for 24 hours. The crude mixture was diluted with ethyl acetate and washed with aqueous NaHCO₃. The organic layer was dried over magnesium sulfate and concentrated under reduced pressure. The residue was purified on silica gel by flash column chromatography to afford the title compound as a colourless glass (188 mg, 84% yield).

MS (ES⁻) 668.

Step 5: 2-((R)-1-(piperidin-4-yl)ethylamino)-4-(1-tosyl-5-(trifluoromethyl)-1H-pyrrolo[2,3-b]pyridin-3-yl)pyrimidine-5-carbonitrile 2,2,2-trifluoroacetate

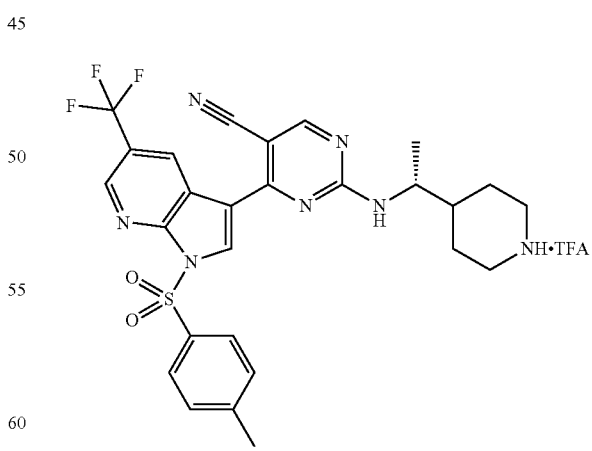

Trifluoroacetic acid (2 mL, 25.96 mmol) was added to a solution of tert-butyl 4-((1R)-1-(5-cyano-4-(1-tosyl-5-(trifluoromethyl)-1H-pyrrolo[2,3-b]pyridin-3-yl)pyrimidin-2-ylamino)ethyl)piperidine-1-carboxylate (1.2 g, 1.79 mmol) in dichloromethane (25 mL) and the reaction mixture was stirred at room temperature for 1 hour. The crude mixture was concentrated to dryness to give the title compound as a white solid (1.021 g, 98% yield).

MS (ES+) 570, (ES−) 568.

Step 6: 2-((R)-1-(1-(2-hydroxyacetyl)piperidin-4-yl)ethylamino)-4-(1-tosyl-5-(trifluoromethyl)-1H-pyrrolo[2,3-b]pyridin-3-yl)pyrimidine-5-carbonitrile

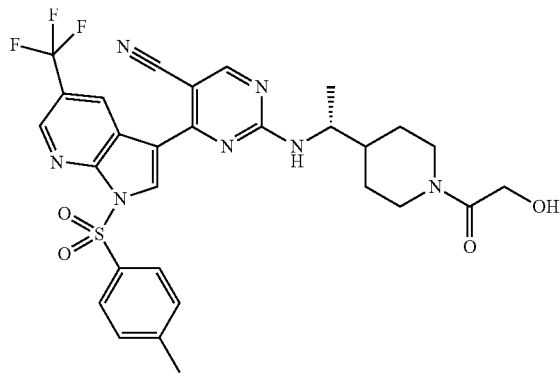 [SMILES: Cc1ccc(S(=O)(=O)n2cc(-c3nc(N[C@H](C)C4CCN(C(=O)CO)CC4)ncc3C#N)c3cc(C(F)(F)F)cnc32)cc1]

Diisopropylethylamine (179 µl, 1.025 mmol) was added to a mixture of 2-((R)-1-(piperidin-4-yl)ethylamino)-4-(1-tosyl-5-(trifluoromethyl)-1H-pyrrolo[2,3-b]pyridin-3-yl)pyrimidine-5-carbonitrile 2,2,2-trifluoroacetate (140 mg, 0.205 mmol), TBTU (131.7 mg, 0.14 mmol) and glycolic acid (15.6 mg, 0.205 mmol) in tetrahydrofuran (3 mL). The reaction mixture was stirred at room temperature for 1 hour. The crude mixture was concentrated to dryness and redissolved in ethyl acetate. The organic phase was washed with a saturated solution of sodium bicarbonate and brine, dried over magnesium sulfate, filtered and concentrated in vacuo. The residue was purified on silica gel by flash column chromatography to afford the title compound (60 mg, 47% yield). Also obtained was 20 mg (21% yield) of the detosylated compound.

MS (ES+) 628, (ES−) 626.

Step 7: 2-((R)-1-(1-(2-hydroxyacetyl)piperidin-4-yl)ethylamino)-4-(5-(trifluoromethyl)-1H-pyrrolo[2,3-b]pyridin-3-yl)pyrimidine-5-carbonitrile

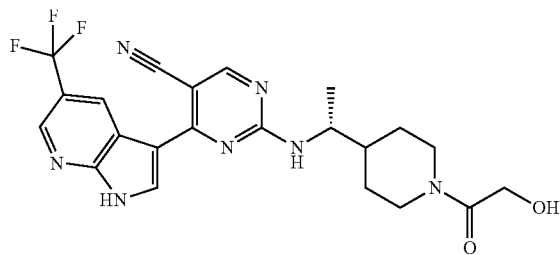 [SMILES: C[C@@H](Nc1ncc(C#N)c(-c2c[nH]c3ncc(C(F)(F)F)cc23)n1)C1CCN(C(=O)CO)CC1]

1M solution of lithium hydroxide (382.5 µl, 0.38 mmol) was added to a solution of 2-((R)-1-(1-(2-hydroxyacetyl)piperidin-4-yl)ethylamino)-4-(1-tosyl-5-(trifluoromethyl)-1H-pyrrolo[2,3-b]pyridin-3-yl)pyrimidine-5-carbonitrile (80 mg, 0.128 mmol) in tetrahydrofuran (2 mL). The reaction mixture was stirred at room temperature for 1 hour. The crude mixture was concentrated to dryness and redissolved in ethyl acetate. The organic phase was washed with water, dried over magnesium sulfate, filtered and concentrated in vacuo. The residue was purified on silica gel by flash column chromatography (ISCO Companion|) to afford the title compound as a white solid (30 mg, 50% yield).

$^1$H NMR (DMSO-d$_6$, 400 MHz) δ 1.05-1.2 (5H, m), 1.75-1.95 (5H, m), 2.85-2.95 (1H, m), 3.63-3.68 (2H, m), 3.97-4.03 (2H, m), 4.4-4.5 (1H, m), 8.23-8.28 (1H, m), 8.7-8.8 (3H, m), 9.1-9.2 (1H, m), 13.1-13.2 (1H, m); MS (ES+) 474, (ES+) 472.

Example 5

Trans-(2R)—N-(4-((1R)-1-(5-cyano-4-(5-(trifluoromethyl)-1H-pyrrolo[2,3-b]pyridin-3-yl)pyrimidin-2-ylamino)ethyl)cyclohexyl)-2-hydroxypropanamide
I-265

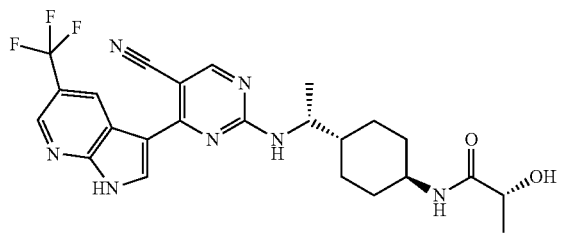 [SMILES: C[C@@H](O)C(=O)N[C@H]1CC[C@H]([C@@H](C)Nc2ncc(C#N)c(-c3c[nH]c4ncc(C(F)(F)F)cc34)n2)CC1]

Step 1: (R)-tert-butyl 1-(4-hydroxycyclohexyl)ethylcarbamate

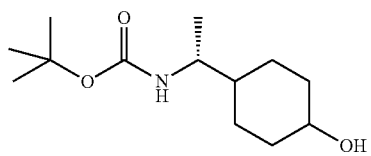 [SMILES: C[C@@H](NC(=O)OC(C)(C)C)C1CCC(O)CC1]

(R)-tert-butyl 1-(4-hydroxyphenyl)ethylcarbamate (described in the literature: WO 2007035154 (A1)) (100 mg, 0.4214 mmol) was dissolved in methanol (5 mL). A methanolic (5 mL) solution of rhodium on alumina (10 Wt %, 10 mg) was added. The reaction mixture was place under a hydrogen atmosphere and stir at room temperature for 18 hours. The rhodium catalyst was filtered off and the mother liquors were concentrated in vacuo. The residue was purified on silica gel by flash column chromatography to afford the title compound (62 mg, 61% yield).

Data for the cis isomer (26 mg as a white solid):

R$_f$ (30% EtOAc/Petrol) 0.40;

$^1$H NMR (DMSO-d$_6$, 400 MHz) δ 1.04 (3H, d), 1.19 (1H, m), 1.30-1.40 (6H, m), 1.37 (9H, s), 1.52-1.62 (2H, m), 3.29 (1H, m), 3.73 (1H, br s), 4.21 (1H, d), 6.59 (1H, d).

Data for the trans isomer (36 mg as a colourless oil):

R$_f$ (30% EtOAc/Petrol) 0.33;

$^1$H NMR (DMSO-d$_6$, 400 MHz) δ 0.85-1.21 (5H, m), 1.03 (3H, d), 1.37 (9H, s), 1.60-1.67 (2H, m), 1.78-1.82 (2H, m), 3.20-3.30 (2H, m), 4.41 (1H, br s), 6.62 (1H, d).

Step 2: Cis-(R)-4-(1-(tert-butoxycarbonylamino)ethyl)cyclohexyl methanesulfonate

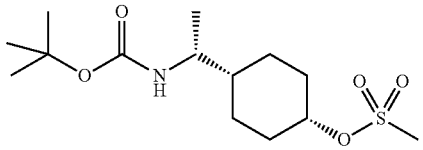 [SMILES: C[C@@H](NC(=O)OC(C)(C)C)[C@H]1CC[C@@H](OS(C)(=O)=O)CC1]

Cis-(R)-tert-butyl 1-(4-hydroxycyclohexyl)ethylcarbamate (575 mg, 2.363 mmol) was dissolved in dichloromethane (10 mL) and cooled to 0° C. under nitrogen. Triethylamine (478.2 mg, 658.7 µL, 4.726 mmol) followed by methanesulfonylchloride (284.2 mg, 192.0 µL, 2.481 mmol) were added dropwise. The reaction mixture was stirred at room temperature for 30 minutes. The crude mixture was washed with 1M HCl, water and a saturated aqueous solution of sodium bicarbonate. The organic extracts were dried over magnesium sulfate, filtered and concentrated in vacuo to give the compound as a white solid (706 mg, 93% yield).

$^1$H NMR (CDCl$_3$, 400 MHz) δ 1.11 (3H, d), 1.38-1.52 (12H, m), 1.54-1.70 (4H, m), 2.06-2.20 (2H, m), 3.03 (3H, s), 3.60 (1H, br s), 4.39 (1H, d), 5.00 (1H, s).

Step 3: Trans-(R)-tert-butyl 1-(4-aminocyclohexyl)ethylcarbamate

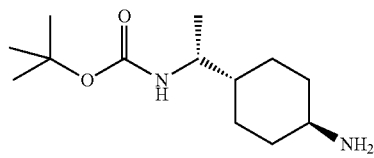 [SMILES: C[C@@H](NC(=O)OC(C)(C)C)[C@H]1CC[C@H](N)CC1]

Cis-(R)-4-(1-(tert-butoxycarbonylamino)ethyl)cyclohexyl methanesulfonate (706 mg, 2.196 mmol) was dissolved in DMF (10 mL). Sodium azide (713.8 mg, 10.98 mmol) was added and the reaction was heated to 80° C. for 18 hours. The reaction mixture was cooled down to ambient temperature and partitioned between EtOAc (50 mL) and water (50 mL). The organic layer was separated, dried over magnesium sulfate and filtered. The ethyl acetate solution was taken into next step without further manipulation.

The above solution was diluted with MeOH (50 mL) and 10% Pd on carbon (Degussa) (120 mg) was added. The reaction mixture was place under a hydrogen atmosphere and stir at room temperature for 18 hours. The catalyst was filtered off and the mother liquors were concentrated in vacuo to afford the title compound as an oil (558.4 mg, quantitative yield).

$^1$H NMR (CDCl$_3$, 400 MHz) δ 1.02-1.32 (8H, m), 1.45 (9H, s), 1.62-1.84 (4H, m), 1.87-1.95 (2H, m), 2.60 (1H, m), 3.53 (1H, m), 4.39 (1H, m).

Step 4: Trans-tert-butyl(R)-1-(4-((R)-2-hydroxypropanamido)cyclohexyl)ethylcarbamate

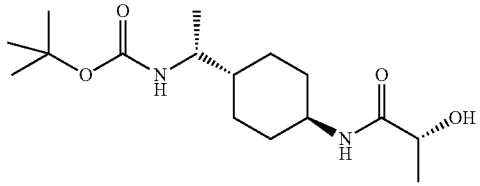 [SMILES: C[C@@H](O)C(=O)N[C@H]1CC[C@H]([C@@H](C)NC(=O)OC(C)(C)C)CC1]

Trans-tert-butyl(R)-1-(4-aminocyclohexyl)ethylcarbamate (125 mg, 0.52 mmol) was dissolved in DMF (3 mL). D-Lactic Acid (49.52 mg, 0.52 mmol), diisopropylethylamine (166.6 mg, 224.5 µL, 1.29 mmol) and TBTU (165.6 mg, 0.5158 mmol) were successively added. The reaction mixture was allowed to stir at ambient temperature for 3 hours. The crude mixture was partitioned between ethyl acetate and brine. The organic extracts were dried over magnesium sulfate, filtered and concentrated in vacuo. The residue was purified on silica gel by column chromatography (ISCO Companion, 12 g column, 0-10% MeOH/DCM) to afford the title compound (66.1 mg, 41% yield).

$^1$H NMR (CDCl$_3$, 400 MHz) δ 1.10 (3H, d), 1.12-1.38 (5H, m), 1.44 (3H, d), 1.46 (9H, s), 1.73-1.88 (2H, m), 1.97-2.08 (2H, m), 2.40 (1H, m), 3.58 (1H, m), 3.72 (1H, m), 4.22 (1H, q), 4.37 (1H, m), 6.24 (1H, m).

Step 5: Trans-(R)—N-(4-((R)-1-aminoethyl)cyclohexyl)-2-hydroxypropanamide

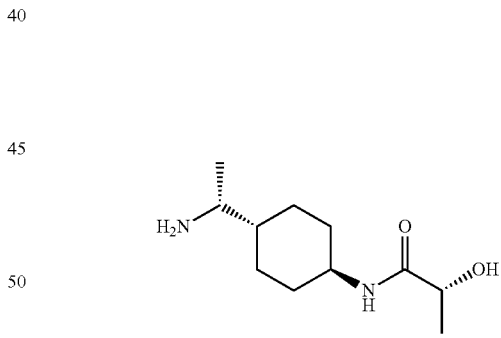

Trans-tert-butyl(R)-1-(4-((R)-2-hydroxypropanamido)cyclohexyl)ethylcarbamate (66 mg, 0.21 mmol) was dissolved in dichloromethane (10 mL). A solution of HCl in dioxane (209.9 µL of 4 M, 0.84 mmol) was added. The reaction mixture was stirred at ambient temperature for 18 hours. The crude mixture was concentrated in vacuo and coevaporated three times with diethylether. The residue was dissolved in methanol (10 mL), passed through a sodium bicarbonate cartridge and concentrated in vacuo to give the desired compound as a white solid (45 mg, quantitative yield).

¹H NMR (DMSO-d₆, 400 MHz) δ 0.80-1.10 (6H, m), 1.12-1.40 (6H, m), 1.50-1.82 (5H, m), 2.54 (1H, m), 3.45 (1H, m), 3.91 (1H, quint), 5.40 (1H, d), 7.35 (1H, d).

Step 6: Trans-(2R)—N-(4-((1R)-1-(5-cyano-4-(5-(trifluoromethyl)-1H-pyrrolo[2,3-b]pyridin-3-yl)pyrimidin-2-ylamino)ethyl)cyclohexyl)-2-hydroxypropanamide I-265

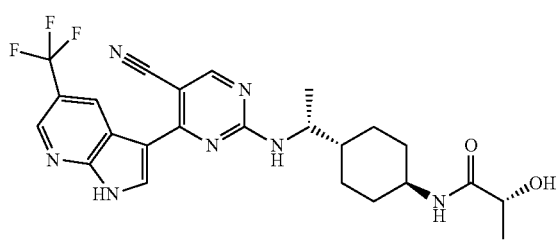 [SMILES: C[C@@H](O)C(=O)N[C@H]1CC[C@H]([C@@H](C)Nc2ncc(C#N)c(-c3c[nH]c4ncc(C(F)(F)F)cc34)n2)CC1]

Trans-(R)—N-(4-((R)-1-aminoethyl)cyclohexyl)-2-hydroxypropanamide (45 mg, 0.21 mmol) was dissolved in THF (6 mL) and DMF (2 mL) and stirred over 4 Å molecular sieves for 10 minutes. 4-(5-(trifluoromethyl)-1-tosyl-1H-pyrrolo[2,3-b]pyridin-3-yl)-2-(methylsulfonyl)pyrimidine-5-carbonitrile (131.9 mg, 0.2100 mmol) was added. The reaction mixture was stirred under nitrogen at ambient temperature for 18 hours. The molecular sieves was removed by filtration and washed with EtOAc. The filtrate was washed with water, dried over magnesium sulfate, filtered and concentrated in vacuo. The residue dissolved in tetrahydrofuran (6 mL). Lithium hydroxide (840.0 μL of 1 M, 0.8400 mmol) was added and the reaction mixture was stirred at room temperature for 18 hours. The crude mixture was partitioned between ethyl acetate and brine. The organic extracts were dried over magnesium sulfate, filtered and concentrated in vacuo. The residue was purified by reverse phase preparative HPLC [Waters Sunfire C18, 10 μM, 100 Å column, gradient 10%-95% B (solvent A: 0.05% TFA in water; solvent B: CH3CN) over 16 minutes at 25 mL/min]. The fractions were collected, passed through a sodium bicarbonate cartridge and freeze-dried to give the title compound as a white solid (19 mg, 18% yield).

¹H NMR (CDCl₃, 400 MHz) δ 1.20-1.35 (8H, m), 1.44 (3H, d), 1.90-2.09 (4H, m), 2.34 (1H, d), 3.69-3.81 (1H, m), 4.18-4.28 (2H, m), 5.52 (0.33H, d), 5.58 (0.67H, d), 6.27 (1H, d), 8.50 (0.66H, s), 8.58 (0.33H, s), 8.72 (1H, s), 8.77 (0.33H, d), 8.86 (0.67H, d), 9.09 (0.33H, s), 9.23 (0.67H, s), 9.64 (1H, br s); MS (ES⁺) 502, (ES⁻) 500.

Example 6

2-(1-(6-(4-hydroxy-1-methylpiperidin-4-yl)pyridin-3-yl)ethylamino)-4-(5-(trifluoromethyl)-1H-pyrrolo[2,3-b]pyridin-3-yl)pyrimidine-5-carbonitrile I-266

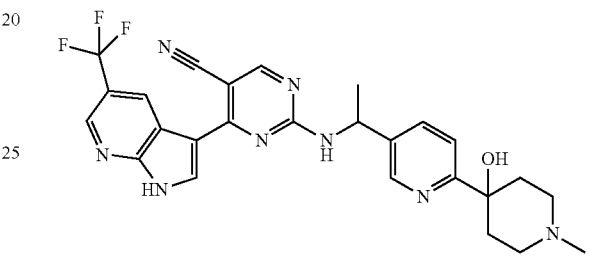

Step 1: 1-methyl-4-(5-(2-methyl-1,3-dioxolan-2-yl)pyridin-2-yl)piperidin-4-ol

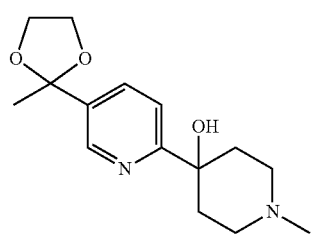

2-bromo-5-(2-methyl-1,3-dioxolan-2-yl)pyridine (500 mg, 2.048 mmol) (described in the literature: Bioorg. Med. Chem., 2005, 13, 6763) was dissolved in anhydrous tetrahydrofuran (10 mL) and cooled to −78° C. under nitrogen. n-BuLi (901.2 μL of 2.5 M, 2.253 mmol) was added dropwise and the reaction mixture was stirred at −78° C. for 30 minutes. 1-Methyl-4-piperidone (602.6 mg, 655.0 μL, 5.325 mmol) was added and the reaction was allowed to stir at −78° C. for 20 minutes then warmed slowly to ambient temperature. The reaction mixture was stirred at room temperature for 18 hours and concentrated in vacuo. The residue was purified on silica gel by flash column chromatography to afford the title compound as a sticky orange solid (483.4 mg, 85% yield).

$^1$H NMR (DMSO-d$_6$, 400 MHz) δ 1.20-1.70 (5H, m), 2.03-2.40 (9H, m), 3.74 (2H, t), 4.00 (2H, t), 5.03 (1H, m), 7.65 (1H, d), 7.77 (1H, dd), 8.54 (1H, s); MS (ES$^+$) 279.

Step 2: 4-(5-(1-aminoethyl)pyridin-2-yl)-1-methylpiperidin-4-ol

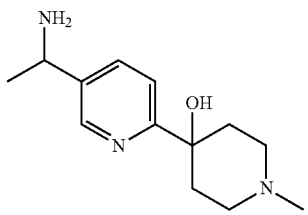 [SMILES: CC(N)c1ccc(C2(O)CCN(C)CC2)nc1]

1-Methyl-4-(5-(2-methyl-1,3-dioxolan-2-yl)pyridin-2-yl)piperidin-4-ol (483 mg, 1.735 mmol) was suspended in tetrahydrofuran (10 mL). 1M HCl (6.97 mL, 6.97 mmol) was added. The reaction mixture was stirred at room temperature for 48 hours and concentrated in vacuo.

The residue was dissolved in MeOH (20 mL). Ammonium acetate (1.337 g, 17.35 mmol), acetic acid (1.5 mL, 26.38 mmol) and MP-CNBH$_3$ (2.871 g, 6.947 mmol) were successively added. The reaction mixture was stirred at room temperature for 18 hours then at 40° C. for a further 7 hours. The reaction mixture was allowed to cool down to room temperature. The resin was filtered off and the mother liquors were concentrated in vacuo. The residue was dissolved in methanol (20 mL) and MP-Carbonate (2.763 g, 8.675 mmol) was added. The reaction mixture was stirred for 6 hours. The resin was filtered off and the mother liquors were concentrated in vacuo. The residue was purified on silica gel by flash column chromatography to afford the title compound as a yellow solid (159 mg, 39% yield).

$^1$H NMR (DMSO-d$_6$, 400 MHz) δ 1.27 (3H, d), 1.44-1.48 (2H, m), 2.08-2.60 (9H, m), 4.02 (1H, q), 4.12 (2H, br s), 4.97 (1H, s), 7.58 (1H, d), 7.75 (1H, dd), 8.46 (1H, d); MS (ES$^+$) 236.

Step 3: 2-(1-(6-(4-hydroxy-1-methylpiperidin-4-yl)pyridin-3-yl)ethylamino)-4-(5-(trifluoromethyl)-1H-pyrrolo[2,3-b]pyridin-3-yl)pyrimidine-5-carbonitrile I-266

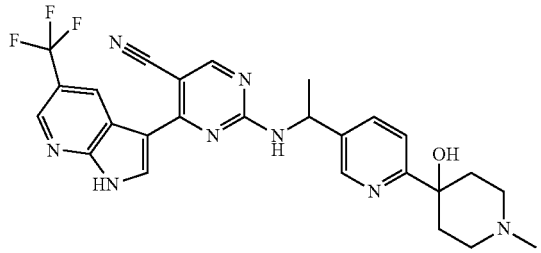 [SMILES: CC(Nc1ncc(C#N)c(-c2c[nH]c3ncc(C(F)(F)F)cc23)n1)c1ccc(C2(O)CCN(C)CC2)nc1]

2-(Methylsulfonyl)-4-(1-tosyl-5-(trifluoromethyl)-1H-pyrrolo[2,3-b]pyridin-3-yl)pyrimidine-5-carbonitrile (160.2 mg, 0.255 mmol) was added to a solution of 4-(5-(1-aminoethyl)pyridin-2-yl)-1-methylpiperidin-4-ol (66.01 mg, 0.28 mmol) in tetrahydrofuran (8 mL). The reaction mixture was stirred under nitrogen at room temperature for 18 hours. 1M Lithium hydroxide (1.020 mL of 1 M, 1.020 mmol) was added and the reaction mixture was stirred at room temperature for 4 hours. The crude mixture was partitioned between ethyl acetate and brine. The organic extracts were dried over magnesium sulfate, filtered and concentrated in vacuo. The residue was purified by reverse phase preparative HPLC [Waters Sunfire C18, 10 μM, 100 Å column, gradient 10%-95% B (solvent A: 0.05% TFA in water; solvent B: CH$_3$CN) over 16 minutes at 25 mL/min] The fractions were collected, passed through a sodium bicarbonate cartridge and freeze-dried to give the title compound as a white solid (12.5 mg, 9% yield).

$^1$H NMR (DMSO-d$_6$, 400 MHz) δ 1.40-1.49 (2H, m), 1.59 (3H, d), 2.05-2.21 (2H, m), 2.16 (1.5H, s), 2.16 (1.5H, s), 2.25-2.33 (2H, m), 2.50-2.55 (2H, m), 4.96 (1H, d), 5.31-5.41 (1H, m), 7.58-7.65 (1H, m), 7.78-7.87 (1H, m), 8.51 (0.5H, s), 8.57 (0.5H, s), 8.70-8.72 (3H, m), 8.52-8.56 (1H, m), 8.97 (0.5H, s), 9.20 (0.5H, s), 13.03 (1H, br s); MS (ES$^+$) 523, (ES$^+$) 521.

Compounds prepared using the methods of Examples 1-6 to give the title compounds I-1 to I-299 are shown in Table I.

The characterization data for these compounds is summarized in Table II-A below and includes LC/MS (observed) and $^1$H NMR data.

TABLE 1

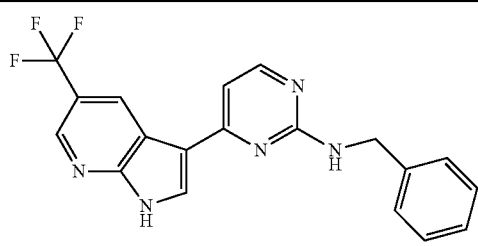

I-1

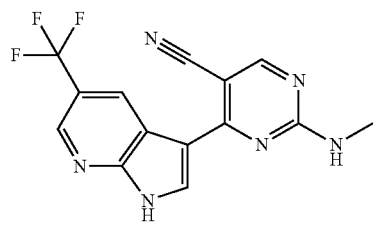 [SMILES: CNc1ncc(C#N)c(-c2c[nH]c3ncc(C(F)(F)F)cc23)n1]

I-2

TABLE 1-continued
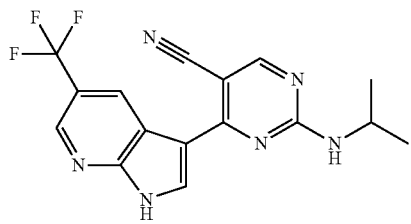 [SMILES: CC(C)Nc1ncc(C#N)c(-c2c[nH]c3ncc(C(F)(F)F)cc23)n1] I-3
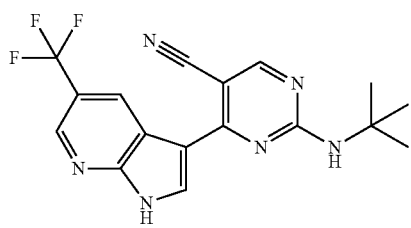 [SMILES: CC(C)(C)Nc1ncc(C#N)c(-c2c[nH]c3ncc(C(F)(F)F)cc23)n1] I-4
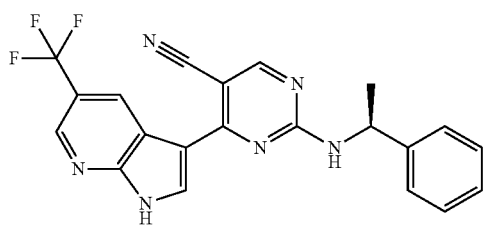 [SMILES: C[C@H](Nc1ncc(C#N)c(-c2c[nH]c3ncc(C(F)(F)F)cc23)n1)c1ccccc1] I-5
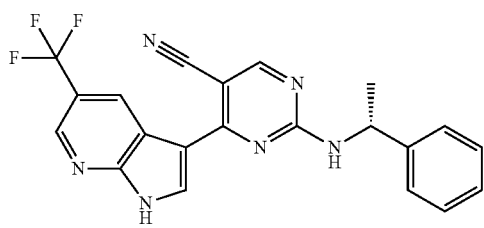 [SMILES: C[C@@H](Nc1ncc(C#N)c(-c2c[nH]c3ncc(C(F)(F)F)cc23)n1)c1ccccc1] I-6
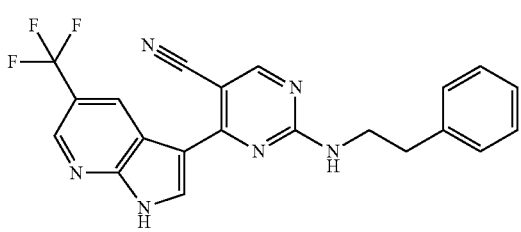 [SMILES: N#Cc1cnc(NCCc2ccccc2)nc1-c1c[nH]c2ncc(C(F)(F)F)cc12] I-7
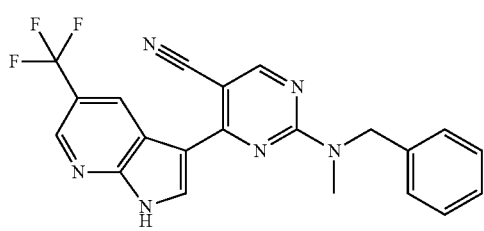 [SMILES: CN(Cc1ccccc1)c1ncc(C#N)c(-c2c[nH]c3ncc(C(F)(F)F)cc23)n1] I-8
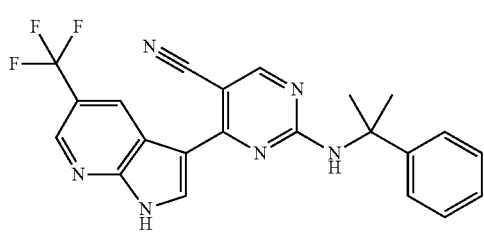 [SMILES: CC(C)(Nc1ncc(C#N)c(-c2c[nH]c3ncc(C(F)(F)F)cc23)n1)c1ccccc1] I-9

TABLE 1-continued
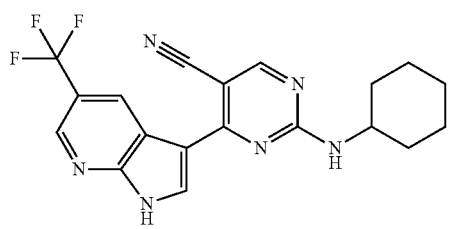 [SMILES: N#Cc1cnc(NC2CCCCC2)nc1-c1c[nH]c2ncc(C(F)(F)F)cc12] I-10
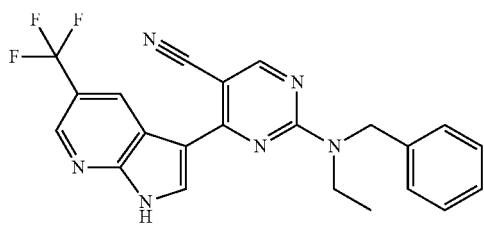 [SMILES: CCN(Cc1ccccc1)c1ncc(C#N)c(-c2c[nH]c3ncc(C(F)(F)F)cc23)n1] I-11
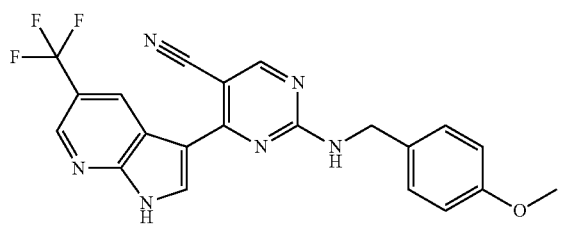 [SMILES: COc1ccc(CNc2ncc(C#N)c(-c3c[nH]c4ncc(C(F)(F)F)cc34)n2)cc1] I-12
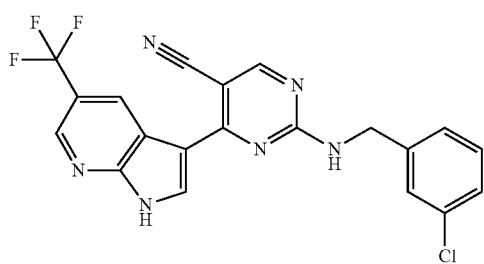 I-13
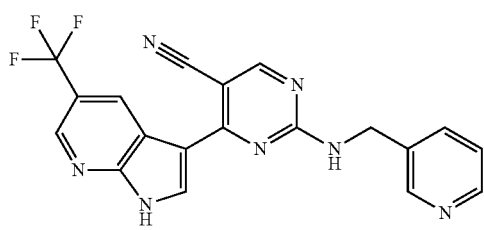 [SMILES: N#Cc1cnc(NCc2cccnc2)nc1-c1c[nH]c2ncc(C(F)(F)F)cc12] I-14
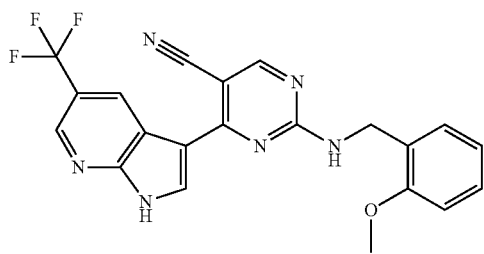 [SMILES: COc1ccccc1CNc1ncc(C#N)c(-c2c[nH]c3ncc(C(F)(F)F)cc23)n1] I-15

TABLE 1-continued
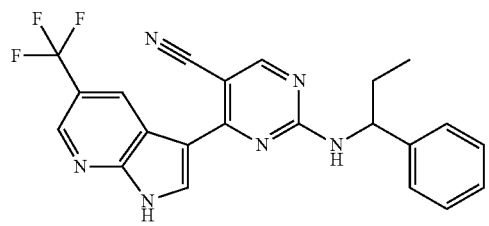 [SMILES: CCC(Nc1ncc(C#N)c(-c2c[nH]c3ncc(C(F)(F)F)cc23)n1)c1ccccc1]
I-16
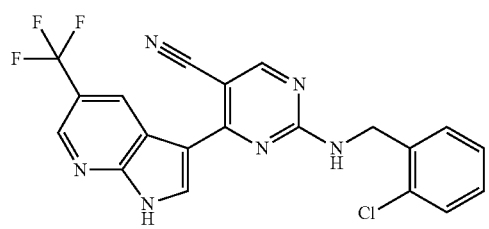
I-17
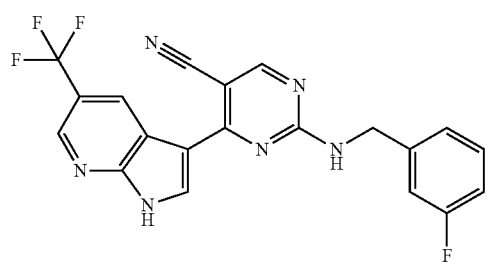 [SMILES: N#Cc1cnc(NCc2cccc(F)c2)nc1-c1c[nH]c2ncc(C(F)(F)F)cc12]
I-18
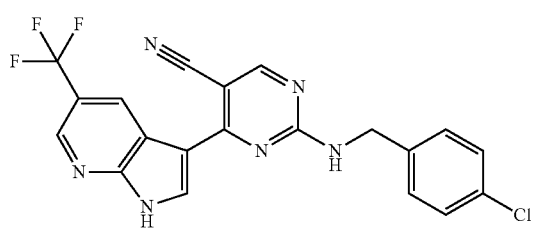 [SMILES: N#Cc1cnc(NCc2ccc(Cl)cc2)nc1-c1c[nH]c2ncc(C(F)(F)F)cc12]
I-19
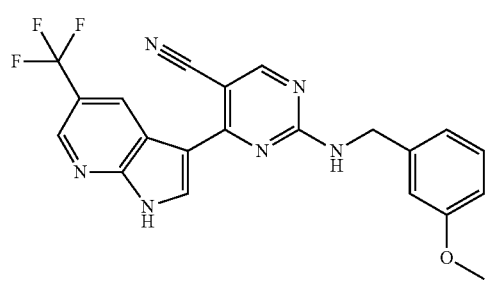 [SMILES: COc1cccc(CNc2ncc(C#N)c(-c3c[nH]c4ncc(C(F)(F)F)cc34)n2)c1]
I-20
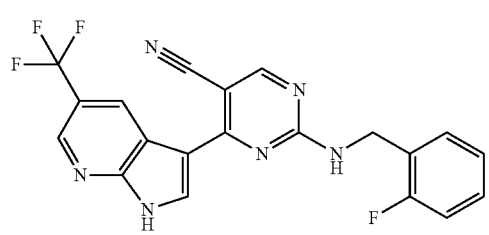 [SMILES: N#Cc1cnc(NCc2ccccc2F)nc1-c1c[nH]c2ncc(C(F)(F)F)cc12]
I-21

TABLE 1-continued
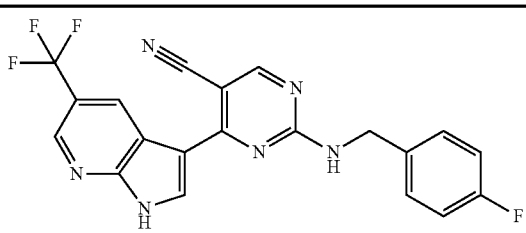
I-22
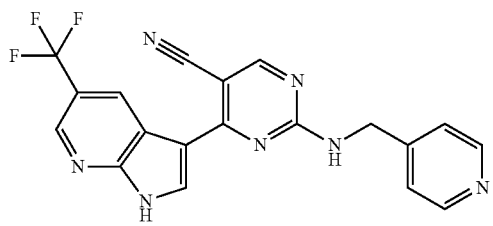 [SMILES: N#Cc1cnc(NCc2ccncc2)nc1-c1c[nH]c2ncc(C(F)(F)F)cc12]
I-23
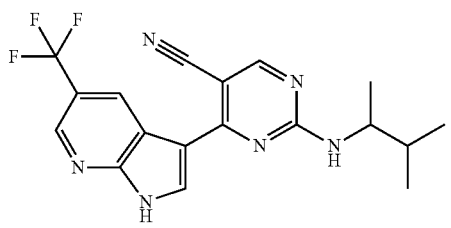 [SMILES: CC(C)C(C)Nc1ncc(C#N)c(-c2c[nH]c3ncc(C(F)(F)F)cc23)n1]
I-24
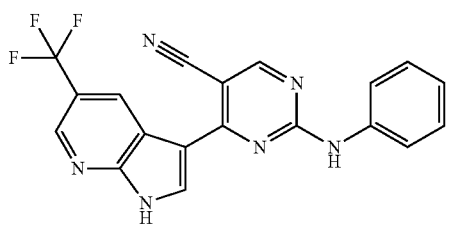 [SMILES: N#Cc1cnc(Nc2ccccc2)nc1-c1c[nH]c2ncc(C(F)(F)F)cc12]
I-25
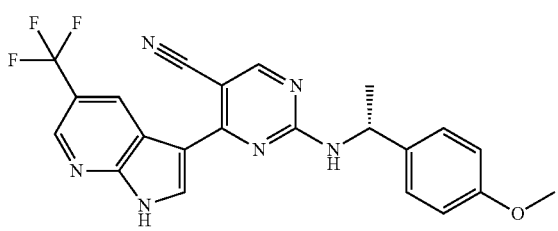 [SMILES: COc1ccc([C@@H](C)Nc2ncc(C#N)c(-c3c[nH]c4ncc(C(F)(F)F)cc34)n2)cc1]
I-26
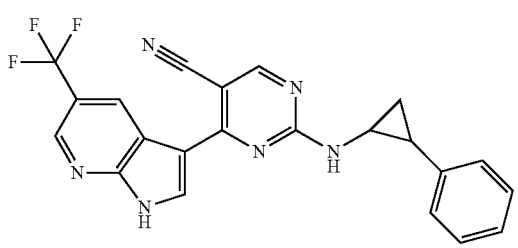 [SMILES: N#Cc1cnc(NC2CC2c2ccccc2)nc1-c1c[nH]c2ncc(C(F)(F)F)cc12]
I-27
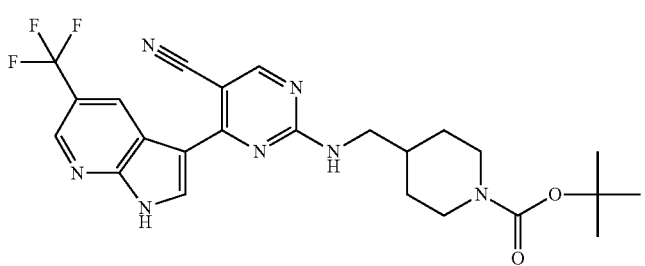 [SMILES: CC(C)(C)OC(=O)N1CCC(CNc2ncc(C#N)c(-c3c[nH]c4ncc(C(F)(F)F)cc34)n2)CC1]
I-28

TABLE 1-continued
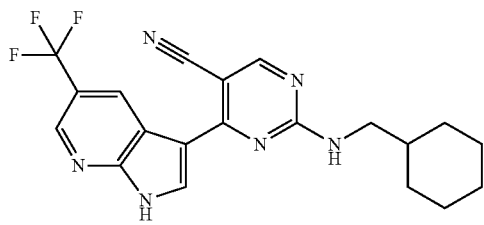 [SMILES: N#Cc1cnc(NCC2CCCCC2)nc1-c1c[nH]c2ncc(C(F)(F)F)cc12]
I-29
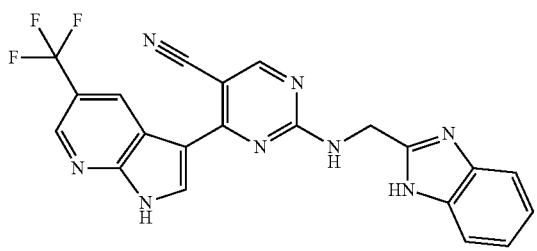 [SMILES: N#Cc1cnc(NCc2nc3ccccc3[nH]2)nc1-c1c[nH]c2ncc(C(F)(F)F)cc12]
I-30
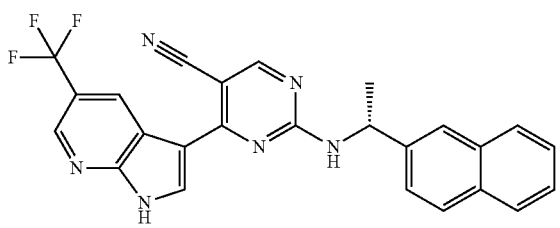 [SMILES: C[C@@H](Nc1ncc(C#N)c(-c2c[nH]c3ncc(C(F)(F)F)cc23)n1)c1ccc2ccccc2c1]
I-31
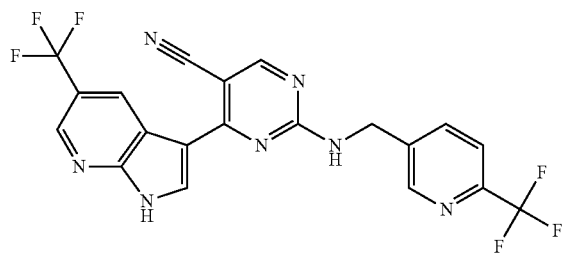 [SMILES: N#Cc1cnc(NCc2ccc(C(F)(F)F)nc2)nc1-c1c[nH]c2ncc(C(F)(F)F)cc12]
I-32
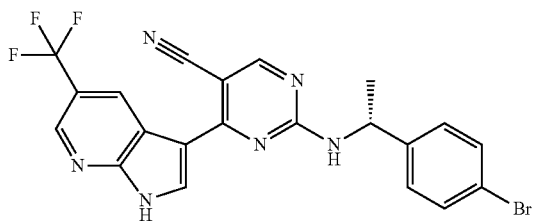 [SMILES: C[C@@H](Nc1ncc(C#N)c(-c2c[nH]c3ncc(C(F)(F)F)cc23)n1)c1ccc(Br)cc1]
I-33
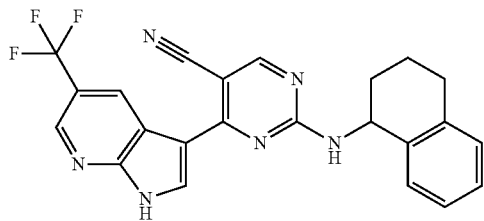 [SMILES: N#Cc1cnc(NC2CCCc3ccccc32)nc1-c1c[nH]c2ncc(C(F)(F)F)cc12]
I-34

TABLE 1-continued
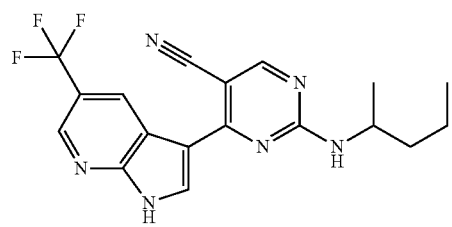 [SMILES: CCCC(C)Nc1ncc(C#N)c(-c2c[nH]c3ncc(C(F)(F)F)cc23)n1] I-35
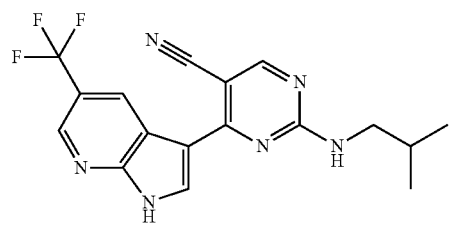 [SMILES: CC(C)CNc1ncc(C#N)c(-c2c[nH]c3ncc(C(F)(F)F)cc23)n1] I-36
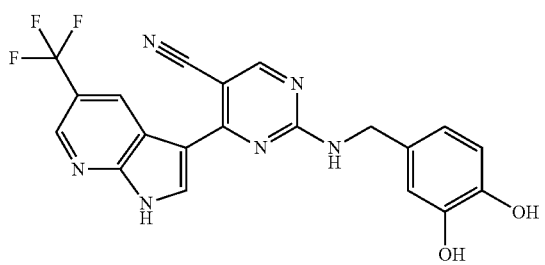 [SMILES: N#Cc1cnc(NCc2ccc(O)c(O)c2)nc1-c1c[nH]c2ncc(C(F)(F)F)cc12] I-37
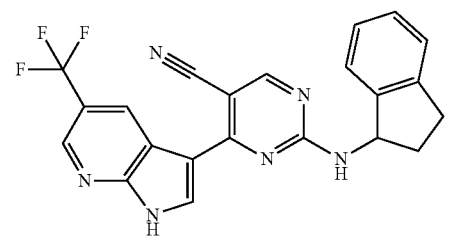 [SMILES: N#Cc1cnc(NC2CCc3ccccc32)nc1-c1c[nH]c2ncc(C(F)(F)F)cc12] I-38
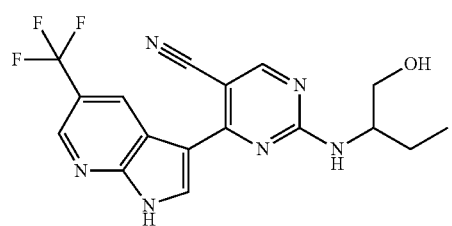 [SMILES: CCC(CO)Nc1ncc(C#N)c(-c2c[nH]c3ncc(C(F)(F)F)cc23)n1] I-39
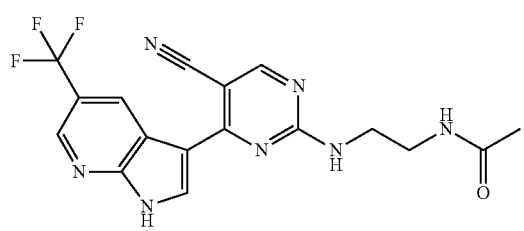 [SMILES: CC(=O)NCCNc1ncc(C#N)c(-c2c[nH]c3ncc(C(F)(F)F)cc23)n1] I-40

TABLE 1-continued
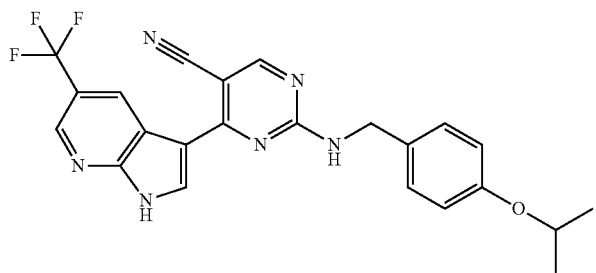 [SMILES: CC(C)Oc1ccc(CNc2ncc(C#N)c(-c3c[nH]c4ncc(C(F)(F)F)cc34)n2)cc1]
I-41
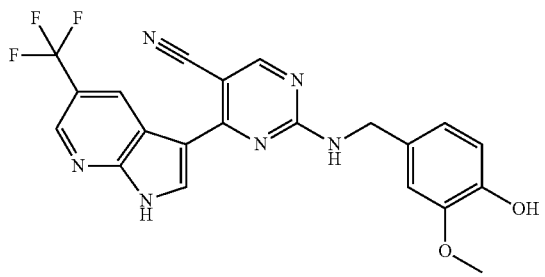 [SMILES: COc1cc(CNc2ncc(C#N)c(-c3c[nH]c4ncc(C(F)(F)F)cc34)n2)ccc1O]
I-42
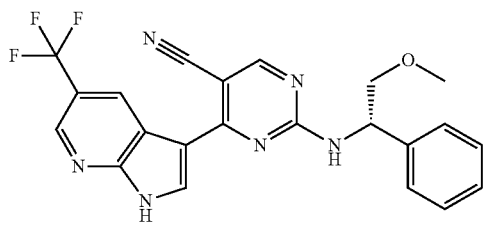 [SMILES: COC[C@@H](Nc1ncc(C#N)c(-c2c[nH]c3ncc(C(F)(F)F)cc23)n1)c1ccccc1]
I-43
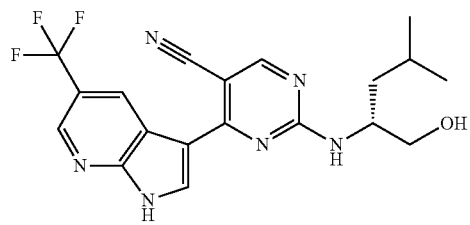 [SMILES: CC(C)C[C@H](CO)Nc1ncc(C#N)c(-c2c[nH]c3ncc(C(F)(F)F)cc23)n1]
I-44
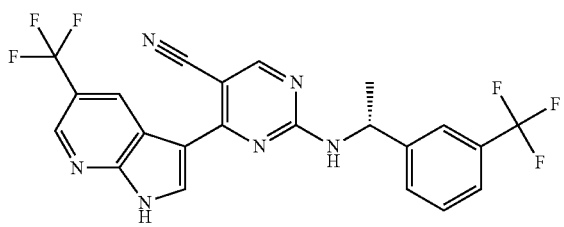 [SMILES: C[C@@H](Nc1ncc(C#N)c(-c2c[nH]c3ncc(C(F)(F)F)cc23)n1)c1cccc(C(F)(F)F)c1]
I-45
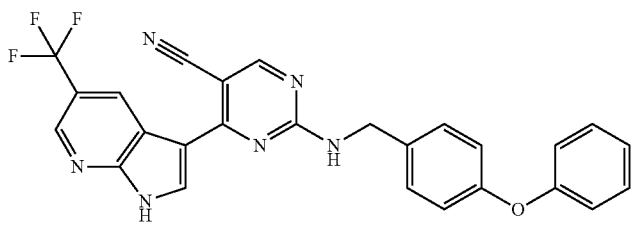 [SMILES: N#Cc1cnc(NCc2ccc(Oc3ccccc3)cc2)nc1-c1c[nH]c2ncc(C(F)(F)F)cc12]
I-46

TABLE 1-continued
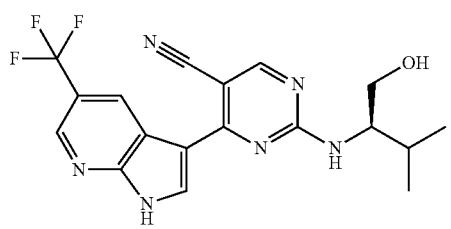 [SMILES: CC(C)[C@H](CO)Nc1ncc(C#N)c(-c2c[nH]c3ncc(C(F)(F)F)cc23)n1]
I-47
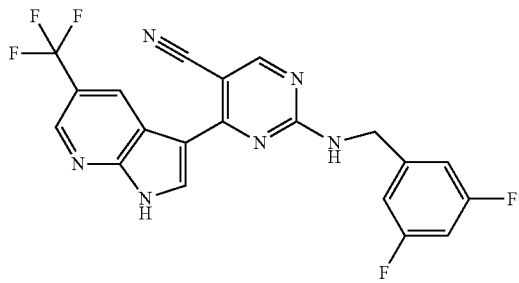 [SMILES: N#Cc1cnc(NCc2cc(F)cc(F)c2)nc1-c1c[nH]c2ncc(C(F)(F)F)cc12]
I-48
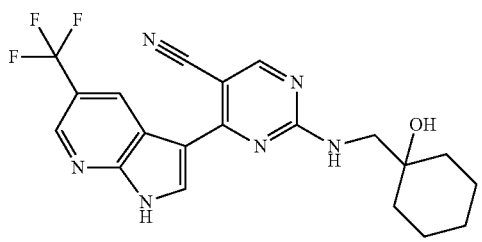 [SMILES: N#Cc1cnc(NCC2(O)CCCCC2)nc1-c1c[nH]c2ncc(C(F)(F)F)cc12]
I-49
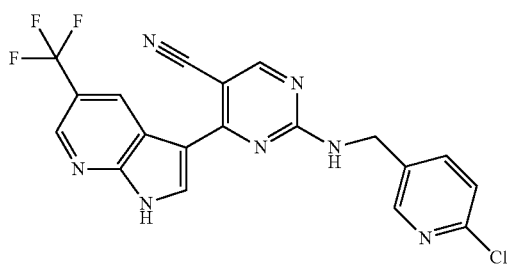 [SMILES: N#Cc1cnc(NCc2ccc(Cl)nc2)nc1-c1c[nH]c2ncc(C(F)(F)F)cc12]
I-50
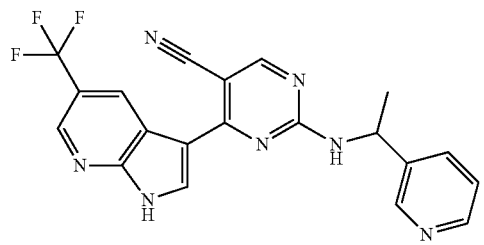 [SMILES: CC(Nc1ncc(C#N)c(-c2c[nH]c3ncc(C(F)(F)F)cc23)n1)c1cccnc1]
I-51
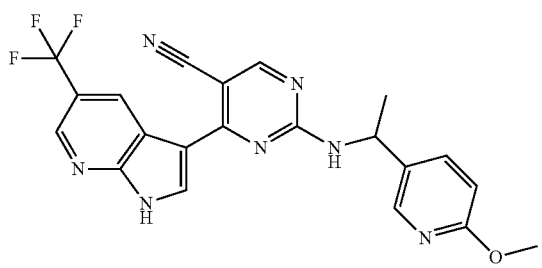 [SMILES: COc1ccc(C(C)Nc2ncc(C#N)c(-c3c[nH]c4ncc(C(F)(F)F)cc34)n2)cn1]
I-52

TABLE 1-continued
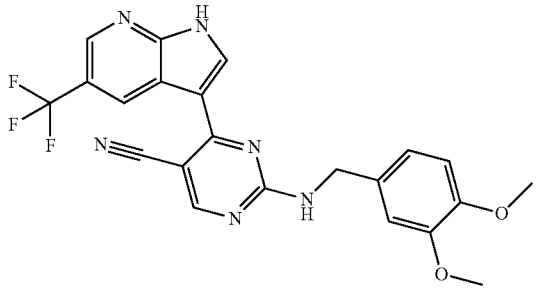 [SMILES: COc1ccc(CNc2ncc(C#N)c(-c3c[nH]c4ncc(C(F)(F)F)cc34)n2)cc1OC]
I-53
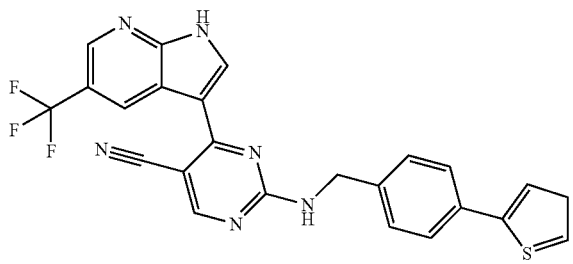
I-54
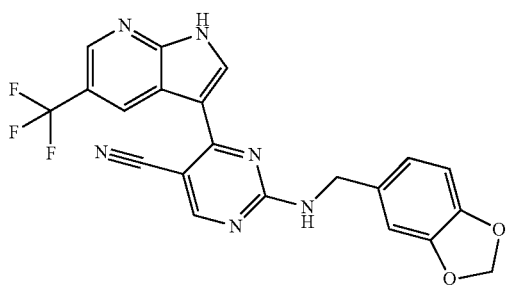 [SMILES: N#Cc1cnc(NCc2ccc3c(c2)OCO3)nc1-c1c[nH]c2ncc(C(F)(F)F)cc12]
I-56
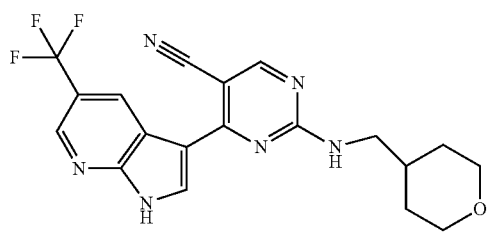 [SMILES: N#Cc1cnc(NCC2CCOCC2)nc1-c1c[nH]c2ncc(C(F)(F)F)cc12]
I-57
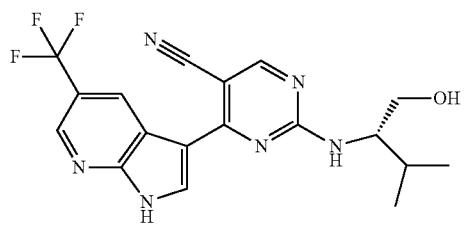 [SMILES: CC(C)[C@@H](CO)Nc1ncc(C#N)c(-c2c[nH]c3ncc(C(F)(F)F)cc23)n1]
I-58
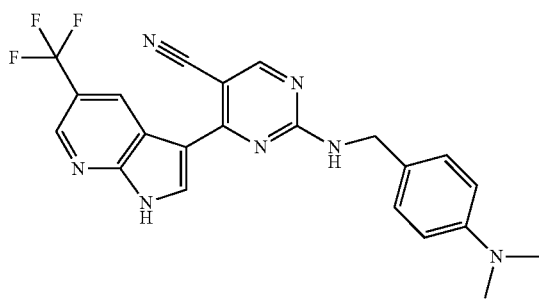 [SMILES: CN(C)c1ccc(CNc2ncc(C#N)c(-c3c[nH]c4ncc(C(F)(F)F)cc34)n2)cc1]
I-59

TABLE 1-continued
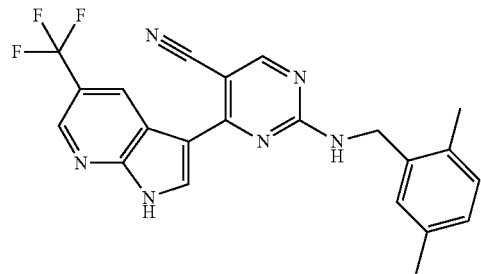 [SMILES: Cc1ccc(C)c(CNc2ncc(C#N)c(-c3c[nH]c4ncc(C(F)(F)F)cc34)n2)c1]
I-60
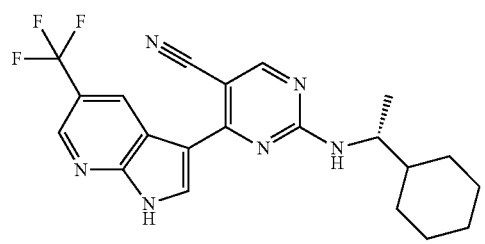 [SMILES: C[C@@H](Nc1ncc(C#N)c(-c2c[nH]c3ncc(C(F)(F)F)cc23)n1)C1CCCCC1]
I-61
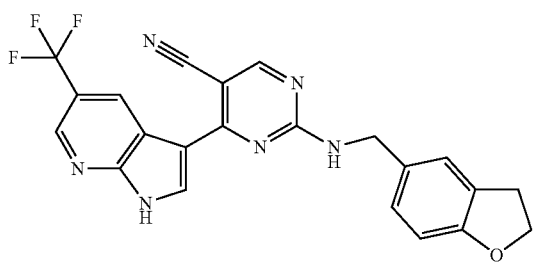 [SMILES: N#Cc1cnc(NCc2ccc3c(c2)CCO3)nc1-c1c[nH]c2ncc(C(F)(F)F)cc12]
I-62
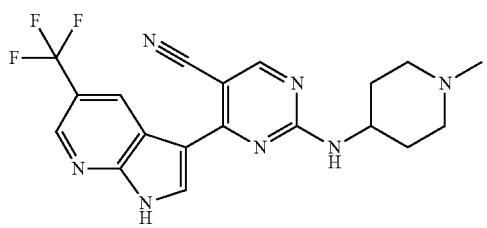 [SMILES: CN1CCC(Nc2ncc(C#N)c(-c3c[nH]c4ncc(C(F)(F)F)cc34)n2)CC1]
I-63
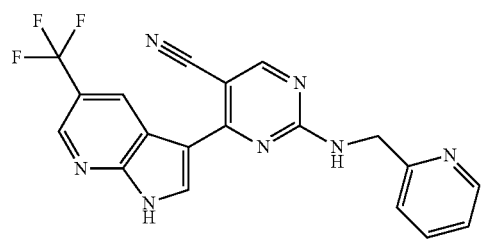 [SMILES: N#Cc1cnc(NCc2ccccn2)nc1-c1c[nH]c2ncc(C(F)(F)F)cc12]
I-64
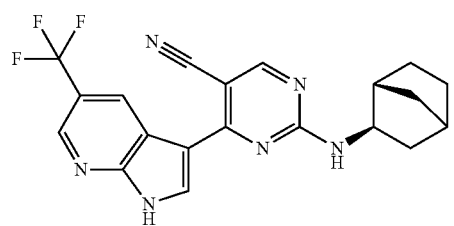 [SMILES: N#Cc1cnc(N[C@@H]2CC3CC[C@@H]2C3)nc1-c1c[nH]c2ncc(C(F)(F)F)cc12]
I-65

TABLE 1-continued
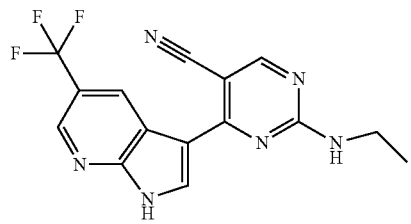 [SMILES: CCNc1ncc(C#N)c(-c2c[nH]c3ncc(C(F)(F)F)cc23)n1] I-66
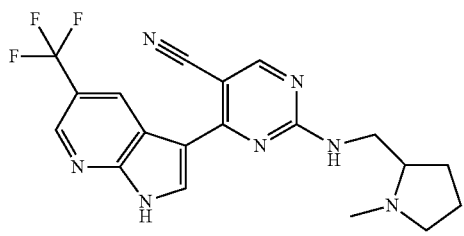 [SMILES: CN1CCCC1CNc1ncc(C#N)c(-c2c[nH]c3ncc(C(F)(F)F)cc23)n1] I-67
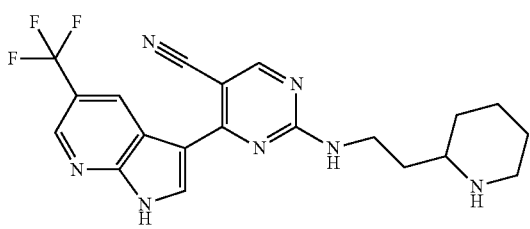 [SMILES: N#Cc1cnc(NCCC2CCCCN2)nc1-c1c[nH]c2ncc(C(F)(F)F)cc12] I-68
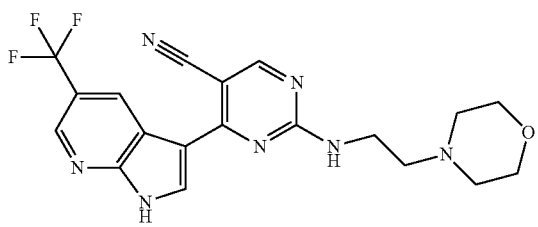 [SMILES: N#Cc1cnc(NCCN2CCOCC2)nc1-c1c[nH]c2ncc(C(F)(F)F)cc12] I-69
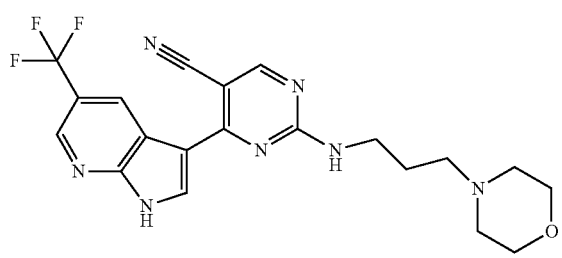 [SMILES: N#Cc1cnc(NCCCN2CCOCC2)nc1-c1c[nH]c2ncc(C(F)(F)F)cc12] I-70
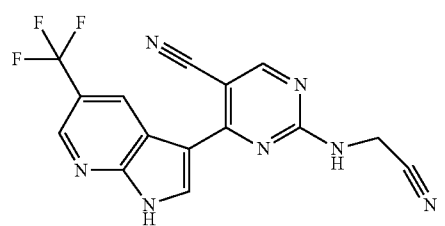 [SMILES: N#CCNc1ncc(C#N)c(-c2c[nH]c3ncc(C(F)(F)F)cc23)n1] I-71

TABLE 1-continued
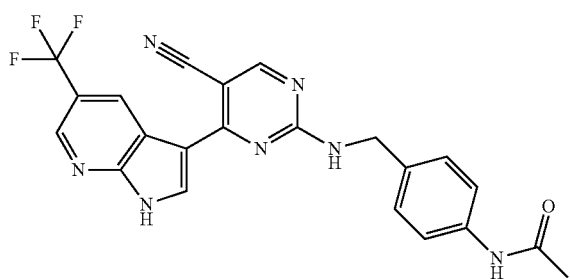 [SMILES: CC(=O)Nc1ccc(CNc2ncc(C#N)c(-c3c[nH]c4ncc(C(F)(F)F)cc34)n2)cc1]
I-72
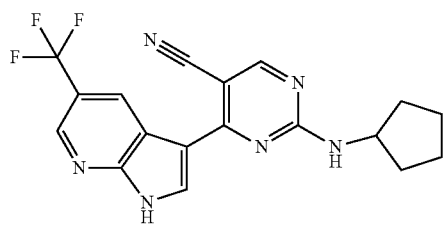 [SMILES: N#Cc1cnc(NC2CCCC2)nc1-c1c[nH]c2ncc(C(F)(F)F)cc12]
I-73
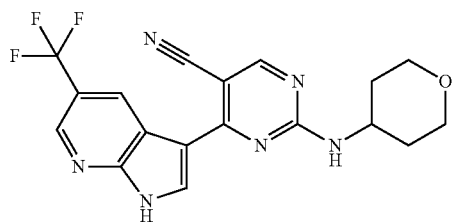 [SMILES: N#Cc1cnc(NC2CCOCC2)nc1-c1c[nH]c2ncc(C(F)(F)F)cc12]
I-74
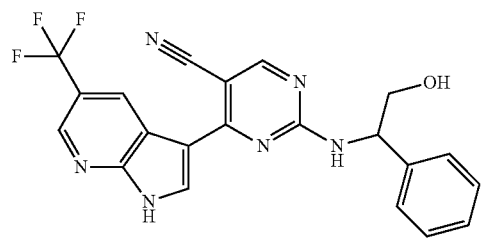 [SMILES: N#Cc1cnc(NC(CO)c2ccccc2)nc1-c1c[nH]c2ncc(C(F)(F)F)cc12]
I-75
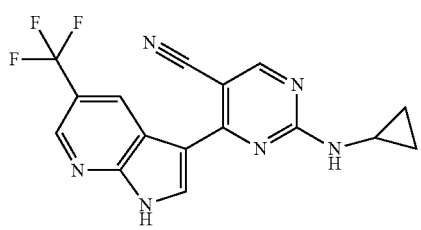 [SMILES: N#Cc1cnc(NC2CC2)nc1-c1c[nH]c2ncc(C(F)(F)F)cc12]
I-76
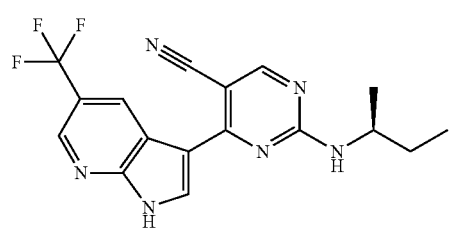 [SMILES: CC[C@H](C)Nc1ncc(C#N)c(-c2c[nH]c3ncc(C(F)(F)F)cc23)n1]
I-77

TABLE 1-continued
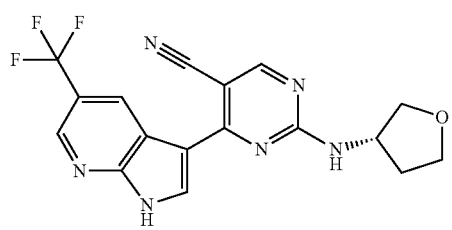 [SMILES: N#Cc1cnc(N[C@H]2CCOC2)nc1-c1c[nH]c2ncc(C(F)(F)F)cc12] I-78
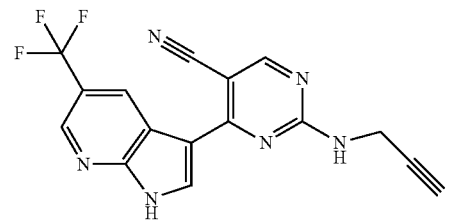 [SMILES: C#CCNc1ncc(C#N)c(-c2c[nH]c3ncc(C(F)(F)F)cc23)n1] I-79
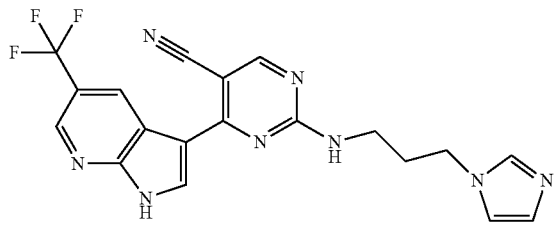 [SMILES: N#Cc1cnc(NCCCn2ccnc2)nc1-c1c[nH]c2ncc(C(F)(F)F)cc12] I-80
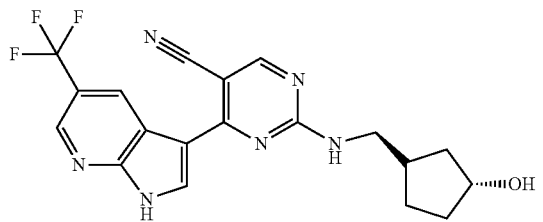 I-81
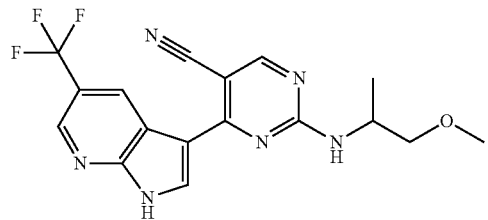 [SMILES: COCC(C)Nc1ncc(C#N)c(-c2c[nH]c3ncc(C(F)(F)F)cc23)n1] I-82
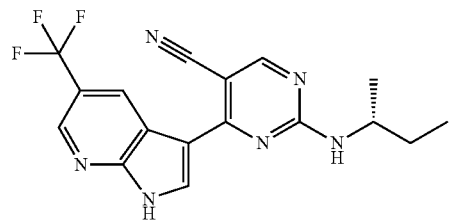 [SMILES: CC[C@@H](C)Nc1ncc(C#N)c(-c2c[nH]c3ncc(C(F)(F)F)cc23)n1] I-83

TABLE 1-continued
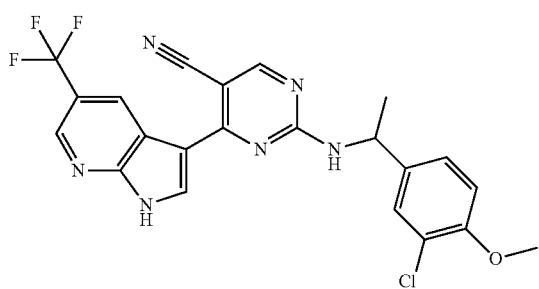 [SMILES: COc1ccc(C(C)Nc2ncc(C#N)c(-c3c[nH]c4ncc(C(F)(F)F)cc34)n2)cc1Cl]
I-84
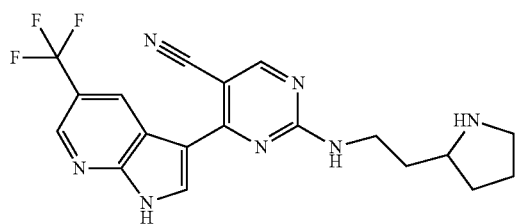 [SMILES: N#Cc1cnc(NCCC2CCCN2)nc1-c1c[nH]c2ncc(C(F)(F)F)cc12]
I-85
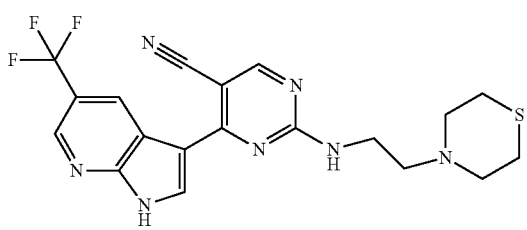 [SMILES: N#Cc1cnc(NCCN2CCSCC2)nc1-c1c[nH]c2ncc(C(F)(F)F)cc12]
I-86
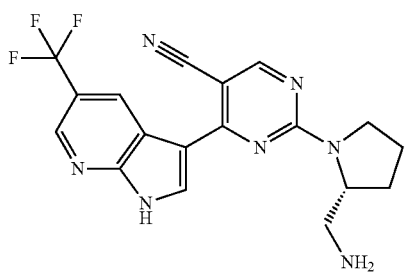 [SMILES: N#Cc1cnc(N2CCC[C@@H]2CN)nc1-c1c[nH]c2ncc(C(F)(F)F)cc12]
I-87
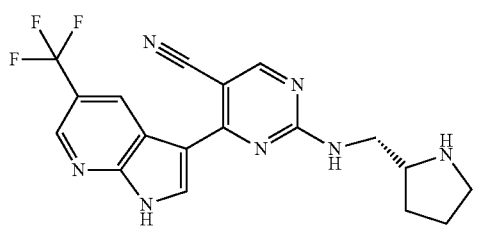
I-88
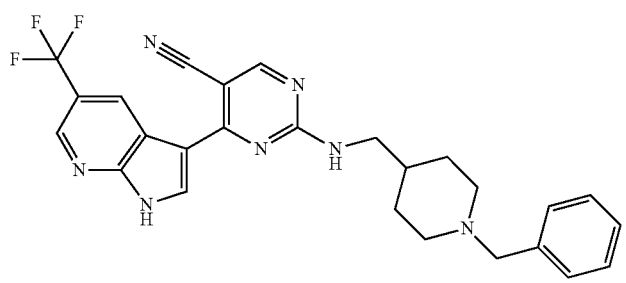 [SMILES: N#Cc1cnc(NCC2CCN(Cc3ccccc3)CC2)nc1-c1c[nH]c2ncc(C(F)(F)F)cc12]
I-89

TABLE 1-continued
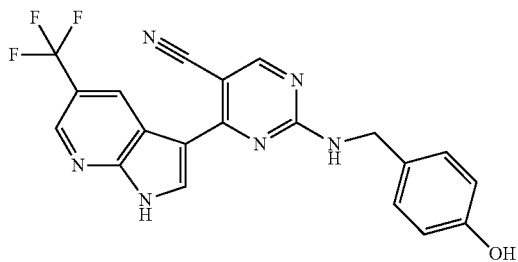 [SMILES: N#Cc1cnc(NCc2ccc(O)cc2)nc1-c1c[nH]c2ncc(C(F)(F)F)cc12]
I-90
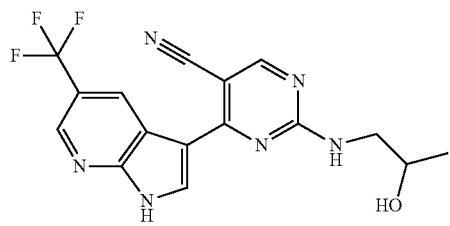 [SMILES: CC(O)CNc1ncc(C#N)c(-c2c[nH]c3ncc(C(F)(F)F)cc23)n1]
I-91
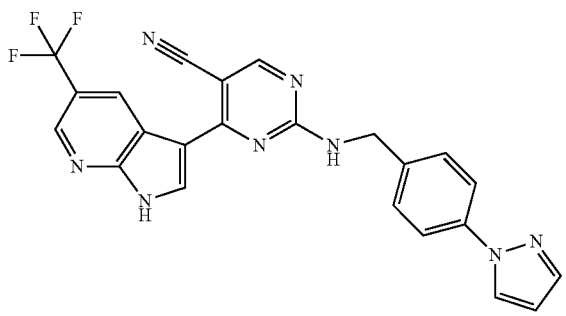 [SMILES: N#Cc1cnc(NCc2ccc(-n3cccn3)cc2)nc1-c1c[nH]c2ncc(C(F)(F)F)cc12]
I-92
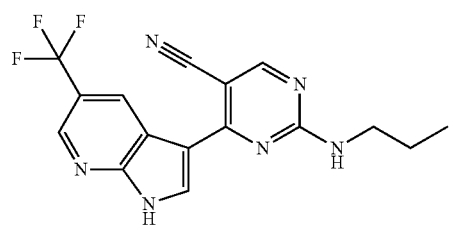 [SMILES: CCCNc1ncc(C#N)c(-c2c[nH]c3ncc(C(F)(F)F)cc23)n1]
I-93
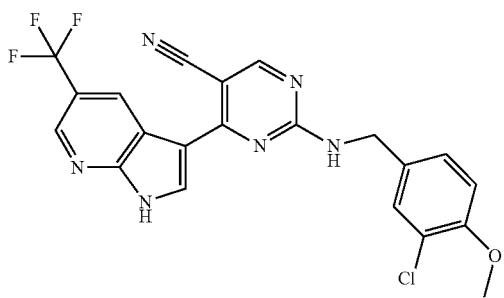 [SMILES: COc1ccc(CNc2ncc(C#N)c(-c3c[nH]c4ncc(C(F)(F)F)cc34)n2)cc1Cl]
I-94
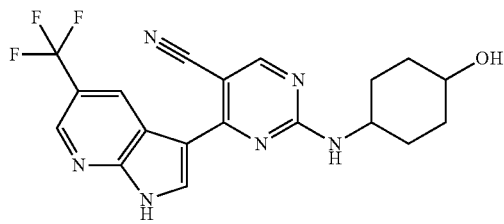 [SMILES: N#Cc1cnc(NC2CCC(O)CC2)nc1-c1c[nH]c2ncc(C(F)(F)F)cc12]
I-95

TABLE 1-continued
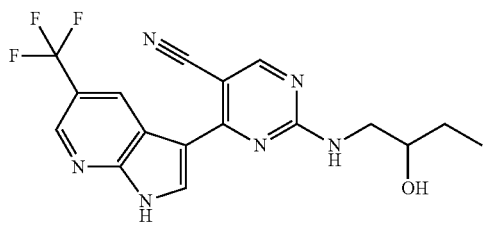 [SMILES: CCC(O)CNc1ncc(C#N)c(-c2c[nH]c3ncc(C(F)(F)F)cc23)n1]
I-96
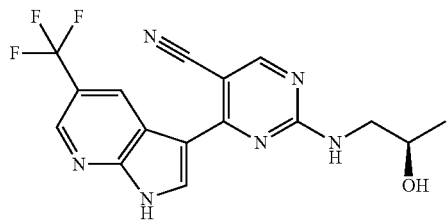 [SMILES: C[C@@H](O)CNc1ncc(C#N)c(-c2c[nH]c3ncc(C(F)(F)F)cc23)n1]
I-97
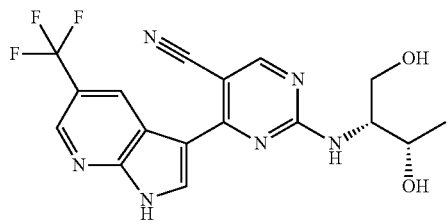 [SMILES: C[C@H](O)[C@@H](CO)Nc1ncc(C#N)c(-c2c[nH]c3ncc(C(F)(F)F)cc23)n1]
I-98
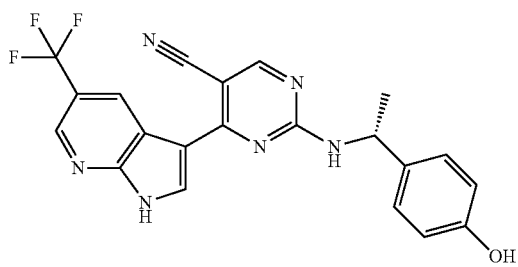 [SMILES: C[C@@H](Nc1ncc(C#N)c(-c2c[nH]c3ncc(C(F)(F)F)cc23)n1)c1ccc(O)cc1]
I-99
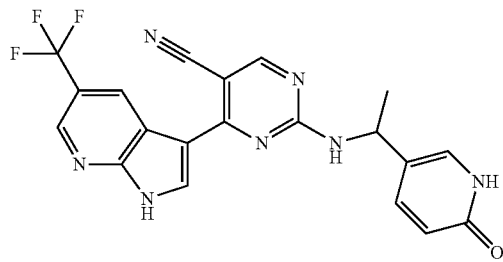 [SMILES: CC(Nc1ncc(C#N)c(-c2c[nH]c3ncc(C(F)(F)F)cc23)n1)c1ccc(=O)[nH]c1]
I-100
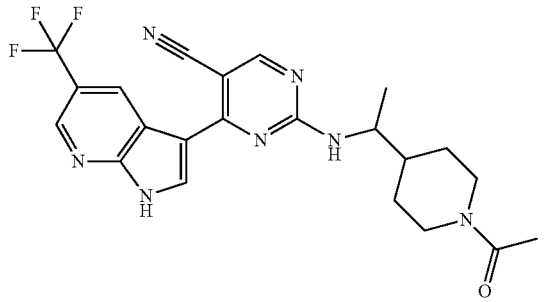 [SMILES: CC(=O)N1CCC(C(C)Nc2ncc(C#N)c(-c3c[nH]c4ncc(C(F)(F)F)cc34)n2)CC1]
I-101

TABLE 1-continued
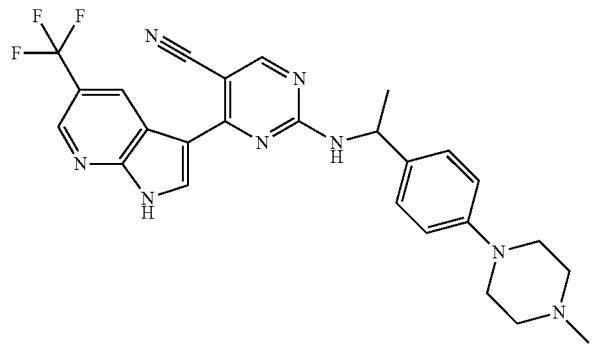 [SMILES: CC(Nc1ncc(C#N)c(-c2c[nH]c3ncc(C(F)(F)F)cc23)n1)c1ccc(N2CCN(C)CC2)cc1]
I-102
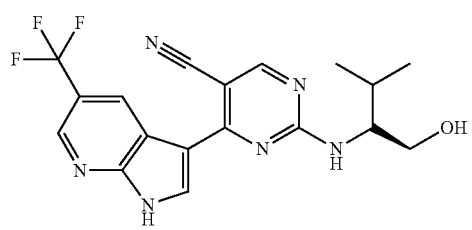
I-103
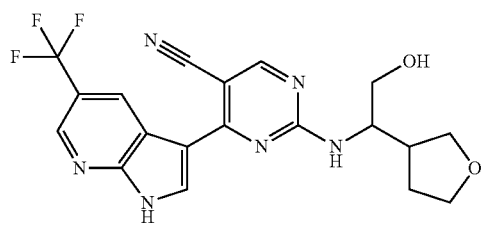 [SMILES: N#Cc1cnc(NC(CO)C2CCOC2)nc1-c1c[nH]c2ncc(C(F)(F)F)cc12]
I-104
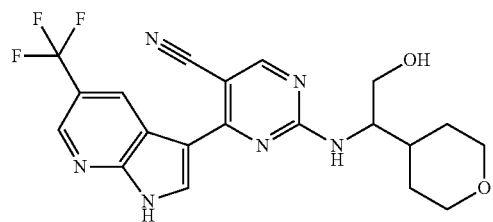 [SMILES: N#Cc1cnc(NC(CO)C2CCOCC2)nc1-c1c[nH]c2ncc(C(F)(F)F)cc12]
I-105
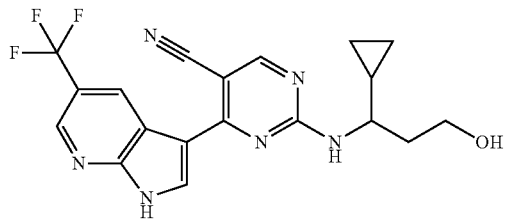 [SMILES: N#Cc1cnc(NC(CCO)C2CC2)nc1-c1c[nH]c2ncc(C(F)(F)F)cc12]
I-106
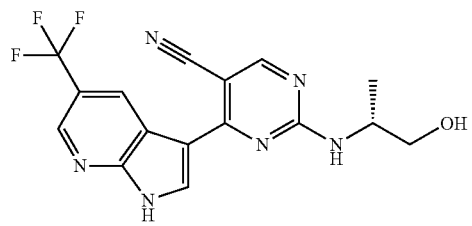 [SMILES: C[C@H](CO)Nc1ncc(C#N)c(-c2c[nH]c3ncc(C(F)(F)F)cc23)n1]
I-107

TABLE 1-continued
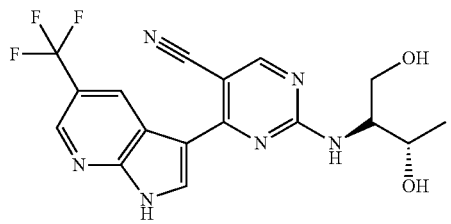 I-108
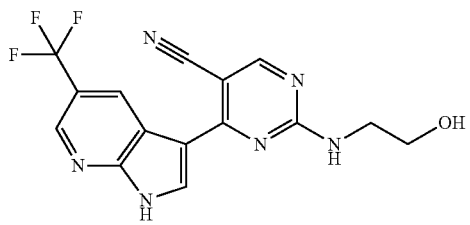 [SMILES: N#Cc1cnc(NCCO)nc1-c1c[nH]c2ncc(C(F)(F)F)cc12] I-109
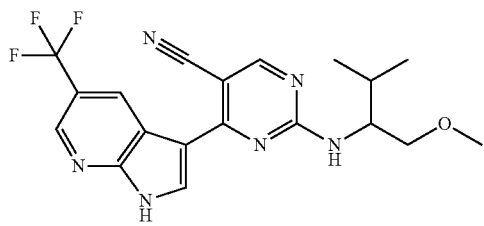 [SMILES: COCC(Nc1ncc(C#N)c(-c2c[nH]c3ncc(C(F)(F)F)cc23)n1)C(C)C] I-110
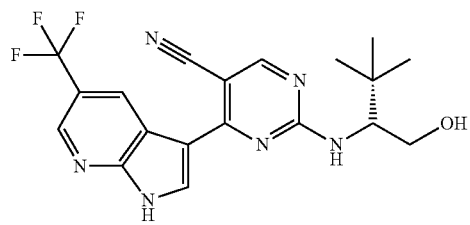 I-111
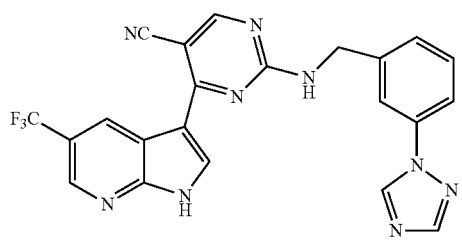 [SMILES: N#Cc1cnc(NCc2cccc(-n3cncn3)c2)nc1-c1c[nH]c2ncc(C(F)(F)F)cc12] I-155
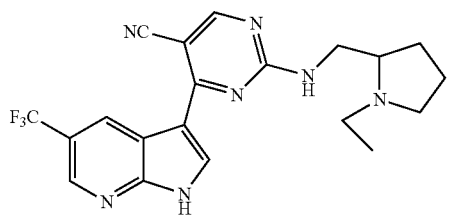 [SMILES: CCN1CCCC1CNc1ncc(C#N)c(-c2c[nH]c3ncc(C(F)(F)F)cc23)n1] I-167
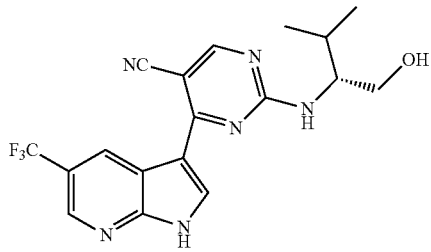 [SMILES: CC(C)[C@H](CO)Nc1ncc(C#N)c(-c2c[nH]c3ncc(C(F)(F)F)cc23)n1] I-103

TABLE 1-continued
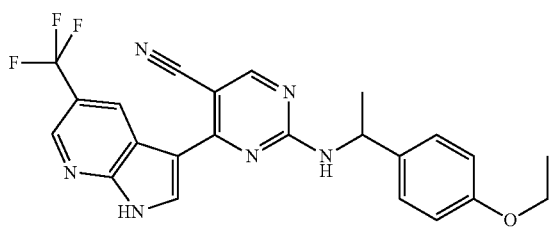 [SMILES: CCOc1ccc(C(C)Nc2ncc(C#N)c(-c3c[nH]c4ncc(C(F)(F)F)cc34)n2)cc1] I-112
 I-113
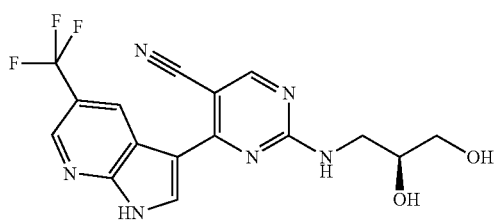 [SMILES: N#Cc1cnc(NC[C@H](O)CO)nc1-c1c[nH]c2ncc(C(F)(F)F)cc12] I-114
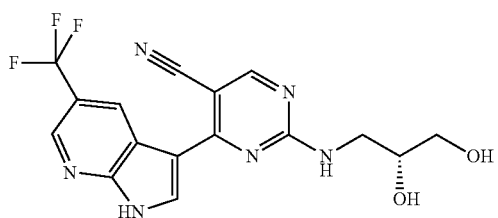 [SMILES: N#Cc1cnc(NC[C@@H](O)CO)nc1-c1c[nH]c2ncc(C(F)(F)F)cc12] I-115
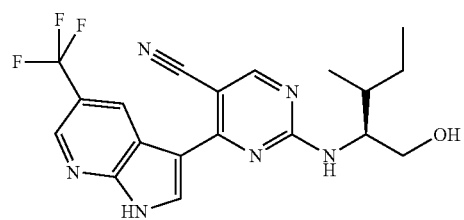 [SMILES: CCC(C)[C@@H](CO)Nc1ncc(C#N)c(-c2c[nH]c3ncc(C(F)(F)F)cc23)n1] I-116
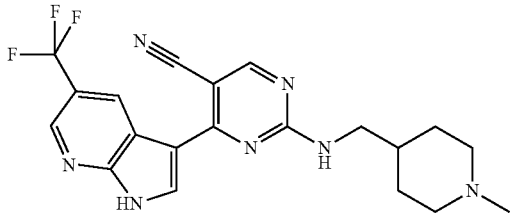 [SMILES: CN1CCC(CNc2ncc(C#N)c(-c3c[nH]c4ncc(C(F)(F)F)cc34)n2)CC1] I-117
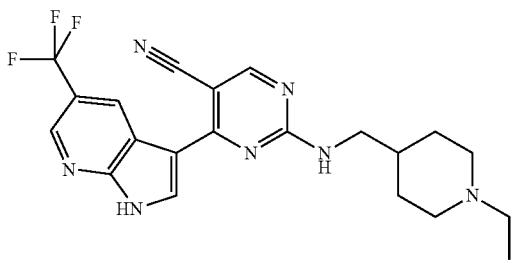 [SMILES: CCN1CCC(CNc2ncc(C#N)c(-c3c[nH]c4ncc(C(F)(F)F)cc34)n2)CC1] I-118

TABLE 1-continued
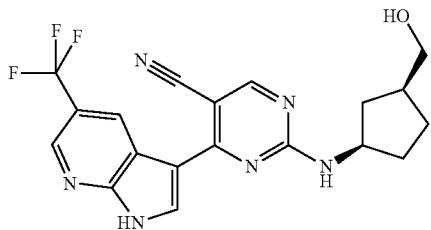 [SMILES: N#Cc1cnc(N[C@@H]2CC[C@H](CO)C2)nc1-c1c[nH]c2ncc(C(F)(F)F)cc12] I-119
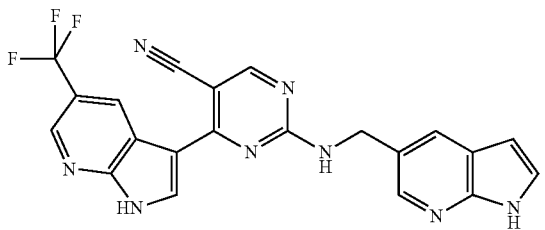 [SMILES: N#Cc1cnc(NCc2cnc3[nH]ccc3c2)nc1-c1c[nH]c2ncc(C(F)(F)F)cc12] I-120
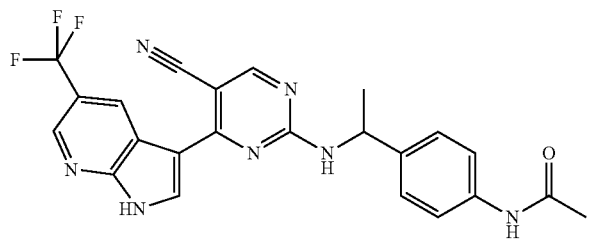 [SMILES: CC(=O)Nc1ccc(C(C)Nc2ncc(C#N)c(-c3c[nH]c4ncc(C(F)(F)F)cc34)n2)cc1] I-121
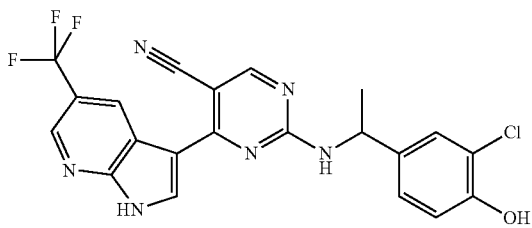 [SMILES: CC(Nc1ncc(C#N)c(-c2c[nH]c3ncc(C(F)(F)F)cc23)n1)c1ccc(O)c(Cl)c1] I-122
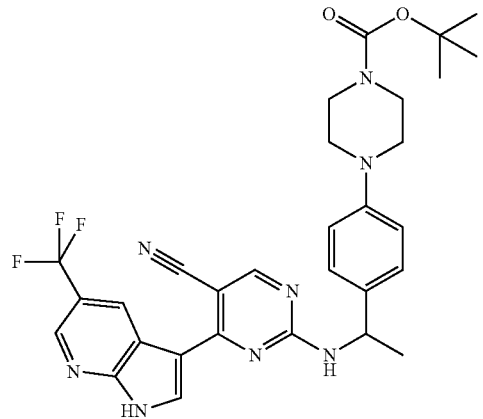 [SMILES: CC(Nc1ncc(C#N)c(-c2c[nH]c3ncc(C(F)(F)F)cc23)n1)c1ccc(N2CCN(C(=O)OC(C)(C)C)CC2)cc1] I-123

TABLE 1-continued
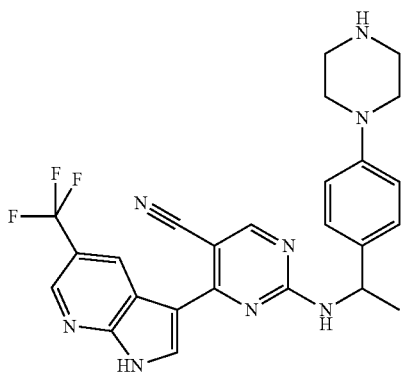 [SMILES: CC(Nc1ncc(C#N)c(-c2c[nH]c3ncc(C(F)(F)F)cc23)n1)c1ccc(N2CCNCC2)cc1]
I-124
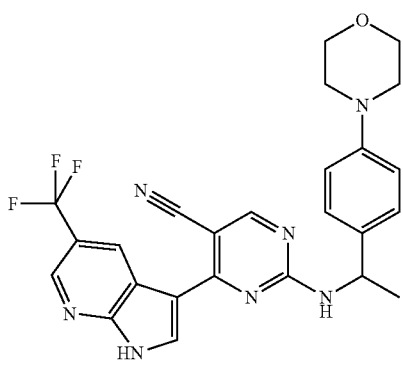 [SMILES: CC(Nc1ncc(C#N)c(-c2c[nH]c3ncc(C(F)(F)F)cc23)n1)c1ccc(N2CCOCC2)cc1]
I-125
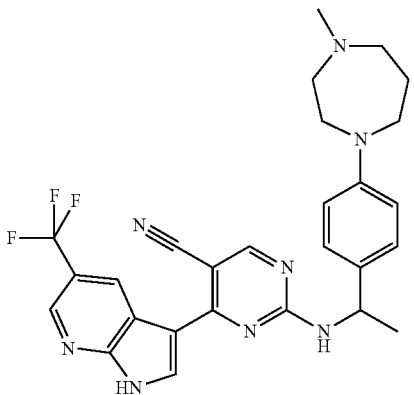 [SMILES: CC(Nc1ncc(C#N)c(-c2c[nH]c3ncc(C(F)(F)F)cc23)n1)c1ccc(N2CCCN(C)CC2)cc1]
I-126
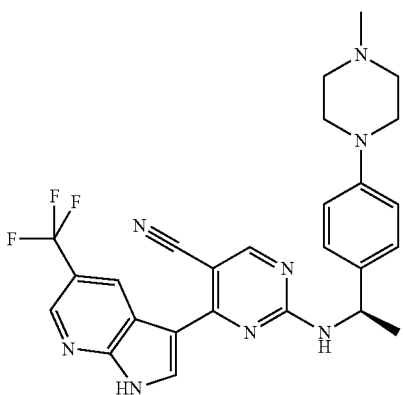 [SMILES: C[C@@H](Nc1ncc(C#N)c(-c2c[nH]c3ncc(C(F)(F)F)cc23)n1)c1ccc(N2CCN(C)CC2)cc1]
I-127

TABLE 1-continued
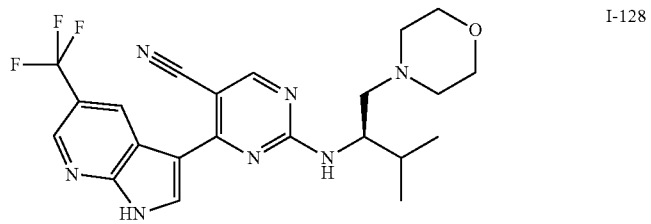
I-128
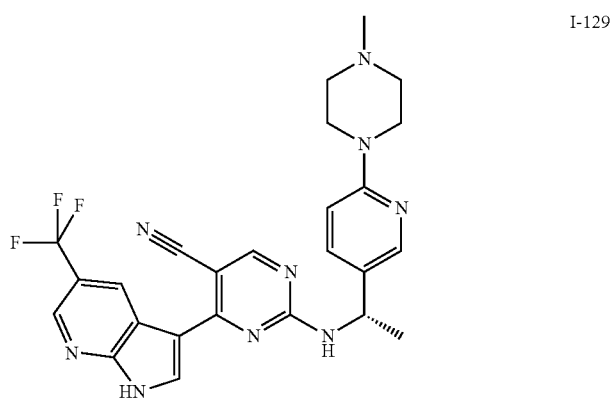
I-129
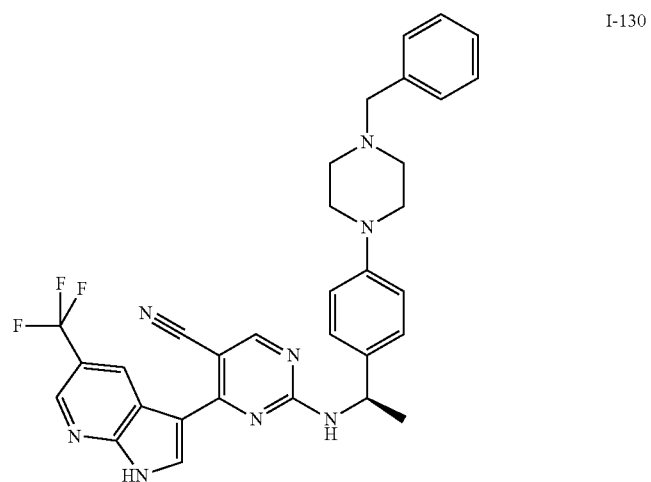
I-130
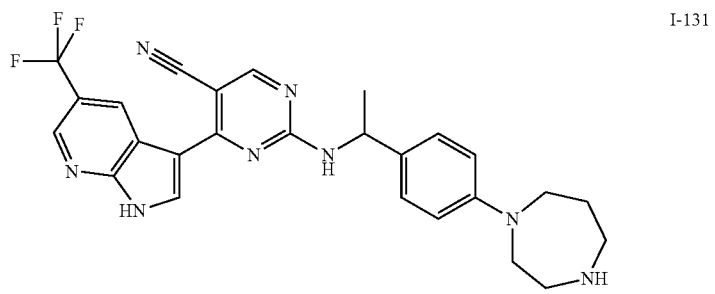
I-131
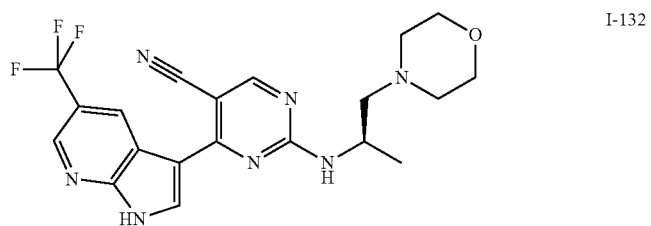
I-132

TABLE 1-continued
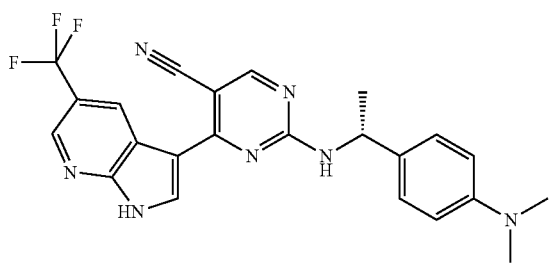 [SMILES: C[C@@H](Nc1ncc(C#N)c(-c2c[nH]c3ncc(C(F)(F)F)cc23)n1)c1ccc(N(C)C)cc1]
I-133
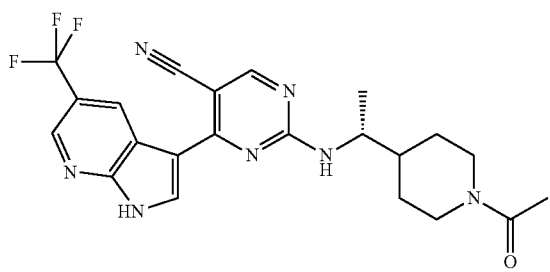 [SMILES: CC(=O)N1CCC([C@@H](C)Nc2ncc(C#N)c(-c3c[nH]c4ncc(C(F)(F)F)cc34)n2)CC1]
I-134
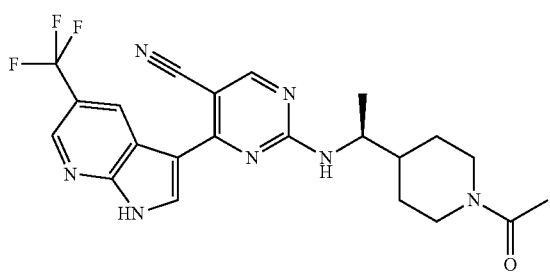 [SMILES: CC(=O)N1CCC([C@H](C)Nc2ncc(C#N)c(-c3c[nH]c4ncc(C(F)(F)F)cc34)n2)CC1]
I-135
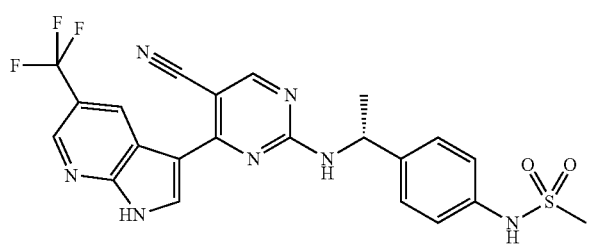 [SMILES: C[C@@H](Nc1ncc(C#N)c(-c2c[nH]c3ncc(C(F)(F)F)cc23)n1)c1ccc(NS(C)(=O)=O)cc1]
I-136
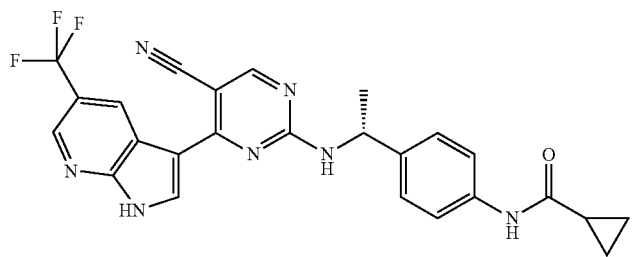 [SMILES: C[C@@H](Nc1ncc(C#N)c(-c2c[nH]c3ncc(C(F)(F)F)cc23)n1)c1ccc(NC(=O)C2CC2)cc1]
I-137

TABLE 1-continued
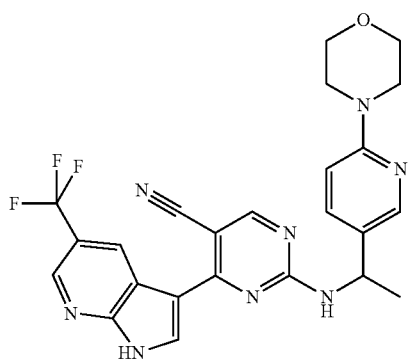 [SMILES: CC(Nc1ncc(C#N)c(-c2c[nH]c3ncc(C(F)(F)F)cc23)n1)c1ccc(N2CCOCC2)nc1]
I-138
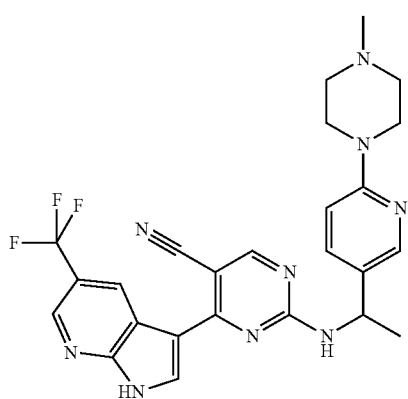
I-139
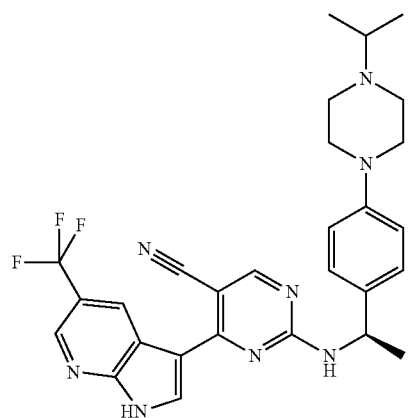 [SMILES: CC(C)N1CCN(c2ccc([C@@H](C)Nc3ncc(C#N)c(-c4c[nH]c5ncc(C(F)(F)F)cc45)n3)cc2)CC1]
I-140
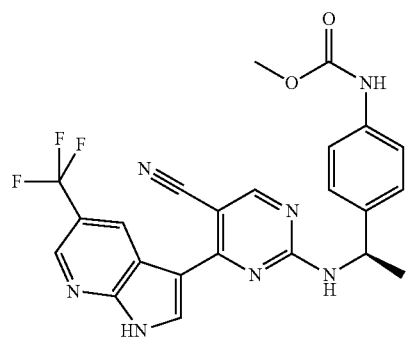 [SMILES: COC(=O)Nc1ccc([C@@H](C)Nc2ncc(C#N)c(-c3c[nH]c4ncc(C(F)(F)F)cc34)n2)cc1]
I-141

TABLE 1-continued
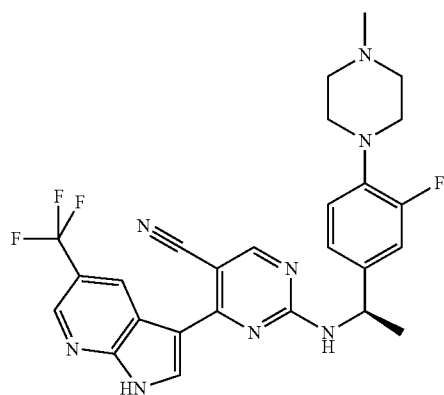 [SMILES: C[C@@H](Nc1ncc(C#N)c(-c2c[nH]c3ncc(C(F)(F)F)cc23)n1)c1ccc(N2CCN(C)CC2)c(F)c1]
I-142
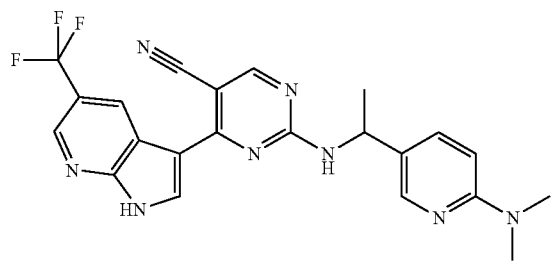 [SMILES: CC(Nc1ncc(C#N)c(-c2c[nH]c3ncc(C(F)(F)F)cc23)n1)c1ccc(N(C)C)nc1]
I-143
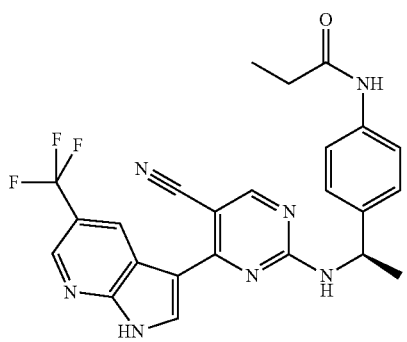 [SMILES: CCC(=O)Nc1ccc([C@@H](C)Nc2ncc(C#N)c(-c3c[nH]c4ncc(C(F)(F)F)cc34)n2)cc1]
I-144
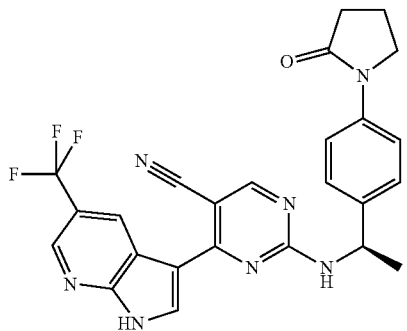 [SMILES: C[C@@H](Nc1ncc(C#N)c(-c2c[nH]c3ncc(C(F)(F)F)cc23)n1)c1ccc(N2CCCC2=O)cc1]
I-145

TABLE 1-continued
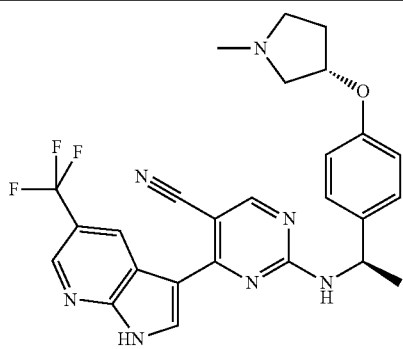 I-146
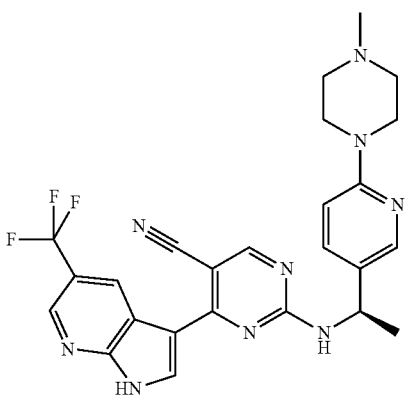 [SMILES: C[C@@H](Nc1ncc(C#N)c(-c2c[nH]c3ncc(C(F)(F)F)cc23)n1)c1ccc(N2CCN(C)CC2)nc1] I-147
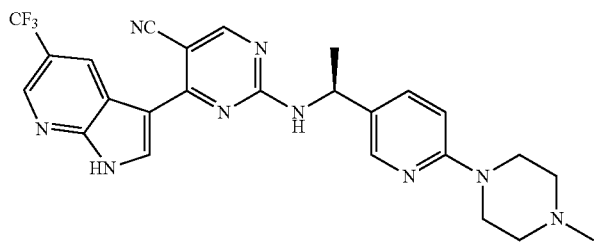 [SMILES: C[C@H](Nc1ncc(C#N)c(-c2c[nH]c3ncc(C(F)(F)F)cc23)n1)c1ccc(N2CCN(C)CC2)nc1] I-148
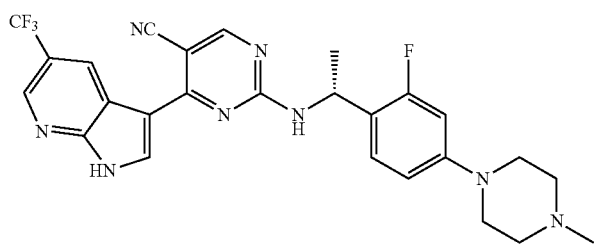 [SMILES: C[C@@H](Nc1ncc(C#N)c(-c2c[nH]c3ncc(C(F)(F)F)cc23)n1)c1ccc(N2CCN(C)CC2)cc1F] I-149
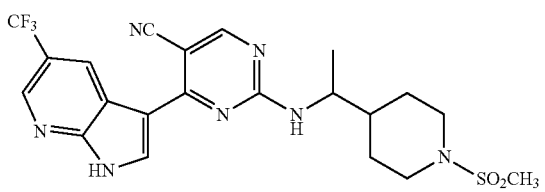 [SMILES: CC(Nc1ncc(C#N)c(-c2c[nH]c3ncc(C(F)(F)F)cc23)n1)C1CCN(S(C)(=O)=O)CC1] I-150
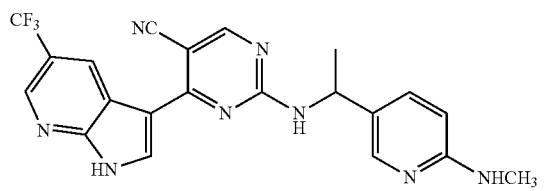 [SMILES: CNc1ccc(C(C)Nc2ncc(C#N)c(-c3c[nH]c4ncc(C(F)(F)F)cc34)n2)cn1] I-151

TABLE 1-continued
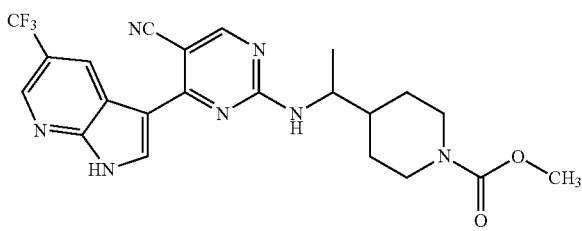 [SMILES: COC(=O)N1CCC(C(C)Nc2ncc(C#N)c(-c3c[nH]c4ncc(C(F)(F)F)cc34)n2)CC1]
I-152
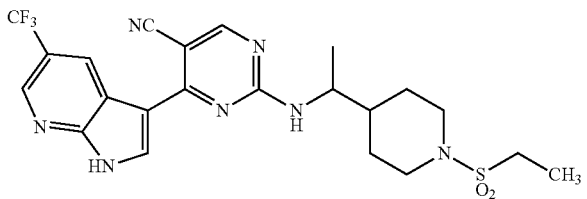 [SMILES: CCS(=O)(=O)N1CCC(C(C)Nc2ncc(C#N)c(-c3c[nH]c4ncc(C(F)(F)F)cc34)n2)CC1]
I-153
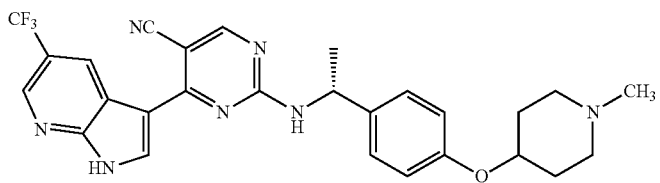 [SMILES: C[C@@H](Nc1ncc(C#N)c(-c2c[nH]c3ncc(C(F)(F)F)cc23)n1)c1ccc(OC2CCN(C)CC2)cc1]
I-154
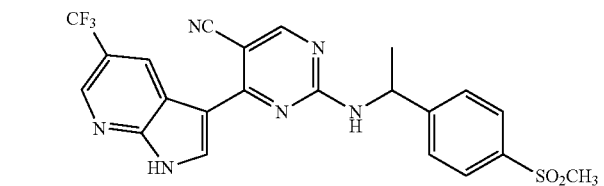 [SMILES: CC(Nc1ncc(C#N)c(-c2c[nH]c3ncc(C(F)(F)F)cc23)n1)c1ccc(S(C)(=O)=O)cc1]
I-155
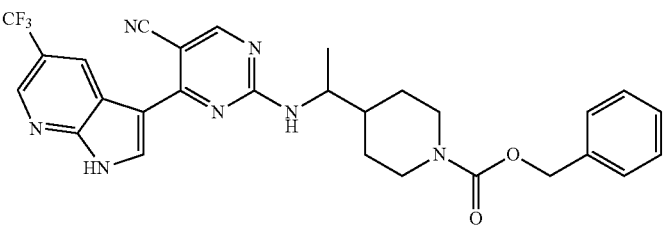 [SMILES: CC(Nc1ncc(C#N)c(-c2c[nH]c3ncc(C(F)(F)F)cc23)n1)C1CCN(C(=O)OCc2ccccc2)CC1]
I-156
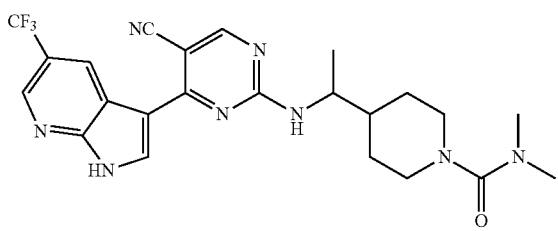
I-157
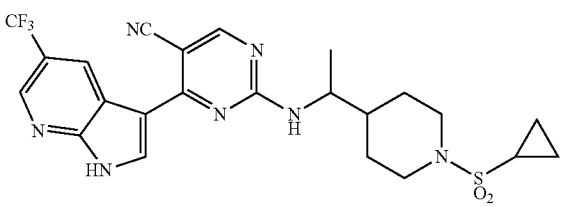 [SMILES: CC(Nc1ncc(C#N)c(-c2c[nH]c3ncc(C(F)(F)F)cc23)n1)C1CCN(S(=O)(=O)C2CC2)CC1]
I-158

TABLE 1-continued
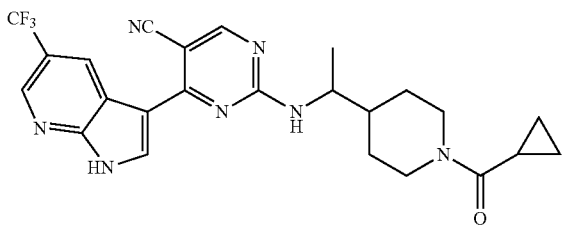 [SMILES: CC(Nc1ncc(C#N)c(-c2c[nH]c3ncc(C(F)(F)F)cc23)n1)C1CCN(C(=O)C2CC2)CC1]
I-159
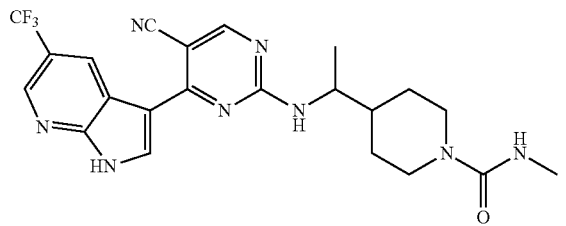 [SMILES: CNC(=O)N1CCC(C(C)Nc2ncc(C#N)c(-c3c[nH]c4ncc(C(F)(F)F)cc34)n2)CC1]
I-160
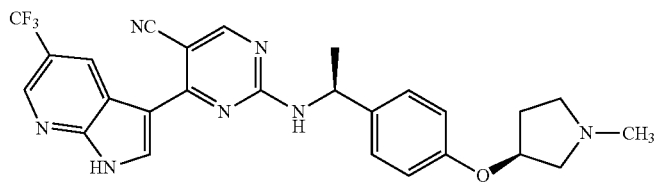 [SMILES: C[C@H](Nc1ncc(C#N)c(-c2c[nH]c3ncc(C(F)(F)F)cc23)n1)c1ccc(O[C@H]2CCN(C)C2)cc1]
I-161
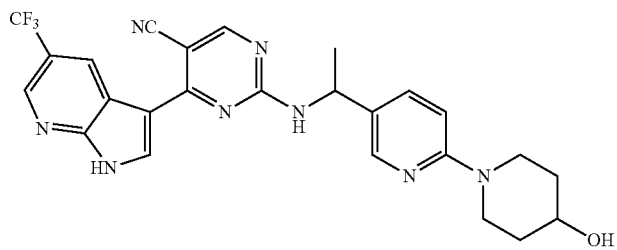 [SMILES: CC(Nc1ncc(C#N)c(-c2c[nH]c3ncc(C(F)(F)F)cc23)n1)c1ccc(N2CCC(O)CC2)nc1]
I-162
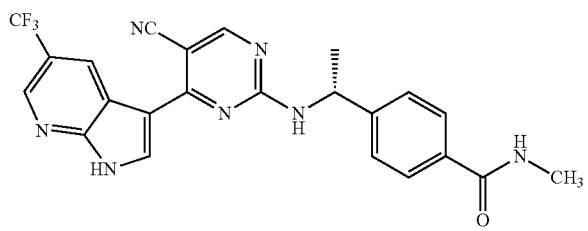 [SMILES: CNC(=O)c1ccc([C@@H](C)Nc2ncc(C#N)c(-c3c[nH]c4ncc(C(F)(F)F)cc34)n2)cc1]
I-163
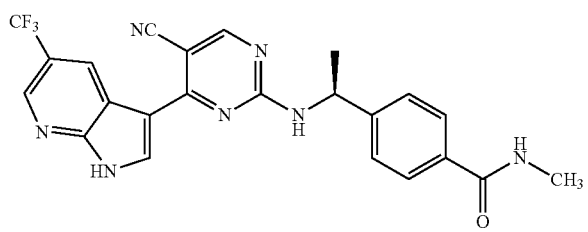 [SMILES: CNC(=O)c1ccc([C@H](C)Nc2ncc(C#N)c(-c3c[nH]c4ncc(C(F)(F)F)cc34)n2)cc1]
I-164
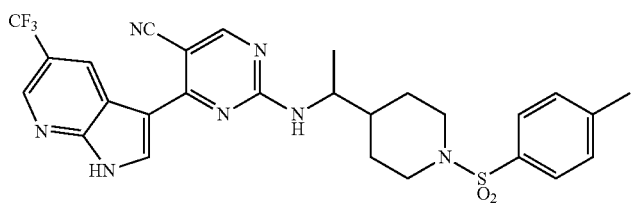 [SMILES: Cc1ccc(S(=O)(=O)N2CCC(C(C)Nc3ncc(C#N)c(-c4c[nH]c5ncc(C(F)(F)F)cc45)n3)CC2)cc1]
I-165

TABLE 1-continued
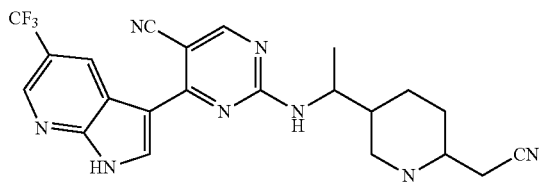 [SMILES: CC(Nc1ncc(C#N)c(-c2c[nH]c3ncc(C(F)(F)F)cc23)n1)C1CCC(CC#N)NC1]
I-166
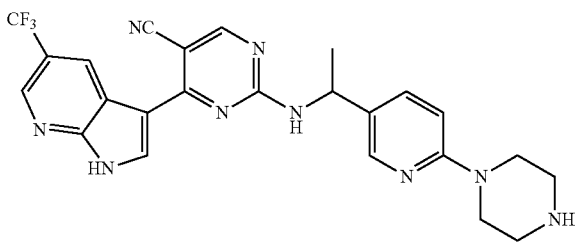 [SMILES: CC(Nc1ncc(C#N)c(-c2c[nH]c3ncc(C(F)(F)F)cc23)n1)c1ccc(N2CCNCC2)nc1]
I-167
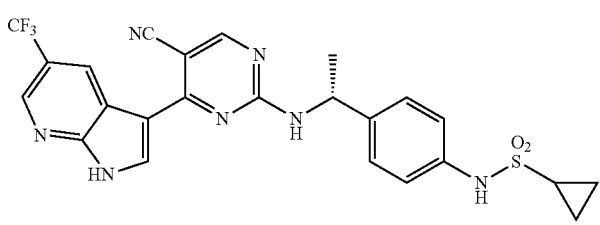 [SMILES: C[C@@H](Nc1ncc(C#N)c(-c2c[nH]c3ncc(C(F)(F)F)cc23)n1)c1ccc(NS(=O)(=O)C2CC2)cc1]
I-168
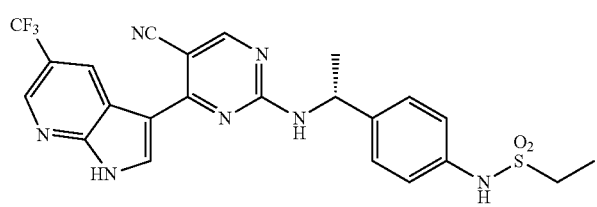 [SMILES: CCS(=O)(=O)Nc1ccc([C@@H](C)Nc2ncc(C#N)c(-c3c[nH]c4ncc(C(F)(F)F)cc34)n2)cc1]
I-169
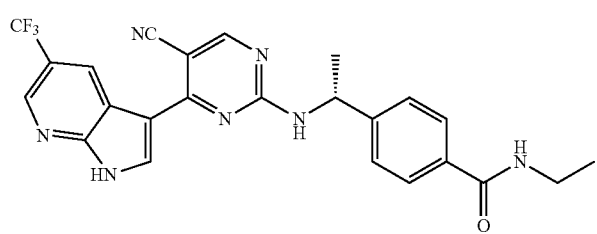 [SMILES: CCNC(=O)c1ccc([C@@H](C)Nc2ncc(C#N)c(-c3c[nH]c4ncc(C(F)(F)F)cc34)n2)cc1]
I-170
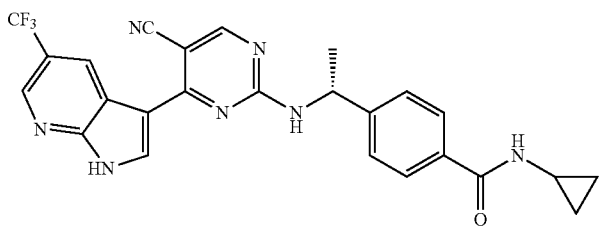 [SMILES: C[C@@H](Nc1ncc(C#N)c(-c2c[nH]c3ncc(C(F)(F)F)cc23)n1)c1ccc(C(=O)NC2CC2)cc1]
I-171
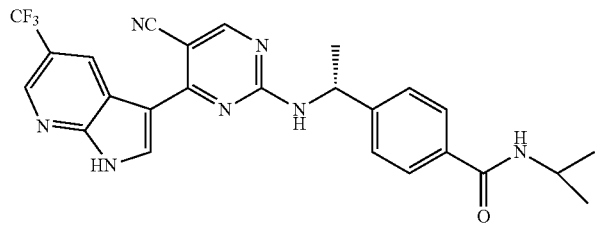 [SMILES: CC(C)NC(=O)c1ccc([C@@H](C)Nc2ncc(C#N)c(-c3c[nH]c4ncc(C(F)(F)F)cc34)n2)cc1]
I-172

TABLE 1-continued
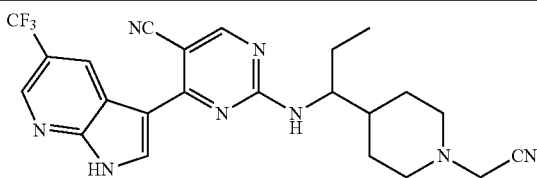 I-173
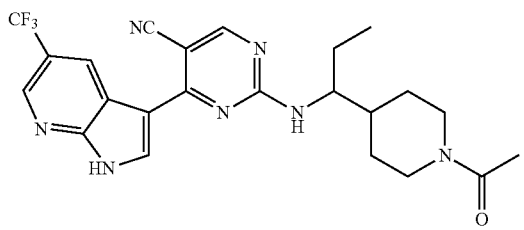 [SMILES: CCC(Nc1ncc(C#N)c(-c2c[nH]c3ncc(C(F)(F)F)cc23)n1)C1CCN(C(C)=O)CC1] I-174
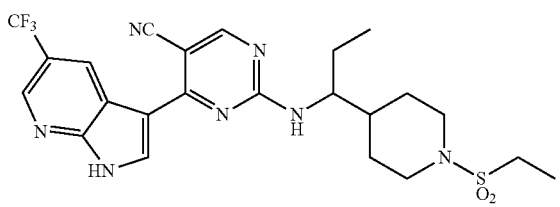 I-175
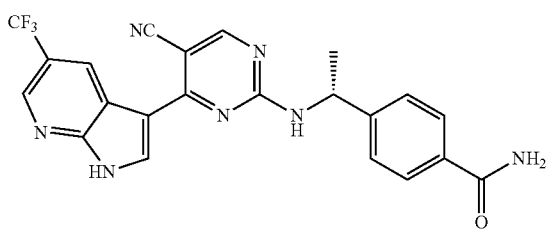 [SMILES: C[C@@H](Nc1ncc(C#N)c(-c2c[nH]c3ncc(C(F)(F)F)cc23)n1)c1ccc(C(N)=O)cc1] I-176
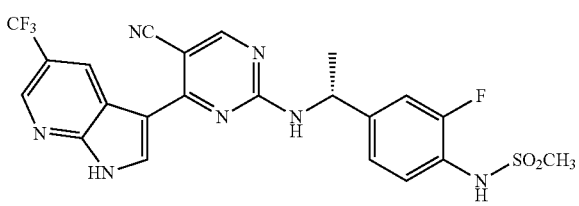 [SMILES: C[C@@H](Nc1ncc(C#N)c(-c2c[nH]c3ncc(C(F)(F)F)cc23)n1)c1ccc(NS(C)(=O)=O)c(F)c1] I-177
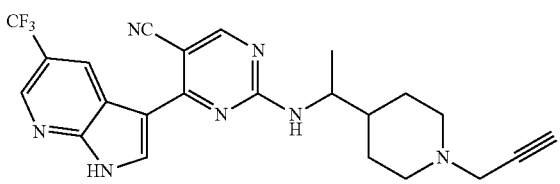 [SMILES: C#CCN1CCC(C(C)Nc2ncc(C#N)c(-c3c[nH]c4ncc(C(F)(F)F)cc34)n2)CC1] I-178
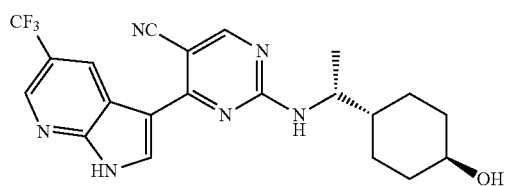 [SMILES: C[C@@H](Nc1ncc(C#N)c(-c2c[nH]c3ncc(C(F)(F)F)cc23)n1)[C@H]1CC[C@H](O)CC1] I-179
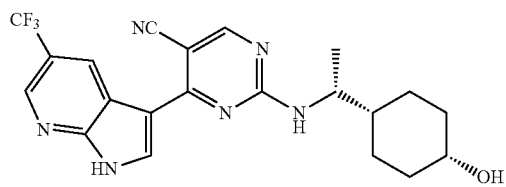 [SMILES: C[C@@H](Nc1ncc(C#N)c(-c2c[nH]c3ncc(C(F)(F)F)cc23)n1)[C@H]1CC[C@@H](O)CC1] I-180

TABLE 1-continued
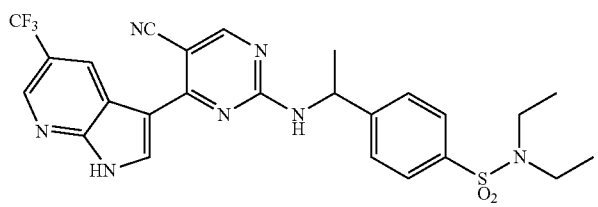 [SMILES: CCN(CC)S(=O)(=O)c1ccc(C(C)Nc2ncc(C#N)c(-c3c[nH]c4ncc(C(F)(F)F)cc34)n2)cc1] I-181
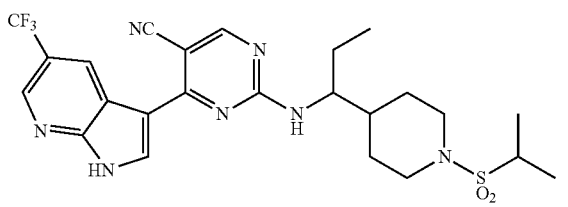 [SMILES: CCC(Nc1ncc(C#N)c(-c2c[nH]c3ncc(C(F)(F)F)cc23)n1)C1CCN(S(=O)(=O)C(C)C)CC1] I-182
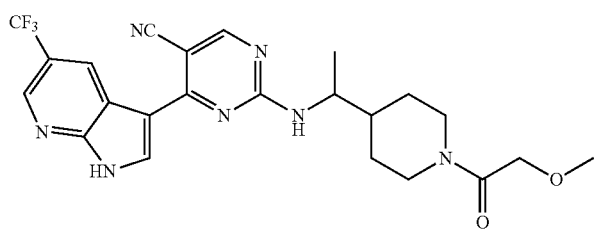 [SMILES: COCC(=O)N1CCC(C(C)Nc2ncc(C#N)c(-c3c[nH]c4ncc(C(F)(F)F)cc34)n2)CC1] I-183
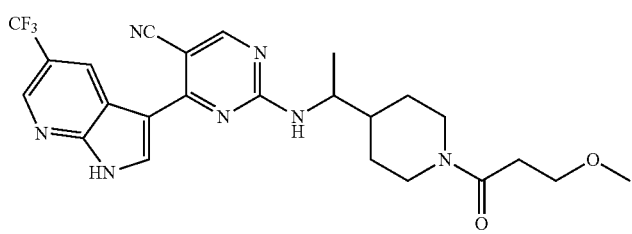 [SMILES: COCCC(=O)N1CCC(C(C)Nc2ncc(C#N)c(-c3c[nH]c4ncc(C(F)(F)F)cc34)n2)CC1] I-184
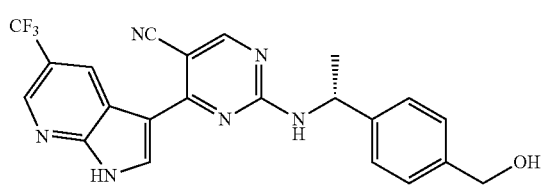 [SMILES: C[C@@H](Nc1ncc(C#N)c(-c2c[nH]c3ncc(C(F)(F)F)cc23)n1)c1ccc(CO)cc1] I-185
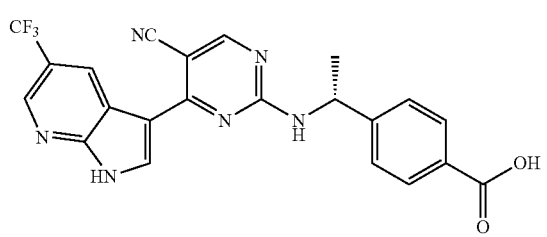 [SMILES: C[C@@H](Nc1ncc(C#N)c(-c2c[nH]c3ncc(C(F)(F)F)cc23)n1)c1ccc(C(=O)O)cc1] I-186
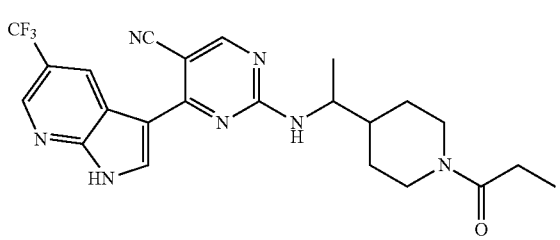 [SMILES: CCC(=O)N1CCC(C(C)Nc2ncc(C#N)c(-c3c[nH]c4ncc(C(F)(F)F)cc34)n2)CC1] I-187

TABLE 1-continued
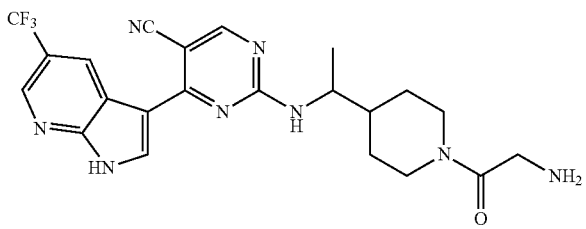 [SMILES: CC(Nc1ncc(C#N)c(-c2c[nH]c3ncc(C(F)(F)F)cc23)n1)C1CCN(C(=O)CN)CC1] I-188
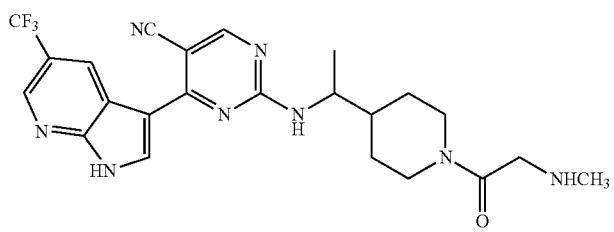 [SMILES: CNCC(=O)N1CCC(C(C)Nc2ncc(C#N)c(-c3c[nH]c4ncc(C(F)(F)F)cc34)n2)CC1] I-189
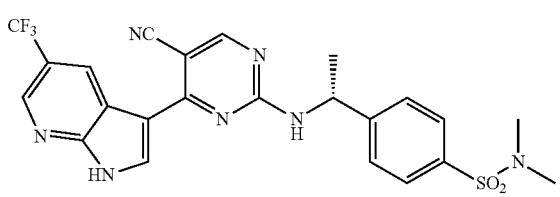 [SMILES: C[C@@H](Nc1ncc(C#N)c(-c2c[nH]c3ncc(C(F)(F)F)cc23)n1)c1ccc(S(=O)(=O)N(C)C)cc1] I-190
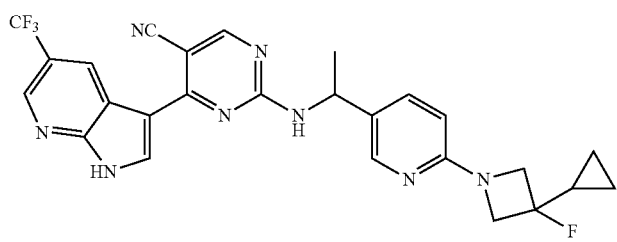 [SMILES: CC(Nc1ncc(C#N)c(-c2c[nH]c3ncc(C(F)(F)F)cc23)n1)c1ccc(N2CC(F)(C3CC3)C2)nc1] I-191
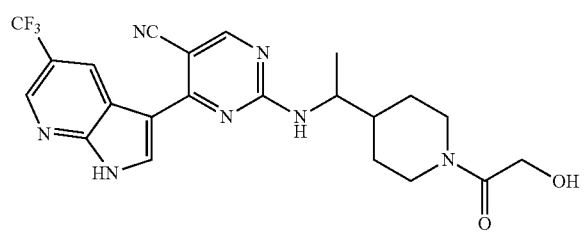 [SMILES: CC(Nc1ncc(C#N)c(-c2c[nH]c3ncc(C(F)(F)F)cc23)n1)C1CCN(C(=O)CO)CC1] I-192
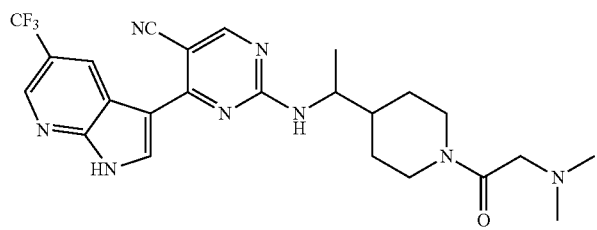 [SMILES: CC(Nc1ncc(C#N)c(-c2c[nH]c3ncc(C(F)(F)F)cc23)n1)C1CCN(C(=O)CN(C)C)CC1] I-193
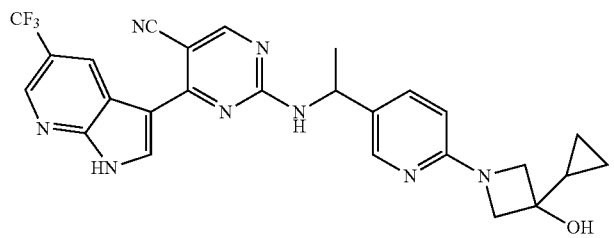 [SMILES: CC(Nc1ncc(C#N)c(-c2c[nH]c3ncc(C(F)(F)F)cc23)n1)c1ccc(N2CC(O)(C3CC3)C2)nc1] I-194

TABLE 1-continued
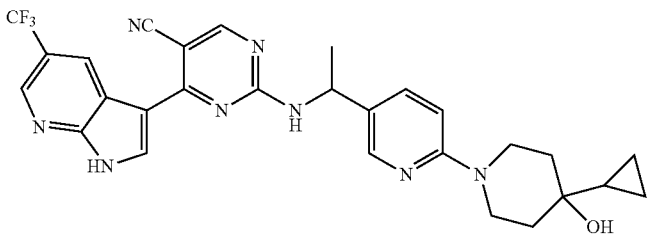 [SMILES: CC(Nc1ncc(C#N)c(-c2c[nH]c3ncc(C(F)(F)F)cc23)n1)c1ccc(N2CCC(O)(C3CC3)CC2)nc1] I-195
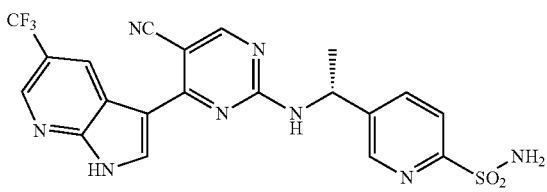 [SMILES: C[C@@H](Nc1ncc(C#N)c(-c2c[nH]c3ncc(C(F)(F)F)cc23)n1)c1ccc(S(N)(=O)=O)nc1] I-196
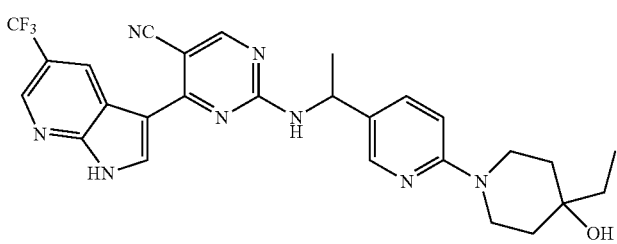 [SMILES: CCC1(O)CCN(c2ccc(C(C)Nc3ncc(C#N)c(-c4c[nH]c5ncc(C(F)(F)F)cc45)n3)cn2)CC1] I-197
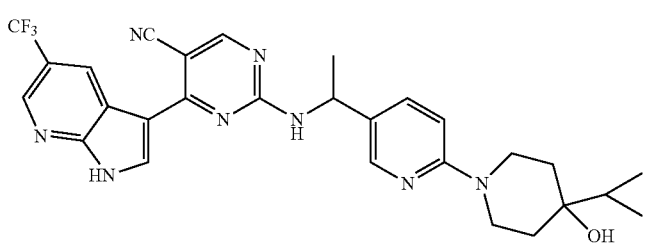 [SMILES: CC(Nc1ncc(C#N)c(-c2c[nH]c3ncc(C(F)(F)F)cc23)n1)c1ccc(N2CCC(O)(C(C)C)CC2)nc1] I-198
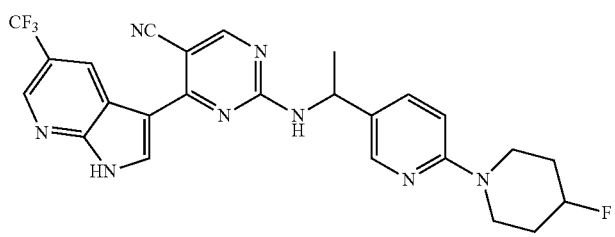 [SMILES: CC(Nc1ncc(C#N)c(-c2c[nH]c3ncc(C(F)(F)F)cc23)n1)c1ccc(N2CCC(F)CC2)nc1] I-199
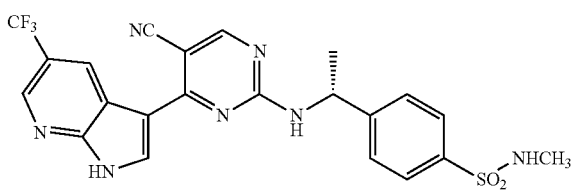 [SMILES: CNS(=O)(=O)c1ccc([C@@H](C)Nc2ncc(C#N)c(-c3c[nH]c4ncc(C(F)(F)F)cc34)n2)cc1] I-200
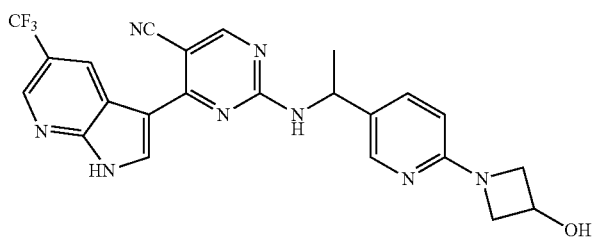 [SMILES: CC(Nc1ncc(C#N)c(-c2c[nH]c3ncc(C(F)(F)F)cc23)n1)c1ccc(N2CC(O)C2)nc1] I-201

TABLE 1-continued
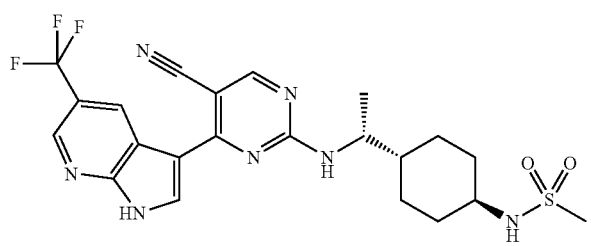 [SMILES: C[C@@H](Nc1ncc(C#N)c(-c2c[nH]c3ncc(C(F)(F)F)cc23)n1)[C@H]1CC[C@H](NS(C)(=O)=O)CC1]
I-202
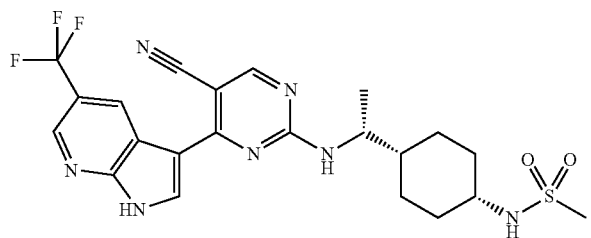 [SMILES: C[C@@H](Nc1ncc(C#N)c(-c2c[nH]c3ncc(C(F)(F)F)cc23)n1)[C@H]1CC[C@@H](NS(C)(=O)=O)CC1]
I-203
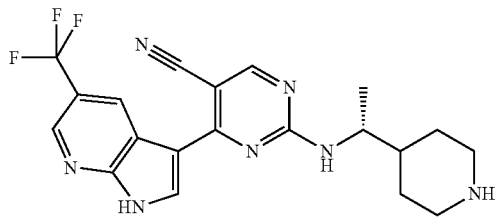 [SMILES: C[C@@H](Nc1ncc(C#N)c(-c2c[nH]c3ncc(C(F)(F)F)cc23)n1)C1CCNCC1]
I-204
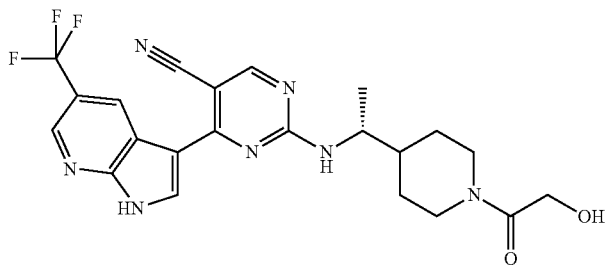 [SMILES: C[C@@H](Nc1ncc(C#N)c(-c2c[nH]c3ncc(C(F)(F)F)cc23)n1)C1CCN(C(=O)CO)CC1]
I-205
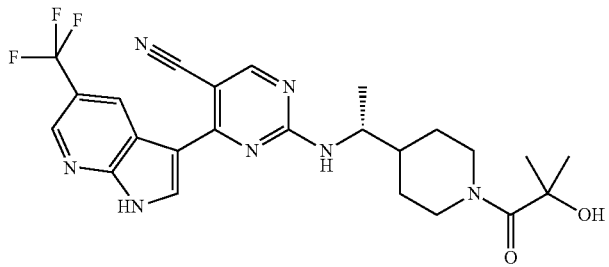 [SMILES: C[C@@H](Nc1ncc(C#N)c(-c2c[nH]c3ncc(C(F)(F)F)cc23)n1)C1CCN(C(=O)C(C)(C)O)CC1]
I-206
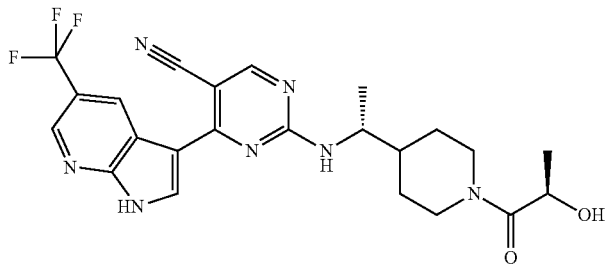 [SMILES: C[C@@H](O)C(=O)N1CCC([C@@H](C)Nc2ncc(C#N)c(-c3c[nH]c4ncc(C(F)(F)F)cc34)n2)CC1]
I-207

TABLE 1-continued
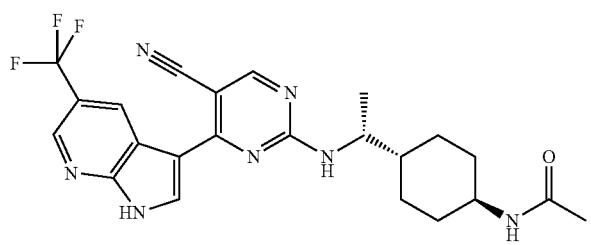 [SMILES: CC(=O)N[C@H]1CC[C@H]([C@@H](C)Nc2ncc(C#N)c(-c3c[nH]c4ncc(C(F)(F)F)cc34)n2)CC1]
I-208
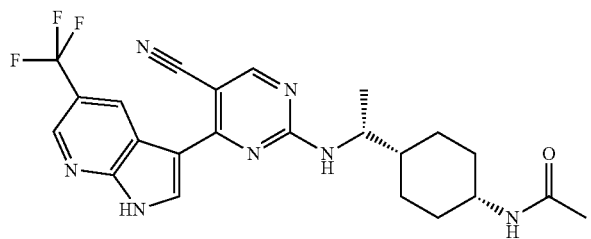 [SMILES: CC(=O)N[C@H]1CC[C@@H]([C@@H](C)Nc2ncc(C#N)c(-c3c[nH]c4ncc(C(F)(F)F)cc34)n2)CC1]
I-209
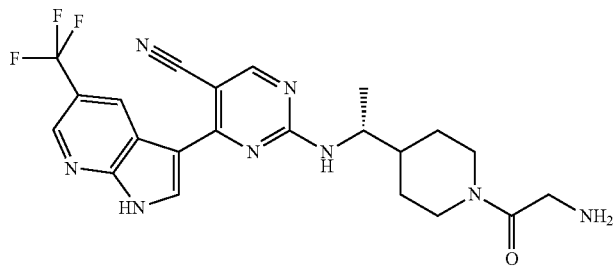 [SMILES: C[C@@H](Nc1ncc(C#N)c(-c2c[nH]c3ncc(C(F)(F)F)cc23)n1)C1CCN(C(=O)CN)CC1]
I-210
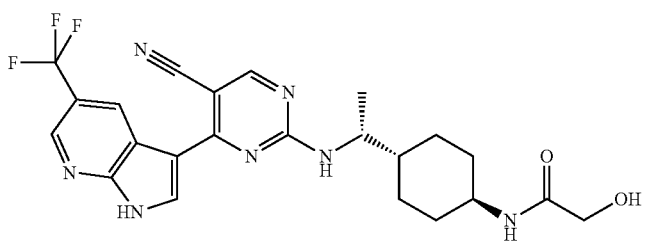 [SMILES: C[C@@H](Nc1ncc(C#N)c(-c2c[nH]c3ncc(C(F)(F)F)cc23)n1)[C@H]1CC[C@H](NC(=O)CO)CC1]
I-211
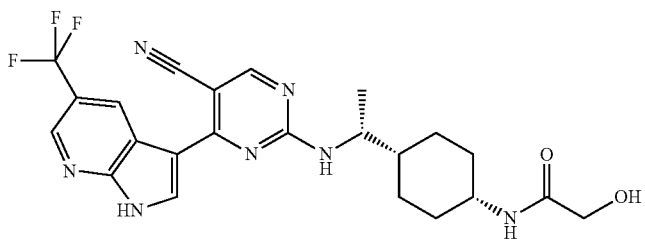 [SMILES: C[C@@H](Nc1ncc(C#N)c(-c2c[nH]c3ncc(C(F)(F)F)cc23)n1)[C@H]1CC[C@@H](NC(=O)CO)CC1]
I-212
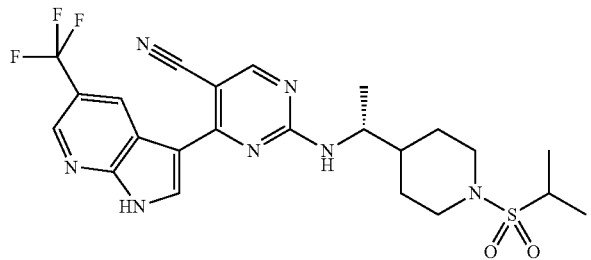 [SMILES: CC(C)S(=O)(=O)N1CCC([C@@H](C)Nc2ncc(C#N)c(-c3c[nH]c4ncc(C(F)(F)F)cc34)n2)CC1]
I-213

TABLE 1-continued
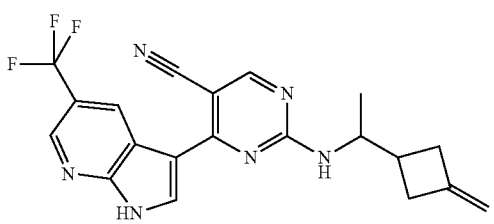 [SMILES: C=C1CC(C(C)Nc2ncc(C#N)c(-c3c[nH]c4ncc(C(F)(F)F)cc34)n2)C1]
I-214
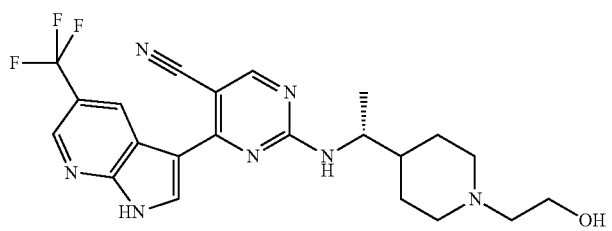 [SMILES: C[C@@H](Nc1ncc(C#N)c(-c2c[nH]c3ncc(C(F)(F)F)cc23)n1)C1CCN(CCO)CC1]
I-215
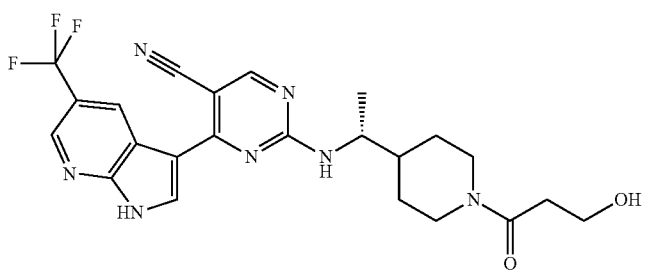 [SMILES: C[C@@H](Nc1ncc(C#N)c(-c2c[nH]c3ncc(C(F)(F)F)cc23)n1)C1CCN(C(=O)CCO)CC1]
I-216
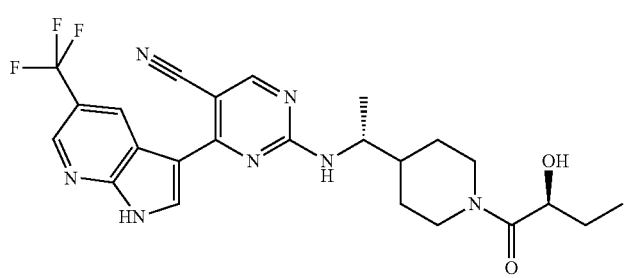 [SMILES: CC[C@H](O)C(=O)N1CCC([C@@H](C)Nc2ncc(C#N)c(-c3c[nH]c4ncc(C(F)(F)F)cc34)n2)CC1]
I-217
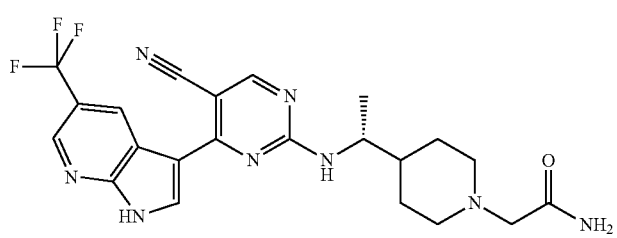 [SMILES: C[C@@H](Nc1ncc(C#N)c(-c2c[nH]c3ncc(C(F)(F)F)cc23)n1)C1CCN(CC(N)=O)CC1]
I-218
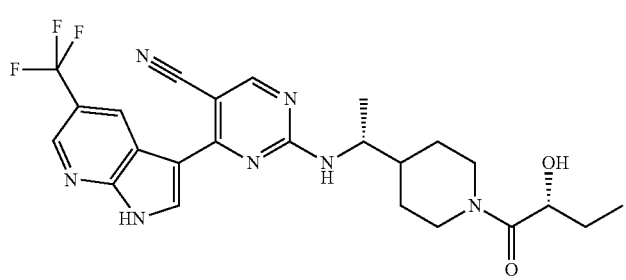 [SMILES: CC[C@@H](O)C(=O)N1CCC([C@@H](C)Nc2ncc(C#N)c(-c3c[nH]c4ncc(C(F)(F)F)cc34)n2)CC1]
I-219

TABLE 1-continued
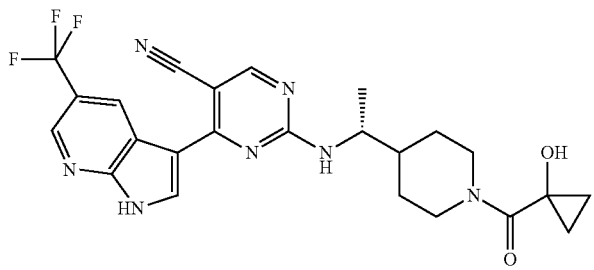 [SMILES: C[C@@H](Nc1ncc(C#N)c(-c2c[nH]c3ncc(C(F)(F)F)cc23)n1)C1CCN(C(=O)C2(O)CC2)CC1]
I-220
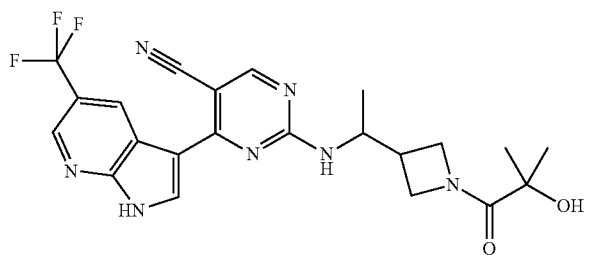 [SMILES: CC(Nc1ncc(C#N)c(-c2c[nH]c3ncc(C(F)(F)F)cc23)n1)C1CN(C(=O)C(C)(C)O)C1]
I-221
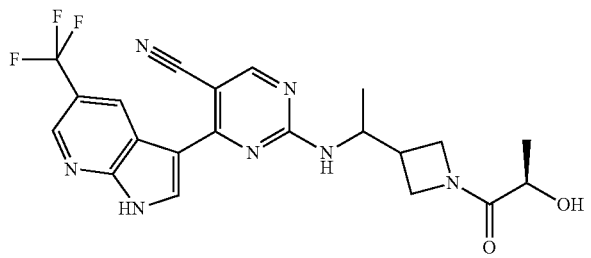 [SMILES: CC(Nc1ncc(C#N)c(-c2c[nH]c3ncc(C(F)(F)F)cc23)n1)C1CN(C(=O)[C@@H](C)O)C1]
I-222
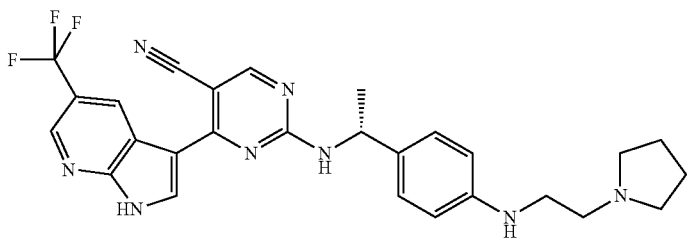 [SMILES: C[C@@H](Nc1ncc(C#N)c(-c2c[nH]c3ncc(C(F)(F)F)cc23)n1)c1ccc(NCCN2CCCC2)cc1]
I-223
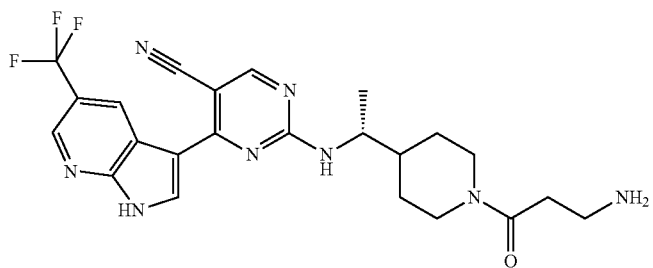 [SMILES: C[C@@H](Nc1ncc(C#N)c(-c2c[nH]c3ncc(C(F)(F)F)cc23)n1)C1CCN(C(=O)CCN)CC1]
I-224
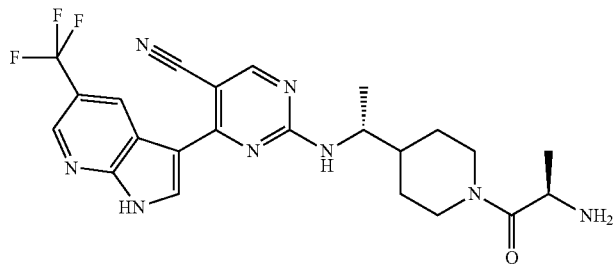 [SMILES: C[C@@H](N)C(=O)N1CCC([C@@H](C)Nc2ncc(C#N)c(-c3c[nH]c4ncc(C(F)(F)F)cc34)n2)CC1]
I-225

TABLE 1-continued
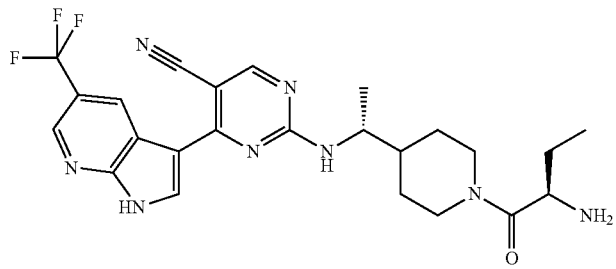 [SMILES: CC[C@@H](N)C(=O)N1CCC([C@@H](C)Nc2ncc(C#N)c(-c3c[nH]c4ncc(C(F)(F)F)cc34)n2)CC1]
I-226
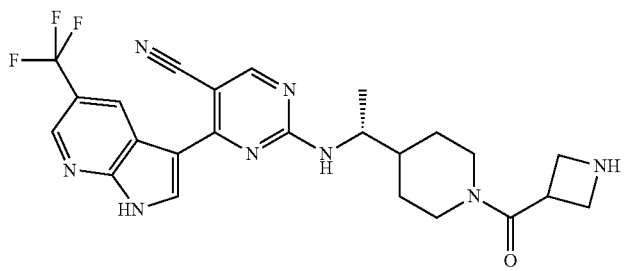 [SMILES: C[C@@H](Nc1ncc(C#N)c(-c2c[nH]c3ncc(C(F)(F)F)cc23)n1)C1CCN(C(=O)C2CNC2)CC1]
I-227
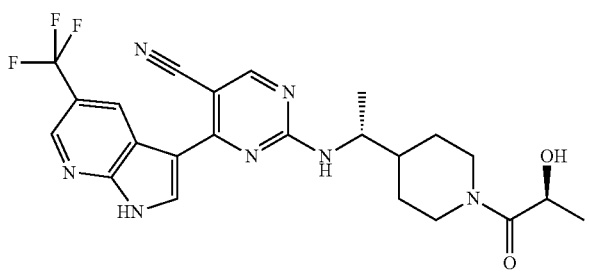 [SMILES: C[C@H](O)C(=O)N1CCC([C@@H](C)Nc2ncc(C#N)c(-c3c[nH]c4ncc(C(F)(F)F)cc34)n2)CC1]
I-228
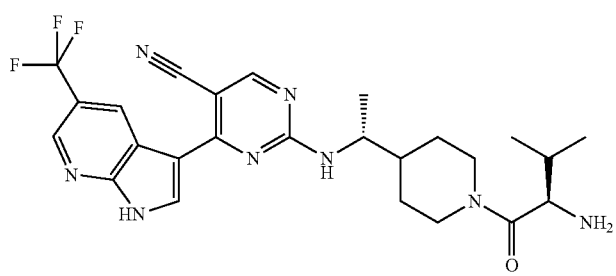 [SMILES: CC(C)[C@@H](N)C(=O)N1CCC([C@@H](C)Nc2ncc(C#N)c(-c3c[nH]c4ncc(C(F)(F)F)cc34)n2)CC1]
I-229
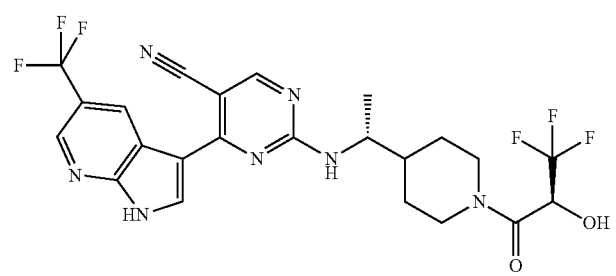 [SMILES: C[C@@H](Nc1ncc(C#N)c(-c2c[nH]c3ncc(C(F)(F)F)cc23)n1)C1CCN(C(=O)[C@H](O)C(F)(F)F)CC1]
I-230
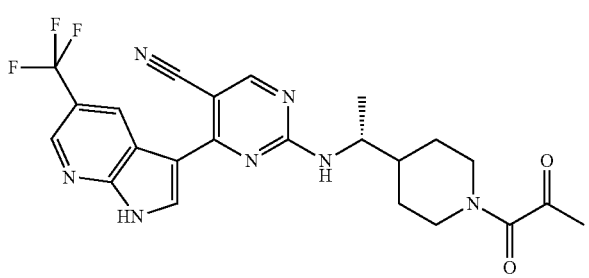 [SMILES: CC(=O)C(=O)N1CCC([C@@H](C)Nc2ncc(C#N)c(-c3c[nH]c4ncc(C(F)(F)F)cc34)n2)CC1]
I-231

TABLE 1-continued
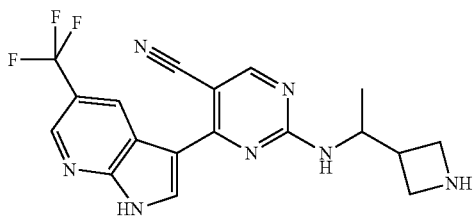 [SMILES: CC(Nc1ncc(C#N)c(-c2c[nH]c3ncc(C(F)(F)F)cc23)n1)C1CNC1]
I-232
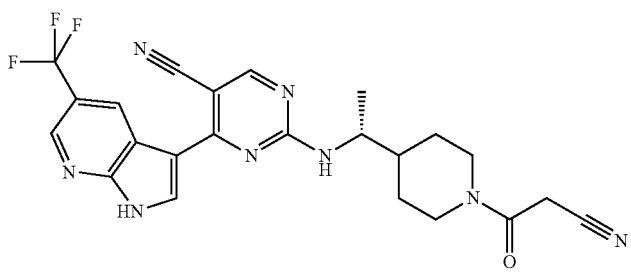 [SMILES: C[C@@H](Nc1ncc(C#N)c(-c2c[nH]c3ncc(C(F)(F)F)cc23)n1)C1CCN(C(=O)CC#N)CC1]
I-233
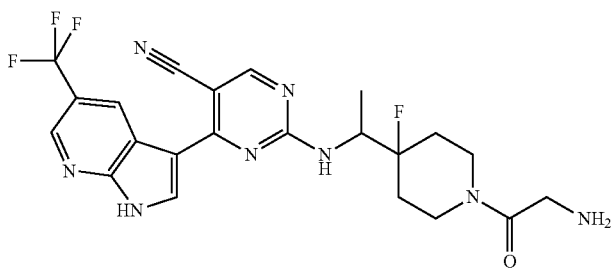 [SMILES: CC(Nc1ncc(C#N)c(-c2c[nH]c3ncc(C(F)(F)F)cc23)n1)C1(F)CCN(C(=O)CN)CC1]
I-234
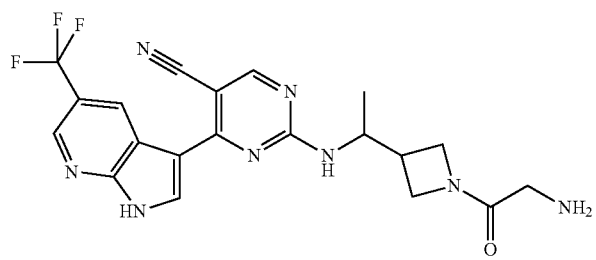 [SMILES: CC(Nc1ncc(C#N)c(-c2c[nH]c3ncc(C(F)(F)F)cc23)n1)C1CN(C(=O)CN)C1]
I-235
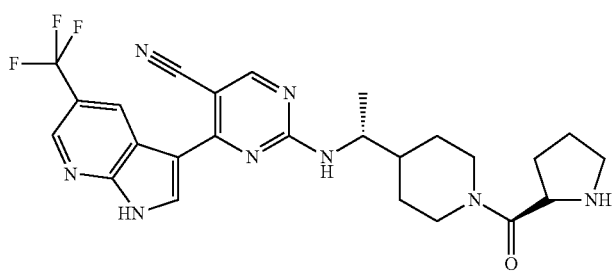
I-236
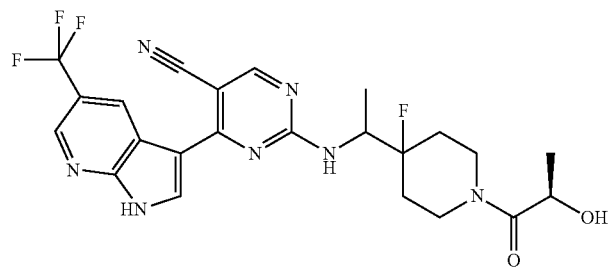 [SMILES: CC(Nc1ncc(C#N)c(-c2c[nH]c3ncc(C(F)(F)F)cc23)n1)C1(F)CCN(C(=O)[C@@H](C)O)CC1]
I-237

TABLE 1-continued
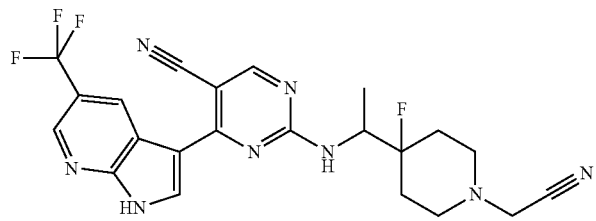 [SMILES: CC(Nc1ncc(C#N)c(-c2c[nH]c3ncc(C(F)(F)F)cc23)n1)C1(F)CCN(CC#N)CC1]
I-238
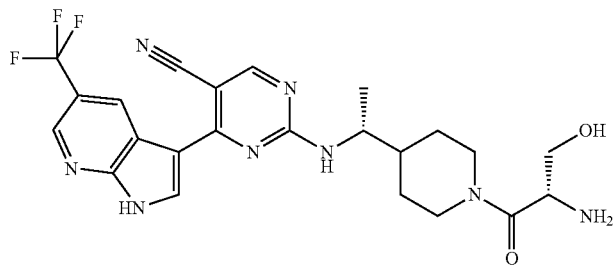 [SMILES: C[C@@H](Nc1ncc(C#N)c(-c2c[nH]c3ncc(C(F)(F)F)cc23)n1)C1CCN(C(=O)[C@@H](N)CO)CC1]
I-239
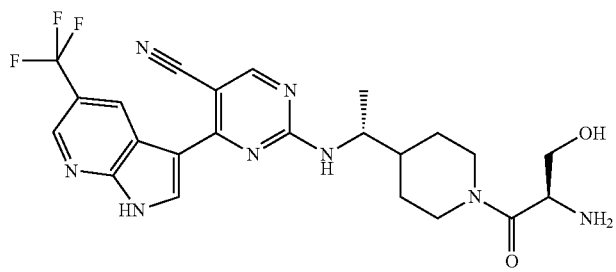 [SMILES: C[C@@H](Nc1ncc(C#N)c(-c2c[nH]c3ncc(C(F)(F)F)cc23)n1)C1CCN(C(=O)[C@H](N)CO)CC1]
I-240
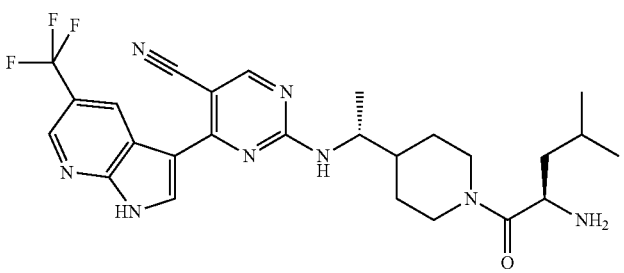 [SMILES: CC(C)C[C@@H](N)C(=O)N1CCC([C@@H](C)Nc2ncc(C#N)c(-c3c[nH]c4ncc(C(F)(F)F)cc34)n2)CC1]
I-241
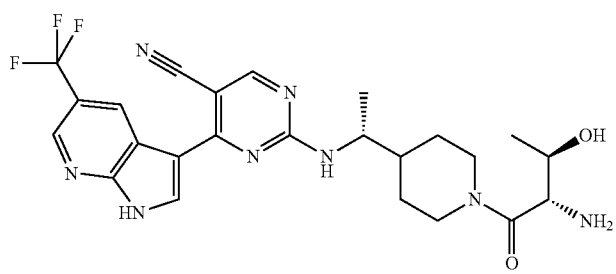 [SMILES: C[C@@H](Nc1ncc(C#N)c(-c2c[nH]c3ncc(C(F)(F)F)cc23)n1)C1CCN(C(=O)[C@@H](N)[C@@H](C)O)CC1]
I-242
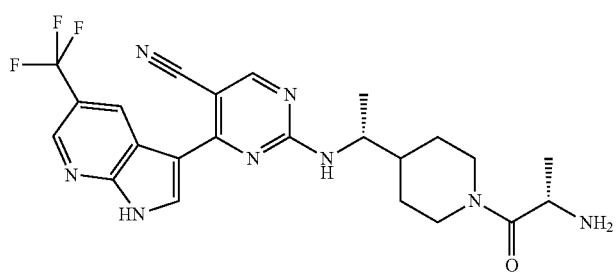 [SMILES: C[C@H](N)C(=O)N1CCC([C@@H](C)Nc2ncc(C#N)c(-c3c[nH]c4ncc(C(F)(F)F)cc34)n2)CC1]
I-243

TABLE 1-continued
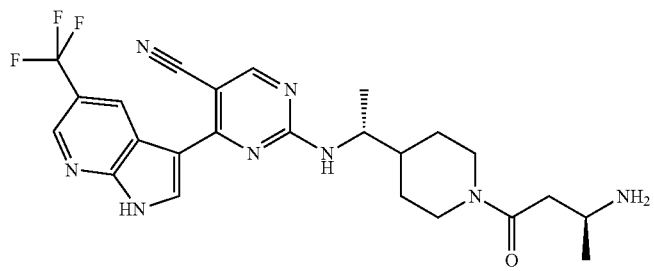 [SMILES: C[C@H](N)CC(=O)N1CCC([C@@H](C)Nc2ncc(C#N)c(-c3c[nH]c4ncc(C(F)(F)F)cc34)n2)CC1]
I-244
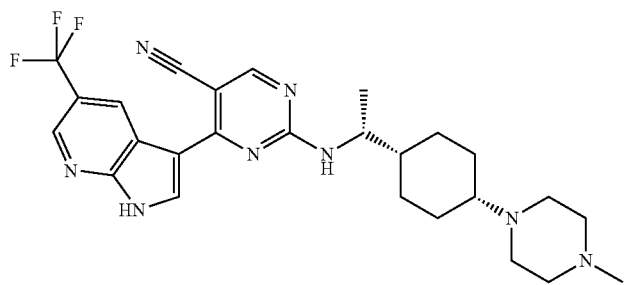 [SMILES: C[C@@H](Nc1ncc(C#N)c(-c2c[nH]c3ncc(C(F)(F)F)cc23)n1)[C@H]1CC[C@@H](N2CCN(C)CC2)CC1]
I-245
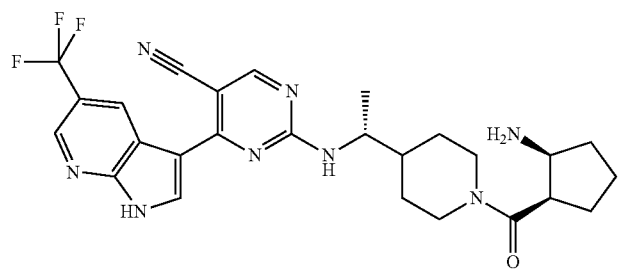 [SMILES: C[C@@H](Nc1ncc(C#N)c(-c2c[nH]c3ncc(C(F)(F)F)cc23)n1)C1CCN(C(=O)[C@@H]2CCC[C@@H]2N)CC1]
I-246
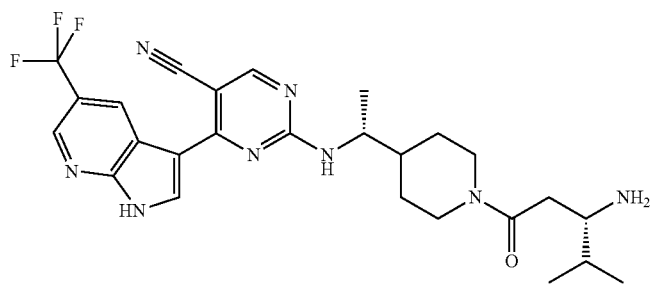 [SMILES: CC(C)[C@@H](N)CC(=O)N1CCC([C@@H](C)Nc2ncc(C#N)c(-c3c[nH]c4ncc(C(F)(F)F)cc34)n2)CC1]
I-247
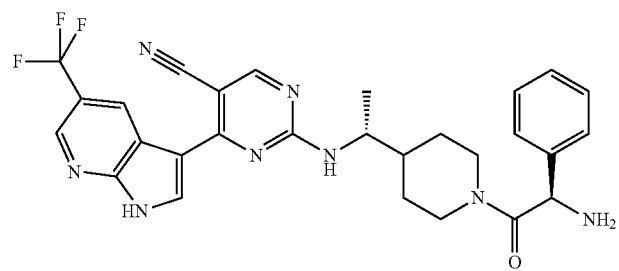 [SMILES: C[C@@H](Nc1ncc(C#N)c(-c2c[nH]c3ncc(C(F)(F)F)cc23)n1)C1CCN(C(=O)[C@H](N)c2ccccc2)CC1]
I-248

TABLE 1-continued
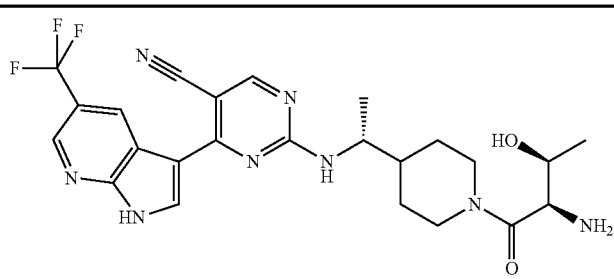
I-249
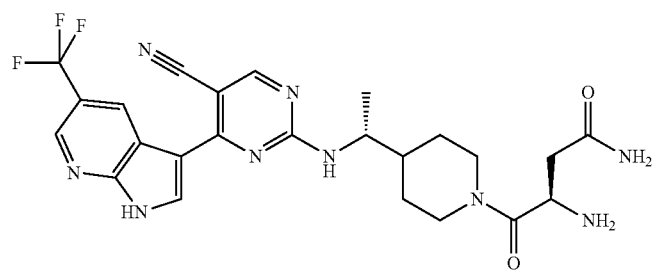 [SMILES: C[C@@H](Nc1ncc(C#N)c(-c2c[nH]c3ncc(C(F)(F)F)cc23)n1)C1CCN(C(=O)[C@H](N)CC(N)=O)CC1]
I-250
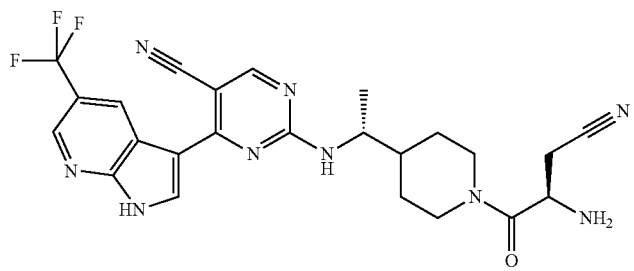 [SMILES: C[C@@H](Nc1ncc(C#N)c(-c2c[nH]c3ncc(C(F)(F)F)cc23)n1)C1CCN(C(=O)[C@H](N)CC#N)CC1]
I-251
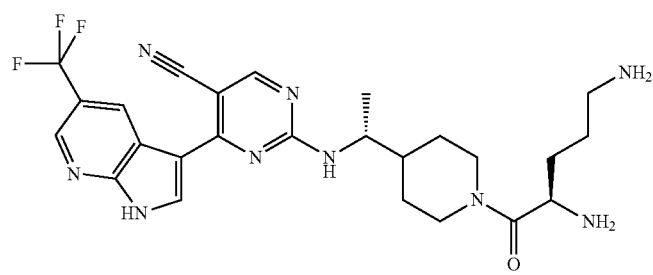 [SMILES: C[C@@H](Nc1ncc(C#N)c(-c2c[nH]c3ncc(C(F)(F)F)cc23)n1)C1CCN(C(=O)[C@H](N)CCCN)CC1]
I-252
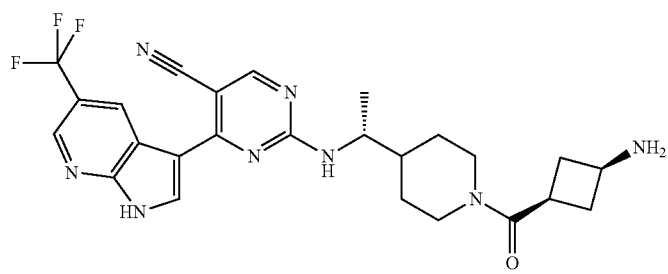 [SMILES: C[C@@H](Nc1ncc(C#N)c(-c2c[nH]c3ncc(C(F)(F)F)cc23)n1)C1CCN(C(=O)[C@H]2C[C@@H](N)C2)CC1]
I-253
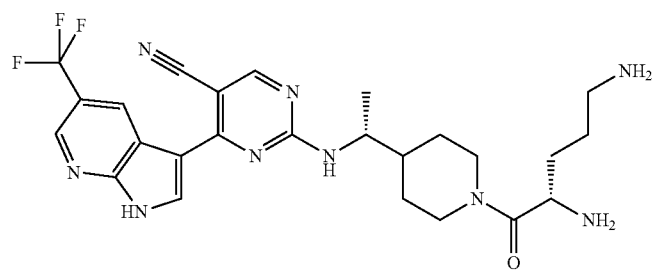 [SMILES: C[C@@H](Nc1ncc(C#N)c(-c2c[nH]c3ncc(C(F)(F)F)cc23)n1)C1CCN(C(=O)[C@@H](N)CCCN)CC1]
I-254

TABLE 1-continued
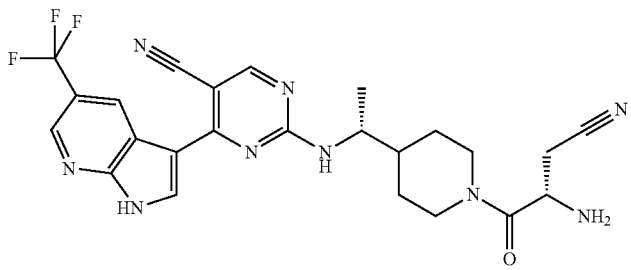 [SMILES: C[C@@H](Nc1ncc(C#N)c(-c2c[nH]c3ncc(C(F)(F)F)cc23)n1)C1CCN(C(=O)[C@@H](N)CC#N)CC1]
I-255
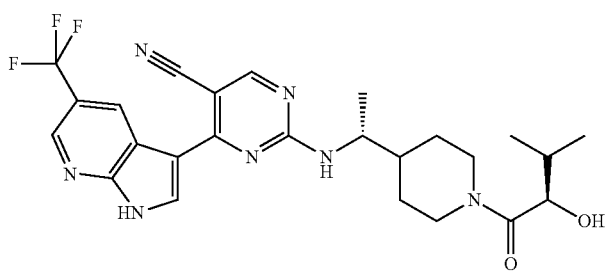 [SMILES: CC(C)[C@@H](O)C(=O)N1CCC([C@@H](C)Nc2ncc(C#N)c(-c3c[nH]c4ncc(C(F)(F)F)cc34)n2)CC1]
I-256
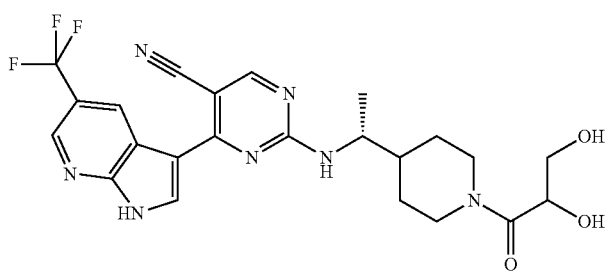 [SMILES: C[C@@H](Nc1ncc(C#N)c(-c2c[nH]c3ncc(C(F)(F)F)cc23)n1)C1CCN(C(=O)C(O)CO)CC1]
I-257
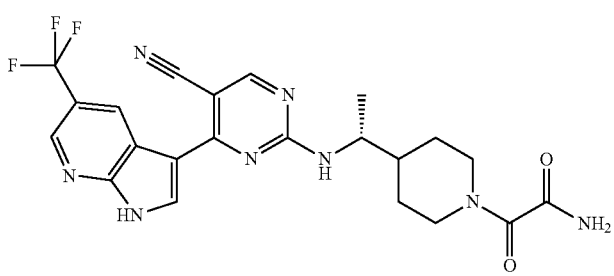 [SMILES: C[C@@H](Nc1ncc(C#N)c(-c2c[nH]c3ncc(C(F)(F)F)cc23)n1)C1CCN(C(=O)C(N)=O)CC1]
I-258
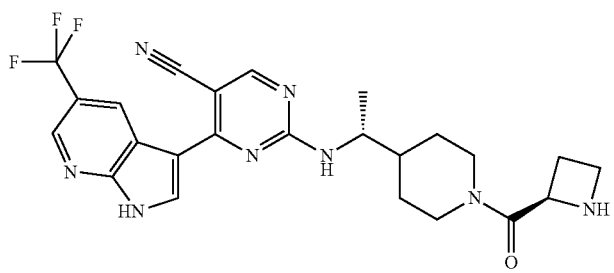 [SMILES: C[C@@H](Nc1ncc(C#N)c(-c2c[nH]c3ncc(C(F)(F)F)cc23)n1)C1CCN(C(=O)[C@H]2CCN2)CC1]
I-259
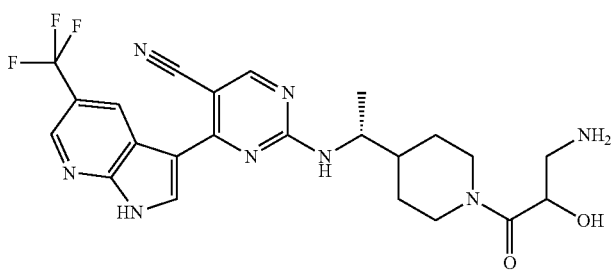 [SMILES: C[C@@H](Nc1ncc(C#N)c(-c2c[nH]c3ncc(C(F)(F)F)cc23)n1)C1CCN(C(=O)C(O)CN)CC1]
I-260

TABLE 1-continued
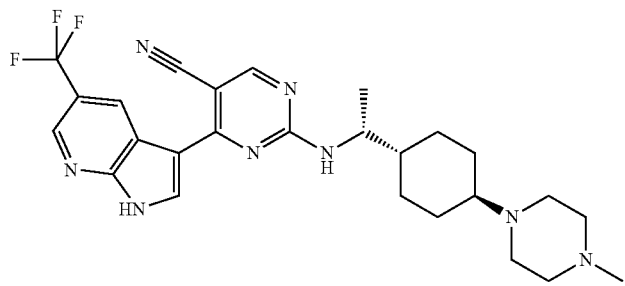 [SMILES: C[C@@H](Nc1ncc(C#N)c(-c2c[nH]c3ncc(C(F)(F)F)cc23)n1)[C@H]1CC[C@H](N2CCN(C)CC2)CC1]
I-261
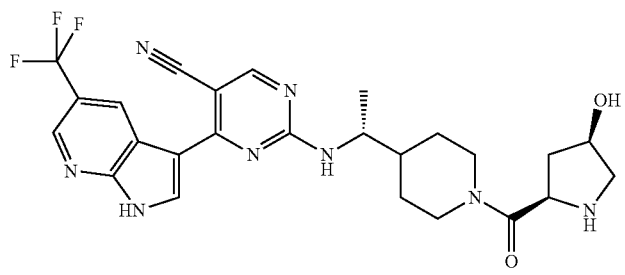 [SMILES: C[C@@H](Nc1ncc(C#N)c(-c2c[nH]c3ncc(C(F)(F)F)cc23)n1)C1CCN(C(=O)[C@H]2C[C@@H](O)CN2)CC1]
I-262
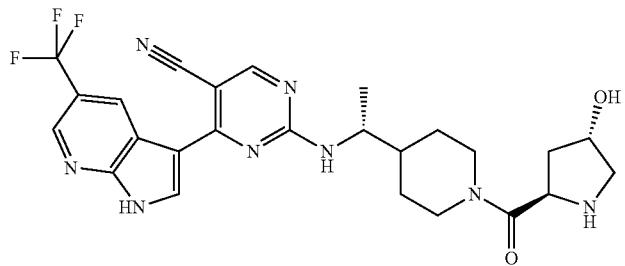 [SMILES: C[C@@H](Nc1ncc(C#N)c(-c2c[nH]c3ncc(C(F)(F)F)cc23)n1)C1CCN(C(=O)[C@H]2C[C@H](O)CN2)CC1]
I-263
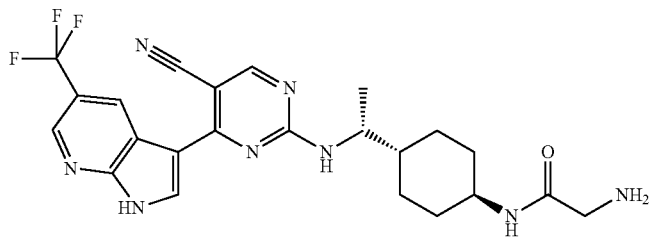 [SMILES: C[C@@H](Nc1ncc(C#N)c(-c2c[nH]c3ncc(C(F)(F)F)cc23)n1)[C@H]1CC[C@H](NC(=O)CN)CC1]
I-264
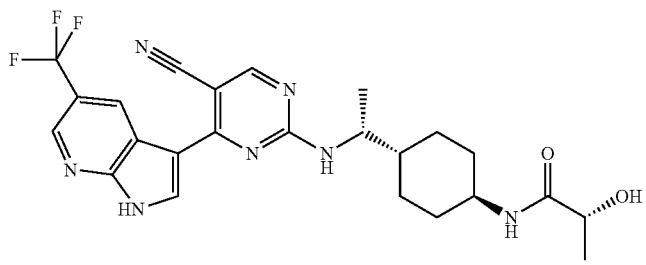 [SMILES: C[C@@H](O)C(=O)N[C@H]1CC[C@H]([C@@H](C)Nc2ncc(C#N)c(-c3c[nH]c4ncc(C(F)(F)F)cc34)n2)CC1]
I-265
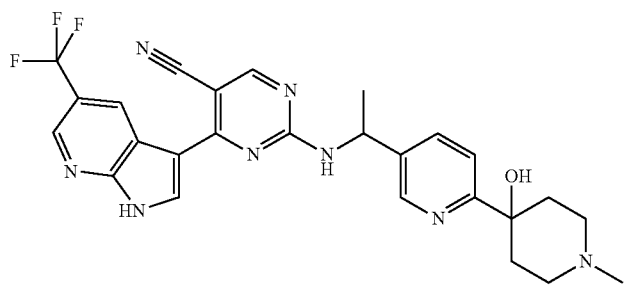 [SMILES: CC(Nc1ncc(C#N)c(-c2c[nH]c3ncc(C(F)(F)F)cc23)n1)c1ccc(C2(O)CCN(C)CC2)nc1]
I-266

TABLE 1-continued
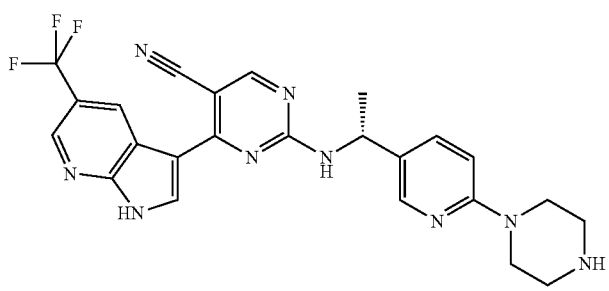 [SMILES: C[C@@H](Nc1ncc(C#N)c(-c2c[nH]c3ncc(C(F)(F)F)cc23)n1)c1ccc(N2CCNCC2)nc1]
I-267
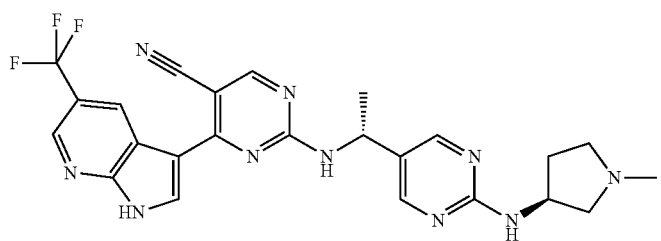 [SMILES: C[C@@H](Nc1ncc(C#N)c(-c2c[nH]c3ncc(C(F)(F)F)cc23)n1)c1cnc(N[C@H]2CCN(C)C2)nc1]
I-268
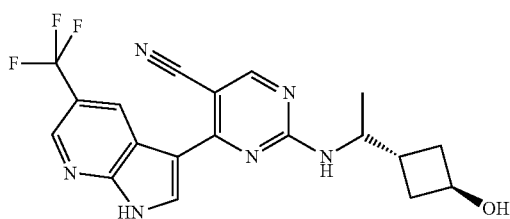 [SMILES: CC(Nc1ncc(C#N)c(-c2c[nH]c3ncc(C(F)(F)F)cc23)n1)[C@H]1C[C@H](O)C1]
I-269
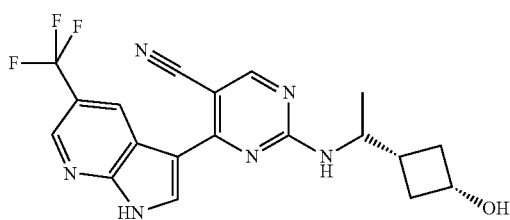 [SMILES: CC(Nc1ncc(C#N)c(-c2c[nH]c3ncc(C(F)(F)F)cc23)n1)[C@H]1C[C@@H](O)C1]
I-270
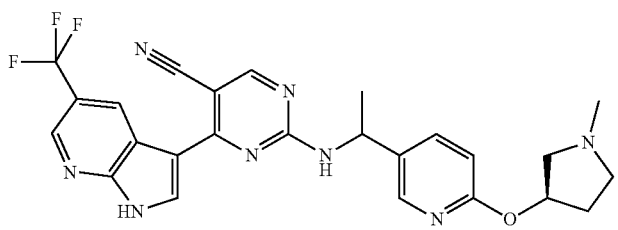 [SMILES: CC(Nc1ncc(C#N)c(-c2c[nH]c3ncc(C(F)(F)F)cc23)n1)c1ccc(O[C@@H]2CCN(C)C2)nc1]
I-271
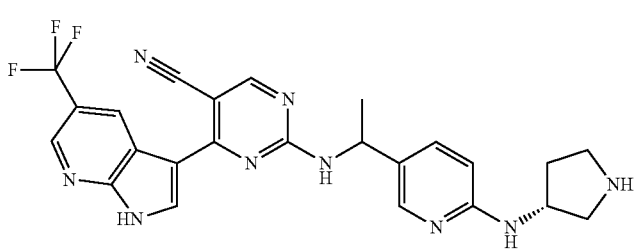 [SMILES: CC(Nc1ncc(C#N)c(-c2c[nH]c3ncc(C(F)(F)F)cc23)n1)c1ccc(N[C@@H]2CCNC2)nc1]
I-272

TABLE 1-continued
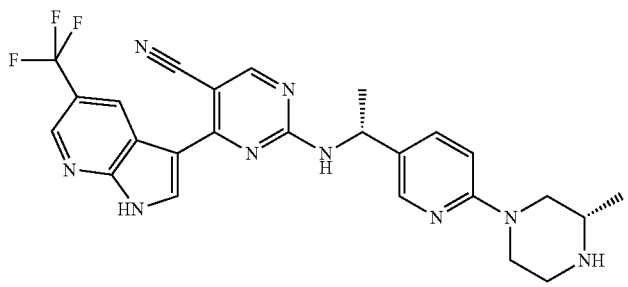 [SMILES: C[C@H]1CN(c2ccc([C@@H](C)Nc3ncc(C#N)c(-c4c[nH]c5ncc(C(F)(F)F)cc45)n3)cn2)CCN1]
I-273
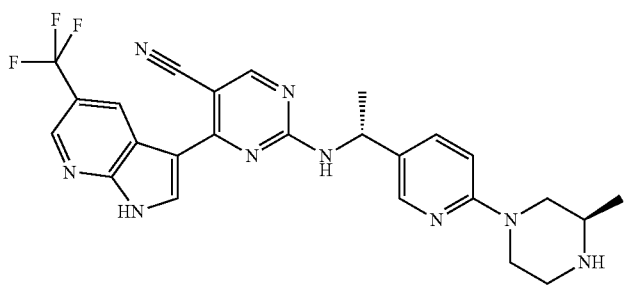 [SMILES: C[C@@H]1CN(c2ccc([C@@H](C)Nc3ncc(C#N)c(-c4c[nH]c5ncc(C(F)(F)F)cc45)n3)cn2)CCN1]
I-274
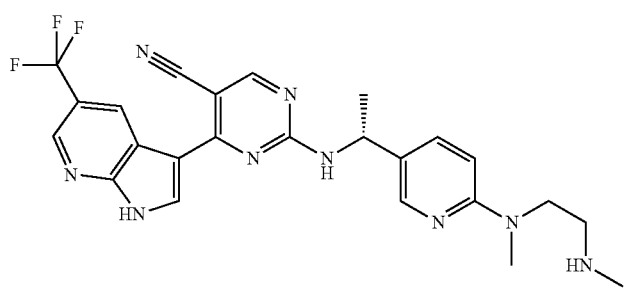 [SMILES: CNCCN(C)c1ccc([C@@H](C)Nc2ncc(C#N)c(-c3c[nH]c4ncc(C(F)(F)F)cc34)n2)cn1]
I-275
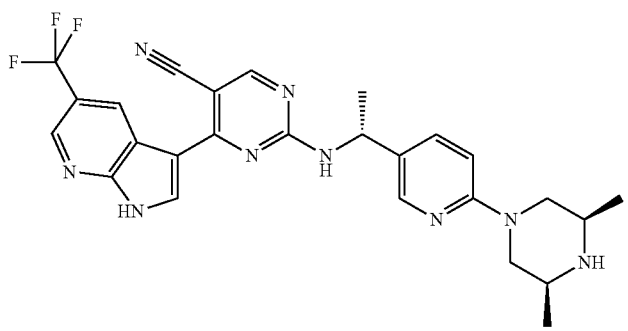 [SMILES: C[C@@H]1CN(c2ccc([C@@H](C)Nc3ncc(C#N)c(-c4c[nH]c5ncc(C(F)(F)F)cc45)n3)cn2)C[C@H](C)N1]
I-276
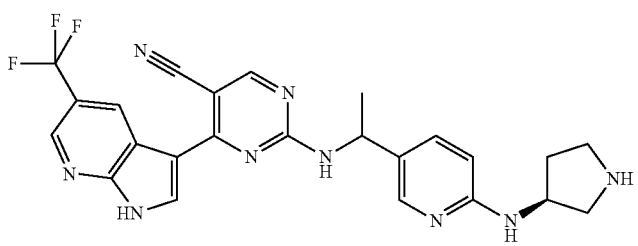 [SMILES: CC(Nc1ncc(C#N)c(-c2c[nH]c3ncc(C(F)(F)F)cc23)n1)c1ccc(N[C@H]2CCNC2)nc1]
I-277

TABLE 1-continued
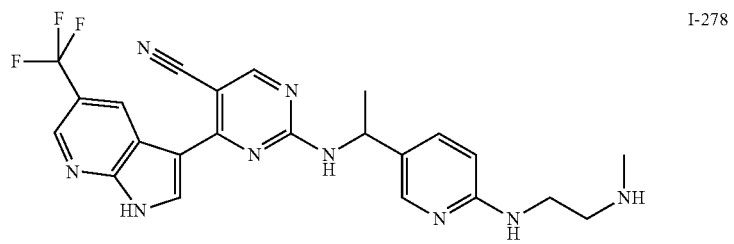
I-278
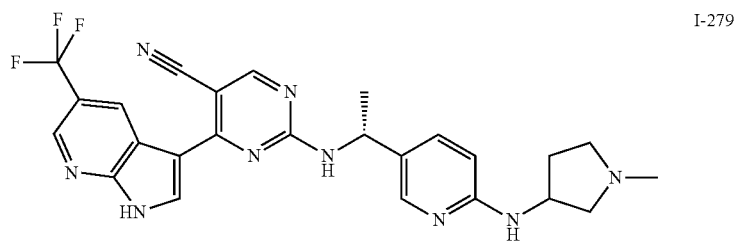
I-279
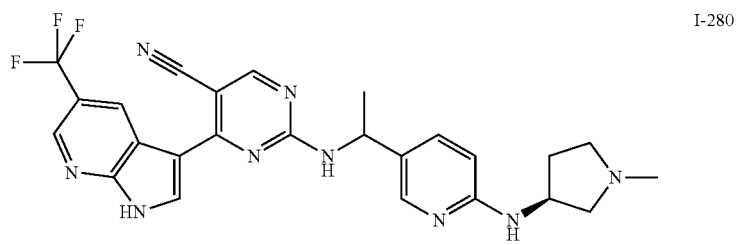
I-280
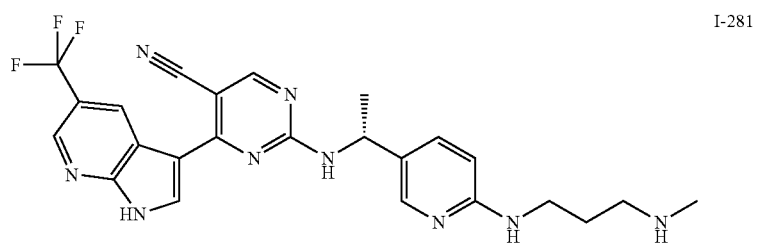
I-281
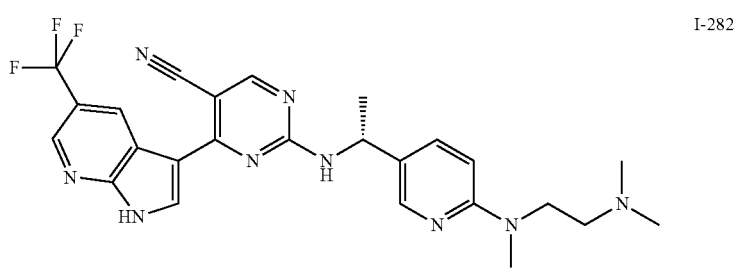
I-282
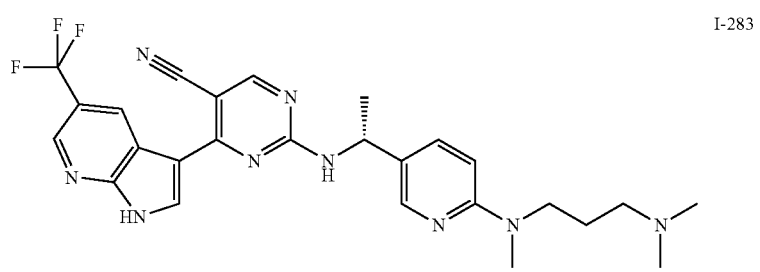
I-283

TABLE 1-continued
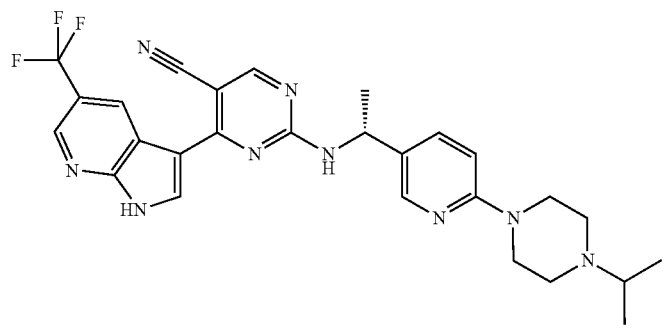 [SMILES: CC(C)N1CCN(c2ccc([C@@H](C)Nc3ncc(C#N)c(-c4c[nH]c5ncc(C(F)(F)F)cc45)n3)cn2)CC1]
I-284
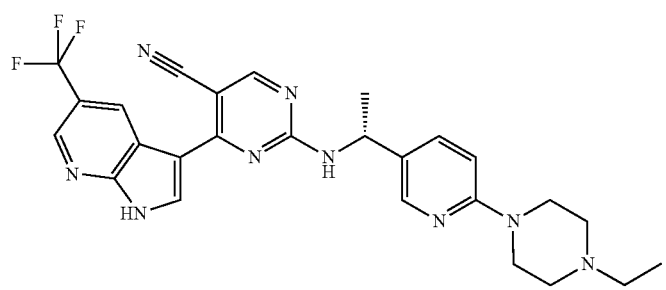 [SMILES: CCN1CCN(c2ccc([C@@H](C)Nc3ncc(C#N)c(-c4c[nH]c5ncc(C(F)(F)F)cc45)n3)cn2)CC1]
I-285
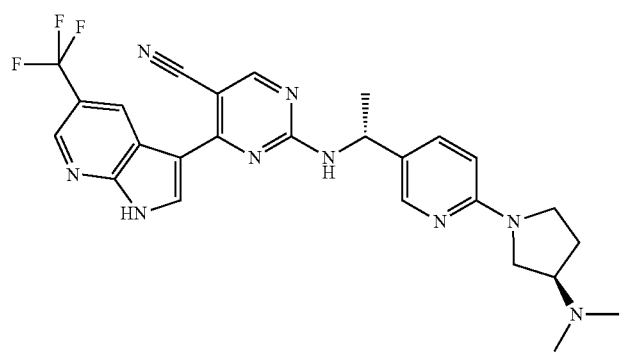 [SMILES: C[C@@H](Nc1ncc(C#N)c(-c2c[nH]c3ncc(C(F)(F)F)cc23)n1)c1ccc(N2CC[C@@H](N(C)C)C2)nc1]
I-286
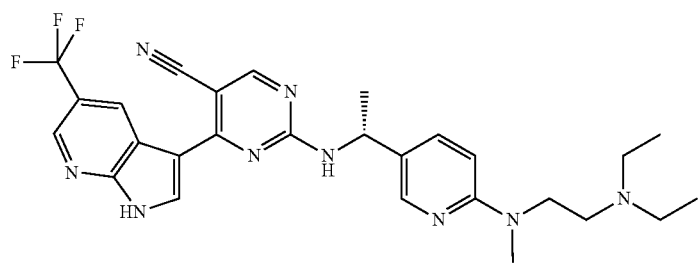 [SMILES: CCN(CC)CCN(C)c1ccc([C@@H](C)Nc2ncc(C#N)c(-c3c[nH]c4ncc(C(F)(F)F)cc34)n2)cn1]
I-287
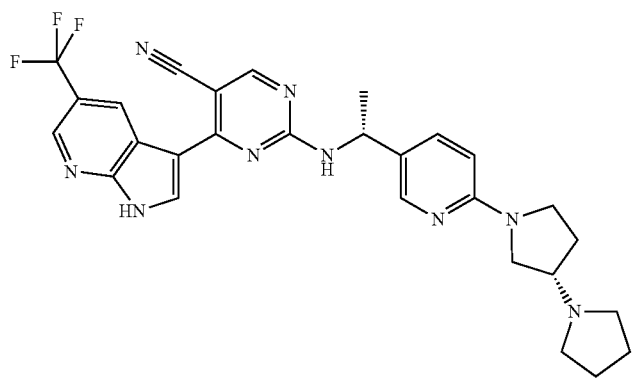 [SMILES: C[C@@H](Nc1ncc(C#N)c(-c2c[nH]c3ncc(C(F)(F)F)cc23)n1)c1ccc(N2CC[C@H](N3CCCC3)C2)nc1]
I-288

TABLE 1-continued
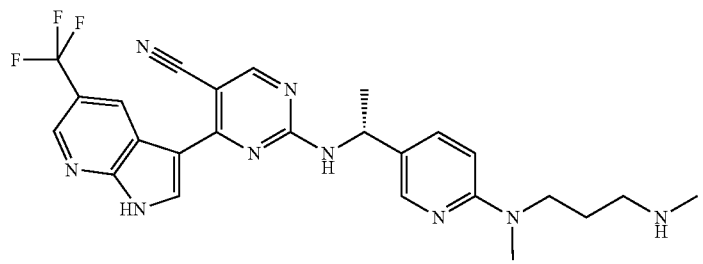 [SMILES: CNCCCN(C)c1ccc([C@@H](C)Nc2ncc(C#N)c(-c3c[nH]c4ncc(C(F)(F)F)cc34)n2)cn1]
I-289
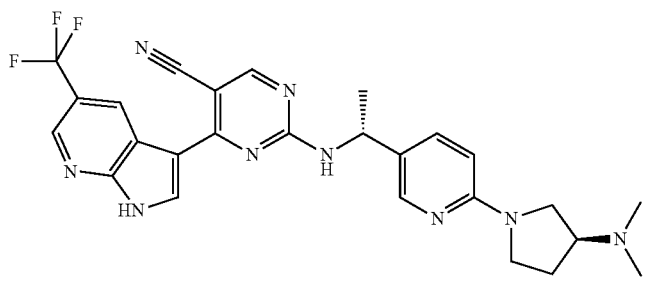 [SMILES: C[C@@H](Nc1ncc(C#N)c(-c2c[nH]c3ncc(C(F)(F)F)cc23)n1)c1ccc(N2CC[C@H](N(C)C)C2)nc1]
I-290
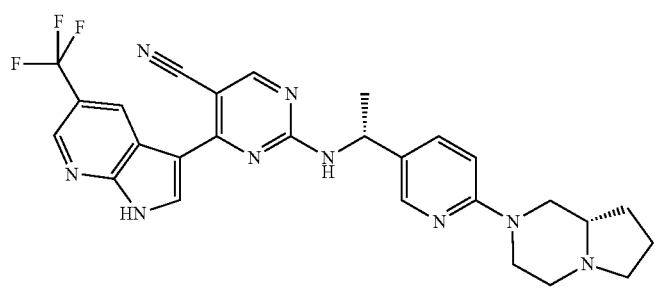 [SMILES: C[C@@H](Nc1ncc(C#N)c(-c2c[nH]c3ncc(C(F)(F)F)cc23)n1)c1ccc(N2CCN3CCC[C@H]3C2)nc1]
I-291
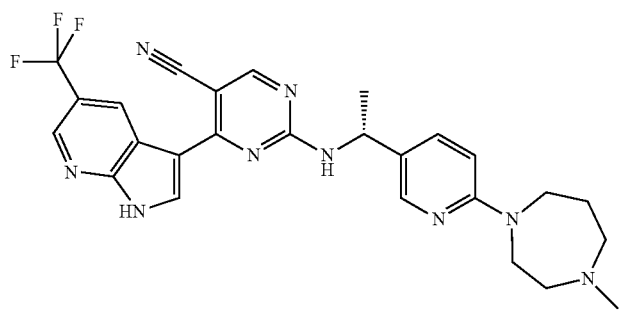 [SMILES: C[C@@H](Nc1ncc(C#N)c(-c2c[nH]c3ncc(C(F)(F)F)cc23)n1)c1ccc(N2CCCN(C)CC2)nc1]
I-292
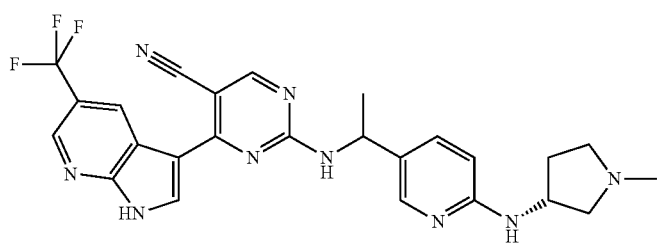
I-293

TABLE 1-continued
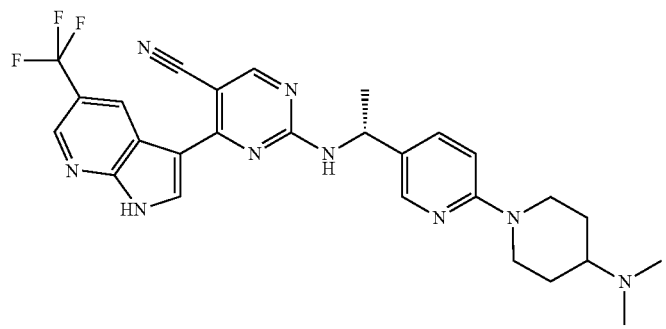 [SMILES: C[C@@H](Nc1ncc(C#N)c(-c2c[nH]c3ncc(C(F)(F)F)cc23)n1)c1ccc(N2CCC(N(C)C)CC2)nc1]
I-294
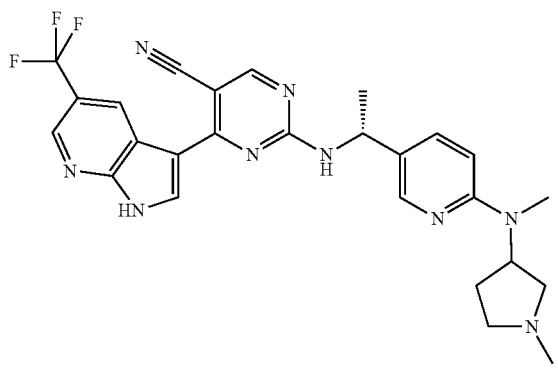 [SMILES: C[C@@H](Nc1ncc(C#N)c(-c2c[nH]c3ncc(C(F)(F)F)cc23)n1)c1ccc(N(C)C2CCN(C)C2)nc1]
I-295
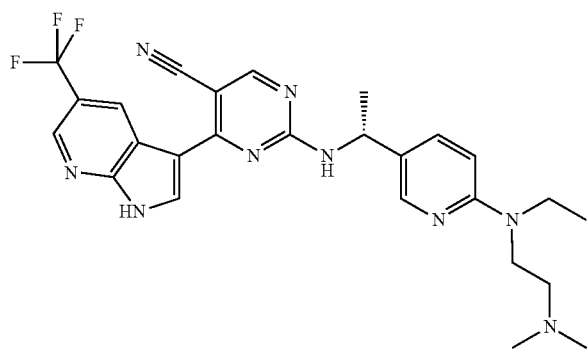 [SMILES: CCN(CCN(C)C)c1ccc([C@@H](C)Nc2ncc(C#N)c(-c3c[nH]c4ncc(C(F)(F)F)cc34)n2)cn1]
I-296
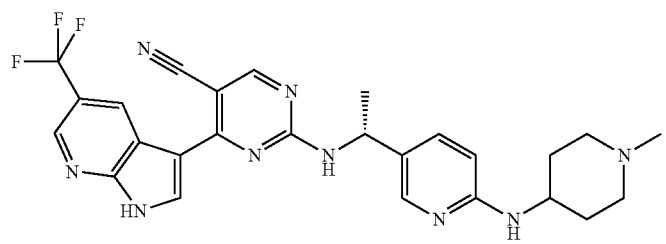 [SMILES: C[C@@H](Nc1ncc(C#N)c(-c2c[nH]c3ncc(C(F)(F)F)cc23)n1)c1ccc(NC2CCN(C)CC2)nc1]
I-297
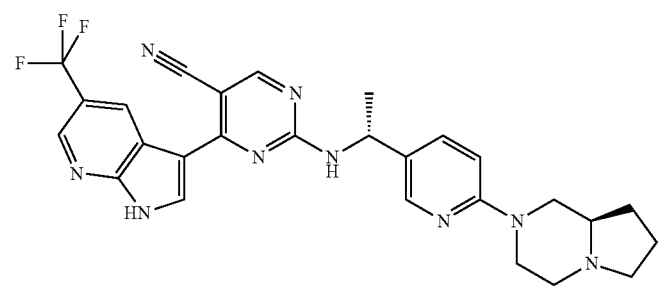 [SMILES: C[C@@H](Nc1ncc(C#N)c(-c2c[nH]c3ncc(C(F)(F)F)cc23)n1)c1ccc(N2CCN3CCC[C@@H]3C2)nc1]
I-298

TABLE 1-continued
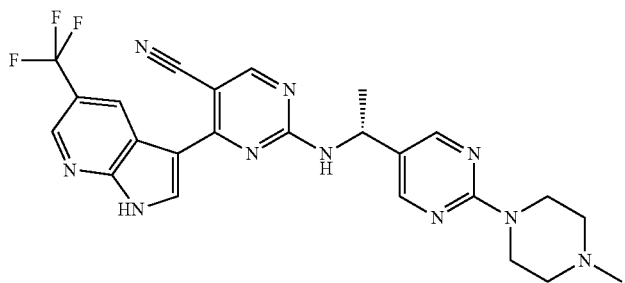 [SMILES: C[C@@H](Nc1ncc(C#N)c(-c2c[nH]c3ncc(C(F)(F)F)cc23)n1)c1cnc(N2CCN(C)CC2)nc1]
I-299
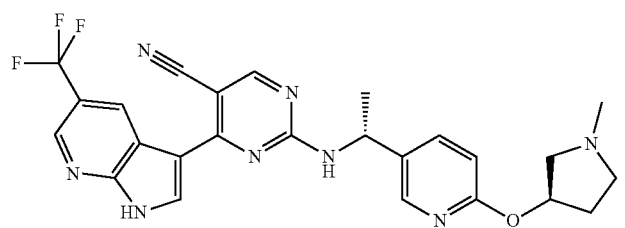 [SMILES: C[C@@H](Nc1ncc(C#N)c(-c2c[nH]c3ncc(C(F)(F)F)cc23)n1)c1ccc(O[C@@H]2CCN(C)C2)nc1]
I-300
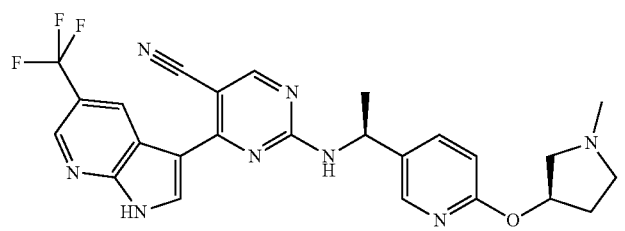 [SMILES: C[C@H](Nc1ncc(C#N)c(-c2c[nH]c3ncc(C(F)(F)F)cc23)n1)c1ccc(O[C@@H]2CCN(C)C2)nc1]
I-301
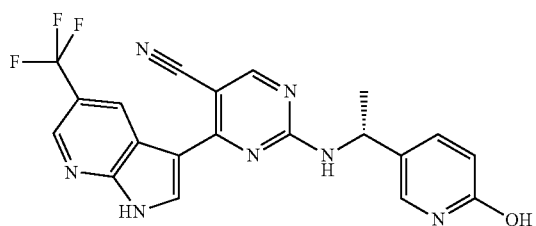 [SMILES: C[C@@H](Nc1ncc(C#N)c(-c2c[nH]c3ncc(C(F)(F)F)cc23)n1)c1ccc(O)nc1]
I-302
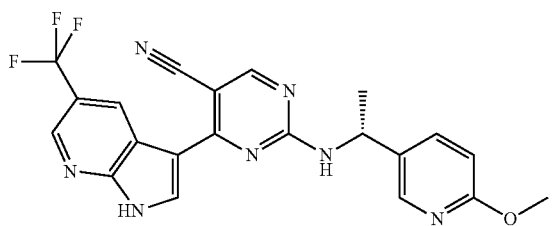
I-303
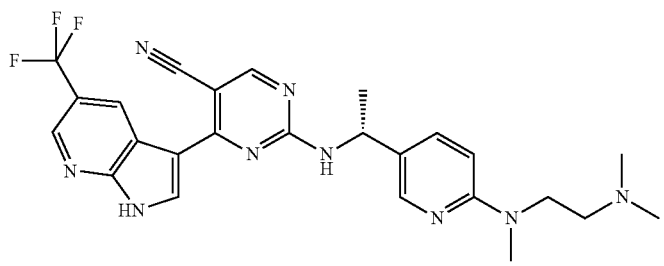 [SMILES: C[C@@H](Nc1ncc(C#N)c(-c2c[nH]c3ncc(C(F)(F)F)cc23)n1)c1ccc(N(C)CCN(C)C)nc1]
I-304

TABLE IIA

| Compound No (I-) | Name | M + 1 (obs) | ¹H NMR (DMSO-D₆) |
|---|---|---|---|
| 2 | 2-(methylamino)-4-(5-(trifluoromethyl)-1H-pyrrolo[2,3-b]pyridin-3-yl)pyrimidine-5-carbonitrile | 319 | 2.95 (3H, d), 3.02 (3H, d), 8.26 (1H, t), 8.44 (1H, t), 8.67 (1H, s), 8.72-8.76 (5H, m), 9.24 (2H, d), 13.04 (1H, brs), 13.10 (1H, brs). [~1:1 mixture of rotamers] |
| 3 | 2-(isopropylamino)-4-(5-(trifluoromethyl)-1H-pyrrolo[2,3-b]pyridin-3-yl)pyrimidine-5-carbonitrile | 347 | 1.24 (6H, d), 1.29 (6H, d), 4.19-4.25 (2H, m), 8.26 (1H, m), 8.67 (1H, s), 8.71-8.76 (4H, m), 9.17 (2H, d), 13.10 (1H, vbrs). [Mixture of rotamers] |
| 4 | 2-(tert-butylamino)-4-(5-(trifluoromethyl)-1H-pyrrolo[2,3-b]pyridin-3-yl)pyrimidine-5-carbonitrile | 361 | 1.47 (9H, s), 1.50 (9H, s), 8.00 (1H, brs), 8.05 (1H, brs), 8.67-8.74 (6H, m), 9.02 (2H, brs), 13.02 (1H, brs), 13.11 (1H, brs). [~1:1 mixture of rotamers]. |
| 5 | 2-((S)-1-phenylethylamino)-4-(5-(trifluoromethyl)-1H-pyrrolo[2,3-b]pyridin-3-yl)pyrimidine-5-carbonitrile | 409 | 1.54-1.57 (6H, m), 5.31-5.35 (2H, m), 7.17-7.44 (10H, m), 8.69-8.71 (4H, m), 8.74 (2H, s), 8.88 (2H, d), 8.97 (1H, s), 9.23 (1H, s), 13.05 (1H, brs), 13.09 (1H, brs). [~1:1 mixture of rotamers] |
| 6 | 2-((R)-1-phenylethylamino)-4-(5-(trifluoromethyl)-1H-pyrrolo[2,3-b]pyridin-3-yl)pyrimidine-5-carbonitrile | 409 | 1.54-1.57 (6H, m), 5.31-5.35 (2H, m), 7.17-7.44 (10H, m), 8.69-8.71 (4H, m), 8.74 (2H, s), 8.88 (2H, d), 8.97 (1H, s), 9.23 (1H, s), 13.05 (1H, brs), 13.09 (1H, brs). [~1:1 mixture of rotamers |
| 7 | 2-(phenethylamino)-4-(5-(trifluoromethyl)-1H-pyrrolo[2,3-b]pyridin-3-yl)pyrimidine-5-carbonitrile | 409 | 2.90-2.97 (4H, m), 3.63-3.65 (2H, m), 3.70-3.75 (2H, m), 7.19-7.31 (10H, m), 8.42 (1H, t), 8.60 (1H, t), 8.68 (1H, s), 8.73-8.77 (5H, m), 9.12 (1H, s), 9.21 (1H, s), 13.05 (1H, brs), 13.10 (1H, brs). [~2:3 mixture of rotamers] |
| 8 | 2-(benzyl(methyl)amino)-4-(5-(trifluoromethyl)-1H-pyrrolo[2,3-b]pyridin-3-yl)pyrimidine-5-carbonitrile | 409 | 3.23 (3H, s), 5.01 (2H, s), 5.10 (2H, s), 7.26-7.35 (10H, m), 8.65 (1H, s), 8.75-8.79 (5H, m), 8.85 (1H, s), 9.16 (1H, s), 13.09 (2H, brs). [1:1 mixture of rotamers]. |
| 9 | 2-(2-phenylpropan-2-ylamino)-4-(5-(trifluoromethyl)-1H-pyrrolo[2,3-b]pyridin-3-yl)pyrimidine-5-carbonitrile | 423 | 1.77 (12H, s), 7.05-7.07 (1H, m), 7.15-7.21 (2H, m), 7.26-7.28 (1H, m), 7.27 (4H, m), 8.34 (1H, s), 8.49 (1H, s), 8.56 (1H, s), 8.61-8.75 (8H, m), 9.27 (1H, s), 13.00 (1H, brs), 13.03 (1H, brs). [~1:1 mixture of rotamers] |
| 10 | 2-(cyclohexylamino)-4-(5-(trifluoromethyl)-1H-pyrrolo[2,3-b]pyridin-3-yl)pyrimidine-5-carbonitrile | 387 | 1.25-1.32 (2H, m), 1.33-1.41 (8H, m), 1.65 (2H, brd), 1.78 (4H, m), 1.95 (4H, m), 3.85-3.95 (2H, m), 8.24 (2H, d), 8.31 (1H, d), 8.64 (2H, s), 8.71-8.76 (4H, m), 9.09 (2H, s), 9.12 (1H, s), 13.09 (2H, brs). [~2:1 mixture of rotamers] |
| 11 | 2-(benzyl(ethyl)amino)-4-(5-(trifluoromethyl)-1H-pyrrolo[2,3-b]pyridin-3-yl)pyrimidine-5-carbonitrile | 423 | 1.15 (3H, t), 1.26 (3H, t), 3.70 (2H, q), 3.79 (2H, q), 4.98 (2H, s), 5.08 (2H, s), 7.27-7.36 (10H, m), 8.63 (1H, s), 8.75-78 (4H, m), 8.80 (1H, s), 8.84 (1H, s), 9.11 (1H, s), 13.11 (2H, brs). [~1:1 mixture of rotamers]. |
| 12 | 2-(4-methoxybenzylamino)-4-(5-(trifluoromethyl)-1H-pyrrolo[2,3-b]pyridin-3-yl)pyrimidine-5-carbonitrile | 425 | 3.68 (3H, s), 3.72 (3H, s), 4.58 (2H, d), 4.66 (2H, d), 6.85 (2H, d), 6.90 (2H, d), 7.25 (2H, d), 7.28 (2H, d), 8.68-8.77 (7H, m), 8.95-8.98 (2H, m), 9.25 (1H, s), 13.06 (2H, brs). [~1:1 mixture of rotamers]. |
| 13 | 2-(3-chlorobenzylamino)-4-(5-(trifluoromethyl)-1H-pyrrolo[2,3-b]pyridin-3-yl)pyrimidine-5-carbonitrile | 429 | 4.68 (2H, d), 4.74 (2H, d), 7.26-7.41 (8H, m), 8.68 (1H, s), 8.71-8.75 (5H, m), 8.83 (2H, s), 9.00 (1H, t), 9.26 (1H, s), 12.13 (2H, vbrs). [~1:1 mixture of rotamers]. |
| 14 | 2-(pyridin-3-ylmethylamino)-4-(5- | 396 | 4.70 (2H, d), 4.76 (2H, d), 7.35-7.39 (1H, m), 7.42-7.45 (1H, m), |

TABLE IIA-continued

| | Name | M + 1 (obs) | ¹H NMR (DMSO-D₆) |
|---|---|---|---|
| | (trifluoromethyl)-1H-pyrrolo[2,3-b]pyridin-3-yl)pyrimidine-5-carbonitrile | | 7.77 (1H, d), 7.85 (1H, d), 8.45 (1H, d), 8.50 (1H, d), 8.56 (1H, s), 8.63 (1H, s), 8.69 (1H, d), 8.72-8.76 (5H, m), 8.88 (2H, m), 9.03 (1H, t), 9.24 (1H, s), 13.07 (1H, s), 13.12 (1H, s). [~1:1 mixture of rotamers] |
| 15 | 2-(2-methoxybenzylamino)-4-(5-(trifluoromethyl)-1H-pyrrolo[2,3-b]pyridin-3-yl)pyrimidine-5-carbonitrile | 425 | 3.81 (3H, s), 3.84 (3H, s), 4.62 (2H, d), 4.69 (2H, d), 6.85 (1H, t), 6.91 (1H, t), 6.99-7.03 (2H, m), 7.14 (1H, d), 7.21-7.26 (3H, m), 8.60 (1H, t), 8.65 (1H, s), 8.70-8.74 (4H, m), 8.81 (1H, s), 8.87 (1H, s), 8.88 (1H, t), 9.29 (1H, s), 12.54 (2H, vbrs). [~1:1 mixture of rotamers] |
| 16 | 2-(1-phenylpropylamino)-4-(5-(trifluoromethyl)-1H-pyrrolo[2,3-b]pyridin-3-yl)pyrimidine-5-carbonitrile | 423 | 0.85-0.89 (3H, m), 1.76-1.85 (2H, m), 4.98-5.06 (1H, m), 7.12-7.38 (5H, m), 8.65 (2H, d), 8.70 (1H, d), 8.84 (1H, d), 9.01 (1H, s), 13.04 (1H, s). [~2:1 mixture of rotamers] |
| 17 | 2-(2-chlorobenzylamino)-4-(5-(trifluoromethyl)-1H-pyrrolo[2,3-b]pyridin-3-yl)pyrimidine-5-carbonitrile | 429 | |
| 18 | 2-(3-fluorobenzylamino)-4-(5-(trifluoromethyl)-1H-pyrrolo[2,3-b]pyridin-3-yl)pyrimidine-5-carbonitrile | 413 | 4.69 (2H, d), 4.75 (2H, d), 7.03-7.21 (6H, m), 7.31-7.42 (2H, m), 8.65 (2H, s), 8.71-8.76 (4H, m), 8.82 (2H, s), 8.99 (1H, t), 9.25 (1H, s), 12.70 (2H, vbrs). [~1:1 mixture of rotamers] |
| 19 | 2-(4-chlorobenzylamino)-4-(5-(trifluoromethyl)-1H-pyrrolo[2,3-b]pyridin-3-yl)pyrimidine-5-carbonitrile | 429 | |
| 20 | 2-(3-methoxybenzylamino)-4-(5-(trifluoromethyl)-1H-pyrrolo[2,3-b]pyridin-3-yl)pyrimidine-5-carbonitrile | 425 | |
| 21 | 2-(2-fluorobenzylamino)-4-(5-(trifluoromethyl)-1H-pyrrolo[2,3-b]pyridin-3-yl)pyrimidine-5-carbonitrile | 413 | 4.68 (2H, m), 6.57 (1H, s), 7.25 (3H, m), 8.50 (1H, s), 8.60 (1H, m), 8.80 (2H, m), 9.20 (1H, s) |
| 22 | 2-(4-fluorobenzylamino)-4-(5-(trifluoromethyl)-1H-pyrrolo[2,3-b]pyridin-3-yl)pyrimidine-5-carbonitrile | 413 | |
| 23 | 2-(pyridin-4-ylmethylamino)-4-(5-(trifluoromethyl)-1H-pyrrolo[2,3-b]pyridin-3-yl)pyrimidine-5-carbonitrile | 396 | |
| 24 | 2-(3-methylbutan-2-ylamino)-4-(5-(trifluoromethyl)-1H-pyrrolo[2,3-b]pyridin-3-yl)pyrimidine-5-carbonitrile | 375 | 0.93 (6H, m), 1.17 (3H, m), 1.87 (1H, m), 4.00 (1H, m), 8.27 (1H, m), 8.70 (3H, m), 9.17 (1H, m) |
| 25 | 2-(phenylamino)-4-(5-(trifluoromethyl)-1H-pyrrolo[2,3-b]pyridin-3-yl)pyrimidine-5-carbonitrile | 381 | 7.14 (1H, t), 7.36 (2H, t), 7.69 (2H, d), 8.72 (1H, s), 8.78 (1H, s), 8.87 (1H, s), 10.38 (1H, s), 13.15 (1H, brs). |
| 26 | 2-((R)-1-(4-methoxyphenyl)ethylamino)-4-(5-(trifluoromethyl)-1H-pyrrolo[2,3-b]pyridin-3-yl)pyrimidine-5-carbonitrile | 440 | 1.53 (3H, d), 3.71 (3H, d), 5.26 (1H, m), 6.88 (2H, m), 7.33 (2H, m), 8.70 (3H, m), 8.81 (1H, m), 8.99 (1H, d), 13.08 (1H, d) |
| 27 | 2-(2-phenylcyclopropylamino)-4-(5-(trifluoromethyl)-1H-pyrrolo[2,3-b]pyridin-3-yl)pyrimidine-5-carbonitrile | 421 | 1.30 (2H, m), 2.17 (H, m), 3.14 (1H, m), 7.17 (5H, m), 8.74 (4H, m), 9.34 (1H, d), 13.12 (1H, m) |
| 28 | tert-butyl 4-((5-cyano-4-(5-(trifluoromethyl)-1H-pyrrolo[2,3-b]pyridin-3-yl)pyrimidin-2- | 502 | 1.04 (3H, m), 1.38 (9H, s), 1.72 (4H, m), 2.67 (2H, br s), 3.37 (1H, m), 3.92 (1H, br s), 8.42 (1H, m), 8.71 (3H, m), 9.20 (1H, |

TABLE IIA-continued

| | Name | M + 1 (obs) | ¹H NMR (DMSO-D₆) |
|---|---|---|---|
| | ylamino)methyl)piperidine-1-carboxylate | | d), 13.11 (1H, d) |
| 29 | 2-(cyclohexylmethylamino)-4-(5-(trifluoromethyl)-1H-pyrrolo[2,3-b]pyridin-3-yl)pyrimidine-5-carbonitrile | 401 | 1.10-1.90 (13H, m), 7.37 (1H, m), 8.52 (1H, m), 8.70 (2H, m), 9.20 (1H, d), 13.10 (1H, d) |
| 30 | 2-((1H-benzo[d]imidazol-2-yl)methylamino)-4-(5-(trifluoromethyl)-1H-pyrrolo[2,3-b]pyridin-3-yl)pyrimidine-5-carbonitrile | 435 | |
| 31 | 2-((R)-1-(naphthalen-2-yl)ethylamino)-4-(5-(trifluoromethyl)-1H-pyrrolo[2,3-b]pyridin-3-yl)pyrimidine-5-carbonitrile | 459 | |
| 32 | 4-(5-(trifluoromethyl)-1H-pyrrolo[2,3-b]pyridin-3-yl)-2-((6-(trifluoromethyl)pyridin-3-yl)methylamino)pyrimidine-5-carbonitrile | 464 | |
| 33 | 2-((R)-1-(4-bromophenyl)ethylamino)-4-(5-(trifluoromethyl)-1H-pyrrolo[2,3-b]pyridin-3-yl)pyrimidine-5-carbonitrile | 487 | |
| 34 | 2-(1,2,3,4-tetrahydronaphthalen-1-ylamino)-4-(5-(trifluoromethyl)-1H-pyrrolo[2,3-b]pyridin-3-yl)pyrimidine-5-carbonitrile | 435 | |
| 35 | 2-(pentan-2-ylamino)-4-(5-(trifluoromethyl)-1H-pyrrolo[2,3-b]pyridin-3-yl)pyrimidine-5-carbonitrile | 375 | MeOD/CDCl₃ (400 MHz): 1.06 (3H, m), 1.39 (3H, m), 1.49 (2H, m), 1.66 (2H, m), 4.29 (1H, m), 7.36 (1H, s), 8.46 (1H, s), 8.61 (1H, s), 8.77 (1H, s), 9.26 (1H, s) |
| 36 | 2-(isobutylamino)-4-(5-(trifluoromethyl)-1H-pyrrolo[2,3-b]pyridin-3-yl)pyrimidine-5-carbonitrile | 361 | MeOD/CDCl₃ (400 MHz): 1.02 (6H, m), 1.31 (2H, m), 2.04 (1H, m), 8.47 (1H, s), 8.62 (1H, s), 8.78 (1H, s), 9.27 (1H, s) |
| 37 | 2-(3,4-dihydroxybenzylamino)-4-(5-(trifluoromethyl)-1H-pyrrolo[2,3-b]pyridin-3-yl)pyrimidine-5-carbonitrile | 427 | MeOD/CDCl₃ (400 MHz): 1.37 (2H, m), 6.74 (3H, m), 6.80 (1H, s), 8.48 (1H, s), 8.67 (1H, s), 9.23 (1H, s) |
| 38 | 2-(2,3-dihydro-1H-inden-1-ylamino)-4-(5-(trifluoromethyl)-1H-pyrrolo[2,3-b]pyridin-3-yl)pyrimidine-5-carbonitrile | 421 | MeOD/CDCl₃ (400 MHz): 1.28 (1H, m), 2.01 (1H, m), 2.64 (2H, m), 5.71 (1H, m), 7.21 (4H, m), 8.48 (3H, m), 8.73 (1H, d), 9.19 (1H, s) |
| 39 | 2-(1-hydroxybutan-2-ylamino)-4-(5-(trifluoromethyl)-1H-pyrrolo[2,3-b]pyridin-3-yl)pyrimidine-5-carbonitrile | 377 | |
| 40 | N-(2-(5-cyano-4-(5-(trifluoromethyl)-1H-pyrrolo[2,3-b]pyridin-3-yl)pyrimidin-2-ylamino)ethyl)acetamide | 390 | MeOD/CDCl₃ (400 MHz): 1.39 (3H, m), 1.96 (1H, m), 3.19 (1H, m), 3.68 (2H, m), 8.51 (1H, s), 8.61 (1H, m), 8.80 (1H, m), 9.27 (1H, s) |
| 41 | 2-(4-isopropoxybenzylamino)-4-(5-(trifluoromethyl)-1H-pyrrolo[2,3-b]pyridin-3-yl)pyrimidine-5-carbonitrile | 453 | MeOD/CDCl₃ (400 MHz): 1.28 (6H, m), 1.31 (2H, m), 4.45 (1H, m), 6.76 (2H, m), 7.20 (2H, m), 8.42 (1H, s), 8.49 (1H, m), 8.68 (1H, m), 9.05 (1H, s) |
| 42 | 2-(4-hydroxy-3-methoxybenzylamino)-4-(5-(trifluoromethyl)-1H-pyrrolo[2,3-b]pyridin-3-yl)pyrimidine-5-carbonitrile | 441 | |
| 43 | 2-((S)-2-methoxy-1-phenylethylamino)-4-(5-(trifluoromethyl)-1H-pyrrolo[2,3-b]pyridin-3-yl)pyrimidine-5-carbonitrile | 439 | MeOD/CDCl₃ (400 MHz): 3.40 (3H, s), 3.78 (2H, m), 5.53 (1H, m), 7.31 (5H, m), 8.51 (1H, s), 8.59 (1H, s), 8.70 (1H, s), 9.04 (1H, s) |

TABLE IIA-continued

| | Name | M + 1 (obs) | $^1$H NMR (DMSO-D$_6$) |
|---|---|---|---|
| 44 | 2-((R)-1-hydroxy-4-methylpentan-2-ylamino)-4-(5-(trifluoromethyl)-1H-pyrrolo[2,3-b]pyridin-3-yl)pyrimidine-5-carbonitrile | 405 | |
| 45 | 4-(5-(trifluoromethyl)-1H-pyrrolo[2,3-b]pyridin-3-yl)-2-((R)-1-(3-(trifluoromethyl)phenyl)ethylamino)pyrimidine-5-carbonitrile | 477 | MeOD/CDCl$_3$ (400 MHz): 1.67 (3H, m), 5.55 (1H, m), 7.49 (3H, m), 8.49 (1H, s), 8.60 (1H, s), 8.72 (1H, s), 9.05 (1H, s), 9.35 (1H, s) |
| 46 | 2-(4-phenoxybenzylamino)-4-(5-(trifluoromethyl)-1H-pyrrolo[2,3-b]pyridin-3-yl)pyrimidine-5-carbonitrile | 487 | MeOD/CDCl$_3$ (400 MHz): 4.75 (2H, m), 6.96 (4H, m), 7.20 (5H, m), 8.43 (2H, m), 8.49 (1H, s), 8.69 (1H, s), 9.03 (1H, s) |
| 47 | 2-((R)-1-hydroxy-3-methylbutan-2-ylamino)-4-(5-(trifluoromethyl)-1H-pyrrolo[2,3-b]pyridin-3-yl)pyrimidine-5-carbonitrile | 391 | (Performed at 110° C.) 1.00 (3H, d), 2.06 (1H, q), 3.67 (1H, m), 4.06 (1H, m), 4.25 (1H, m), 7.40 (1H, m), 8.60 (1H, s), 8.68 (2H, s), 9.14 (1H, s), 12.64 (1H, br s) |
| 48 | 2-(3,5-difluorobenzylamino)-4-(5-(trifluoromethyl)-1H-pyrrolo[2,3-b]pyridin-3-yl)pyrimidine-5-carbonitrile | 431 | |
| 49 | 2-((1-hydroxycyclohexyl)methylamino)-4-(5-(trifluoromethyl)-1H-pyrrolo[2,3-b]pyridin-3-yl)pyrimidine-5-carbonitrile | 417 | |
| 50 | 2-((6-chloropyridin-3-yl)methylamino)-4-(5-(trifluoromethyl)-1H-pyrrolo[2,3-b]pyridin-3-yl)pyrimidine-5-carbonitrile | 430 | |
| 51 | 2-(1-(pyridin-3-yl)ethylamino)-4-(5-(trifluoromethyl)-1H-pyrrolo[2,3-b]pyridin-3-yl)pyrimidine-5-carbonitrile | 411 | 1.57 (3H, d), 5.33 (1H, m), 7.47-7.60 (1H, m), 7.94-7.96 (1H, m), 8.47-8.86 (7H, m), 13.02 (1H, m) mixture of rotamers |
| 52 | 2-(1-(6-methoxypyridin-3-yl)ethylamino)-4-(5-(trifluoromethyl)-1H-pyrrolo[2,3-b]pyridin-3-yl)pyrimidine-5-carbonitrile | 441 | 1.57 (3H, d), 3.78-3.82 (3H, d), 5.29 (1H, m), 6.79 (1H, m), 7.73-7.79 (1H, m), 8.12-8.21 (1H, m), 8.70-8.75 (3H, m), 8.82 (1H, m), 8.97 (1H, m), 13.06 (1H, m) 1:1 mixture of rotamers |
| 53 | 2-(3,4-dimethoxybenzylamino)-4-(5-(trifluoromethyl)-1H-pyrrolo[2,3-b]pyridin-3-yl)pyrimidine-5-carbonitrile | 455 | |
| 54 | 2-(4-(thiophen-2-yl)benzylamino)-4-(5-(trifluoromethyl)-1H-pyrrolo[2,3-b]pyridin-3-yl)pyrimidine-5-carbonitrile | 477 | |
| 55 | 2-(4-(1H-1,2,4-triazol-1-yl)benzylamino)-4-(5-(trifluoromethyl)-1H-pyrrolo[2,3-b]pyridin-3-yl)pyrimidine-5-carbonitrile | 462 | 4.75 (2H, d), 7.35 (1H, d), 7.41 (1H, d), 7.49 (1H, t), 7.54 (1H, t), 7.75 (2H, t), 7.87 (2H, s), 8.19 (1H, s), 8.22 (1H, s), 8.67 (1H, s), 8.72-8.76 (6H, m), 8.86 (1H, s), 8.92 (1H, t), 9.09 (1H, t), 9.23 (1H, s), 9.27 (1H, s), 9.30 (1H, s), 13.10 (2H, brs). [1:1 mix of rotamers] |
| 56 | nzo[d][1,3]dioxol-5-ylmethylamino)-4-(5-(trifluoromethyl)-1H-pyrrolo[2,3-b]pyridin-3-yl)pyrimidine-5-carbonitrile | 439 | 4.56 (2H, d), 4.64 (2H, d), 6.77-6.89 (5H, m), 6.93 (1H, s), 8.71-8.75 (6H, m), 8.80 (1H, t), 8.94 (2H, brs), 9.25 (1H, s), 13.07 (2H, vbrs). [1:1 mixture of rotamers] |
| 57 | 2-((tetrahydro-2H-pyran-4-yl)methylamino)-4-(5-(trifluoromethyl)-1H-pyrrolo[2,3-b]pyridin-3-yl)pyrimidine-5-carbonitrile | 403 | 1.19-1.27 (2H, m), 1.62-1.68 (2H, m), 1.91 (1H, brs), 3.22-3.39 (4H, m), 3.83-3.87 (2H, m), 8.43 and 8.56 (1H total, 2t), 8.67 (1H, s), 8.71-8.76 (2H, m), 9.15 and 9.21 (1H, total, 2s), 13.03 and |

TABLE IIA-continued

| | Name | M + 1 (obs) | ¹H NMR (DMSO-D₆) |
|---|---|---|---|
| | | | 13.12 (1H total, 2brs). [~2:3 mix of rotamers] |
| 58 | 2-((S)-1-hydroxy-3-methylbutan-2-ylamino)-4-(5-(trifluoromethyl)-1H-pyrrolo[2,3-b]pyridin-3-yl)pyrimidine-5-carbonitrile | 391 | 0.92-0.97 (6H, m), 1.91-2.02 (1H, m), 3.55-3.58 and 3.61-3.70 (2H total, 2m), 3.99 (1H, brs), 4.68 and 4.72 (1H total, 2t), 8.07 and 8.20 (1H total, 2d), 8.66-8.75 (3H, m), 9.13 and 9.23 (1H total, 2s), 13.05 (1H, brs). |
| 59 | 2-(4-(dimethylamino)benzylamino)-4-(5-(trifluoromethyl)-1H-pyrrolo[2,3-b]pyridin-3-yl)pyrimidine-5-carbonitrile | 438 | MeOD/CDCl₃ 1.26 (2H, s), 3.09 (6H, s), 7.18 (2H, d), 7.45 (2H, d), 8.56 (2H, m), 8.78 (1H, s), 9.01 (1H, s) |
| 60 | 2-(2,5-dimethylbenzylamino)-4-(5-(trifluoromethyl)-1H-pyrrolo[2,3-b]pyridin-3-yl)pyrimidine-5-carbonitrile | 423 | MeOD/CDCl₃ 2.24 (3H, s), 2.28 (2H, s), 2.33 (3H, s), 7.08 (3H, m), 8.57 (2H, m), 8.76 (1H, s), 9.07 (1H, s) |
| 61 | 2-((R)-1-cyclohexylethylamino)-4-(5-(trifluoromethyl)-1H-pyrrolo[2,3-b]pyridin-3-yl)pyrimidine-5-carbonitrile | 415 | (CDCl₃) 1.30 (8H, m), 4.18 (7H, m), 4.18 (1H, m), 7.54 (1H, s), 8.47 (1H, s), 8.69 (1H, s), 9.01 (1H, s), 9.34 (1H, s) |
| 62 | 2-((2,3-dihydrobenzofuran-5-yl)methylamino)-4-(5-(trifluoromethyl)-1H-pyrrolo[2,3-b]pyridin-3-yl)pyrimidine-5-carbonitrile | 437 | |
| 63 | 2-(1-methylpiperidin-4-ylamino)-4-(5-(trifluoromethyl)-1H-pyrrolo[2,3-b]pyridin-3-yl)pyrimidine-5-carbonitrile | 402 | |
| 64 | 2-(pyridin-2-ylmethylamino)-4-(5-(trifluoromethyl)-1H-pyrrolo[2,3-b]pyridin-3-yl)pyrimidine-5-carbonitrile | 396 | 4.80 (2H, m), 7.33 (2H, m), 7.73 (1H, m), 8.51 (1H, d), 8.70 (4H, m), 9.09 (1H, d) |
| 65 | 2-((1R,2R)-bicyclo[2.2.1]heptan-2-ylamino)-4-(5-(trifluoromethyl)-1H-pyrrolo[2,3-b]pyridin-3-yl)pyrimidine-5-carbonitrile | 399 | |
| 66 | 2-(ethylamino)-4-(5-(trifluoromethyl)-1H-pyrrolo[2,3-b]pyridin-3-yl)pyrimidine-5-carbonitrile | 333 | |
| 67 | 2-((1-ethylpyrrolidin-2-yl)methylamino)-4-(5-(trifluoromethyl)-1H-pyrrolo[2,3-b]pyridin-3-yl)pyrimidine-5-carbonitrile | 416 | |
| 68 | 2-(2-(piperidin-2-yl)ethylamino)-4-(5-(trifluoromethyl)-1H-pyrrolo[2,3-b]pyridin-3-yl)pyrimidine-5-carbonitrile | 416 | |
| 69 | 2-(2-morpholinoethylamino)-4-(5-(trifluoromethyl)-1H-pyrrolo[2,3-b]pyridin-3-yl)pyrimidine-5-carbonitrile | 418 | |
| 70 | 2-(3-morpholinopropylamino)-4-(5-(trifluoromethyl)-1H-pyrrolo[2,3-b]pyridin-3-yl)pyrimidine-5-carbonitrile | 432 | |
| 71 | 2-(cyanomethylamino)-4-(5-(trifluoromethyl)-1H-pyrrolo[2,3-b]pyridin-3-yl)pyrimidine-5-carbonitrile | | 4.49-4.53 (2H, m), 8.76-8.85 (3H, m), 8.92 (0.5H, s), 9.00 (0.5H, t), 9.23 (1H, s), 13.14 (0.5H, brs), 13.18 (0.5H, brs). |
| 72 | N-(4-((5-cyano-4-(5-(trifluoromethyl)-1H-pyrrolo[2,3-b]pyridin-3-yl)pyrimidin-2- | | 2.00 (3H, d), 4.60 (1H, d), 4.68 (1H, d), 7.25 (2H, dd), 7.51 (2H, dd), 8.71-8.74 (3H, m), 8.80-8.82 (0.5H, m), 8.97-8.99 (1H, m), |

TABLE IIA-continued

| | Name | M + 1 (obs) | ¹H NMR (DMSO-D₆) |
|---|---|---|---|
| | ylamino)methyl)phenyl)acetamide | | 9.26 (0.5H, s), 9.87 (0.5H, s), 9.92 (0.5H, s), 13.06 (0.5H, brs), 13.09 (0.5H, brs). |
| 73 | 2-(cyclopentylamino)-4-(5-(trifluoromethyl)-1H-pyrrolo[2,3-b]pyridin-3-yl)pyrimidine-5-carbonitrile | | 1.59-1.65 (4H, m), 1.66-1.74 (2H, m), 1.99-2.08 (2H, m), 4.30-4.39 (1H, m), 8.38-8.41 (1H, m), 8.66-8.75 (3H, m), 9.18 and 9.20 (1H total, 2s), 13.03 and 13.09 (1H total, 2s). |
| 74 | 2-(tetrahydro-2H-pyran-4-ylamino)-4-(5-(trifluoromethyl)-1H-pyrrolo[2,3-b]pyridin-3-yl)pyrimidine-5-carbonitrile | | 1.38-1.45 (2H, m), 1.63-1.70 (2H, m), 3.15-3.21 (2H, partly obscured m), 3.69-3.74 (2H, m), 3.89-3.94 (1H, m), 8.14-8.18 (1H, m), 8.46-8.54 (3H, m), 8.85 and 8.95 (1H total, 2s), 12.81 and 12.89 (1H total, 2brs). |
| 75 | 2-(2-hydroxy-1-phenylethylamino)-4-(5-(trifluoromethyl)-1H-pyrrolo[2,3-b]pyridin-3-yl)pyrimidine-5-carbonitrile | | 3.69-3.78 (2H, m), 5.04-5.09 (1H, m), 5.22-5.27 (1H, m), 7.19-7.44 (5H, m), 8.68-8.82 (4H, m), 8.97 (0.5H, s), 9.25 (0.5H, s), 13.06 and 13.09 (1H total, 2brs). |
| 76 | 2-(cyclopropylamino)-4-(5-(trifluoromethyl)-1H-pyrrolo[2,3-b]pyridin-3-yl)pyrimidine-5-carbonitrile | | 0.63-0.69 (2H, m), 0.78-0.87 (2H, m), 2.85-2.88 (1H, m), 8.53-8.79 (4H, m), 9.18 and 9.46 (1H total, 2s), 13.01 (1H, vbrs). |
| 77 | 2-(sec-butylamino)-4-(5-(trifluoromethyl)-1H-pyrrolo[2,3-b]pyridin-3-yl)pyrimidine-5-carbonitrile | | 0.85-0.91 (3H, m), 1.22-1.26 (3H, m), 1.54-1.69 (2H, m), 4.03-4.08 (1H, m), 8.23-8.27 (1H, m), 8.66-8.75 (3H, m), 9.14 and 9.18 (1H total, 2s), 13.03 and 13.09 (1H total, 2s). |
| 78 | 2-((S)-tetrahydrofuran-3-ylamino)-4-(5-(trifluoromethyl)-1H-pyrrolo[2,3-b]pyridin-3-yl)pyrimidine-5-carbonitrile | | 2.25-2.29 (1H, m), 2.33-2.38 (1H, m), 3.67-3.88 (2H, m), 3.89-3.96 (2H, m), 4.57-4.59 (1H, m), 8.57-8.63 (1H, m), 8.71-8.76 (3H, m), 9.11 (0.5H, s), 9.20 (0.5H, s), 13.07 (1H, brs). |
| 79 | 2-(prop-2-ynylamino)-4-(5-(trifluoromethyl)-1H-pyrrolo[2,3-b]pyridin-3-yl)pyrimidine-5-carbonitrile | | 3.11 and 3.19 (1H total, 2s), 4.21 (2H, m), 8.68-8.91 (4H, m), 9.26 and 9.36 (1H total, 2s), 13.08 and 13.12 (1H total, 2brs). |
| 80 | 2-(3-(1H-imidazol-1-yl)propylamino)-4-(5-(trifluoromethyl)-1H-pyrrolo[2,3-b]pyridin-3-yl)pyrimidine-5-carbonitrile | | 2.15-2.24 (2H, m), 4.27-4.31 (2H, m), 7.64 (0.5H, s), 7.70 (0.5H, s), 7.83 (1H, d), 8.43 (0.5H, t), 8.51 (0.5H, t), 8.72-8.76 (3H, m), 9.05 (0.5H, s), 9.10 (0.5H, s). 9.14 (0.5H, s), 9.19 (0.5H, s), 13.08 (0.5H, s), 13.13 (0.5H, s), 14.25 (1H, vbrs). |
| 81 | 2-(((1S,3R)-3-hydroxycyclopentyl)methylamino)-4-(5-(trifluoromethyl)-1H-pyrrolo[2,3-b]pyridin-3-yl)pyrimidine-5-carbonitrile | | 1.20-1.35 (1H, m), 1.40-1.55 (2H, m), 1.82-1.91 (3H, m), 3.31-3.47 (2H, partly obscured m), 4.13 (1H, m), 4.38-4.40 (1H, m), 8.44 and 8.54 (1H total, 2t), 8.66-8.74 (3H, m), 9.17 and 9.20 (1H total, 2s), 13.03 and 13.11 (1H total, 2brs). |
| 82 | 2-(1-methoxypropan-2-ylamino)-4-(5-(trifluoromethyl)-1H-pyrrolo[2,3-b]pyridin-3-yl)pyrimidine-5-carbonitrile | | 1.21-1.25 (3H, m), 3.25 (3H, d), 3.36-3.51 (2H, partly obscured m), 4.33-4.39 (1H, m), 8.23 and 8.32 (1H total, 2d), 8.68-8.75 (3H, m), 9.13 and 9.20 (1H total, 2s), 13.09 (1H, brs). |
| 83 | 2-(sec-butylamino)-4-(5-(trifluoromethyl)-1H-pyrrolo[2,3-b]pyridin-3-yl)pyrimidine-5-carbonitrile | | 0.85-0.91 (3H, m), 1.22-1.26 (3H, m), 1.54-1.69 (2H, m), 4.03-4.08 (1H, m), 8.23-8.27 (1H, m), 8.66-8.75 (3H, m), 9.14 and 9.18 (1H total, 2s), 13.03 and 13.09 (1H total, 2s). |
| 84 | 2-(1-(3-chloro-4-methoxyphenyl)ethylamino)-4-(5-(trifluoromethyl)-1H-pyrrolo[2,3-b]pyridin-3-yl)pyrimidine-5-carbonitrile | 474 | 1.54 (3H, d), 3.82 masked signal, 5.25 (1H, m), 7.04-7.47 (3H, m), 8.70-8.80 (4H, m), 8.97-9.20 (1H, m), 13.05 (1H, m) 1:1 mixture of rotamers |
| 85 | 2-(2-(pyrrolidin-2-yl)ethylamino)-4-(5-(trifluoromethyl)-1H- | 402 | |

TABLE IIA-continued

| | Name | M + 1 (obs) | ¹H NMR (DMSO-D₆) |
|---|---|---|---|
| 86 | pyrrolo[2,3-b]pyridin-3-yl)pyrimidine-5-carbonitrile 2-(2-thiomorpholinoethylamino)-4-(5-(trifluoromethyl)-1H-pyrrolo[2,3-b]pyridin-3-yl)pyrimidine-5-carbonitrile | 434 | |
| 87 | 2-((R)-2-(aminomethyl)pyrrolidin-1-yl)-4-(5-(trifluoromethyl)-1H-pyrrolo[2,3-b]pyridin-3-yl)pyrimidine-5-carbonitrile | 388 | |
| 88 | 2-((R)-pyrrolidin-2-ylmethylamino)-4-(5-(trifluoromethyl)-1H-pyrrolo[2,3-b]pyridin-3-yl)pyrimidine-5-carbonitrile | 388 | |
| 89 | 2-((1-benzylpiperidin-4-yl)methylamino)-4-(5-(trifluoromethyl)-1H-pyrrolo[2,3-b]pyridin-3-yl)pyrimidine-5-carbonitrile | 492 | |
| 90 | 4-(5-(1,1-Trifluoromethyl)-1H-pyrrolo[2,3-b]pyridin-3-yl)-2-(4-hydroxybenzylamino)pyrimidine-5-carbonitrile | 411 | |
| 91 | 2-(2-hydroxypropylamino)-4-(5-(trifluoromethyl)-1H-pyrrolo[2,3-b]pyridin-3-yl)pyrimidine-5-carbonitrile | 363 | |
| 92 | 2-(4-(1H-pyrazol-1-yl)benzylamino)-4-(5-(trifluoromethyl)-1H-pyrrolo[2,3-b]pyridin-3-yl)pyrimidine-5-carbonitrile | 461 | |
| 93 | 2-(propylamino)-4-(5-(trifluoromethyl)-1H-pyrrolo[2,3-b]pyridin-3-yl)pyrimidine-5-carbonitrile | 347 | |
| 94 | 2-(3-chloro-4-methoxybenzylamino)-4-(5-(trifluoromethyl)-1H-pyrrolo[2,3-b]pyridin-3-yl)pyrimidine-5-carbonitrile | 459 | |
| 95 | 2-(4-hydroxycyclohexylamino)-4-(5-(trifluoromethyl)-1H-pyrrolo[2,3-b]pyridin-3-yl)pyrimidine-5-carbonitrile | 403 | |
| 96 | 2-(2-hydroxybutylamino)-4-(5-(trifluoromethyl)-1H-pyrrolo[2,3-b]pyridin-3-yl)pyrimidine-5-carbonitrile | 377 | |
| 97 | 2-((R)-2-hydroxypropylamino)-4-(5-(trifluoromethyl)-1H-pyrrolo[2,3-b]pyridin-3-yl)pyrimidine-5-carbonitrile | 363 | |
| 98 | 2-((2R,3S)-1,3-dihydroxybutan-2-ylamino)-4-(5-(trifluoromethyl)-1H-pyrrolo[2,3-b]pyridin-3-yl)pyrimidine-5-carbonitrile | 393 | |
| 99 | 2-((R)-1-(4-hydroxyphenyl)ethylamino)-4-(5-(trifluoromethyl)-1H-pyrrolo[2,3-b]pyridin-3-yl)pyrimidine-5-carbonitrile | 425 | 1.51 (3H, m), 5.23 (1H, m), 6.65-6.73 (2H, m), 6.96-7.18 (1H, m), 7.18-7.23 (2H, m), 8.69-8.79 (4H, m), 9.02-9.21 (1H, m), 9.27 (1H, m), 13.04 (1H, m) mixture of rotamers |
| 100 | 2-(1-(6-oxo-1,6-dihydropyridin-3-yl)ethylamino)-4-(5-(trifluoromethyl)-1H-pyrrolo[2,3-b]pyridin-3-yl)pyrimidine-5-carbonitrile | 426 | 1.51 (3H, m), 5.10 (1H, m), 6.33 (1H, m), 6.96-7.22 (2H, m), 7.51 (1H, m), 8.66-8.74 (4H, m), 8.98-9.18 (1H, m), 11.46 (1H, s), 13.06 (1H, m) mixture of rotamers |

TABLE IIA-continued

| | Name | M + 1 (obs) | ¹H NMR (DMSO-D₆) |
|---|---|---|---|
| 101 | 2-(1-(1-acetylpiperidin-4-yl)ethylamino)-4-(5-(trifluoromethyl)-1H-pyrrolo[2,3-b]pyridin-3-yl)pyrimidine-5-carbonitrile | 458 | 1.15-1.23 (5H, m), 1.76 (3H, m), 1.93-1.98 (3H, m), 2.96 (1H, m), 3.80 (1H, m), 4.04 (1H, m), 4.41 (1H, m), 8.30 (1H, m), 8.67-8.75 (3H, m), 9.10 (1H, m), 13.10 (1H, m) mixture of rotamers |
| 102 | 2-(1-(4-(4-methylpiperazin-1-yl)phenyl)ethylamino)-4-(5-(trifluoromethyl)-1H-pyrrolo[2,3-b]pyridin-3-yl)pyrimidine-5-carbonitrile | 507 | 1.51 (3H, m), 2.82-2.89 (5H, m), 3.09 (2H, m), 3.43 (2H, m), 3.78 (2H, m), 5.26 (1H, m), 6.92-6.99 (2H, m), 7.28-7.33 (2H, m), 8.70 (2H, m), 8.80 (1H, m), 9.03-9.21 (1H, m), 9.57 (1H, m), 13.10 (1H, m) mixture of rotamers |
| 103 | 2-((R)-1-hydroxy-3-methylbutan-2-ylamino)-4-(5-(trifluoromethyl)-1H-pyrrolo[2,3-b]pyridin-3-yl)pyrimidine-5-carbonitrile | 366 | 0.95-0.97 (6H, m), 1.97-2.03 (1H, m), 3.55-3.61 (2H, m), 3.94 (1H, m), 4.60 (1H, m), 6.75 (1H, vbrs), 7.09 (1H, d), 8.20 (1H, d), 8.62 (1H, s), 8.66 (1H, s), 9.20 (1H, brs), 12.75 (1H, s). |
| 104 | 2-(2-hydroxy-1-(tetrahydrofuran-3-yl)ethylamino)-4-(5-(trifluoromethyl)-1H-pyrrolo[2,3-b]pyridin-3-yl)pyrimidine-5-carbonitrile | 419 | |
| 105 | 2-(2-hydroxy-1-(tetrahydro-2H-pyran-4-yl)ethylamino)-4-(5-(trifluoromethyl)-1H-pyrrolo[2,3-b]pyridin-3-yl)pyrimidine-5-carbonitrile | 433 | |
| 106 | 2-(1-cyclopropyl-3-hydroxypropylamino)-4-(5-(trifluoromethyl)-1H-pyrrolo[2,3-b]pyridin-3-yl)pyrimidine-5-carbonitrile | 403 | |
| 107 | 2-((R)-1-hydroxypropan-2-ylamino)-4-(5-(trifluoromethyl)-1H-pyrrolo[2,3-b]pyridin-3-yl)pyrimidine-5-carbonitrile | 363 | |
| 108 | 2-((2R,3S)-1,3-dihydroxybutan-2-ylamino)-4-(5-(trifluoromethyl)-1H-pyrrolo[2,3-b]pyridin-3-yl)pyrimidine-5-carbonitrile | 393 | |
| 109 | 2-(2-hydroxyethylamino)-4-(5-(trifluoromethyl)-1H-pyrrolo[2,3-b]pyridin-3-yl)pyrimidine-5-carbonitrile | 349 | |
| 110 | 2-(1-methoxy-3-methylbutan-2-ylamino)-4-(5-(trifluoromethyl)-1H-pyrrolo[2,3-b]pyridin-3-yl)pyrimidine-5-carbonitrile | 405 | |
| 111 | 2-((S)-1-hydroxy-3,3-dimethylbutan-2-ylamino)-4-(5-(trifluoromethyl)-1H-pyrrolo[2,3-b]pyridin-3-yl)pyrimidine-5-carbonitrile | 405 | |
| 112 | 2-(1-(4-ethoxyphenyl)ethylamino)-4-(5-(trifluoromethyl)-1H-pyrrolo[2,3-b]pyridin-3-yl)pyrimidine-5-carbonitrile | 453 | (DMSO) 1.28 (3H, q), 1.52 (1H, d), 3.98 (2H, m), 5.26 (1H, m), 6.82-6.90 (2H, m), 7.28-7.34 (2H, m), 8.70-8.81 (4H, m), 9.01-9.22 (1H, m), 13.05 (1H, m) 1:1 mixture of rotamers |
| 113 | 2-(2-hydroxy-1-(pyridin-3-yl)ethylamino)-4-(5-(trifluoromethyl)-1H-pyrrolo[2,3-b]pyridin-3-yl)pyrimidine-5-carbonitrile | 426 | (DMSO) 3.80 masked signal, 5.30 (1H, m), 7.49-7.63 (1H, m), 7.98-8.14 (1H, m), 8.52-9.24 (8H, m), 13.09 (1H, m) 1:1 mixture of rotamers |
| 114 | 2-((S)-2,3-dihydroxypropylamino)-4-(5-(trifluoromethyl)-1H-pyrrolo[2,3-b]pyridin-3-yl)pyrimidine-5-carbonitrile | 379 | |
| 115 | 2-((R)-2,3-dihydroxypropylamino)-4- | 379 | |

TABLE IIA-continued

| | Name | M + 1 (obs) | ¹H NMR (DMSO-D₆) |
|---|---|---|---|
| | (5-(trifluoromethyl)-1H-pyrrolo[2,3-b]pyridin-3-yl)pyrimidine-5-carbonitrile | | |
| 116 | 2-((2S,3R)-1-hydroxy-3-methylpentan-2-ylamino)-4-(5-(trifluoromethyl)-1H-pyrrolo[2,3-b]pyridin-3-yl)pyrimidine-5-carbonitrile | 405 | |
| 117 | 2-((1-methylpiperidin-4-yl)methylamino)-4-(5-(trifluoromethyl)-1H-pyrrolo[2,3-b]pyridin-3-yl)pyrimidine-5-carbonitrile | 416 | |
| 118 | 2-((1-ethylpiperidin-4-yl)methylamino)-4-(5-(trifluoromethyl)-1H-pyrrolo[2,3-b]pyridin-3-yl)pyrimidine-5-carbonitrile | 430 | |
| 119 | 2-((1R,3S)-3-(hydroxymethyl)cyclopentylamino)-4-(5-(trifluoromethyl)-1H-pyrrolo[2,3-b]pyridin-3-yl)pyrimidine-5-carbonitrile | 403 | CDCl₃/MeOD 1.40-2.40 (9H, m), 4.51 (1H, m), 8.44 (1H, s), 8.52 (1H, d), 8.60 (1H, s), 9.26 (1H, m) |
| 120 | 2-((1H-pyrrolo[2,3-b]pyridin-5-yl)methylamino)-4-(5-(trifluoromethyl)-1H-pyrrolo[2,3-b]pyridin-3-yl)pyrimidine-5-carbonitrile | 435 | CDCl₃/MeOD: 2.04 (2H, s), 2.66 (1H, s), 6.70 (1H, d), 7.55 (1H, d), 8.58 (3H, m), 8.90 (1H, s), 9.35 (1H, s) |
| 121 | N-(4-(1-(5-cyano-4-(5-(trifluoromethyl)-1H-pyrrolo[2,3-b]pyridin-3-yl)pyrimidin-2-ylamino)ethyl)phenyl)acetamide | 466 | CDCl₃/MeOD: 1.63 (3H, m), 2.09 (3H, d), 5.39 (1H, m), 7.39 (2H, d), 7.49 (2H, d), 8.56 (1H, d), 8.65 (1H, s), 8.78 (1H, s), 9.14 (1H, s), 9.40 (1H, s), 9.85 (1H, m) |
| 122 | 2-(1-(3-chloro-4-hydroxyphenyl)ethylamino)-4-(5-(trifluoromethyl)-1H-pyrrolo[2,3-b]pyridin-3-yl)pyrimidine-5-carbonitrile | 459 | CDCl₃: 1.68 (3H, s), 5.32 (1H, m), 6.13 (1H, br s), 7.00 (1H, m), 7.22 (2H, m), 7.40 (1H, m), 8.54 (1H, d), 8.69 (1H, s), 8.84 (1H, d), 9.11 (1H, s), 10.06 (1H, s) |
| 123 | tert-butyl 4-(4-(1-(5-cyano-4-(5-(trifluoromethyl)-1H-pyrrolo[2,3-b]pyridin-3-yl)pyrimidin-2-ylamino)ethyl)phenyl)piperazine-1-carboxylate | 593 | |
| 124 | 2-(1-(4-(piperazin-1-yl)phenyl)ethylamino)-4-(5-(trifluoromethyl)-1H-pyrrolo[2,3-b]pyridin-3-yl)pyrimidine-5-carbonitrile | 493 | 1.52 (3H, s), 3.24 (8H, m), 5.30 (1H, m), 6.96 (2H, m), 7.29 (2H, m), 8.71 (6H, m), 9.21 (1H, d), 13.08 (1H, m) |
| 125 | 2-(1-(4-morpholinophenyl)ethylamino)-4-(5-(trifluoromethyl)-1H-pyrrolo[2,3-b]pyridin-3-yl)pyrimidine-5-carbonitrile | 494 | 1.53 (3H, s), 3.03 (4H, m), 3.69 (4H, m), 5.26 (1H, m), 6.90 (2H, m), 7.26 (2H, m), 8.74 (4H, m), 9.21 (1H, d), 13.06 (1H, m) |
| 126 | 2-(1-(4-(4-methyl-1,4-diazepan-1-yl)phenyl)ethylamino)-4-(5-(trifluoromethyl)-1H-pyrrolo[2,3-b]pyridin-3-yl)pyrimidine-5-carbonitrile | 521 | 1.63 (3H, d), 2.01 (2H, m), 2.35 (3H, s), 2.59 (2H, m), 2.72 (2H, m), 3.44 (2H, m), 3.54 (2H, m), 5.33 (1H, d), 6.64 (2H, d), 7.24 (2H, d), 8.45 (1H, s), 8.59 (1H, s), 8.67 (1H, s), 9.19 (1H, s) |
| 127 | 2-((R)-1-(4-(4-methylpiperazin-1-yl)phenyl)ethylamino)-4-(5-(trifluoromethyl)-1H-pyrrolo[2,3-b]pyridin-3-yl)pyrimidine-5-carbonitrile | 507 | 1.53 (3H, d), 2.20-2.25 (3H, m), 2.4-2.5 (4H, m), 3.02-3.08 (4H, m), 5.2-5.3 (1H, m), 6.83-6.9 (2H, m), 7.23-7.28 (2H, m), 8.68-8.8 (4H, m), 9.1 (0.6H, s), 9.25 (0.4H, s), 13.2 (1H, s) |
| 128 | 2-((R)-3-methyl-1-morpholinobutan-2-ylamino)-4-(5-(trifluoromethyl)-1H-pyrrolo[2,3-b]pyridin-3-yl)pyrimidine-5-carbonitrile | 460 | (at 110° C.) 0.99 (6H, m), 2.33-2.51 (6H, m), 3.47 (4H, br m), 4.27 (1H, m), 7.56 (1H, m), 8.61 (1H, s), 8.70 (2H, s), 9.12 (1H, s), 12.66 (1H, br s) |
| 129 | 2-((S)-1-(6-(4-methylpiperazin-1-yl)pyridin-3-yl)ethylamino)- | 508 | ¹H NMR (DMSO-d₆, 400 MHz) δ 1.54 (3H, m), 2.18 (3H, m), 2.33-2.37 (4H, m), 3.38-3.43 (4H, m), |

TABLE IIA-continued

| | Name | M + 1 (obs) | ¹H NMR (DMSO-D₆) |
|---|---|---|---|
| | 4-(5-(trifluoromethyl)-1H-pyrrolo[2,3-b]pyridin-3-yl)pyrimidine-5-carbonitrile | | 5.18-5.27 (1H, m), 6.77-6.84 (1H, m), 7.56-7.62 (1H, m), 8.08-8.16 (1H, m), 8.70-8.77 (4H, m), 9.04-9.18 (1H, m), 12.98 (1H, m) mixture of rotamers |
| 130 | 2-((R)-1-(4-(4-benzylpiperazin-1-yl)phenyl)ethylamino)-4-(5-(trifluoromethyl)-1H-pyrrolo[2,3-b]pyridin-3-yl)pyrimidine-5-carbonitrile | 583 | CDCl³: 1.70 (3H, m), 2.61 (4H, s), 3.20 (4H, s), 3.58 (2H, s), 3.80 (1H, m), 6.31 (1H, m), 6.92 (2H, m), 7.34 (7H, m), 8.59 (1H, d), 8.75 (1H, s), 8.86 (1H, d), 9.24 (1H, d) |
| 131 | 2-(1-(4-(1,4-diazepan-1-yl)phenyl)ethylamino)-4-(5-(trifluoromethyl)-1H-pyrrolo[2,3-b]pyridin-3-yl)pyrimidine-5-carbonitrile | 507 | |
| 132 | 2-((R)-1-morpholinopropan-2-ylamino)-4-(5-(trifluoromethyl)-1H-pyrrolo[2,3-b]pyridin-3-yl)pyrimidine-5-carbonitrile | 432 | (at 110° C.) 1.30 (3H, d), 2.50-2.67 (6H, m), 3.55 (4H, m), 4.39 (1H, m), 7.63 (1H m), 8.62 (1H, s), 8.69 (2H, s), 9.11 (1H, s), 12.66 (1H, br s) |
| 133 | 2-((R)-1-(4-(dimethylamino)phenyl)ethylamino)-4-(5-(trifluoromethyl)-1H-pyrrolo[2,3-b]pyridin-3-yl)pyrimidine-5-carbonitrile | 452 | 1.51 (3H, m), 2.81 (6H, m), 5.23 (1H, m), 6.63-6.71 (2H, m), 7.20-7.25 (2H, m), 8.70 (4H, m), 9.07-9.22 (1H, m), 13.07 (1H, m) mixture of rotamers |
| 134 | 2-((R)-1-(1-acetylpiperidin-4-yl)ethylamino)-4-(5-(trifluoromethyl)-1H-pyrrolo[2,3-b]pyridin-3-yl)pyrimidine-5-carbonitrile | 458 | 1.03 (1H, m), 1.19-1.23 (4H, m), 1.76-1.84 (3H, m), 1.93-1.98 (3H, m), 2.96 (1H, m), 3.80 (1H, m), 4.07 (1H, m), 4.41 (1H, m), 8.10 (1H, m), 8.57-8.65 (2H, m), 8.81 (1H, m), 9.12 (1H, m), 13.10 (1H, m) mixture of rotamers |
| 135 | 2-((S)-1-(1-acetylpiperidin-4-yl)ethylamino)-4-(5-(trifluoromethyl)-1H-pyrrolo[2,3-b]pyridin-3-yl)pyrimidine-5-carbonitrile | 458 | 1.02 (1H, m), 1.21 (4H, m), 1.76-1.84 (3H, m), 1.93-1.96 (3H, m), 2.96 (1H, m), 3.80 (1H, m), 4.05 (1H, m), 4.41 (1H, m), 8.14 (1H, m), 8.58-8.79 (3H, m), 9.12 (1H, m), 13.10 (1H, m) mixture of rotamers |
| 136 | N-(4-((1R)-1-(5-cyano-4-(5-(trifluoromethyl)-1H-pyrrolo[2,3-b]pyridin-3-yl)pyrimidin-2-ylamino)ethyl)phenyl)methanesulfonamide | 502 | 1.54 (3H, m), 2.91 (3H, m), 5.29 (1H, m), 7.12-7.19 (2H, m), 7.34-7.40 (2H, m), 8.69-8.74 (3H, m), 8.82 (1H, m), 8.97-9.21 (1H, m), 9.66 (1H, m), 13.06 (1H, m) mixture of rotamers |
| 137 | N-(4-((1R)-1-(5-cyano-4-(5-(trifluoromethyl)-1H-pyrrolo[2,3-b]pyridin-3-yl)pyrimidin-2-ylamino)ethyl)phenyl)cyclopropanecarboxamide | 492 | 0.75 (4H, m), 1.54 (3H, m), 1.74 (1H, m), 5.26 (1H, m), 7.29-7.35 (2H, m), 7.48-7.55 (2H, m), 8.69-8.74 (3H, m), 8.80 (1H, m), 9.00-9.22 (1H, m), 10.14 (1H, m), 13.07 (1H, m) mixture of rotamers |
| 138 | 2-(1-(6-morpholinopyridin-3-yl)ethylamino)-4-(5-(trifluoromethyl)-1H-pyrrolo[2,3-b]pyridin-3-yl)pyrimidine-5-carbonitrile | 495 | 1.55 (3H, d), 3.38-3.42 (2H, m), 3.63-3.69 (4H, m), 5.20-5.27 (1H, m), 6.78-6.85 (1H, m), 7.59-7.65 (1H, m), 8.11 (0.5H, s), 8.19 (0.5H, s), 8.71-8.77 (4H, m), 9.05 (0.5H, s), 9.19 (0.5H, s), 13.03 (0.5H, s), 13.09 (0.5H, s). ~1:1 mixture of rotamers, water peak obscures some signals |
| 139 | 2-(1-(6-(4-methylpiperazin-1-yl)pyridin-3-yl)ethylamino)-4-(5-(trifluoromethyl)-1H-pyrrolo[2,3-b]pyridin-3-yl)pyrimidine-5-carbonitrile | 508 | 1.54 (3H, d), 2.17 (1.5H, s), 2.20 (1.5H, s), 2.33-2.37 (4H, m), 3.37-3.43 (4H, m), 5.20-5.24 (1H, m), 6.77-6.83 (1H, m), 7.57-7.62 (1H, m), 8.08 (0.5H, s), 8.16 (0.5H, s), 8.69-8.73 (4H, m), 9.05 (0.5H, s), 9.18 (0.5H, s), 12.95 (1H, vbrs). ~1:1 mixture of rotamers |
| 140 | 2-((R)-1-(4-(4-isopropylpiperazin-1-yl)phenyl)ethylamino)-4-(5-(trifluoromethyl)-1H-pyrrolo[2,3-b]pyridin-3-yl)pyrimidine-5-carbonitrile | 535 | |

TABLE IIA-continued

| | Name | M + 1 (obs) | ¹H NMR (DMSO-D₆) |
|---|---|---|---|
| 141 | methyl 4-((1R)-1-(5-cyano-4-(5-(trifluoromethyl)-1H-pyrrolo[2,3-b]pyridin-3-yl)pyrimidin-2-ylamino)ethyl)phenylcarbamate | 482 | 1.53 (3H, m), 3.62 (3H, m), 5.28 (1H, m), 7.28-7.41 (4H, m), 8.69-8.78 (4H, m), 8.99-9.21 (1H, m), 9.58 (1H, m), 13.03 (1H, br s) mixture of rotamers |
| 142 | 2-((R)-1-(3-fluoro-4-(4-methylpiperazin-1-yl)phenyl)ethylamino)-4-(5-(trifluoromethyl)-1H-pyrrolo[2,3-b]pyridin-3-yl)pyrimidine-5-carbonitrile | 525 | CDCl3 1.55 (3H, d), 2.17-2.24 (3H, m), 2.4-2.5 (4H, m), 2.95-3.02 (4H, m), 5.22-5.28 (1H, m), 6.95-7.02 (1H, m), 7.02-7.18 (2H, m), 8.7-8.8 (3H, m), 8.97 (0.5H, s), 9.12 (0.5H, s), 13.1 (1H, brs) |
| 143 | 2-(1-(6-(dimethylamino)pyridin-3-yl)ethylamino)-4-(5-(trifluoromethyl)-1H-pyrrolo[2,3-b]pyridin-3-yl)pyrimidine-5-carbonitrile | 453 | 1.54 (3H, d), 2.94 (3H, s), 2.98 (3H, s), 5.18-5.26 (1H, m), 6.61 (1H, dd), 7.54-7.59 (1H, m), 8.05 (0.5H, s), 8.13 (0.5H, s), 8.70-8.75 (4H, m), 9.07 (0.5H, s), 9.19 (0.5H, s), 13.02 (0.5H, brs), 13.09 (0.5H, brs). ~1:1 mixture of rotamers |
| 144 | N-(4-((1R)-1-(5-cyano-4-(5-(trifluoromethyl)-1H-pyrrolo[2,3-b]pyridin-3-yl)pyrimidin-2-ylamino)ethyl)phenyl)propionamide. | 480 | 1.05 (3H, m), 1.54 (3H, m), 2.25-2.30 (2H, m), 5.26 (1H, m), 7.21-7.35 (2H, m), 7.48-7.55 (2H, m), 8.69-8.74 (3H, m), 8.78 (1H, m), 9.00-9.22 (1H, m), 9.78 (1H, m), 13.03 (1H, m) mixture of rotamers |
| 145 | 2-((R)-1-(4-(2-oxopyrrolidin-1-yl)phenyl)ethylamino)-4-(5-(trifluoromethyl)-1H-pyrrolo[2,3-b]pyridin-3-yl)pyrimidine-5-carbonitrile | 492 | 1.54 (3H, m), 1.99-2.06 (2H, m), 3.74-3.82 (3H, m), 5.29 (1H, m), 7.36-7.42 (2H, m), 7.54-7.61 (2H, m), 8.67-8.71 (3H, m), 8.78 (1H, m), 8.99-9.21 (1H, m). Mixture of rotamers |
| 146 | 2-((R)-1-(4-((S)-1-methylpyrrolidin-3-yloxy)phenyl)ethylamino)-4-(5-(trifluoromethyl)-1H-pyrrolo[2,3-b]pyridin-3-yl)pyrimidine-5-carbonitrile | 508 | MeOD 1.59 (3H, m), 2.34 (2H, m), 2.96 (3H, m), 3.32 (3H, m), 3.82 (2H, m), 5.25 (2H, m), 6.90 (2H, d), 7.39 (2H, d), 8.45 (1H, s), 8.60 (1H, s), 8.71 (1H, s), 9.04 (1H, d) |
| 147 | 2-((R)-1-(6-(4-methylpiperazin-1-yl)pyridin-3-yl)ethylamino)-4-(5-(trifluoromethyl)-1H-pyrrolo[2,3-b]pyridin-3-yl)pyrimidine-5-carbonitrile | 508 | |
| Compound No I- | | | |
| 149 | 2-((R)-1-(2-fluoro-4-(4-methylpiperazin-1-yl)phenyl)ethylamino)-4-(5-(trifluoromethyl)-1H-pyrrolo[2,3-b]pyridin-3-yl)pyrimidine-5-carbonitrile | 525 | 1.48-1.52 (3H, m), .212 (3H, s), 2.7-2.76 (2H, m), 2.9-3.03 (2H, m), 3.07-3.2 (2H, m), 3.8-3.9 (2H, m), 5.4-5.5 (0.4H, m), 5.53-5.6 (0.6H, m), 6.7-6.85 (2H, m), 7.3-7.4 (1H, m), 8.7-8.9 (4H, m), 8.97 (0.6H, s), 9.22 (0.4H, s), 9.63 (1H, br s), 13.0-13.15 (1H, m) |
| 150 | 2-(1-(1-(methylsulfonyl)piperidin-4-yl)ethylamino)-4-(5-(trifluoromethyl)-1H-pyrrolo[2,3-b]pyridin-3-yl)pyrimidine-5-carbonitrile | 494 | 1.2-1.35 (5H, m), 1.5-1.62 (1H, m), 1.8-1.97 (2H, m), 2.6-2.74 (2H, m), 2.82-2.87 (3H, m), 3.5-3.65 (2H, m), 4.0-4.1 (1H, m), 8.3-8.36 (1H, m), 8.67-8.8 (3H, m), 9.1-9.2 (1H, m), 13.0-13.15 (1H, m) |
| 151 | 2-(1-(6-(methylamino)pyridin-3-yl)ethylamino)-4-(5-(trifluoromethyl)-1H-pyrrolo[2,3-b]pyridin-3-yl)pyrimidine-5-carbonitrile | 439 | 1.55 (3H, d), 2.85 (1.5H, brs), 2.89 (1.5H, brs), 5.17-5.22 (1H, m), 6.99 (1H, vbrs), 7.73 (0.5H, brs), 7.87 (1H, s), 7.96 (0.5H, m), 8.72-8.79 (4H, m), 8.91 (0.5H, s), 9.18 (0.5H, s), 13.08 (0.5H, s), 13.12 (0.5H, s); ~1:1 mixture of rotamers |
| 152 | methyl 4-(1-(5-cyano-4-(5-(trifluoromethyl)-1H-pyrrolo[2,3-b]pyridin-3-yl)pyrimidin-2-ylamino)ethyl)piperidine-1-carboxylate | 474 | 1.0-1.3 (6H, m), 1.68-1.72 (4H, m), 2.65-2.85 (2H, m), 3.52-3.58 (3H, m), 3.9-4.1 (3H, m), 8.25-8.29 (1H, m), 8.66-8.8 (3H, m), 9.12 (0.7H, s), 9.18 (0.3H, s), 13.0-13.15 (1H, m) |
| 153 | 2-(1-(1-(ethylsulfonyl)piperidin-4- | 508 | 1.15-1.3 (8H, m), 1.52-1.6 (1H, m), 1.82-1.95 (2H, m), |

TABLE IIA-continued

| | Name | M + 1 (obs) | ¹H NMR (DMSO-D₆) |
|---|---|---|---|
| | yl)ethylamino)-4-(5-(trifluoromethyl)-1H-pyrrolo[2,3-b]pyridin-3-yl)pyrimidine-5-carbonitrile | | 2.7-2.85 (2H, m), 2.92-2.98 (2H, m), 3.58-3.65 (2H, m), 4.03-4.1 (1H, m), 8.28-8.31 (1H, m), 8.7-8.8 (3H, m), 9.12-9.18 (1H, m), 13.0-13.1 (1H, m) |
| 154 | 2-((R)-1-(4-(1-methylpiperidin-4-yloxy)phenyl)ethylamino)-4-(5-(trifluoromethyl)-1H-pyrrolo[2,3-b]pyridin-3-yl)pyrimidine-5-carbonitrile | 522 | |
| 155 | 2-(1-(4-(methylsulfonyl)phenyl)ethylamino)-4-(5-(trifluoromethyl)-1H-pyrrolo[2,3-b]pyridin-3-yl)pyrimidine-5-carbonitrile | 487 | |
| 156 | benzyl 4-(1-(5-cyano-4-(5-(trifluoromethyl)-1H-pyrrolo[2,3-b]pyridin-3-yl)pyrimidin-2-ylamino)ethyl)piperidine-1-carboxylate | 550 | 1.21 (5H, m), 1.76 (3H, m), 2.77 (2H, m), 4.05 (3H, m), 5.03 (2H, m), 7.34 (5H, m), 8.27 (1H, m), 8.66 (3H, m), 9.13 (1H, m), 13.04 (1H) |
| 157 | 4-(1-(5-cyano-4-(5-(trifluoromethyl)-1H-pyrrolo[2,3-b]pyridin-3-yl)pyrimidin-2-ylamino)ethyl)-N,N-dimethylpiperidine-1-carboxamide | 487 | 1.21 (5H, m), 1.63 (3H, m), 2.68 (2H, m), 2.70 (6H, m), 2.74 (2H, m), 4.03 (1H, m), 8.26 (1H, m), 8.66 (3H, m), 9.11 (1H, m), 13.08 (1H) |
| 158 | 2-(1-(1-(cyclopropylsulfonyl)piperidin-4-yl)ethylamino)-4-(5-(trifluoromethyl)-1H-pyrrolo[2,3-b]pyridin-3-yl)pyrimidine-5-carbonitrile | 520 | 0.85-0.98 (4H, m), 1.15-1.3 (5H, m), 1.6-1.7 (1H, m), 1.8-1.9 (2H, m), 2..7-2.85 (2H, m), 3.6-3.7 (2H, m), 4.05-4.15 (1H, m), 8.3-8.37 (1H, m), 8.65-8.8 (3H, m), 9.1-9.2 (1H, m), 13.05-13.15 (1H, m) |
| 159 | 2-(1-(1-(cyclopropanecarbonyl)piperidin-4-yl)ethylamino)-4-(5-(trifluoromethyl)-1H-pyrrolo[2,3-b]pyridin-3-yl)pyrimidine-5-carbonitrile | 484 | 0.65 (4H, m), 1.22 (6H, m), 1.84 (4H, m), 3.02 (1H, m), 4.06 (1H, m), 4.35 (2H, m), 8.27 (1H, m), 8.67 (3H, m), 9.14 (1H, m), 13.08 (1H, m) |
| 160 | 4-(1-(5-cyano-4-(5-(trifluoromethyl)-1H-pyrrolo[2,3-b]pyridin-3-yl)pyrimidin-2-ylamino)ethyl)-N-methylpiperidine-1-carboxamide | 473 | 1.04 (2H, m), 1.22 (3H, m), 1.70 (3H, m), 2.50 (3H, m), 2.54 (2H, m), 3.99 (3H, m), 6.30 (1H, br s), 8.26 (1H, m), 8.67 (3H, m), 9.14 (1H, m), 13.03 (1H, s) |
| 161 | 2-((S)-1-(4-((S)-1-methylpyrrolidin-3-yloxy)phenyl)ethylamino)-4-(5-(trifluoromethyl)-1H-pyrrolo[2,3-b]pyridin-3-yl)pyrimidine-5-carbonitrile | 508 | 1.55 (3H, m), 1.99 (1H, m), 2.23 (1H, m), 2.84-2.90 (3H, m), 3.67 (2H, m), 5.10 (1H, m), 5.30 (1H, m), 6.88-6.96 (2H, m), 7.34-7.40 (2H, m), 8.70-8.75 (3H, m), 8.82 (1H, m), 9.00-9.21 (1H, m), 9.99 (1H, m), 13.09 (1H, m) mixture of rotamers |
| 162 | 2-(1-(6-(4-hydroxypiperidin-1-yl)pyridin-3-yl)ethylamino)-4-(5-(trifluoromethyl)-1H-pyrrolo[2,3-b]pyridin-3-yl)pyrimidine-5-carbonitrile | 509 | 1.33-1.47 (2H, m), 1.54 (3H, d), 1.70-1.76 (2H, m), 2.95-3.05 (2H, m), 3.60-3.73 (1H, m), 3.90-3.99 (2H, m), 4.62-4.66 (1H, m), 5.18-5.24 (1H, m), 6.80 (1H, dd), 7.54-7.59 (1H, m), 8.07 (0.5H, s), 8.14 (0.5H, s), 8.69-8.74 (4H, m), 9.06 (0.5H, s), 9.19 (0.5H, s), 13.04 (1H, br s); ~1:1 mixture of rotamers |
| 163 | 4-((1R)-1-(5-cyano-4-(5-(trifluoromethyl)-1H-pyrrolo[2,3-b]pyridin-3-yl)pyrimidin-2-ylamino)ethyl)-N-methylbenzamide | 466 | 1.57 (3H, m), 2.72-2.77 (3H, m), 5.34 (1H, m), 7.44-7.50 (2H, m), 7.73-7.80 (2H, m), 8.31-8.36 (1H, m), 8.67-8.73 (3H, m), 8.86 (1H, m), 8.94-9.22 (1H, m), 13.02 (1H, m) mixture of rotamers |
| 164 | 4-((1S)-1-(5-cyano-4-(5-(trifluoromethyl)-1H-pyrrolo[2,3-b]pyridin-3- | 466 | 1.56 (3H, m), 2.72-2.77 (3H, m), 5.34 (1H, m), 7.44-7.50 (2H, m), 7.73-7.80 (2H, m), 8.31-8.36 (1H, |

TABLE IIA-continued

| | Name | M + 1 (obs) | ¹H NMR (DMSO-D₆) |
|---|---|---|---|
| | yl)pyrimidin-2-ylamino)ethyl)-N-methylbenzamide | | m), 8.67-8.73 (3H, m), 8.85 (1H, m), 8.94-9.22 (1H, m), 13.00 (1H, m) mixture of rotamers |
| 165 | 2-(1-(1-tosylpiperidin-4-yl)ethylamino)-4-(5-(trifluoromethyl)-1H-pyrrolo[2,3-b]pyridin-3-yl)pyrimidine-5-carbonitrile | 570 | 1.17 (5H, m), 1.46 (1H, m), 1.83 (2H, m), 2.15 (2H, m), 2.34 (3H, s), 3.66 (2H, m), 3.96 (1H, m), 7.40 (2H, m), 7.60 (2H, m), 8.19 (1H, m), 8.69 (3H, m), 9.06 (1H, m), 13.08 (1H, s) |
| 166 | 2-(1-(1-(cyanomethyl)piperidin-4-yl)ethylamino)-4-(5-(trifluoromethyl)-1H-pyrrolo[2,3-b]pyridin-3-yl)pyrimidine-5-carbonitrile | 455 | 1.2-1.4 (4H, m), 1.5-1.65 (1H, m), 1.85-1.98 (2H, m), 2.90-3.12 (1H, m), 3.7-4.1 (3H, m), 8.23-8.3 (1H, m), 8.65-8.8 (3H, m), 9.1-9.2 (1H, m) |
| 167 | 2-(1-(6-(piperazin-1-yl)pyridin-3-yl)ethylamino)-4-(5-(trifluoromethyl)-1H-pyrrolo[2,3-b]pyridin-3-yl)pyrimidine-5-carbonitrile | 494 | 1.54 (3H, d), 2.72-2.76 (4H, m), 5.18-5.26 (1H, m), 6.76 (1H, dd), 7.56-7.61 (1H, m), 8.08 (0.5H, s), 8.16 (0.5H, s), 8.68-8.72 (4H, m), 9.05 (0.5H, s), 9.18 (0.5H, s). Water peak obscures some signals, ~1:1 mixture of rotamers |
| 168 | N-(4-((1R)-1-(5-cyano-4-(5-(trifluoromethyl)-1H-pyrrolo[2,3-b]pyridin-3-yl)pyrimidin-2-ylamino)ethyl)phenyl)cyclopropanesulfonamide | 528 | 0.72-0.9 (4H, m), 1.48 (3H, d), 3.12-3.14 (2H, m), 4.02-4.05 (1H, m), 5.25-5.32 (1H, m), 7.05-7.16 (2H, m), 7.25-7.33 (2H, m), 8.63-8.71 (3H, m), 8.75-8.8 (1H, m), 8.92 (0.6H, s), 9.18 (0.4H, s), 9.5-9.6 (1H, m), 12.92-12.98 (1H, m) |
| 169 | N-(4-((1R)-1-(5-cyano-4-(5-(trifluoromethyl)-1H-pyrrolo[2,3-b]pyridin-3-yl)pyrimidin-2-ylamino)ethyl)phenyl)ethanesulfonamide | 516 | 1.1-1.25 (3H, m), 1.58 (3H, d), 2.95-3.07 (2H, m), 5.3-5.37 (1H, m), 7.12-7.22 (2H, m), 7.32-7.42 (2H, m), 8.7-8.8 (3H, m), 8.8-8.82 (1H, m), 8.95 (0.6H, s), 9.22 (0.4H, s), 9.71-9.76 (1H, m), 13.0-13.1 (1H, m) |
| 170 | 4-((1R)-1-(5-cyano-4-(5-(trifluoromethyl)-1H-pyrrolo[2,3-b]pyridin-3-yl)pyrimidin-2-ylamino)ethyl)-N-ethylbenzamide | 480 | 1.05-1.10 (3H, m), 1.56 (3H, m), 3.21 (2H, m), 5.30-5.37 (1H, m), 7.43-7.49 (2H, m), 7.74-7.81 (2H, m), 8.34 (1H, m), 8.67-8.74 (3H, m), 8.88 (1H, m), 8.95-9.23 (1H, m), 13.04 (1H, br s) |
| 171 | 4-((1R)-1-(5-cyano-4-(5-(trifluoromethyl)-1H-pyrrolo[2,3-b]pyridin-3-yl)pyrimidin-2-ylamino)ethyl)-N-cyclopropylbenzamide | 492 | 0.51-0.54 (2H, m), 0.64-0.69 (2H, m), 1.55 (3H, m), 2.78-2.82 (1H, m), 5.33 (1H, m), 7.42-7.49 (2H, m), 7.71-7.78 (2H, m), 8.29 (1H, m), 8.67-8.74 (3H, m), 8.88 (1H, m), 8.96-9.22 (1H, m), 13.06 (1H, br s) |
| 172 | 4-((1R)-1-(5-cyano-4-(5-(trifluoromethyl)-1H-pyrrolo[2,3-b]pyridin-3-yl)pyrimidin-2-ylamino)ethyl)-N-isopropylbenzamide | 494 | 1.10-1.15 (6H, m), 1.56 (3H, m), 4.03-4.08 (1H, m), 5.31-5.37 (1H, m), 7.43-7.49 (2H, m), 7.74-7.81 (2H, m), 8.08 (1H, m), 8.67-8.74 (3H, m), 8.89 (1H, m), 8.97-9.23 (1H, m), 13.05 (1H, br s) |
| 173 | 2-(1-(1-(cyanomethyl)piperidin-4-yl)propylamino)-4-(5-(trifluoromethyl)-1H-pyrrolo[2,3-b]pyridin-3-yl)pyrimidine-5-carbonitrile | 469 | 0.914 (3H, m), 1.34-1.40 (2H, m), 1.50-1.98 (7H, m), 2.55 (1H, m), 3.13 (2H, m), 3.79 (2H, m), 8.16 (1H, m), 8.71 (3H, m), 9.14 (1H, m), 13.05 (1H, s) |
| 174 | 2-(1-(1-acetylpiperidin-4-yl)propylamino)-4-(5-(trifluoromethyl)-1H-pyrrolo[2,3-b]pyridin-3-yl)pyrimidine-5-carbonitrile | 472 | 1.04 (3H, m), 1.05-1.16 (2H, m), 1.52 (1H, m), 1.74 (5H, m), 1.96 (3H, m), 2.92 (1H, m), 3.99 (2H, m), 4.41 (1H, m), 8.19 (1H, m), 8.69 (3H, m), 9.11 (1H, m), 13.08 (1H, s) |
| 175 | 2-(1-(1-(ethylsulfonyl)piperidin-4-yl)propylamino)-4-(5-(trifluoromethyl)-1H-pyrrolo[2,3-b]pyridin-3-yl)pyrimidine-5-carbonitrile | 522 | 0.91 (3H, m), 1.25 (5H, m), 1.72 (1H, m), 1.74-1.80 (6H, m), 2.72 (2H, m), 3.01 (2H, m), 4.01 (1H, m), 8.23 (1H, m), 8.73 (3H, m), 9.12 (1H, m), 13.09 (1H, s) |
| 176 | 4-((1R)-1-(5-cyano-4-(5-(trifluoromethyl)-1H-pyrrolo[2,3-b]pyridin-3- | 452 | 1.56 (3H, m), 5.30-5.37 (1H, m), 7.28 (1H, m), 7.43-7.49 (2H, m), 7.77-7.92 (3H, M), 8.68-8.73 (3H, |

TABLE IIA-continued

| | Name | M + 1 (obs) | ¹H NMR (DMSO-D₆) |
|---|---|---|---|
| | yl)pyrimidin-2-ylamino)ethyl)benzamide | | m), 8.90-9.23 (2H, m), 13.06 (1H, m) |
| 177 | N-(4-((1R)-1-(5-cyano-4-(5-(trifluoromethyl)-1H-pyrrolo[2,3-b]pyridin-3-yl)pyrimidin-2-ylamino)ethyl)-2-fluorophenyl)methanesulfonamide | 520 | 1.54 (3H, m), 2.95-3.00 (3H, m), 5.25-5.34 (1H, m), 7.11-7.34 (3H, m), 8.68-8.73 (3H, m), 8.82 (1H, m), 8.90-9.21 (1H, m), 9.53 (1H, m), 13.04 (1H, m) |
| 178 | 2-(1-(1-(prop-2-ynyl)piperidin-4-yl)ethylamino)-4-(5-(trifluoromethyl)-1H-pyrrolo[2,3-b]pyridin-3-yl)pyrimidine-5-carbonitrile | 454 | 1.22-1.26 (3H, m), 1.41-1.47 (2H, m), 1.78 (1H, m), 2.02 (2H, m), 2.97 (2H, m), 3.89 (2H, m), 4.04 (3H, m), 8.29-8.35 (1H, m), 8.70-8.77 (3H, m), 9.10-9.17 (1H, m), 9.78 (1H, m), 13.06 (1H, m) |
| 179 | 2-((R)-1-((1r,4R)-4-hydroxycyclohexyl)ethylamino)-4-(5-(trifluoromethyl)-1H-pyrrolo[2,3-b]pyridin-3-yl)pyrimidine-5-carbonitrile | 431 | (CDCl₃) 1.18-1.36 (7H, m), 1.90-2.07 (4H, m), 3.61 (1H, m), 4.12-4.22 (2H, m), 5.64-5.65 (1H, m), 8.58.55 (1H, m), 8.74 (1H, s), 8.8.83 (1H, m), 9.18 (1H, m), 10.09 (1H, s) |
| 180 | 2-((R)-1-((1s,4S)-4-hydroxycyclohexyl)ethylamino)-4-(5-(trifluoromethyl)-1H-pyrrolo[2,3-b]pyridin-3-yl)pyrimidine-5-carbonitrile | 431 | |
| 181 | 4-(1-(5-cyano-4-(5-(trifluoromethyl)-1H-pyrrolo[2,3-b]pyridin-3-yl)pyrimidin-2-ylamino)ethyl)-N,N-diethylbenzenesulfonamide | 544 | (CDCl₃) 1.05 (6H, m), 1.75 (3H, m), 3.19 (4H, m), 5.46 (1H, s), 7.08 (1H, d), 7.53 (2H, d), 7.78 (2H, d), 8.55 (1H, s), 8.70 (1H, s), 8.91 (1H, s), 9.22 (1H, d), 11.27 (1H, d) |
| 182 | 2-(1-(1-(isopropylsulfonyl)piperidin-4-yl)propylamino)-4-(5-(trifluoromethyl)-1H-pyrrolo[2,3-b]pyridin-3-yl)pyrimidine-5-carbonitrile | 536 | 0.91 (3H, m), 1.26 (8H, m), 1.55 (1H, m), 1.91 (5H, m), 2.75 (2H, m), 3.54 (2H, m), 4.01 (1H, m), 8.19 (1H, m), 8.73 (3H, m), 9.12 (1H, m), 13.08 (1H, s) |
| 183 | 2-(1-(1-(2-methoxyacetyl)piperidin-4-yl)ethylamino)-4-(5-(trifluoromethyl)-1H-pyrrolo[2,3-b]pyridin-3-yl)pyrimidine-5-carbonitrile | 488 | 1.22 (5H, m), 1.83 (3H, m), 2.93 (1H, m), 3.30 (3H, m), 3.95 (2H, m), 4.01 (3H, m), 4.41 (1H, m), 8.28 (1H, m), 8.73 (3H, m), 9.15 (1H, m), 13.08 (1H, s) |
| 184 | 2-(1-(1-(3-methoxypropanoyl)piperidin-4-yl)ethylamino)-4-(5-(trifluoromethyl)-1H-pyrrolo[2,3-b]pyridin-3-yl)pyrimidine-5-carbonitrile | 502 | 1.23 (5H, m), 1.81 (3H, m), 3.10 (1H, m), 3.21 (3H, m), 3.51 (2H, m), 4.05 (3H, m), 4.58 (3H, m), 8.28 (1H, m), 8.73 (3H, m), 9.15 (1H, m), 13.08 (1H, s) |
| 185 | 2-((R)-1-(4-(hydroxymethyl)phenyl)ethylamino)-4-(5-(trifluoromethyl)-1H-pyrrolo[2,3-b]pyridin-3-yl)pyrimidine-5-carbonitrile | 439 | 1.55 (3H, m), 4.41 (2H, m), 5.28-3.34 (1H, m), 7.21-7.29 (2H, m), 7.33-7.38 (2H, m), 8.67-8.74 (3H, m), 8.84 (1H, m), 9.01-9.23 (1H, m), 13.03 (1H, m) |
| 186 | 4-((1R)-1-(5-cyano-4-(5-(trifluoromethyl)-1H-pyrrolo[2,3-b]pyridin-3-yl)pyrimidin-2-ylamino)ethyl)benzoic acid | 453 | 1.57 (3H, m), 5.34 (1H, m), 7.49-7.55 (2H, m), 7.86-7.93 (2H, m), 8.68-8.74 (2H, m), 8.85-9.23 (2H, m), 12.82 (1H, br s), 13.05 (1H, m) |
| 187 | 2-(1-(1-propionylpiperidin-4-yl)ethylamino)-4-(5-(trifluoromethyl)-1H-pyrrolo[2,3-b]pyridin-3-yl)pyrimidine-5-carbonitrile | 472 | 1.03 (4H, m), 1.25 (5H, m), 1.75 (3H, m), 2.26 (2H, m), 2.95 (1H, m), 3.90 (1H, m), 4.05 (1H, m), 4.51 (1H, m), 4.58 (3H, m), 8.25 (1H, m), 8.73 (3H, m), 9.15 (1H, m), 13.09 (1H, s) |
| 188 | 2-(1-(1-(2-aminoacetyl)piperidin-4-yl)ethylamino)-4-(5-(trifluoromethyl)-1H-pyrrolo[2,3-b]pyridin-3-yl)pyrimidine-5-carbonitrile | 473 | 1.24 (6H, m), 1.89 (3H, m), 2.51 (1H, m), 2.63 (1H, m), 3.01 (1H, m), 4.12 (2H, m), 4.24 (1H, m), 7.98 (2H, m), 8.30 (1H, m), 8.73 (3H, m), 9.16 (1H, m), 13.06 (1H, s) |
| 189 | 2-(1-(1-(2-(methylamino)acetyl)piperidin-4-yl)ethylamino)-4-(5-(trifluoromethyl)-1H- | 487 | 1.22 (5H, m), 1.87 (3H, m), 2.51 (3H, m), 2.53 (1H, m), 3.11 (1H, m), 4.05 (4H, m), 4.41 (1H, m), 8.31 (1H, m), 8.59 (2H, m), |

TABLE IIA-continued

| | Name | M + 1 (obs) | ¹H NMR (DMSO-D₆) |
|---|---|---|---|
| | pyrrolo[2,3-b]pyridin-3-yl)pyrimidine-5-carbonitrile | | 8.74 (3H, m), 9.16 (1H, m), 13.10 (1H, s) |
| 190 | 4-((1R)-1-(5-cyano-4-(5-(trifluoromethyl)-1H-pyrrolo[2,3-b]pyridin-3-yl)pyrimidin-2-ylamino)ethyl)-N,N-dimethylbenzenesulfonamide | 516 | 1.61 (3H, m), 2.55 (6H, m masked), 5.48 (1H, m), 7.67 (4H, m), 8.71 (3H, m), 8.80 (1H, m), 8.90 (1H, m), 13.08 (1H, s) |
| 191 | 2-(1-(6-(3-cyclopropyl-3-fluoroazetidin-1-yl)pyridin-3-yl)ethylamino)-4-(5-(trifluoromethyl)-1H-pyrrolo[2,3-b]pyridin-3-yl)pyrimidine-5-carbonitrile | 523 | 0.39-0.44 (2H, m), 0.57-0.61 (2H, m), 1.36-1.39 (1H, m), 1.55 (3H, d), 3.83-3.95 (4H, m), 5.22-5.27 (1H, m), 6.46 (1H, dd), 7.64 (1H, dd), 8.06 (0.5H, s), 8.15 (0.5H, s), 8.71-8.77 (4H, m), 9.03 (0.5H, s), 9.18 (0.5H, s), 13.03 (0.5H, s), 13.09 (0.5H, s); 1:1 mixture of rotamers |
| 192 | 2-(1-(1-(2-hydroxyacetyl)piperidin-4-yl)ethylamino)-4-(5-(trifluoromethyl)-1H-pyrrolo[2,3-b]pyridin-3-yl)pyrimidine-5-carbonitrile | 474 | 1.23 (5H, m), 1.82 (3H, m), 2.59 (1H, m), 2.85 (1H, m), 3.72 (1H, m), 4.02 (3H, m), 4.40 (1H, m), 8.31 (1H, m), 8.68 (3H, m), 9.13 (1H, m), 13.08 (1H, s) |
| 193 | 2-(1-(1-(2-(dimethylamino)acetyl)piperidin-4-yl)ethylamino)-4-(5-(trifluoromethyl)-1H-pyrrolo[2,3-b]pyridin-3-yl)pyrimidine-5-carbonitrile | 501 | 1.23 (5H, m), 1.87 (3H, m), 2.54 (1H, m), 2.77 (6H, m), 3.03 (1H, m), 3.72 (1H, m), 4.02-4.45 (5H, m), 8.31 (1H, m), 8.68 (3H, m), 9.16 (1H, m), 9.46 (1H, m), 13.08 (1H, s) |
| 194 | 2-(1-(6-(3-cyclopropyl-3-hydroxyazetidin-1-yl)pyridin-3-yl)ethylamino)-4-(5-(trifluoromethyl)-1H-pyrrolo[2,3-b]pyridin-3-yl)pyrimidine-5-carbonitrile | 521 | 0.29-0.41 (4H, m), 1.14-1.19 (1H, m), 1.53 (3H, d), 3.60-3.75 (4H, m), 5.19-5.25 (1H, m), 5.47 (1H, d), 6.36 (1H, dd), 7.55-7.60 (1H, m), 8.02 (0.5H, s), 8.11 (0.5H, s), 8.70-8.76 (4H, m), 9.06 (0.5H, s), 9.18 (0.5H, s), 13.05 (0.5H, br s), 13.11 (0.5H, br s); ~1:1 mixture of rotamers |
| 195 | 2-(1-(6-(4-cyclopropyl-4-hydroxypiperidin-1-yl)pyridin-3-yl)ethylamino)-4-(5-(trifluoromethyl)-1H-pyrrolo[2,3-b]pyridin-3-yl)pyrimidine-5-carbonitrile | 549 | 1.55 (4H, d), 2.05-2.25 (7H, m), 3.45-3.55 (4H, m), 4.45-4.55 (1H, m). 5.15-5.30 (2H, m), 6.80-6.85 (1H, m), 7.55-7.65 (1H, m), 8.09-8.16 (1H, m), 8.69-8.72 (4H, m), 9.06-9.18 (1H, m) |
| 196 | 4-((1R)-1-(5-cyano-4-(5-(trifluoromethyl)-1H-pyrrolo[2,3-b]pyridin-3-yl)pyrimidin-2-ylamino)ethyl)benzenesulfonamide | 488 | 1.57 (3H, m), 5.28-5.39 (1H, m), 7.22 (2H, m), 7.54-7.61 (2H, m), 7.73-7.80 (2H, m), 8.67-8.74 (3H, m), 8.94-9.24 (2H, m), 13.06 (1H, m) |
| 197 | 2-(1-(6-(4-ethyl-4-hydroxypiperidin-1-yl)pyridin-3-yl)ethylamino)-4-(5-(trifluoromethyl)-1H-pyrrolo[2,3-b]pyridin-3-yl)pyrimidine-5-carbonitrile | 537 | 0.81 (3H, q), 1.31-1.47 (6H, m), 1.54 (3H, d), 3.11-3.22 (2H, m), 3.81-3.89 (2H, m), 4.10 (1H, d), 5.19-5.26 (1H, m), 6.79 (1H, dd), 7.55 (1H, dd), 8.09 (1H, d), 8.67-8.73 (4H, m), 9.12 (1H, d), 13.05 (1H, br s) |
| 198 | 2-(1-(6-(4-hydroxy-4-isopropylpiperidin-1-yl)pyridin-3-yl)ethylamino)-4-(5-(trifluoromethyl)-1H-pyrrolo[2,3-b]pyridin-3-yl)pyrimidine-5-carbonitrile | 551 | 0.78-0.83 (6H, m), 1.36-1.49 (6H, m), 1.53 (3H, d), 2.99-3.10 (2H, m), 3.97-4.03 (3H, m), 5.17-5.26 (1H, m), 6.78 (1H, dd), 7.56 (1H, dd), 8.09 (1H, d), 8.49-8.65 (3H, m), 8.77 (1H, d), 9.07 (1H, d) |
| 199 | 2-(1-(6-(4-fluoropiperidin-1-yl)pyridin-3-yl)ethylamino)-4-(5-(trifluoromethyl)-1H-pyrrolo[2,3-b]pyridin-3-yl)pyrimidine-5-carbonitrile | 511 | 1.53 (3H, d), 1.58-1.69 (2H, m), 1.80-1.94 (2H, m), 3.32-3.42 (2H, m), 3.64-3.75 (2H, m), 4.77-4.88 (1H, d), 5.21-5.27 (1H, m), 6.86 (1H, dd), 7.60 (1H, d), 8.12 (1H, d), 8.50-8.65 (3H, m), 8.77 (1H, d), 9.16 (1H, d) |
| 200 | 4-((1R)-1-(5-cyano-4-(5-(trifluoromethyl)-1H-pyrrolo[2,3-b]pyridin-3-yl)pyrimidin-2-ylamino)ethyl)-N-methylbenzenesulfonamide | 502 | 1.59 (3H, d), 2.31 (1.5H, m), 2.40 (1.5H, m), 5.32-5.42 (1H, m), 7.36-7.41 (1H, m), 7.62 (2H, dd), 7.73 (2H, dd), 8.85 (0.5H, s), 8.94-8.97 (1H, m), 9.23 (0.5H, s), 13.08 (1H, brd); ~1:1 mix of rotamers |

TABLE IIA-continued

| | Name | M + 1 (obs) | ¹H NMR (DMSO-D₆) |
|---|---|---|---|
| 201 | 2-(1-(6-(3-hydroxyazetidin-1-yl)pyridin-3-yl)ethylamino)-4-(5-(trifluoromethyl)-1H-pyrrolo[2,3-b]pyridin-3-yl)pyrimidine-5-carbonitrile | 481 | 1.53 (3H, d), 3.55-3.61 (2H, m), 4.04-4.12 (2H, m), 5.19-5.25 (1H, m), 5.59 (1H, dd), 6.36 (1H, dd), 7.54-7.59 (1H, m), 8.02 (0.5H, s), 8.11 (0.5H, s), 8.70-8.77 (4H, m), 9.06 (0.5H, s), 9.18 (0.5H, s), 13.07 (2H, br s); ~1:1 mixture of rotamers |
| 202 | N-((1R,4r)-4-((1R)-1-(5-cyano-4-(5-(trifluoromethyl)-1H-pyrrolo[2,3-b]pyridin-3-yl)pyrimidin-2-ylamino)ethyl)cyclohexyl)methanesulfonamide | 508 | 1.19-1.27 (7H, m), 1.85-1.97 (2H, m), 2.06-2.10 (2H, m), 2.91 (3H, s), 3.16-3.22 (1H, m), 4.08-4.17 (2H, m), 5.47-5.55 (1H, m), 8.43-8.50 (1H, m), 8.65-8.80 (2H, m), 9.02-9.14 (1H, m), 10.07 (1H, br d) |
| 203 | N-((1S,4s)-4-((1R)-1-(5-cyano-4-(5-(trifluoromethyl)-1H-pyrrolo[2,3-b]pyridin-3-yl)pyrimidin-2-ylamino)ethyl)cyclohexyl)methanesulfonamide | 508 | 1.39-1.86 (11H, m), 2.97 & 3.00 (3H rotamer s), 3.70-3.74 (1H, m), 4.27-4.32 (1H, s), 4.46-4.58 (1H, m), 5.49-5.64 (1H, m), 8.48-8.58 (1H, m), 8.71-8.88 (2H, m), 9.10-9.23 (1H, m), 9.56-10.10 (1H, m) |
| 204 | 2-((R)-1-(piperidin-4-yl)ethylamino)-4-(5-(trifluoromethyl)-1H-pyrrolo[2,3-b]pyridin-3-yl)pyrimidine-5-carbonitrile | 416 | 1.1-1.35 (5H, m), 1.6-1.85 (4H, m), 3.0-3.15 (1H, m), 4.0-4.1 (1H, m), 8.2-8.3 (1H, m), 8.7-8.9 (3H, m), 9.1-9.2 (1H, m) |
| 205 | 2-((R)-1-(1-(2-hydroxyacetyl)piperidin-4-yl)ethylamino)-4-(5-(trifluoromethyl)-1H-pyrrolo[2,3-b]pyridin-3-yl)pyrimidine-5-carbonitrile | 474 | 1.05-1.2 (5H, m), 1.75-1.95 (5H, m), 2.85-2.95 (1H, m), 3.63-3.68 (2H, m), 3.97-4.03 (2H, m), 4.4-4.5 (1H, m), 8.23-8.28 (1H, m), 8.7-8.8 (3H, m), 9.1-9.2 (1H, m), 13.1-13.2 (1H, m) |
| 206 | 2-((R)-1-(1-(2-hydroxy-2-methylpropanoyl)piperidin-4-yl)ethylamino)-4-(5-(trifluoromethyl)-1H-pyrrolo[2,3-b]pyridin-3-yl)pyrimidine-5-carbonitrile | 502 | 1.1-1.35 (10H, m), 1.8-1.9 (5H, m), 4.0-4.1 (1H, m), 8.3-8.33 (1H, m), 8.7-8.8 (3H, m), 9.1-9.17 (1H, m), 13.1-13.16 (1H, m) |
| 207 | 2-((R)-1-(1-((R)-2-hydroxypropanoyl)piperidin-4-yl)ethylamino)-4-(5-(trifluoromethyl)-1H-pyrrolo[2,3-b]pyridin-3-yl)pyrimidine-5-carbonitrile | 488 | 1.05-1.25 (5H, m), 1.75-1.95 (3H, m), 2.8-2.96 (1H, m), 4.4-4.55 (1H, m), 8.3-8.37 (1H, m), 8.65-8.8 (3H, m), 9.1-9.2 (1H, m), 13.1-13.17 (1H, m) |
| 208 | N-((1R,4r)-4-((1R)-1-(5-cyano-4-(5-(trifluoromethyl)-1H-pyrrolo[2,3-b]pyridin-3-yl)pyrimidin-2-ylamino)ethyl)cyclohexyl)acetamide | 472 | (CDCl₃) 1.07-1.31 (4H, m), 1.34 (3H, d), 1.51-1.62 (2H, m), 1.88-1.92 (1H, m), 1.97 (3H, s), 2.06-2.12 (2H, m), 3.71-3.81 (1H, m), 4.14-4.25 (1H, m), 5.26 (1H, d), 5.52-5.64 (1H, 2 × d), 8.51-8.59 (1H, 2 × s), 8.73-8.88 (2H, m), 9.10-9.23 (1H, 2 × s), 9.96-10.00 (1H, 2 × s) |
| 209 | N-((1S,4s)-4-((1R)-1-(5-cyano-4-(5-(trifluoromethyl)-1H-pyrrolo[2,3-b]pyridin-3-yl)pyrimidin-2-ylamino)ethyl)cyclohexyl)acetamide | 472 | (CDCl₃) 1.27-2.16 (14H, m), 4.24-4.29 (2H, m), 5.54-5.79 (1H, m), 6.10-6.32 (1H, m), 8.44 (1H, s), 8.60-8.81 (2H, m), 9.07-9.09 (1H, 2 × s), 9.23 (1H, s), 10.09-10.53 (1H, 2 × s) |
| 210 | 2-((R)-1-(1-(2-aminoacetyl)piperidin-4-yl)ethylamino)-4-(5-(trifluoromethyl)-1H-pyrrolo[2,3-b]pyridin-3-yl)pyrimidine-5-carbonitrile | 473 | 0.8-0.9 (1H, m), 0.9-1.0 (5H, m), 1.6-1.7 (4H, m), 2.4-2.5 (1H, m), 2.7-2.8 (1H, m), 3.8-3.9 (1H, m), 4.15-4.22 (1H, m), 7.7-7.8 (3H, m), 8.1-8.14 (1H, m), 8.5-8.58 (3H, m), 8.85-8.95 (1H, m), 13.1-13.17 (1H, m) |
| 211 | N-((1R,4r)-4-((1R)-1-(5-cyano-4-(5-(trifluoromethyl)-1H-pyrrolo[2,3-b]pyridin-3-yl)pyrimidin-2-ylamino)ethyl)cyclohexyl)-2-hydroxyacetamide | 488 | (CDCl₃) 1.27-1.34 (5H, m), 1.35 (3H, d), 1.85-2.14 (4H, m), 2.37-2.41 (1H, m), 3.77-3.83 (1H, m), 4.11 (1H, s), 4.18-4.29 (1H, m), 5.52-5.65 (1H, 2 × d), 6.21 (1H, d), 8.51-8.87 (3H, m), 9.10-9.23 (1H, 2 × s), 9.74-9.80 (1H, 2 × br s) |
| 212 | N-((1S,4s)-4-((1R)-1-(5-cyano-4-(5- | 488 | (CDCl₃) 1.04-1.74 (12H, m), 2.01-2.47 (1H, m), 3.94-4.22 (4H, |

TABLE IIA-continued

| | Name | M + 1 (obs) | ¹H NMR (DMSO-D₆) |
|---|---|---|---|
| | (trifluoromethyl)-1H-pyrrolo[2,3-b]pyridin-3-yl)pyrimidin-2-ylamino)ethyl)cyclohexyl)-2-hydroxyacetamide | | m), 5.52-5.65 (1H, 2 × d), 6.40 (1H, d), 8.41-8.86 (3H, m), 9.01-9.17 (1H, 2 × s), 9.62-9.71 (1H, 2 × br s) |
| 213 | 2-((R)-1-(1-(isopropylsulfonyl)piperidin-4-yl)ethylamino)-4-(5-(trifluoromethyl)-1H-pyrrolo[2,3-b]pyridin-3-yl)pyrimidine-5-carbonitrile | 522 | 1.15-1.28 (11H, m), 1.7-1.8 (1H, m), 1.85-1.95 (2H, m), 2.75-2.9 (2H, m), 3.28-3.33 (1H, m), 3.6-3.7 (2H, m), 4.02-4.1 (1H, m), 8.3-8.36 (1H, m), 8.7-8.8 (3H, m), 9.1-9.17 (1H, m), 13.05-13.12 (1H, m) |
| 214 | 2-(1-(3-methylenecyclobutyl)ethylamino)-4-(5-(trifluoromethyl)-1H-pyrrolo[2,3-b]pyridin-3-yl)pyrimidine-5-carbonitrile | 399 | Mixture of rotamers 1.10-1.25 (3H, m), 2.35-2.85 (5H, m), 4.20-4.35 (1H, m), 4.65-4.80 (2H, m), 8-8.15 (1H, m), 8.55-8.7 (2H, m), 8.80 (0.3H, s), 8.90 (0.7H, s), 9.10 (1H, s), 12.80-13.40 (1H, br s), Mixture of rotamers |
| 215 | 2-((R)-1-(1-(2-hydroxyethyl)piperidin-4-yl)ethylamino)-4-(5-(trifluoromethyl)-1H-pyrrolo[2,3-b]pyridin-3-yl)pyrimidine-5-carbonitrile | 460 | 1.25-1.4 (3H, m), 1.5-1.7 (2H, m), 1.8-2.0 (3H, m), 2.85-3.0 (2H, m), 3.1-3.25 (2H, m), 3.5-3.6 (2H, m), 3.75-3.85 (2H, m), 4.1-4.23 (1H, m), 5.255.35 (1H, m), 8.3-8.4 (1H, m), 8.7-8.83 (3H, m), 8.9-9.02 (1H, m), 9.1-9.2 (1H, m), 13.1-13.15 (1H, m) |
| 216 | 2-((R)-1-(1-(3-hydroxypropanoyl)piperidin-4-yl)ethylamino)-4-(5-(trifluoromethyl)-1H-pyrrolo[2,3-b]pyridin-3-yl)pyrimidine-5-carbonitrile | 488 | 1.0-1.22 (5H, m), 1.7-1.87 (3H, m), 2.55-2.65 (2H, m), 2.9-3.02 (1H, m), 3.6-3.9 (6H, m), 4.4-4.5 (1H, m), 8.32-8.36 (1H, m), 8.75-8.82 (3H, m), 9.1-9.08 (1H, m), 13.1-13.15 (1H, m) |
| 217 | 2-((R)-1-(1-((S)-2-hydroxybutanoyl)piperidin-4-yl)ethylamino)-4-(5-(trifluoromethyl)-1H-pyrrolo[2,3-b]pyridin-3-yl)pyrimidine-5-carbonitrile | 502 | 0.75-0.82 (H, m), 0.8-0.9 (2H, m), 1.0-1.25 (4H, m), 1.35-1.52 (1H, m), 1.8-1.95 (3H, m), 2.9-3.1 (1H, m), 4.1-4.2 (1H, m), 4.2-4.3 (1H, m), 4.4-4.5 (1H, m), 8.34-8.37 (1H, m), 8.7-8.82 (2H, m), 9.12-9.2 1H, m), 13.1-13.15 (1H, m) |
| 218 | 2-(4-((1R)-1-(5-cyano-4-(5-(trifluoromethyl)-1H-pyrrolo[2,3-b]pyridin-3-yl)pyrimidin-2-ylamino)ethyl)piperidin-1-yl)acetamide | 473 | 1.2-1.3 (3H, m), 1.55-1.7 (2H, m), 1.75-1.95 (3H, m), 2.9-3.1 (2H, m), 3.5-3.57 (2H, m), 3.82-3.87 (2H, m), 4.1-4.2 (1H, m), 7.72 (1H, s), 7.95 (1H, s), 8.32-8.42 (1H, m), 8.8-8.9 (3H, m), 9.1-9.2 (1H, m), 9.35-9.45 (1H, m), 13.1-13.15 (1H, m) |
| 219 | 2-((R)-1-(1-((R)-2-hydroxybutanoyl)piperidin-4-yl)ethylamino)-4-(5-(trifluoromethyl)-1H-pyrrolo[2,3-b]pyridin-3-yl)pyrimidine-5-carbonitrile | 502 | 0.8-0.9 (2H, m), 1.1-1.15 (2H, m), 1.2-1.26 (3H, m), 1.32-1.53 (2H, m), 1.78-1.9 (3H, m), 2.88-3.0 (1H, m), 3.95-4.1 (2H, m), 4.1-4.2 (2H, m), 4.4-4.5 (1H, m), 8.3-8.34 (1H, m), 8.7-8.8 (3H, m), 9.1-9.2 (1H, m), 13.1-13.15 (1H, m) |
| 220 | 2-((R)-1-(1-(1-hydroxycyclopropanecarbonyl)piperidin-4-yl)ethylamino)-4-(5-(trifluoromethyl)-1H-pyrrolo[2,3-b]pyridin-3-yl)pyrimidine-5-carbonitrile | 500 | 0.72-0.78 (2H, m), 0.85-0.92 (2H, m), 1.1-1.27 (4H, m), 1.75-1.9 (4H, m),, 4.0-4.1 (2H, m), 4.3-4.5 (2H, m), 8.3-8.34 (1H, m), 8.7-8.82 (3H, m), 9.1-9.2 (1H, m), 13.1-13.15 (1H, m) |
| 221 | 2-(1-(1-(2-hydroxy-2-methylpropanoyl)azetidin-3-yl)ethylamino)-4-(5-(trifluoromethyl)-1H-pyrrolo[2,3-b]pyridin-3-yl)pyrimidine-5-carbonitrile | 474 | 1.06-1.24 (9H, m), 2.76-2.81 (1H, m), 3.60 masked signal, 3.84-3.96 (1H, m), 4.07-4.16 (1H, m), 4.34-4.51 (2H, m), 8.31-8.39 (1H, m), 8.69-8.75 (3H, m), 9.13 (1H, m)13.06-13.13 (1H, m) |
| 222 | 2-(1-(1-((R)-2-hydroxypropanoyl)azetidin-3-yl)ethylamino)-4-(5-(trifluoromethyl)-1H-pyrrolo[2,3-b]pyridin-3-yl)pyrimidine-5-carbonitrile | 460 | 0.34-0.40 (1H, m), 0.47-0.56 (5H, m), 2.15 (1H, m), 3.01-3.10 (1H, m), 3.30-3.47 (3H, m), 3.62-3.78 (2H, m), 4.10 masked signal, 7.76-7.87 (2H, m), 8.00-8.05 (1H, m), 8.49-8.53 (1H, m) |
| 223 | 2-((R)-1-(6-(2-(pyrrolidin-1-yl)ethylamino)pyridin-3-yl)ethylamino)-4-(5-(trifluoromethyl)-1H-pyrrolo[2,3-b]pyridin-3-yl)pyrimidine-5-carbonitrile | 522 | 1.56 (3H, d), 1.89-1.93 (4H, m), 2.50 (2H, masked by DMSO), 3.33 (4H, masked by water), 3.54-3.60 (2H, m), 5.10-5.30 (1H, m), 6.55-6.85 (1H, br s), 7.55-7.80 (1H, br s). 7.95 (0.5 H, s), 8.04 (0.5H, s), 8.65-8.80 (4H, m), |

TABLE IIA-continued

| | Name | M + 1 (obs) | ¹H NMR (DMSO-D₆) |
|---|---|---|---|
| 224 | 2-((R)-1-(1-(3-aminopropanoyl)piperidin-4-yl)ethylamino)-4-(5-(trifluoromethyl)-1H-pyrrolo[2,3-b]pyridin-3-yl)pyrimidine-5-carbonitrile | 487 | 9.01 (0.5H, s), 9.18 (0.5H, s), 9.50-9.70 (1H, br s), 13.15 (1H, d) 1.04-1.24 (6H, m), 1.79 (3H, m), 2.59-2.67 (1H, m), 2.94-2.99 (3H, m), 3.82 (1H, m), 4.04 (1H, m), 4.45 (1H, m), 7.58 (3H, br s), 8.32 (1H, m), 8.68-8.76 (3H, m), 9.10 (1H, m), 13.06-13.12 (1H, m) mixture of rotamers |
| 225 | 2-((R)-1-(1-((R)-2-aminopropanoyl)piperidin-4-yl)ethylamino)-4-(5-(trifluoromethyl)-1H-pyrrolo[2,3-b]pyridin-3-yl)pyrimidine-5-carbonitrile | 487 | 1.04-1.31 (8H, m), 1.79-1.91 (3H, m), 2.64 (1H, m), 3.03 (1H, m), 3.84-4.02 (2H, m), 4.35-4.45 (1H, m), 7.99-8.01 (3H, m), 8.35 (1H, m), 8.68-8.76 (3H, m), 9.10-9.17 (1H, m), 13.06-13.12 (1H, m) |
| 226 | 2-((R)-1-(1-((R)-2-aminobutanoyl)piperidin-4-yl)ethylamino)-4-(5-(trifluoromethyl)-1H-pyrrolo[2,3-b]pyridin-3-yl)pyrimidine-5-carbonitrile | 501 | 0.85-0.90 (3H, m), 0.92-1.24 (5H, m), 1.63-1.91 (5H, m), 2.62 (1H, m), 2.99-3.10 (1H, m), 3.88-4.07 (1H, m), 4.32 (1H, m), 4.43 (1H, m), 8.02-8.05 (3H, m), 8.34 (1H, m), 8..67-8.75 (3H, m), 9.09-9.17 (1H, m), 13.14 (1H, m) mixture of rotamers |
| 227 | 2-((R)-1-(1-(azetidine-3-carbonyl)piperidin-4-yl)ethylamino)-4-(5-(trifluoromethyl)-1H-pyrrolo[2,3-b]pyridin-3-yl)pyrimidine-5-carbonitrile | 499 | 1.03-1.28 (5H, m), 1.79 (3H, m), 2.62 (1H, m), 2.91 (1H, m), 3.51 (1H, m), 3.82 masked signal, 4.42 (1H, m), 8.29-8.33 (1H, m), 8.67-8.74 (4H, m), 8.87 (1H, br s), 9.09-9.16 (1H, m), 13.07-13.14 (1H, m) |
| 228 | 2-((R)-1-(1-((S)-2-hydroxypropanoyl)piperidin-4-yl)ethylamino)-4-(5-(trifluoromethyl)-1H-pyrrolo[2,3-b]pyridin-3-yl)pyrimidine-5-carbonitrile | 488 | / |
| 229 | 2-((R)-1-(1-((R)-2-amino-3-methylbutanoyl)piperidin-4-yl)ethylamino)-4-(5-(trifluoromethyl)-1H-pyrrolo[2,3-b]pyridin-3-yl)pyrimidine-5-carbonitrile | 515 | 0.84-1.24 (11H, m), 1.82-1.99 (4H, m), 2.64 (1H, m), 3.02 (1H, m), 4.03 masked signal, 4.25 (1H, br s), 4.56 (1H, m), 7.98-8.01 (3H, m), 8.33 (1H, m), 8.67-8.75 (3H, m), 9.09-9.17 (1H, m), 13.09-13.15 (1H, m) rotamers observed |
| 230 | 2-((R)-1-(1-((S)-3,3,3-trifluoro-2-hydroxypropanoyl)piperidin-4-yl)ethylamino)-4-(5-(trifluoromethyl)-1H-pyrrolo[2,3-b]pyridin-3-yl)pyrimidine-5-carbonitrile | 542 | / |
| 231 | 2-((R)-1-(1-(2-oxopropanoyl)piperidin-4-yl)ethylamino)-4-(5-(trifluoromethyl)-1H-pyrrolo[2,3-b]pyridin-3-yl)pyrimidine-5-carbonitrile | 486 | 1.0-1.22 (5H, m), 1.8-1.95 (3H, m), 2.3-2.4 (3H, m), 2.65-2.8 (1H, m), 3.0-3.14 (1H, m), 3.6-3.72 (1H, m), 4.08-4.12 (1H, m), 4.3-4.4 (1H, m), 8.2-8.6 (1H, m), 8.7-8.82 (3H, m), 9.1-9.2 (1H, m), 13.1-13.17 (1H, m) |
| 232 | 2-(1-(azetidin-3-yl)ethylamino)-4-(5-(trifluoromethyl)-1H-pyrrolo[2,3-b]pyridin-3-yl)pyrimidine-5-carbonitrile | 388 | 1.41 (3H, d), 2.43 (1H, m), 3.02 (2H, m), 3.91 (1H, m), 4.28 (1H, m), 4.42 (1H, m), 8.10 (3H, br s), 8.84-9.22 (4H, m), 10.82 (1H, br s) |
| 233 | 2-((R)-1-(1-(2-cyanoacetyl)piperidin-4-yl)ethylamino)-4-(5-(trifluoromethyl)-1H-pyrrolo[2,3-b]pyridin-3-yl)pyrimidine-5-carbonitrile | 483 | 1.0-1.25 (5H, m), 1.75-1.9 (3H, m), 2.5-2.7 (1H, m), 2.95-3.1 (1H, m), 3.65-3.8 (1H, m), 3.95-4.1 (3H, m), 4.38-4.46 (1H, m), 8.3-8.37 (1H, m), 8.7-8.82 (3H, m), 9.1-9.2 (1H, m), 13.1-13.15 (1H, m) |
| 234 | 2-(1-(1-(2-aminoacetyl)-4-fluoropiperidin-4-yl)ethylamino)-4-(5-(trifluoromethyl)-1H-pyrrolo[2,3-b]pyridin-3-yl)pyrimidine-5-carbonitrile | 491 | 1.3-1.38 (3H, m), 1.65-2.0 (4H, m), 2.8-2.9 (1H, m), 3.3-3.4 (1H, m), 3.68-3.78 (1H, m), 3.8-4.0 (2H, m), 4.33-4.43 (1H, m), 4.43-4.53 (1H, m), 7.95-8.07 (2H, m), 8.45-8.58 (1H, m), 8.72-8.77 (3H, m), 9.1-9.13 (0.5H, m), 9.26-9.28 (0.5H, m), 13.1-13.15 (1H, m) |
| 235 | 2-(1-(1-(2-aminoacetyl)azetidin-3-yl)ethylamino)-4-(5-(trifluoromethyl)-1H- | 445 | / |

TABLE IIA-continued

| | Name | M + 1 (obs) | ¹H NMR (DMSO-D₆) |
|---|---|---|---|
| | pyrrolo[2,3-b]pyridin-3-yl)pyrimidine-5-carbonitrile | | |
| 236 | 2-((R)-1-(1-((S)-pyrrolidine-2-carbonyl)piperidin-4-yl)ethylamino)-4-(5-(trifluoromethyl)-1H-pyrrolo[2,3-b]pyridin-3-yl)pyrimidine-5-carbonitrile | 513 | 1.06-1.25 (5H, m), 1.68-1.92 (6H, m), 2.33 (1H, m), 2.65 (1H, m), 3.00-3.23 (3H, m), 3.86 (1H, m), 4.06 (1H, m), 4.40 (1H, m), 4.54 (1H, m), 8.33 (1H, m), 8.45 (1H, m), 8.68-8.76 (3H, m), 9.09-9.27 (2H, m), 13.06-13.13 (1H, m) |
| 237 | 2-(1-(4-fluoro-1-((R)-2-hydroxypropanoyl)piperidin-4-yl)ethylamino)-4-(5-(trifluoromethyl)-1H-pyrrolo[2,3-b]pyridin-3-yl)pyrimidine-5-carbonitrile | 506 | 1.1-1.2 (3H, m), 1.27-1.33 (3H, m), 1.6-2.0 (5H, m), 2.75-2.85 (1H, m), 3.2-3.3 (1H, m), 4.0-4.1 (1H, m), 4.3-4.6 (3H, m), 8.4-8.55 (1H, m), 8.73-8.82 (3H, m), 9.1-9.15 (0.6H, m), 9.26-9.28 (0.4H, m), 13.1-13.15 (1H, m) |
| 238 | 2-(1-(1-(cyanomethyl)-4-fluoropiperidin-4-yl)ethylamino)-4-(5-(trifluoromethyl)-1H-pyrrolo[2,3-b]pyridin-3-yl)pyrimidine-5-carbonitrile | 473 | 1.25-1.3 (3H, m), 1.7-2.0 (5H, m), 2.72-2.82 (1H, m), 4.5-4.6 (1H, m), 8.45 (0.6H, d), 8.55 (0.4H, d), 8.74-8.82 (3H, m), 9.12 (0.6H, s), 9.27 (0.4H, s), 13.1-3.18 (1H, m) |
| 239 | 2-((R)-1-(1-((S)-2-amino-3-hydroxypropanoyl)piperidin-4-yl)ethylamino)-4-(5-(trifluoromethyl)-1H-pyrrolo[2,3-b]pyridin-3-yl)pyrimidine-5-carbonitrile | 503 | 1.04-1.25 (5H, m), 1.85 (3H, m), 2.56-2.67 (1H, m), 3.04 (1H, m), 3.17 (2H, s), 3.68 (2H, m), 3.89 (1H, m), 4.06 (1H, m), 4.28-4.45 (2H, m), 8.04 (3H, br s), 8.32 (1H, m), 8.68-8.75 (3H, m), 9.10 (1H, m), 13.06-13.13 (1H, m) |
| 240 | 2-((R)-1-(1-((R)-2-amino-3-hydroxypropanoyl)piperidin-4-yl)ethylamino)-4-(5-(trifluoromethyl)-1H-pyrrolo[2,3-b]pyridin-3-yl)pyrimidine-5-carbonitrile | 503 | / |
| 241 | 2-((R)-1-(1-((R)-2-amino-4-methylpentanoyl)piperidin-4-yl)ethylamino)-4-(5-(trifluoromethyl)-1H-pyrrolo[2,3-b]pyridin-3-yl)pyrimidine-5-carbonitrile | 529 | 0.87-0.93 (6H, m), 1.04-1.24 (5H, m), 1.39-1.93 (6H, m), 2.62 (1H, m), 3.74 (2H, m), 4.35-4.47 (2H, m), 8.04-8.36 (4H, m), 8.67-8.75 (3H, m), 9.10-9.17 (1H, m), 13.08-13.14 (1H, m) |
| 242 | 2-((R)-1-(1-((2S,3R)-2-amino-3-hydroxybutanoyl)piperidin-4-yl)ethylamino)-4-(5-(trifluoromethyl)-1H-pyrrolo[2,3-b]pyridin-3-yl)pyrimidine-5-carbonitrile | 517 | 0.97-1.26 (8H, m), 1.82-1.88 (3H, m), 2.57-2.63 (1H, m), 2.95-3.04 (1H, m), 4.12 masked signal, 4.28 (1H, m), 4.45 (1H, m), 7.93-7.98 (3H, m), 8.33 (1H, m), 8.68-8.75 (3H, m), 9.10-9.16 (1H, m), 13.07-13.13 (1H, m) |
| 243 | 2-((R)-1-(1-((S)-2-aminopropanoyl)piperidin-4-yl)ethylamino)-4-(5-(trifluoromethyl)-1H-pyrrolo[2,3-b]pyridin-3-yl)pyrimidine-5-carbonitrile | 487 | 1.03-1.29 (8H, m), 1.84 (3H, m), 2.65 (1H, m), 2.94-3.16 (2H, m), 3.83 (1H, m), 4.06 (1H, m), 4.28-4.44 (2H, m), 8.01 (3H, br s), 8.30-8.34 (1H, m), 8.68-8.75 (3H, m), 9.09-9.16 (1H, m), 13.06-13.13 (1H, m) |
| 244 | 2-((R)-1-(1-((S)-3-aminobutanoyl)piperidin-4-yl)ethylamino)-4-(5-(trifluoromethyl)-1H-pyrrolo[2,3-b]pyridin-3-yl)pyrimidine-5-carbonitrile | 501 | 1.03-1.24 (8H, m), 1.78 (3H, m), 2.66 (1H, m), 2.97 (1H, m), 3.84 (1H, m), 4.05 (1H, m), 4.45 (1H, m), 7.68 (3H, br s), 8.31-8.34 (1H, m), 8.67-8.74 (3H, m), 9.09-9.17 (1H, m), 13.06-13.13 (1H, m) |
| 245 | 2-((R)-1-((1s,4S)-4-(4-methylpiperazin-1-yl)cyclohexyl)ethylamino)-4-(5-(trifluoromethyl)-1H-pyrrolo[2,3-b]pyridin-3-yl)pyrimidine-5-carbonitrile | 513 | (CDCl₃) 1.06-1.13 (2H, m), 1.24-1.32 (2H, m), 1.28 (3H, d), 1.46 (3H, s), 1.54-1.98 (7H, m), 2.28-2.34 (3H, m), 2.38-2.70 (4H, m), 3.70 (1H, 2 s br s), 4.34-4.37 (1H, m), 5.63-5.69 (1H, m), 8.50-8.83 (3H, m), 9.23 (1H, 2 × s) |
| 246 | 2-((R)-1-(1-((1R,2S)-2-aminocyclopentanecarbonyl)piperidin-4-yl)ethylamino)-4-(5-(trifluoromethyl)-1H-pyrrolo[2,3-b]pyridin-3-yl)pyrimidine-5-carbonitrile | 527 | 1.10-1.24 (5H, m), 1.65-1.99 (9H, m), 2.95-3.06 (1H, m), 3.16-3.24 (1H, m), 3.98-4.05 (2H, m), 4.45 (1H, m), 7.78 (3H, br s), 8.31-8.35 (1H, m), 8.68-8.75 (3H, m), 9.10-9.16 (1H, m), 13.06-13.13 (1H, m) rotamers observed |
| 247 | 2-((R)-1-(1-((S)-3-amino-4-methylpentanoyl)piperidin-4- | 529 | 0.84-0.93 (6H, m), 1.03-1.26 (5H, m), 1.77-1.86 (4H, m), 2.37 (1H, m), |

TABLE IIA-continued

| | Name | M + 1 (obs) | ¹H NMR (DMSO-D₆) |
|---|---|---|---|
| | yl)ethylamino)-4-(5-(trifluoromethyl)-1H-pyrrolo[2,3-b]pyridin-3-yl)pyrimidine-5-carbonitrile | | 2.57-2.73 (1H, m), 2.89-3.02 (1H, m), 3.26 (1H, m), 3.90- (1H, m), 4.06 (1H, m), 4.44-4.52 (1H, m), 7.64 (3H, br s), 8.32-8.35 (1H, m), 8.68-8.75 (3H, m), 9.09-9.16 (1H, m), 13.06-13.13 (1H, m) rotamers observed |
| 248 | 2-((R)-1-(1-((R)-2-amino-2-phenylacetyl)piperidin-4-yl)ethylamino)-4-(5-(trifluoromethyl)-1H-pyrrolo[2,3-b]pyridin-3-yl)pyrimidine-5-carbonitrile | 549 | 0.90-1.26 (5H, m), 1.70-1.90 (2H, m), 2.62 (1H, m), 2.99 (1H, m), 3.75-4.05 (2H, m), 4.47 (1H, m), 5.53 (1H, m), 7.35-7.46 (5H, m), 8.14-8.34 (1H, m), 8.49 (3H, m), 8.66-8.78 (3H, m), 8.95-9.18 (1H, m), 13.06-13.13 (1H, m) rotamers observed |
| 249 | 2-((R)-1-(1-((2R,3S)-2-amino-3-hydroxybutanoyl)piperidin-4-yl)ethylamino)-4-(5-(trifluoromethyl)-1H-pyrrolo[2,3-b]pyridin-3-yl)pyrimidine-5-carbonitrile | 517 | 1.06-1.25 (8H, m), 1.82-1.86 (3H, m), 2.58-2.67)1H, m), 2.96-3.02 (1H, m), 3.86 (1H, m), 3.97-4.05 (2H, m), 4.22 (1H, m), 4.42-4.48 (1H, m), 7.92-7.98 (3H, m), 8.33-8.36 (1H, m), 8.68-8.75 (3H, m), 9.10-9.17 (1H, m), 13.06-13.13 (1H, m) |
| 250 | (3R)-3-amino-4-(4-((1R)-1-(5-cyano-4-(5-(trifluoromethyl)-1H-pyrrolo[2,3-b]pyridin-3-yl)pyrimidin-2-ylamino)ethyl)piperidin-1-yl)-4-oxobutanamide | 530 | 1.03-1.09 (1H, m), 1.21-1.25 (4H, m), 2.43 masked signal, 2.59-2.67 (1H, m), 2.96-3.08 (1H, m), 3.80-4.04 (3H, m), 4.41-4.55 (2H, m), 7.26 (1H, m), 7.64 (1H, m), 8.02-8.07 (3H, m), 8.31-8.35 (1H, m), 8.69-8.76 (3H, m), 9.07-9.17 (1H, m), 13.05-13.12 (1H, m) rotamers observed |
| 251 | 2-((R)-1-(1-((R)-2-amino-3-cyanopropanoyl)piperidin-4-yl)ethylamino)-4-(5-(trifluoromethyl)-1H-pyrrolo[2,3-b]pyridin-3-yl)pyrimidine-5-carbonitrile | 512 | 1.04-1.32 (5H, m), 1.86 (3H, m), 2.60-2.67 (1H, m), 2.92-3.17 (3H, m), 3.93-4.04 (2H, m), 4.43 (1H, m), 4.75 (1H, m), 8.32-8.43 (4H, m), 8.68-8.76 (3H, m), 9.09-9.17 (1H, m), 13.06-13.12 (1H, m) rotamers observed |
| 252 | 2-((R)-1-(1-((R)-2,5-diaminopentanoyl)piperidin-4-yl)ethylamino)-4-(5-(trifluoromethyl)-1H-pyrrolo[2,3-b]pyridin-3-yl)pyrimidine-5-carbonitrile | 530 | 1.04-1.26 (5H, m), 1.50-1.92 (7H, m), 2.58-2.77 (3H, m), 2.99-3.07 (1H, m), 3.88-3.91 (1H, m), 4.04-4.06 (1H, m), 4.44 (2H, m), 7.74 (3H, m), 8.10-8.13 (3H, m), 8.35 (1H, t), 8.70-8.76 (3H, m), 9.10-9.17 (1H, m), 13.08-13.14 (1H, m) |
| 253 | 2-((R)-1-(1-((1s,3S)-3-aminocyclobutanecarbonyl)piperidin-4-yl)ethylamino)-4-(5-(trifluoromethyl)-1H-pyrrolo[2,3-b]pyridin-3-yl)pyrimidine-5-carbonitrile | 513 | 0.98-1.05 (2H, m), 1.19-1.23 (3H, m), 1.77-1.86 (3H, m), 2.17-2.24 (2H, m), 2.33-2.46 (2H, m), 2.85-2.98 (1H, m), 3.05-3.16 (1H, m), 4.02 (1H, m), 4.40 (1H, m), 7.90 (3H, m), 8.31 (1H, m), 8.68-8.75 (3H, m), 9.10-9.16 (1H, m), 1306-13.12 (1H, m) |
| 254 | 2-((R)-1-(1-((S)-2,5-diaminopentanoyl)piperidin-4-yl)ethylamino)-4-(5-(trifluoromethyl)-1H-pyrrolo[2,3-b]pyridin-3-yl)pyrimidine-5-carbonitrile | 530 | 1.06-1.27 (5H, m), 1.40-1.66 (4H, m), 1.83-1.90 (3H, m), 2.67-2.77 (2H, m), 2.99-3.08 (1H, m), 3.87-4.12 (2H, m), 4.37-4.47 (2H, m), 7.68-7.73 (3H, m), 8.11 (3H, m), 8.34 (1H, m), 8.69-8.76 (3H, m), 9.09-9.16 (1H, m), 13.07-13.14 (1H, m), rotamers observed |
| 255 | 2-((R)-1-(1-((S)-2-amino-3-cyanopropanoyl)piperidin-4-yl)ethylamino)-4-(5-(trifluoromethyl)-1H-pyrrolo[2,3-b]pyridin-3-yl)pyrimidine-5-carbonitrile | 512 | 1.10-1.26 (5H, m), 1.81-1.88 (3H, m), 2.62-2.67 (1H, m), 2.92-3.10 (3H, m), 3.96-4.10 (2H, m), 4.43 (1H, m), 4.71-4.81 (1H, m), 8.30-8.43 (4H, m), 8.69-8.76 (3H, m), 9.10-9.17 (1H, m), 13.06-13.12 (1H, m) rotamers observed |
| 256 | 2-((R)-1-(1-((R)-2-hydroxy-3-methylbutanoyl)piperidin-4-yl)ethylamino)-4-(5-(trifluoromethyl)-1H-pyrrolo[2,3-b]pyridin-3-yl)pyrimidine-5-carbonitrile | 516 | 0.70-0.87 (6H, m), 0.85-1.23 (6H, m), 1.76-1.81 (4H, m), 2.94 (1H, m), 4.02 (3H, m), 4.40 (1H, m), 8.31-8.33 (1H, m), 8.67-8.75 (3H, m), 9.10-9.16 (1H, m), 13.04-13.10 (1H, m) rotamers observed |
| 257 | 2-((1R)-1-(1-(2,3-dihydroxypropanoyl)piperidin- | 504 | 1.05-1.24 (5H, m), 1.78-1.80 (3H, m), 2.93 (1H, m), 4.05 (2H, m), |

TABLE IIA-continued

| | Name | M + 1 (obs) | ¹H NMR (DMSO-D₆) |
|---|---|---|---|
| | 4-yl)ethylamino)-4-(5-(trifluoromethyl)-1H-pyrrolo[2,3-b]pyridin-3-yl)pyrimidine-5-carbonitrile | | 4.29 (1H, m), 4.43 (1H, m), 8.31 (1H, m), 8.67-8.75 (3H, m), 9.10-9.17 (1H, m), 13.04-13.10 (1H, m) |
| 258 | 2-(4-((1R)-1-(5-cyano-4-(5-(trifluoromethyl)-1H-pyrrolo[2,3-b]pyridin-3-yl)pyrimidin-2-ylamino)ethyl)piperidin-1-yl)-2-oxoacetamide | 487 | 1.11-1.24 (5H, m), 1.82 (3H, m), 2.62 (1H, m), 3.03 (1H, m), 3.75-3.78 (1H, m), 4.05 (1H, m), 4.31 (1H, m), 7.60 (1H, m), 8.00 (1H, m), 8.32 (1H, m), 8.67-8.76 (3H, m), 9.10-9.17 (1H, m), 13.03-13.10 (1H, m) rotamers observed |
| 259 | 2-((R)-1-(1-((R)-azetidine-2-carbonyl)piperidin-4-yl)ethylamino)-4-(5-(trifluoromethyl)-1H-pyrrolo[2,3-b]pyridin-3-yl)pyrimidine-5-carbonitrile | 499 | 1.06-1.24 (5H, m), 1.78-1.87 (3H, m), 2.36 (1H, m), 2.61-2.82 (2H, m), 2.91 (1H, m), 3.41 (1H, m), 3.70 (1H, m), 4.38 (1H, m), 5.27 (1H, m), 8.32 (1H, m), 8.68-8.75 (4H, m), 9.10-9.16 (1H, m), 9.23 (1H, br s), 13.07-13.13 (1H, m) |
| 260 | 2-((1R)-1-(1-(3-amino-2-hydroxypropanoyl)piperidin-4-yl)ethylamino)-4-(5-(trifluoromethyl)-1H-pyrrolo[2,3-b]pyridin-3-yl)pyrimidine-5-carbonitrile | 503 | 1.08-1.24 (5H, m), 1.83 (3H, m), 2.60 (1H, m), 2.87-3.09 (3H, m), 4.47 (2H, m), 7.75 (3H, br s), 8.32 (1H, m), 8.67-8.75 (3H, m), 9.10-9.17 (1H, m), 13.07-13.13 (1H, m) rotamers observed |
| 261 | 2-((R)-1-((1r,4R)-4-(4-methylpiperazin-1-yl)cyclohexyl)ethylamino)-4-(5-(trifluoromethyl)-1H-pyrrolo[2,3-b]pyridin-3-yl)pyrimidine-5-carbonitrile | 513 | (CDCl₃) 1.20-1.34 (6H, m), 1.38-2.23 (10H, m), 2.84 (3H, s), 3.00-3.09 (1H, m), 3.45-3.75 (6H, m), 4.18-4.21 (1H, m), 5.47-5.92 (1H, m), 8.48-8.87 (3H, m), 9.08-9.16 (1H, m), 9.92-10.03 (1H, m) |
| 262 | 2-((R)-1-(1-((2R,4R)-4-hydroxypyrrolidine-2-carbonyl)piperidin-4-yl)ethylamino)-4-(5-(trifluoromethyl)-1H-pyrrolo[2,3-b]pyridin-3-yl)pyrimidine-5-carbonitrile | 529 | 1.10-1.25 (5H, m), 1.67-1.91 (4H, m), 2.60-2.73 (1H, m), 2.97-3.16 (3H, m), 3.72 (1H, m), 4.06 (1H, m), 4.36-4.51 (3H, m), 5.29 (1H, m), 8.34 (1H, m), 8.50 (1H, m), 8.69-8.76 (3H, m), 9.11-9.17 (1H, m), 9.34 (1H, m), 13.06-13.12 (1H, m) |
| 263 | 2-((R)-1-(1-((2R,4S)-4-hydroxypyrrolidine-2-carbonyl)piperidin-4-yl)ethylamino)-4-(5-(trifluoromethyl)-1H-pyrrolo[2,3-b]pyridin-3-yl)pyrimidine-5-carbonitrile | 529 | 1.05-1.25 (5H, m), 1.83-1.94 (4H, m), 2.27 (1H, m), 2.65 (1H, m), 2.97-3.13 (2H, m), 3.26 (2H, m), 3.80 (1H, m), 4.06 (1H, m), 4.40 (2H, m), 4.67 (1H, m), 8.34 (1H, m), 8.60 (1H, m), 8.69-8.76 (3H, m), 9.11-9.17 (1H, m), 9.54 (1H, m), 13.06-13.12 (1H, m) rotamers observed |
| 264 | 2-amino-N-((1R,4r)-4-((1R)-1-(5-cyano-4-(5-(trifluoromethyl)-1H-pyrrolo[2,3-b]pyridin-3-yl)pyrimidin-2-ylamino)ethyl)cyclohexyl)acetamide | 487 | (CDCl₃) 1.12-1.35 (10H, m), 1.86-2.10 (4H, m), 3.34 (3H, s), 3.35-3.42 (1H, m), 4.18-4.25 (1H, m), 5.52-5.60 (1H, 2 × d), 7.11-7.13 (1H, m), 8.51-8.59 (1H, 2 × s), 8.72-8.86 (2H, m), 9.10-9.23 (1H, 2 × s), 9.73 (1H, br s) |
| 265 | (2R)—N-((1R,4R)-4-((1R)-1-(5-cyano-4-(5-(trifluoromethyl)-1H-pyrrolo[2,3-b]pyridin-3-yl)pyrimidin-2-ylamino)ethyl)cyclohexyl)-2-hydroxypropanamide | 502 | (CDCl₃) 1.20-1.35 (8H, m), 1.44 (3H, d), 1.90-2.09 (4H, m), 2.34 (1H, d), 3.69-3.81 (1H, m), 4.18-4.28 (2H, m), 5.52 (0.33H, d), 5.58 (0.67H, d), 6.27 (1H, d), 8.50 (0.66H, s), 8.58 (0.33H, s), 8.72 (1H, s), 8.77 (0.33H, d), 8.86 (0.67H, d), 9.09 (0.33H, s), 9.23 (0.67H, s), 9.64 (1H, br s) |
| 266 | 2-(1-(6-(4-hydroxy-1-methylpiperidin-4-yl)pyridin-3-yl)ethylamino)-4-(5-(trifluoromethyl)-1H-pyrrolo[2,3-b]pyridin-3-yl)pyrimidine-5-carbonitrile | 523 | 1.40-1.49 (2H, m), 1.59 (3H, d), 2.05-2.21 (2H, m), 2.16 (1.5H, s), 2.16 (1.5H, s), 2.25-2.33 (2H, m), 2.50-2.55 (2H, m), 4.96 (1H, d), 5.31-5.41 (1H, m), 7.58-7.65 (1H, m), 7.78-7.87 (1H, m), 8.51 (0.5H, s), 8.57 (0.5H, s), 8.70-8.72 (3H, m), 8.52-8.56 (1H, m), 8.97 (0.5H, s), 9.20 (0.5H, s), 13.03 (1H, br s) |
| 267 | 2-((R)-1-(6-(piperazin-1-yl)pyridin-3-yl)ethylamino)-4-(5-(trifluoromethyl)-1H-pyrrolo[2,3-b]pyridin-3-yl)pyrimidine-5-carbonitrile | 494 | 1.58 (3H, d), 2.3 (3H, s), 3.1-3.22 (4H, m), 3.63-3.73 (4H, m), 5.2-5.3 (1H, m), 6.87-6.96 (1H, m), 7.65-7.75 (1H, m), 8.15 (0.6H, s), 8.26 (0.4H, s), 8.7-8.83 (5H, m), 9.03 (0.6H, s), 9.22 (0.4H, s) |
| 268 | 2-((R)-1-(2-((S)-1-methylpyrrolidin-3- | 509 | 1.52-1.6 (3H, m), 1.85-2.0 (2H, m), 2.82-2.93 (2H, m), 3.08-3.3 (1.5H, |

TABLE IIA-continued

| | Name | M + 1 (obs) | $^1$H NMR (DMSO-D$_6$) |
|---|---|---|---|
| | ylamino)pyrimidin-5-yl)ethylamino)-4-(5-(trifluoromethyl)-1H-pyrrolo[2,3-b]pyridin-3-yl)pyrimidine-5-carbonitrile | | m), 3.52-3.8 (1.5H, m), 3.85-3.95 (1H, m), 4.45-4.55 (1H, m), 5.2-5.33 (1H, m), 7.51-7.53 (0.55H, m), 7.67-7.70 (0.45H, m), 8.4-8.52 (2H, m), 8.7-8.8 (4H, m), 9.05 90.55H, s), 9.18 (0.45H, s), 9.67-9.8 (1H, m) |
| 269 | 2-((S)-1-((1r,3S)-3-hydroxycyclobutyl)ethylamino)-4-(5-(trifluoromethyl)-1H-pyrrolo[2,3-b]pyridin-3-yl)pyrimidine-5-carbonitrile | 403 | 1.1-1.5 (4H, m), 1.80-1.95 (1H, m), 1.95-2.10 (3H, m), 4.1-4.4 (2H, m), 4.90 (1H, br s), 7.20-7.90 (2H, m), 8.35 (2H, d), 8.95 (2H, s) |
| 270 | 2-((S)-1-((1s,3R)-3-hydroxycyclobutyl)ethylamino)-4-(5-(trifluoromethyl)-1H-pyrrolo[2,3-b]pyridin-3-yl)pyrimidine-5-carbonitrile | 403 | 1.05-1.20 (4H, m), 1.40-1.60 (2H, m), 1.80-2.00 (1H, m), 2.20-2.35 (3H, m), 3.80-3.90 (1H, m), 4.0-4.15 (1H, m), 4.85-4.95 (1H, d), 8.45-8.65 (2H, m), 8.70-8.80 (1H, m), 9.10 (1H, s) |
| 271 | 2-(1-(6-((R)-1-methylpyrrolidin-3-yloxy)pyridin-3-yl)ethylamino)-4-(5-(trifluoromethyl)-1H-pyrrolo[2,3-b]pyridin-3-yl)pyrimidine-5-carbonitrile | 509 | 1.56 (3H, d), 1.99 (1H, m), 2.33 (2H, m), 2.80-3.17 (4H, m), 5.27-5.41 (2H, m), 6.79 (1H, t), 7.78 (1H, m), 8.13-8.20 (1H, m), 8.71-8.82 (4H, m), 8.96-9.18 (1H, m), 13.05 (1H, m) |
| 272 | 2-(1-(6-((R)-pyrrolidin-3-ylamino)pyridin-3-yl)ethylamino)-4-(5-(trifluoromethyl)-1H-pyrrolo[2,3-b]pyridin-3-yl)pyrimidine-5-carbonitrile | 494 | 1.52 (3H, d), 1.91-2.15 (1H, m), 2.50-2.71 (1H, m), 2.72-3.3.15 (3H, m), 3.20-3.58 (1H, m), 4.08-4.22 (1H, m), 5.10-5.27 (1H, m), 6.38-6.55 (2H, m), 7.35-7.50 (1H, m), 7.88-8.05 (1H, m), 8.42-8.80 (4H, m), 9.05 + 9.17 (1H, 2 × s) |
| 273 | 2-((R)-1-(6-((S)-3-methylpiperazin-1-yl)pyridin-3-yl)ethylamino)-4-(5-(trifluoromethyl)-1H-pyrrolo[2,3-b]pyridin-3-yl)pyrimidine-5-carbonitrile | 508 | 1.2-1.3 (3H, m), 1.5-1.6 (3H, m), 2.8-2.9 (1H, m), 3.0-3.13 (2H, m), 3.2-3.4 (2H, m), 4.22-4.35 (2H, m), 5.2-5.3 (1H, m), 6.87-7.0 (1H, m), 7.65-7.75 (1H, m), 8.15-8.25 (1H, m), 8.55-8.8 (4H, m), 8.9-9.0 (1H, m), 9.08 (0.6H, s), 9.18 (0.4H, s), 13.1-13.2 (1H, m) |
| 274 | 2-((R)-1-(6-((R)-3-methylpiperazin-1-yl)pyridin-3-yl)ethylamino)-4-(5-(trifluoromethyl)-1H-pyrrolo[2,3-b]pyridin-3-yl)pyrimidine-5-carbonitrile | 508 | 1.2-1.3 (3H, m), 1.5-1.6 (3H, m), 2.8-2.9 (1H, m), 3.0-3.13 (2H, m), 3.2-3.4 (2H, m), 4.22-4.35 (2H, m), 5.2-5.3 (1H, m), 6.87-7.0 (1H, m), 7.65-7.75 (1H, m), 8.15-8.25 (1H, m), 8.55-8.8 (4H, m), 8.9-9.0 (1H, m), 9.08 (0.6H, s), 9.18 (0.4H, s), 13.1-13.2 (1H, m) |
| 275 | 2-((R)-1-(6-(methyl(2-(methylamino)ethyl)amino)pyridin-3-yl)ethylamino)-4-(5-(trifluoromethyl)-1H-pyrrolo[2,3-b]pyridin-3-yl)pyrimidine-5-carbonitrile | 496 | 1.5-1.6 (3H, m), 2.5-2.6 (3H, m), 2.9-3.0 (3H, m), 3.07-3.12 (2H, m), 3.7-3.8 (2H, m), 5.25-5.35 (1H, m), 6.7-6.85 (1H, m), 7.7-7.82 (1H, m), 8.07-8.15 (1H, m), 8.32-8.47 (2H, m), 8.7-8.84 (4H, m), 9.1 (0.6H, s), 9.2 (0.4H, s), 13.05-13.1 (1H, m) |
| 276 | 2-((R)-1-(6-((3S,5R)-3,5-dimethylpiperazin-1-yl)pyridin-3-yl)ethylamino)-4-(5-(trifluoromethyl)-1H-pyrrolo[2,3-b]pyridin-3-yl)pyrimidine-5-carbonitrile | 522 | 1.2-1.3 (6H, m), 1.52-1.57 (3H, m), 2.68-2.72 (1H, m), 3.25-3.35 (2H, m), 4.38-4.45 (2H, m), 5.22-5.32 (1H, m), 6.9-7.0 (1H, m), 7.65-7.75 (1H, m), 8.15 (0.6H, s), 8.25 (0.4H, s), 8.38-8.45 (1H, m), 8.7-8.82 (4H, m), 8.9-9.0 (1H, m), 9.1 (0.6H, s), 9.2 (0.4H, s), 13.1-13.2 (1H, m) |
| 277 | 2-(1-(6-((S)-pyrrolidin-3-ylamino)pyridin-3-yl)ethylamino)-4-(5-(trifluoromethyl)-1H-pyrrolo[2,3-b]pyridin-3-yl)pyrimidine-5-carbonitrile | 494 | 1.52 (3H, d), 1.85-2.01 (1H, m), 2.51-2.65 (1H, m), 2.72-3.01 (3H, m), 3.18-3-55 (1H, m), 4.08-4.23 (1H, m), 5.12-5.30 (1H, m), 6.37-6.55 (2H, m), 7.35-7.48 (1H, m), 7.90-8.05 (1H, m), 8.55-8.77 (4H, m), 9.05 + 9.16 (1H, 2 × s) |
| 278 | 2-(1-(6-(2-(methylamino)ethylamino)pyridin-3-yl)ethylamino)-4-(5-(trifluoromethyl)-1H-pyrrolo[2,3-b]pyridin-3-yl)pyrimidine-5-carbonitrile | 482 | 1.54 (3H, m), 2.56 (3H, m), 3.04-3.09 (2H, m), 3.46-3.52 (2H, m), 2.19 (1H, m), 6.63 (1H, m), 7.62 (1H, m), 7.96-8.04 (1H, m), 8.40 (1H, m), 8.72 (4H, m), 9.03-9.18 (1H, m), 13.06-13.11 (1H, m) |
| 279 | 2-((1R)-1-(4-(1-methylpyrrolidin-3- | 507 | 1.49-1.50 (4H, m), 2.11-2.40 (7H, m), 2.62-2.74 (1H, m), |

TABLE IIA-continued

| | Name | M + 1 (obs) | ¹H NMR (DMSO-D₆) |
|---|---|---|---|
| | ylamino)phenyl)ethylamino)-4-(5-(trifluoromethyl)-1H-pyrrolo[2,3-b]pyridin-3-yl)pyrimidine-5-carbonitrile | | 3.72-3.88 (1H br, s), 5.20 (1H, m), 5.60 (1H, m), 6.46 (1.2H, d), 6.51 (0.8H, d), 7.10-7.14 (2H, m), 8.67-8.74 (4H, m), 9.07 (0.6H, s), 9.21 (0.4H, s) and 13.05 (1H, br s) |
| 280 | 2-(1-(6-((S)-1-methylpyrrolidin-3-ylamino)pyridin-3-yl)ethylamino)-4-(5-(trifluoromethyl)-1H-pyrrolo[2,3-b]pyridin-3-yl)pyrimidine-5-carbonitrile | 508 | 2.08-2.40 (4H, m), 2.45-2.55 (1H, m), 2.61-2.75 (1H, m), 4.15-4.25 (1H, m), 5.12-5.22 (1H, m), 6.40-6.46 (1H, dd), 6.56 (1H, t), 7.43 (1H, t), 7.92 + 8.00 (1H, 2 × s), 8.69-8.74 (4H, m), 9.07 + 9.19 (1H, 2 × s), 13.00 (1H, br s) |
| 281 | 2-((R)-1-(4-(3-(methylamino)propylamino)phenyl)ethylamino)-4-(5-(trifluoromethyl)-1H-pyrrolo[2,3-b]pyridin-3-yl)pyrimidine-5-carbonitrile | 496 | (MeOH-d₄) 1.62-1.75 (3H, m), 2.0-2.1 (2H, m), 2.7-2.8 (3H, m), 3.07-3.15 (2H, m), 3.4-3.55 (2H, m), 5.25-5.42 (1H, m), 7.03-7.1 (1H, m), 7.85 (0.5H, s), 7.95 (0.5H, s), 8.0-8.1 (1H, m), 8.6-8.73 (2H, m), 8.8 (1H, s), 9.02 (1H, s), 9.42 (1H, s) |
| 282 | 2-((R)-1-(6-((2-(dimethylamino)ethyl)(methyl)amino)pyridin-3-yl)ethylamino)-4-(5-(trifluoromethyl)-1H-pyrrolo[2,3-b]pyridin-3-yl)pyrimidine-5-carbonitrile | 510 | 1.2-1.3 (3H, m). 1.5-1.6 (3H, m), 2.8 (3H, d), 2.92 (3H, d), 3.2-3.3 (2H, m), 3.8-3.9 (2H, m), 5.2-5.35 (1H, m), 6.65-6.8 (1H, m), 8.1-8.22 (1H, m), 8.7-8.85 (3H, m), 9.05-9.25 (1H, m), 9.3-9.55 (1H, m), 13.05-13.1 (1H, m) |
| 283 | 2-((R)-1-(6-((3-(dimethylamino)propyl)(methyl)amino)pyridin-3-yl)ethylamino)-4-(5-(trifluoromethyl)-1H-pyrrolo[2,3-b]pyridin-3-yl)pyrimidine-5-carbonitrile | 525 | 1.25-1.35 (2H, m). 1.5-1.6 (3H, m), 1.85-1.95 (3H, m), 2.74 (3H, d), 2.82 (3H, d), 2.95-3.1 (4H, m), 3.55-3.65 (2H, m), 5.2-5.3 (1H, m), 6.7-6.8 (1H, m), 7.7-7.8 (1H, m), 8.08-8.17 (1H, m), 8.72-8.85 (3H, m), 9.1 (0.5H, s), 9.23 (0.5H, s), 9.4-9.55 (1H, m), 13.05-13.15 (1H, m) |
| 284 | 2-((R)-1-(6-(4-isopropylpiperazin-1-yl)pyridin-3-yl)ethylamino)-4-(5-(trifluoromethyl)-1H-pyrrolo[2,3-b]pyridin-3-yl)pyrimidine-5-carbonitrile | 536 | |
| 285 | 2-((R)-1-(6-(4-ethylpiperazin-1-yl)pyridin-3-yl)ethylamino)-4-(5-(trifluoromethyl)-1H-pyrrolo[2,3-b]pyridin-3-yl)pyrimidine-5-carbonitrile | 522 | 1.2-1.28 (3H, m). 1.53-1.58 (3H, m), 2.95-3.1 (4H, d), 3.15-3.25 (2H, m), 3.5-3.6 (2H, m), 5.22-5.32 (1H, m), 6.9-7.0 (1H, m), 7.7-7.8 (1H, m), 8.18 (0.6H, m), 8.25 (0.4H, s), 8.7-8.85 (3H, m), 9.05 (0.6H, s), 9.18 (0.4H, s), 9.4-9.55 (1H, m), 13.05-13.1 (1H, m) |
| 286 | 2-((R)-1-(6-((R)-3-(dimethylamino)pyrrolidin-1-yl)pyridin-3-yl)ethylamino)-4-(5-(trifluoromethyl)-1H-pyrrolo[2,3-b]pyridin-3-yl)pyrimidine-5-carbonitrile | 522 | 1.55 (3H, d), 2.1-2.3 (2H, m), 2.8-2.9 (6H, m), 3.35-3.45 (1H, m), 3.5-3.7 (2H, m), 3.75-4.0 (2H, m), 5.25-5.35 (1H, m), 6.7-6.9 (1H, m), 7.75-7.85 (0.55H, m), 7.85-7.95 (0.45H, m), 8.05 (0.55H, s), 8.15 (0.45H, s), 8.75-8.9 (3H, m), 9.05 (0.5H, s), 9.18 (0.5H, s), 9.95-10.05 (1H, m), 13.05-13.1 (1H, m) |
| 287 | 2-((R)-1-(6-((2-(diethylamino)ethyl)(methyl)amino)pyridin-3-yl)ethylamino)-4-(5-(trifluoromethyl)-1H-pyrrolo[2,3-b]pyridin-3-yl)pyrimidine-5-carbonitrile | 538 | 1.02 (3H, t). 1.1 (3H, t), 1.42 (3H, d), 2.8-2.9 (3H, m), 2.95-3.15 (6H, m), 3.6-3.75 (2H, m), 5.1-5.2 (1H, m), 6.6-6.7 (1H, m), 7.55-7.65 (1H, m), 7.95 (0.55H, s), 8.05 (0.45H, s), 8.6-8.72 (4H, m), 8.95 (0.55H, s), 9.1-9.2 (1H, m), 13.05-13.1 (1H, m) |
| 288 | 2-((R)-1-(6-((S)-1,3'-bipyrrolidin-1'-yl)pyridin-3-yl)ethylamino)-4-(5-(trifluoromethyl)-1H-pyrrolo[2,3-b]pyridin-3-yl)pyrimidine-5-carbonitrile | 548 | |
| 289 | 2-((R)-1-(6-(methyl(3-(methylamino)propyl)amino)pyridin-3-yl)ethylamino)-4-(5-(trifluoromethyl)-1H-pyrrolo[2,3-b]pyridin-3-yl)pyrimidine-5-carbonitrile | 510 | 0.8-0.9 (3H, m). 1.2-1.35 (2H, m), 1.85-2.0 (3H, m), 2.2-2.3 (1H, m), 2.35-2.5 (2H, m), 2.8-3.0 (2H, m), 4.45-4.6 (1H, m), 6.35-6.45 (1H, m), 7.2-7.35 (2H, m), 7.7-7.85 (2H, m), 8.0 (1H, s), 8.25 (0.5H, m), 8.6 (0.5H, s) |

TABLE IIA-continued

| | Name | M + 1 (obs) | ¹H NMR (DMSO-D₆) |
|---|---|---|---|
| 290 | 2-((R)-1-(6-((S)-3-(dimethylamino)pyrrolidin-1-yl)pyridin-3-yl)ethylamino)-4-(5-(trifluoromethyl)-1H-pyrrolo[2,3-b]pyridin-3-yl)pyrimidine-5-carbonitrile | 522 | 1.55 (3H, d), 2.2-2.35 (2H, m), 2.8-2.9 (6H, m), 3.4-3.75 (3H, m), 3.75-4.0 (2H, m), 5.25-5.35 (1H, m), 6.7-6.9 (1H, m), 7.75-7.85 (0.55H, m), 7.85-7.95 (0.45H, m), 8.05 (0.55H, s), 8.15 (0.45H, s), 8.75-8.9 (3H, m), 9.05 (0.5H, s), 9.18 (0.5H, s), 9.95-10.05 (1H, m), 13.05-13.1 (1H, m) |
| 291 | 2-((R)-1-(6-((S)-hexahydropyrrolo[1,2-a]pyrazin-2(1H)-yl)pyridin-3-yl)ethylamino)-4-(5-(trifluoromethyl)-1H-pyrrolo[2,3-b]pyridin-3-yl)pyrimidine-5-carbonitrile | 534 | 1.55 (3H, d), 1.8-2.2 (4H, m), 3.0-3.08 (1H, m), 3.3-3.4 (1H, m), 3.5-3.8 (2H, m), 3.8-3.95 (1H, m), 5.25-5.35 (1H, m), 6.85-7.0 (1H, m), 7.7-7.8 (1H, m), 8.15 (0.65H, d), 8.25 (0.35H, d), 8.75-8.9 (3H, m), 9.05 (0.6H, s), 9.18 (0.4H, s), 9.7-9.8 (0.5H, m), 10.07-10.12 (0.5H, m), 13.05-13.1 (1H, m) |
| 292 | 2-((R)-1-(6-(4-methyl-1,4-diazepan-1-yl)pyridin-3-yl)ethylamino)-4-(5-(trifluoromethyl)-1H-pyrrolo[2,3-b]pyridin-3-yl)pyrimidine-5-carbonitrile | 522 | 1.55 (3H, d), 2.1-2.2 (2H, m), 2.7-2.8 (1.5H, m), 3.08-3.2 (1.5H, m), 3.45-3.65 (4H, m), 4.2-4.33 (1H, m), 5.25-5.35 (1H, m), 6.75-6.9 (1H, m), 7.7-7.85 (1H, m), 8.12 (0.5H, s), 8.2 (0.5H, s), 8.75-8.9 (3H, m), 9.15 (0.5H, s), 9.23 (0.5H, s), 9.5-9.65 (1H, m), 10.05-10.15 (1H, m) |
| 293 | 2-(1-(6-((R)-1-methylpyrrolidin-3-ylamino)pyridin-3-yl)ethylamino)-4-(5-(trifluoromethyl)-1H-pyrrolo[2,3-b]pyridin-3-yl)pyrimidine-5-carbonitrile | 508 | 1.54 (3H, d), 1.85-2.10 (1H, br s), 2.80-2.95 (4H, m), 3.47 (4H, masked by water peak), 4.30-4.50 (1H, br s), 5.15-5.30 (1H, br s), 6.55-6.75 (1H, m), 7.55-7.75 (1H, m), 8.70-8.80 (4H, m), 9.05-9.20 (2 × 0.5H, 2 s), 9.65-10.0 (1H, br m), 13.10 (1H, d) |
| 294 | 2-((R)-1-(6-(4-(dimethylamino)piperidin-1-yl)pyridin-3-yl)ethylamino)-4-(5-(trifluoromethyl)-1H-pyrrolo[2,3-b]pyridin-3-yl)pyrimidine-5-carbonitrile | 536 | 1.45-1.6 (6H, m), 1.95-2.1 (3H, m), 2.7-2.9 (8H, m), 3.3-3.4 (1H, m), 4.4-4.5 (2H, m), 5.2-5.3 (1H, m), 6.93-7.05 (1H, m), 7.65-7.79 (1H, m), 8.05 (0.55H, s), 8.15 (0.45H, s), 8.72-8.9 (4H, m), 9.05 (0.5H, s), 9.18 (0.5H, s), 9.4-9.55 (1H, m), 13.05-13.1 (1H, m) |
| 295 | 2-((1R)-1-(6-(methyl(1-methylpyrrolidin-3-yl)amino)pyridin-3-yl)ethylamino)-4-(5-(trifluoromethyl)-1H-pyrrolo[2,3-b]pyridin-3-yl)pyrimidine-5-carbonitrile | 522 | / |
| 296 | 2-((R)-1-(6-((2-(dimethylamino)ethyl)(ethyl)amino)pyridin-3-yl)ethylamino)-4-(5-(trifluoromethyl)-1H-pyrrolo[2,3-b]pyridin-3-yl)pyrimidine-5-carbonitrile | 524 | / |
| 297 | 2-((R)-1-(6-(1-methylpiperidin-4-ylamino)pyridin-3-yl)ethylamino)-4-(5-(trifluoromethyl)-1H-pyrrolo[2,3-b]pyridin-3-yl)pyrimidine-5-carbonitrile | 522 | / |
| 298 | 2-((R)-1-(6-((R)-hexahydropyrrolo[1,2-a]pyrazin-2(1H)-yl)pyridin-3-yl)ethylamino)-4-(5-(trifluoromethyl)-1H-pyrrolo[2,3-b]pyridin-3-yl)pyrimidine-5-carbonitrile | 534 | 1.55 (3H, d), 1.8-2.2 (4H, m), 3.0-3.08 (1H, m), 3.3-3.4 (1H, m), 3.5-3.8 (2H, m), 3.8-3.95 (1H, m), 4.45-4.55 (0.5H, m), 4.65-4.75 (0.5H, m), 5.25-5.35 (1H, m), 6.85-7.02 (1H, m), 7.68-7.78 (1H, m), 8.15 (0.6H, d), 8.25 (0.4H, d), 8.75-8.9 (3H, m), 9.05 (0.6H, s), 9.18 (0.4H, s), 9.68-9.8 (0.5H, m), 10.07-10.15 (0.5H, m), 13.05-13.15 (1H, m) |
| 299 | 2-((R)-1-(2-(4-methylpiperazin-1-yl)pyrimidin-5-yl)ethylamino)-4-(5-(trifluoromethyl)-1H-pyrrolo[2,3-b]pyridin-3-yl)pyrimidine-5-carbonitrile | 509 | 1.52-1.56 (3H, m), 2.2 (3H, d), 2.3-2.4 (4H, m), 3.65-3.75 (4H, m), 5.1-5.22 (1H, m), 8.38-8.47 (1H, m), 8.72-8.8 (4H, m), 9.02 (0.5H, s), 9.15 (0.5H, s), 13.05-13.1 (1H, m) |

TABLE IIA-continued

| | Name | M + 1 (obs) | $^1$H NMR (DMSO-D$_6$) |
|---|---|---|---|
| 300 | 2-(I-1-(6-(I-1-methylpyrrolidin-3-yloxy)pyridin-3-yl)ethylamino)-4-(5-(trifluoromethyl)-1H-pyrrolo[2,3-b]pyridin-3-yl)pyrimidine-5-carbonitrile | 509 | 1.56 (3H, d), 1.99-2.30 (2H, m), 2.81-2.91 (3H, m), 3.10-3.27 (1H, m), 3.64-3.75 (2H, m), 5.27-5.35 (1H, m), 5.51-5.55 (1H, m), 6.80 (1H, t), 7.79 (1H, m), 8.13-8.22 (1H, m), 8.71-8.86 (4H, m), 8.96-9.18 (1H, m), 10.01 (1H, m), 13.08 (1H, m) |
| 301 | 2-((S)-1-(6-(I-1-methylpyrrolidin-3-yloxy)pyridin-3-yl)ethylamino)-4-(5-(trifluoromethyl)-1H-pyrrolo[2,3-b]pyridin-3-yl)pyrimidine-5-carbonitrile | 509 | 1.56 (3H, d), 1.99-2.30 (2H, m), 2.81-2.91 (3H, m), 3.10-3.27 (1H, m), 3.67 (2H, m), 5.27-5.35 (1H, m), 5.51-5.55 (1H, m), 6.83 (1H, t), 7.79 (1H, m), 8.14-8.22 (1H, m), 8.72-8.86 (4H, m), 8.96-9.18 (1H, m), 10.01 (1H, m), 13.08 (1H, m) |
| 302 | 2-(I-1-(2-hydroxypyrimidin-5-yl)ethylamino)-4-(5-(trifluoromethyl)-1H-pyrrolo[2,3-b]pyridin-3-yl)pyrimidine-5-carbonitrile | 427 | (MeOH-d$_4$) 1.65-1.75 (3H, m), 5.1-5.2 (0.8H, m), 5.3-5.4 (0.6H, m), 8.42-8.55 (2H, m), 8.6-8.7 (2H, m), 8.82 (1H, s), 9.15 (0.4H, s), 9.4 (0.6H, s) |
| 303 | 2-(I-1-(2-methoxypyrimidin-5-yl)ethylamino)-4-(5-(trifluoromethyl)-1H-pyrrolo[2,3-b]pyridin-3-yl)pyrimidine-5-carbonitrile | 441 | 1.62-1.68 (3H, m), 3.87-3.92 (3H, m), 5.26-5.32 (1H, m), 8.42-8.55 (2H, m), 8.62 (1H, s), 8.7-8.8 (4H, m), 8.82 (1H, d), 8.9 (0.6H, s), 9.2 (0.4H, s), 15.1-15.2 (1H, m) |
| 304 | 2-((R)-1-(4-((2-(dimethylamino)ethyl)(methyl)amino)phenyl)ethylamino)-4-(5-(trifluoromethyl)-1H-pyrrolo[2,3-b]pyridin-3-yl)pyrimidine-5-carbonitrile | 509 | 1.48-1.52 (3H, m), 2.13-2.16 (6H, m), 2.25-2.40 (2H, m), 2.80-2.87 (3H, m), 3.33-3.55 (3H, m), 6.56-6.66 (2H, m), 7.15-7.25 (2H, m), 8.65-8.75 (4H, m), 9.05 + 9.21 (1H, 2 × s), 13.02 (1H, br s) |

Preparation 4: 2-(4-chloro-5-cyanopyrimidin-2-ylamino)-2-methyl-N-(2,2,2-trifluoroethyl)propanamide

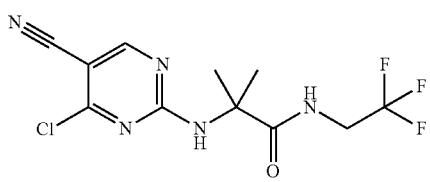 [SMILES: CC(C)(Nc1ncc(C#N)c(Cl)n1)C(=O)NCC(F)(F)F]

2,4-dichloropyrimidine-5-carbonitrile (E. F. Godefroi, J. Org. Chem., 1962, 27(6), 2264-6) (0.10 g, 0.57 mmol), 2-amino-2-methyl-N-(2,2,2-trifluoroethyl)propanamide.1TFA (Meinke, Peter T.; Shih, Thomas L.; Fisher, Michael H., U.S. Pat. No. 6,221,894 B1) (0.171 g, 1.14 mmol) and DIPEA (0.39 mL, 2.29 mmol) were combined in anhydrous THF (5 mL) in a sealed tube and heated to 90° C. for 18 hours, before cooling to room temperature. The solvent was evaporated in vacuo and the residue purified by flash chromatography (40 g SiO$_2$, pentane/ethyl acetate, 30-70% over 14 column volumes) to afford the title compound as a colorless waxy solid (0.036 g, 19.7%).
MS (ES+): 322.28.
MS (ES−): 320.39.

Example 5

2-(5-cyano-4-(5-(trifluoromethyl)-1H-pyrrolo[2,3-b]pyridin-3-yl)pyrimidin-2-ylamino)-2-methyl-N-(2,2,2-trifluoroethyl)propanamide Step 1: 2-(5-cyano-4-(1-tosyl-5-(trifluoromethyl)-1H-pyrrolo[2,3-b]pyridin-3-yl)pyrimidin-2-ylamino)-2-methyl-N-(2,2,2-trifluoroethyl)propanamide

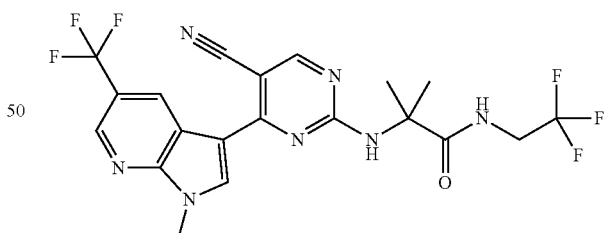

A mixture of 5-trifluoro-3-(4,4,5,5-tetramethyl-1,3,2-dioxaborolan-2-yl)-1-tosyl-1H-pyrrolo[2,3-b]pyridine (23 mg, 0.07 mmol, 1.0 Eq.) and 2-(4-chloro-5-cyanopyrimidine-2-ylamino)-2-methyl-N-(2,2,2-trifluoromethyl)propanamide (33 mg, 0.07 mmol, 1.0 Eq.) was suspended in toluene (2.0 mL) and EtOH (0.5 mL) and treated with 2M K$_2$CO$_3$ (105 ul, 0.21 mmol, 3.0 Eq.). The mixture was sonicated under an atmosphere of nitrogen for 20 minutes and then treated with Pd(PPh$_3$)$_4$ (8 mg, 0.007 mmol, 0.1 Eq.). After sonication for a further 5 minutes the reaction was heated under microwave conditions at 140° C. for 20 minutes. The reaction was partitioned between EtOAc and water and the aqueous phase extracted with EtOAc (3×). The combined organic layers were dried (MgSO₄) and concentrated in vacuo. The crude product was purified by column chromatography (ISCO Companion™, 12 g column, 0-100% EtOAc/Petroleum Ether) to give the title compound as a white solid (29 mg, 66%).

Step 2: 2-(5-cyano-4-(5-(trifluoromethyl)-1H-pyrrolo[2,3-b]pyridin-3-yl)pyrimidin-2-ylamino)-2-methyl-N-(2,2,2-trifluoroethyl)propanamide

IA-0

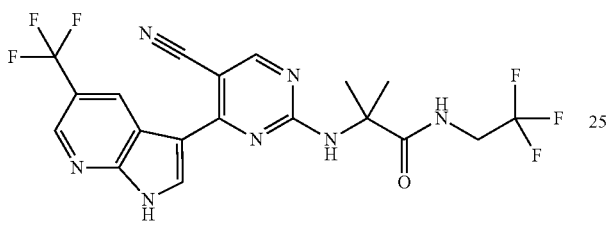

2-(5-cyano-4-(1-tosyl-5-(trifluoromethyl)-1H-pyrrolo[2,3-b]pyridin-3-yl)pyrimidin-2-ylamino)<sub>2</sub>-methyl-N-(2,2,2-trifluoroethyl)propanamide (29 mg, 0.046 mmol, 1.0 Eq.) was dissolved in THF (4 mL) and water (1 mL) and treated with LiOH.H₂O (10 mg, 0.23 mmol, 15 eq) and allowed to stir at room temperature overnight. The reaction mixture was concentrated and the residue partitioned between EtOAc and water. The organic phase was washed with saturated aqueous NaHCO₃ followed by brine, dried over MgSO₄, filtered and the solvent evaporated. The residue was purified by column chromatography (ISCO Companion™, 12 g column, 0-100% EtOAc/Petroleum Ether) to give the title compound as a white solid (13 mg, 60%). MS (ES⁺) m/e=472. ¹H NMR (DMSO) 1.53 (6H, s), 1.58 (6H, s), 3.65-3.69 (2H, m), 3.75-3.79 (2H, m), 8.26-8.34 (2H, m), 8.45 (1H, s), 8.65-8.78 (6H, m), 8.96 (1H, s), 9.29 (1H, s), 13.05 (2H, brs) [1:1 Mixture of rotamers]

A variety of other compounds of Formula I have been prepared by the methods of Example 5. The characterization data for these compounds is summarized in Table II-B below and includes LC/MS (observed) and ¹H NMR data.

IA-1

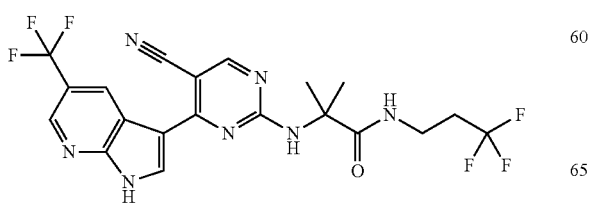

-continued

IA-2

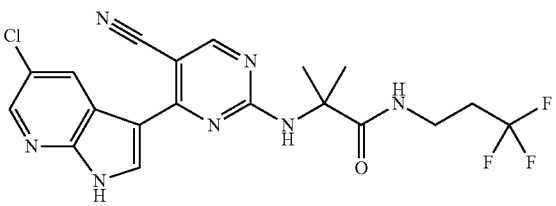

IA-3

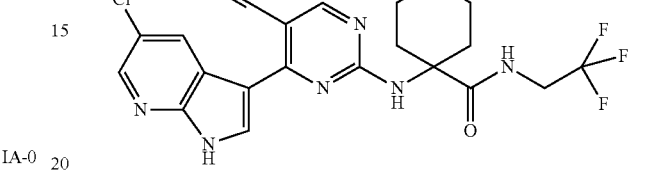

IA-4

IA-5

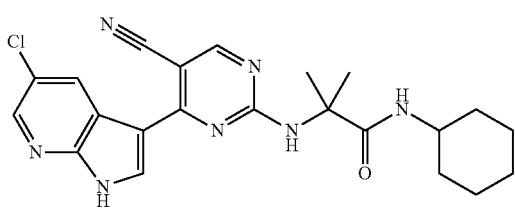

IA-6

IA-7

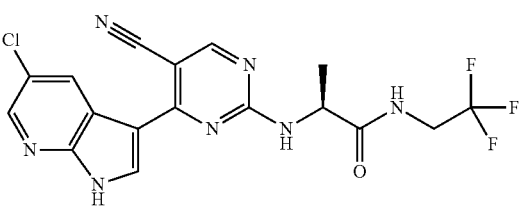

IA-8

-continued

IA-9
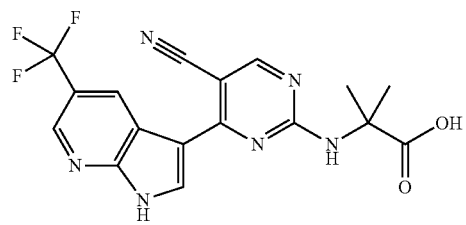

IA-10
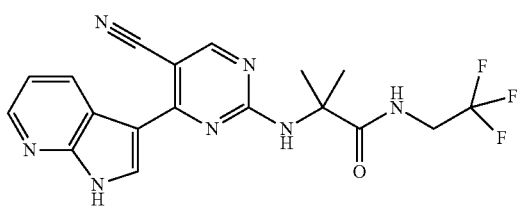

IA-11
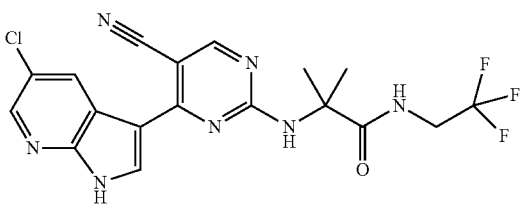

-continued

IA-12
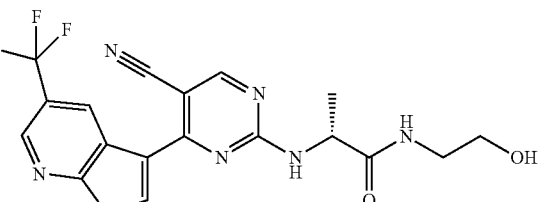

IA-13
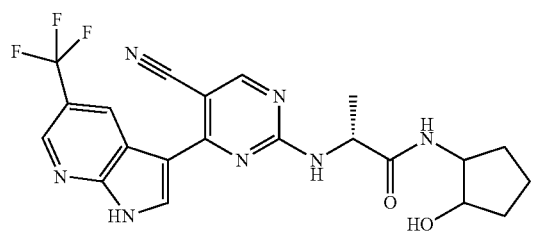

IA-14
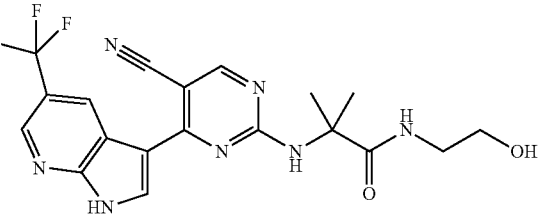

TABLE II-B

| Compound No. | Name | M + 1 (obs) | $^1$H NMR |
|---|---|---|---|
| IA-1 | 2-(5-cyano-4-(5-(trifluoromethyl)-1H-pyrrolo[2,3-b]pyridin-3-yl)pyrimidin-2-ylamino)-2-methyl-N-(3,3,3-trifluoropropyl)propanamide | 486 | (DMSO) 1.51 (6H, s), 1.56 (6H, s), 1.76-1.91 (2H, m), 2.01-2.39 (2H, m), 3.06 (2H, brq), 3.24 (2H, brq), 7.90 (2H, t), 8.33 (1H, s), 8.42 (1H, s), 8.70-8.77 (6H, m), 8.99 (1H, s), 9.28 (1H, s), 13.04 (1H, brs). [1:1 Mixture of rotamers.] |
| IA-2 | 1-(4-(5-chloro-1H-pyrrolo[2,3-b]pyridin-3-yl)-5-cyanopyrimidin-2-ylamino)-N-(2,2,2-trifluoroethyl)cyclohexanecarboxamide | 452 | (DMSO) 1.54 (6H, d), 2.10 (1H, m), 2.35 (1H, m), 3.25 (2H, m), 6.56 (1H, br s), 7.90 (1H, m), 8.38 (2H, m), 8.66 (2H, m), 9.20 (1H, d), 12.80 (1H, s) |
| IA-3 | 1-(4-(5-chloro-1H-pyrrolo[2,3-b]pyridin-3-yl)-5-cyanopyrimidin-2-ylamino)-N-(2,2,2-trifluoroethyl)cyclohexanecarboxamide478 | 478 | |
| IA-4 | 2-(4-(5-chloro-1H-pyrrolo[2,3-b]pyridin-3-yl)-5-cyanopyrimidin-2-ylamino)-N-cyclopentyl-2-methylpropanamide | 424 | |
| IA-5 | 2-(4-(5-chloro-1H-pyrrolo[2,3-b]pyridin-3-yl)-5-cyanopyrimidin-2-ylamino)-N-cyclohexyl-2-methylpropanamide | 438 | |
| IA-6 | (2S)-2-(4-(5-chloro-1H-pyrrolo{2,3-b]pyridin-3-yl)-5-cyanopyrimidin-2-ylamino)-N-(2,2,2-trifluoroethyl)propanamide | 424 | (DMSO) 1.47 (3H, m), 3.81 (3H, m), 7.53 (1H, m), 8.20 (1H, s), 8.26 (2H, br s), 8.43 (1H, s), 8.57 (1H, s), 8.65 (1H, s), 8.97 (1H, s) |

TABLE II-B-continued

| Compound No. | Name | M + 1 (obs) | $^1$H NMR |
|---|---|---|---|
| IA-7 | 1-(4-(5-chloro-1H-pyrrolo[2,3-b]pyridin-3-yl)-5-cyanopyrimidin-2-ylamino)-N-(2,2,2-trifluoroethyl)cyclopentane-carboxamide | 464 | (MeOD) 1.87 (4H, br s), 2.20 (2H, m), 2.45 (2H, m), 3.83 (2H, m), 8.29 (1H, s), 8.41 (2H, m), 8.52 (1H, s), 8.72 (1H, s), 8.83 (1H, s), 9.30 (1H, s) |
| IA-8 | 2-(4-(5-chloro-1H-pyrrolo[2,3-b]pyridin-3-yl)-5-cyanopyrimidin-2-ylamino)-N,2-dimethylpropanamide | 370 | (MeOD/CDCl3) 1.63 (6H, br s), 2.71 (3H, m), 8.29 (1H, s), 8.54 (1H, s), 8.69 (1H, s), 9.25 (1H, br s) |
| IA-9 | 2-(5-cyano-4-(5-(trifluoromethyl)-1H-pyrrolo[2,3-b]pyridin-3-yl)pyrimidin-2-ylamino)-2-methylpropanoic acid | 391 | (MeOD) 1.58 (3H, s), 1.67 (3H, s), 8.49 (1H, s), 8.55 (1H, s), 8.70 (1H, s), 9.13 (1H, s), 9.31 (1H, s) |
| IA-10 | 2-(5-cyano-4-(1H-pyrrolo[2,3-b]pyridin-3-yl)pyrimidin-2-ylamino)-2-methyl-N-(2,2,2-trifluoroethyl)propanamide | 404 | (MeOD) 1.64 (br, 6H), 3.80 (br, 2H), 7.37 (s, 1H), 8.58-8.36 (m, 2.78H), 8.69 (br, 1H), 8.92 (br, 0.44H), 9.30 (br, 0.47H) |
| IA-11 | 2-(4-(5-chloro-1H-pyrrolo[2,3-b]pyridin-3-yl)-5-cyanopyrimidin-2-ylamino)-2-methyl-N-(2,2,2-trifluoroethyl)propanamide | 438 | (CD3OD/CDCl3) 1.64 (6H, s), 3.82 (2H, m), 7.60 (1H, br s), 8.25 (1H, s), 8.47 (1H, s), 8.64 (1H, s), 8.75 (1H, br s), 8.99 (1H, br s) |
| IA-12 | (2R)-2-(5-cyano-4-(5-(trifluoromethyl)-1H-pyrrolo[2,3-b]pyridin-3-yl)pyrimidin-2-ylamino)-N-(2-hydroxyethyl)-propanamide | 420 | 1.42 (3H, m), 3.13 (2H, m), 3.46 masked signal, 4.54-4.58 (2H, m), 7.84-8.03 (1H, m), 8.23-8.61 (1H, m), 8.70-8.76 (3H, m), 8.93-9.30 (1H, m), 13.07 (1H, m) rotamers observed |
| IA-13 | (2R)-2-(5-cyano-4-(5-(trifluoromethyl)-1H-pyrrolo[2,3-b]pyridin-3-yl)pyrimidin-2-ylamino)-N-(2-hydroxycyclopentyl)propanamide | 460 | 1.24-1.44 (7H, m), 1.76-1.99 (2H, m), 3.77-3.83 (2H, m), 4.54-4.72 (2H, m), 7.91-8.12 (1H, m), 8.57-8.82 (4H, m), 8.96-9.30 (1H, m), 13.07 (1H, m) rotamers observed |
| IA-14 | 2-(5-cyano-4-(5-(trifluoromethyl)-1H-pyrrolo[2,3-b]pyridin-3-yl)pyrimidin-2-ylamino)-N-(2-hydroxyethyl)-2-methylpropanamide | 434 | 0.84 (6H, m), 2.34 (2H, m), 2.75 (2H, m), 7.06 (1H, br s), 7.78 (2H, m), 7.99 (1H, s), 8.30-8.61 (1H, m) |

Example 6

2-(phenylthio)-4-(5-(trifluoromethyl)-1H-pyrrolo[2,3-b]pyridin-3-yl)pyrimidine-5-carbonitrile

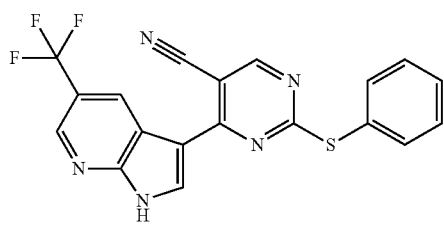

II-0

2-(methylsulfonyl)-4-(1-tosyl-5-(trifluoromethyl)-1H-pyrrolo[2,3-b]pyridin-3-yl)pyrimidine-5-carbonitrile (75 mg, 0.15 mmol) was heated with benzenethiol (31 uL, 0.30 mmol, 2.0 Eq.) and DIPEA (78 uL, 0.45 mmol, 3.0 Eq.) in THF (2 mL) under microwave conditions at 100° C. for 10 minutes. A solution of LiOH.H$_2$O (32 mg, 0.75 mmol, 5.0 Eq.) in water (1 mL) was added to the mixture and the reaction left to stir for 90 minutes. The reaction was partitioned between EtOAc and water and the aqueous phase extracted with EtOAc. The combined organic layers were dried (Na$_2$SO$_4$) and concentrated in vacuo. The resultant solid was purified by column chromatography (ISCO Companion™, 12 g column, 0-30% EtOAc/Petroleum Ether) and lyophilized to give the title compound as a pale yellow solid (28 mg, 47% over 2 steps).

MS (ES$^+$) m/e=398. $^1$H NMR (DMSO) 7.48-7.50 (3H, m), 7.68-7.71 (2H, m), 8.37 (1H, s), 8.70 (1H, s), 8.80 (1H, s), 9.02 (1H, s), 13.25 (1H, brs).

Other compounds of Formula I prepared by the methods of Example 3 are illustrated in Table III-A. The characterization data for these compounds is summarized in Table III-B below and includes LC/MS (observed) and $^1$H NMR data.

TABLE III-A

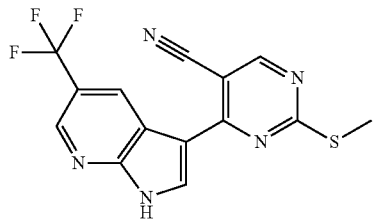

II-1

TABLE III-A-continued
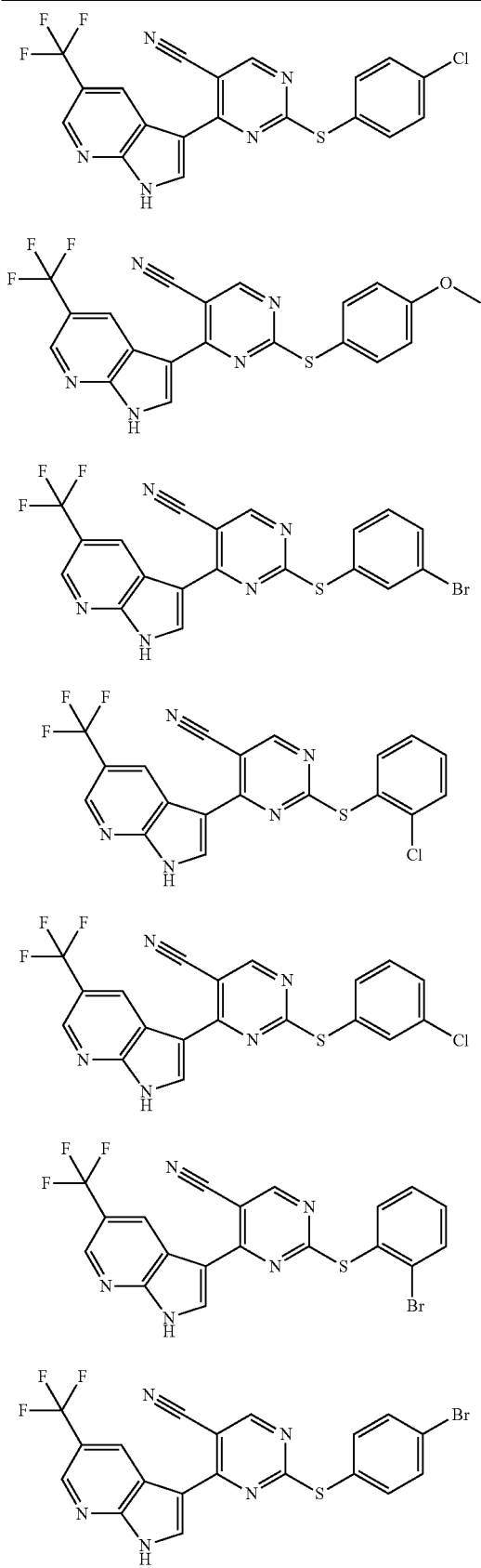
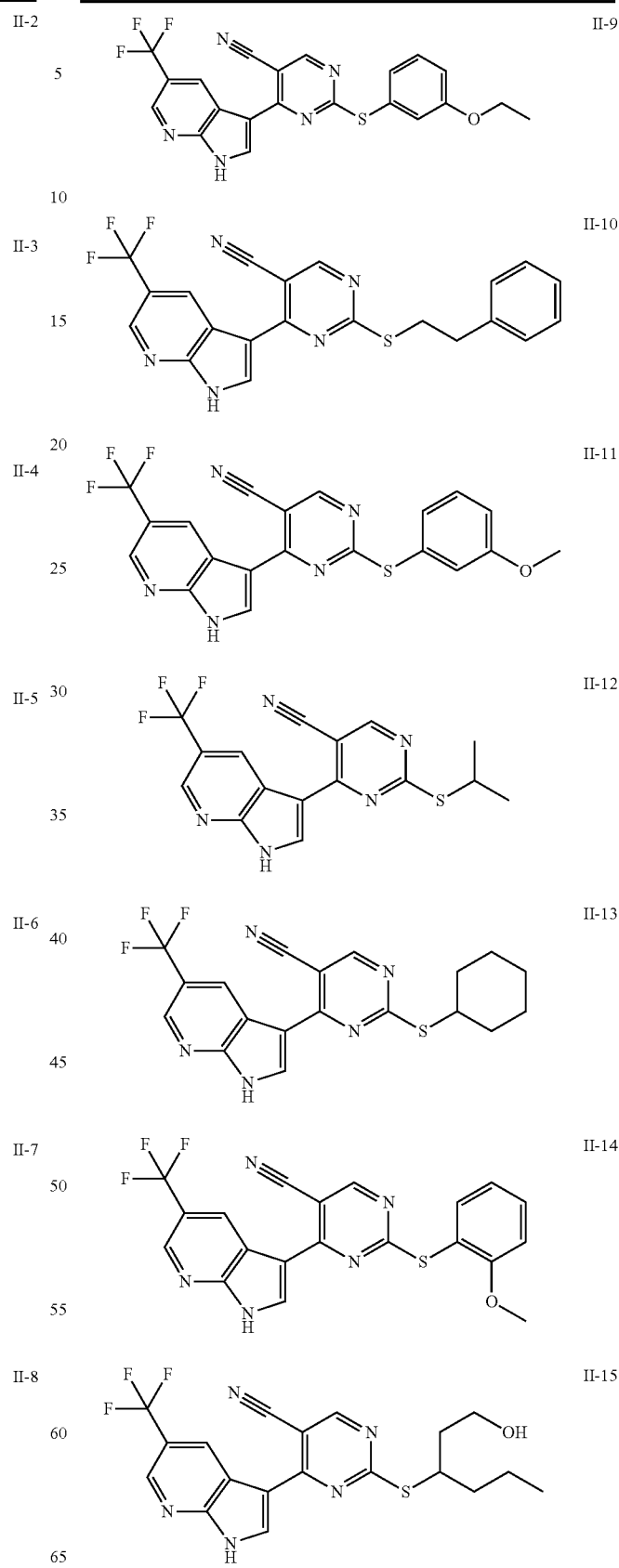

TABLE III-A-continued

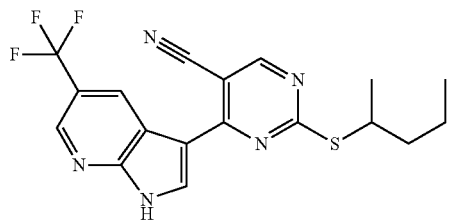 [SMILES: CCCC(C)Sc1ncc(C#N)c(-c2c[nH]c3ncc(C(F)(F)F)cc23)n1]
II-16

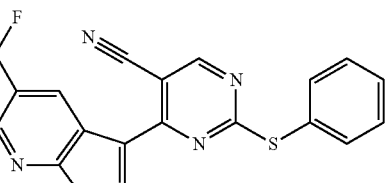
II-0

TABLE IIIB

| Compound No (II-) | Name | M + 1 (obs) | $^1$H NMR (DMSO-D$_6$ Except where noted) |
|---|---|---|---|
| 1 | 2-(methylthio)-4-(5-(trifluoromethyl)-1H-pyrrolo[2,3-b]pyridin-3-yl)pyrimidine-5-carbonitrile | 336 | 2.70 (3H, s), 8.79 (1H, s), 8.85 (1H, s), 9.04 (1H, s), 9.13 (1H, s), 13.32 (1H, brs). |
| 2 | 2-(4-chlorophenylthio)-4-(5-(trifluoromethyl)-1H-pyrrolo[2,3-b]pyridin-3-yl)pyrimidine-5-carbonitrile | 432 | 7.55 (2H, d), 7.74 (2H, d), 8.39 (1H, s), 8.81 (1H, s), 8.83 (1H, s), 9.04 (1H, s), 13.30 (1H, brs). |
| 3 | 2-(4-methoxyphenylthio)-4-(5-(trifluoromethyl)-1H-pyrrolo[2,3-b]pyridin-3-yl)pyrimidine-5-carbonitrile | 428 | 3.80 (3H, s), 7.03 (2H, d), 7.60 (2H, d), 8.40 (1H, s), 8.71 (1H, s), 8.81 (1H, s), 9.02 (1H, s), 13.28 (1H, brs). |
| 4 | 2-(3-bromophenylthio)-4-(5-(trifluoromethyl)-1H-pyrrolo[2,3-b]pyridin-3-yl)pyrimidine-5-carbonitrile | 476 | 7.45 (1H, t), 7.71 (2H, t), 7.92 (1H, s), 8.39 (1H, s), 8.69 (1H, s), 8.86 (1H, s), 9.01 (1H, s), 13.32 (1H, brs). |
| 5 | 2-(2-chlorophenylthio)-4-(5-(trifluoromethyl)-1H-pyrrolo[2,3-b]pyridin-3-yl)pyrimidine-5-carbonitrile | 432 | 7.47 (1H, t), 7.56 (1H, t), 7.67 (1H, d), 7.89 (1H, d), 8.35 (1H, s), 8.72 (1H, s), 8.81 (1H, s), 9.06 (1H, s), 13.31 (1H, brs). |
| 6 | 2-(3-chlorophenylthio)-4-(5-(trifluoromethyl)-1H-pyrrolo[2,3-b]pyridin-3-yl)pyrimidine-5-carbonitrile | 432 | |
| 7 | 2-(2-bromophenylthio)-4-(5-(trifluoromethyl)-1H-pyrrolo[2,3-b]pyridin-3-yl)pyrimidine-5-carbonitrile | 476 | 7.27 (2H, m), 7.63 (1H, d), 7.70 (1H, d), 8.14 (1H, s), 8.49 (1H, s), 8.61 (1H, s), 8.84 (1H, s) |
| 8 | 2-(4-bromophenylthio)-4-(5-(trifluoromethyl)-1H-pyrrolo[2,3-b]pyridin-3-yl)pyrimidine-5-carbonitrile | 476 | |
| 9 | 2-(3-ethoxyphenylthio)-4-(5-(trifluoromethyl)-1H-pyrrolo[2,3-b]pyridin-3-yl)pyrimidine-5-carbonitrile | 442 | |
| 10 | 2-(phenethylthio)-4-(5-(trifluoromethyl)-1H-pyrrolo[2,3-b]pyridin-3-yl)pyrimidine-5-carbonitrile | 426 | |
| 11 | 2-(3-methoxyphenylthio)-4-(5-(trifluoromethyl)-1H-pyrrolo[2,3-b]pyridin-3-yl)pyrimidine-5-carbonitrile | 428 | |
| 12 | 2-(isopropylthio)-4-(5-(trifluoromethyl)-1H-pyrrolo[2,3-b]pyridin-3-yl)pyrimidine-5-carbonitrile | 364 | 1.45 (6H, d), 4.07 (1H, m), 8.79 (1H, s), 8.85 (1H, s), 9.04 (2H, m), 13.32 (1H, s) |
| 13 | 2-(cyclohexylthio)-4-(5-(trifluoromethyl)-1H-pyrrolo[2,3-b]pyridin-3-yl)pyrimidine-5-carbonitrile | 404 | 1.44 (8H, m), 2.09 (2H, m), 3.91 (1H, m), 8.79 (2H, d), 9.00 (2H, d), 13.31 (1H, s) |
| 14 | 2-(2-methoxyphenylthio)-4-(5-(trifluoromethyl)-1H-pyrrolo[2,3-b]pyridin-3-yl)pyrimidine-5-carbonitrile | 428 | 3.71 (3H, s), 7.05 (1H, t), 7.16 (1H, d), 7.51 (1H, t), 7.64 (1H, d), 8.40 (1H, s), 8.74 (1H, d), 8.80 (1H, d), 8.99 (1H, s), 13.31 (1H, s) |
| 15 | 2-(1-hydroxyhexan-3-ylthio)-4-(5-(trifluoromethyl)-1H-pyrrolo[2,3-b]pyridin-3-yl)pyrimidine-5-carbonitrile | 422 | |

TABLE IIIB-continued

| Compound No (II-) | Name | M + 1 (obs) | $^1$H NMR (DMSO-D$_6$ Except where noted) |
|---|---|---|---|
| 16 | 2-(pentan-2-ylthio)-4-(5-(trifluoromethyl)-1H-pyrrolo[2,3-b]pyridin-3-yl)pyrimidine-5-carbonitrile | 392 | (MeOD/CDCl$_3$) 0.97 (6H, d), 1.69 (2H, m), 1.80 (1H, m), 3.36 (2H, m), 8.65 (1H, s), 8.75 (1H, s), 8.87 (1H, s), 9.20 (1H, s) |
| 17 | 2-(phenylthio)-4-(5-(trifluoromethyl)-1H-pyrrolo[2,3-b]pyridin-3-yl)pyrimidine-5-carbonitrile | 398 | 7.48-7.50 (3H, m), 7.68-7.71 (2H, m), 8.37 (1H, s), 8.70 (1H, s), 8.80 (1H, s), 9.02 (1H, s), 13.25 (1H, brs) |

Using the methods of Example 3, compounds wherein R$^2$ is –OR$^6$ were prepared as follows.

Example 7

2-Phenoxy-4-(5-(trifluoromethyl)-1H-pyrrolo[2,3-b]pyridin-3-yl)pyrimidine-5-carbonitrile

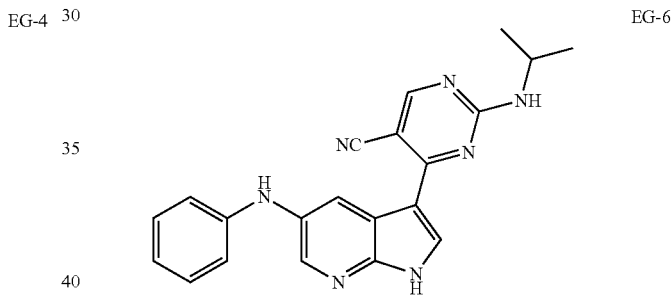

EG-4

MS (ES$^+$) m/e=382. $^1$H NMR (DMSO) 7.4-7.45 (3H, m), 7.48-7.53 (2H, m), 8.3 (1H, s), 8.72 (1H, s), 8.9 (1H, s), 9.23 (1H, s)

Example 8

2-isopropoxy-4-(5-(trifluoromethyl)-1H-pyrrolo[2,3-b]pyridin-3-yl)pyrimidine-5-carbonitrile

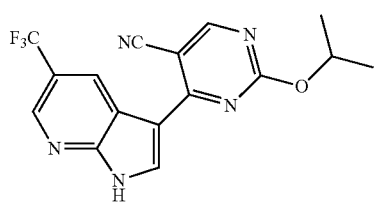

EG-5

MS (ES$^+$) m/e=349. $^1$H NMR (MeOH) 1.55 (6H, d), 5.55 (1H, m), 8.95 (1H, s), 8.9 (1H, s), 8.97 (1H, s), 9.32 (1H, s)

Example 9

2-(isopropylamino)-4-(5-(phenylamino)-1H-pyrrolo[2,3-b]pyridin-3-yl)pyrimidine-5-carbonitrile

EG-6

Step 1: 1H-pyrrolo[2,3-b]pyridin-5-amine

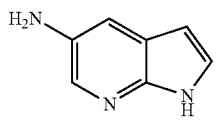

5-bromo-1H-pyrrolo[2,3-b]pyridine (6.0 g, 30.45 mmol) in ammonium hydroxide (120 mL) was treated with copper sulphate pentahydrate (1.50 g, 6.09 mmol, 0.2 eq) and heated in a sealed tube overnight. The reaction was diluted with EtOAc and the insoluble black solid was filtered off. The filtrate was extracted (EtOAc/Water) and the organic layer washed with saturated aqueous ammonium chloride, followed by water and brine. The organics were dried over

Step 2: Benzyl 1H-pyrrolo[2,3-b]pyridin-5-ylcarbamate

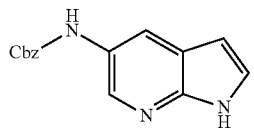 [SMILES: O=C(Nc1cnc2[nH]ccc2c1)OCc1ccccc1]

1H-pyrrolo[2,3-b]pyridin-5-amine (9.45 g, 71.05 mmol) was dissolved in THF (150 mL) and stirred at 0° C. under an atmosphere of nitrogen. Benzyl chloroformate (20.3 mL, 142.10 mmol, 2.0 Eq) was added dropwise over a period of 15 minutes and the mixture allowed to stir at room temperature for 30 minutes. The mixture was treated with 4M NaOH (aq) (53.3 mL, 213.16 mmol, 3.0 Eq) over a period of 15 minutes and the resultant brown solution left to stir for 16 hours. The reaction mixture was taken to pH 4 (125 mL of 10% aq. citric acid) and the 2 layers were separated. The aqueous layer was back extracted with EtOAc and the combined organics were dried over magnesium sulphate, filtered and dried under vacuum. The crude product was purified by column chromatography (50% EtOAc/Petroleum Ether) to give 14.59 g (77%) of pale yellow solid.

Step 3: Benzyl 3-bromo-1H-pyrrolo[2,3-b]pyridin-5-ylcarbamate

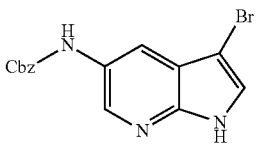 [SMILES: O=C(Nc1cnc2[nH]cc(Br)c2c1)OCc1ccccc1]

Benzyl 1H-pyrrolo[2,3-b]pyridin-5-ylcarbamate (9.48 g, 35.5 mmol) in chloroform (100 mL) was cooled to 5° C. and treated dropwise with bromine (1.86 mL, 36.21 mmol, 1.02 Eq). The reaction was allowed to to stir at 0° C. for 1 hour and then at room temperature for 1 hour. The mixture was diluted with DCM and washed with a 1:1 sat. aq. sodium thiosulfate/sodium bicarbonate solution (200 mL). The organic layer was separated and the aqueous layer taken to pH 12 and re-extracted with EtOAc. The combined organics were dried over magnesium sulphate, filtered and dried under vacuum and the resultant brown solid triturated with diethyl ether/EtOAc to give 10.24 g (83%) of the title compound.

Step 4: Benzyl 3-bromo-1-tosyl-1H-pyrrolo[2,3-b]pyridin-5-ylcarbamate

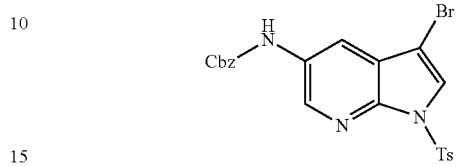

Benzyl 3-bromo-1H-pyrrolo[2,3-b]pyridin-5-ylcarbamate (10.22 g, 29.53 mmol) in dry THF (120 mL) was cooled to 0° C. and treated portionwise with sodium hydride (1.193 g, 29.83 mmol, 1.01 Eq). The mixture was allowed to stir at this temperature for 1 hour and then treated with tosyl chloride (5.744 g, 30.13 mmol, 1.02 Eq) in THF (15 mL) over a period of 10 minutes. The mixture was left to stir at room temperature for a further 4 hours and then quenched with sat. aq. ammonium chloride. The mixture was diluted with EtOAc and the organic layer separated, washed with brine, dried over magnesium sulphate, filtered and evaporated to dryness. The crude product was purified by column chromatography (5% MeOH/DCM) to give 11.09 g (75%) of brown solid.

Step 5: Benzyl 3-(4,4,5,5-tetramethyl-1,3,2-dioxaborolan-2-yl)-1-tosyl-1H-pyrrolo[2,3-b]pyridin-5-ylcarbamate

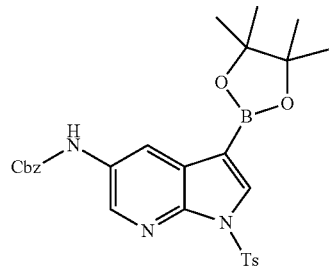 [SMILES: Cc1ccc(S(=O)(=O)n2cc(B3OC(C)(C)C(C)(C)O3)c3cc(NC(=O)OCc4ccccc4)cnc32)cc1]

Benzyl 3-bromo-1-tosyl-1H-pyrrolo[2,3-b]pyridin-5-ylcarbamate (3.51 g, 7.02 mmol) in dry dioxane (35 mL) was treated with bis(pinacolato)diboron (2.14 g, 8.42 mmol, 1.2 Eq) and potassium acetate (2.06 g, 98.15 mmol, 3.0 Eq), the reaction mixture was degassed and stirred under nitrogen for 20 minutes and then treated with Pd(PPh$_3$)$_4$ (0.811 g, 0.70 mmol, 0.1 Eq). The mixture was degassed and heated at reflux under nitrogen for 2 hours. The mixture was partitioned between EtOAc and sat. aq ammonium chloride, the organic layer was separated, washed with brine, dried over magnesium sulphate and evaporated to dryness. The residue was filtered through a plug of Florisil eluting with 50% EtOAc/

Petroleum ether and the resultant solid triturated with EtOAc to give the title compound as an off-white solid (2.805 g, 73%).

Step 6: Benzyl 3-(5-cyano-2-(methylthio)pyrimidin-4-yl)-1-tosyl-1H-pyrrolo[2,3-b]pyridin-5-ylcarbamate

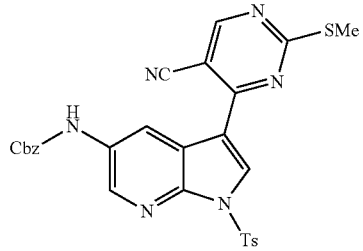 [SMILES: CSc1ncc(C#N)c(-c2cn(S(=O)(=O)c3ccc(C)cc3)c3ncc(NC(=O)OCc4ccccc4)cc23)n1]

Benzyl 3-(4,4,5,5-tetramethyl-1,3,2-dioxaborolan-2-yl)-1-tosyl-1H-pyrrolo[2,3-b]pyridin-5-ylcarbamate (0.50 g, 0.91 mmol) in toluene/ethanol (7.5 mL:2.0 mL) was treated with 4-chloro-2-(methylthio)pyrimidine-5-carbonitrile (0.186 g, 1.00 mmol, 1.1 Eq) and 2M aqueous potassium carbonate (1.37 mL, 2.74 mmol, 3.0 Eq), degassed and stirred under nitrogen for 20 minutes. $Pd(dppf)_2Cl_2$ (0.075 g, 0.1 Eq) was added and the mixture allowed to heat at 100° C. for 1.5 hours. The reaction was partitioned between EtOAc and saturated aqueous sodium carbonate and the organic layer separated, dried over magnesium sulphate and evaporated to dryness. The mixture was purified by column chromatography eluting with 10% EtOAc/Petroleum ether to yield a white solid (0.219 g, 42%).

Step 7: Benzyl 3-(5-cyano-2-(methylsulfonyl)pyrimidin-4-yl)-1-tosyl-1H-pyrrolo[2,3-b]pyridin-5-ylcarbamate

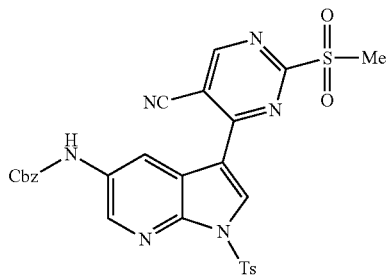 [SMILES: Cc1ccc(S(=O)(=O)n2cc(-c3nc(S(C)(=O)=O)ncc3C#N)c3cc(NC(=O)OCc4ccccc4)cnc32)cc1]

Benzyl 3-(5-cyano-2-(methylthio)pyrimidin-4-yl)-1-tosyl-1H-pyrrolo[2,3-b]pyridin-5-ylcarbamate (1.316 g, 2.308 mmol) in DCM (75 mL) was treated with mCPBA (0.877 g, 5.08 mmol, 0.2 Eq) and allowed to stir at room temperature overnight. The mixture was evaporated to a smaller volume and the resultant solid filtered off and washed with EtOAc (0.826 g, 60%).

Step 8: Benzyl 3-(5-cyano-2-(isopropylamino)pyrimidin-4-yl)-1-tosyl-1H-pyrrolo[2,3-b]pyridin-5-ylcarbamate

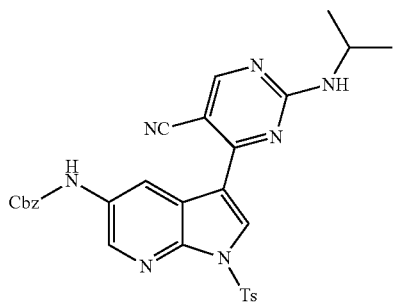 [SMILES: Cc1ccc(S(=O)(=O)n2cc(-c3nc(NC(C)C)ncc3C#N)c3cc(NC(=O)OCc4ccccc4)cnc32)cc1]

Benzyl 3-(5-cyano-2-(methylsulfonyl)pyrimidin-4-yl)-1-tosyl-1H-pyrrolo[2,3-b]pyridin-5-ylcarbamate (0.826 g, 1.372 mmol) in THF (30 mL) was treated with isopropylamine (0.234 mL, 2.744 mmol, 2.0 Eq) and DIPEA (0.478 mL, 2.744 mmol, 2.0 Eq) and allowed to heat at reflux for 1 hour. The mixture was concentrated in vacuo and purified by column chromatography (ISCO Companion™, 40 g column, 0-100% EtOAc/Petroleum ether) to give 0.651 g (82%) of the title compound.

Step 9: 4-(5-amino-1-tosyl-1H-pyrrolo[2,3-b]pyridin-3-yl)-2-(isopropylamino)pyrimidine-5-carbonitrile

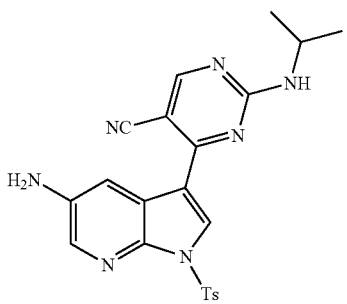 [SMILES: Cc1ccc(S(=O)(=O)n2cc(-c3nc(NC(C)C)ncc3C#N)c3cc(N)cnc32)cc1]

Benzyl 3-(5-cyano-2-(isopropylamino)pyrimidin-4-yl)-1-tosyl-1H-pyrrolo[2,3-b]pyridin-5-ylcarbamate (0.199 g, 0.342 mmol) in EtOH (15 mL) was charged with ammonium formate (0.129 g, 2.055 mmol, 6.0 Eq) and 10% Pd/C (0.040 g, 0.2 Eq) and heated at reflux for 3 hours.

Reaction mixture allowed to cool and filtered through a plug of celite washing through with further EtOAc. The mixture was concentrated in vacuo and purified by column chromatography (ISCO Companion™, 12g column, 0-100% (EtOAc/Petroleum ether) to give the title compound as a yellow solid (0.103 g 67%).

Step 10: 2-(isopropylamino)-4-(5-(phenylamino)-1-tosyl-1H-pyrrolo[2,3-b]pyridin-3-yl)pyrimidine-5-carbonitrile

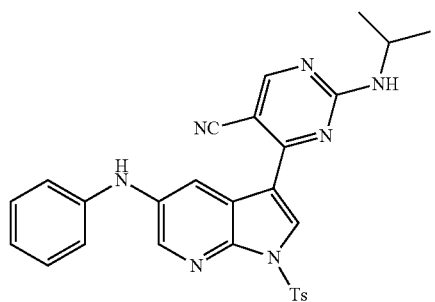 [SMILES: Cc1ccc(S(=O)(=O)n2cc(-c3nc(NC(C)C)ncc3C#N)c3cc(Nc4ccccc4)cnc32)cc1]

4-(5-amino-1-tosyl-1H-pyrrolo[2,3-b]pyridin-3-yl)-2-(isopropylamino)pyrimidine-5-carbonitrile (0.204 g, 0.455 mmol) in DCM (12 mL) was treated with phenylboronic acid (0.111 g, 0.910 mmol, 2.0 Eq), copper acetate (0.124 g, 0.682 mmol, 1.5 Eq), pyridine (0.074 mL, 0.910 mmol, 2.0 Eq) and 4 Angstrom molecular sieves (0.600 g) and the reaction was allowed to stir at room temperature for 16 hours. The reaction mixture was quenched with 4M Ammonia in MeOH (12 mL) and filtered through a plug of celite whilst washing through with further DCM/MeOH. The combined washes were evaporated to dryness and purified by column chromatography (ISCO Companion™, 12 g column, 0-100% EtOAc/Petroleum Ether) to give the title compound as a yellow solid (85 mg, 36%).

Step 11: 2-(isopropylamino)-4-(5-(phenylamino)-1H-pyrrolo[2,3-b]pyridin-3-yl)pyrimidine-5-carbonitrile

EG-6

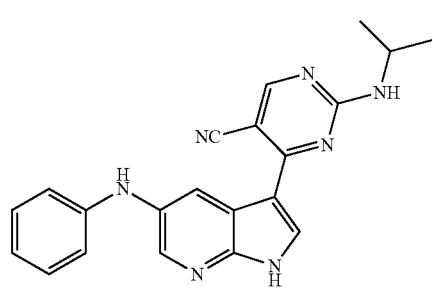

2-(isopropylamino)-4-(5-(phenylamino)-1-tosyl-1H-pyrrolo[2,3-b]pyridin-3-yl)pyrimidine-5-carbonitrile (0.083 g, 0.158 mmol) was stirred in THF (7 mL) and water (1.5 mL) and treated with LiOH.H$_2$O (0.066 g, 1.60 mmol, 10.0 Eq) and allowed to stir at room temperature for 16 hours. The reaction mixture was concentrated and purified by column chromatography (50% EtOAc/Petroleum ether) to yield the product as a yellow solid (29 mg, 50%)

MS (ES$^+$) m/e=370. $^1$H NMR (DMSO) 1.12 (6H, m), 4.13 (1H, m), 6.79 (1H, m), 7.03 (2H, m), 7.22 (2H, m), 7.31 (1H), 8.19 (1H, m), 8.51 (2H, m), 8.63 (1H, m), 11.98 (1H)

Example 10

3-(3-(5-cyano-2-(isopropylamino)pyrimidin-4-yl)-1H-pyrrolo[2,3-b]pyridin-5-ylamino)-N-methylbenzamide

EG-7

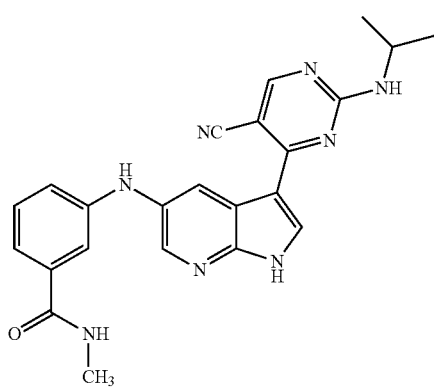

The title compound prepared from 4-(5-amino-1-tosyl-1H-pyrrolo[2,3-b]pyridin-3-yl)-2-(isopropylamino) pyrimidine-5-carbonitrile using the methods described in Example 9.

MS (ES$^+$) m/e=427. $^1$H NMR (DMSO) 1.12 (6H, m), 2.80 (3H, m), 4.15 (1H, m), 7.12 (1H, m), 7.24 (3H, m), 7.53 (1H, m), 7.83 (2H, br s), 8.20 (1H, m), 8.52 (2H, m), 8.66 (1H, m), 12.00 (1H).

Example 11

2-((R)-1-hydroxy-3-methylbutan-2-ylamino)-4-(5-methyl-1H-pyrrolo[2,3-b]pyridin-3-yl)pyrimidine-5-carbonitrile

EG-8

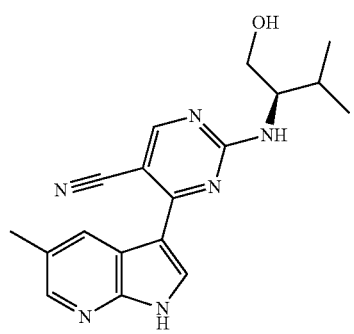

Step 1: 5-methyl-1-tosyl-1H-pyrrolo[2,3-b]pyridine

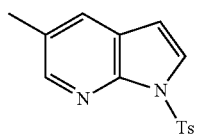 [SMILES: Cc1ccc(S(=O)(=O)n2ccc3cc(C)cnc32)cc1]

A solution of 5-bromo-1-tosyl-1H-pyrrolo[2,3-b]pyridine (5 g, 14.29 mmol), potassium trifluoro(methyl)borate (2.62 g, 21.43 mmol), cesium carbonate (12.56 g, 38.57 mmol) and [1,1'-bis(diphenylphosphino)ferrocene]dichloropalladium (II) (1.16 g, 1.43 mmol) in THF (150 mL) and water (15 mL) was heated at reflux for 18 hours. The reaction mixture was cooled down to ambient and partitioned between EtOAc (100 mL) and water (100 mL). The organic phase was separated, washed with 1N HCl (100 mL) and brine (100 mL), then, dried over magnesium sulfate and concentrated in vacuo. The residue was purified on silica gel by flash column chromatography to give the title compound as a white solid (1.903 g, 47% yield).

$^1$H NMR (DMSO-D$_6$, 400 MHz) δ 2.33 (3H, s), 2.34 (3H, s), 6.74 (1H, d), 7.40 (2H, d), 7.83 (2H, s), 7.95 (2H, d), 8.20 (1H, s); MS (ES+) 287.

Step 2: 3-bromo-5-methyl-1-tosyl-1H-pyrrolo[2,3-b]pyridine

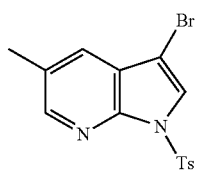 [SMILES: Cc1ccc(S(=O)(=O)n2cc(Br)c3cc(C)cnc32)cc1]

5-methyl-1-tosyl-1H-pyrrolo[2,3-b]pyridine (1.9 g, 6.62 mmol) in dichloromethane (40 mL) was treated dropwise with a solution of bromine (0.678 mL, 13.24 mmol) in dichloromethane (3 mL). The resulting solution was stirred at room temperature for 3 hours. The reaction mixture was partitioned between dichloromethane (150 mL) and a 1:1 mixture of a saturated aqueous solution of NaHCO3 and a saturated aqueous solution of Na2S2O3 (250 mL). The organic phase was separated and the aqueous phase was re-extracted twice with DCM (50 mL). The combined organic phases were dried over magnesium sulfate and concentrated in vacuo to give the desired compound as an off-white solid (2.381 g, 99% yield).

$^1$H NMR (DMSO-D$_6$, 400 MHz) δ 2.34 (3H, s), 2.39 (3H, s), 7.42 (2H, d), 7.75 (1H, s), 7.99 (2H, d), 8.14 (1H, s), 8.21 (1H, s); MS (ES+) 365.

Step 3: 5-methyl-3-(4,4,5,5-tetramethyl-1,3,2-dioxaborolan-2-yl)-1-tosyl-1H-pyrrolo[2,3-b]pyridine

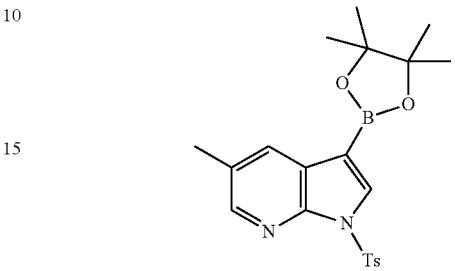

A mixture of 3-bromo-5-methyl-1-tosyl-1H-pyrrolo[2,3-b]pyridine (1.0 g, 2.75 mmol), bis(pinacolato)diboron (1.046 g, 4.12 mmol) and potassium acetate (0.851 g, 8.67 mmol) in dioxane (25 mL) was degassed and stirred under nitrogen for 30 minutes. The reaction mixture was treated with tetrakis(triphenylphosphine)palladium(0) (0.317 g, 0.27 mmol) and degassed again. The reaction mixture was then heated at reflux for 16 hours. The resulting mixture was cooled down to room temperature and filtered through a pad of celite washing with ethyl acetate. The filtrate was concentrated in vacuo and purified on florisil by flash column chromatography to afford the title compound as a white solid (0.779 g, 69% yield).

$^1$H NMR (DMSO-D$_6$, 400 MHz) δ 1.32 (12H, s), 2.34 (3H, s), 2.37 (3H, s), 7.42 (2H, d), 7.89 (1H, s), 7.99 (1H, s), 8.04 (2H, d), 8.22 (1H, s); MS (ES+) 413.

Step 4: 4-(5-methyl-1-tosyl-1H-pyrrolo[2,3-b]pyridin-3-yl)-2-(methylthio)pyrimidine-5-carbonitrile

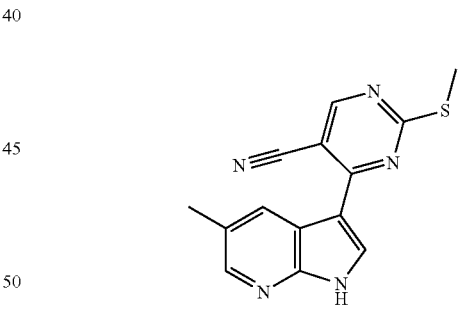

A mixture of 5-methyl-3-(4,4,5,5-tetramethyl-1,3,2-dioxaborolan-2-yl)-1-tosyl-1H-pyrrolo[2,3-b]pyridine (306 mg, 0.74 mmol) and 4-chloro-2-(methylthio)pyrimidine-5-carbonitrile (207 mg, 1.12 mmol) in dioxane (9 mL) was degassed and stirred under nitrogen for 10 minutes. The reaction mixture was treated with potassium carbonate (336 mg, 2.23 mmol) and bis(tri-t-butylphosphine)palladium(0) (38 mg, 0.074 mmol) and degassed again. The reaction mixture and stirred under nitrogen for 10 minutes. Water (1.35 mL) was added and the reaction mixture was degassed and stirred under nitrogen for 2 hours. A suspension was observed. The resulting mixture was filtered and the solid was washed with dioxane and water. The solid was dried in a vacuum oven to afford the title compound as a white solid (282 mg, 87% yield).

¹H NMR (DMSO-D₆, 400 MHz) δ 2.36 (3H, s), 2.42 (3H, s), 2.68 (3H, s), 7.46 (2H, d), 8.07 (2H, d), 8.36 (1H, s), 8.49 (1H, s), 8.93 (1H, s), 9.15 (1H, s); MS (ES+) 436.

Step 5: 4-(5-methyl-1-tosyl-1H-pyrrolo[2,3-b]pyridin-3-yl)-2-(methylsulfonyl)pyrimidine-5-carbonitrile

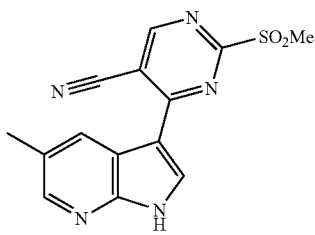 [SMILES: Cc1cnc2[nH]cc(-c3nc(S(C)(=O)=O)ncc3C#N)c2c1]

4-(5-Methyl-1-tosyl-1H-pyrrolo[2,3-b]pyridin-3-yl)-2-(methylthio)pyrimidine-5-carbonitrile (216 mg, 0.498 mmol) in dichloromethane (15 mL) was treated with m-chloroperbenzoic acid (215 mg, 1.244 mmol). The resulting suspension was allowed to stir at room temperature for 18 hours. The reaction mixture was partitioned between dichloromethane and a 1:1 mixture of a saturated aqueous solution of NaHCO3 and a saturated aqueous solution of Na2S2O3 (50 mL). The organic phase was separated and the aqueous phase was re-extracted twice with DCM. The combined organic phases were dried over magnesium sulfate and concentrated in vacuo. The resulting solid was triturated with EtOH and filtered to afford the title compound as an off-white solid (186 mg, 80% yield, 10:90 sulfoxide:sulfone mixture by LCMS).
¹H NMR (DMSO-D₆, 400 MHz) δ 2.37 (3H, s), 2.42 (3H, s), 3.54 (3H, s), 7.48 (2H, d), 8.10 (2H, d), 8.40 (1H, s), 8.61 (1H, s), 9.09 (1H, s), 9.64 (1H, s); MS (ES+) 468 (sulfone), (ES+) 452 (sulfoxide).

Step 6: 2-((R)-1-hydroxy-3-methylbutan-2-ylamino)-4-(5-methyl-1-tosyl-1H-pyrrolo[2,3-b]pyridin-3-yl)pyrimidine-5-carbonitrile

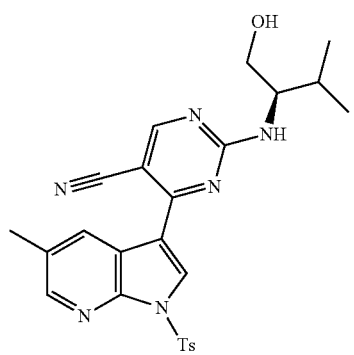 [SMILES: Cc1ccc(S(=O)(=O)n2cc(-c3nc(N[C@@H](CO)C(C)C)ncc3C#N)c3cc(C)cnc32)cc1]

A mixture of 4-(5-methyl-1-tosyl-1H-pyrrolo[2,3-b]pyridin-3-yl)-2-(methylsulfonyl)pyrimidine-5-carbonitrile (120 mg, 0.257 mmol), (R)-(+)2-amino-3-methyl-1-butanol (57 l, 0.515 mmol) and diisopropylethylamine (90 l, 0.515 mmol) in THF (4 mL) was heated at reflux for 1 hour. The reaction mixture was concentrated in vacuo and the residue was purified on silica gel by flash column chromatography to give the title compound as a colourless glassy solid (97 mg, 77% yield).
¹H NMR (DMSO-D₆, 400 MHz) δ 0.92 (3H, d), 0.94 (3H, d), 1.98 (1H, m), 2.36 (3H, s), 2.40 and 2.45 (3H, 2 s rotamers), 3.50-3.64 (2H, m), 3.97 (1H, m), 4.68 (1H, dt), 7.45 (2H, d), 8.05 (2H, dd), 8.19 (1H, t), 8.33 (1H, dd), 8.54 and 8.80 (1H, 2 br s rotamers), 8.73 and 8.76 (1H, 2 s rotamers), 8.82 and 8.86 (1H, 2 s rotamers); MS (ES+) 491, (ES−) 489.

Step 7: 2-((R)-1-hydroxy-3-methylbutan-2-ylamino)-4-(5-methyl-1H-pyrrolo[2,3-b]pyridin-3-yl)pyrimidine-5-carbonitrile

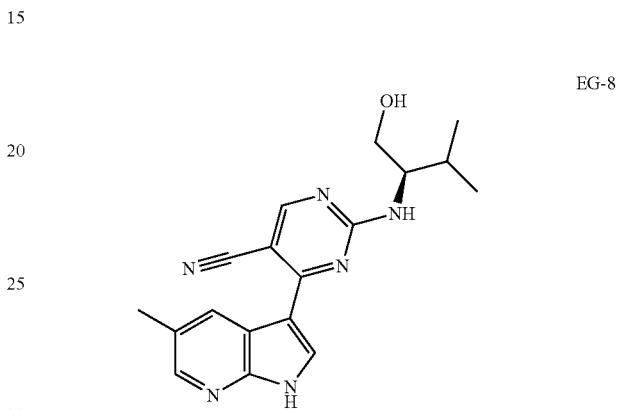

EG-8

2-((R)-1-Hydroxy-3-methylbutan-2-ylamino)-4-(5-methyl-1-tosyl-1H-pyrrolo[2,3-b]pyridin-3-yl)pyrimidine-5-carbonitrile (97 mg, 0.198 mmol) in THF (7 mL) and water (1.5 mL) was treated with lithium hydroxide monohydrate (83 mg, 1.98 mmol). The reaction mixture was stirred at room temperature for 18 hours. The reaction mixture was partitioned between EtOAc and water. The organic layer was separated and the aqueous phase was re-extracted twice with EtOAc and twice with DCM. The combined organic layers were dried over magnesium sulfate and concentrated in vacuo. The residue was purified on silica gel by flash column chromatography then via reverse phase preparative HPLC [Waters Sunfire C18, 10 M, 100 Å column, gradient 10%-95% B (solvent A: 0.05% TFA in water; solvent B: CH3CN) over 16 minutes at 25 mL/min] to afford the title compound as an off-white solid and a TFA salt (12.5 mg, 14% yield).
¹H NMR (DMSO-D₆, 400 MHz) δ 0.94 (6H, m), 2.01 (1H, m), 2.05 (3H, s), 3.59 (2H, m), 4.08 (1H, m), 4.68 (1H, m), 7.89 (1H, m), 8.21 (1H, m), 8.51 (1H, m), 8.61 (2H, m), 8.87 (1H, s), 12.42 (1H, s); MS (ES+) 337, (ES−) 335

Example 12

PLK Assays

The compounds of the present invention are evaluated as inhibitors of human PLK kinase using the following assays.
PLK1 Inhibition Assay I:
Compounds were screened for their ability to inhibit PLK1 using a radioactive-phosphate incorporation assay. Assays were carried out in a mixture of 25 mM HEPES (pH 7.5), 10 mM MgCl₂, and 1 mM DTT. Final substrate concentrations were 350 µM [γ-33P]ATP (136 mCi 33P ATP/mmol ATP, Amersham Pharmacia Biotech/Sigma Chemicals) and 450 µM peptide (KKKISDELMDATFADQEAK) [SEQ. ID:1]. Assays were carried out at 25° C. in the presence of 2 nM PLK1. An assay stock buffer solution was prepared containing all of the reagents listed above, with the exception of ATP and the test compound of interest. 30 μL of the stock solution was placed in a 96 well plate followed by addition of 2 μL of DMSO stock containing serial dilutions of the test compound (typically starting from a final concentration of 10 μM with 2-fold serial dilutions) in duplicate (final DMSO concentration 5%). The plate was pre-incubated for 10 minutes at 25° C. and the reaction initiated by addition of 8 μL [γ-33P]ATP (final concentration 350 μM).

The reaction was stopped after 240 minutes by the addition of 1000 μL, 0.14M phosphoric acid. A multiscreen phosphocellulose filter 96-well plate (Millipore, Cat No. MAPHN0B50) was pretreated with 100 μL 0.1 M phosphoric acid prior to the addition of 125 μL of the stopped assay mixture. The plate was washed with 4×200 μL 0.1 M phosphoric acid. After drying, 100 μL Optiphase 'SuperMix' liquid scintillation cocktail (Perkin Elmer) was added to the well prior to scintillation counting (1450 Microbeta Liquid Scintillation Counter, Wallac).

After removing mean background values for all of the data points, Ki(app) data were calculated from non-linear regression analysis of the initial rate data using the Prism software package (GraphPad Prism version 3.0cx for Macintosh, GraphPad Software, San Diego Calif., USA).

PLK1 Inhibition Assay II:

Compounds were screened for their ability to inhibit PLK1 using a radioactive-phosphate incorporation assay. Assays were carried out in a mixture of 25 mM HEPES (pH 7.5), 10 mM MgCl$_2$, 0.1% BSA, and 2 mM DTT. Final substrate concentrations were 150 μM [γ-33P]ATP (115 mCi 33P ATP/mmol ATP, Amersham Pharmacia Biotech/Sigma Chemicals) and 300 μM peptide (KKKISDELMDATFADQEAK) [SEQ. ID:2]. Assays were carried out at 25° C. in the presence of 4 nM PLK1. An assay stock buffer solution was prepared containing all of the reagents listed above, with the exception of ATP and the test compound of interest. 30 μL of the stock solution was placed in a 96 well plate followed by addition of 2 μL of DMSO stock containing serial dilutions of the test compound (typically starting from a final concentration of 10 μM with 2-fold serial dilutions) in duplicate (final DMSO concentration 5%). The plate was pre-incubated for 10 minutes at 25° C. and the reaction initiated by addition of 8 μL [γ-33P]ATP (final concentration 150 μM).

The reaction was stopped after 90 minutes by the addition of 100 μL 0.14 M phosphoric acid. A multiscreen phosphocellulose filter 96-well plate (Millipore, Cat No. MAPHN0B50) was pretreated with 100 μL 0.1 M phosphoric acid prior to the addition of 125 μL of the stopped assay mixture. The plate was washed with 4×200 μL 0.1 M phosphoric acid. After drying, 100 μL Optiphase 'SuperMix' liquid scintillation cocktail (Perkin Elmer) was added to the well prior to scintillation counting (1450 Microbeta Liquid Scintillation Counter, Wallac).

After removing mean background values for all of the data points, Ki(app) data were calculated from non-linear regression analysis of the initial rate data using the Prism software package (GraphPad Prism version 3.0cx for Macintosh, GraphPad Software, San Diego Calif., USA).

The following table contains results for the compounds in these assays. In the table, PLK1 inhibition $K_i$<3 nM is +++, PLK1 inhibition $K_i$ between 3 nM and 40 nM is ++, and PLK1 $K_i$>40 nM is +; NT means the compound has not been evaluated.

| Compound | Activity |
|---|---|
| IA-0 | ++ |
| IA-1 | + |
| I-1 | + |
| II-1 | + |
| I-2 | + |
| I-3 | ++ |
| I-4 | + |
| I-5 | + |
| I-6 | +++ |
| I-7 | + |
| I-8 | + |
| II-0 | ++ |
| IA-9 | + |
| I-9 | ++ |
| I-10 | ++ |
| I-11 | + |
| I-12 | + |
| I-13 | + |
| I-14 | ++ |
| I-15 | + |
| I-16 | ++ |
| I-17 | + |
| I-18 | ++ |
| I-19 | + |
| I-20 | + |
| I-21 | + |
| I-22 | + |
| I-23 | + |
| I-24 | ++ |
| I-25 | ++ |
| II-2 | + |
| II-3 | + |
| II-4 | + |
| II-5 | + |
| II-6 | + |
| II-7 | + |
| II-8 | + |
| II-9 | + |
| II-10 | + |
| II-11 | + |
| I-26 | +++ |
| I-27 | + |
| II-12 | + |
| II-13 | + |
| I-28 | + |
| I-29 | ++ |
| II-14 | + |
| I-30 | + |
| I-31 | ++ |
| I-32 | + |
| I-33 | + |
| I-34 | + |
| I-35 | ++ |
| I-36 | ++ |
| II-15 | + |
| I-37 | + |
| I-38 | + |
| I-39 | ++ |
| I-40 | + |
| I-41 | + |
| I-42 | + |
| II-16 | + |
| I-43 | + |
| I-44 | + |
| I-45 | ++ |
| I-46 | + |
| I-47 | +++ |
| I-48 | + |
| I-49 | ++ |
| I-50 | + |
| I-51 | +++ |
| I-52 | +++ |
| I-53 | + |
| I-54 | + |
| I-55 | ++ |
| I-56 | ++ |
| I-57 | ++ |
| I-58 | ++ |
| EG4 | + |
| I-59 | ++ |
| I-60 | ++ |

| | |
|---|---|
| I-61 | +++ |
| I-62 | ++ |
| I-63 | ++ |
| I-64 | + |
| I-65 | ++ |
| I-66 | + |
| I-67 | + |
| I-68 | + |
| I-69 | + |
| I-70 | + |
| I-71 | + |
| I-72 | ++ |
| I-73 | ++ |
| I-74 | ++ |
| I-75 | ++ |
| I-76 | + |
| I-77 | ++ |
| I-78 | ++ |
| I-79 | + |
| I-80 | + |
| I-81 | ++ |
| I-82 | ++ |
| I-83 | +++ |
| I-84 | +++ |
| I-85 | + |
| I-86 | + |
| I-87 | + |
| I-88 | + |
| I-89 | + |
| I-90 | ++ |
| I-91 | ++ |
| I-92 | + |
| I-93 | ++ |
| I-94 | ++ |
| I-95 | ++ |
| I-96 | ++ |
| I-97 | ++ |
| I-99 | +++ |
| I-100 | +++ |
| EG5 | + |
| I-101 | +++ |
| I-102 | +++ |
| I-104 | + |
| I-105 | ++ |
| I-106 | ++ |
| I-107 | ++ |
| I-108 | ++ |
| I-109 | ++ |
| I-110 | ++ |
| I-111 | +++ |
| I-98 | ++ |
| I-112 | +++ |
| I-113 | + |
| I-114 | ++ |
| I-115 | ++ |
| I-116 | ++ |
| I-117 | + |
| I-118 | + |
| I-119 | ++ |
| I-120 | ++ |
| I-121 | +++ |
| I-122 | +++ |
| I-123 | ++ |
| I-124 | +++ |
| I-125 | +++ |
| I-126 | +++ |
| I-127 | +++ |
| I-128 | ++ |
| I-130 | +++ |
| I-131 | +++ |
| I-132 | ++ |
| I-133 | +++ |
| I-134 | +++ |
| I-135 | ++ |
| I-136 | +++ |
| I-137 | +++ |
| I-138 | +++ |
| I-139 | +++ |
| I-140 | +++ |
| I-141 | +++ |
| I-142 | +++ |
| I-143 | +++ |
| I-144 | +++ |
| I-145 | +++ |
| I-146 | +++ |
| I-147 | +++ |
| I-148 | ++ |
| I-149 | +++ |
| I-150 | +++ |
| I-151 | +++ |
| I-152 | +++ |
| I-153 | +++ |
| I-154 | ++ |
| I-155 | +++ |
| I-156 | NT |
| I-157 | +++ |
| I-158 | +++ |
| I-159 | +++ |
| I-160 | +++ |
| I-161 | +++ |
| I-162 | +++ |
| I-163 | +++ |
| I-164 | ++ |
| I-165 | ++ |
| I-166 | +++ |
| I-167 | +++ |
| I-168 | +++ |
| I-169 | +++ |
| I-170 | +++ |
| I-171 | ++ |
| I-172 | ++ |
| I-173 | +++ |
| I-174 | +++ |
| I-175 | +++ |
| I-176 | +++ |
| I-177 | +++ |
| I-178 | ++ |
| I-179 | +++ |
| I-180 | +++ |
| I-181 | ++ |
| I-182 | ++ |
| I-183 | +++ |
| I-184 | +++ |
| I-185 | +++ |
| I-186 | +++ |
| I-187 | +++ |
| I-188 | +++ |
| I-189 | +++ |
| I-190 | +++ |
| I-191 | ++ |
| I-192 | +++ |
| I-193 | +++ |
| I-194 | ++ |
| I-195 | ++ |
| I-196 | +++ |
| I-197 | ++ |
| I-198 | ++ |
| I-199 | ++ |
| I-200 | +++ |
| I-201 | +++ |
| I-202 | +++ |
| I-203 | +++ |
| I-204 | ++ |
| I-205 | +++ |
| I-206 | +++ |
| I-207 | +++ |
| I-208 | +++ |
| I-209 | ++ |
| I-210 | +++ |
| I-211 | +++ |
| I-212 | +++ |
| I-213 | +++ |
| IA-12 | ++ |
| IA-13 | ++ |
| I-214 | ++ |
| I-215 | +++ |
| I-216 | +++ |
| I-217 | +++ |

| | |
|---|---|
| I-218 | +++ |
| I-219 | +++ |
| I-220 | +++ |
| I-221 | ++ |
| I-222 | +++ |
| IA-14 | + |
| I-223 | ++ |
| I-224 | +++ |
| I-225 | +++ |
| I-226 | +++ |
| I-227 | +++ |
| I-228 | +++ |
| I-229 | +++ |
| I-230 | +++ |
| I-231 | +++ |
| I-232 | NT |
| I-233 | +++ |
| I-234 | +++ |
| I-235 | + |
| I-236 | +++ |
| I-237 | +++ |
| I-238 | +++ |
| I-239 | +++ |
| I-240 | +++ |
| I-241 | ++ |
| I-242 | +++ |
| I-243 | +++ |
| I-244 | +++ |
| I-245 | + |
| I-246 | +++ |
| I-247 | +++ |
| I-248 | ++ |
| I-249 | +++ |
| I-250 | +++ |
| I-251 | +++ |
| I-252 | ++ |
| I-253 | +++ |
| I-254 | +++ |
| I-255 | +++ |
| I-256 | +++ |
| I-257 | +++ |
| I-258 | +++ |
| I-259 | +++ |
| I-260 | +++ |
| I-261 | +++ |
| I-262 | +++ |
| I-263 | +++ |
| I-264 | +++ |
| I-265 | +++ |
| I-266 | +++ |
| I-267 | +++ |
| I-268 | +++ |
| I-269 | ++ |
| I-270 | +++ |
| I-271 | ++ |
| I-272 | +++ |
| I-273 | +++ |
| I-274 | +++ |
| I-275 | +++ |
| I-276 | +++ |
| I-277 | +++ |
| I-278 | +++ |
| I-279 | ++ |
| I-280 | ++ |
| I-281 | +++ |
| I-282 | +++ |
| I-283 | ++ |
| I-284 | +++ |
| I-285 | +++ |
| I-286 | ++ |
| I-287 | ++ |
| I-288 | ++ |
| I-289 | +++ |
| I-290 | ++ |
| I-291 | +++ |
| I-292 | +++ |
| I-293 | +++ |
| I-294 | ++ |
| I-295 | +++ |
| I-296 | +++ |
| I-297 | +++ |
| I-298 | +++ |
| I-299 | +++ |
| IA-2 | + |
| IA-3 | ++ |
| IA-4 | ++ |
| IA-5 | ++ |
| IA-6 | + |
| IA-7 | + |
| IA-8 | + |
| EG6 | ++ |
| EG7 | ++ |
| EG8 | ++ |
| IA-10 | + |
| IA-11 | ++ |
| I-300 | +++ |
| I-301 | + |
| I-302 | +++ |
| I-303 | +++ |
| I-304 | NT |

PLK2 Inhibition Assay:

Compounds were screened for their ability to inhibit PLK2 using a radioactive-phosphate incorporation assay. Assays were carried out in a mixture of 25 mM HEPES (pH 7.5), 10 mM MgCl$_2$, 0.1% BSA, and 2 mM DTT. Final substrate concentrations were 200 μM [γ-33P]ATP (57 mCi 33P ATP/mmol ATP, Amersham Pharmacia Biotech/Sigma Chemicals) and 300 μM peptide (KKKISDELMDATFADQEAK) [SEQ ID:3]. Assays were carried out at 25° C. in the presence of 25 nM PLK2. An assay stock buffer solution was prepared containing all of the reagents listed above, with the exception of ATP and the test compound of interest. 30 μL of the stock solution was placed in a 96 well plate followed by addition of 2 μL of DMSO stock containing serial dilutions of the test compound (typically starting from a final concentration of 10 μM with 2-fold serial dilutions) in duplicate (final DMSO concentration 5%). The plate was pre-incubated for 10 minutes at 25° C. and the reaction initiated by addition of 8 μL [γ-33P]ATP (final concentration 200 μM).

The reaction was stopped after 90 minutes by the addition of 100 μL 0.14 M phosphoric acid. A multiscreen phosphocellulose filter 96-well plate (Millipore, Cat No. MAPHN0B50) was pretreated with 100 μL 0.2M phosphoric acid prior to the addition of 125 μL of the stopped assay mixture. The plate was washed with 4×200 μL 0.2 M phosphoric acid. After drying, 100 μL Optiphase 'SuperMix' liquid scintillation cocktail (Perkin Elmer) was added to the well prior to scintillation counting (1450 Microbeta Liquid Scintillation Counter, Wallac).

After removing mean background values for all of the data points, Ki(app) data were calculated from non-linear regression analysis of the initial rate data using the Prism software package (GraphPad Prism version 3.0cx for Macintosh, GraphPad Software, San Diego Calif., USA).

PLK3 Inhibition Assay:

Compounds were screened for their ability to inhibit PLK3 using a radioactive-phosphate incorporation assay. Assays were carried out in a mixture of 25 mM HEPES (pH 7.5), 10 mM MgCl$_2$, and 1 mM DTT. Final substrate concentrations were 75 μM [γ-33P]ATP (60 mCi 33P ATP/mmol ATP, Amersham Pharmacia Biotech/Sigma Chemicals) and 10 μM peptide (SAM68 protein Δ332-443). Assays were carried out at 25° C. in the presence of 5 nM PLK3 (S38-A340). An assay stock buffer solution was prepared containing all of the reagents listed above, with the exception of ATP and the test compound of interest. 30 μL of the stock solution was placed in a 96 well plate followed by addition of 2 μL of DMSO stock containing serial dilutions of the test compound (typically starting from a final concentration of 10 μM with 2-fold serial dilutions) in duplicate (final DMSO concentration 5%). The plate was pre-incubated for 10 minutes at 25° C. and the reaction initiated by addition of 8 μL [γ-33P]ATP (final concentration 75 μM).

The reaction was stopped after 60 minutes by the addition of 100 μL 0.14M phosphoric acid. A multiscreen phosphocellulose filter 96-well plate (Millipore, Cat No. MAPHN0B50) was pretreated with 100 μL 0.2M phosphoric acid prior to the addition of 125 μL of the stopped assay mixture. The plate was washed with 4×200 μL 0.2 M phosphoric acid. After drying, 100 μL Optiphase 'SuperMix' liquid scintillation cocktail (Perkin Elmer) was added to the well prior to scintillation counting (1450 Microbeta Liquid Scintillation Counter, Wallac).

After removing mean background values for all of the data points, Ki(app) data were calculated from non-linear regression analysis of the initial rate data using the Prism software package (GraphPad Prism version 3.0cx for Macintosh, GraphPad Software, San Diego Calif., USA).

PLK4 Inhibition Assay:

Compounds are screened for their ability to inhibit PLK4 using a radioactive-phosphate incorporation assay. Assays are carried out in a mixture of 8 mM MOPS (pH 7.5), 10 mM $MgCl_2$, 0.1% BSA and 2 mM DTT. Final substrate concentrations are 15 μM [γ-33P]ATP (227 mCi 33P ATP/mmol ATP, Amersham Pharmacia Biotech/Sigma Chemicals) and 300 μM peptide (KKKMDATFADQ) [SEQ ID:4]. Assays are carried out at 25° C. in the presence of 25 nM PLK4. An assay stock buffer solution is prepared containing all of the reagents listed above, with the exception of ATP and the test compound of interest. 30 μL of the stock solution is placed in a 96 well plate followed by addition of 2 μL of DMSO stock containing serial dilutions of the test compound (typically starting from a final concentration of 10 μM with 2-fold serial dilutions) in duplicate (final DMSO concentration 5%). The plate is pre-incubated for 10 minutes at 25° C. and the reaction initiated by addition of 8 μL [γ-33P]ATP (final concentration 15 μM).

The reaction is stopped after 180 minutes by the addition of 100 μL 0.14M phosphoric acid. A multiscreen phosphocellulose filter 96-well plate (Millipore, Cat No. MAPHN0B50) is pretreated with 100 μL 0.2 M phosphoric acid prior to the addition of 125 μL of the stopped assay mixture. The plate is washed with 4×200 μL 0.2 M phosphoric acid. After drying, 100 μL Optiphase 'SuperMix' liquid scintillation cocktail (Perkin Elmer) is added to the well prior to scintillation counting (1450 Microbeta Liquid Scintillation Counter, Wallac).

After removing mean background values for all of the data points, Ki(app) data are calculated from non-linear regression analysis of the initial rate data using the Prism software package (GraphPad Prism version 3.0cx for Macintosh, GraphPad Software, San Diego Calif., USA).

Compounds of formula Id show selectivity for PLK1 over PLK2 and PLK3 as illustrated in the following table.

| Compound No. | $\frac{Ki_{(PLK2)}}{Ki_{(PLK1)}}$ | $\frac{Ki_{(PLK3)}}{Ki_{(PLK1)}}$ |
|---|---|---|
| I-102 | 113 | 28 |
| I-124 | 323 | 185 |
| I-126 | 211 | 126 |
| I-127 | 210 | 140 |
| I-131 | 180 | 163 |
| I-139 | 1000 | 456 |
| I-142 | <30 | <23 |

-continued

| Compound No. | $\frac{Ki_{(PLK2)}}{Ki_{(PLK1)}}$ | $\frac{Ki_{(PLK3)}}{Ki_{(PLK1)}}$ |
|---|---|---|
| I-147 | 523 | 186 |
| I-148 | 63 | 70 |
| I-149 | <130 | <100 |
| I-167 | 914 | 586 |
| I-267 | 1152 | |
| I-268 | 293 | 141 |
| I-272 | 67 | 14 |
| I-273 | 1813 | 581 |
| I-274 | 4074 | |
| I-275 | 313 | 919 |
| I-276 | 2952 | |
| I-277 | | 39 |
| I-278 | 208 | 142 |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of inhibiting PLK protein kinase activity in a biological sample, comprising contacting the biological sample with a compound represented by Structural Formula (I):

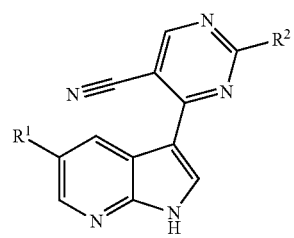

or a pharmaceutically acceptable salt thereof; wherein:
$R^1$ is —H, halogen, $C_{1-6}$ aliphatic optionally substituted with 1-3 $R^3$, —O($C_{1-6}$ aliphatic) optionally substituted with 1-3 $R^3$, or —N(H)R;
Each R is independently H, $C_{1-6}$ aliphatic, aryl, heteroaryl, $C_{3-8}$ cycloalkyl, or 4-12 membered heterocyclic ring optionally containing 1-3 groups selected from —N($R_{17}$)—, —O—, or —S—; wherein each of the aliphatic, aryl, heteroaryl, cycloalkyl, and heterocyclic ring are optionally substituted with 1-3 of Q;
Each Q is independently selected from halogen, hydroxy, $C_{1-6}$ alkyl, benzyl, oxo, —$CF_3$, W, —CN, —$NH_2$, —N(H)—W, —N(W)$_2$, —N(H)—$SO_2$—W, —S(O)$_2$—N(H)—W, —S(O)$_2$—N(W)$_2$, —C(O)—W, —C(O)—N(W)$_2$, —N(H)—C(O)—W, —O—C(O)—W, —C(O)—O—W, —$SO_2$—W, SW or —OW;
Two Q can be linked together to form a 4- to 8-membered carbocyclic or heterocyclic ring optionally substituted with $C_{1-3}$ alkyl or $CF_3$;
Each W is independently selected from —H, $C_{1-6}$ alkyl, aralkyl, cycloalkyl or heterocyclic ring; each $C_{1-6}$ alkyl, aralkyl, cycloalkyl or heterocyclic ring is optionally substituted with 1-3 of halogen, —$OR^6$, —CN, $C_{1-6}$ alkyl or $NR^{18}R^{19}$; or One W, together with the nitrogen atom to which it is attached and a carbon atom of R, form a 4- to 8-membered ring; or Two W, together with the same or different nitrogen atom or carbon atom to which they are attached, form a 4- to 8-membered heterocyclic ring;

Each $R^{18}$ and $R^{19}$ is independently hydrogen or $C_{1-3}$ alkyl; or $R^{18}$ and $R^{19}$, together with the nitrogen atom to which they are attached, form a 4- to 8-memebered heterocyclic ring, optionally substituted with $C_{1-3}$ alkyl or $CF_3$;

Two W can be linked together to form a 4- to 8-membered cycloalkyl or heterocycloalkyl optionally substituted with $C_{1-3}$ alkyl or $CF_3$;

$R^2$ is —$NR^4R^5$, —$OR^6$, —$SR^6$, or —$NR^{10\,R11}$;

Each $R^3$ is independently halogen, $C_{1-6}$ alkyl, aryl, or heteroaryl;

Each $R^4$ is independently —H or $C_{1-6}$ aliphatic optionally substituted with 1-3 $R^7$;

Each $R^5$ is independently $C_{1-6}$ aliphatic optionally substituted with 1-4 $R^7$ or a 4- to 8-membered monocyclic or 6- to 10-membered bicyclic ring optionally substituted with 1-4 $R^7$, or $R^4$ and $R^5$ can be joined together to form a monocyclic or bicyclic ring optionally substituted with 1-3 $R^9$;

Each $R^6$ is independently H, $C_{1-6}$ alkyl, -L-aryl, or -L-heteroaryl, wherein each of the $C_{1-6}$ alkyl, -L-aryl, or -L-heteroaryl is optionally and independently substituted with 1-3 $R^8$;

L is $C_{0-3}$ alkyl;

Each $R^7$ is independently oxo, alkyl, halogen, —CN, —$OR^9$, —$SR^9$, —$N(R^9)_2$, $C_{3-8}$ cycloalkyl, aryl, heteroaryl or a 4- to 8-membered heterocyclic ring containing 1-3 groups selected from —$N(R^{17})$—, —O—, or —S—, wherein each alkyl, cycloalkyl, 4-8 membered heterocyclic monocyclic or bicyclic ring, aryl, and heteroaryl is optionally and independently substituted with 1-3 $R^8$, or Two $R^7$ on the same atom or adjacent atoms is joined to form a carbocyclic ring or a 4- to 8-membered heterocyclic ring containing 1-3 groups selected from —$N(R^{17})$—, —O—, or —S—, wherein each of the carbocyclic ring and the 4- to 8-membered heterocyclic ring is optionally and independently substituted with 1-3 $R^8$;

Each $R^8$ is independently —R, -Q, —$R^9$, —$OR^9$, —$N(R^9)_2$, halogen, or —CN;

Each $R^9$ is independently —H, —$N(R^{16})_2$, $C_{3-6}$ carbocyclic ring, $C_{3-6}$ heterocyclic ring, or $C_{1-3}$ aliphatic, wherein $C_{3-6}$ carbocyclic ring, $C_{3-6}$ heterocyclic ring and $C_{1-3}$ aliphatic are each optionally substituted with 1-3 Q; or Two $R^9$ groups together with the N atom to which they are bound form a 4-8 membered ring additionally containing 1 or 2 groups each independently selected from —$N(R^{17})$—, —O—, or —S—, wherein the 4- to 8-membered ring is optionally and independently substituted with 1-3 of W;

Each $R^{16}$ is independently hydrogen or $C_{1-6}$ alkyl, or

Two $R^{16}$ groups together with the N atom to which they are bound form a 4- to 8-membered ring containing 1 or 2 groups selected from $NR^{17}$, O, or S;

Each $R^{17}$ is independently, hydrogen, $Q_1$ or $C_{1-4}$ aliphatic or cycloaliphatic, wherein each $C_{1-4}$ aliphatic or cycloaliphatic is optionally substituted with 1-3 of Q;

$Q_1$ is $C_{1-6}$ alkyl, benzyl, —$SO_2$—W, —$S(O)_2$—N(H)—W, —$S(O)_2$—$N(W)_2$, —C(O)—W, —C(O)—$N(W)_2$—C(O)—N(H)—W, —N(H)—C(O)—W, —O—C(O)—W, —C(O)—O—W, or —$SO_2$—W;

$R^{10}$ is —H or $C_{1-6}$ aliphatic optionally substituted with 1-3 of $R^7$;

$R^{11}$ is —$C(R^{12}R^{13})C(=O)NR^{14}R^{15}$;

Each of $R^{12}$ and $R^{13}$ is independently H or $C_{1-6}$ aliphatic optionally substituted with 1-3 $R^7$; or $R^{12}$ and $R^{13}$ can be joined together to form a ring optionally substituted with 1-3 of $R^9$; or $R^{10}$ and $R^{12}$ can be joined together to form a ring optionally substituted with 1-3 of $R^9$; and Each $R^{14}$ and $R^{15}$ is independently H, $C_{1-6}$ alkyl, carbocyclic, or heterocyclic optionally substituted with 1-3 of $R^7$; or $R^{14}$ and $R^{15}$ can be joined together to form a ring optionally substituted with 1-3 of $R^9$.

2. A method of treating, melanoma, multiple myeloma, leukemia, colon cancer, breast cancer, gastric cancer, ovarian cancer, cervical cancer, lung cancer, renal cancer, prostate cancer, bladder cancer, pancreatic cancer, or malignant mesothelioma in a patient wherein said method comprises administering to said patient a compound represented by Structural Formula (I):

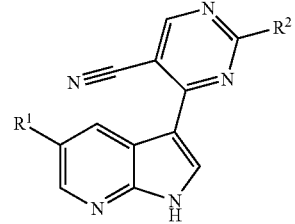

or a pharmaceutically acceptable salt thereof; wherein:

$R^1$ is —H, halogen, $C_{1-6}$ aliphatic optionally substituted with 1-3 $R^3$, —$O(C_{1-6}$ aliphatic) optionally substituted with 1-3 $R^3$, or —N(H)R;

Each R is independently H, $C_{1-6}$ aliphatic, aryl, heteroaryl, $C_{3-8}$ cycloalkyl, or 4-12 membered heterocyclic ring optionally containing 1-3 groups selected from —$N(R_{17})$—, —O—, or —S—;

wherein each of the aliphatic, aryl, heteroaryl, cycloalkyl, and heterocyclic ring are optionally substituted with 1-3 of Q;

Each Q is independently selected from halogen, hydroxy, $C_{1-6}$ alkyl, benzyl, oxo, —$CF_3$, W, —CN, —$NH_2$, —N(H)—W, —$N(W)_2$, —N(H)—$SO_2$—W, —$S(O)_2$—N(H)—W, —$S(O)_2$—$N(W)_2$, —C(O)—W, —C(O)—$N(W)_2$, —N(H)—C(O)—W, —O—C(O)—W, —C(O)—O—W, —$SO_2$—W, SW or —OW;

Two Q can be linked together to form a 4- to 8-membered carbocyclic or heterocyclic ring optionally substituted with $C_{1-3}$ alkyl or $CF_3$;

Each W is independently selected from —H, $C_{1-6}$ alkyl, aralkyl, cycloalkyl or heterocyclic ring; each $C_{1-6}$ alkyl, aralkyl, cycloalkyl or heterocyclic ring is optionally substituted with 1-3 of halogen, —$OR^6$, —CN, $C_{1-6}$ alkyl or $NR^{18}R^{19}$; or One W, together with the nitrogen atom to which it is attached and a carbon atom of R, form a 4- to 8-membered ring; or Two W, together with the same or different nitrogen atom or carbon atom to which they are attached, form a 4- to 8-membered heterocyclic ring;

Each $R^{18}$ and $R^{19}$ is independently hydrogen or $C_{1-3}$ alkyl; or $R^{18}$ and $R^{19}$, together with the nitrogen atom to which they are attached, form a 4- to 8-membered heterocyclic ring, optionally substituted with $C_{1-3}$ alkyl or $CF_3$;

Two W can be linked together to form a 4- to 8-membered cycloalkyl or heterocycloalkyl optionally substituted with $C_{1-3}$ alkyl or $CF_3$;

$R^2$ is —$NR^4R^5$, —$OR^6$, —$SR^6$, or —$NR^{10}R^{11}$;

Each $R^3$ is independently halogen, $C_{1-6}$ alkyl, aryl, or heteroaryl;

Each $R^4$ is independently —H or $C_{1-6}$ aliphatic optionally substituted with 1-3 $R^7$;

Each $R^5$ is independently $C_{1-6}$ aliphatic optionally substituted with 1-4 $R^7$ or a 4- to 8-membered monocyclic or 6- to 10-membered bicyclic ring optionally substituted with 1-4 $R^7$, or $R^4$ and $R^5$ can be joined together to form a monocyclic or bicyclic ring optionally substituted with 1-3 $R^9$;

Each $R^6$ is independently H, $C_{1-6}$ alkyl, -L-aryl, or -L-heteroaryl, wherein each of the $C_{1-6}$ alkyl, -L-aryl, or -L-heteroaryl is optionally and independently substituted with 1-3 $R^8$;

L is $C_{0-3}$ alkyl;

Each $R^7$ is independently oxo, alkyl, halogen, —CN, —$OR^9$, —$SR^9$, —$N(R^9)_2$, $C_{3-8}$ cycloalkyl, aryl, heteroaryl or a 4- to 8-membered heterocyclic ring containing 1-3 groups selected from —$N(R^{17})$—, —O—, or —S—, wherein each alkyl, cycloalkyl, 4-8 membered heterocyclic monocyclic or bicyclic ring, aryl, and heteroaryl is optionally and independently substituted with 1-3 $R^8$, or Two $R^7$ on the same atom or adjacent atoms is joined to form a carbocyclic ring or a 4- to 8-membered heterocyclic ring containing 1-3 groups selected from —$N(R^{17})$—, —O—, or —S—, wherein each of the carbocyclic ring and the 4- to 8-membered heterocyclic ring is optionally and independently substituted with 1-3 $R^8$;

Each $R^8$ is independently —R, -Q, —$R^9$, —$OR^9$, —$N(R^9)_2$, halogen, or —CN;

Each $R^9$ is independently —H, —$N(R^{16})_2$, $C_{3-6}$ carbocyclic ring, $C_{3-6}$ heterocyclic ring, or $C_{1-3}$ aliphatic, wherein $C_{3-6}$ carbocyclic ring, $C_{3-6}$ heterocyclic ring and $C_{1-3}$ aliphatic are each optionally substituted with 1-3 Q; or Two $R^9$ groups together with the N atom to which they are bound form a 4-8 membered ring additionally containing 1 or 2 groups each independently selected from —$N(R^{17})$—, —O—, or —S—, wherein the 4- to 8-membered ring is optionally and independently substituted with 1-3 of W;

Each $R^{16}$ is independently hydrogen or $C_{1-6}$ alkyl, or

Two $R^{16}$ groups together with the N atom to which they are bound form a 4- to 8-membered ring containing 1 or 2 groups selected from $NR^{17}$, O, or S;

Each $R^{17}$ is independently, hydrogen, $Q_1$ or $C_{1-4}$ aliphatic or cycloaliphatic, wherein each $C_{1-4}$ aliphatic or cycloaliphatic is optionally substituted with 1-3 of Q;

$Q_1$ is $C_{1-6}$ alkyl, benzyl, —$SO_2$—W, —$S(O)_2$—N(H)—W, —$S(O)_2$—$N(W)_2$, —C(O)—W, —C(O)—$N(W)_2$, —C(O)—N(H)—W, —N(H)—C(O)—W, —O—C(O)—W, —C(O)—O—W, or —$SO_2$—W;

$R^{10}$ is —H or $C_{1-6}$ aliphatic optionally substituted with 1-3 of $R^7$;

$R^{11}$ is —$C(R^{12}R^{13})C(=O)NR^{14}R^{15}$;

Each of $R^{12}$ and $R^{13}$ is independently H or $C_{1-6}$ aliphatic optionally substituted with 1-3 $R^7$; or $R^{12}$ and $R^{13}$ can be joined together to form a ring optionally substituted with 1-3 of $R^9$; or $R^{10}$ and $R^{12}$ can be joined together to form a ring optionally substituted with 1-3 of $R^9$; and Each $R^{14}$ and $R^{15}$ is independently H, $C_{1-6}$ alkyl, carbocyclic, or heterocyclic optionally substituted with 1-3 of $R^7$; or $R^{14}$ and $R^{15}$ can be joined together to form a ring optionally substituted with 1-3 of $R^9$.

3. The method of claim 2, wherein $R^1$ is halogen.

4. The method of claim 2, wherein $R^1$ is methyl optionally substituted with 1-3 $R^3$ and each $R^3$ is independently halo.

5. The c method of claim 4, wherein $R^1$ is —$CF_3$.

6. The method of claim 4, wherein $R^1$ is —NHR and R is H, $C_{1-6}$ aliphatic, aryl, or $C_{3-8}$ cycloalkyl.

7. The method of claim 6, wherein R is H, $C_{1-6}$ alkyl, or aryl.

8. The method of claim 6, wherein $R^2$ is —$NR^4R^5$, wherein $R^4$ is H or $C_{1-6}$ aliphatic optionally substituted with 1-3 $R^7$, and $R^5$ is $C_{1-6}$ aliphatic optionally substituted with 1-4 $R^7$ or a 3- to 6-membered monocyclic or 6- to 10-membered bicyclic ring optionally substituted with 1-4 $R^7$.

9. The method of claim 8, wherein $R^4$ is H, and $R^5$ is $C_{1-4}$ alkyl and optionally substituted with 1-4 $R^7$.

10. The method of claim 9, wherein $R^5$ is ethyl substituted at the carbon atom attached to the nitrogen atom with $R^7$.

11. The method of claim 10, wherein $R^7$ is phenyl, pyridyl, or pyrimidyl, and is optionally substituted with 1-3 of $R^8$.

12. The method of claim 8, wherein $R^7$ is phenyl substituted at the para-position with —R or —$N(R^9)_2$;

R is 4- to 8-membered heterocyclic ring optionally containing 1-3 groups each independently selected from —$N(R^{17})$—, —O—, or —S—, and the heterocyclic ring is optionally substituted with 1-3 of Q;

Each Q is independently selected from halogen, hydroxy, $C_{1-6}$ alkyl, benzyl, —$CF_3$, W, —C(O)—W, —C(O)—N(W)$_2$, —C(O)—O—W;

Each W is independently selected from —H, $C_{1-6}$ alkyl, or cycloalkyl;

Each $R^9$ is independently —H, $C_{3-6}$ heterocyclic ring, or $C_{1-3}$ aliphatic, wherein $C_{3-6}$ heterocyclic ring and $C_{1-3}$ aliphatic are each optionally substituted with 1-3 Q; or Two $R^9$ groups together with the N atom to which they are bound form a 4- to 8-membered ring containing additional 1 or 2 groups each independently selected from —$bN(R^{17})$—, —O—, or —S—, wherein the 4- to 8-membered ring is optionally and independently substituted with 1-3 of W.

13. The method of claim 8, wherein $R^7$ is

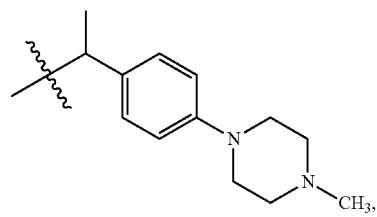

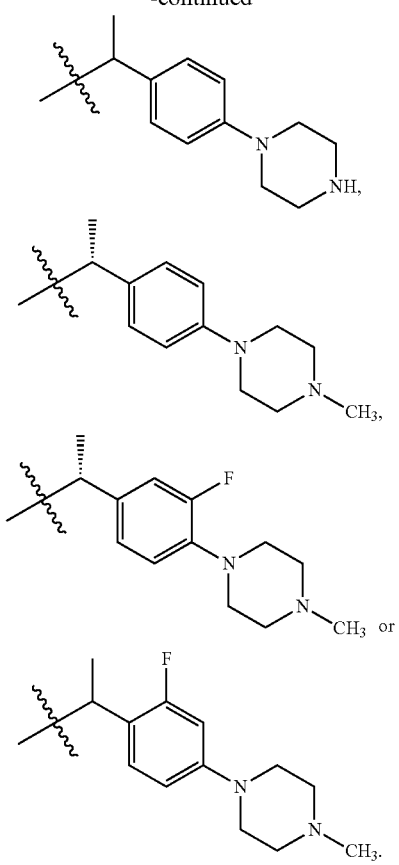

14. The method of claim 8, wherein R⁷ is pyrimidinyl optionally substituted with 1-3 of R⁸,5-pyrimidyl optionally substituted at the 2-position with R⁸, or pyridinyl optionally substituted with 1-3 of R⁸.

15. The method of claim 14, wherein R⁷ is

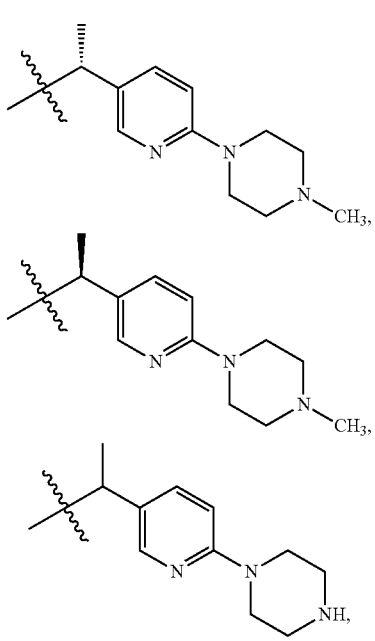

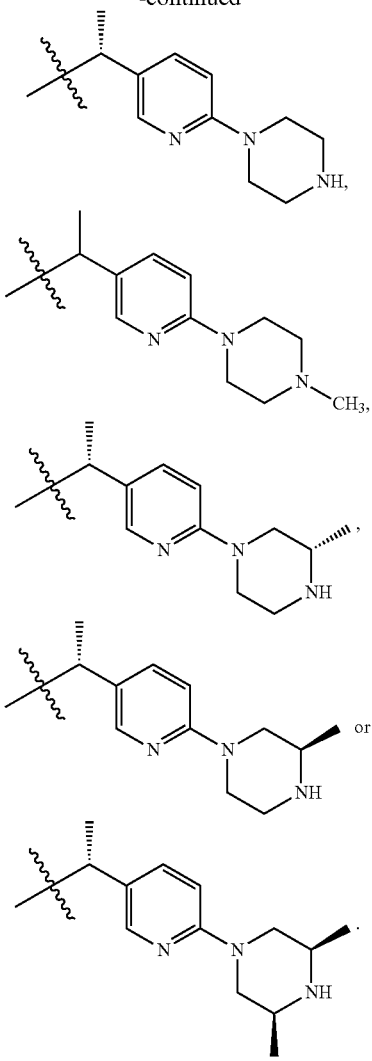

16. The method of claim 11, wherein one R⁸ is aryl, heteroaryl, $C_3$-$C_8$ cycloalkyl, or 4- to 8-membered heterocyclic ring each optionally substituted with 1-3 of Q.

17. The method of claim 11, wherein one R⁸ is Q, and wherein Q is —NHW, —NW₂, —NH—SO₂W, —NH—COW, —CO—NHW, —CO—NW₂, —SO₂NHW, —SO₂—NW₂, —SW, —OW, or —W.

18. The method of claim 17, wherein W is $C_{1-6}$ alkyl, aralkyl, cycloalkyl or heterocyclic ring; each $C_{1-6}$ alkyl, aralkyl, cycloalkyl or heterocyclic ring is optionally substituted with 1-3 of halogen, —OR⁶, —CN, $C_{1-6}$ alkyl, $C_{1-6}$ alkyl or —NR¹⁸R¹⁹.

19. The method of claim 18, wherein W is $C_{1-6}$ alkyl or heterocyclic ring; each $C_{1-6}$ alkyl, aralkyl, cycloalkyl or heterocyclic ring is optionally substituted with 1-3 of halogen, —OR⁶, —CN, $C_{1-6}$ alkyl, $C_{1-6}$ alkyl or —NR¹⁸R¹⁹.

20. The method of claim 11, wherein one R⁸ is —R⁹, —OR⁹ or —N(R⁹)₂.

21. The method of claim 20, wherein R⁹ is independently H, $C_{3-6}$ carbocyclic ring, $C_{3-6}$ heterocyclic ring, or $C_{1-3}$ aliphatic, wherein $C_{3-6}$ carbocyclic ring, $C_{3-6}$ heterocyclic ring and $C_{1-3}$ aliphatic are each optionally substituted with 1-3 Q; or Two R⁹ groups, together with the N atom to which they are bound, form a 4- to 8-membered ring optionally containing additional 1 or 2 groups selected from —N(R¹⁷)—, —O—, or —S—, wherein the 4- to 8-membered ring is optionally and independently substituted with 1-3 of W.

22. The method of claim 8, wherein $R^7$ is a 4- to 10-membered heterocyclic monocyclic or bicyclic ring optionally substituted with 1-3 of $R^8$.

23. The method of claim 22, wherein $R^7$ is a 4- to 6-membered heterocyclic monocyclic ring optionally substituted with 1-3 of $R^8$.

24. The method of claim 23, wherein $R^8$ is Q selected from —C(O)—W, —C(O)—N(W)₂—C(O)—O—W or —SO₂—W.

25. The method of claim 22, wherein $R^7$ is a $C_3$-$C_8$ carbocycle optionally substituted with 1-3 $R^8$.

26. The method of claim 25, wherein one $R^8$ is Q selected from hydroxy, —NH₂, —N(H)—W, —N(W)₂, —N(H)—SO₂—W, —C(O)—N(W)₂, —N(H)—C(O)—W, or —O—C(O)—W.

27. The method of claim 6, wherein $R^2$ is —NR¹⁰R¹¹.

28. The method of claim 27, wherein $R^{10}$ is —H and $R^{11}$ is —C(R¹²R¹³)C(═O)NR¹⁴R¹⁵, wherein $R^{12}$ is H; $R^{13}$ is $C_{1-3}$ alkyl; $R^{14}$ is H; and $R^{15}$ is alkyl substituted with trifluoromethyl or hydroxy, or $R^{15}$ is cycloalkyl substituted with hydroxy.

29. The method of claim 6, wherein $R^2$ is –OR⁶ or —SR⁶; and $R^6$ is optionally substituted phenyl.

30. The method of claim 1, wherein the compounds of structural formula (I) is any one of compounds I-1 through I-304 or a pharmaceutically acceptable salt thereof:

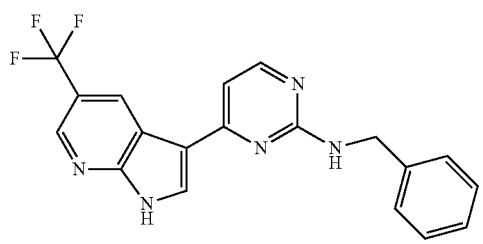

I-1

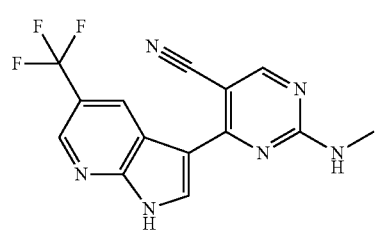

I-2

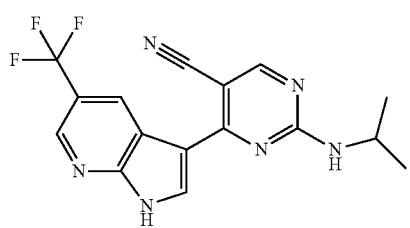

I-3

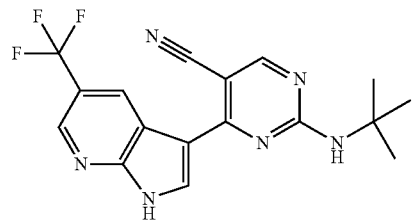

I-4

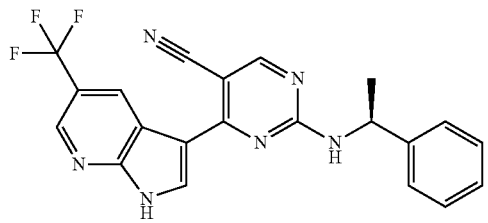

I-5

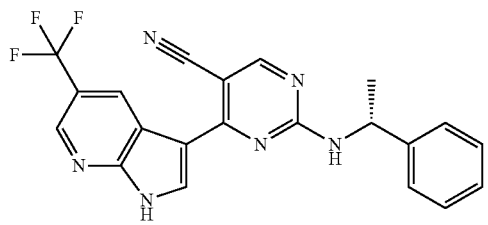

I-6

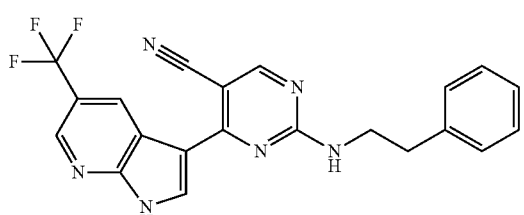

I-7

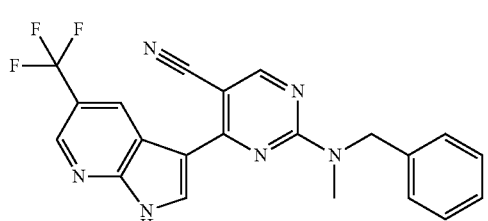

I-8

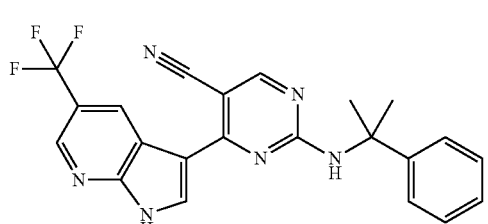

I-9

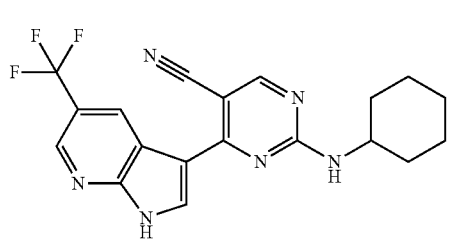

I-10

I-11
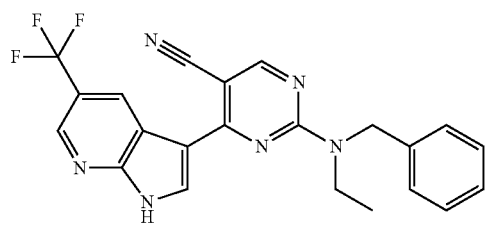
I-12
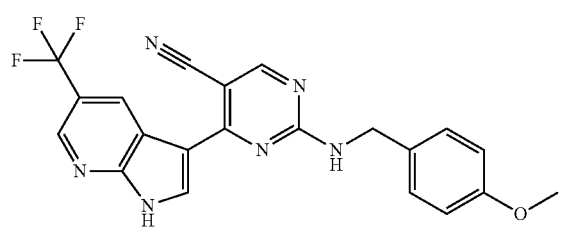
I-13
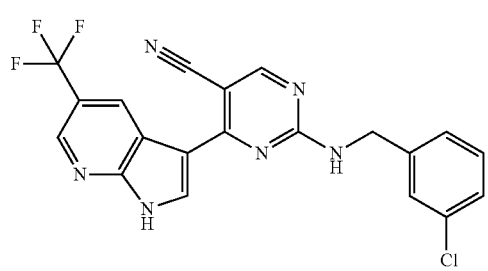
I-14
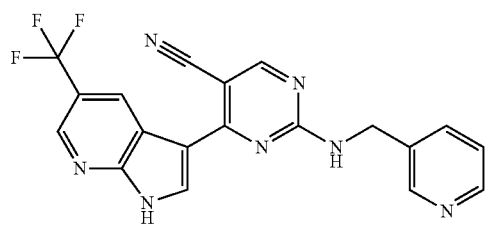
I-15
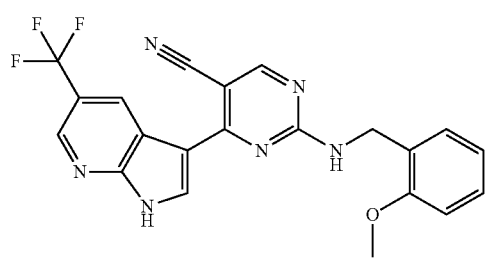
I-16
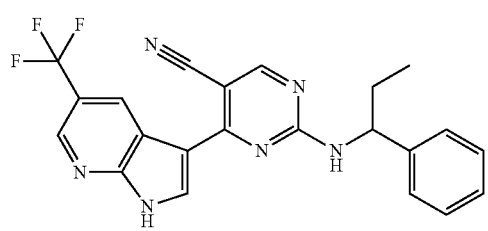
I-17
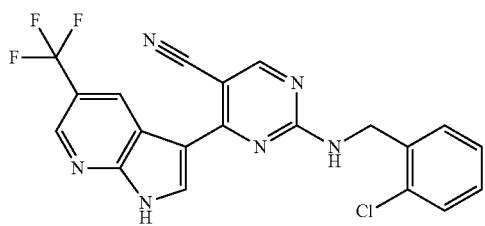
I-18
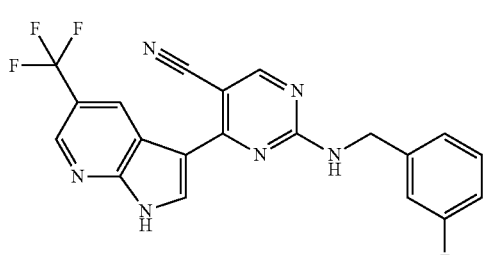
I-19
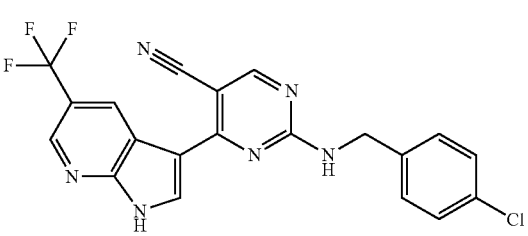
I-20
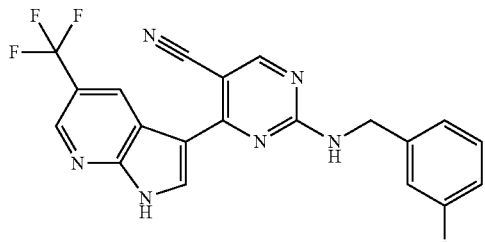
I-21
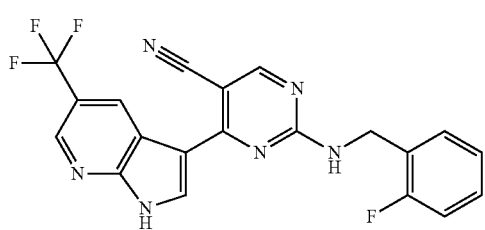
I-22
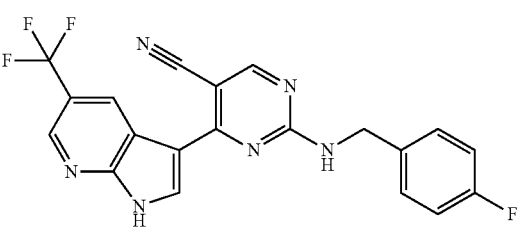

I-23 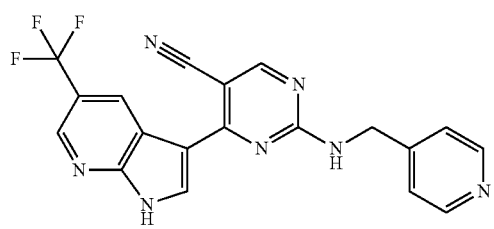
I-24 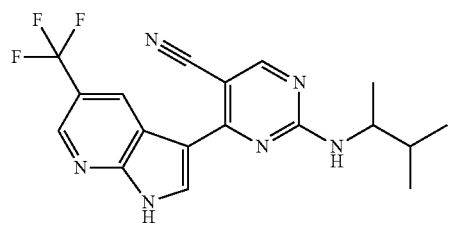
I-25 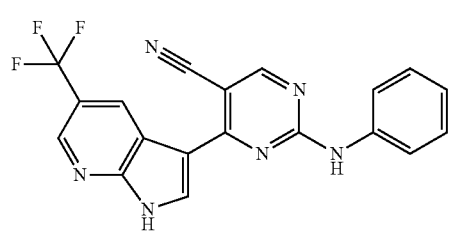
I-26 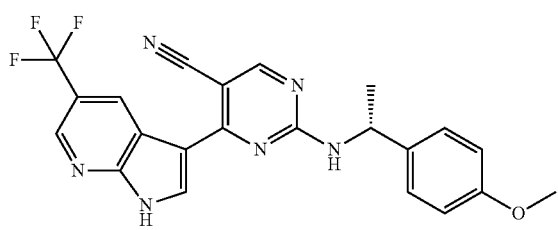
I-27 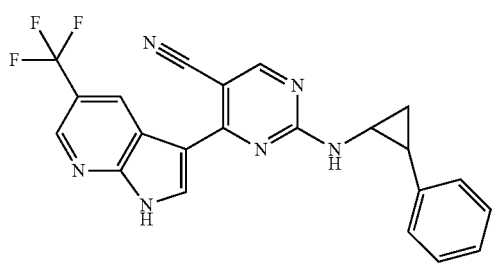
I-28 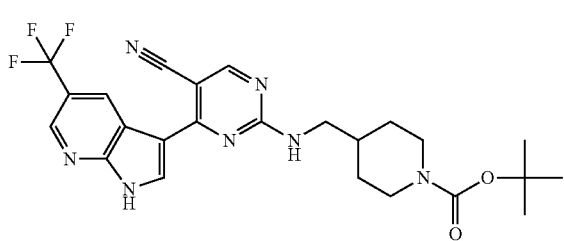
I-29 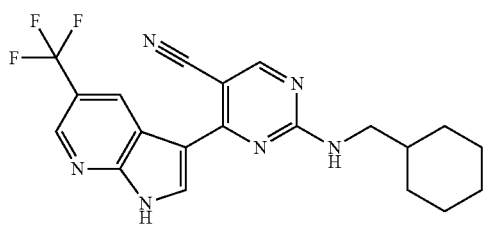
I-30 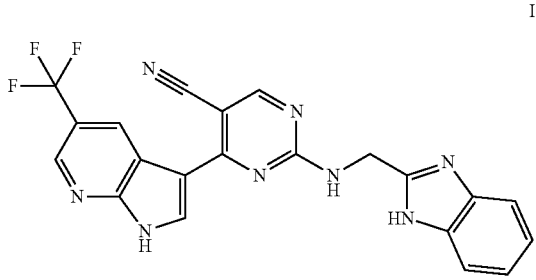
I-31 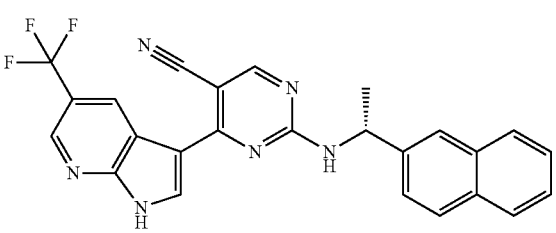
I-32 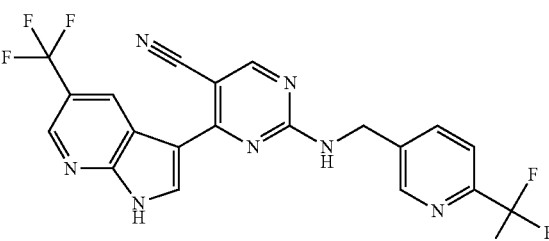
I-33 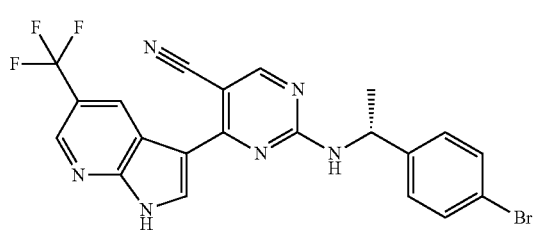
I-34 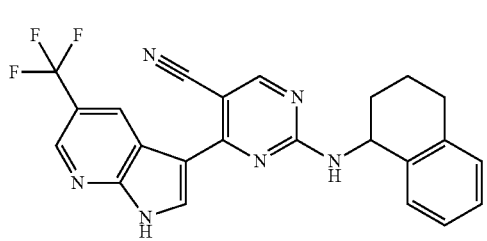

-continued
I-35
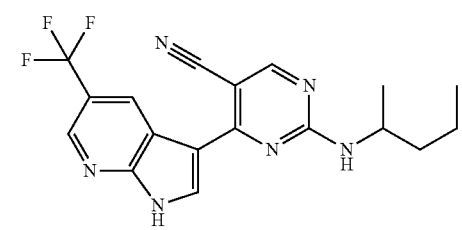
I-36
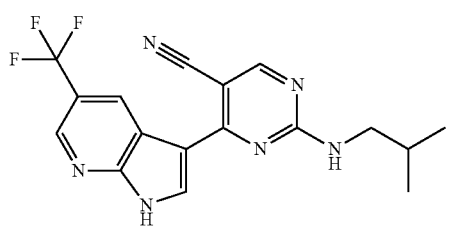
I-37
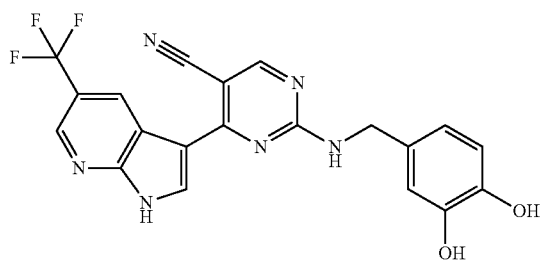
I-38
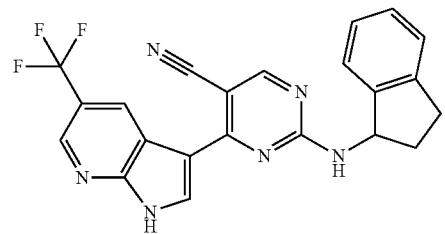
I-39
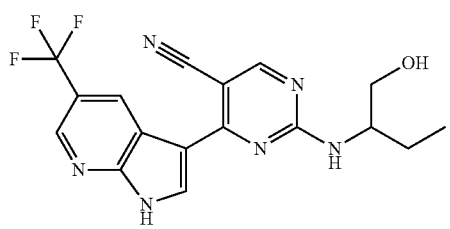
I-40
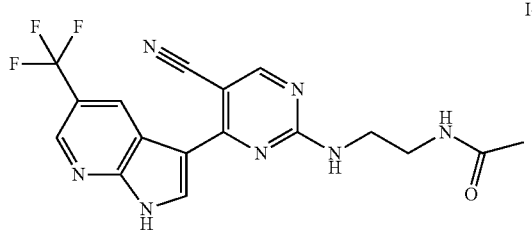
-continued
I-41
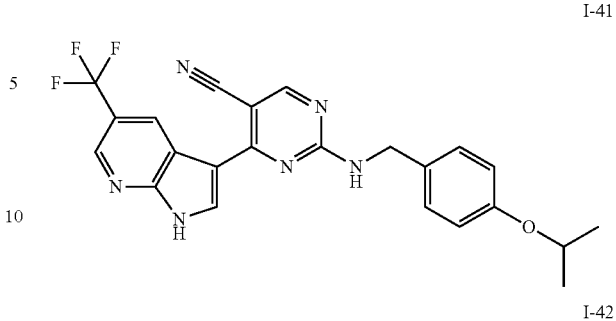
I-42
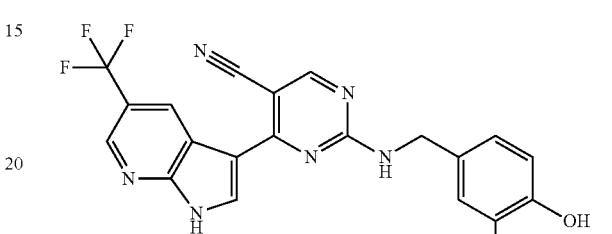
I-43
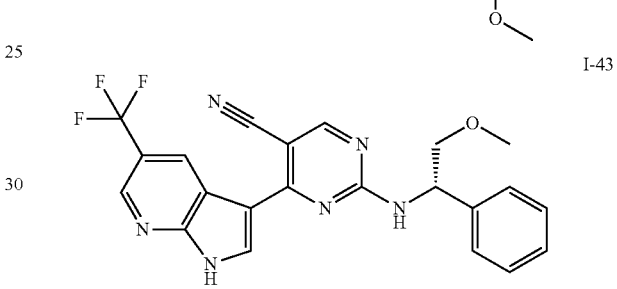
I-44
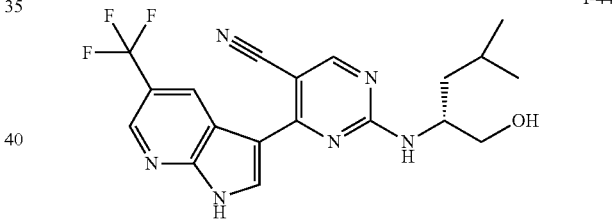
I-45
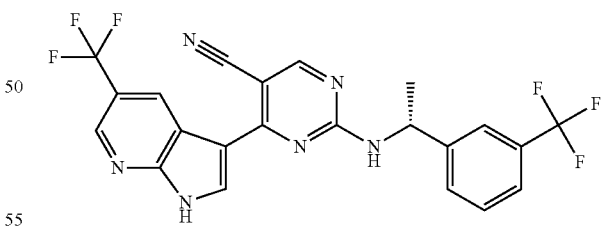
I-46
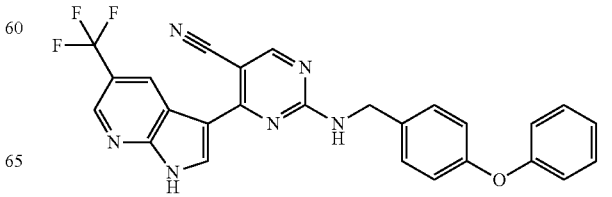

I-47
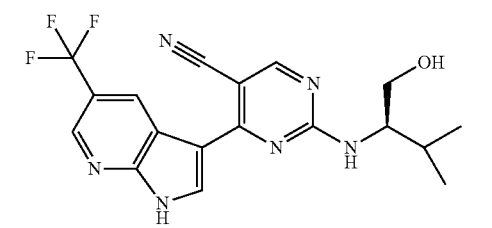
I-48
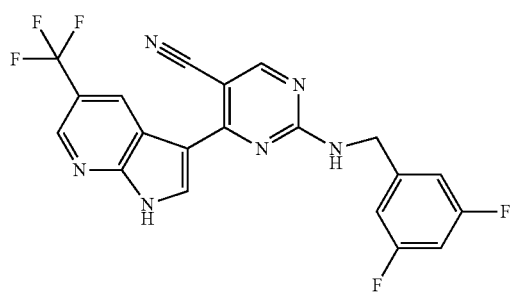
I-49
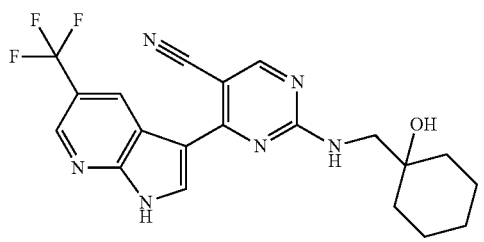
I-50
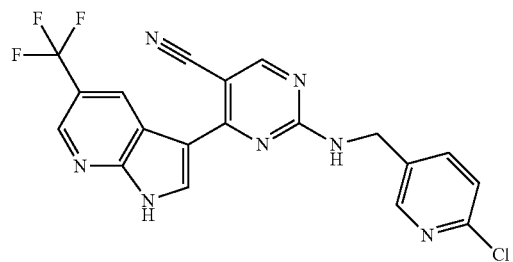
I-51
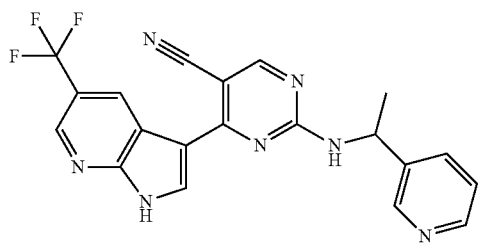
I-52
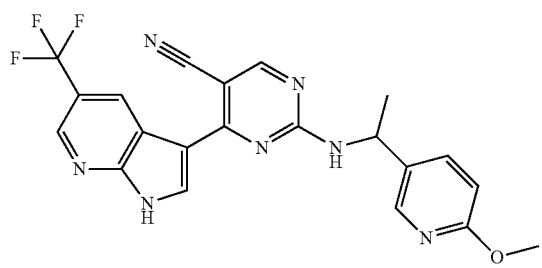
I-53
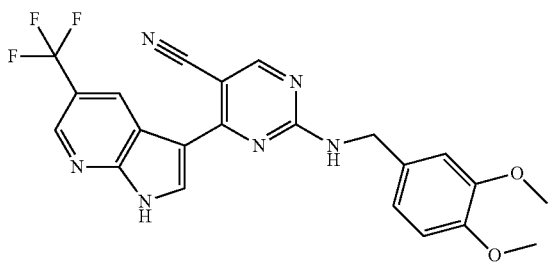
I-54
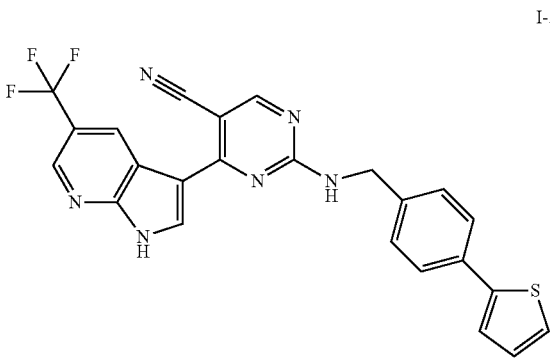
I-56
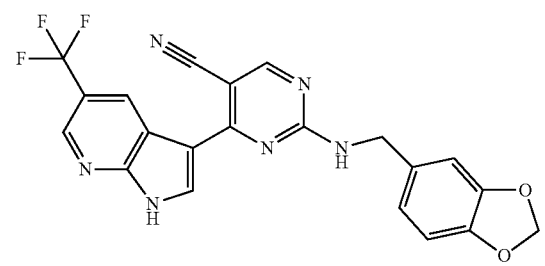
I-57
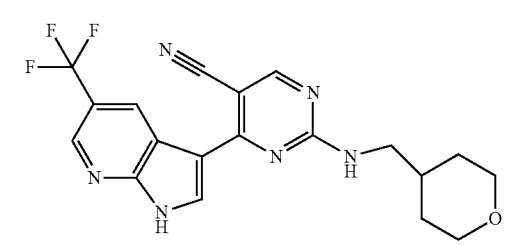
I-58
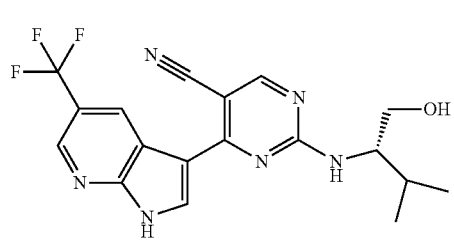

301
-continued
I-59
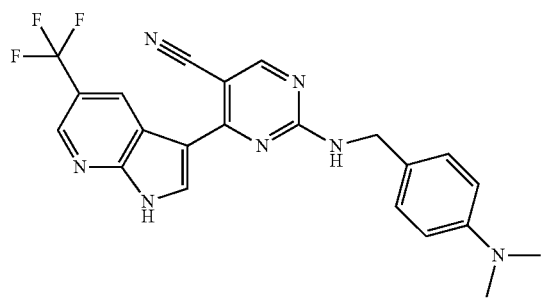
I-60
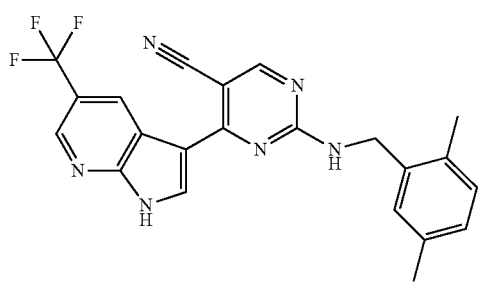
I-61
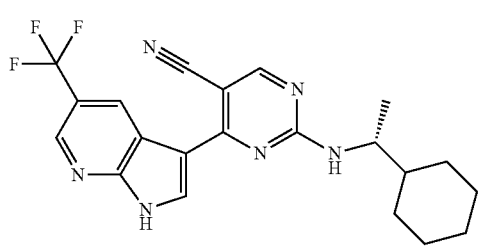
I-62
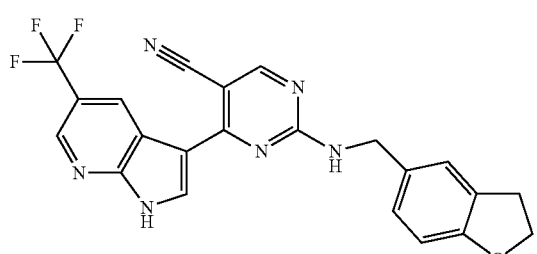
I-63
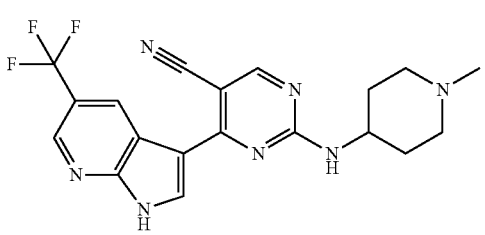
I-64
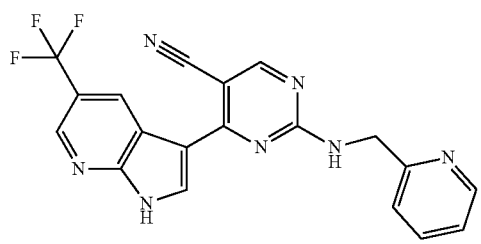
302
-continued
I-65
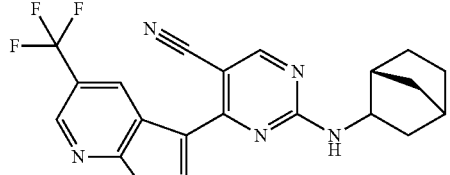
I-66
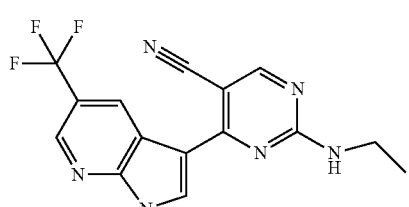
I-68
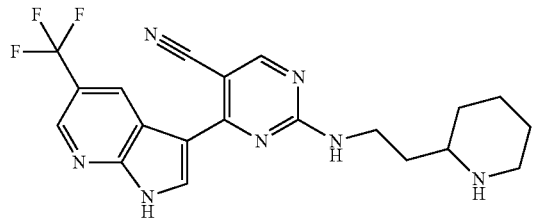
I-69
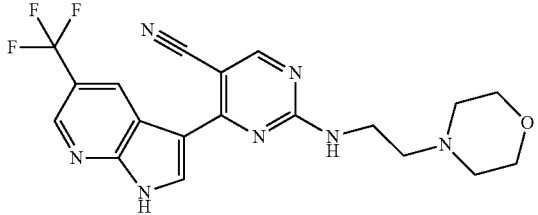
I-70
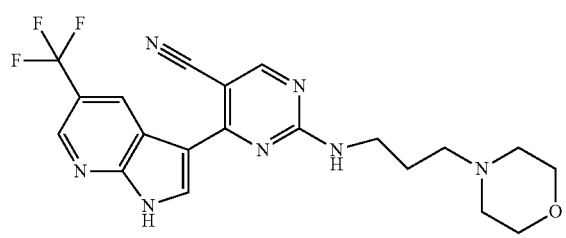
I-71
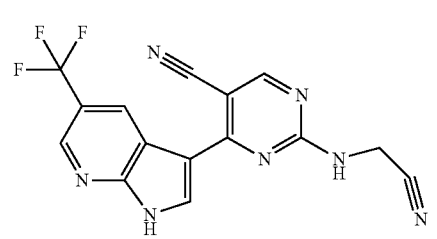

303
-continued
I-72
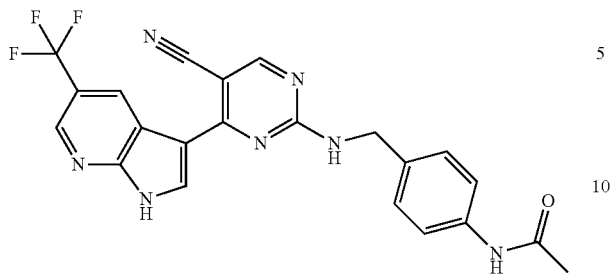
I-73
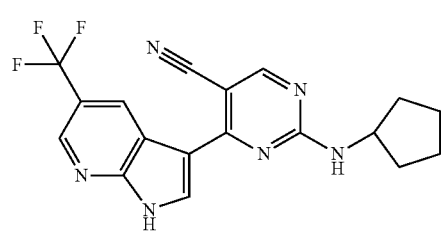
I-74
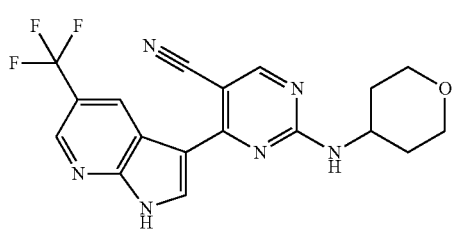
I-75
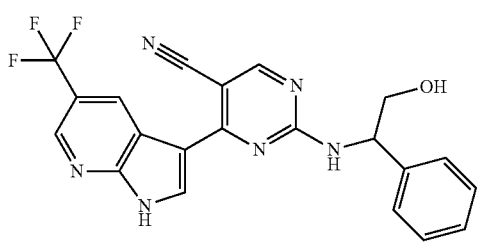
I-76
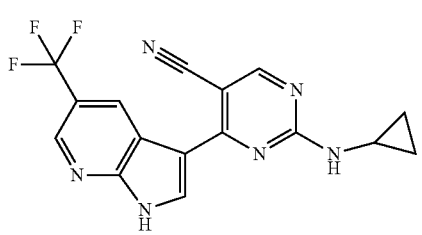
I-77
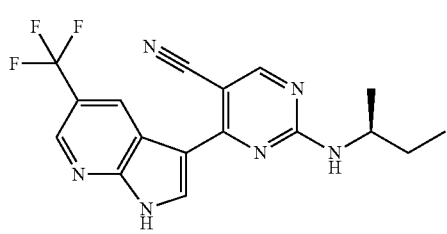
304
-continued
I-78
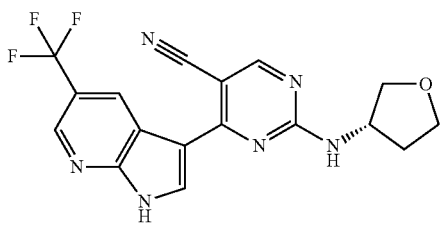
I-79
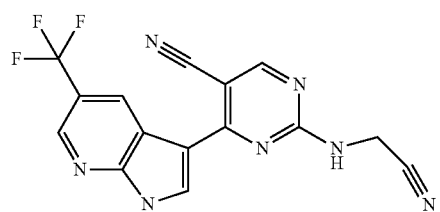
I-80
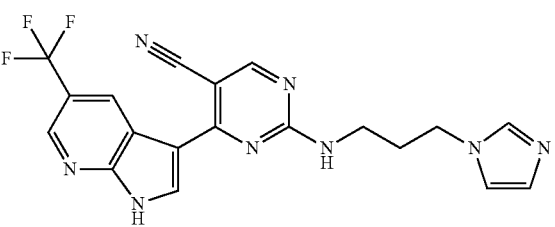
I-81
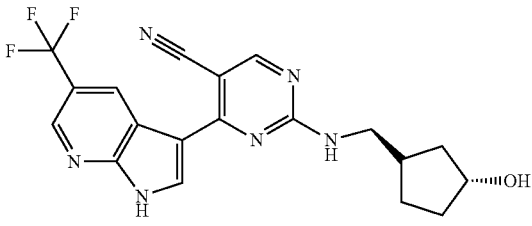
I-82
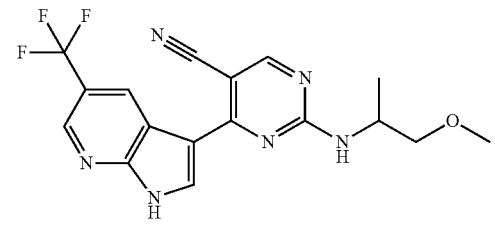
I-83
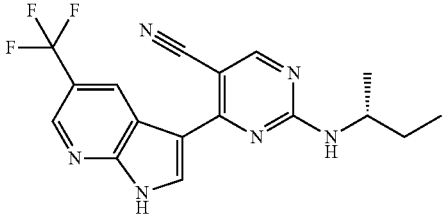

I-84
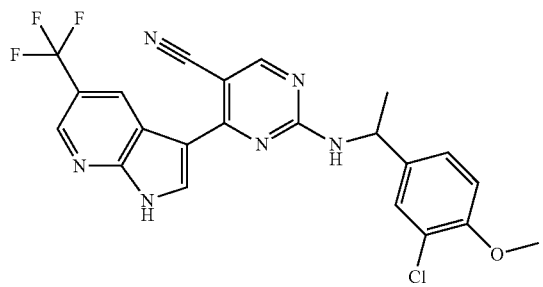
I-85
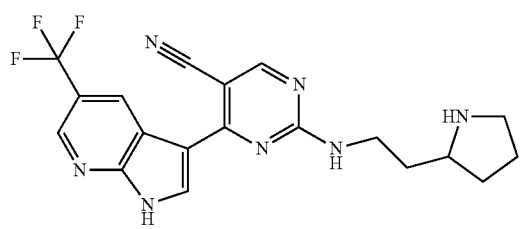
I-86
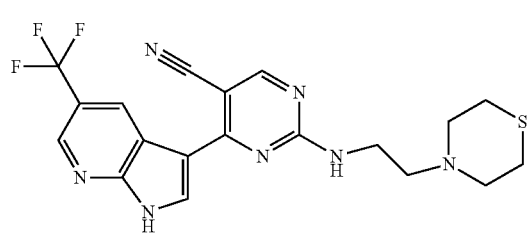
I-87
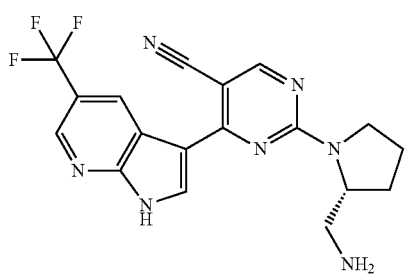
I-88
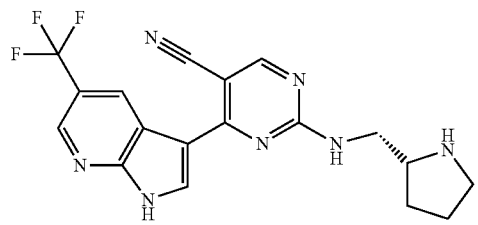
I-89
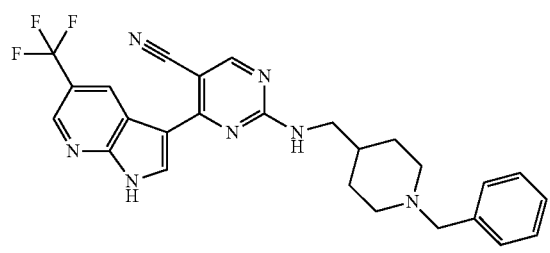
I-90
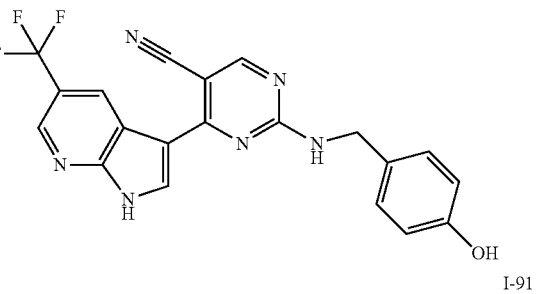
I-91
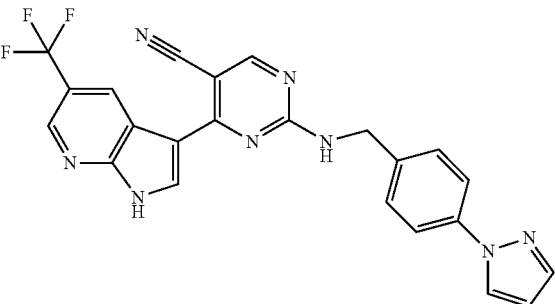
I-92
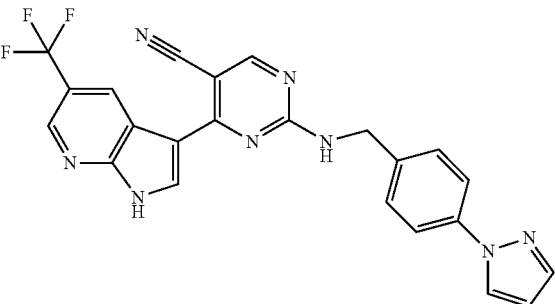
I-93
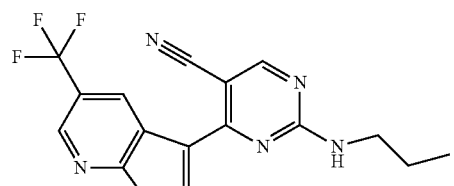
I-94
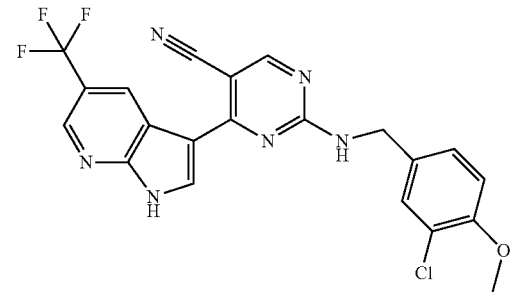
I-95
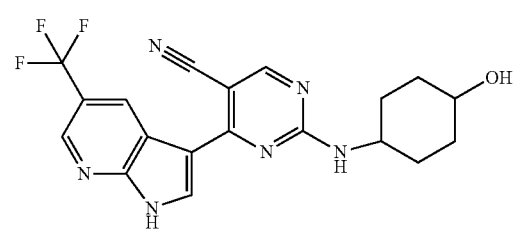

307
-continued
I-96
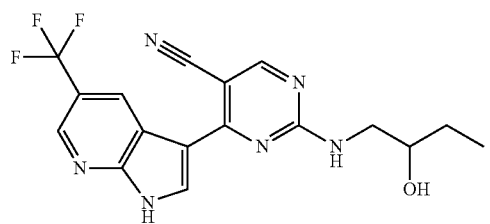
I-97
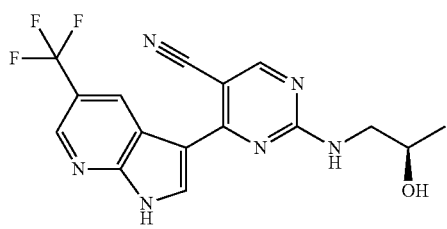
I-98
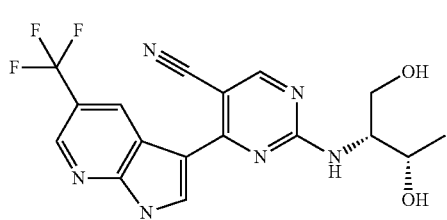
I-99
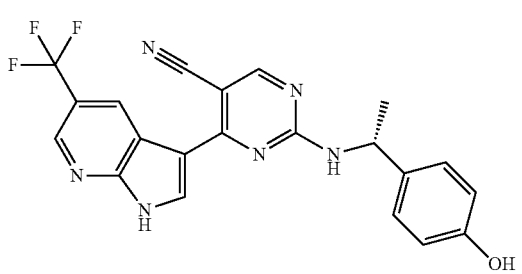
I-100
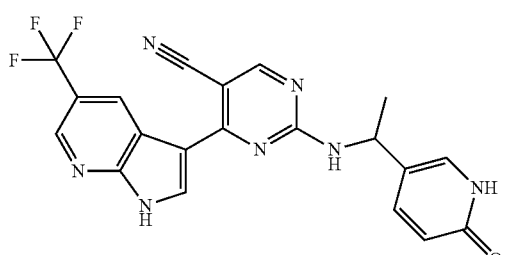
I-101
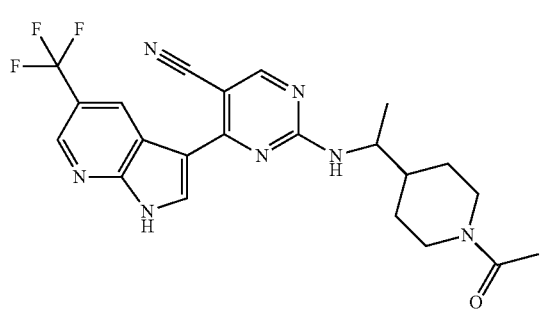
308
-continued
I-102
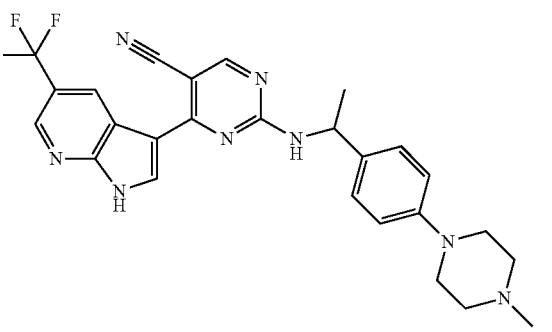
I-104
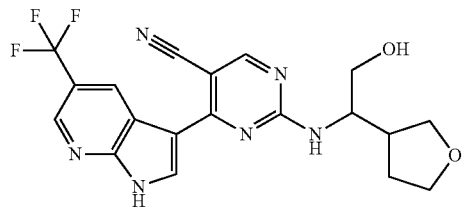
I-105
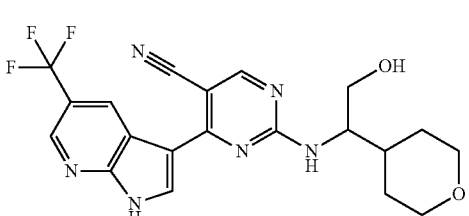
I-106
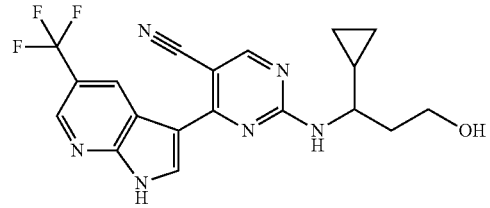
I-107
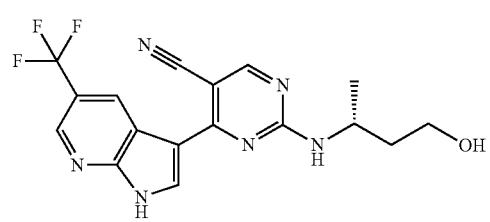
I-108
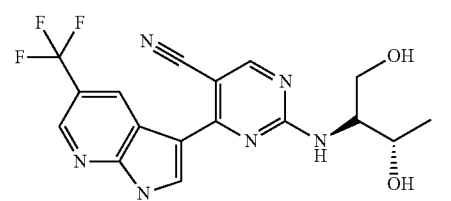
I-109
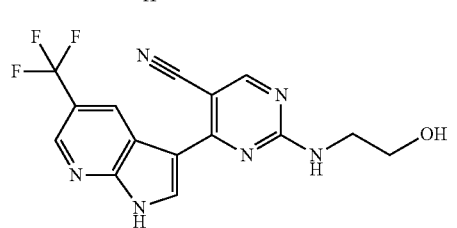

I-110
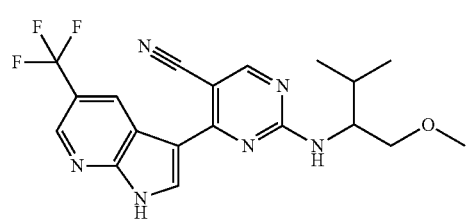
I-111
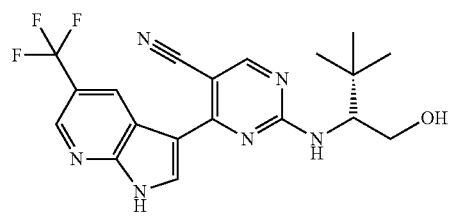
I-55
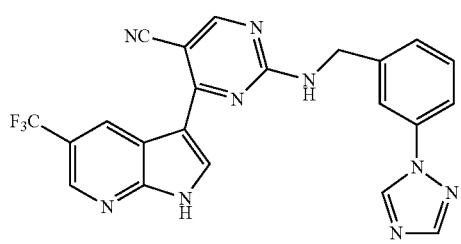
I-67
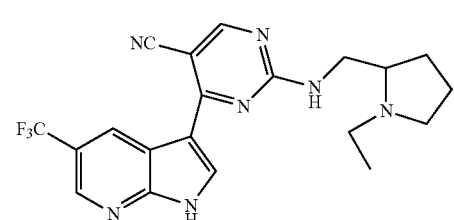
I-103
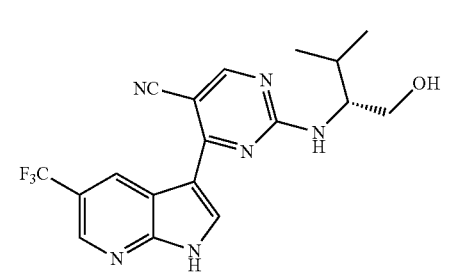
I-112
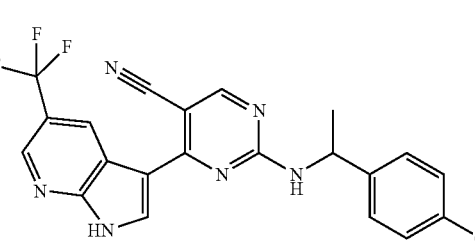
I-113
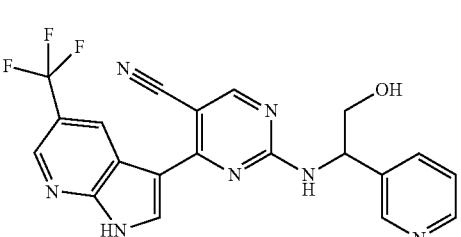
I-114
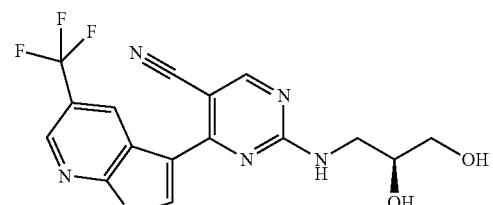
I-115
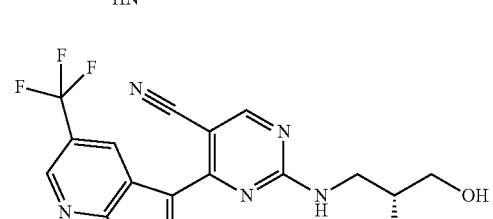
I-116
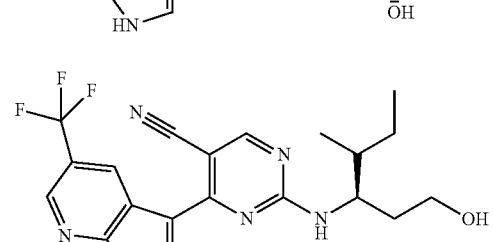
I-117
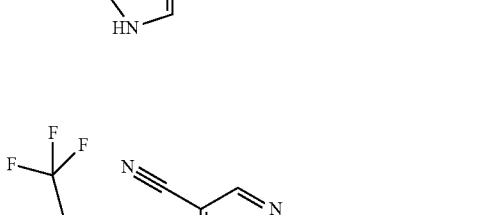
I-118
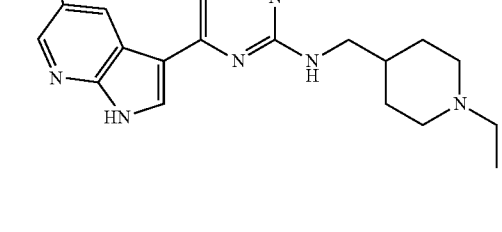
I-119
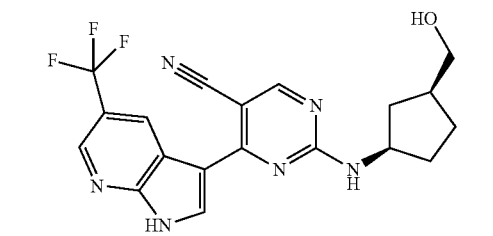

I-120
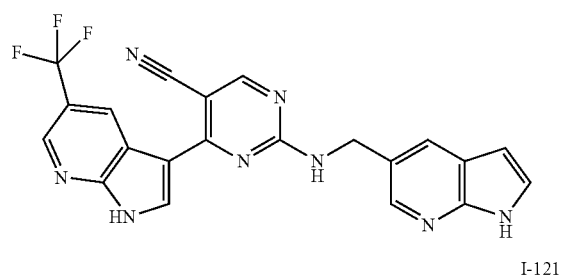
I-121
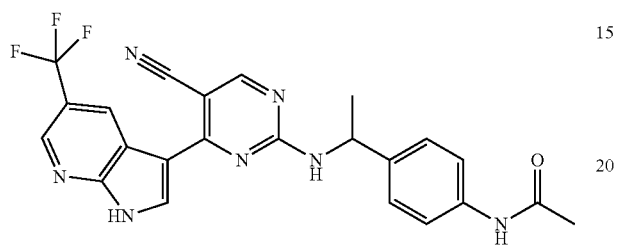
I-122
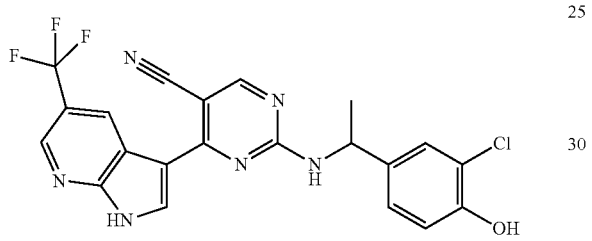
I-123
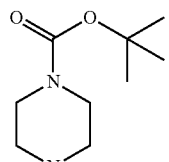
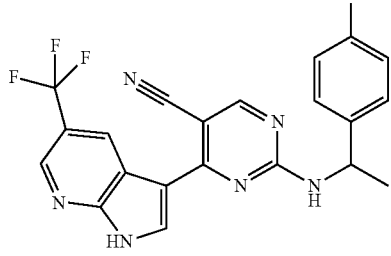
I-124
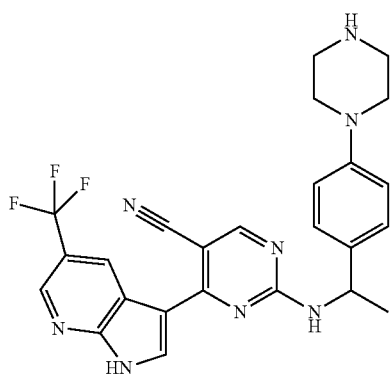
I-125
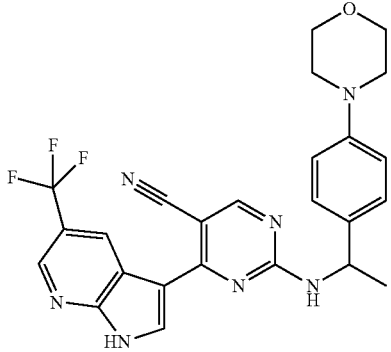
I-126
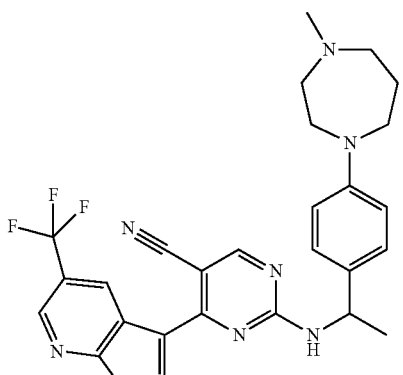
I-127
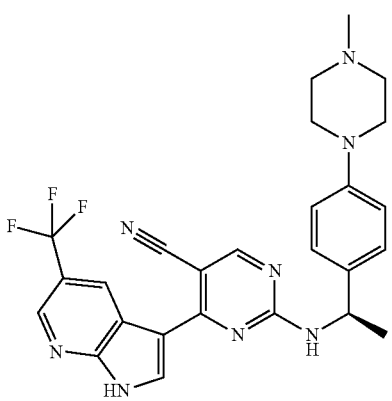
I-128
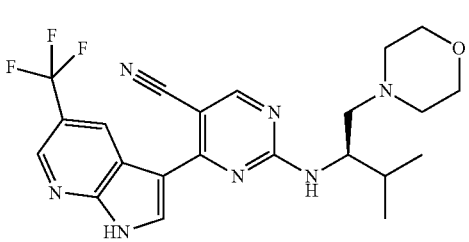

I-129
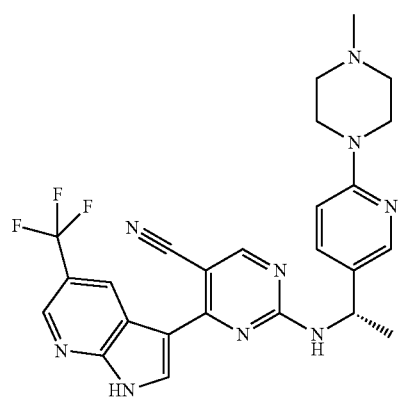
I-130
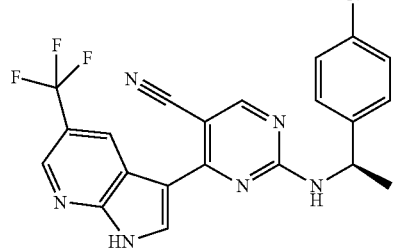
I-131
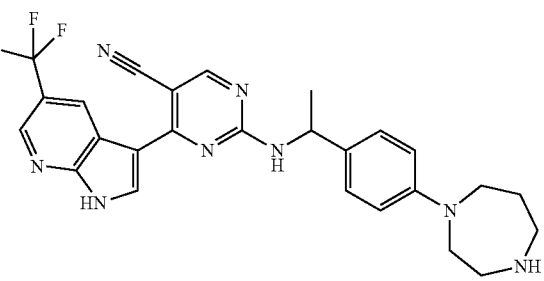
I-132
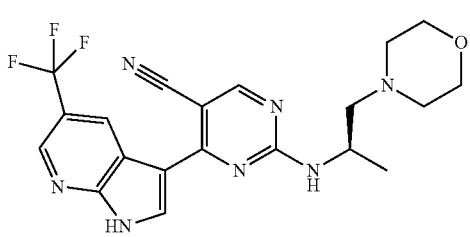
I-133
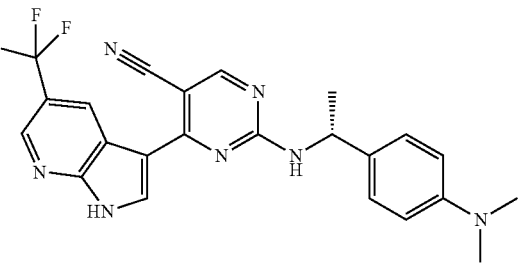
I-134
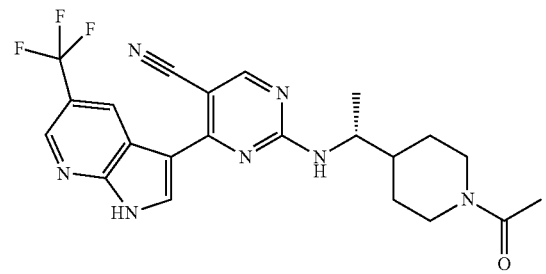
I-135
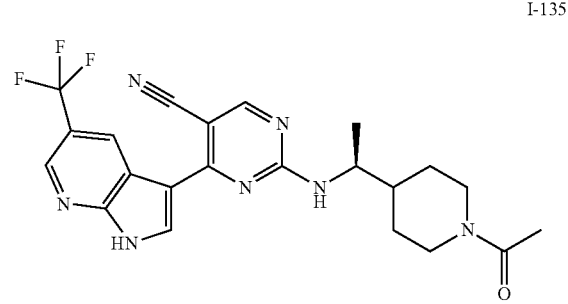
I-136
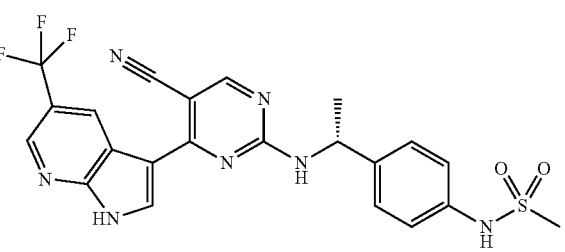
I-137
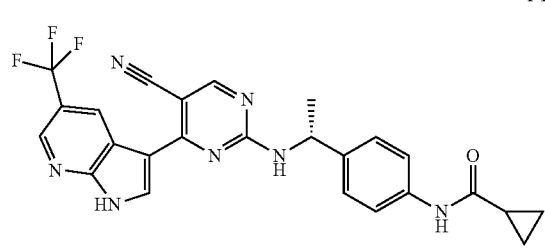

-continued
I-138
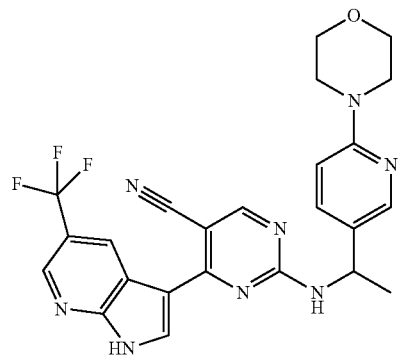
I-139
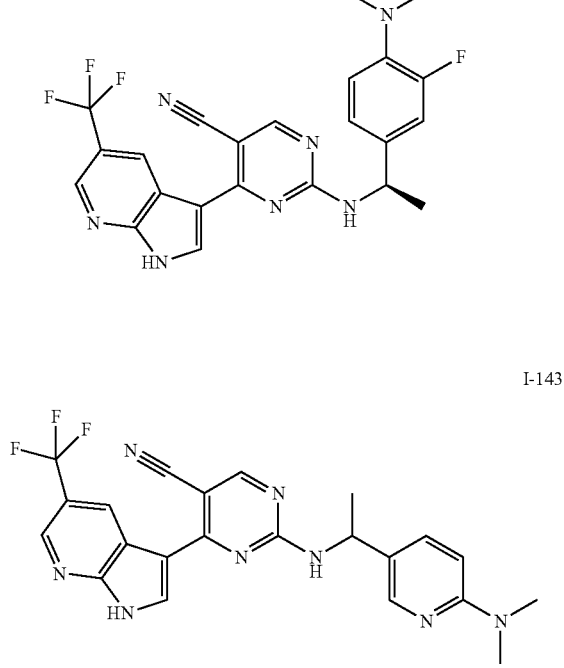
I-140
I-141
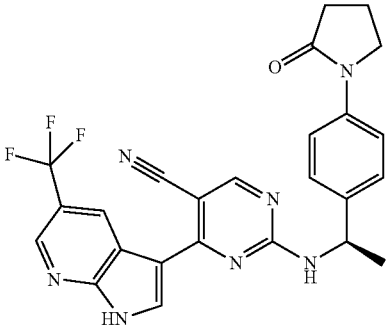
-continued
I-142
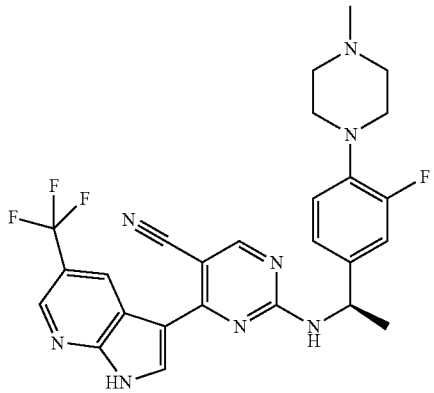
I-143
I-144
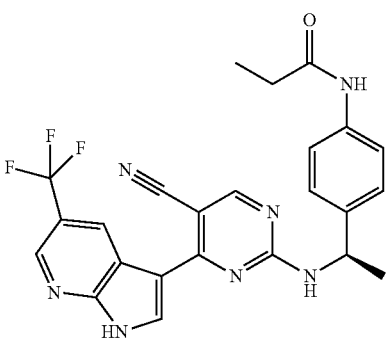
I-145
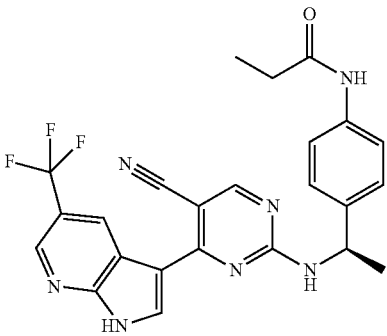

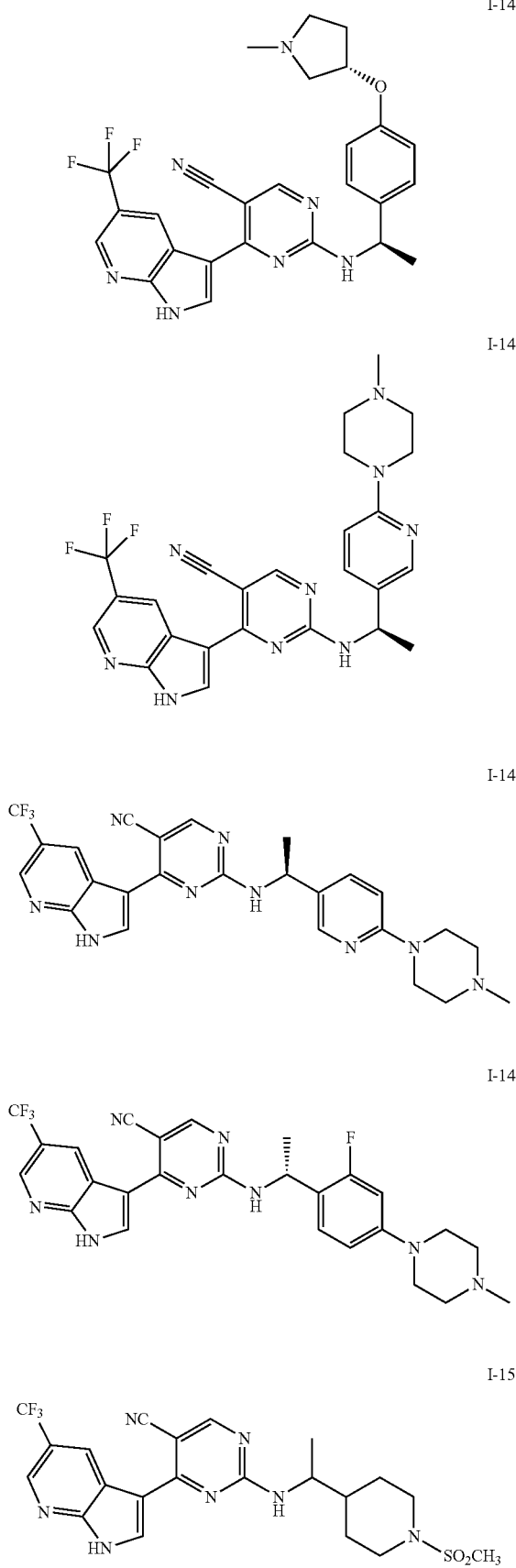
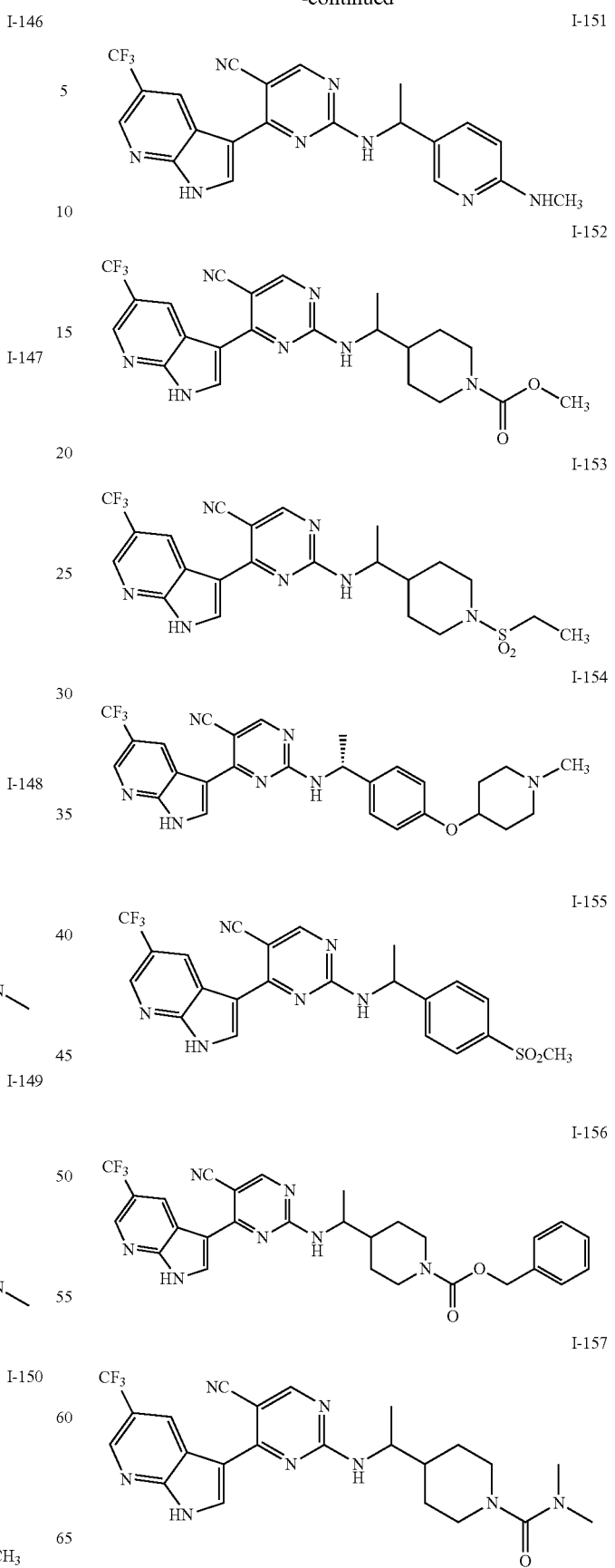

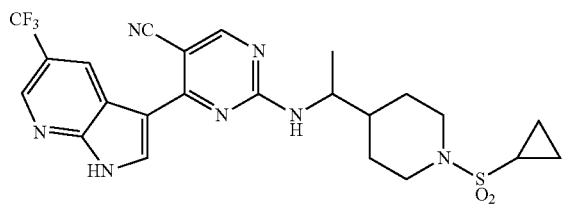
I-158
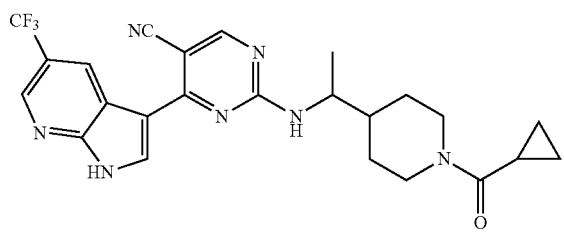
I-159
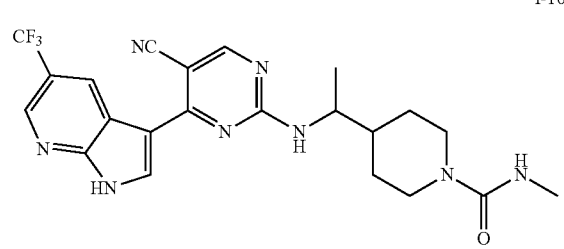
I-160
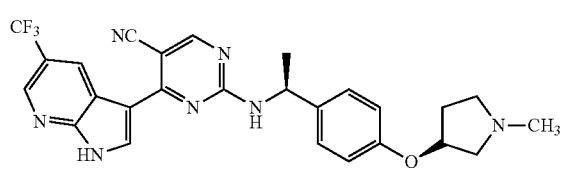
I-161
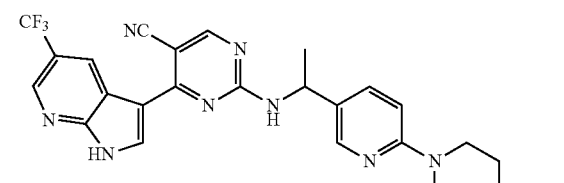
I-162
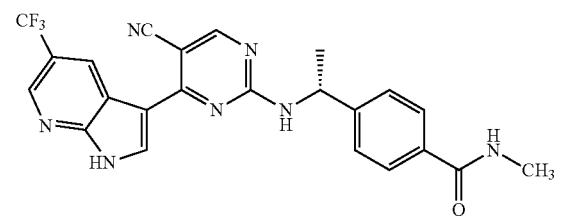
I-163
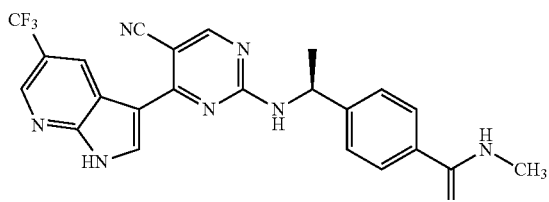
I-164
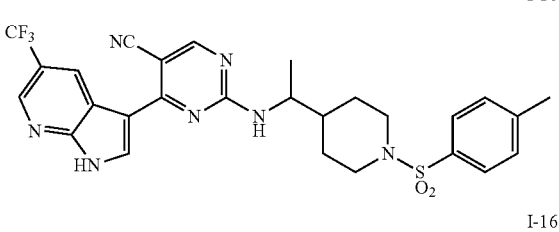
I-165
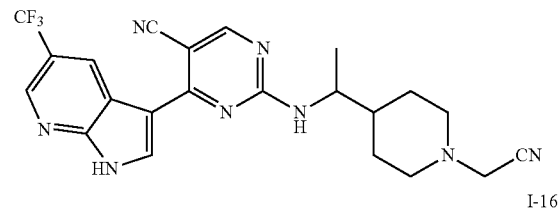
I-166
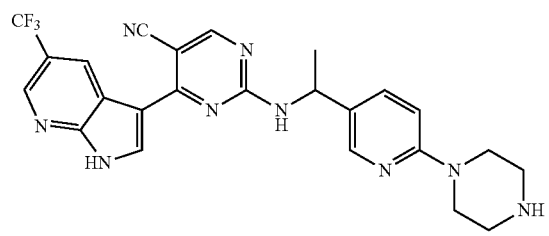
I-167
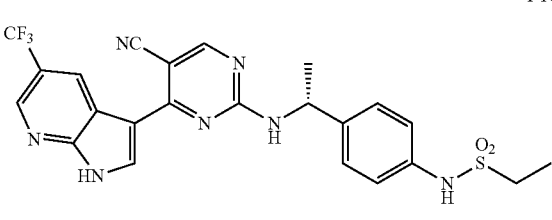
I-168
I-169
I-170

I-171
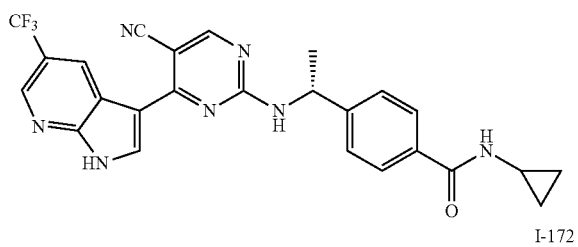
I-172
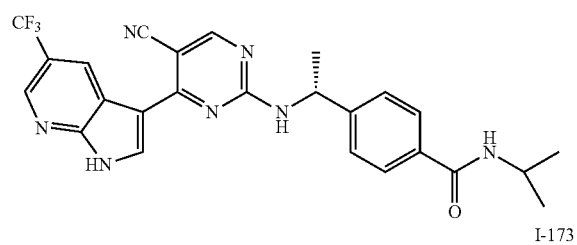
I-173
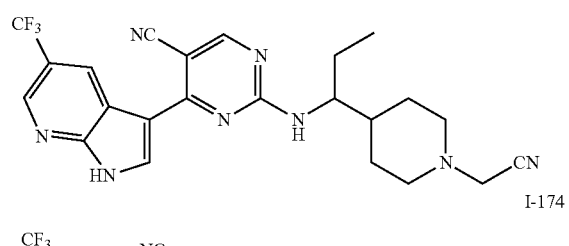
I-174
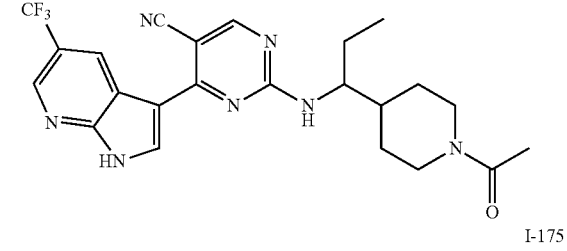
I-175
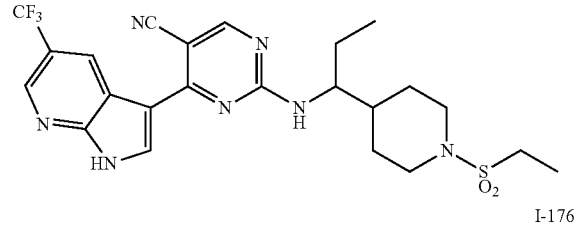
I-176
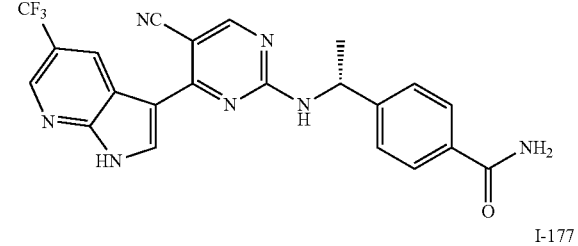
I-177
I-178
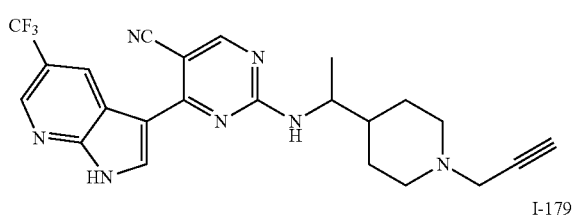
I-179
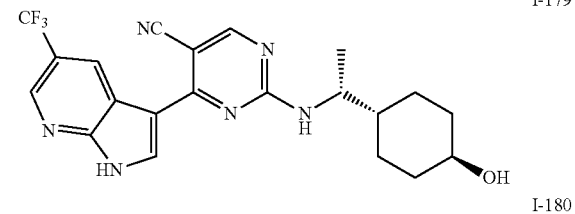
I-180
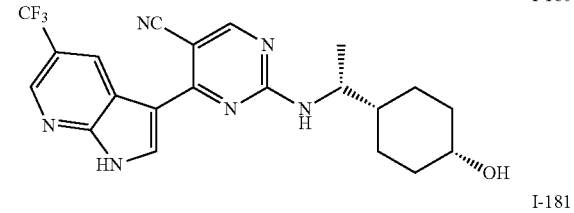
I-181
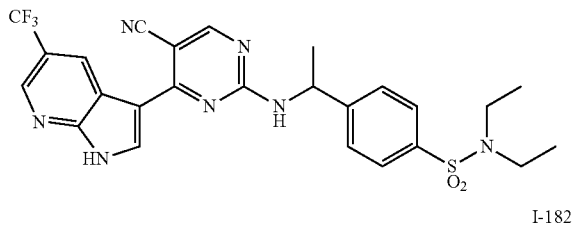
I-182
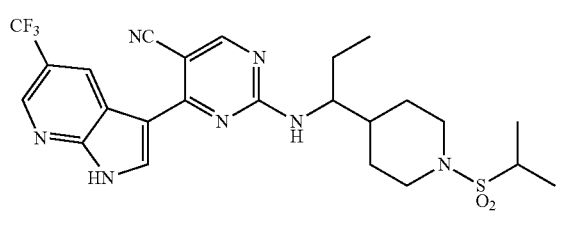
I-183
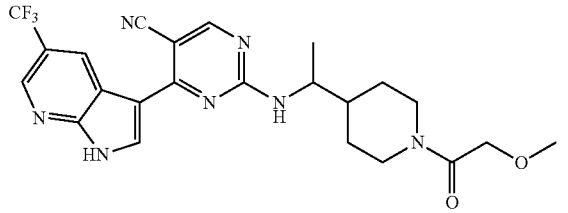
I-184
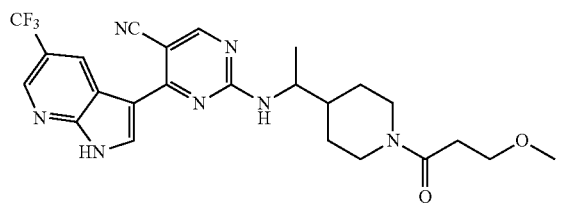

I-185 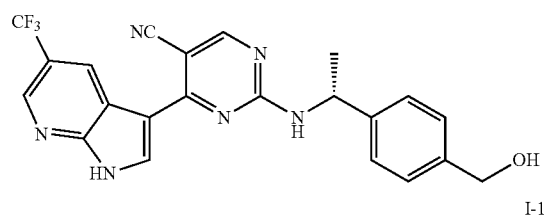
I-186 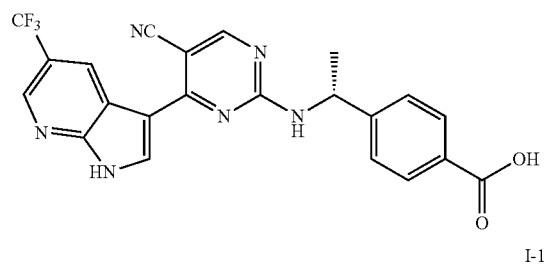
I-187 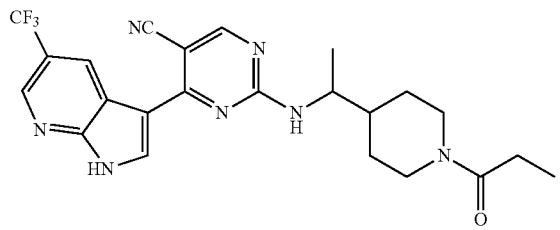
I-188 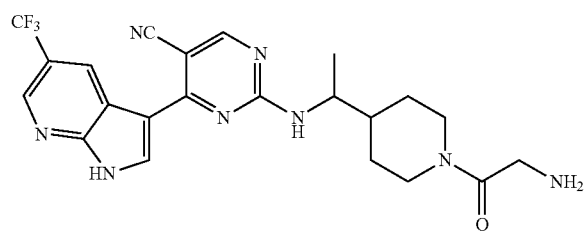
I-189 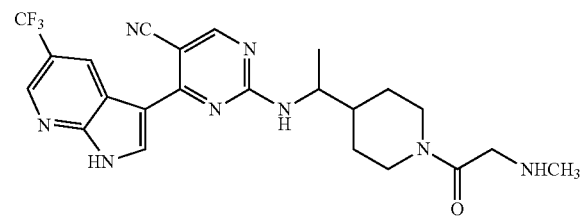
I-190 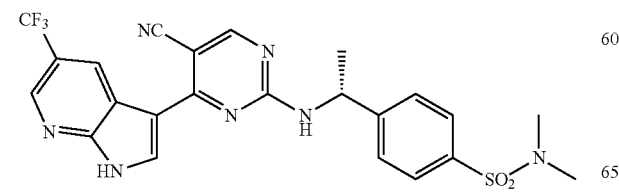
I-191 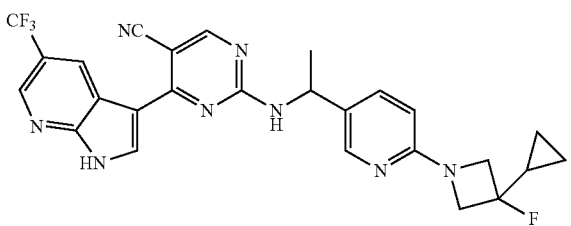
I-192 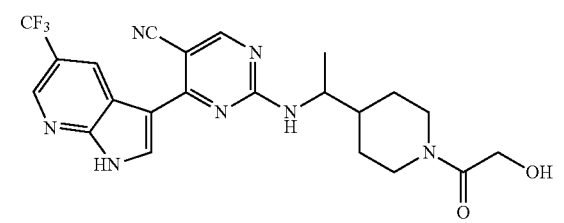
I-193 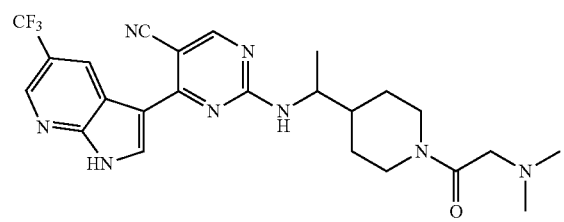
I-194 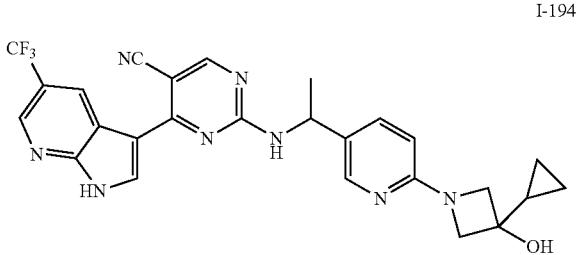
I-195 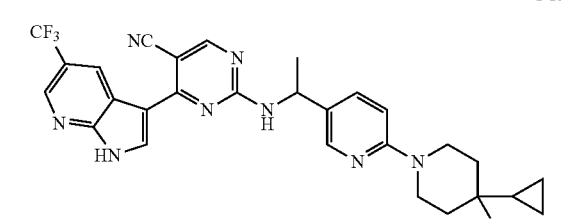
I-196 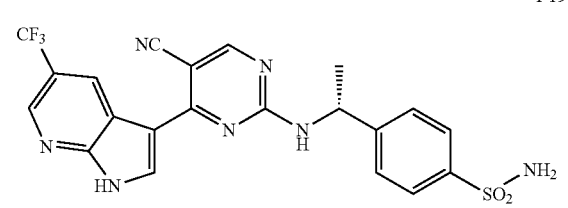

I-197
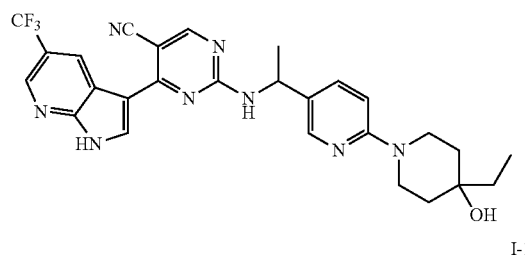
I-198
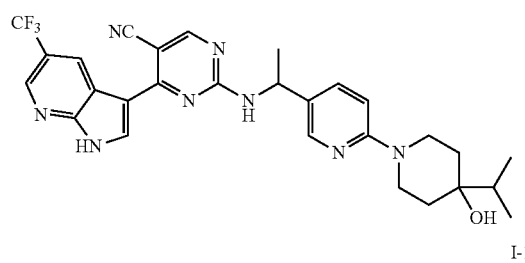
I-199
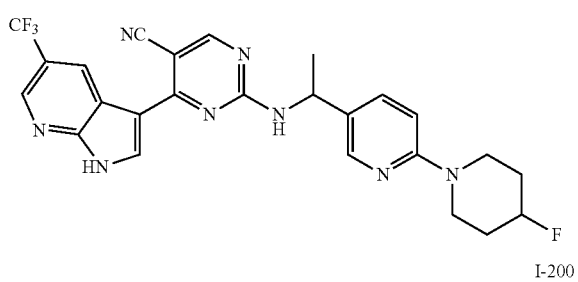
I-200
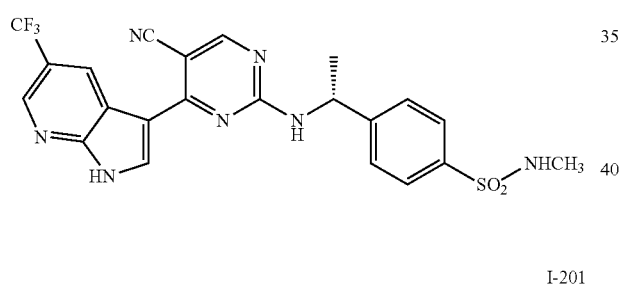
I-201
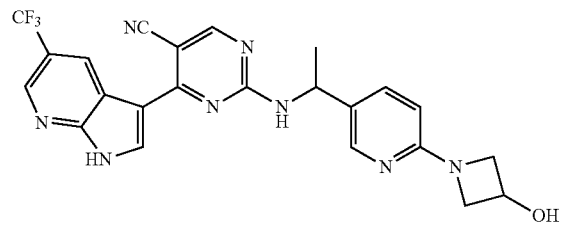
I-202
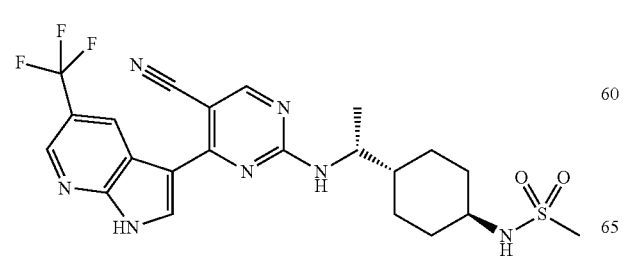
I-203
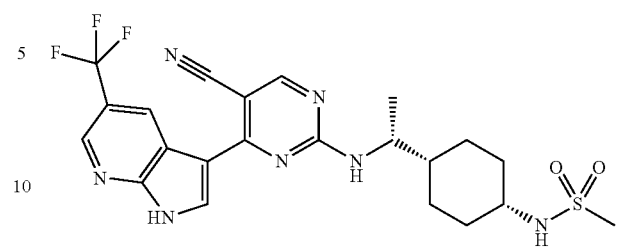
I-204
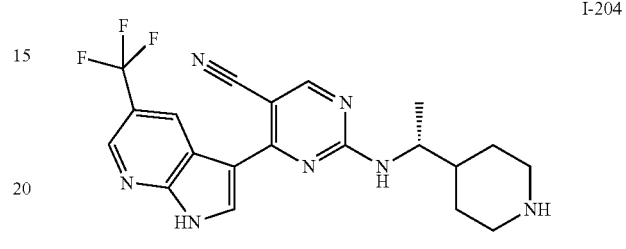
I-205
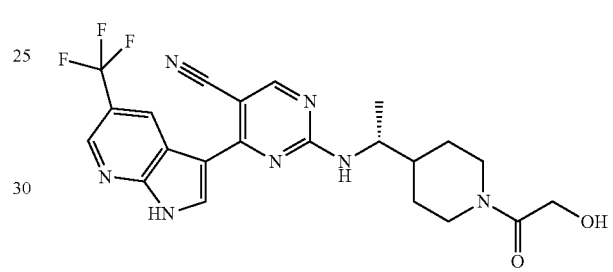
I-206
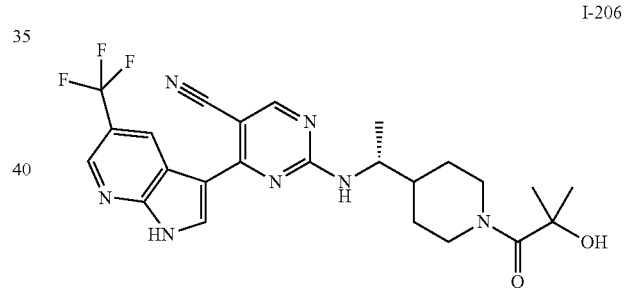
I-207
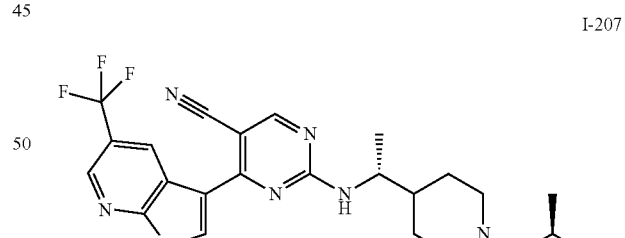
I-208
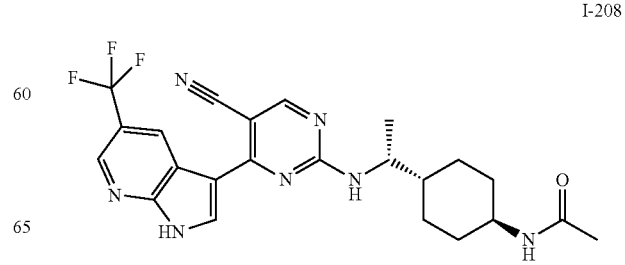

I-209
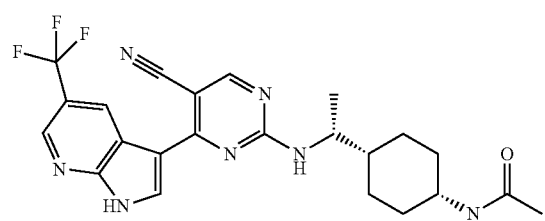
I-210
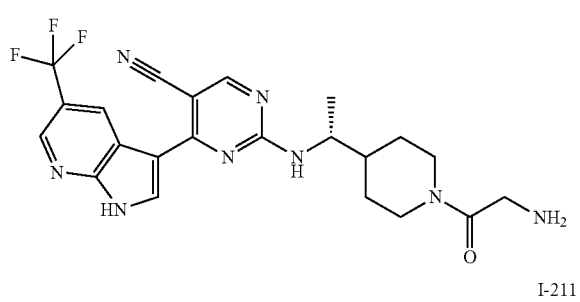
I-211
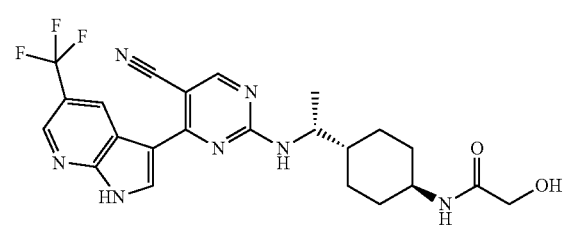
I-212
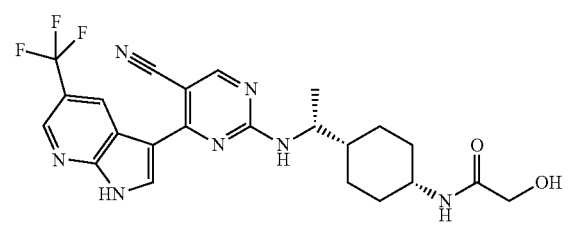
I-213
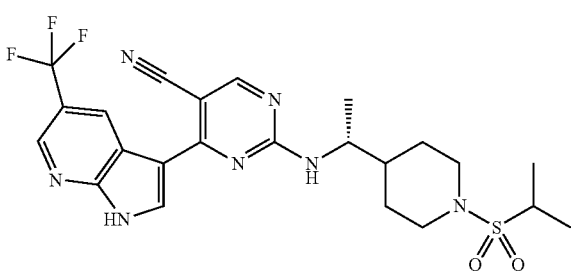
I-214
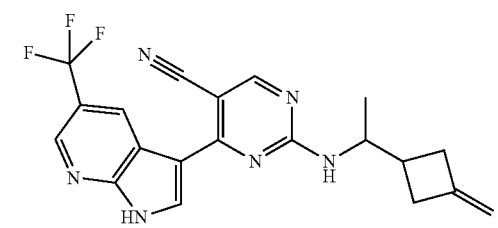
I-215
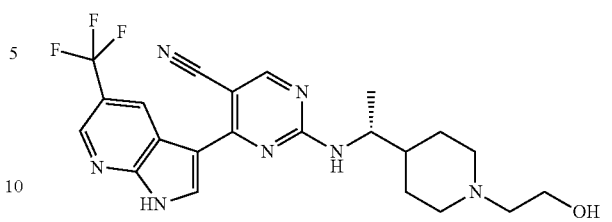
I-216
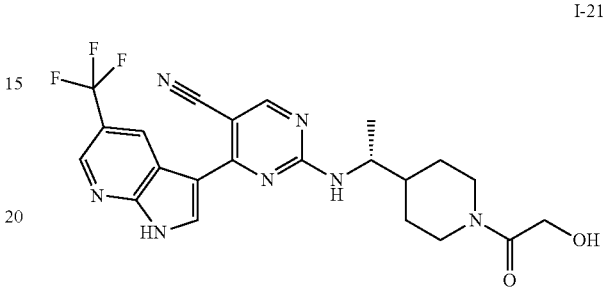
I-217
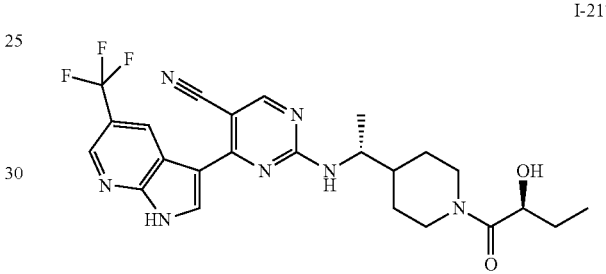
I-218
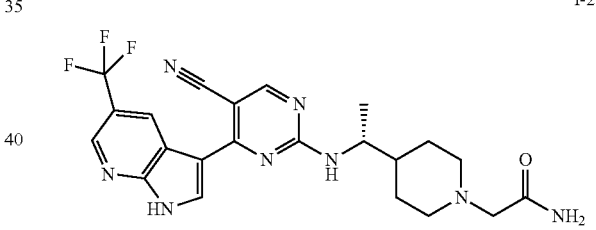
I-219
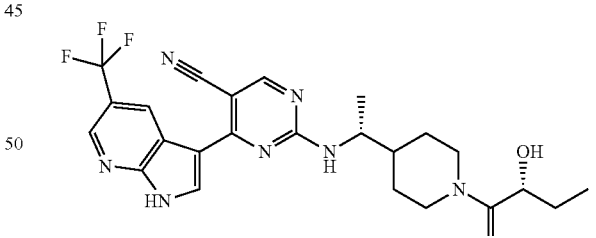
I-220
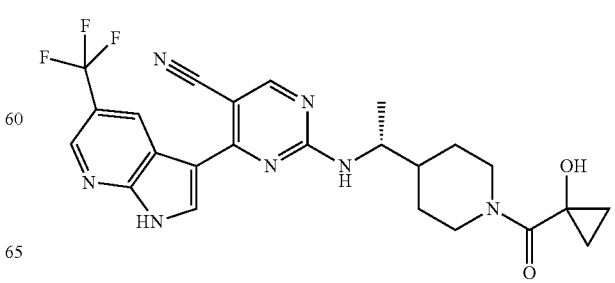

I-221
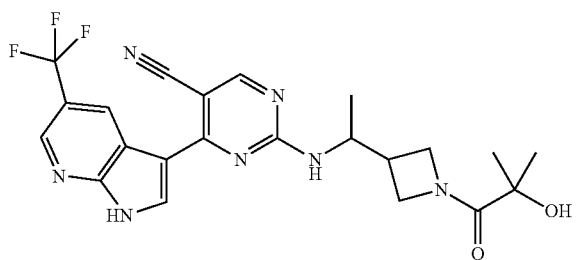
I-222
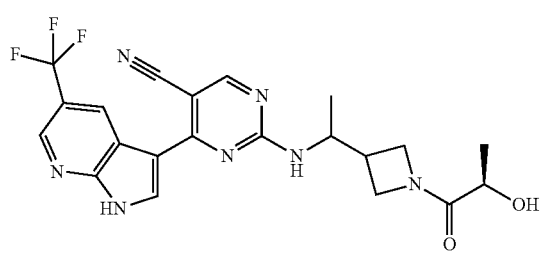
I-223
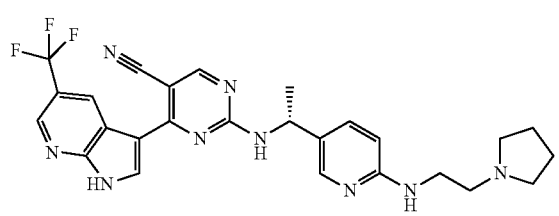
I-224
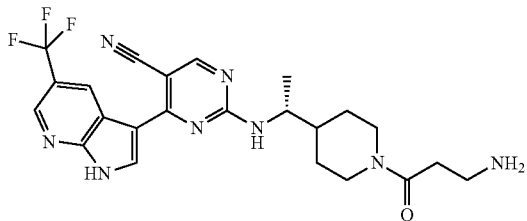
I-225
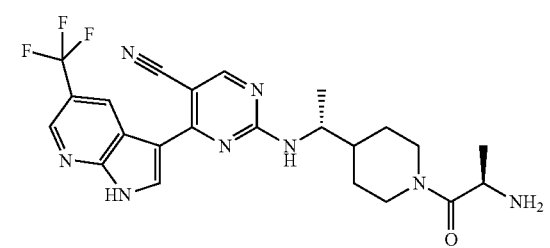
I-226
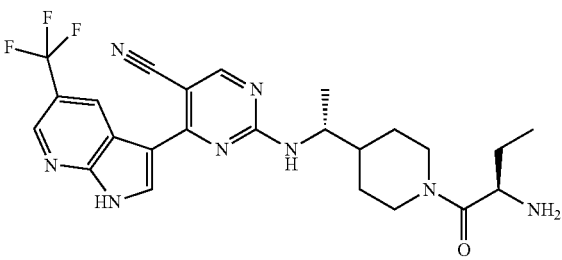
I-227
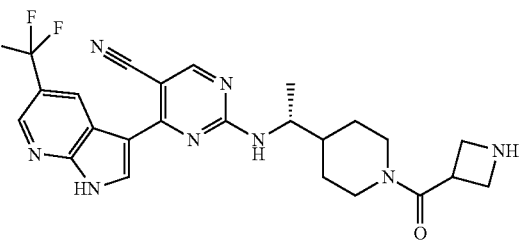
I-228
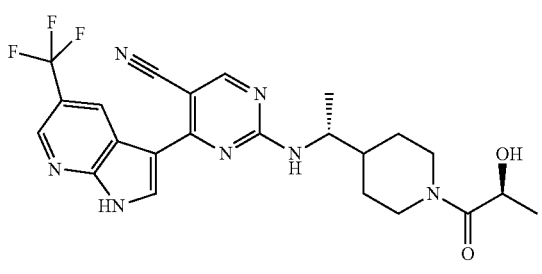
I-229
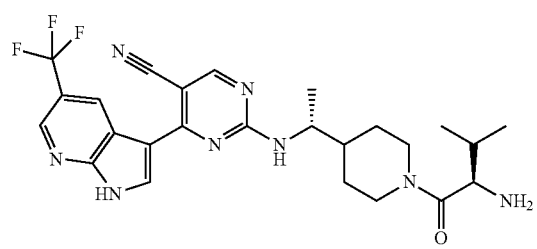
I-230
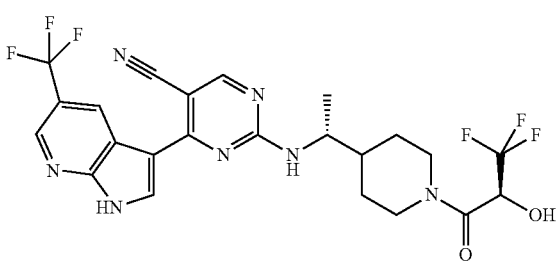
I-231
I-232
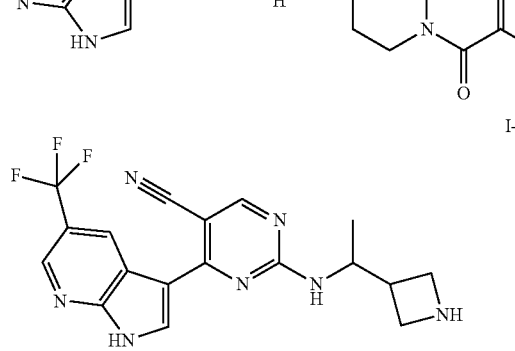

I-233
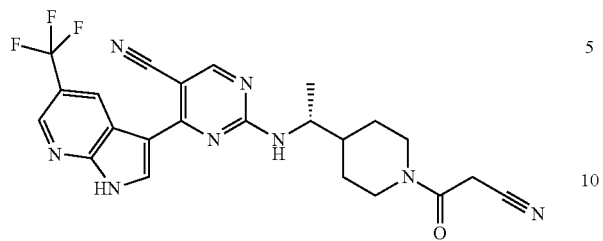
I-234
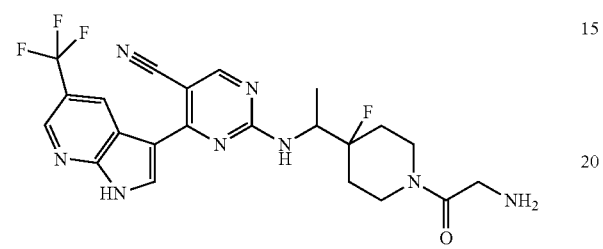
I-235
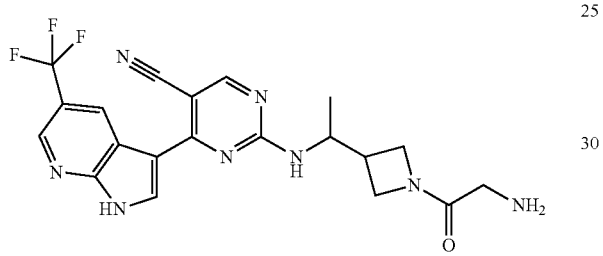
I-236
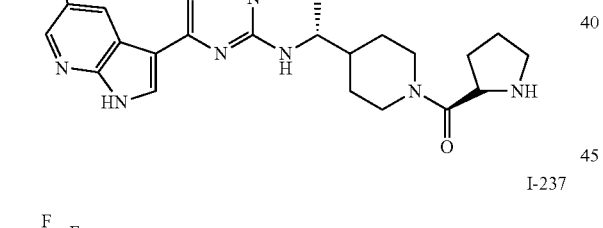
I-237
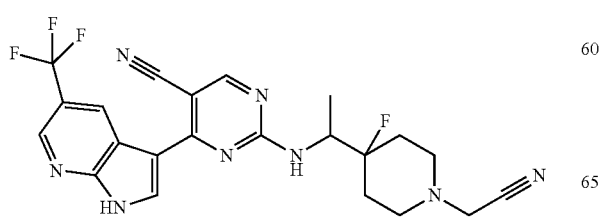
I-239
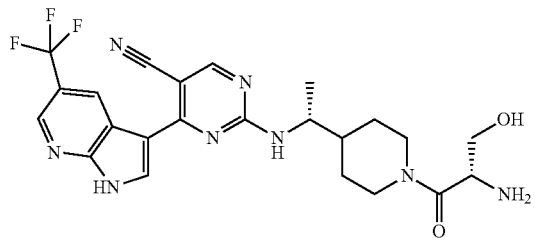
I-240
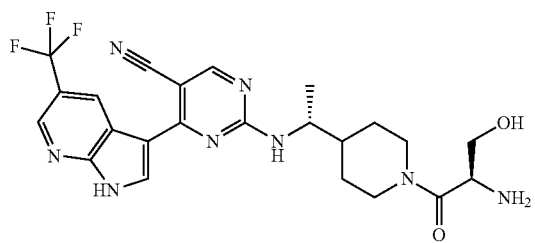
I-241
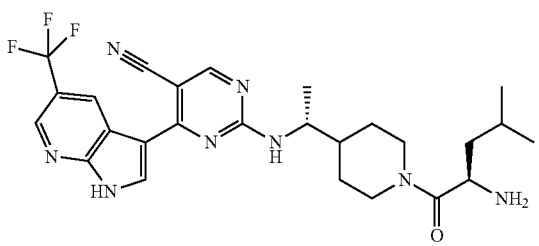
I-242
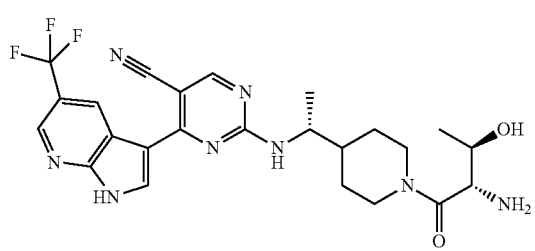
I-243
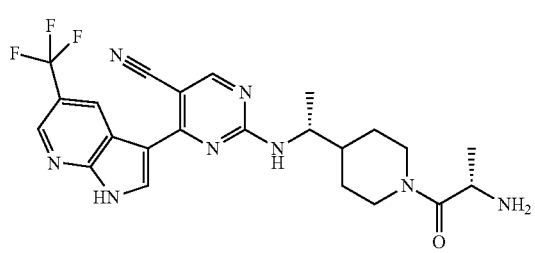
I-244
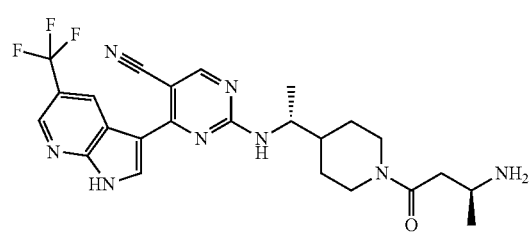

I-245
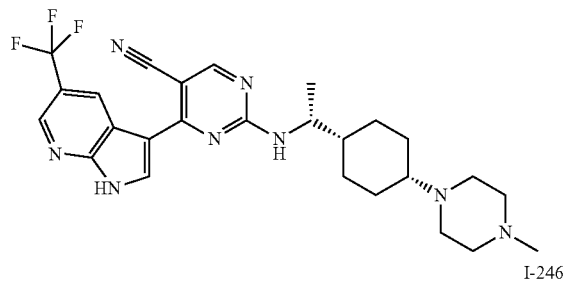
I-246
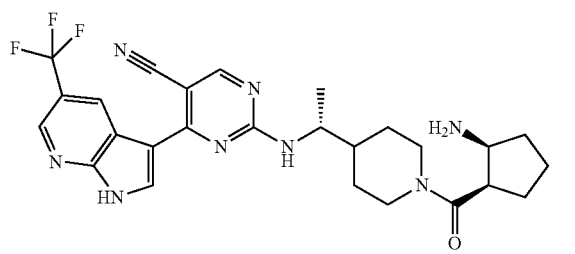
I-247
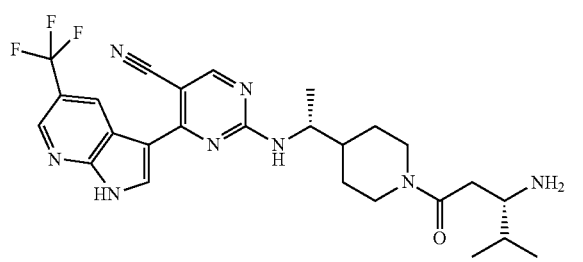
I-248
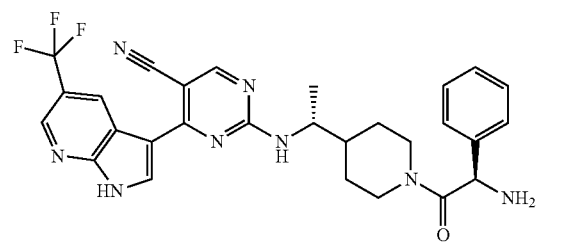
I-249
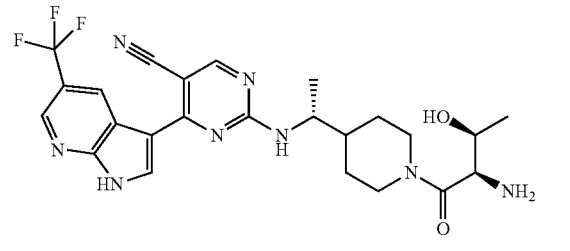
I-250
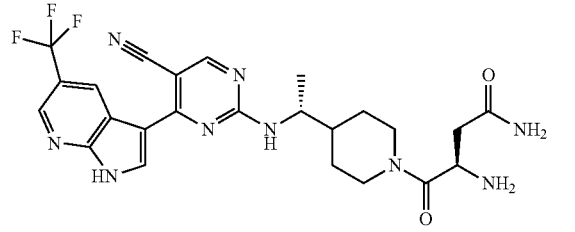
I-251
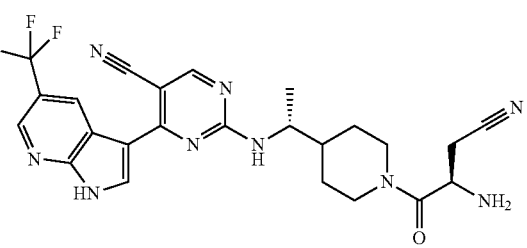
I-252
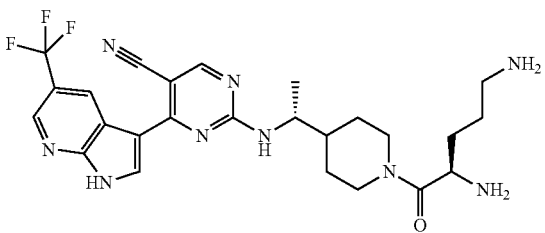
I-253
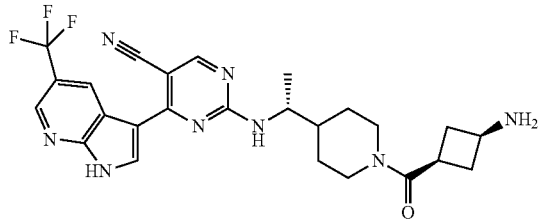
I-254
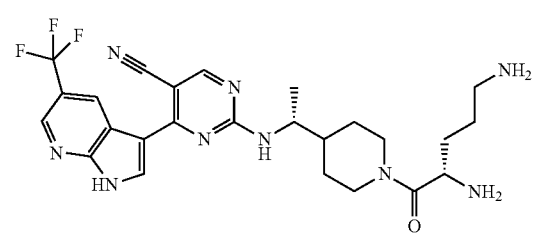
I-255
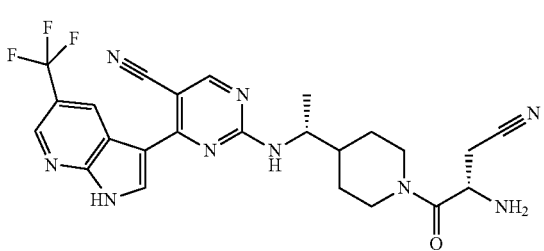
I-256
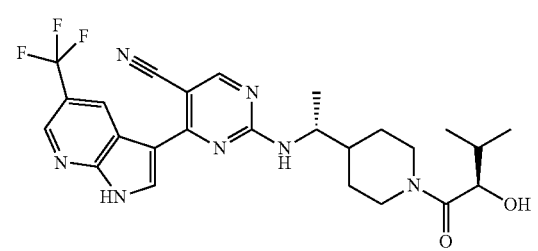

335
-continued
I-257
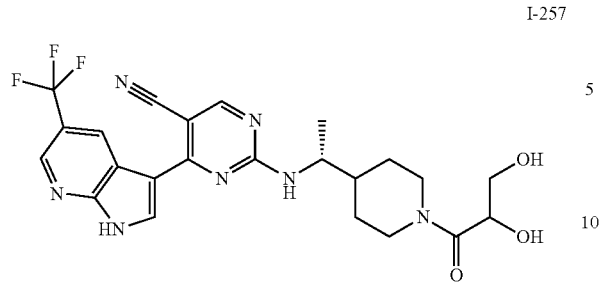
I-258
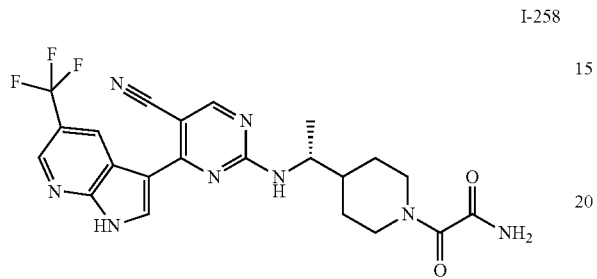
I-259
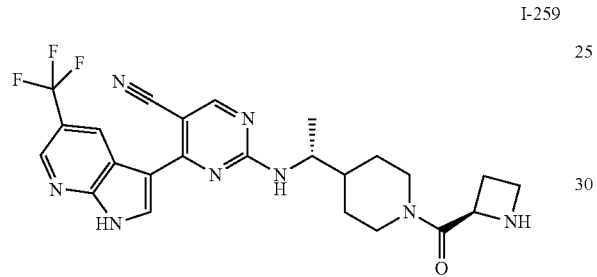
I-260
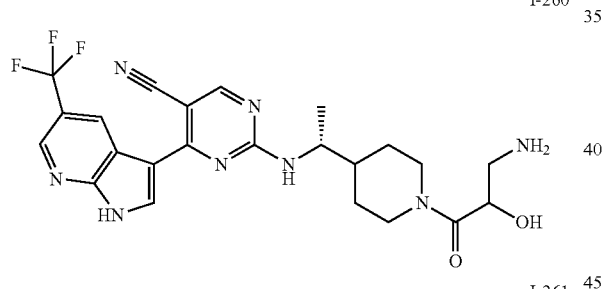
I-261
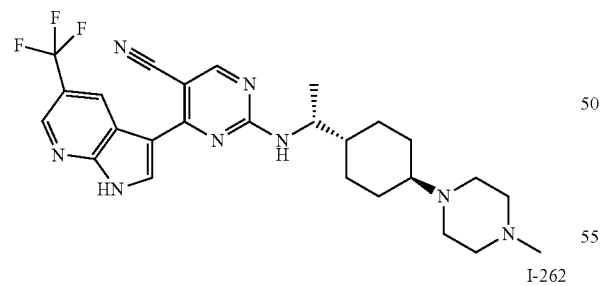
I-262
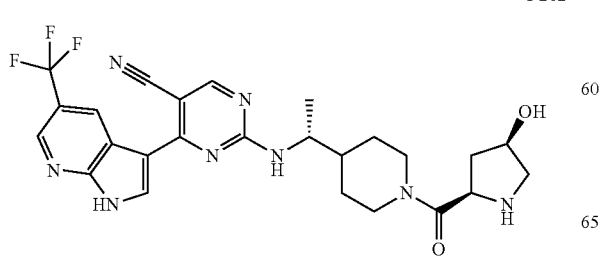
336
-continued
I-263
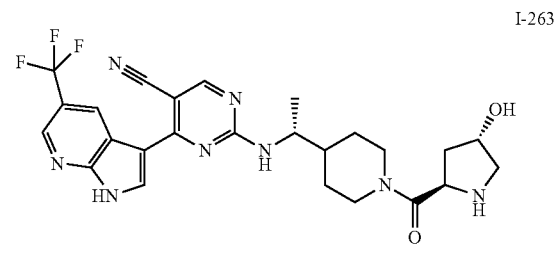
I-264
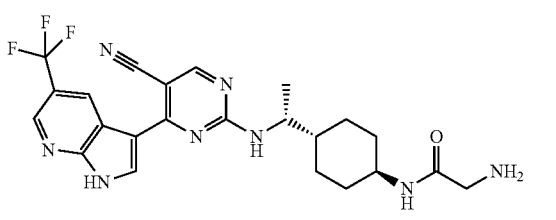
I-265
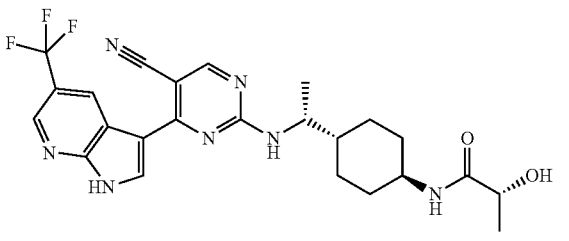
I-266
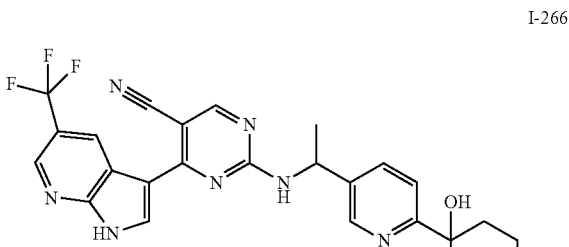
I-267
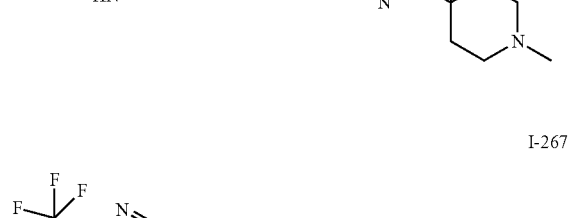
I-268
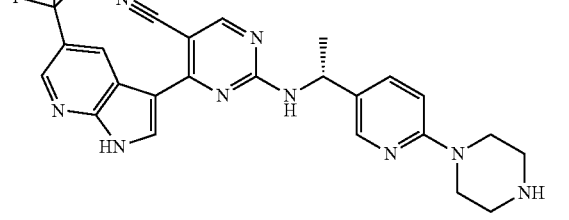
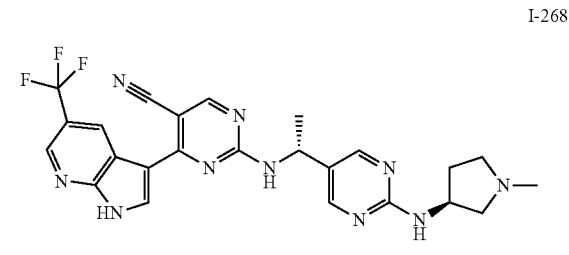

I-269
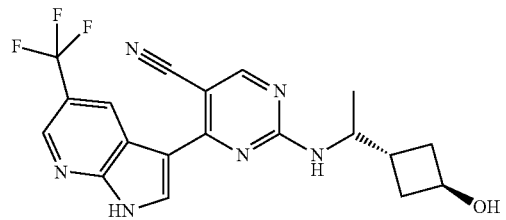
I-270
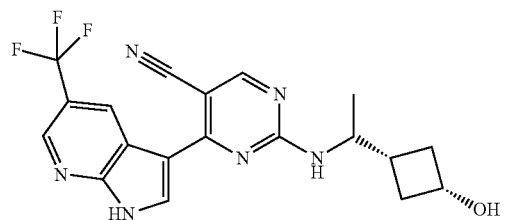
I-271
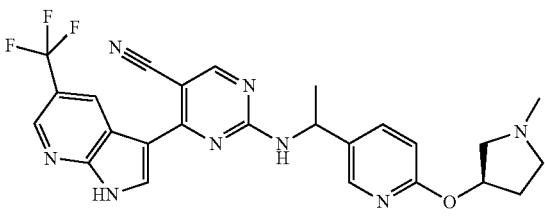
I-272
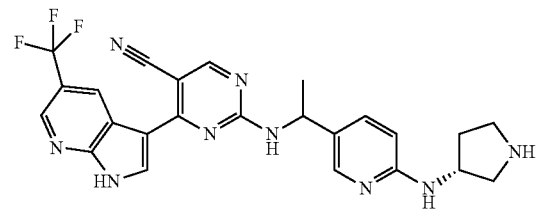
I-273
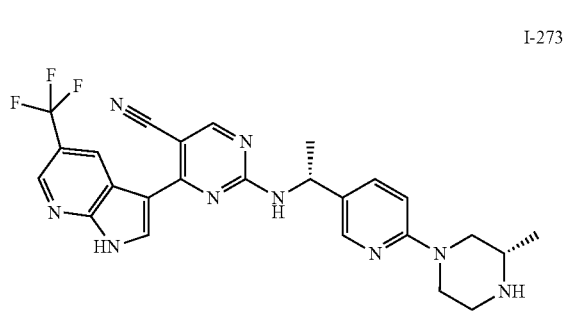
I-274
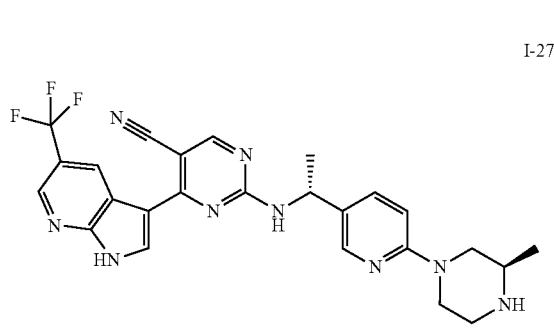
I-275
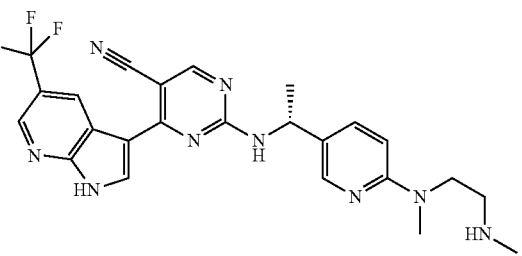
I-276
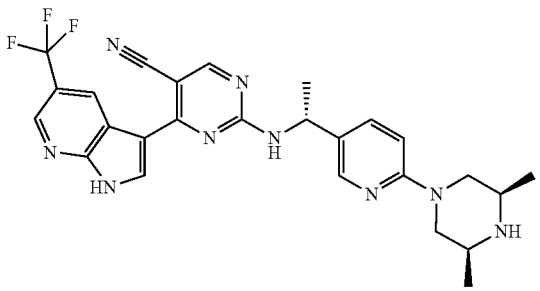
I-277
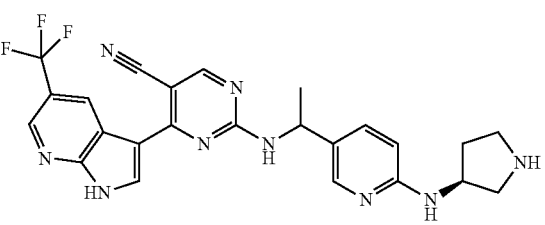
I-278
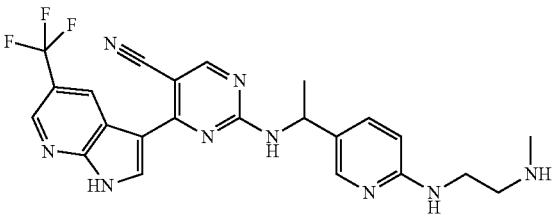
I-279
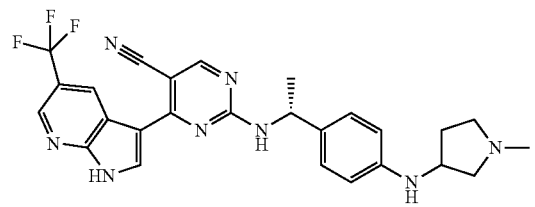
I-280
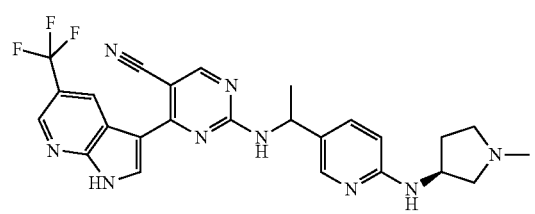

339
-continued
I-281
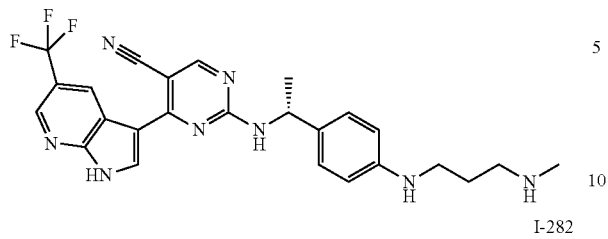
I-282
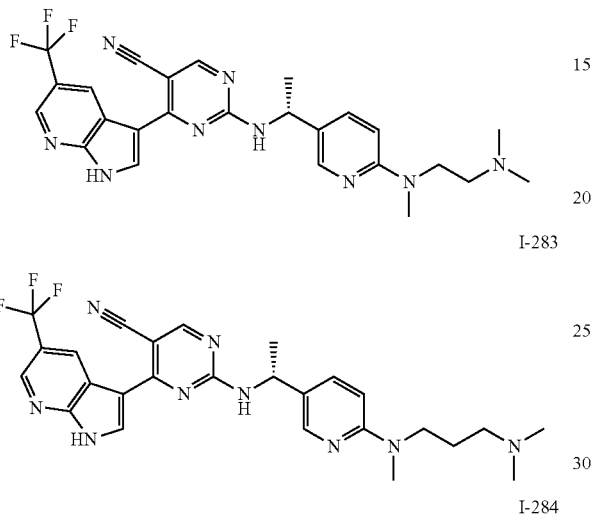
I-283
I-284
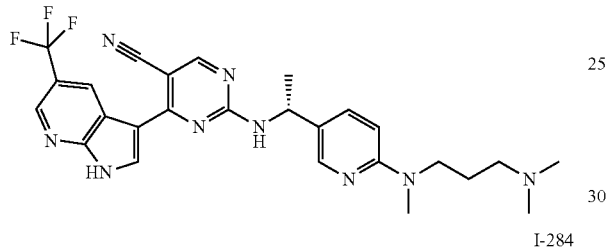
I-285
I-286
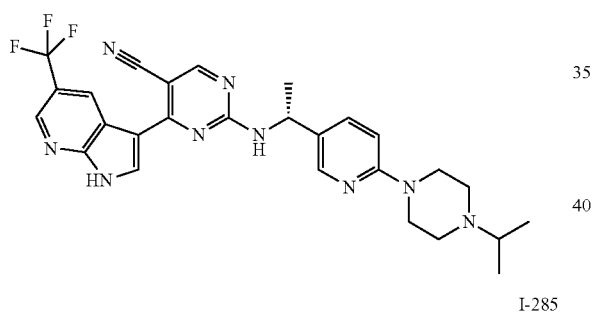
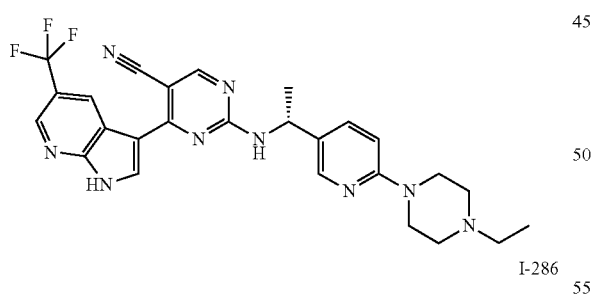
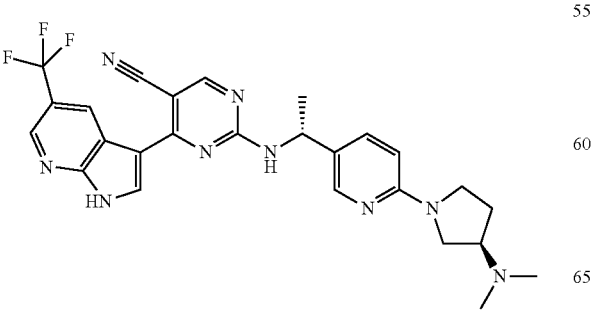
340
-continued
I-287
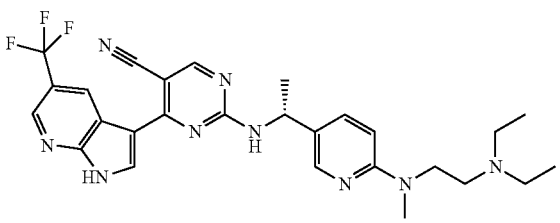
I-288
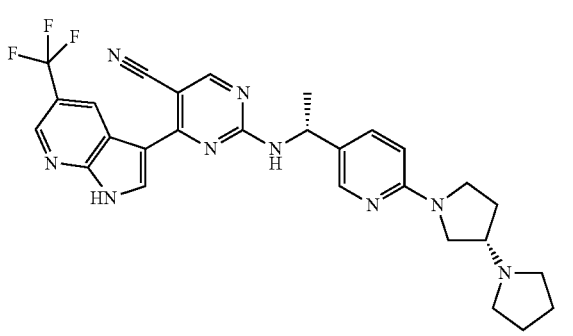
I-289
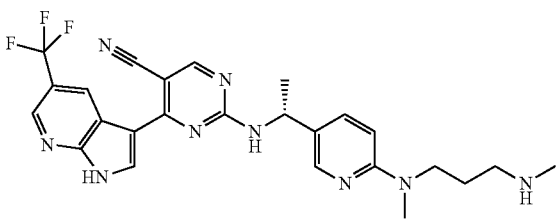
I-290
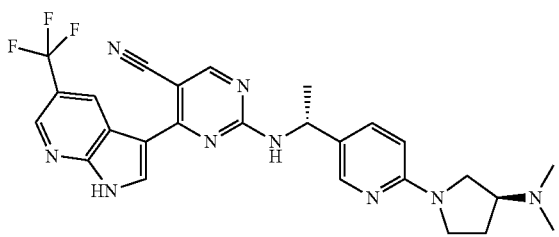
I-291
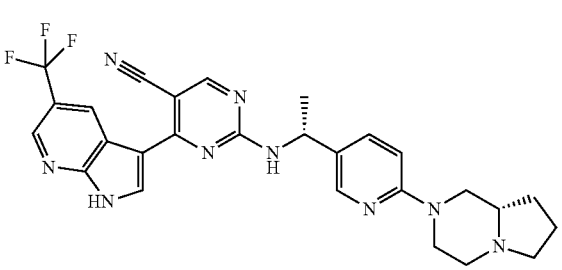

I-292
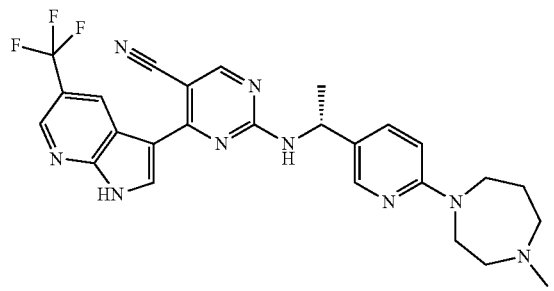
I-293
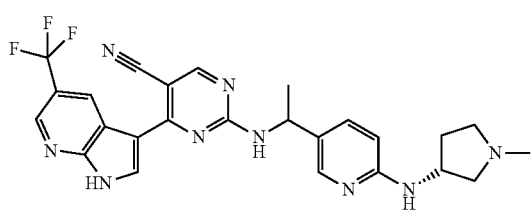
I-294
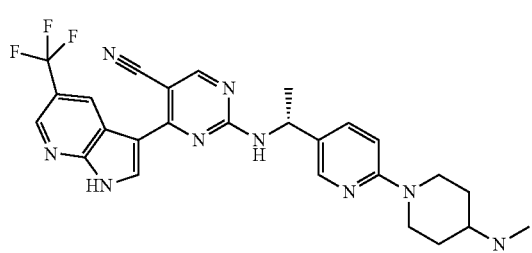
I-295
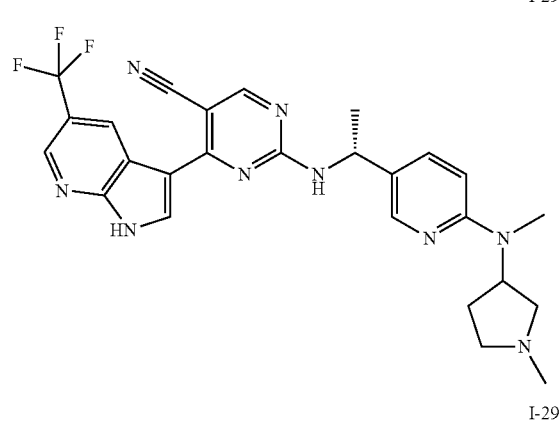
I-296
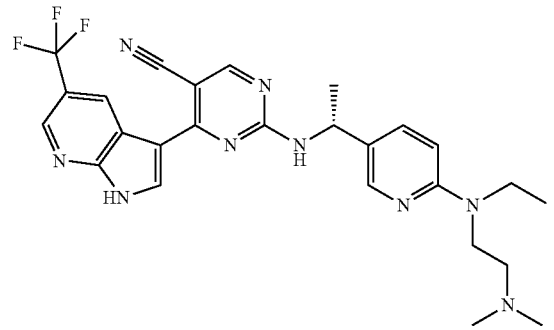
I-297
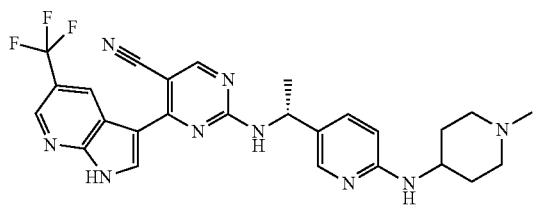
I-298
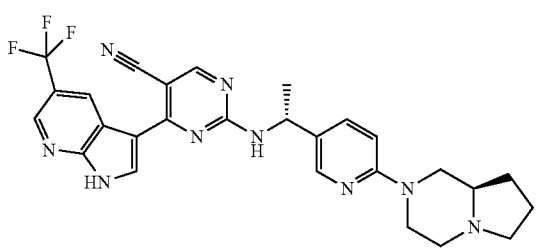
I-299
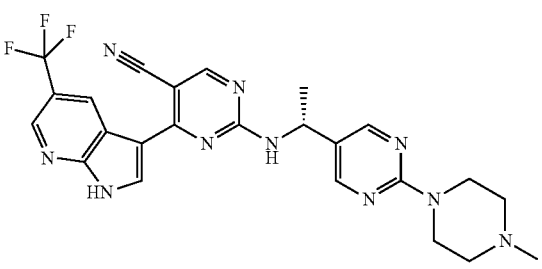
I-300
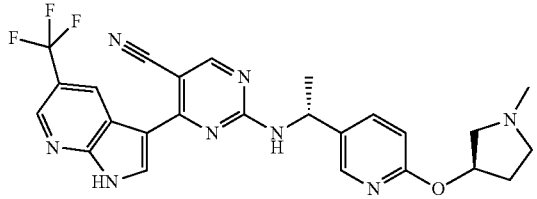
I-301
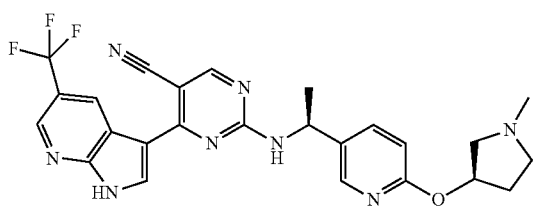
I-302
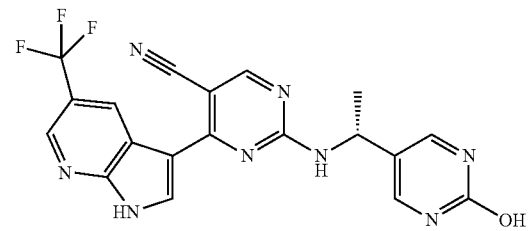

31. The method of claim 2, wherein the compound of structural formula (I) is any one of compounds IA-1 through IA-14 or a pharmaceutically acceptable salt thereof:

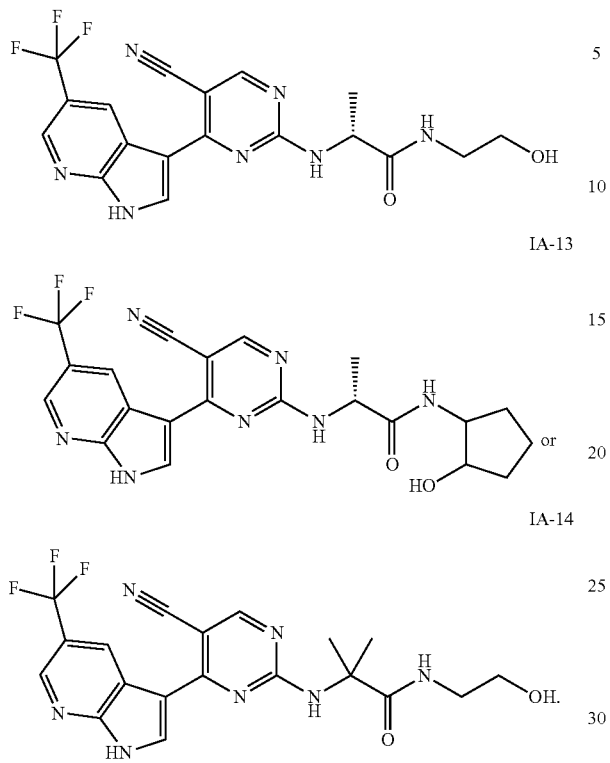
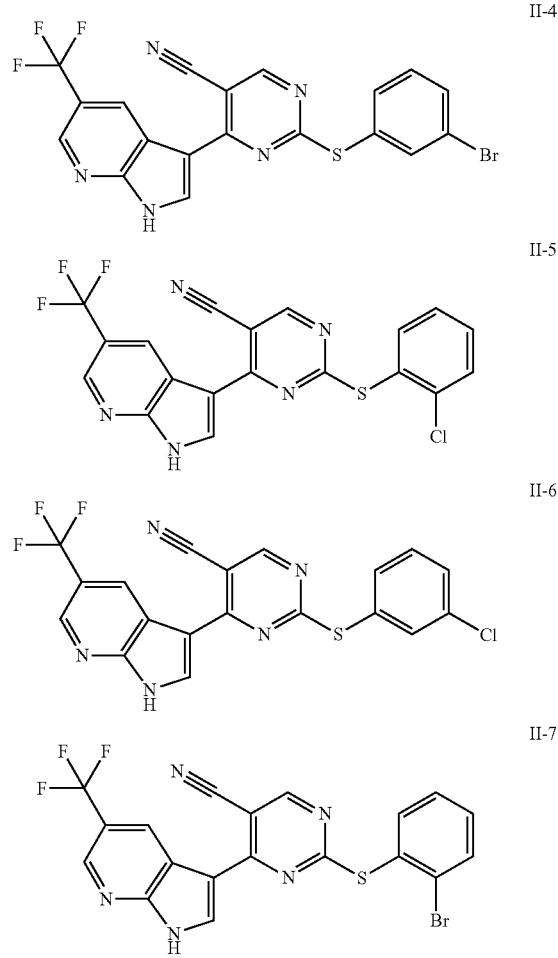
32. The method of claim 2, wherein the compound of structural formula (I) is any one of compounds II-1 through II-16, or II-0, or a pharmaceutically acceptable salt thereof:
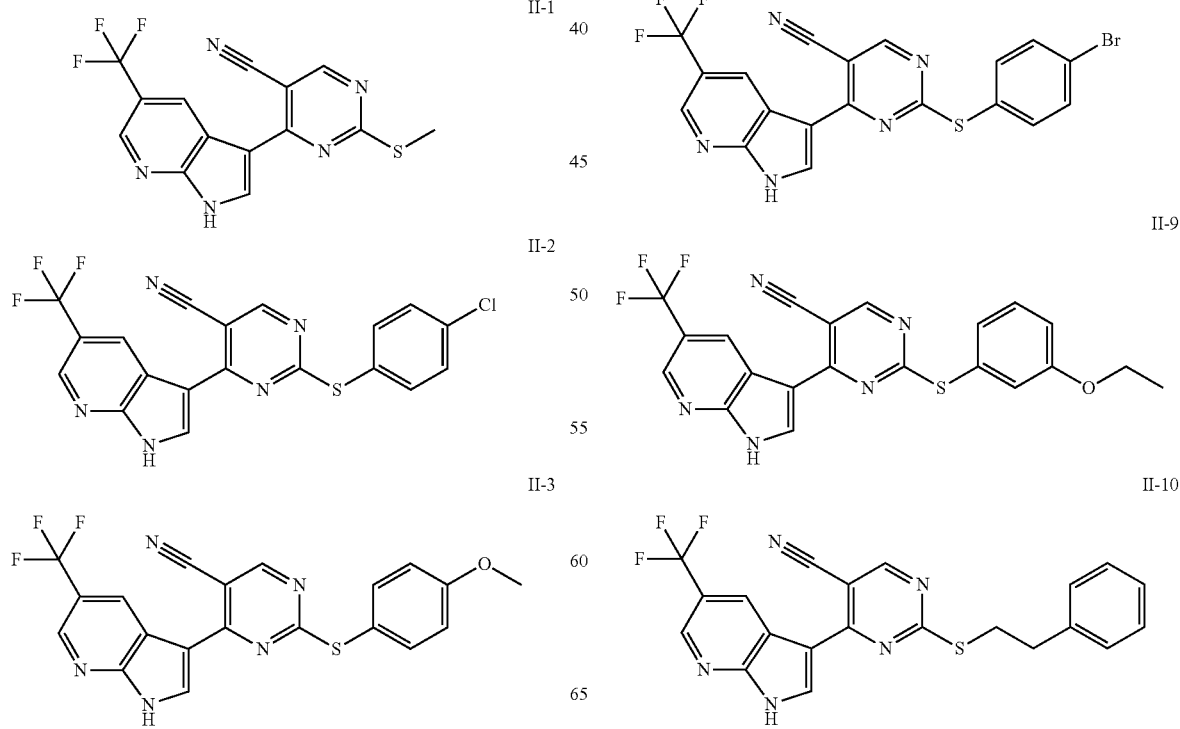

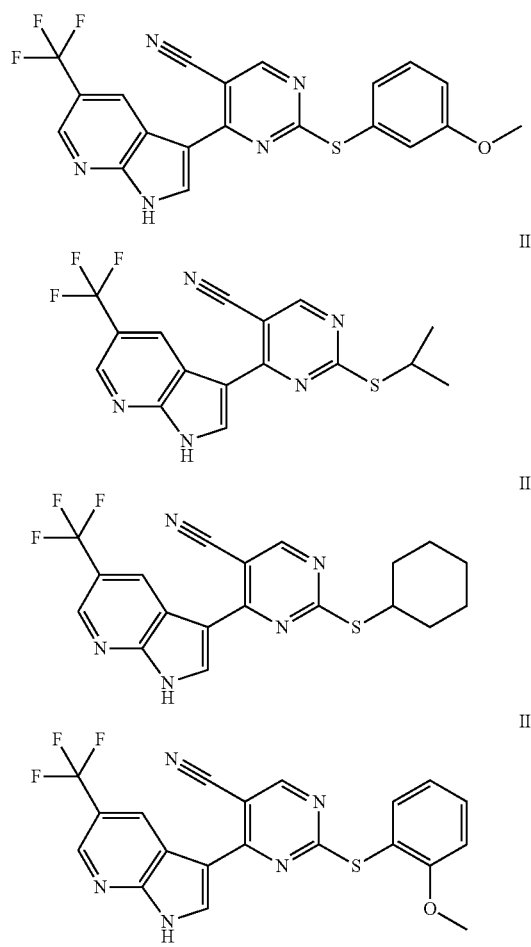
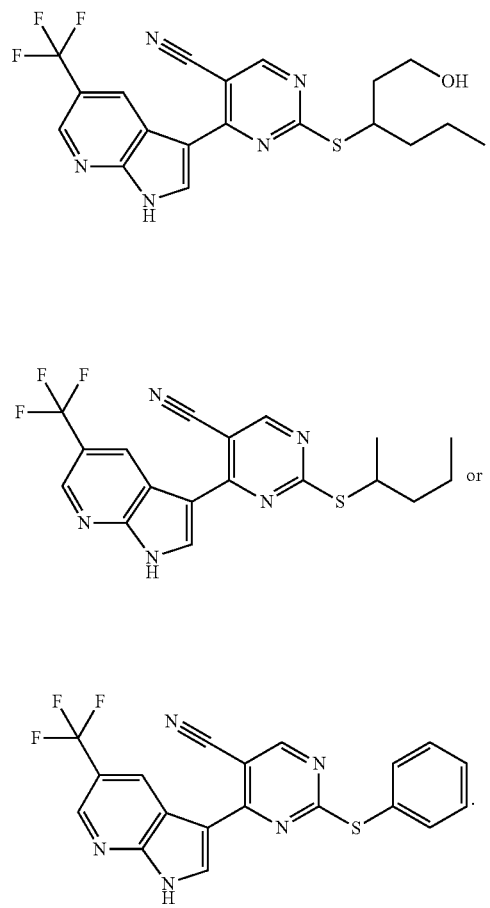
* * * * *